US012655125B2

(12) United States Patent
Zhang et al.

(10) Patent No.: US 12,655,125 B2

(45) Date of Patent: Jun. 16, 2026

(54) AZETIDINE CYCLIC UREAS

(71) Applicant: SIRONAX LTD., Grand Cayman (KY)

(72) Inventors: Zhaolan Zhang, Beijing (CN); Zhiyuan Zhang, San Diego, CA (US); Yaning Su, Beijing (CN); Yanping Xu, Beijing (CN)

(73) Assignee: SIRONAX LTD., Grand Cayman (KY)

(*) Notice: Subject to any disclaimer, the term of this patent is extended or adjusted under 35 U.S.C. 154(b) by 679 days.

(21) Appl. No.: 17/998,552

(22) PCT Filed: May 20, 2021

(86) PCT No.: PCT/CN2021/094991

§ 371 (c)(1),
(2) Date: Nov. 11, 2022

(87) PCT Pub. No.: WO2021/233396

PCT Pub. Date: Nov. 25, 2021

(65) Prior Publication Data

US 2023/0416226 A1 Dec. 28, 2023

(30) Foreign Application Priority Data

May 20, 2020 (WO) ................ PCT/CN2020/091416

(51) Int. Cl.

| | |
|---|---|
| ***C07D 401/14*** | (2006.01) |
| ***C07D 403/14*** | (2006.01) |
| ***C07D 405/14*** | (2006.01) |
| ***C07D 413/14*** | (2006.01) |
| ***C07D 417/14*** | (2006.01) |

(52) U.S. Cl.

CPC ......... *C07D 401/14* (2013.01); *C07D 403/14* (2013.01); *C07D 405/14* (2013.01); *C07D 413/14* (2013.01); *C07D 417/14* (2013.01)

(58) Field of Classification Search

CPC .. C07D 401/14; C07D 403/14; C07D 405/14; C07D 413/14; C07D 417/14

See application file for complete search history.

(56) References Cited

U.S. PATENT DOCUMENTS

| | | | |
|---|---|---|---|
| 6,756,394 | B1 | 6/2004 | Yuan et al. |
| 8,278,344 | B2 | 10/2012 | Cuny et al. |
| 9,974,762 | B2 | 5/2018 | Zhang et al. |
| 10,092,529 | B2 | 10/2018 | Zhang et al. |
| 2003/0083386 | A1 | 5/2003 | Yuan et al. |
| 2009/0099242 | A1 | 4/2009 | Cuny et al. |
| 2010/0317701 | A1 | 12/2010 | Cuny et al. |
| 2011/0144169 | A1 | 6/2011 | Cuny et al. |
| 2012/0122889 | A1 | 5/2012 | Yuan et al. |
| 2012/0309795 | A1 | 12/2012 | Cuny et al. |
| 2017/0304237 | A1 | 10/2017 | Zhang et al. |

FOREIGN PATENT DOCUMENTS

| | | | | |
|---|---|---|---|---|
| CN | 107624111 A | 1/2018 | | |
| JP | 2005526091 A | 9/2005 | | |
| JP | 2018515555 A | 6/2018 | | |
| JP | 2019535728 A | 12/2019 | | |
| JP | 7577655 B | 11/2024 | | |
| WO | WO 2003/079973 A2 | 10/2003 | | |
| WO | WO 03079973 A2 | 10/2003 | | |
| WO | WO 2009023272 A1 | 2/2009 | | |
| WO | 2009109743 41 | 9/2009 | | |
| WO | WO 2010075290 A1 | 7/2010 | | |
| WO | WO 2010075561 A1 | 7/2010 | | |
| WO | WO 2012125544 A2 | 9/2012 | | |
| WO | WO 2016/101887 A1 | 6/2016 | | |
| WO | 2016185423 A1 | 11/2016 | | |
| WO | 2018092089 A1 | 5/2018 | | |
| WO | WO 2019/224774 A1 | 11/2019 | | |
| WO | WO 2019224773 A1 | 11/2019 | | |
| WO | WO-2020103884 A1 | * | 5/2020 | ........... A61K 31/397 |
| WO | WO 2021062199 A1 | 4/2021 | | |

OTHER PUBLICATIONS

Liu et.al., RIP1/RIP3-regulated necroptosis as a target for multifaceted disease therapy (Review). Int J Mol Med. Sep. 2019;44(3): 771-786. (Year: 2019).*

Fearnhead et al., ell Death and Differentiation (2017) 24, 1991-1998. (Year: 2017).*

Harris et a;., ACS Med Chem Lett. May 9, 2019;10(6):857-862. (Year: 2019).*

Philip A. Harris, et al., Journal of Medicinal Chemistry 2019 62 (10), 5096-5110. (Year: 2019).*

Holler, N. et al., Fas triggers an alternative, caspase-8-independent cell death pathway using the kinase RIP as effector molecule, *Nature Immunology*, 2000, 1(6), pp. 489-495.

Degterev, A. et al., Identification of RIP1 kinase as a specific cellular target of necrostatins, *Nature Chemical Biology*, 2008, 4(5), pp. 313-321.

Dunai, Z., et al., Necroptosis: Biochemical, Physiological and Pathological Aspects, *Pathology & Oncology Research*, 2011, 17(4), pp. 791-800.

Degterev, A. et al., Chemical inhibitor of nonapoptotic cell death with therapeutic potential for ischemic brain injury, *Nature Chemical Biology*, 2005, 1(2), pp. 112-119.

Manguso, R. T. et al., In vivo CRISPR screening identifies Ptpn2 as a cancer immunotherapy target, *Nature*, 2017, 547(7664), pp. 413-418.

Wang, W. et al., RIP1 Kinase Drives Macrophage-Mediated Adaptive Immune Tolerance in Pancreatic Cancer, *Cancer Cell*, 2018, 34(5), pp. 757-774.

Berge, S. M., et al., Pharmaceutical Salts, *Journal of Pharmaceutical Sciences*, 1977, 66(1), pp. 1-19.

(Continued)

*Primary Examiner* — George W Kosturko

*Assistant Examiner* — Izabela Schmidt

(74) *Attorney, Agent, or Firm* — Troutman Pepper Locke LLP

(57) ABSTRACT

Provided are azetidine cyclic urea compounds that inhibit cellular necrosis and/or human receptor interacting protein 1 kinase (RIP1), including corresponding sulfonamides, and pharmaceutically acceptable salts, hydrates and stereoisomers thereof. The compounds are employed in pharmaceutical compositions, and methods of making and use, including treating a person in need thereof with an effective amount of the compound or composition, and detecting a resultant improvement in the persons health or condition.

27 Claims, No Drawings

(56) References Cited

OTHER PUBLICATIONS

Cox, C. D. et al., Kinesin spindle protein (KSP) inhibitors. Part 4: Structure-based design of 5-alkylamino-3,5-diaryl-4,5-dihydropyrazoles as potent, water-soluble inhibitors of the mitotic kinesin KSP, *Bioorganic & Medicinal Chemistry Letters*, 2006, 16(12), pp. 3175-3179.
Sebastian, J., Dihydropyrazole and dihydropyrrole structures based design of Kif15 inhibitors as novel therapeutic agents for cancer, *Computational Biology and Chemistry*, 2017, 68, pp. 164-174.
International Search Report and Written Opinion in counterpart PCT application No. PCT/CN2021/094991, mailed Aug. 24, 2021.
Extended European Search Report issued in European Application No. 21808475.4 on Sep. 14, 2023, 8 pgs.
Harris, Philip A. et al., "Discovery and Lead-Organization of 4,5-Dihydropyrazoles as Mono-Kinase Selective, Orally Bioavailable and Efficacious Inhibitors of Receptor Interacting Protein 1 (RIP1) Kinase," *Journal of Medicinal Chemistry*, 2019, 62, 5096-5110, © 2019 American Chemical Society, 15 pgs.
PCT International Preliminary Report on Patentability issued in International Application No. PCT/CN2021/094991 on Nov. 17, 2022, 8 pgs.
A.K. Ghosh et al., Urea Derivatives in Modern Drug Discovery and Medicinal Chemistr, *Journal of Medicinal Chemistry*, 63(6), pp. 2751-2788 (2019).

* cited by examiner

AZETIDINE CYCLIC UREAS

CROSS-REFERENCE TO RELATED APPLICATIONS

This is a national stage application of International Application No. PCT/CN2021/094991, filed May 20, 2021, which claims priority to PCT/CN2020/091416, filed May 20, 2020, all of which are incorporated herein by reference.

INTRODUCTION

Tumor necrosis factor alpha (TNF-α)-induced NF-κB activation plays a central role in the immune system and inflammatory responses. Receptor-interacting protein 1 (RIP1) is a multi-functional signal transducer involved in mediating nuclear factor κB (NF-κB) activation, apoptosis, and necroptosis. The kinase activity of RIP1 is critically involved in mediating necroptosis, a caspase-independent pathway of necrotic cell death. Holler et al. Nat Immunol 2000; 1: 489-495; Degterev et al. Nat Chem Biol 2008; 4: 313-321.

Necroptosis plays a role in various pathological forms of cell death, including ischemic brain injury, neurodegenerative diseases and viral infections. Dunai, et al., December 2011, Pathol. Oncol. Res.: POR 17 (4): 791-800. Necrostatin-1 (Nec-1), a small molecule inhibitor of RIP1 kinase activity, can block necroptosis. Degterev et al. Nat Chem Biol 2005; 1: 112-119.

RIP1 can contribute to D-1 immunotherapy resistance (e.g. Manguso et al., 2017 Nature 547, 413-418) and can act as a checkpoint kinase governing tumor immunity (e.g. Wang et al, Cancer Cell 34, 757-774, Nov. 12, 2018).

Related patent publications include: U.S. Pat. Nos. 9,974,762, 10,092,529, 6,756,394, 8,278,344, US20120122889, US20090099242, US20100317701, US20110144169, US20030083386, US201200309795, WO2009023272, WO2010075290, WO2010075561, WO2012125544, and WO 2020/103884.

SUMMARY OF THE INVENTION

The invention provides compounds that are inhibitors of necrosis, necroptosis, ferroptosis, human receptor interacting protein 1 kinase (RIP1) or related indications, and prodrugs thereof, which are hydrolyzed, typically in the gut or blood, to yield the corresponding inhibitors. In embodiments the inhibitors provide unexpectedly exceptional metabolic stability, evidenced by liver microsome data and PK data.

In an aspect the invention provides a compound of formula I:

I

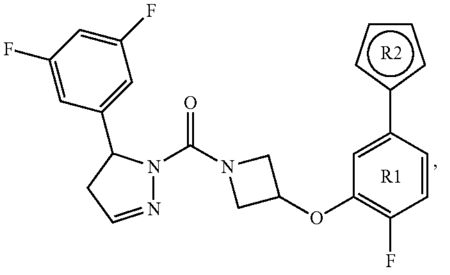

wherein:

R1 is 1-F substituted C6 aryl comprising 0, 1 or 2 N heteroatoms; and

R2 is C5 aryl comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl;

or a salt, hydrate or stereoisomer thereof.

In embodiments:

the R2 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3);

R1 comprises N2, N4 or N2/N4 ("/" means "and", unless otherwise specified);

R2 comprises N1, N1/N2, N2/N3, N3/N4, N2/N5; N2/N4, S2/N4, N2/S4, S3/N4, N2/S3, N3/O4, N2/N3/S5, N2/N3/O5, N2/N3/N5 or N2/N3/N4; or any combination of the foregoing substituents.

In an aspect the invention provides a compound having a structure disclosed herein.

In an aspect the invention provides a pharmaceutical composition comprising a therapeutically effective amount of a compound, a salt, hydrate or stereoisomer thereof, disclosed herein and one or more pharmaceutically acceptable excipients, in predetermined, unit dosage form.

In an aspect the invention provides use of a compound, a salt, hydrate or stereoisomer thereof, or composition disclosed herein in the manufacture of a medicament for inhibiting necrosis, necroptosis, ferroptosis, human RIP1, or related indications, in a person in need thereof.

In an aspect the invention provides a compound, a salt, hydrate or stereoisomer thereof, or composition disclosed herein for use in inhibiting necrosis, necroptosis, ferroptosis, human RIP1, or related indications in a person in need thereof, or in the manufacture of a medicament thereof in a person in need thereof.

In an aspect the invention provides a method of using a compound, a salt, hydrate or stereoisomer thereof, or composition disclosed herein for to inhibit necrosis, necroptosis, ferroptosis, human RIP1, or related indications in a person in need thereof, or in the manufacture of a medicament thereof in a person in need thereof.

The invention encompasses all combination of the particular embodiments recited herein, as if each combination had been laboriously recited.

DESCRIPTION OF PARTICULAR EMBODIMENTS OF THE INVENTION

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

The term "alkyl" refers to a hydrocarbon group selected from linear and branched saturated hydrocarbon groups of 1-18, or 1-12, or 1-6, or 1-3 carbon atoms. Examples of the alkyl group include methyl, ethyl, 1-propyl or n-propyl ("n-Pr"), 2-propyl or isopropyl ("i-Pr"), 1-butyl or n-butyl ("n-Bu"), 2-methyl-1-propyl or isobutyl ("i-Bu"), 1-methylpropyl or s-butyl ("s-Bu"), and 1,1-dimethylethyl or t-butyl ("t-Bu"). Other examples of the alkyl group include 1-pentyl, 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl and 3,3-dimethyl-2-butyl groups.

Lower alkyl means 1-8, preferably 1-6, more preferably 1-4 carbon atoms, e.g., 1-3 carbon atoms, lower alkenyl or alkynyl means 2-8, 2-6 or 2-4 carbon atoms.

The term "alkenyl" refers to a hydrocarbon group selected from linear and branched hydrocarbon groups comprising at least one C═C double bond and of 2-18, or 2-12, or 2-6 carbon atoms. Examples of the alkenyl group may be selected from ethenyl or vinyl, prop-1-enyl, prop-2-enyl, 2-methylprop-1-enyl, but-1-enyl, but-2-enyl, but-3-enyl, buta-1,3-dienyl, 2-methylbuta-1,3-diene, hex-1-enyl, hex-2-enyl, hex-3-enyl, hex-4-enyl, and hexa-1,3-dienyl groups.

The term "alkynyl" refers to a hydrocarbon group selected from linear and branched hydrocarbon group, comprising at least one C≡C triple bond and of 2-18, or 2-12, or 2-6 carbon atoms. Examples of the alkynyl group include ethynyl, 1-propynyl, 2-propynyl (propargyl), 1-butynyl, 2-butynyl, and 3-butynyl groups.

The term "cycloalkyl" refers to a hydrocarbon group selected from saturated and partially unsaturated cyclic hydrocarbon groups, comprising monocyclic and polycyclic (e.g., bicyclic and tricyclic) groups. For example, the cycloalkyl group may be of 3-12, or 3-8, or 3-6, or 3-4, carbon atoms. Even further for example, the cycloalkyl group may be a monocyclic group of 3-12, or 3-8, or 3-6 carbon atoms. Examples of the monocyclic cycloalkyl group include cyclopropyl, cyclobutyl, cyclopentyl, 1-cyclopent-1-enyl, 1-cyclopent-2-enyl, 1-cyclopent-3-enyl, cyclohexyl, 1-cyclohex-1-enyl, 1-cyclohex-2-enyl, 1-cyclohex-3-enyl, cyclohexadienyl, cycloheptyl, cyclooctyl, cyclononyl, cyclodecyl, cycloundecyl, and cyclododecyl groups. Examples of the bicyclic cycloalkyl groups include those having 7-12 ring atoms arranged as a bicycle ring selected from [4,4], [4,5], [5,5], [5,6] and [6,6] ring systems, or as a bridged bicyclic ring selected from bicyclo[2.2.1]heptane, bicyclo[2.2.2]octane, and bicyclo[3.2.2]nonane. The ring may be saturated or have at least one double bond (i.e. partially unsaturated), but is not fully conjugated, and is not aromatic, as aromatic is defined herein.

The term "aryl" herein refers to a group selected from: 5- and 6-membered carbocyclic aromatic rings, for example, phenyl; bicyclic ring systems such as 7-12 membered bicyclic ring systems wherein at least one ring is carbocyclic and aromatic, selected, for example, from naphthalene, indane, and 1,2,3,4-tetrahydroquinoline; and tricyclic ring systems such as 10-15 membered tricyclic ring systems wherein at least one ring is carbocyclic and aromatic, for example, fluorene. 5- or 6-membered "aryl" may comprise 0, 1, 2 or 3 heteroatoms selected from the group consisting of N, S or O.

For example, the aryl group is selected from 5- and 6-membered carbocyclic aromatic rings fused to a 5- to 7-membered cycloalkyl or heterocyclic ring optionally comprising at least one heteroatom selected from N, O, and S, provided that the point of attachment is at the carbocyclic aromatic ring when the carbocyclic aromatic ring is fused with a heterocyclic ring, and the point of attachment can be at the carbocyclic aromatic ring or at the cycloalkyl group when the carbocyclic aromatic ring is fused with a cycloalkyl group. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene.

The term "halogen" or "halo" refers to F, Cl, Br or I.

The term "heteroalkyl" refers to alkyl comprising at least one heteroatom.

The term "heteroaryl" refers to a group selected from:

- 5- to 7-membered aromatic, e.g., 5- to 6-membered aromatic, monocyclic rings comprising 1, 2, 3 or 4 heteroatoms selected from N, O, and S, with the remaining ring atoms being carbon;
- 8- to 12-membered bicyclic rings comprising 1, 2, 3 or 4 heteroatoms, selected from N, O, and S, with the remaining ring atoms being carbon and wherein at least one ring is aromatic and at least one heteroatom is present in the aromatic ring; and
- 11- to 14-membered tricyclic rings comprising 1, 2, 3 or 4 heteroatoms, selected from N, O, and S, with the remaining ring atoms being carbon and wherein at least one ring is aromatic and at least one heteroatom is present in an aromatic ring.

For example, the heteroaryl group includes a 5- to 7-membered heterocyclic aromatic ring fused to a 5- to 7-membered cycloalkyl ring. For such fused, bicyclic heteroaryl ring systems wherein only one of the rings comprises at least one heteroatom, the point of attachment may be at the heteroaromatic ring or at the cycloalkyl ring.

When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1.

Examples of the heteroaryl group include, but are not limited to, (as numbered from the linkage position assigned priority 1) pyridyl (such as 2-pyridyl, 3-pyridyl, or 4-pyridyl), cinnolinyl, pyrazinyl, 2,4-pyrimidinyl, 3,5-pyrimidinyl, 2,4-imidazolyl, imidazopyridinyl, isoxazolyl, oxazolyl, thiazolyl, isothiazolyl, thiadiazolyl, tetrazolyl, thienyl, triazinyl, benzothienyl, furyl, benzofuryl, benzoimidazolyl, indolyl, isoindolyl, indolinyl, phthalazinyl, pyrazinyl, pyridazinyl, pyrrolyl, triazolyl, quinolinyl, isoquinolinyl, pyrazolyl, pyrrolopyridinyl (such as 1H-pyrrolo[2,3-b]pyridin-5-yl), pyrazolopyridinyl (such as 1H-pyrazolo[3,4-b]pyridin-5-yl), benzoxazolyl (such as benzo[d]oxazol-6-yl), pteridinyl, purinyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, furazanyl, benzofurazanyl, benzothiophenyl, benzothiazolyl, benzoxazolyl, quinazolinyl, quinoxalinyl, naphthyridinyl, furopyridinyl, benzothiazolyl (such as benzo[d]thiazol-6-yl), indazolyl (such as 1H-indazol-5-yl) and 5,6,7,8-tetrahydroisoquinoline.

The term "heterocyclic" or "heterocycle" or "heterocyclyl" refers to a ring selected from 4- to 12-membered, e.g., 3- to 6-membered, or 3 to 5-membered, or 4 to 5-membered, or 5 to 6-membered, or 4- to 6-membered, monocyclic, bicyclic and tricyclic, saturated and partially unsaturated rings comprising at least one carbon atoms in addition to 1, 2, 3 or 4 heteroatoms, selected from oxygen, sulfur, and nitrogen. "Heterocycle" also refers to a 5- to 7-membered heterocyclic ring comprising at least one heteroatom selected from N, O, and S fused with 5-, 6-, and/or 7-membered cycloalkyl, carbocyclic aromatic or heteroaromatic ring, provided that the point of attachment is at the heterocyclic ring when the heterocyclic ring is fused with a carbocyclic aromatic or a heteroaromatic ring, and that the point of attachment can be at the cycloalkyl or heterocyclic ring when the heterocyclic ring is fused with cycloalkyl.

"Heterocycle" also refers to an aliphatic spirocyclic ring comprising at least one heteroatom selected from N, O, and S, provided that the point of attachment is at the heterocyclic ring. The rings may be saturated or have at least one double bond (i.e. partially unsaturated). The heterocycle may be substituted with oxo. The point of the attachment may be carbon or heteroatom in the heterocyclic ring. A heterocycle is not a heteroaryl as defined herein.

Examples of the heterocycle include, but not limited to, (as numbered from the linkage position assigned priority 1) 1-pyrrolidinyl, 2-pyrrolidinyl, 2,4-imidazolidinyl, 2,3-pyrazolidinyl, 1-piperidinyl, 2-piperidinyl, 3-piperidinyl, 4-piperidinyl, 2,5-piperazinyl, pyranyl, 2-morpholinyl, 3-morpholinyl, oxiranyl, aziridinyl, thiiranyl, azetidinyl, oxetanyl, thietanyl, 1,2-dithietanyl, 1,3-dithietanyl, dihydropyridinyl, tetrahydropyridinyl, thiomorpholinyl, thioxanyl, piperazinyl, homopiperazinyl, homopiperidinyl, azepanyl, oxepanyl, thiepanyl, 1,4-oxathianyl, 1,4-dioxepanyl, 1,4-oxathiepanyl, 1,4-oxaazepanyl, 1,4-dithiepanyl, 1,4-thiazepanyl and 1,4-diazepane 1,4-dithianyl, 1,4-azathianyl, oxazepinyl, diazepinyl, thiazepinyl, dihydrothienyl, dihydropyranyl, dihydrofuranyl, tetrahydrofuranyl, tetrahydrothienyl, tetrahydropyranyl, tetrahydrothiopyranyl, 1-pyrrolinyl, 2-pyrrolinyl, 3-pyrrolinyl, indolinyl, 2H-pyranyl, 4H-pyranyl, 1,4-dioxanyl, 1,3-dioxolanyl, pyrazolinyl, pyrazolidinyl, dithianyl, dithiolanyl, pyrazolidinylimidazolinyl, pyrimidinonyl, 1,1-dioxo-thiomorpholinyl, 3-azabicyclo [3.1.0]hexanyl, 3-azabicyclo[4.1.0]heptanyl and azabicyclo [2.2.2]hexanyl. Substituted heterocycle also includes ring systems substituted with one or more oxo moieties, such as piperidinyl N-oxide, morpholinyl-N-oxide, 1-oxo-1-thiomorpholinyl and 1, 1-dioxo-1-thiomorpholinyl.

The term "fused ring" herein refers to a polycyclic ring system, e.g., a bicyclic or tricyclic ring system, in which two rings share only two ring atoms and one bond in common. Examples of fused rings may comprise a fused bicyclic cycloalkyl ring such as those having from 7 to 12 ring atoms arranged as a bicyclic ring selected from [4,4], [4,5], [5,5], [5,6] and [6,6] ring systems as mentioned above; a fused bicyclic aryl ring such as 7 to 12 membered bicyclic aryl ring systems as mentioned above, a fused tricyclic aryl ring such as 10 to 15 membered tricyclic aryl ring systems mentioned above; a fused bicyclic heteroaryl ring such as 8- to 12-membered bicyclic heteroaryl rings as mentioned above, a fused tricyclic heteroaryl ring such as 11- to 14-membered tricyclic heteroaryl rings as mentioned above; and a fused bicyclic or tricyclic heterocyclyl ring as mentioned above.

In embodiments substituents are selected from optionally substituted heteroatom and optionally substituted, optionally hetero-, optionally cyclic C1-C18 hydrocarbyl, particularly wherein the optionally substituted, optionally hetero-, optionally cyclic C1-C18 hydrocarbyl is optionally-substituted, optionally hetero-, optionally cyclic alkyl, alkenyl or alkynyl, or optionally-substituted, optionally hetero-aryl; and/or the optionally substituted heteroatom is halogen, optionally substituted hydroxyl (such as alkoxy, aryloxy), optionally substituted acyl (such as formyl, alkanoyl, carbamoyl, carboxyl, amido), optionally substituted amino (such as amino, alkylamino, dialkylamino, amido, sulfamidyl), optionally substituted thiol (such as mercapto, alkylthiol, aryl thiol), optionally substituted sulfinyl or sulfonyl (such as alkylsulfinyl, arylsulfinyl, alkyl sulfonyl, arylsulfonyl), nitro, or cyano.

In embodiments, substituents are selected from: halogen, —R', —OR', =O, =NR', =N—OR', —NR'R", —SR', —SiR'R"R"', —OC(O)R', —C(O)R', —CO2R', —CONR'R", —OC(O)NR'R", —NR"C(O)R', —NR'—C(O)NR"R"', —NR'—SO2NR"', —NR"CO2R', —NH—C(NH2)=NH, —NR'C(NH2)=NH, —NH—C(NH2)=NR', —S(O)R', —SO2R', —SO2NR'R", —NR"SO2R, —CN and —NO2, —N3, —CH(Ph)2, perfluoro(C1-C4)alkoxy and perfluoro(C1-C4)alkyl, in a number ranging from zero to three, with those groups having zero, one or two substituents being particularly preferred. R', R" and R"' each independently refer to hydrogen, unsubstituted (C1-C8)alkyl and heteroalkyl, (C1-C8)alkyl and heteroalkyl substituted with one to three halogens, unsubstituted aryl, aryl substituted with one to three halogens, unsubstituted alkyl, alkoxy or thioalkoxy groups, or aryl-(C1-C4)alkyl groups. When R' and R" are attached to the same nitrogen atom, they can be combined with the nitrogen atom to form a 5-, 6- or 7-membered ring. Hence, —NR'R" includes 1-pyrrolidinyl and 4-morpholinyl, "alkyl" includes groups such as trihaloalkyl (e.g., —CF3 and —CH2CF3), and when the aryl group is 1,2,3,4-tetrahydronaphthalene, it may be substituted with a substituted or unsubstituted (C3-C7)spirocycloalkyl group. The (C3-C7)spirocycloalkyl group may be substituted in the same manner as defined herein for "cycloalkyl".

Preferred substituents are selected from: halogen, —R', —OR', =O, —NR'R", —SR', —SiR'R"R"', —OC(O)R', —C(O)R', —CO2R', —CONR'R", —OC(O)NR'R", —NR"C(O)R', —NR"CO2R', —NR'—SO2NR"R$^{1'}$, —S(O)R', —SO2R', —SO2NR'R", —NR"SO2R, —CN and —NO2, perfluoro(C1-C4)alkoxy and perfluoro(C1-C4)alkyl, where R' and R" are as defined above.

Preferred substituents are disclosed herein and exemplified in the tables, structures, examples, and claims, and may be applied across different compounds of the invention, i.e. substituents of any given compound may be combinatorically used with other compounds.

In particular embodiments applicable substituents are independently substituted or unsubstituted heteroatom, substituted or unsubstituted, 0-3 heteroatom C1-C6 alkyl, C1-C3 alkyl, or C1-C2 alkyl, substituted or unsubstituted, 0-3 heteroatom C2-C6 alkenyl, substituted or unsubstituted, 0-3 heteroatom C2-C6 alkynyl, or substituted or unsubstituted, 0-3 heteroatom C6-C14 aryl, or C5-C6 aryl, wherein each heteroatom is independently oxygen, phosphorus, sulfur or nitrogen.

In more particular embodiments, applicable substituents are independently aldehyde, aldimine, alkanoyloxy, alkoxy, alkoxycarbonyl, alkyloxy, alkyl, alkenyl, alkynyl, amine, azo, halogen, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or trifluromethyl ether (OCF3). It shall be noted that, when used in the context of substituents, terms such as aldehyde, aldimine, amine, azo, ester, imine, isocyanide, iscyante, nitrate, nitrile, nitrite, phosphate, sulfide or trifluromethyl ether equal to aldehyde group, aldimine group, amino, azo group, ester group, imino, isocyanide group, iscyante group, nitrate group, nitrile group, nitrite group, phosphate group, sulfide group or trifluromethyl ether group, respectively.

Combinations of substituents as disclosed herein are those that result in the formation of stable or chemically feasible compounds. For abbreviation or according to common practice, certain hydrogen atoms attached to a certain atom (e.g., a carbon atom C or a nitrogen atom N) are not specifically spelled out in a chemical structure, formula, or notation; hydrogen atoms are deemed to be present to the extent the valences of the certain atom (e.g., C or N) are completed.

The compounds may contain an asymmetric center and may thus exist as enantiomers. Where the compounds possess two or more asymmetric centers, they may additionally exist as diastereomers. Enantiomers and diastereomers fall within the broader class of stereoisomers. All such possible stereoisomers as substantially pure resolved enantiomers, racemic mixtures thereof, as well as mixtures of diastereomers are intended to be included. All stereoisomers of the compounds and/or pharmaceutically acceptable salts thereof are intended to be included. Unless specifically mentioned otherwise, reference to one isomer applies to any of the possible isomers. Whenever the isomeric composition is unspecified, all possible isomers are included.

The term "substantially pure" means that the target stereoisomer contains no more than 35%, such as no more than 30%, further such as no more than 25%, even further such as no more than 20%, by weight of any other stereoisomer (s). In some embodiments, the term "substantially pure" means that the target stereoisomer contains no more than 10%, for example, no more than 5%, such as no more than 1%, by weight of any other stereoisomer(s).

When compounds contain olefin double bonds, unless specified otherwise, such double bonds are meant to include both E and Z geometric isomers.

Some of the compounds may exist with different points of attachment of hydrogen, referred to as tautomers. For example, compounds including carbonyl —$CH_2C(O)$— groups (keto forms) may undergo tautomerism to form hydroxyl —CH=C(OH)— groups (enol forms). Both keto and enol forms, individually as well as mixtures thereof, are also intended to be included where applicable.

It may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example: reverse-phase and normal phase; size exclusion; ion exchange; high, medium and low pressure liquid chromatography methods and apparatus; small scale analytical; simulated moving bed ("SMB") and preparative thin or thick layer chromatography, as well as techniques of small scale thin layer and flash chromatography. One skilled in the art will apply techniques most likely to achieve the desired separation.

Diastereomeric mixtures can be separated into their individual diastereomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereoisomers to the corresponding pure enantiomers. Enantiomers can also be separated by use of a chiral HPLC column.

A single stereoisomer, e.g., a substantially pure enantiomer, may be obtained by resolution of the racemic mixture using a method such as formation of diastereomers using optically active resolving agents. Racemic mixtures of chiral compounds of the invention can be separated and isolated by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure stereoisomers, and (3) separation of the substantially pure or enriched stereoisomers directly under chiral conditions.

"Pharmaceutically acceptable salts" include, but are not limited to salts with inorganic acids, selected, for example, from hydrochlorates, phosphates, diphosphates, hydrobromates, sulfates, sulfinates, and nitrates; as well as salts with organic acids, selected, for example, from malates, maleates, fumarates, tartrates, succinates, citrates, lactates, methanesulfonates, p-toluenesulfonates, 2-hydroxyethylsulfonates, benzoates, salicylates, stearates, alkanoates such as acetate, and salts with HOOC—$(CH_2)$n-COOH, wherein n is selected from 0 to 4. Similarly, examples of pharmaceutically acceptable cations include, but are not limited to, sodium, potassium, calcium, aluminum, lithium, and ammonium.

In addition, if a compound is obtained as an acid addition salt, the free base can be obtained by basifying a solution of the acid salt. Conversely, if the product is a free base, an addition salt, such as a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used without undue experimentation to prepare non-toxic pharmaceutically acceptable addition salts.

"Treating," "treat," or "treatment" refers to administering at least one compound and/or at least one stereoisomer thereof, and/or at least one hydrate thereof, and/or at least one pharmaceutically acceptable salt thereof to a subject in recognized need thereof.

An "effective amount" refers to an amount of at least one compound and/or at least one stereoisomer thereof, and/or at least one pharmaceutically acceptable salt thereof effective to "treat" a disease or disorder in a subject, and that will elicit, to some significant extent, the biological or medical response of a tissue, system, animal or human that is being sought, such as when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The term "at least one substituent" includes, for example, from 1 to 4, such as from 1 to 3, further as 1 or 2, substituents. For example, "at least one substituent $R^{16}$" herein includes from 1 to 4, such as from 1 to 3, further as 1 or 2, substituents selected from the list of $R^{16}$ as described herein.

The subject compounds and stereoisomers thereof, hydrates thereof, and pharmaceutically acceptable salts thereof may be employed alone or in combination with at least one other therapeutic agent for treatment. In some embodiments, the compounds, stereoisomers thereof, hydrates thereof, and pharmaceutically acceptable salts thereof can be used in combination with at least one additional therapeutic agent. The compound and/or one pharmaceutically acceptable salt disclosed herein may be administered with the at least one other therapeutic agent in a single dosage form or as a separate dosage form. When administered as a separate dosage form, the at least one other therapeutic agent may be administered prior to, at the same time as, or following administration of the compound and/or one pharmaceutically acceptable salt disclosed herein.

Also provided is a composition comprising a subject compound and stereoisomers thereof, hydrates thereof, and pharmaceutically acceptable salts thereof, and at least one pharmaceutically acceptable carrier.

The composition comprising a subject compound and stereoisomers thereof, hydrates thereof, and pharmaceutically acceptable salts thereof can be administered in various known manners, such as orally, topically, rectally, parenterally, by inhalation spray, or via an implanted reservoir, although the most suitable route in any given case will depend on the particular host, and nature and severity of the conditions for which the active ingredient is being administered. The term "parenteral" as used herein includes subcutaneous, intracutaneous, intravenous, intramuscular, intraarticular, intraarterial, intrasynovial, intrasternal, intrathecal, intralesional and intracranial injection or infusion techniques. The compositions disclosed herein may be conveniently presented in unit dosage form and prepared by any of the methods well known in the art.

The subject compounds and stereoisomers thereof, and pharmaceutically acceptable salts thereof can be administered orally in solid dosage forms, such as capsules, tablets, troches, dragées, granules and powders, or in liquid dosage forms, such as elixirs, syrups, emulsions, dispersions, and suspensions. The subject compounds and stereoisomers thereof, and pharmaceutically acceptable salts thereof disclosed herein can also be administered parenterally, in sterile liquid dosage forms, such as dispersions, suspensions or solutions. Other dosages forms that can also be used to administer the subject compounds and stereoisomers thereof, and pharmaceutically acceptable salts thereof disclosed herein as an ointment, cream, drops, transdermal patch or powder for topical administration, as an ophthalmic solution or suspension formation, i.e., eye drops, for ocular administration, as an aerosol spray or powder composition for inhalation or intranasal administration, or as a cream, ointment, spray or suppository for rectal or vaginal administration.

Gelatin capsules containing the compound and/or the at least one pharmaceutically acceptable salt thereof disclosed herein and powdered carriers, such as lactose, starch, cellulose derivatives, magnesium stearate, stearic acid, and the like, can also be used. Similar diluents can be used to make compressed tablets. Both tablets and capsules can be manufactured as sustained release products to provide for continuous release of medication over a period of time. Compressed tablets can be sugar coated or film coated to mask any unpleasant taste and protect the tablet from the atmosphere, or enteric coated for selective disintegration in the gastrointestinal tract.

Liquid dosage forms for oral administration can further comprise at least one agent selected from coloring and flavoring agents to increase patient acceptance.

In general, water, a suitable oil, saline, aqueous dextrose (glucose), and related sugar solutions and glycols such as propylene glycol or polyethylene glycols can be examples of suitable carriers for parenteral solutions. Solutions for parenteral administration may comprise a water soluble salt of the at least one compound describe herein, at least one suitable stabilizing agent, and if necessary, at least one buffer substance. Antioxidizing agents such as sodium bisulfite, sodium sulfite, or ascorbic acid, either alone or combined, can be examples of suitable stabilizing agents. Citric acid and its salts and sodium EDTA can also be used as examples of suitable stabilizing agents. In addition, parenteral solutions can further comprise at least one preservative, selected, for example, from benzalkonium chloride, methyl- and propylparaben, and chlorobutanol.

A pharmaceutically acceptable carrier is, for example, selected from carriers that are compatible with active ingredients of the composition (and in some embodiments, capable of stabilizing the active ingredients) and not deleterious to the subject to be treated. For example, solubilizing agents, such as cyclodextrins (which can form specific, more soluble complexes with the at least one compound and/or at least one pharmaceutically acceptable salt disclosed herein), can be utilized as pharmaceutical excipients for delivery of the active ingredients. Examples of other carriers include colloidal silicon dioxide, magnesium stearate, cellulose, sodium lauryl sulfate, and pigments such as D&C Yellow #10. Suitable pharmaceutically acceptable carriers are described in *Remington's Pharmaceutical Sciences*, A. Osol, a standard reference text in the art.

For administration by inhalation, the subject compounds and stereoisomers thereof, and pharmaceutically acceptable salts thereof may be conveniently delivered in the form of an aerosol spray presentation from pressurized packs or nebulisers. The subject compounds and stereoisomers thereof, and pharmaceutically acceptable salts thereof may also be delivered as powders, which may be formulated and the powder composition may be inhaled with the aid of an insufflation powder inhaler device. One exemplary delivery system for inhalation can be metered dose inhalation (MDI) aerosol, which may be formulated as a suspension or solution of a subject compound and stereoisomers thereof, hydrates thereof, and pharmaceutically acceptable salts thereof disclosed herein in at least one suitable propellant, selected, for example, from fluorocarbons and hydrocarbons.

For ocular administration, an ophthalmic preparation may be formulated with an appropriate weight percentage of a solution or suspension of the subject compound and stereoisomers thereof, hydrates thereof, and pharmaceutically acceptable salts thereof in an appropriate ophthalmic vehicle, such that the subject compound and stereoisomers thereof, hydrates thereof, and at least one pharmaceutically acceptable salts thereof is maintained in contact with the ocular surface for a sufficient time period to allow the compound to penetrate the corneal and internal regions of the eye.

Useful pharmaceutical dosage-forms for administration of the subject compounds and stereoisomers thereof, and pharmaceutically acceptable salts thereof disclosed herein include, but are not limited to, hard and soft gelatin capsules, tablets, parenteral injectables, and oral suspensions.

The dosage administered will be dependent on factors, such as the age, health and weight of the recipient, the extent of disease, type of concurrent treatment, if any, frequency of treatment, and the nature of the effect desired. In general, a daily dosage of the active ingredient can vary, for example, from 0.1 to 2000 milligrams per day. For example, 10-500 milligrams once or multiple times per day may be effective to obtain the desired results.

In some embodiments, a large number of unit capsules can be prepared by filling standard two-piece hard gelatin capsules each with, for example, 100 milligrams of the subject compound and stereoisomers thereof, hydrates thereof, and pharmaceutically acceptable salt thereof disclosed herein in powder, 150 milligrams of lactose, 50 milligrams of cellulose, and 6 milligrams magnesium stearate.

In some embodiments, a mixture of the compound, stereoisomers thereof, and pharmaceutically acceptable salts thereof a digestible oil such as soybean oil, cottonseed oil or olive oil can be prepared and injected by means of a positive displacement pump into gelatin to form soft gelatin capsules containing 100 milligrams of the active ingredient. The capsules are washed and dried.

In some embodiments, a large number of tablets can be prepared by conventional procedures so that the dosage unit comprises, for example, 100 milligrams of the compound, stereoisomers thereof, and pharmaceutically acceptable salts thereof, 0.2 milligrams of colloidal silicon dioxide, 5 milligrams of magnesium stearate, 275 milligrams of microcrystalline cellulose, 11 milligrams of starch and 98.8 milligrams of lactose. Appropriate coatings may be applied to increase palatability or delay absorption.

In some embodiments, a parenteral composition suitable for administration by injection can be prepared by stirring 1.5% by weight of the compound and/or at least an enantiomer, a diastereomer, or pharmaceutically acceptable salt thereof disclosed herein in 10% by volume propylene glycol. The solution is made to the expected volume with water for injection and sterilized.

In some embodiment, an aqueous suspension can be prepared for oral administration. For example, each 5 milliliters of an aqueous suspension comprising 100 milligrams of finely divided compound, stereoisomers thereof, and pharmaceutically acceptable salts thereof, 100 milligrams of sodium carboxymethyl cellulose, 5 milligrams of sodium benzoate, 1.0 grams of sorbitol solution, U.S.P., and 0.025 milliliters of vanillin can be used.

The same dosage forms can generally be used when the compound, stereoisomers thereof, and pharmaceutically acceptable salts thereof are administered stepwise or in conjunction with at least one other therapeutic agent. When drugs are administered in physical combination, the dosage form and administration route should be selected depending on the compatibility of the combined drugs. Thus the term coadministration is understood to include the administration of at least two agents concomitantly or sequentially, or alternatively as a fixed dose combination of the at least two active components.

The compounds, stereoisomers thereof, hydrates thereof, and pharmaceutically acceptable salts thereof disclosed herein can be administered as the sole active ingredient or in combination with at least one second active ingredient.

The subject compounds, stereoisomers thereof, hydrates thereof, and/or pharmaceutically acceptable salts are incorporated into pharmaceutical compositions or formulations. The compositions will contain pharmaceutically acceptable diluents and/or carriers, i. e. diluents or carriers that are physiologically compatible and substantially free from pathogenic impurities. Suitable excipients or carriers and methods for preparing administrable compositions are known or apparent to those skilled in the art and are described in more detail in such publications as Remington's Pharmaceutical Science, Mack Publishing Co, NJ (1991). The compositions may also be in the form of controlled release or sustained release compositions as known in the art. For many applications the subject compounds are administered for morning/daytime dosing, with off period at night.

The subject compounds may be used per se, or in the form of their pharmaceutically acceptable salts, such as hydrochlorides, hydrobromides, acetates, sulfates, citrates, carbonates, trifluoroacetates and the like. When compounds contain relatively acidic functionalities, salts can be obtained by addition of the desired base, either neat or in a suitable inert solvent. Examples of pharmaceutically acceptable base addition salts include sodium, potassium, calcium, ammonium, organic amino, or magnesium salts, or the like. When compounds contain relatively basic functionalities, salts can be obtained by addition of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galacturonic acids and the like (see, for example, Berge et al, "Pharmaceutical Salts", Journal of Pharmaceutical Science, 1977, 66, 1-19).

The neutral forms of the compounds may be regenerated by contacting the salt with a base or acid, and isolating the parent compound in the conventional manner. The parent form of the compound differs from the various salt forms in certain physical properties, such as solubility in polar solvents, but otherwise the salts are equivalent to the parent form of the compound for the purposes of this invention.

In addition to salt forms, this invention provides compounds which are in a prodrug form. Prodrugs of the compounds described herein are those compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the present invention which is administered as an ester (the "prodrug"), but then is metabolically hydrolyzed to the carboxylic acid, the active entity.

Certain compounds of the invention can exist in unsolvated forms as well as solvated forms, including hydrated forms. In general, the solvated forms are equivalent to unsolvated forms and are intended to be encompassed within the scope of the present invention. Certain compounds of the invention may exist in multiple crystalline or amorphous forms. In general, all physical forms are equivalent for the uses contemplated by the present invention and are intended to be within the scope of the invention.

Some of the subject compounds possess asymmetric carbon atoms (optical centers) or double bonds; the racemates, diastereomers, geometric isomers and individual isomers are all intended to be encompassed within the scope of the present invention.

The compounds of the invention may also contain unnatural proportions of atomic isotopes at one or more of the atoms that constitute such compounds, such as deuterium, e.g. —$CD_3$, $CD_2H$ or $CDH_2$ in place of methyl. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

The compounds are generally administered in a "therapeutically effective amount", i.e. the amount of the subject compound that will elicit the biological or medical response of a tissue, system, animal or human that is being sought by the researcher, veterinarian, medical doctor or other clinician. The term "therapeutically effective amount" includes that amount of a compound that, when administered, is sufficient to prevent development of, or alleviate to some extent, one or more of the symptoms of the condition or disorder being treated. The therapeutically effective amount will vary depending on the compound, the disease and its severity and the age, weight, etc., of the mammal to be treated.

The contacting is generally effected by administering to the subject an effective amount of one or more compounds having the general formula I (supra), including the various embodiments described above. Generally administration is adjusted to achieve a therapeutic dosage of about 0.1 to 50, preferably 0.5 to 10, more preferably 1 to 10 mg/kg, though optimal dosages are compound specific, and generally empirically determined for each compound.

The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, lozenges or the like in the case of solid compositions. In such compositions, the mimetic is usually a minor component (from about 0.1 to about 50% by weight or preferably from about 1 to about 40% by weight) with the remainder being various vehicles or carriers and processing aids helpful for forming the desired dosing form. Unit dosage formulations are preferably about of 5, 10, 25, 50, 100, 250, 500, or 1,000 mg per unit. In a particular embodiment, unit dosage forms are packaged in a multipack adapted for sequential use, such as blisterpack comprising sheets of at least 6, 9 or 12 unit dosage forms.

The subject compositions may also be coformulated and/or coadministered with a different compound to treat applicable indications, or to treat programmed cell death. In embodiments applicable indications include brain injury, neurodegenerative diseases, viral infections, immune tolerance, and cancer e.g. promote tumor immunity in pancreatic cancer and melanoma.

In one embodiment, a compound of this disclosure is a compound of the following structural formula I:

I

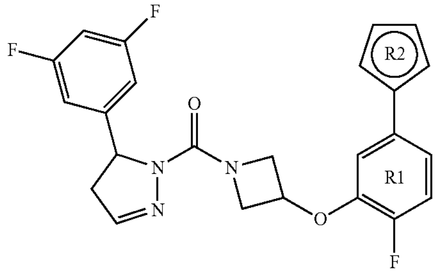

R1 is 1-F substituted C6 aryl comprising 0, 1 or 2 N heteroatoms; and R2 is C5 aryl comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl; or a salt, hydrate or stereoisomer thereof.

In one embodiment, the R2 substituents are independently C0-C6: aldehyde, aldimine, alkanoyloxy, alkoxy, alkoxycarbonyl, alkyloxy, alkyl, alkenyl, alkynyl, amine, azo, halogens, carbamoyl, carbonyl, carboxamido, carboxyl, cyanyl, ester, haloformyl, hydroperoxyl, hydroxyl, imine, isocyanide, iscyante, N-tert-butoxycarbonyl, nitrate, nitrile, nitrite, nitro, nitroso, phosphate, phosphono, sulfide, sulfonyl, sulfo, sulfhydryl, thiol, thiocyanyl, trifluoromethyl or triflurommethyl ether (OCF3); R1 comprises N2, N4 or N2/N4; R2 comprises N1, N1/N2, N2/N3, N3/N4, N2/N5; N2/N4, S2/N4, N2/S4, S3/N4, N2/S3, N3/O4, N2/N3/S5, N2/N3/O5, N2/N3/N5 or N2/N3/N4; or any combination of the foregoing substituents.

In one embodiment, the present disclosure provides a compound, a salt, hydrate or stereoisomer thereof, wherein the compound has the following structural formula II(1):

II(1)

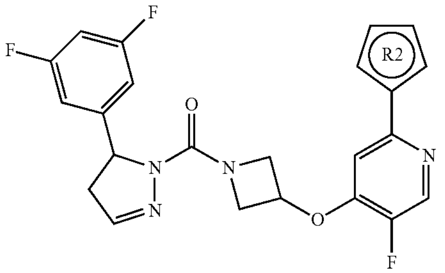

wherein R2 (Ring 2) is C5 aryl (5-membered aryl) comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula II(2):

II(2)

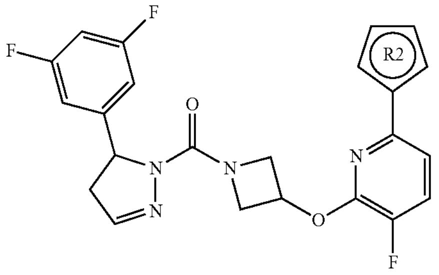

wherein R2 (Ring 2) is C5 aryl (5-membered aryl) comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula II(3):

II(3)

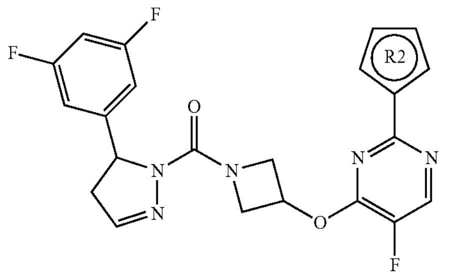

wherein R2 (Ring 2) is C5 aryl (5-membered aryl) comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula II(4):

II(4)

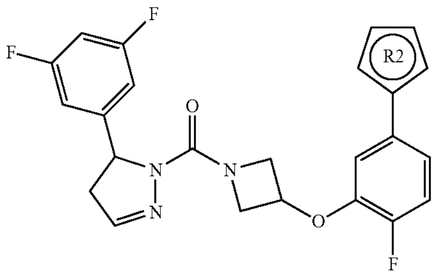

wherein R2 (Ring 2) is C5 aryl (5-membered aryl) comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula II(5):

II(5)

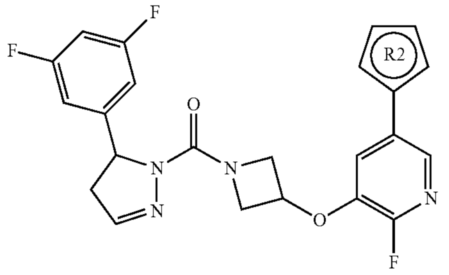

wherein R2 (Ring 2) is C5 aryl (5-membered aryl) comprising 1, 2 or 3 N heteroatoms, or 1 or 2 N heteroatoms and an O or S heteroatom, substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein R2 is

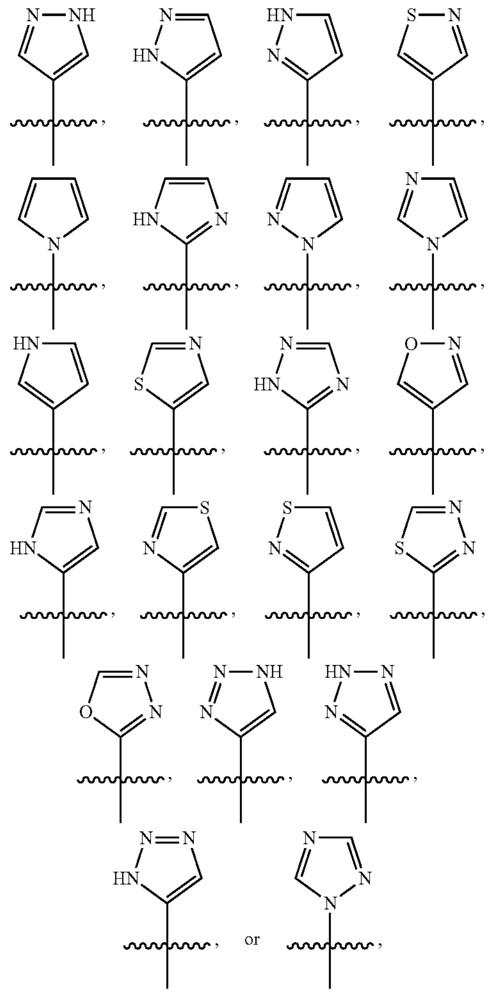

substituted with 0-3 substituents selected from halide, optionally-substituted N, S or O, and optionally-substituted hydrocarbyl, and all other variables not specifically defined herein are as defined in any one of the appropriate preceding embodiments.

In one embodiment, the present disclosure provides a compound, a salt, hydrate or stereoisomer thereof, wherein the compound has the following structural formula III(1):

III(1)

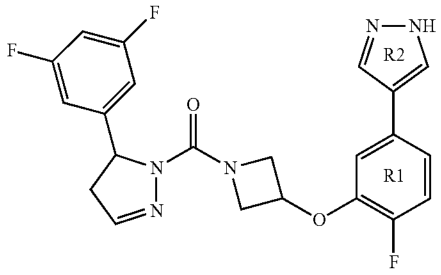

wherein R1 (Ring 1) is 1-F substituted C6 aryl (6-membered aryl) comprising 0, 1 or 2 N heteroatoms; and wherein R2 (Ring 2) is a C5 aryl as set forth in structural formula III(1), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula III(2):

III(2)

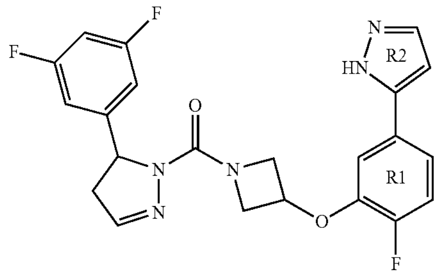

wherein R1 (Ring 1) is 1-F substituted C6 aryl (6-membered aryl) comprising 0, 1 or 2 N heteroatoms; and wherein R2 (Ring 2) is a C5 aryl as set forth in structural formula III(2), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has the following structural formula III(3):

III(3)

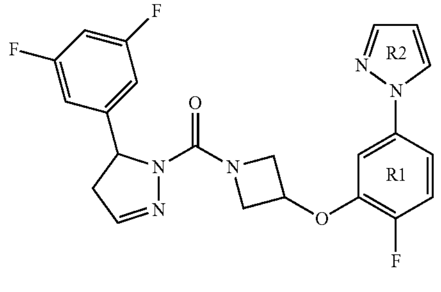

wherein R1 (Ring 1) is 1-F substituted C6 aryl (6-membered aryl) comprising 0, 1 or 2 N heteroatoms; and wherein R2 (Ring 2) is a C5 aryl as set forth in structural formula III (3), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has one of the following structural formulae IV(1)-IV(5):

IV(1)

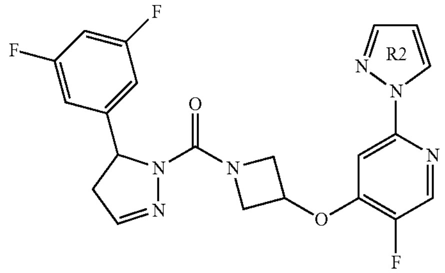

IV(2)

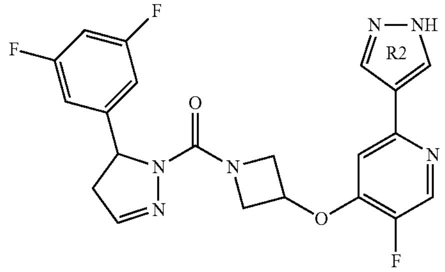

IV(3)

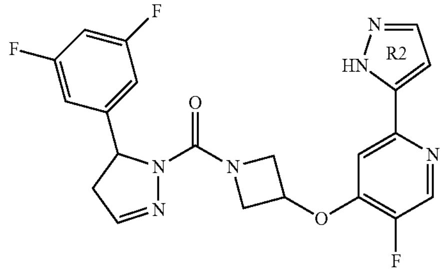

IV(4)

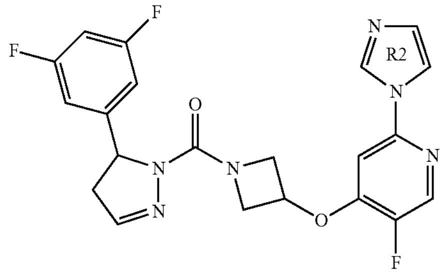

IV(5)

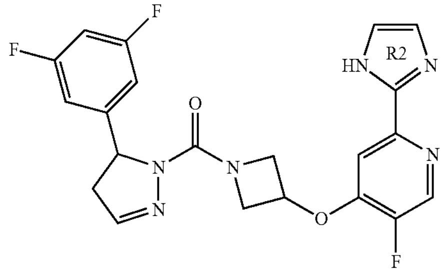

wherein R2 is a C5 aryl as set forth in structural formulae IV(1)-IV(5), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has one of the following structural formulae IV(6)-IV(10):

IV(6)

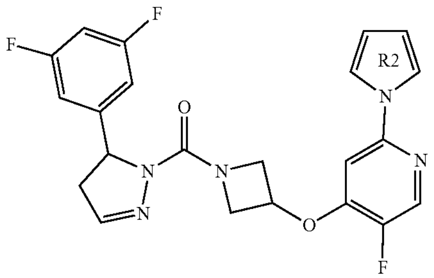

IV(7)

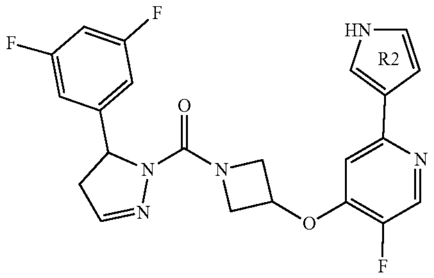

IV(8)

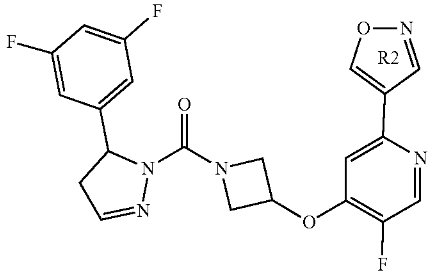

IV(9)

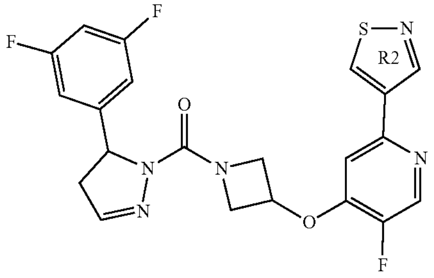

IV(10)

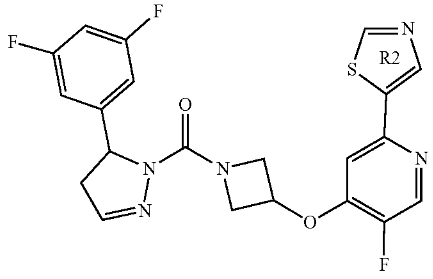

wherein R2 is a C5 aryl as set forth in structural formulae IV(11)-IV(15), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein the compound has one of the following structural formulae IV(11)-IV(15):

IV(11)

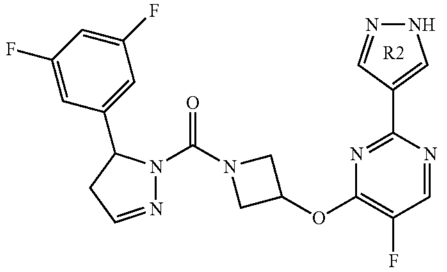

IV(12)

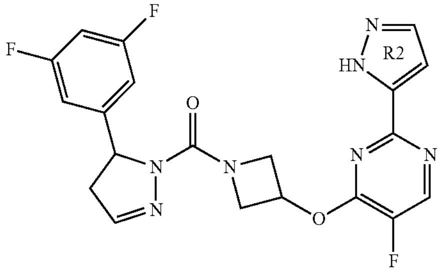

IV(13)

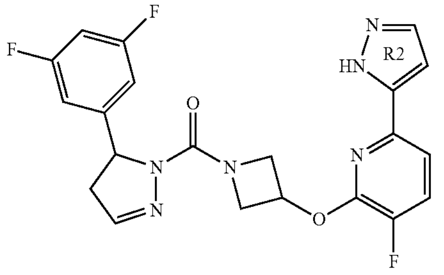

IV(14)

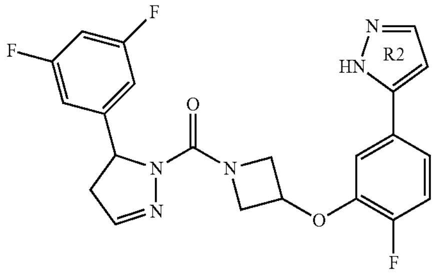

IV(15)

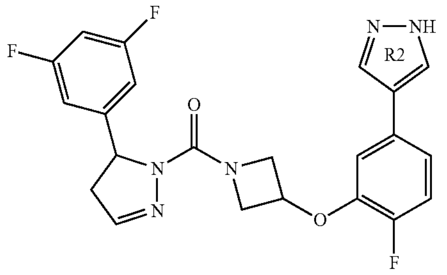

wherein R2 is a C5 aryl as set forth in structural formulae IV(11)-IV(15), substituted with 0-3 substituents selected from halide, optionally-substituted N, S or O, and optionally-substituted hydrocarbyl.

In one embodiment, the present disclosure provides a compound, a salt, hydrate or stereoisomer thereof, wherein R2 is substituted with 0-3 $R^a$, wherein $R^a$, for each occurrence, is independently selected from: halogen, cyano, $C_1$-$C_6$ alkyl, $C_3$-$C_6$ cycloalkyl, 3- to 6-membered heterocyclyl, $C_2$-$C_6$ alkenyl, $C_1$-$C_6$ alkoxy, —C(═O)($C_1$-$C_6$ alkyl), —C(═O)($C_3$-$C_6$ cycloalkyl), —C(═O)(3- to 6-membered heterocyclyl), ═O, —$NO_2$, —C(═O)$OR^s$, —C(═O)$NR^pR^q$, —$NR^pR^q$, —$NR^p$C(═O)$R^s$, —$NR^p$C(═O)$OR^s$, —$NR^p$C(═O)$NR^qR^r$, —$NR^p$S(═O)$_wR^s$, —$OR^s$, —OC(═O)$R^s$, —OC(═O)$OR^s$, —OC(═O)$NR^pR^q$, —S(═O)$_wR^s$, and —S(═O)$_wNR^pR^q$; wherein the $C_1$-$C_6$ alkyl, $C_3$-$C_6$ cycloalkyl, 3- to 6-membered heterocyclyl, $C_2$-$C_6$ alkenyl, and $C_1$-$C_6$ alkoxy of $R^a$, the $C_1$-$C_6$ alkyl of —C(═O)($C_1$-$C_6$ alkyl), the $C_3$-$C_6$ cycloalkyl of —C(═O)($C_3$-$C_6$ cycloalkyl), and the 3- to 6-membered heterocyclyl of —C(═O)(3- to 6-membered heterocyclyl) are each optionally substituted with 1 to 3 groups selected from halogen, cyano, ═O, —C(═O)$R^s$, —C(═O)$OR^s$, —C(═O)$NR^pR^q$, —$NR^pR^q$, —$NR^p$C(═O)$R^s$, —$NR^p$C(═O)$OR^s$, —$NR^p$C(═O)$NR^qR^r$, —$NR^p$S(═O)$R^s$, —$OR^s$, —OC(═O)$R^s$, —OC(═O)$OR^s$, —OC(═O)$NR^pR^q$, —S(═O)$_wR^s$, —S(═O)$_wNR^pR^q$, $C_3$-$C_6$ cycloalkyl, and 3- to 6-membered heterocyclyl; wherein $R^p$, $R^q$, $R^r$, and $R^s$, for each occurrence, are each independently selected from hydrogen, OH, $NH_2$, $C_1$-$C_4$ alkyl, $C_3$-$C_6$ cycloalkyl, and 3- to 6-membered heterocyclyl; wherein the $C_1$-$C_4$ alkyl, $C_3$-$C_6$ cycloalkyl, and 3- to 6-membered heterocyclyl of any one of $R^p$, $R^q$, $R^r$, and $R^s$ are optionally substituted with 1 to 3 groups selected from halogen, cyano, —OH, $C_1$-$C_6$ alkyl, —O($C_1$-$C_6$ alkyl), —C(═O)N($C_1$-$C_6$ alkyl)($C_1$-$C_6$ alkyl), —C(═O)NH($C_1$-$C_6$ alkyl), —C(═O)(3- to 6-membered heterocyclyl), —C(═O)($C_3$-$C_6$ cycloalkyl), $C_3$-$C_6$ cycloalkyl, phenyl, and 3- to 6-membered heterocyclyl; and wherein w is an integer selected from 0, 1, and 2; and all other variables not specifically defined herein are as defined in any one of the appropriate preceding embodiments.

In one embodiment, the present disclosure provides a compound, a salt, hydrate or stereoisomer thereof, wherein R2 is substituted with 1-3 $R^a$, wherein $R^a$, for each occurrence, is independently selected from: halogen; cyano; 4- to 6-membered heterocyclyl optionally substituted with oxo; —C(═O)($C_1$-$C_6$ alkyl); —C(═O)($C_3$-$C_6$ cycloalkyl); —C(═O)(4- to 6-membered heterocyclyl); 3- to 4-membered cycloalkyl;

—C(═O)$OR^s$, wherein $R^s$ is H or $C_1$-$C_3$ alkyl;

$C_1$-$C_3$ alkyl, optionally substituted with OH, $NH_2$, cyano, halogen, $C_1$-$C_3$ alkoxyl, 3- to 4-membered cycloalkyl, 4- to 6-membered heterocyclyl, —C(═O)OH, —C(═O)(4- to 6-membered heterocyclyl), —C(═O)NH$(CH_2)_2$OH, or —C(═O)$NH_2$;

—C(═O)$NR^pR^q$, wherein $R^p$ and $R^q$ each are independently selected from H, OH, CN, 4- to 6-membered heterocyclyl, $C_1$-$C_3$ alkyl optionally substituted with OH, and 3- to 4-membered cycloalkyl optionally substituted with OH;

—$NR^pR^q$, wherein $R^p$ and $R^q$ each are independently selected from H, OH, —C(═O)$CH_3$, and $C_1$-$C_3$ alkyl optionally substituted with OH, 3- to 4-membered cycloalkyl, or 6-membered heterocyclyl;

—$NR^p$C(═O)$NR^qR^q$, wherein $R^p$, $R^q$ and $R^r$ each are independently selected from H and $C_1$-$C_3$ alkyl;

—$NR^p$C(═O)$R^s$, wherein $R^p$ is selected from H and $C_1$-$C_3$ alkyl, and $R^s$ is selected from $C_1$-$C_3$ alkyl and 3- to 4-membered cycloalkyl;

—S(═O)$_wR^s$, wherein $R^s$ is selected from $C_1$-$C_3$ alkyl optionally substituted with phenyl or $NH_2$, and wherein w is 0 or 2; and —S(═O)$_wNR^pR^q$, wherein $R^p$ and $R^q$ each are independently selected from H, 3- to 6-membered cycloalkyl, 4- to 6-membered heterocyclyl, and $C_1$-$C_3$ alkyl optionally substituted with OH, $C_1$-$C_3$ alkoxyl or phenyl, and wherein w is 2; and all other variables not specifically defined herein are as defined in any one of the appropriate preceding embodiments.

In one embodiment, the present disclosure provides a compound, a salt, hydrate or stereoisomer thereof, wherein R2 is substituted with 1-3 $R^a$, wherein $R^a$, for each occurrence, is independently selected from methyl, ethyl, —$NH_2$, —CN, —$OCH_3$, —$O(CH_2)_2N(CH_3)_2$, —$NHCH_3$, —$O(CH_2)_2OCH_3$, —$N(CH_3)_2$, —$NH(CH_2)OCH_3$, —NHC(═O)$CH_3$, —NHC(═O)$CH_2CH_3$, —NHC(═O)$CH(CH_3)_2$, —NHC(═O)$CH_2CH(CH_3)_2$, —$NHCH_2$C(═O)$NHCH_3$, —$NHCH_2$C(═O)$NHCH_3$,

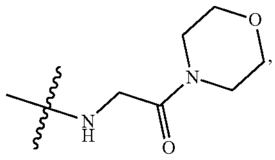 [SMILES: *NCC(=O)N1CCOCC1]

—$NHCH_2$C(═O)$N(CH_3)_2$, —C(═O)$OCH_3$, —C(═O)OH, —C(═O)$CH_3$, —C(═O)$NH_2$, —C(═O)$NHCH_3$, —C(═O)$NH(CH_2)_2N(CH_3)_2$, —C(═O)$NHCH_2N(CH_3)_2$, —C(═O)$NHCH_2CH_3$,

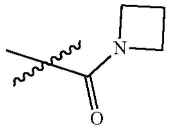
,
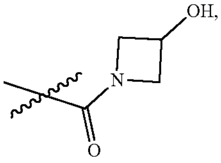
,
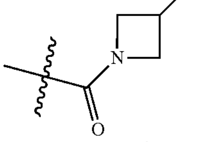
,
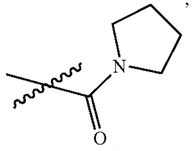
,
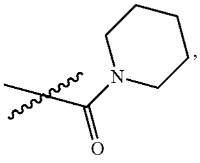
,
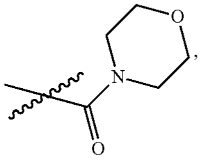
,

—$CH_2OH$, —$CH_2N(CH_3)_2$, —$CH_2OCH_3$, —F, —Cl, —$(CH_2)_2OCH_3$, —$CH_2$C(═O)$NH_2$, —$CH_2$C(═O)$N(CH_3)_2$,

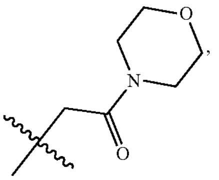 [SMILES: *CC(=O)N1CCOCC1]
$—CH_2C(=O)NHCH_3$, $—NO_2$, $—(CH_2)_2OH$, $—CH_2C(=O)CH_3$, $—NH(CH_2)_2N(CH_3)_2$,
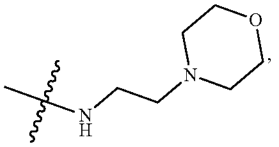 [SMILES: *NCCN1CCOCC1]
$—NHC(=O)CH_2OCH_3$, $—NHC=OCH_2N(CH_3)_2$,
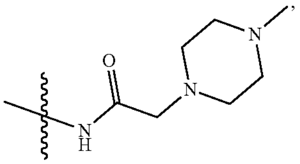 [SMILES: *NC(=O)CN1CCN(C)CC1]
$—NHC_3$, $—C(=O)OCH_2CH_3$,
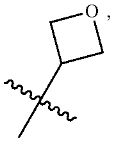
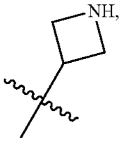
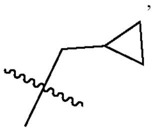
$—C(=O)NHCH(CH_3)_2$,
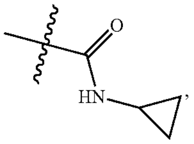 [SMILES: *C(=O)NC1CC1]
$—N(C(=O)CH_3)_2$,
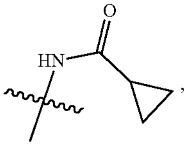
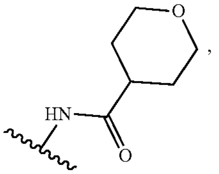
-continued
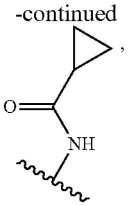
$—NHC(=O)NHCH(CH_3)_2$, $—NHC(=O)NHCH_3$, $—NHCH_2C(=O)NH_2$, $—CH_2CH_2OH$,
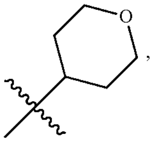 [SMILES: *C1CCOCC1]
$—NH(CH_2)_2CH_3$, $—NHCH(CH_3)_2$,
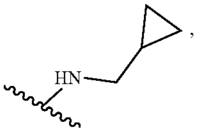
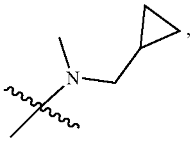
$—NH(CH_3)_2$, $—S(=O)_2CH_2CH_3$, $—CF_3$,
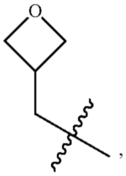 [SMILES: *CC1COC1]
$—C(=O)N(CH_3)_2$, $—SCH_3$, $—S(=O)CH_3$, $—CHOHCH_3$,
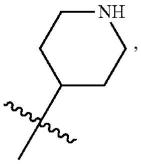 [SMILES: *C1CCNCC1]
$—S(=O)_2CH_3$, $—CH_2F$, $—CH_2NH_2$, $—NH(CH_2)_2OH$,
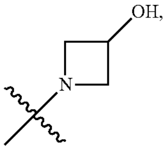 [SMILES: *N1CC(O)C1]
$—C(=O)NH(CH_2)_2OH$,

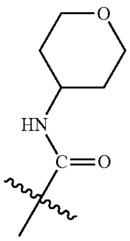,
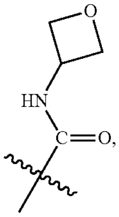,
—S(=O)$_2$NH$_2$,
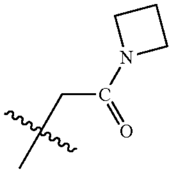,
—CH$_2$C(=O)NH(CH$_2$)$_2$OH,
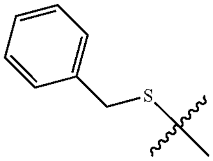,
—S(=O)$_2$NHCH$_3$,
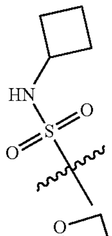, 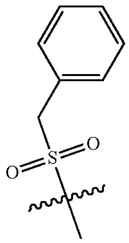,
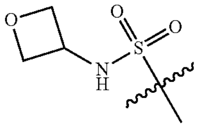,
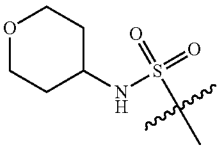,
-continued
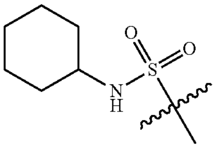,
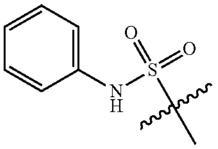,
—S(=O)$_2$NH(CH$_2$)$_2$OH, —S(=O)$_2$NHOCH$_3$,
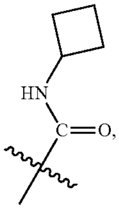 [SMILES: *C(=O)NC1CCC1],
—C(=O)NHOH, —C(=O)NHCN,
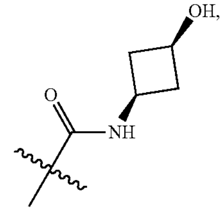, 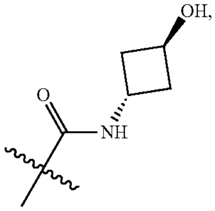,
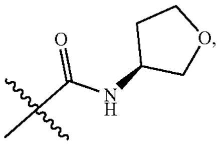, 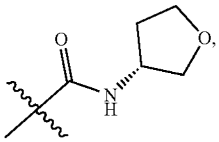,
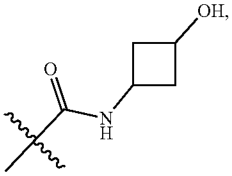,
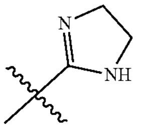, 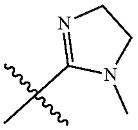,
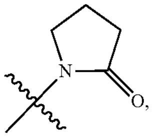,
—CH$_2$CN,

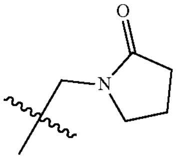, $—CH_2C(=O)OH$, $—C(CH_3)_2C(=O)OH$, and $—C(CH_3)_2C(=O)NH_2$, and all other variables not specifically defined herein are as defined in any one of the appropriate preceding embodiments.

In one embodiment, the present disclosure provides a compound, a salt, hydrate or stereoisomer thereof, wherein R2 is substituted with 1-3 $R^a$, wherein $R^a$, for each occurrence, is independently selected from methyl, ethyl, $—NH_2$, $—NHCH_3$, $—CN$, $—CH_2CH_2OH$,

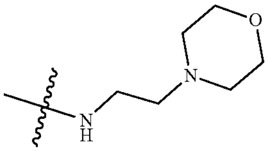, $—NHC(=O)CH_3$, $—C(=O)OCH_3$,

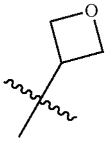, 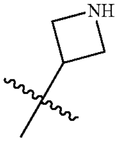,

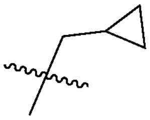

$—N(C=OCH_3)_2$, $—NHCH_2C(=O)NH_2$,

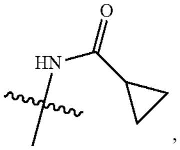 [SMILES: *NC(=O)C1CC1], $—C(=O)OCH_2CH_3$, $—NHCH_3$, $—CH_2OCH_3$, $—CH_2CH_2OH$,

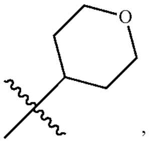 [SMILES: *C1CCOCC1], $—NHCH_2CH_2OCH_3$, $—NHCH(CH_3)_2$,

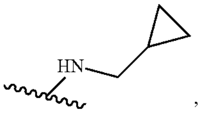, 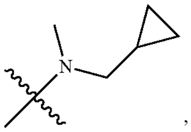, $—N(CH_3)_2$, $—C(=O)N(CH_3)_2$, $—C(=O)NH_2$, $—Cl$, $—SCH_3$, $—S(=O)_2CH_3$, $CH_2OH$,

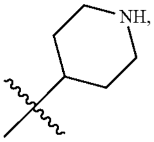 [SMILES: *C1CCNCC1]

$—C(=O)NHCH_3$, $CH_2F$, $—NHCH_2OH$, $—C(=O)NHCH_2CH_2OH$,

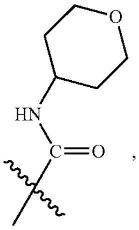, 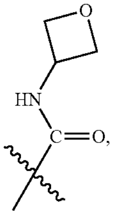

$—S(=O)_2NH_2$, $—CH_2C(=O)NH_2$,

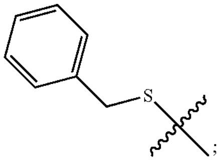 [SMILES: *SCc1ccccc1];

$—C(=O)NHCH_2CH_3$, $—C(=O)OH$,

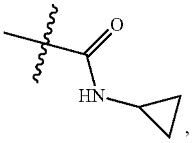, 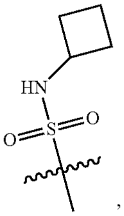, 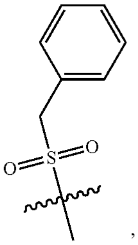,

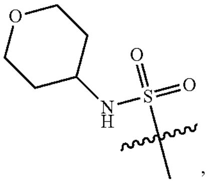, 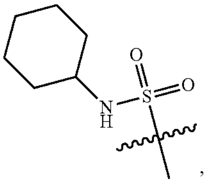, $—C(=O)NHCH_3$, $—S(=O)_2NHOCH_3$,

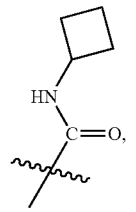 [SMILES: *C(=O)NC1CCC1]

—C(=O)NHOH,

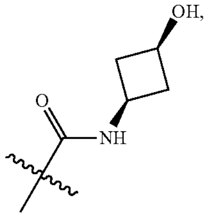 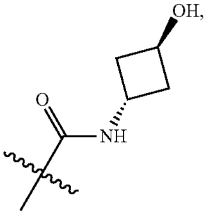

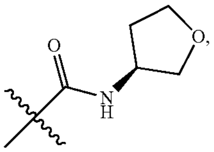 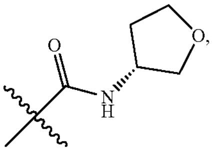

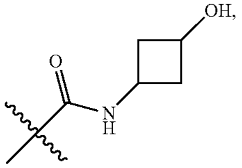

—C(=O)NHCH$_2$CH$_2$OH, and —CH$_2$CN, and all other variables not specifically defined herein are as defined in any one of the appropriate preceding embodiments.

In one embodiment, the present disclosure provides a compound, a salt, hydrate or stereoisomer thereof, wherein R2 is substituted with 1-3 R$^a$, wherein R$^a$, for each occurrence, is independently selected from methyl, ethyl, —NH$_2$, —C(=O)NH$_2$, —NHCH$_3$, —CN, —CH$_2$CN, —NHCH$_2$OH, —CH$_2$NH$_2$, —SCH$_3$, CONHCH$_3$, —SO$_2$CH$_3$, —CH$_2$OH, —Cl, —N(CH$_3$)$_2$, —NHCH(CH$_3$)$_2$, —NHCH$_2$CH$_2$OCH$_3$, —CH$_2$CH$_2$OH, —C(=O)OCH$_2$CH$_3$, —C(=O)OCH$_3$, —C(=O)OH, —S(=O)$_2$NH$_2$, —CH$_2$C(=O)NH$_2$, —C(=O)NHCH$_2$CH$_2$OH,

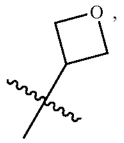 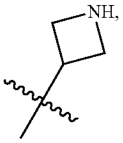 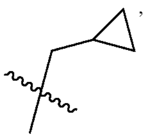

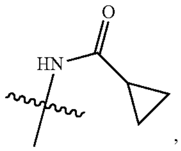 , 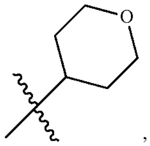 , 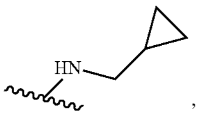 ,

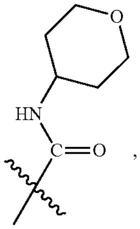 , 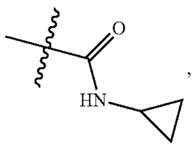 , and 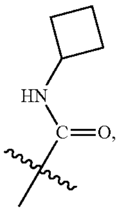

and all other variables not specifically defined herein are as defined in any one of the appropriate preceding embodiments.

In one embodiment, the present disclosure provides a compound, a salt, hydrate or stereoisomer thereof, wherein the compound has one of structural formulae in Tables 1 and 3.

TABLE 1

| Active Compounds 1-116: Structures | |
|---|---|
| 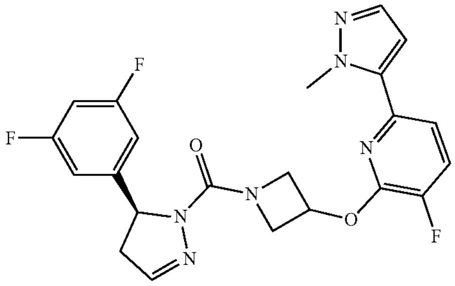 [SMILES: Cn1nccc1-c1ccc(F)c(OC2CN(C(=O)N3N=CC[C@H]3c3cc(F)cc(F)c3)C2)n1] | 1 |
| 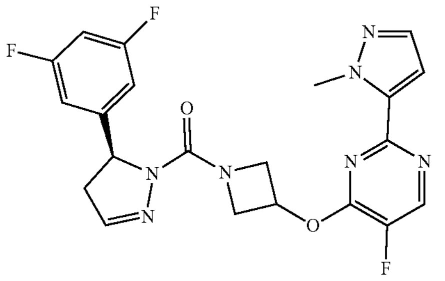 [SMILES: Cn1nccc1-c1ncc(F)c(OC2CN(C(=O)N3N=CC[C@H]3c3cc(F)cc(F)c3)C2)n1] | 2 |

TABLE 1-continued
| Active Compounds 1-116: Structures | |
|---|---|
| 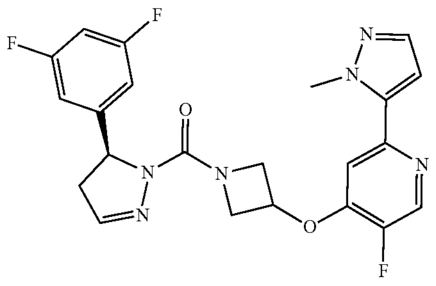 [SMILES: Cn1nccc1-c1cc(OC2CN(C(=O)N3N=CC[C@H]3c3cc(F)cc(F)c3)C2)c(F)cn1] | 3 |
| 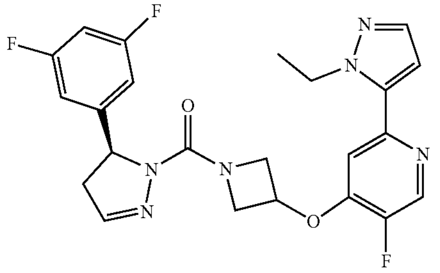 [SMILES: CCn1nccc1-c1cc(OC2CN(C(=O)N3N=CC[C@H]3c3cc(F)cc(F)c3)C2)c(F)cn1] | 4 |
| 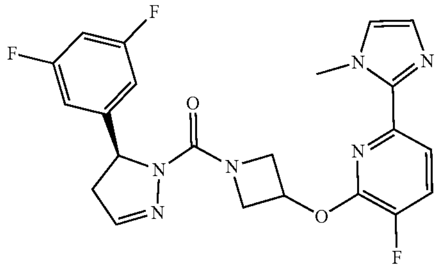 [SMILES: Cn1ccnc1-c1ccc(F)c(OC2CN(C(=O)N3N=CC[C@H]3c3cc(F)cc(F)c3)C2)n1] | 5 |
| 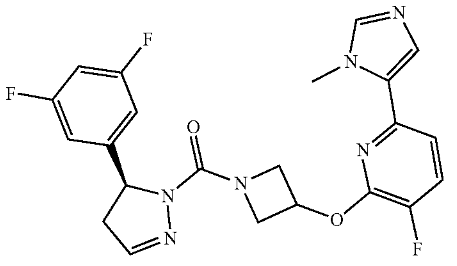 [SMILES: Cn1cncc1-c1ccc(F)c(OC2CN(C(=O)N3N=CC[C@H]3c3cc(F)cc(F)c3)C2)n1] | 6 |
| 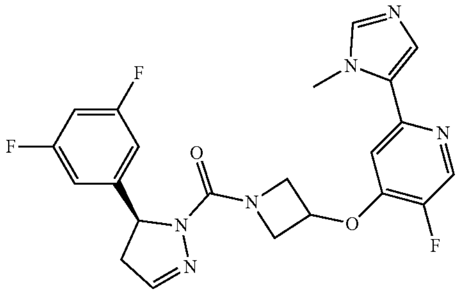 [SMILES: Cn1cncc1-c1cc(OC2CN(C(=O)N3N=CC[C@H]3c3cc(F)cc(F)c3)C2)c(F)cn1] | 7 |

TABLE 1-continued
| Active Compounds 1-116: Structures | |
|---|---|
| 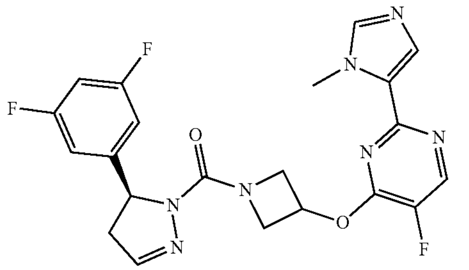 [SMILES: Cn1cncc1-c1ncc(F)c(OC2CN(C(=O)N3N=CC[C@H]3c3cc(F)cc(F)c3)C2)n1] | 8 |
| 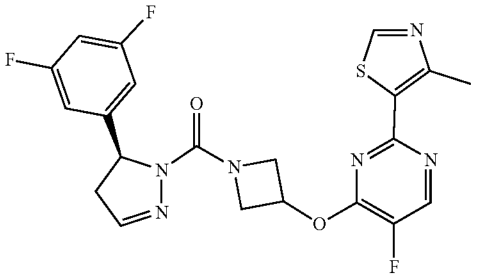 [SMILES: Cc1ncsc1-c1ncc(F)c(OC2CN(C(=O)N3N=CC[C@H]3c3cc(F)cc(F)c3)C2)n1] | 9 |
| 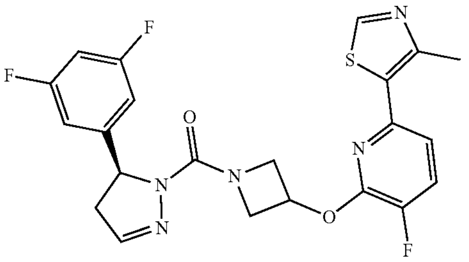 [SMILES: Cc1ncsc1-c1ccc(F)c(OC2CN(C(=O)N3N=CC[C@H]3c3cc(F)cc(F)c3)C2)n1] | 10 |
| 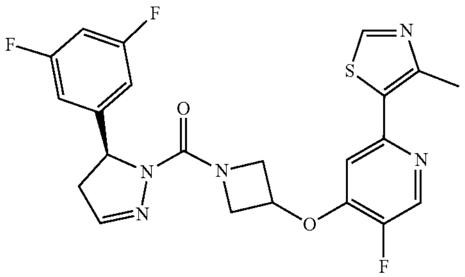 [SMILES: Cc1ncsc1-c1cc(OC2CN(C(=O)N3N=CC[C@H]3c3cc(F)cc(F)c3)C2)c(F)cn1] | 11 |
| 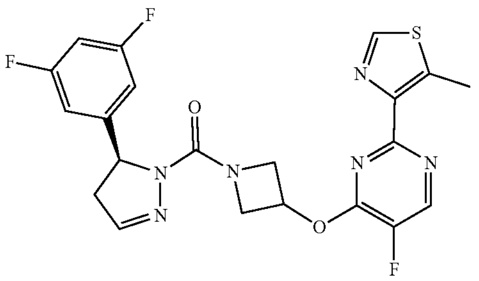 [SMILES: Cc1scnc1-c1ncc(F)c(OC2CN(C(=O)N3N=CC[C@H]3c3cc(F)cc(F)c3)C2)n1] | 12 |

TABLE 1-continued
| Active Compounds 1-116: Structures | |
|---|---|
| 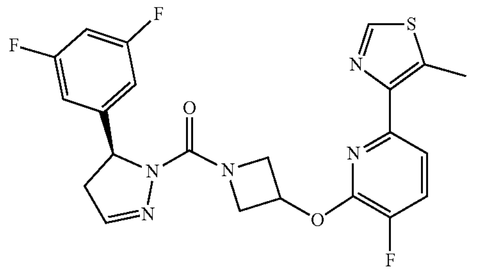 [SMILES: Cc1scnc1-c1ccc(F)c(OC2CN(C(=O)N3N=CC[C@H]3c3cc(F)cc(F)c3)C2)n1] | 13 |
| 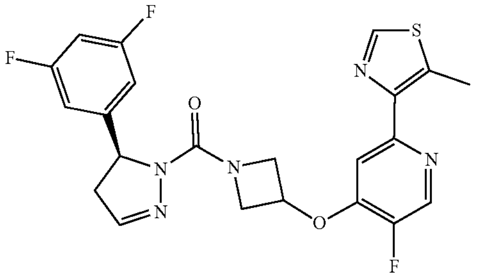 [SMILES: Cc1scnc1-c1cc(OC2CN(C(=O)N3N=CC[C@H]3c3cc(F)cc(F)c3)C2)c(F)cn1] | 14 |
| 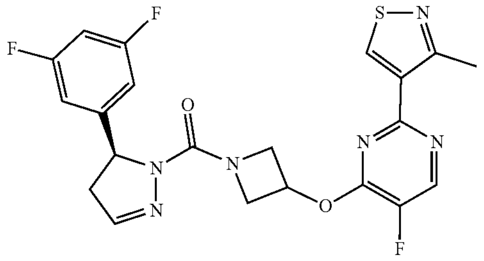 [SMILES: Cc1nscc1-c1ncc(F)c(OC2CN(C(=O)N3N=CC[C@H]3c3cc(F)cc(F)c3)C2)n1] | 15 |
| 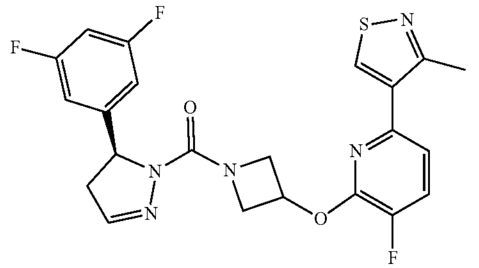 [SMILES: Cc1nscc1-c1ccc(F)c(OC2CN(C(=O)N3N=CC[C@H]3c3cc(F)cc(F)c3)C2)n1] | 16 |
| 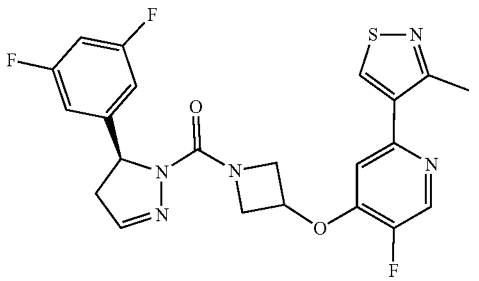 [SMILES: Cc1nscc1-c1cc(OC2CN(C(=O)N3N=CC[C@H]3c3cc(F)cc(F)c3)C2)c(F)cn1] | 17 |

TABLE 1-continued
| Active Compounds 1-116: Structures |
| --- |
| 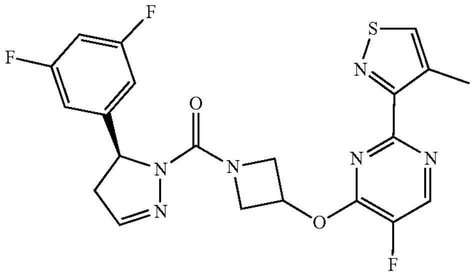 [SMILES: Cc1csnc1-c1ncc(F)c(OC2CN(C(=O)N3N=CC[C@H]3c3cc(F)cc(F)c3)C2)n1] 18 |
| 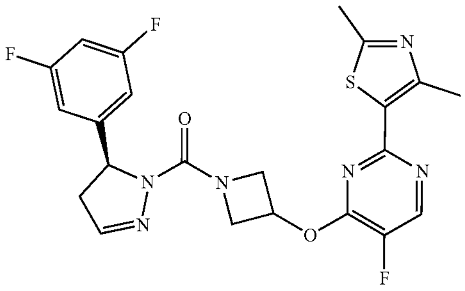 [SMILES: Cc1nc(C)c(-c2ncc(F)c(OC3CN(C(=O)N4N=CC[C@H]4c4cc(F)cc(F)c4)C3)n2)s1] 19 |
| 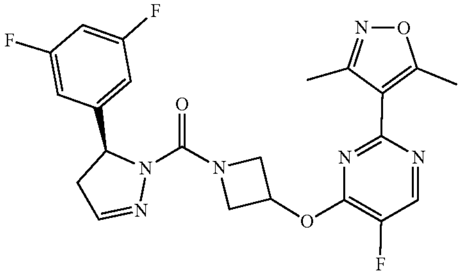 [SMILES: Cc1noc(C)c1-c1ncc(F)c(OC2CN(C(=O)N3N=CC[C@H]3c3cc(F)cc(F)c3)C2)n1] 20 |
| 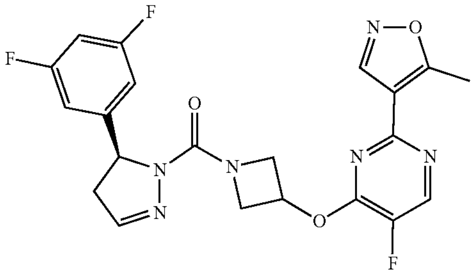 [SMILES: Cc1oncc1-c1ncc(F)c(OC2CN(C(=O)N3N=CC[C@H]3c3cc(F)cc(F)c3)C2)n1] 21 |
| 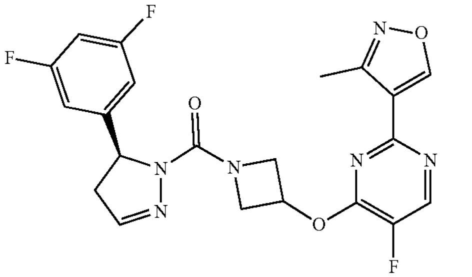 [SMILES: Cc1nocc1-c1ncc(F)c(OC2CN(C(=O)N3N=CC[C@H]3c3cc(F)cc(F)c3)C2)n1] 22 |

TABLE 1-continued
| Active Compounds 1-116: Structures | |
| --- | --- |
| 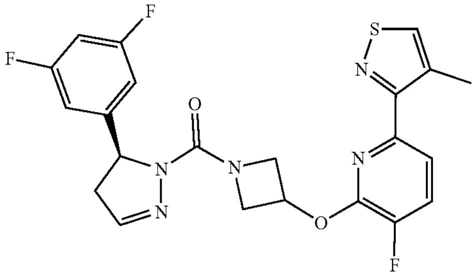 [SMILES: Cc1csnc1-c1ccc(F)c(OC2CN(C(=O)N3N=CC[C@H]3c3cc(F)cc(F)c3)C2)n1] | 23 |
| 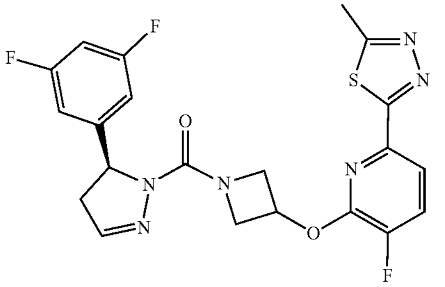 [SMILES: Cc1nnc(-c2ccc(F)c(OC3CN(C(=O)N4N=CC[C@H]4c4cc(F)cc(F)c4)C3)n2)s1] | 24 |
| 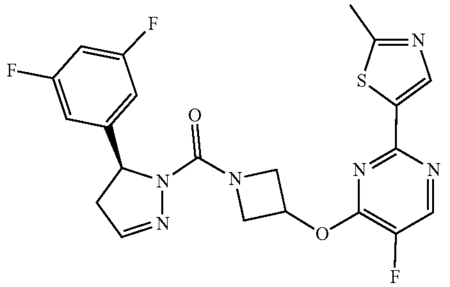 [SMILES: Cc1ncc(-c2ncc(F)c(OC3CN(C(=O)N4N=CC[C@H]4c4cc(F)cc(F)c4)C3)n2)s1] | 25 |
| 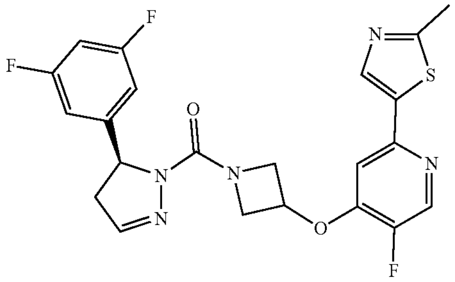 [SMILES: Cc1ncc(-c2cc(OC3CN(C(=O)N4N=CC[C@H]4c4cc(F)cc(F)c4)C3)c(F)cn2)s1] | 26 |
| 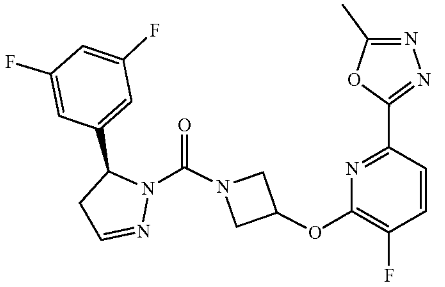 [SMILES: Cc1nnc(-c2ccc(F)c(OC3CN(C(=O)N4N=CC[C@H]4c4cc(F)cc(F)c4)C3)n2)o1] | 27 |

TABLE 1-continued
| Active Compounds 1-116: Structures |
| --- |
| 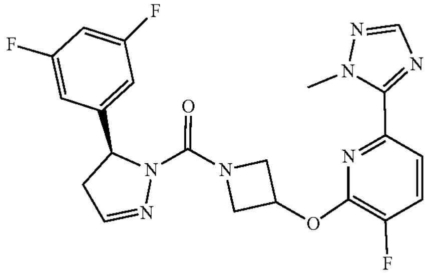 [SMILES: Cn1ncnc1-c1ccc(F)c(OC2CN(C(=O)N3N=CC[C@H]3c3cc(F)cc(F)c3)C2)n1] 28 |
| 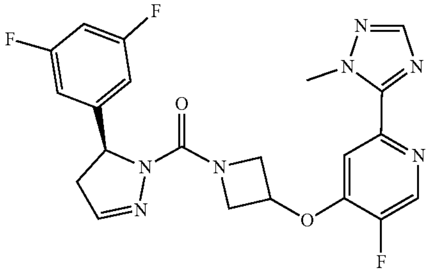 [SMILES: Cn1ncnc1-c1cc(OC2CN(C(=O)N3N=CC[C@H]3c3cc(F)cc(F)c3)C2)c(F)cn1] 29 |
| 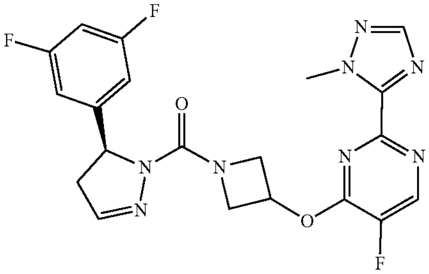 [SMILES: Cn1ncnc1-c1ncc(F)c(OC2CN(C(=O)N3N=CC[C@H]3c3cc(F)cc(F)c3)C2)n1] 30 |
| 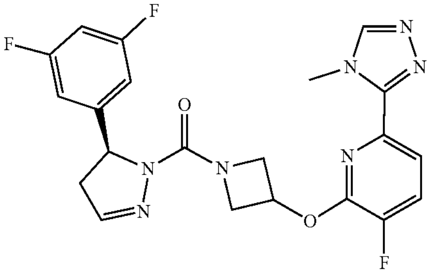 [SMILES: Cn1cnnc1-c1ccc(F)c(OC2CN(C(=O)N3N=CC[C@H]3c3cc(F)cc(F)c3)C2)n1] 31 |
| 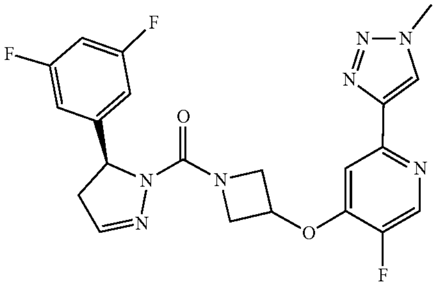 [SMILES: Cn1cc(-c2cc(OC3CN(C(=O)N4N=CC[C@H]4c4cc(F)cc(F)c4)C3)c(F)cn2)nn1] 32 |

TABLE 1-continued
| Active Compounds 1-116: Structures |
| --- |
| 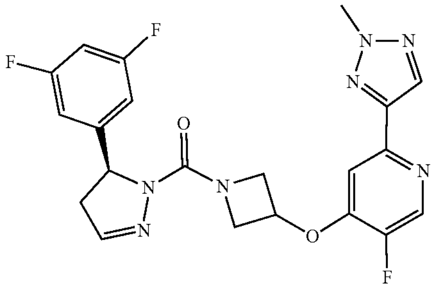 [SMILES: Cn1ncc(-c2cc(OC3CN(C(=O)N4N=CC[C@H]4c4cc(F)cc(F)c4)C3)c(F)cn2)n1] 33 |
| 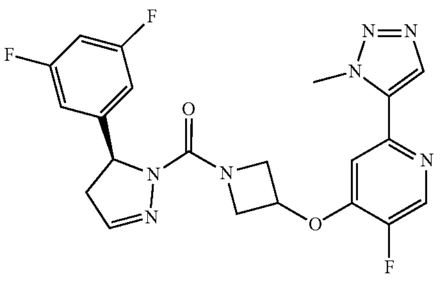 [SMILES: Cn1nncc1-c1cc(OC2CN(C(=O)N3N=CC[C@H]3c3cc(F)cc(F)c3)C2)c(F)cn1] 34 |
| 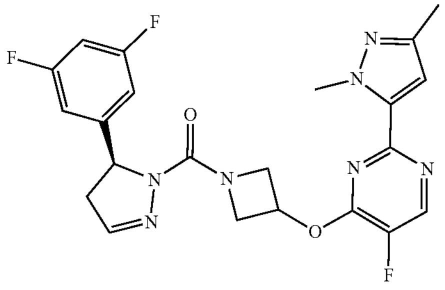 [SMILES: Cc1cc(-c2ncc(F)c(OC3CN(C(=O)N4N=CC[C@H]4c4cc(F)cc(F)c4)C3)n2)n(C)n1] 35 |
| 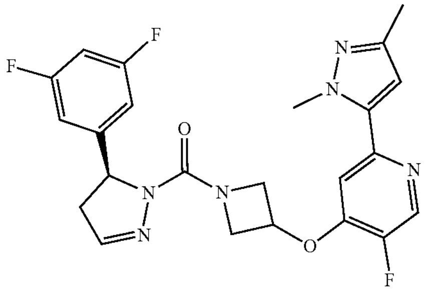 [SMILES: Cc1cc(-c2cc(OC3CN(C(=O)N4N=CC[C@H]4c4cc(F)cc(F)c4)C3)c(F)cn2)n(C)n1] 36 |
| 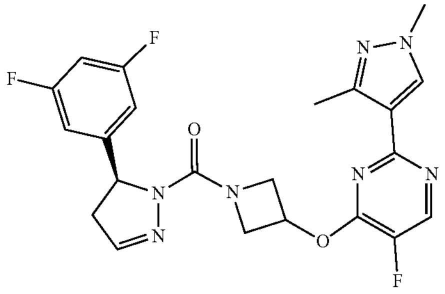 [SMILES: Cc1nn(C)cc1-c1ncc(F)c(OC2CN(C(=O)N3N=CC[C@H]3c3cc(F)cc(F)c3)C2)n1] 37 |

TABLE 1-continued
| Active Compounds 1-116: Structures | |
|---|---|
| 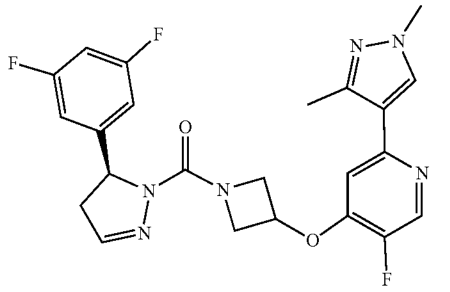 [SMILES: Cc1nn(C)cc1-c1cc(OC2CN(C(=O)N3N=CC[C@H]3c3cc(F)cc(F)c3)C2)c(F)cn1] | 38 |
| 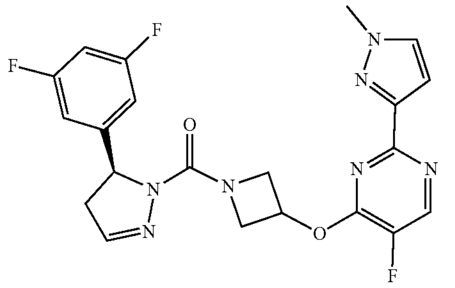 [SMILES: Cn1ccc(-c2ncc(F)c(OC3CN(C(=O)N4N=CC[C@H]4c4cc(F)cc(F)c4)C3)n2)n1] | 39 |
| 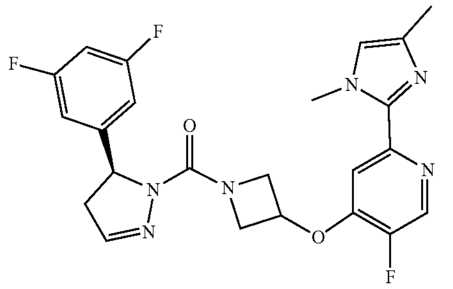 [SMILES: Cc1cn(C)c(-c2cc(OC3CN(C(=O)N4N=CC[C@H]4c4cc(F)cc(F)c4)C3)c(F)cn2)n1] | 40 |
| 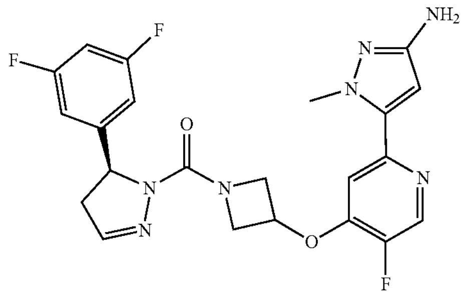 [SMILES: Cn1nc(N)cc1-c1cc(OC2CN(C(=O)N3N=CC[C@H]3c3cc(F)cc(F)c3)C2)c(F)cn1] | 41 |
| 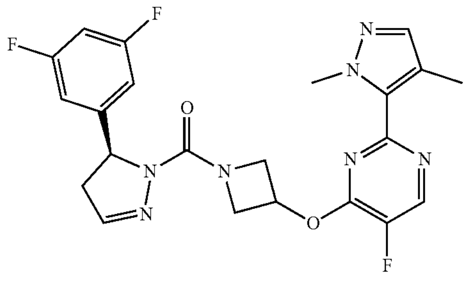 | 42 |

TABLE 1-continued
| Active Compounds 1-116: Structures | |
| --- | --- |
| 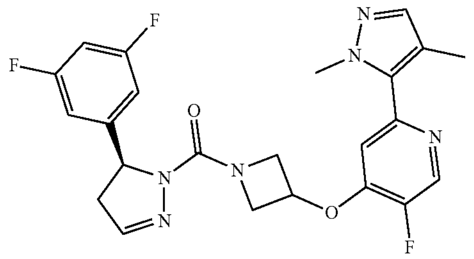 [SMILES: Cc1cnn(C)c1-c1cc(OC2CN(C(=O)N3N=CC[C@H]3c3cc(F)cc(F)c3)C2)c(F)cn1] | 43 |
| 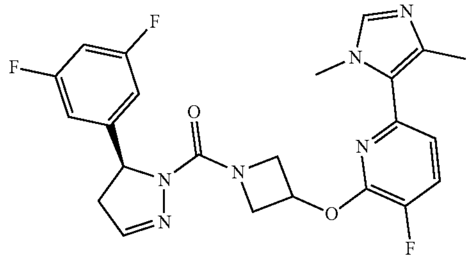 [SMILES: Cc1ncn(C)c1-c1ccc(F)c(OC2CN(C(=O)N3N=CC[C@H]3c3cc(F)cc(F)c3)C2)n1] | 44 |
| 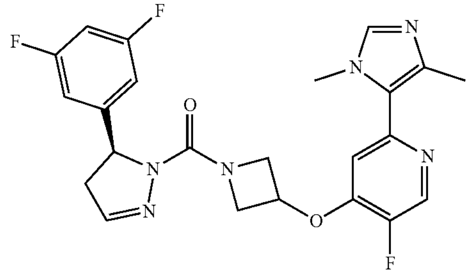 | 45 |
| 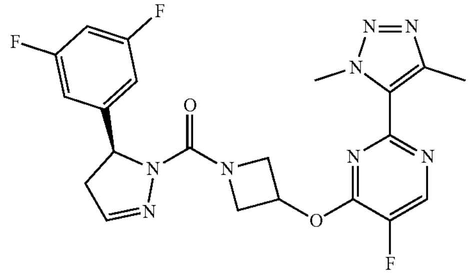 [SMILES: Cc1nnn(C)c1-c1ncc(F)c(OC2CN(C(=O)N3N=CC[C@H]3c3cc(F)cc(F)c3)C2)n1] | 46 |
| 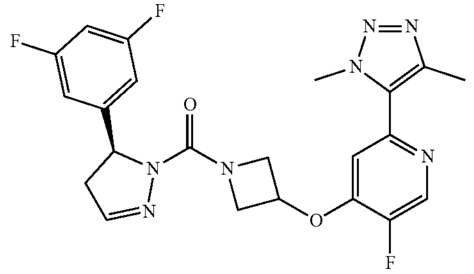 [SMILES: Cc1nnn(C)c1-c1cc(OC2CN(C(=O)N3N=CC[C@H]3c3cc(F)cc(F)c3)C2)c(F)cn1] | 47 |

TABLE 1-continued
| Active Compounds 1-116: Structures | |
|---|---|
| 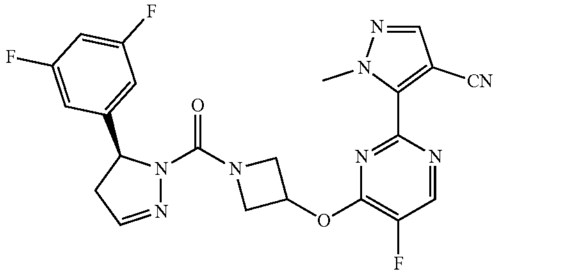 [SMILES: Cn1ncc(C#N)c1-c1ncc(F)c(OC2CN(C(=O)N3N=CC[C@H]3c3cc(F)cc(F)c3)C2)n1] | 48 |
| 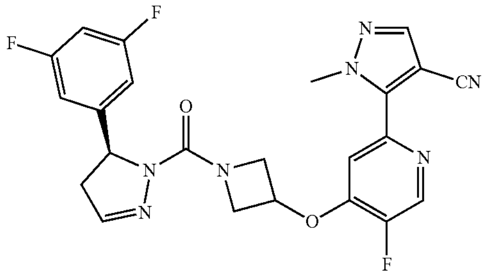 [SMILES: Cn1ncc(C#N)c1-c1cc(OC2CN(C(=O)N3N=CC[C@H]3c3cc(F)cc(F)c3)C2)c(F)cn1] | 49 |
| 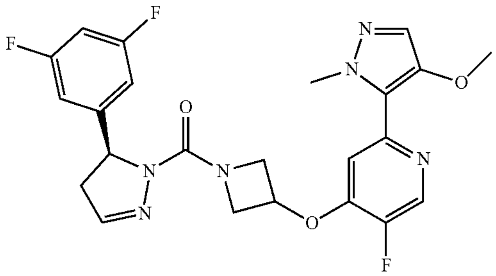 [SMILES: COc1cnn(C)c1-c1cc(OC2CN(C(=O)N3N=CC[C@H]3c3cc(F)cc(F)c3)C2)c(F)cn1] | 50 |
| 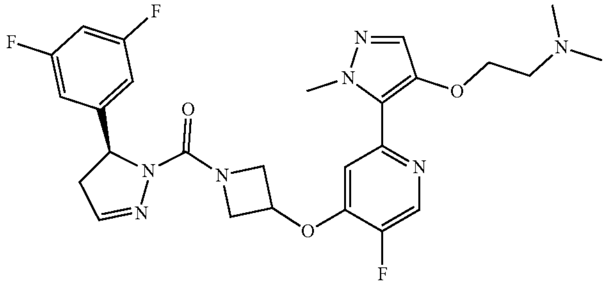 [SMILES: CN(C)CCOc1cnn(C)c1-c1cc(OC2CN(C(=O)N3N=CC[C@H]3c3cc(F)cc(F)c3)C2)c(F)cn1] | 51 |
| 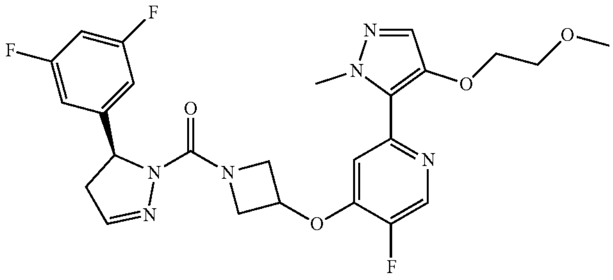 [SMILES: COCCOc1cnn(C)c1-c1cc(OC2CN(C(=O)N3N=CC[C@H]3c3cc(F)cc(F)c3)C2)c(F)cn1] | 52 |

TABLE 1-continued
| Active Compounds 1-116: Structures |
|---|
| 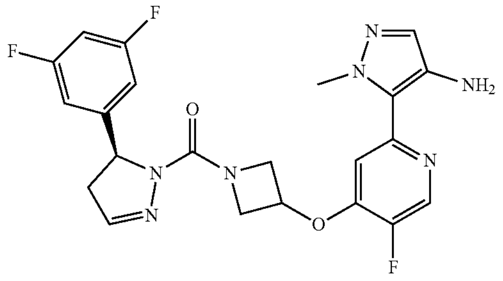 [SMILES: Cn1ncc(N)c1-c1cc(OC2CN(C(=O)N3N=CC[C@H]3c3cc(F)cc(F)c3)C2)c(F)cn1] 53 |
| 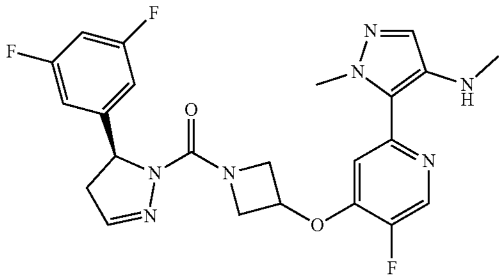 [SMILES: CNc1cnn(C)c1-c1cc(OC2CN(C(=O)N3N=CC[C@H]3c3cc(F)cc(F)c3)C2)c(F)cn1] 54 |
| 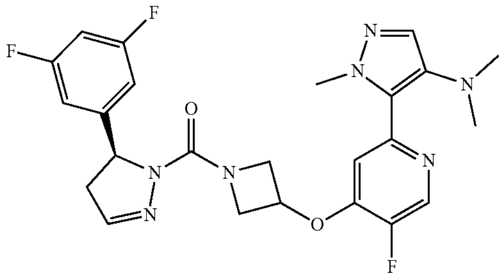 [SMILES: CN(C)c1cnn(C)c1-c1cc(OC2CN(C(=O)N3N=CC[C@H]3c3cc(F)cc(F)c3)C2)c(F)cn1] 55 |
| 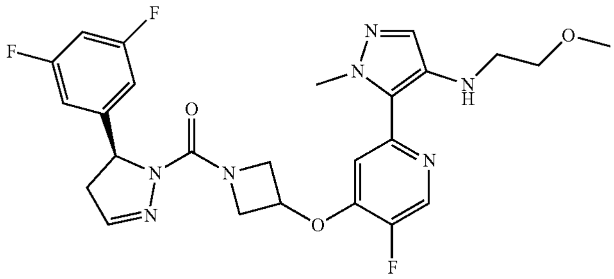 [SMILES: COCCNc1cnn(C)c1-c1cc(OC2CN(C(=O)N3N=CC[C@H]3c3cc(F)cc(F)c3)C2)c(F)cn1] 56 |
| 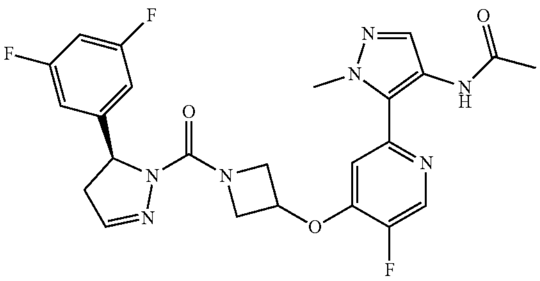 [SMILES: CC(=O)Nc1cnn(C)c1-c1cc(OC2CN(C(=O)N3N=CC[C@H]3c3cc(F)cc(F)c3)C2)c(F)cn1] 57 |

TABLE 1-continued
| Active Compounds 1-116: Structures | |
|---|---|
| 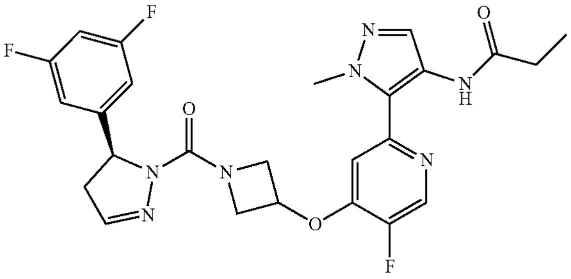 [SMILES: CCC(=O)Nc1cnn(C)c1-c1cc(OC2CN(C(=O)N3N=CC[C@H]3c3cc(F)cc(F)c3)C2)c(F)cn1] | 58 |
| 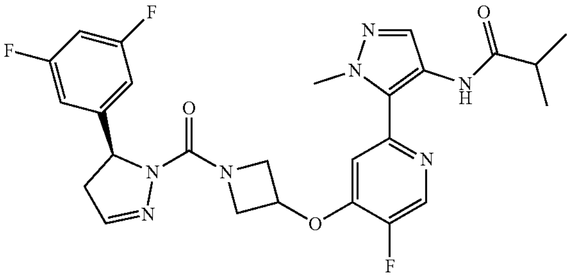 [SMILES: CC(C)C(=O)Nc1cnn(C)c1-c1cc(OC2CN(C(=O)N3N=CC[C@H]3c3cc(F)cc(F)c3)C2)c(F)cn1] | 59 |
| 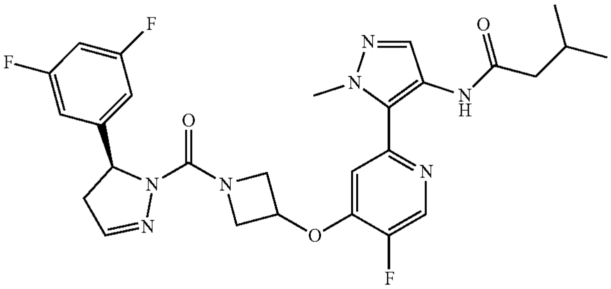 [SMILES: CC(C)CC(=O)Nc1cnn(C)c1-c1cc(OC2CN(C(=O)N3N=CC[C@H]3c3cc(F)cc(F)c3)C2)c(F)cn1] | 60 |
| 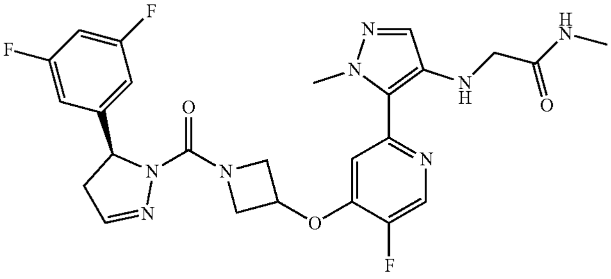 [SMILES: CNC(=O)CNc1cnn(C)c1-c1cc(OC2CN(C(=O)N3N=CC[C@H]3c3cc(F)cc(F)c3)C2)c(F)cn1] | 61 |
| 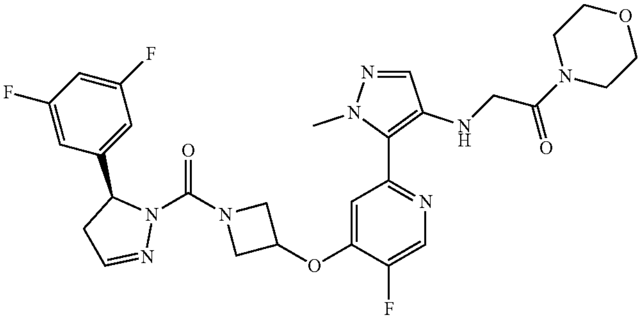 [SMILES: Cn1ncc(NCC(=O)N2CCOCC2)c1-c1cc(OC2CN(C(=O)N3N=CC[C@H]3c3cc(F)cc(F)c3)C2)c(F)cn1] | 62 |

TABLE 1-continued
| Active Compounds 1-116: Structures |
|---|
| 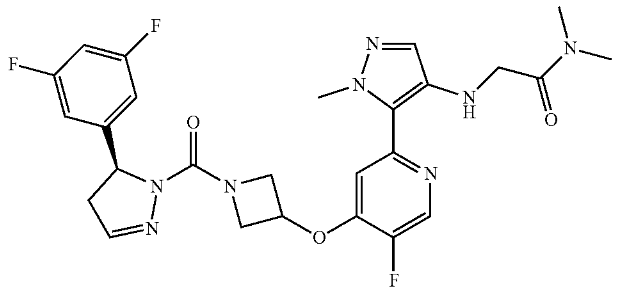 [SMILES: CN(C)C(=O)CNc1cnn(C)c1-c1cc(OC2CN(C(=O)N3N=CC[C@H]3c3cc(F)cc(F)c3)C2)c(F)cn1] 63 |
| 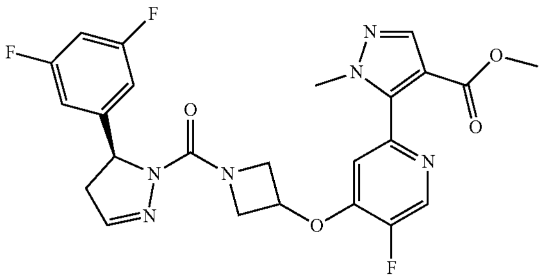 [SMILES: COC(=O)c1cnn(C)c1-c1cc(OC2CN(C(=O)N3N=CC[C@H]3c3cc(F)cc(F)c3)C2)c(F)cn1] 64 |
| 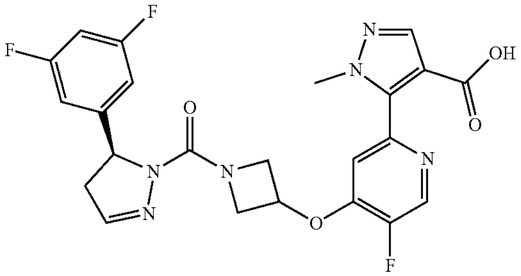 [SMILES: Cn1ncc(C(=O)O)c1-c1cc(OC2CN(C(=O)N3N=CC[C@H]3c3cc(F)cc(F)c3)C2)c(F)cn1] 65 |
| 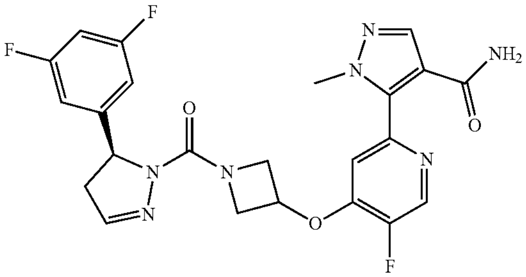 [SMILES: Cn1ncc(C(N)=O)c1-c1cc(OC2CN(C(=O)N3N=CC[C@H]3c3cc(F)cc(F)c3)C2)c(F)cn1] 66 |
| 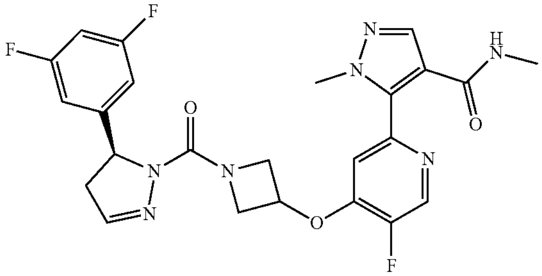 [SMILES: CNC(=O)c1cnn(C)c1-c1cc(OC2CN(C(=O)N3N=CC[C@H]3c3cc(F)cc(F)c3)C2)c(F)cn1] 67 |

TABLE 1-continued
| Active Compounds 1-116: Structures |
|---|
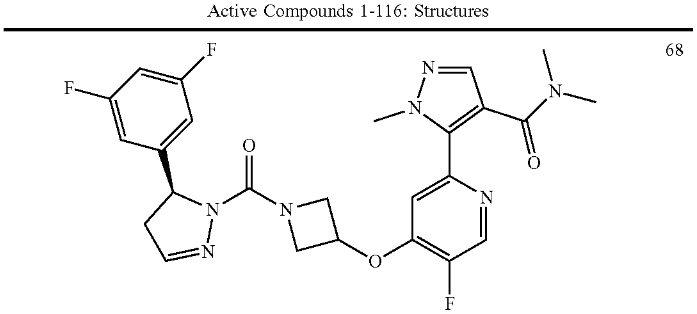
68
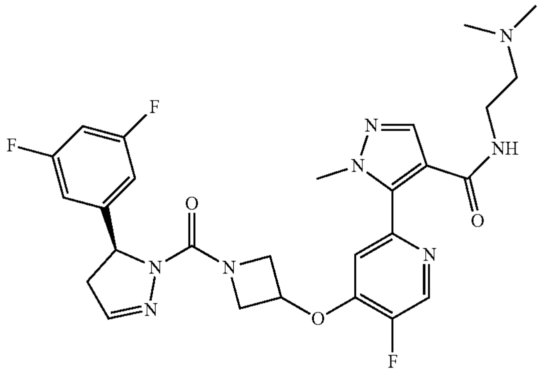 [SMILES: CN(C)CCNC(=O)c1cnn(C)c1-c1cc(OC2CN(C(=O)N3N=CC[C@H]3c3cc(F)cc(F)c3)C2)c(F)cn1]
69
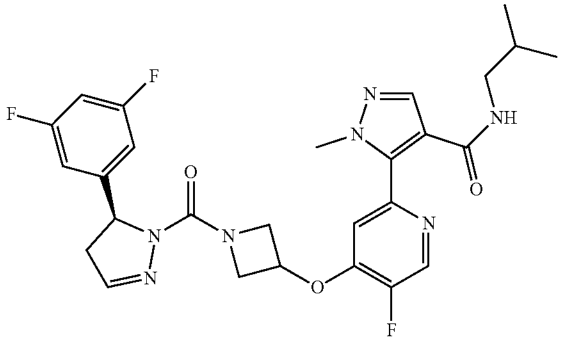 [SMILES: CC(C)CNC(=O)c1cnn(C)c1-c1cc(OC2CN(C(=O)N3N=CC[C@H]3c3cc(F)cc(F)c3)C2)c(F)cn1]
70
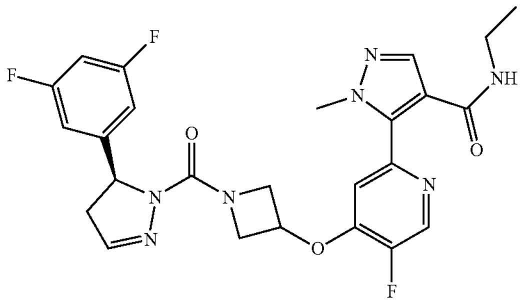 [SMILES: CCNC(=O)c1cnn(C)c1-c1cc(OC2CN(C(=O)N3N=CC[C@H]3c3cc(F)cc(F)c3)C2)c(F)cn1]
71
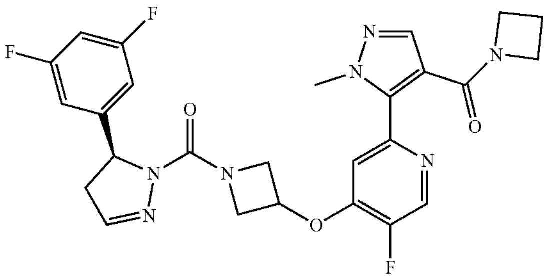 [SMILES: Cn1ncc(C(=O)N2CCC2)c1-c1cc(OC2CN(C(=O)N3N=CC[C@H]3c3cc(F)cc(F)c3)C2)c(F)cn1]
72

TABLE 1-continued
| Active Compounds 1-116: Structures | |
|---|---|
| 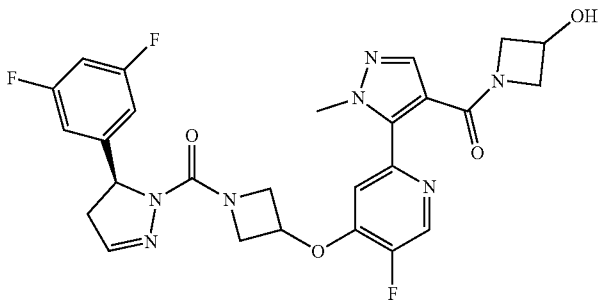 [SMILES: Cn1ncc(C(=O)N2CC(O)C2)c1-c1cc(OC2CN(C(=O)N3N=CC[C@H]3c3cc(F)cc(F)c3)C2)c(F)cn1] | 73 |
| 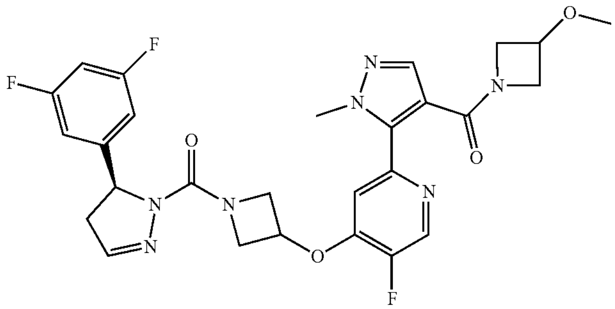 [SMILES: COC1CN(C(=O)c2cnn(C)c2-c2cc(OC3CN(C(=O)N4N=CC[C@H]4c4cc(F)cc(F)c4)C3)c(F)cn2)C1] | 74 |
| 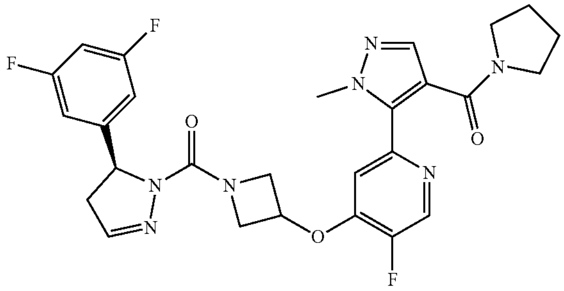 [SMILES: Cn1ncc(C(=O)N2CCCC2)c1-c1cc(OC2CN(C(=O)N3N=CC[C@H]3c3cc(F)cc(F)c3)C2)c(F)cn1] | 75 |
| 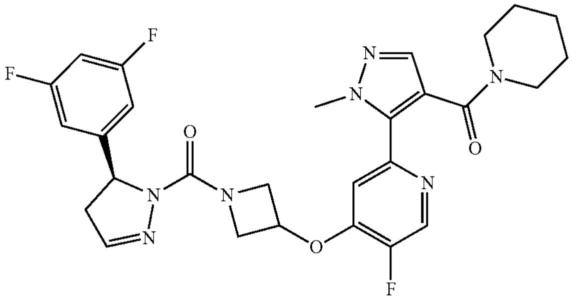 [SMILES: Cn1ncc(C(=O)N2CCCCC2)c1-c1cc(OC2CN(C(=O)N3N=CC[C@H]3c3cc(F)cc(F)c3)C2)c(F)cn1] | 76 |
| 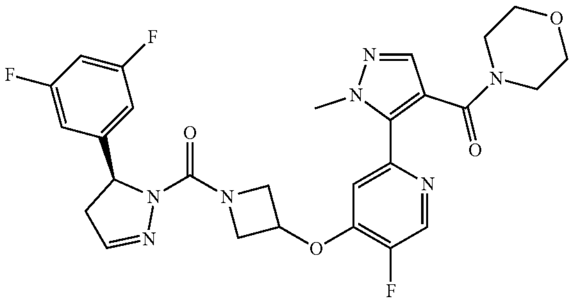 [SMILES: Cn1ncc(C(=O)N2CCOCC2)c1-c1cc(OC2CN(C(=O)N3N=CC[C@H]3c3cc(F)cc(F)c3)C2)c(F)cn1] | 77 |

TABLE 1-continued
| Active Compounds 1-116: Structures |
| --- |
| 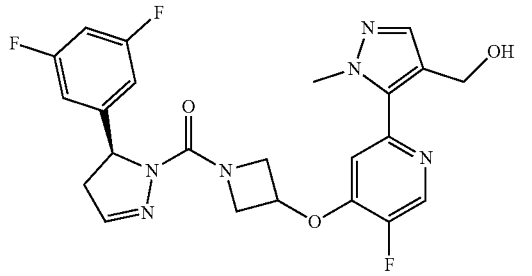 [SMILES: Cn1ncc(CO)c1-c1cc(OC2CN(C(=O)N3N=CC[C@H]3c3cc(F)cc(F)c3)C2)c(F)cn1] 78 |
| 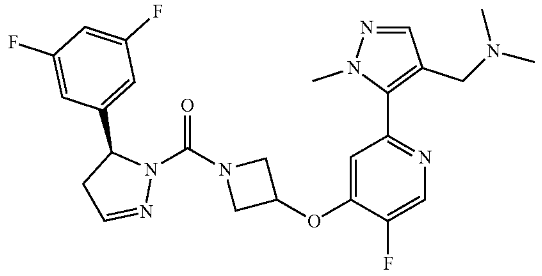 [SMILES: CN(C)Cc1cnn(C)c1-c1cc(OC2CN(C(=O)N3N=CC[C@H]3c3cc(F)cc(F)c3)C2)c(F)cn1] 79 |
| 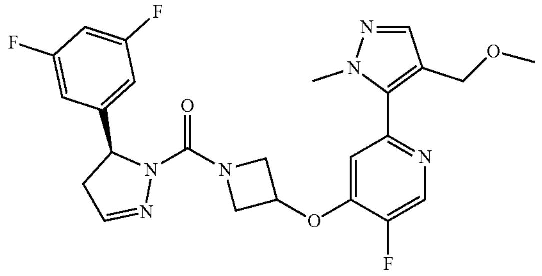 [SMILES: COCc1cnn(C)c1-c1cc(OC2CN(C(=O)N3N=CC[C@H]3c3cc(F)cc(F)c3)C2)c(F)cn1] 80 |
| 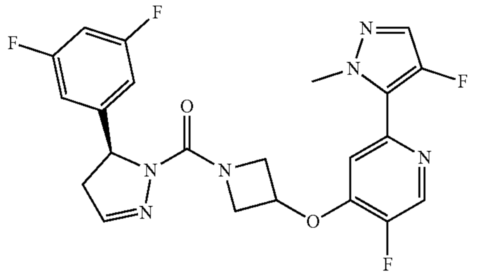 [SMILES: Cn1ncc(F)c1-c1cc(OC2CN(C(=O)N3N=CC[C@H]3c3cc(F)cc(F)c3)C2)c(F)cn1] 81 |
| 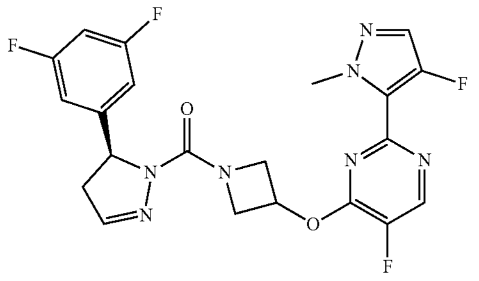 [SMILES: Cn1ncc(F)c1-c1ncc(F)c(OC2CN(C(=O)N3N=CC[C@H]3c3cc(F)cc(F)c3)C2)n1] 82 |

TABLE 1-continued
| Active Compounds 1-116: Structures | |
|---|---|
| 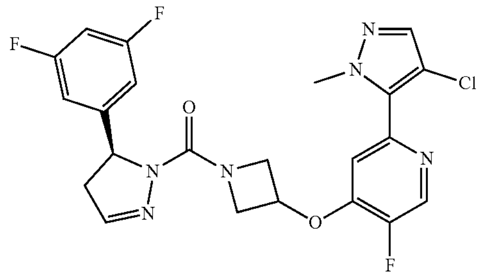 [SMILES: Cn1ncc(Cl)c1-c1cc(OC2CN(C(=O)N3N=CC[C@H]3c3cc(F)cc(F)c3)C2)c(F)cn1] | 83 |
| 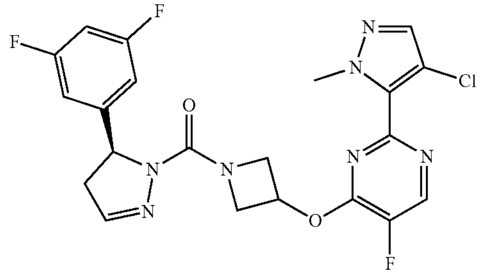 [SMILES: Cn1ncc(Cl)c1-c1ncc(F)c(OC2CN(C(=O)N3N=CC[C@H]3c3cc(F)cc(F)c3)C2)n1] | 84 |
| 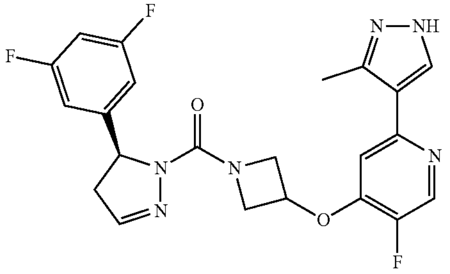 [SMILES: Cc1n[nH]cc1-c1cc(OC2CN(C(=O)N3N=CC[C@H]3c3cc(F)cc(F)c3)C2)c(F)cn1] | 85 |
| 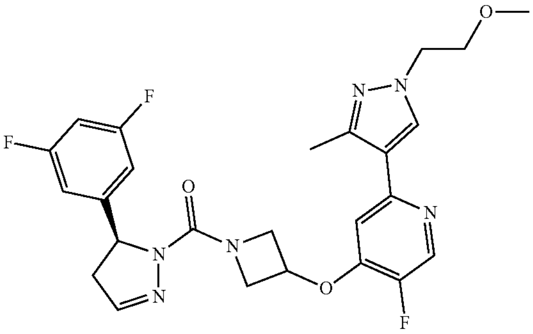 [SMILES: COCCn1cc(-c2cc(OC3CN(C(=O)N4N=CC[C@H]4c4cc(F)cc(F)c4)C3)c(F)cn2)c(C)n1] | 86 |
| 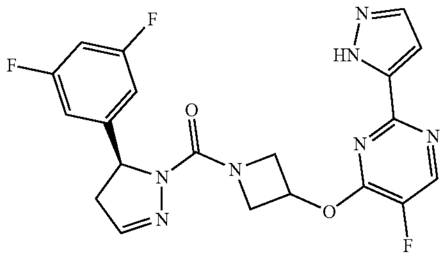 [SMILES: O=C(N1CC(Oc2nc(-c3ccn[nH]3)ncc2F)C1)N1N=CC[C@H]1c1cc(F)cc(F)c1] | 87 |

TABLE 1-continued
| Active Compounds 1-116: Structures | |
|---|---|
| 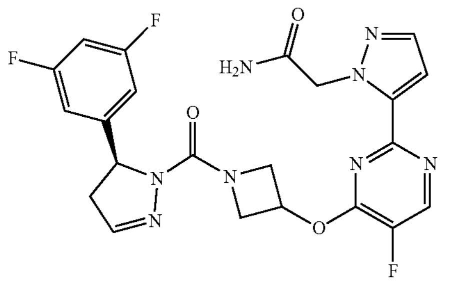 [SMILES: NC(=O)Cn1nccc1-c1ncc(F)c(OC2CN(C(=O)N3N=CC[C@H]3c3cc(F)cc(F)c3)C2)n1] | 88 |
| 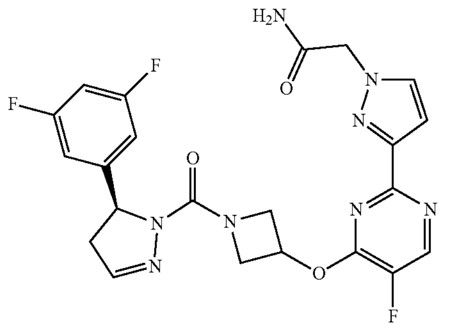 [SMILES: NC(=O)Cn1ccc(-c2ncc(F)c(OC3CN(C(=O)N4N=CC[C@H]4c4cc(F)cc(F)c4)C3)n2)n1] | 89 |
| 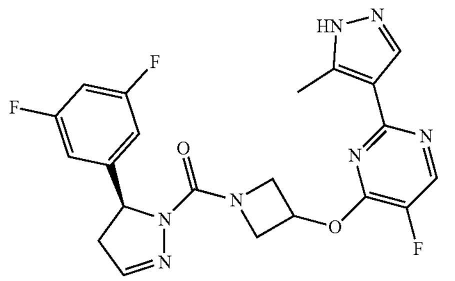 [SMILES: Cc1[nH]ncc1-c1ncc(F)c(OC2CN(C(=O)N3N=CC[C@H]3c3cc(F)cc(F)c3)C2)n1] | 90 |
| 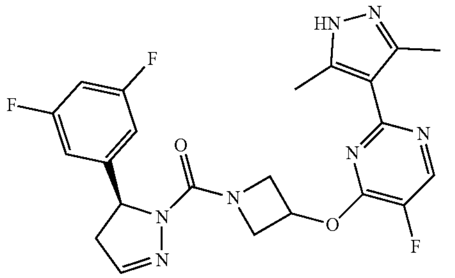 [SMILES: Cc1n[nH]c(C)c1-c1ncc(F)c(OC2CN(C(=O)N3N=CC[C@H]3c3cc(F)cc(F)c3)C2)n1] | 91 |
| 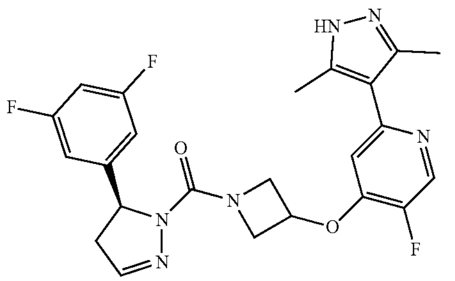 [SMILES: Cc1n[nH]c(C)c1-c1cc(OC2CN(C(=O)N3N=CC[C@H]3c3cc(F)cc(F)c3)C2)c(F)cn1] | 92 |

TABLE 1-continued
| Active Compounds 1-116: Structures | |
|---|---|
| 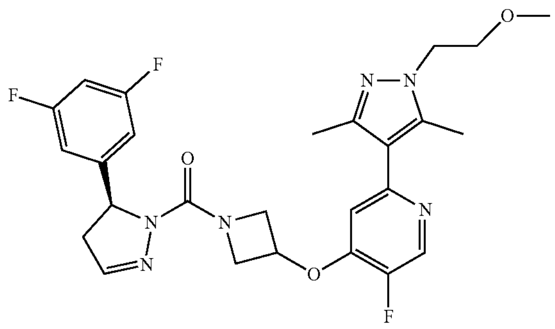 [SMILES: COCCn1nc(C)c(-c2cc(OC3CN(C(=O)N4N=CC[C@H]4c4cc(F)cc(F)c4)C3)c(F)cn2)c1C] | 93 |
| 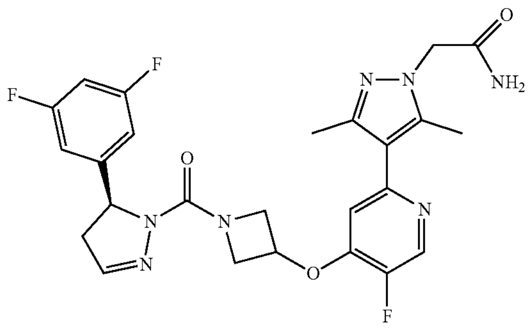 [SMILES: Cc1nn(CC(N)=O)c(C)c1-c1cc(OC2CN(C(=O)N3N=CC[C@H]3c3cc(F)cc(F)c3)C2)c(F)cn1] | 94 |
| 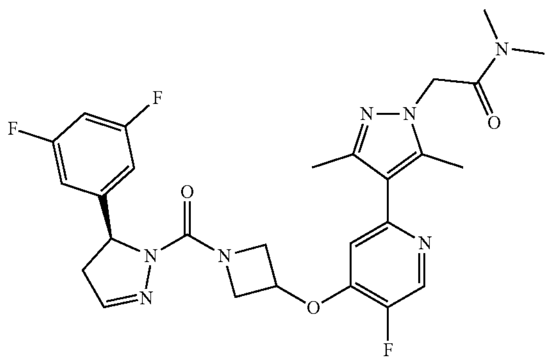 [SMILES: Cc1nn(CC(=O)N(C)C)c(C)c1-c1cc(OC2CN(C(=O)N3N=CC[C@H]3c3cc(F)cc(F)c3)C2)c(F)cn1] | 95 |
| 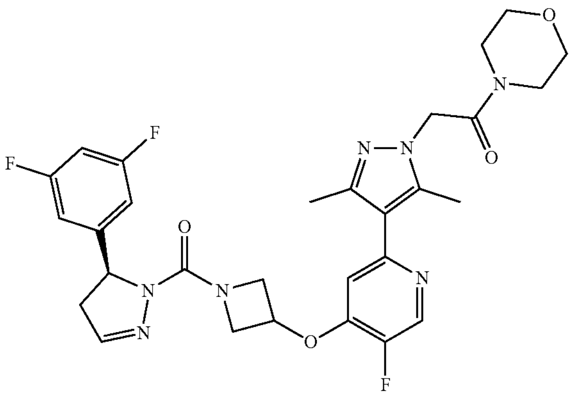 [SMILES: Cc1nn(CC(=O)N2CCOCC2)c(C)c1-c1cc(OC2CN(C(=O)N3N=CC[C@H]3c3cc(F)cc(F)c3)C2)c(F)cn1] | 96 |

TABLE 1-continued
| Active Compounds 1-116: Structures |
| --- |
| 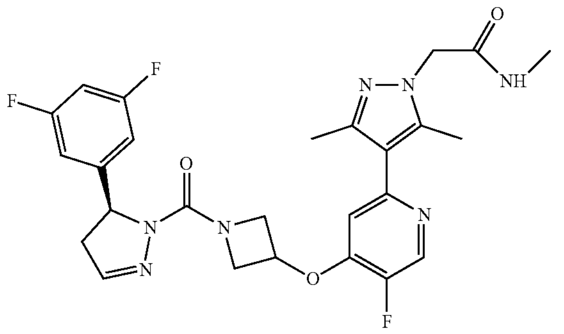 [SMILES: CNC(=O)Cn1nc(C)c(-c2cc(OC3CN(C(=O)N4N=CC[C@H]4c4cc(F)cc(F)c4)C3)c(F)cn2)c1C] 97 |
| 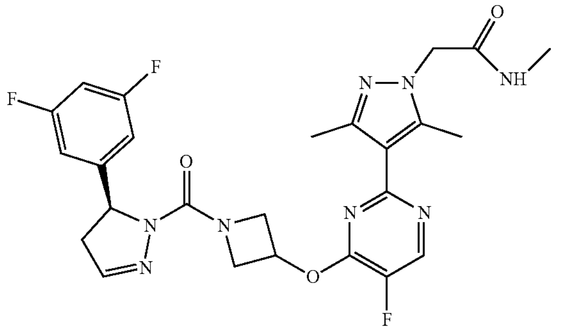 [SMILES: CNC(=O)Cn1nc(C)c(-c2ncc(F)c(OC3CN(C(=O)N4N=CC[C@H]4c4cc(F)cc(F)c4)C3)n2)c1C] 98 |
| 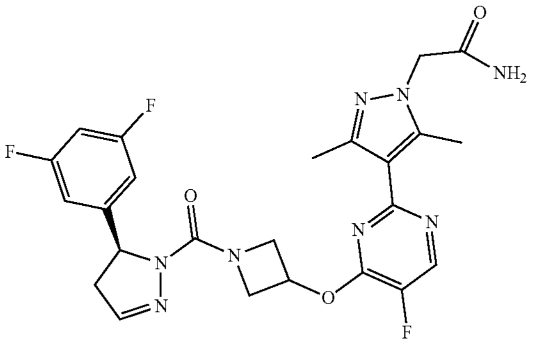 [SMILES: Cc1nn(CC(N)=O)c(C)c1-c1ncc(F)c(OC2CN(C(=O)N3N=CC[C@H]3c3cc(F)cc(F)c3)C2)n1] 99 |
| 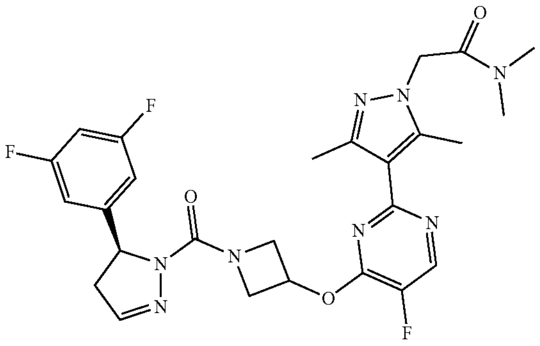 [SMILES: Cc1nn(CC(=O)N(C)C)c(C)c1-c1ncc(F)c(OC2CN(C(=O)N3N=CC[C@H]3c3cc(F)cc(F)c3)C2)n1] 100 |

TABLE 1-continued
| Active Compounds 1-116: Structures | |
|---|---|
| 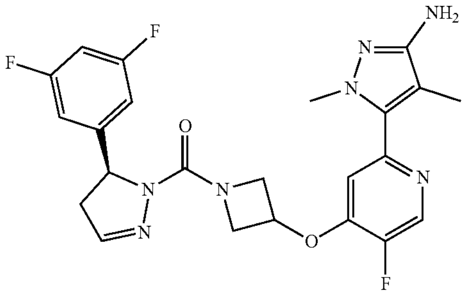 | 101 |
| 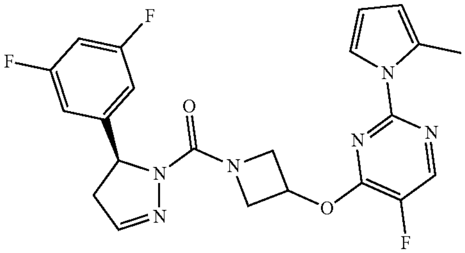 [SMILES: Cc1cccn1-c1ncc(F)c(OC2CN(C(=O)N3N=CC[C@H]3c3cc(F)cc(F)c3)C2)n1] | 102 |
| 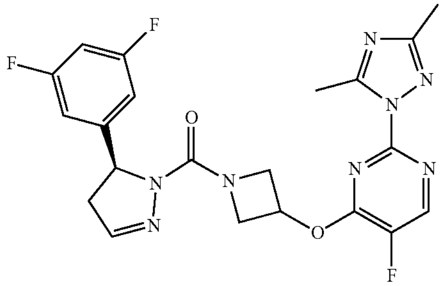 [SMILES: Cc1nc(C)n(-c2ncc(F)c(OC3CN(C(=O)N4N=CC[C@H]4c4cc(F)cc(F)c4)C3)n2)n1] | 103 |
| 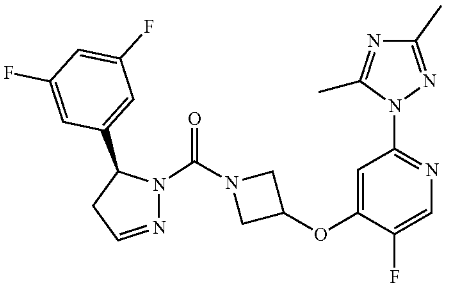 [SMILES: Cc1nc(C)n(-c2cc(OC3CN(C(=O)N4N=CC[C@H]4c4cc(F)cc(F)c4)C3)c(F)cn2)n1] | 104 |
| 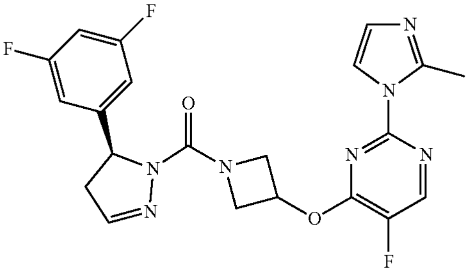 [SMILES: Cc1nccn1-c1ncc(F)c(OC2CN(C(=O)N3N=CC[C@H]3c3cc(F)cc(F)c3)C2)n1] | 105 |

TABLE 1-continued
| Active Compounds 1-116: Structures | |
|---|---|
| 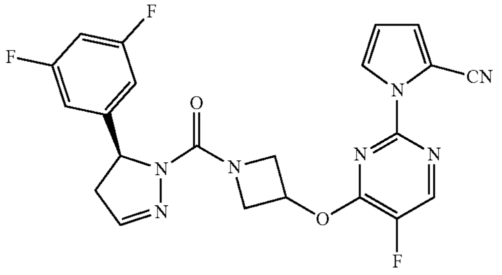 [SMILES: N#Cc1cccn1-c1ncc(F)c(OC2CN(C(=O)N3N=CC[C@H]3c3cc(F)cc(F)c3)C2)n1] | 106 |
| 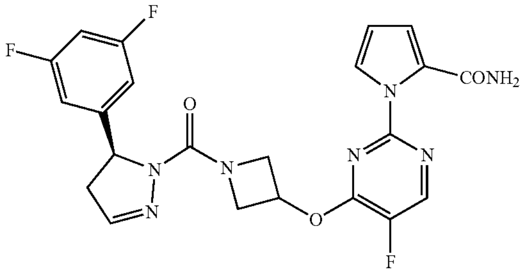 [SMILES: NC(=O)c1cccn1-c1ncc(F)c(OC2CN(C(=O)N3N=CC[C@H]3c3cc(F)cc(F)c3)C2)n1] | 107 |
| 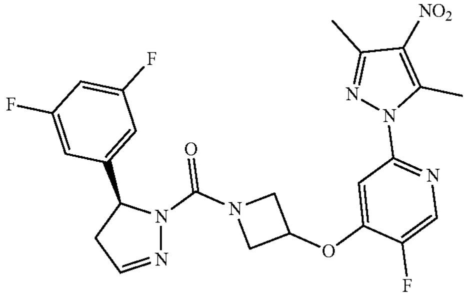 [SMILES: Cc1nn(-c2cc(OC3CN(C(=O)N4N=CC[C@H]4c4cc(F)cc(F)c4)C3)c(F)cn2)c(C)c1[N+](=O)[O-]] | 108 |
| 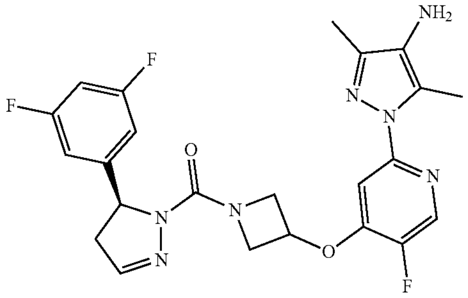 [SMILES: Cc1nn(-c2cc(OC3CN(C(=O)N4N=CC[C@H]4c4cc(F)cc(F)c4)C3)c(F)cn2)c(C)c1N] | 109 |
| 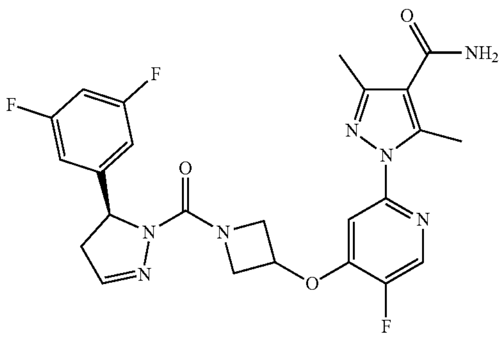 [SMILES: Cc1nn(-c2cc(OC3CN(C(=O)N4N=CC[C@H]4c4cc(F)cc(F)c4)C3)c(F)cn2)c(C)c1C(N)=O] | 110 |

TABLE 1-continued
| Active Compounds 1-116: Structures | |
|---|---|
| 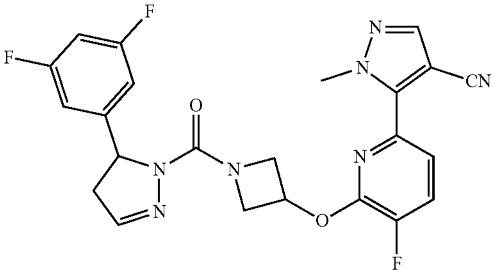 [SMILES: Cn1ncc(C#N)c1-c1ccc(F)c(OC2CN(C(=O)N3N=CCC3c3cc(F)cc(F)c3)C2)n1] | 111 |
| 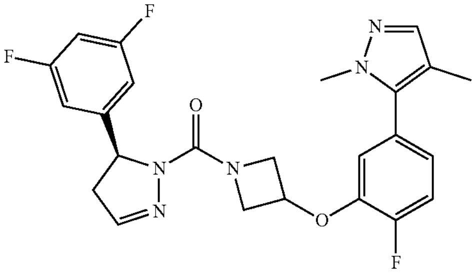 [SMILES: Cc1cnn(C)c1-c1ccc(F)c(OC2CN(C(=O)N3N=CC[C@H]3c3cc(F)cc(F)c3)C2)c1] | 112 |
| 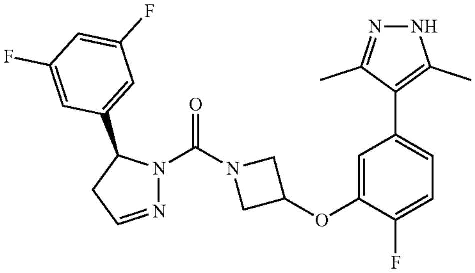 [SMILES: Cc1n[nH]c(C)c1-c1ccc(F)c(OC2CN(C(=O)N3N=CC[C@H]3c3cc(F)cc(F)c3)C2)c1] | 113 |
| 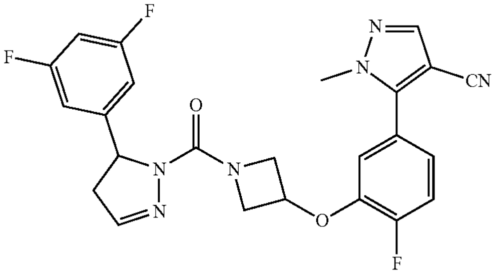 [SMILES: Cn1ncc(C#N)c1-c1ccc(F)c(OC2CN(C(=O)N3N=CCC3c3cc(F)cc(F)c3)C2)c1] | 114 |
| 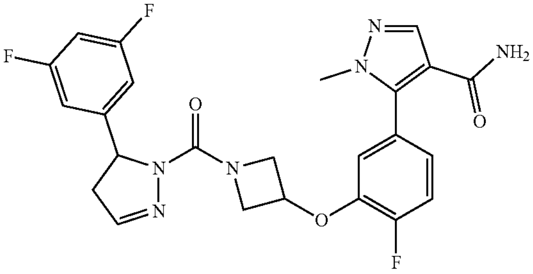 [SMILES: Cn1ncc(C(N)=O)c1-c1ccc(F)c(OC2CN(C(=O)N3N=CCC3c3cc(F)cc(F)c3)C2)c1] | 115 |

TABLE 1-continued

| Active Compounds 1-116: Structures | |
|---|---|
| 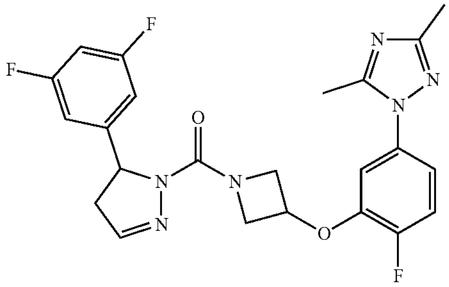 [SMILES: Cc1nc(C)n(-c2ccc(F)c(OC3CN(C(=O)N4N=CCC4c4cc(F)cc(F)c4)C3)c2)n1] | 116 |

TABLE 2

Cell activity ($EC_{50}$) of Compounds 1-116

| # | EC50 |
|---|---|
| 1 | +++ |
| 2 | +++ |
| 3 | +++ |
| 4 | +++ |
| 5 | +++ |
| 6 | +++ |
| 7 | +++ |
| 8 | +++ |
| 9 | +++ |
| 10 | +++ |
| 11 | +++ |
| 12 | +++ |
| 13 | +++ |
| 14 | +++ |
| 15 | +++ |
| 16 | +++ |
| 17 | +++ |
| 18 | +++ |
| 19 | +++ |
| 20 | +++ |
| 21 | +++ |
| 22 | +++ |
| 23 | +++ |
| 24 | +++ |
| 25 | +++ |
| 26 | +++ |
| 27 | ++ |
| 28 | +++ |
| 29 | +++ |
| 30 | +++ |
| 31 | +++ |
| 32 | +++ |
| 33 | +++ |
| 34 | +++ |
| 35 | +++ |
| 36 | +++ |
| 37 | +++ |
| 38 | +++ |
| 39 | ++ |
| 40 | +++ |
| 41 | +++ |
| 42 | +++ |
| 43 | +++ |
| 44 | +++ |
| 45 | +++ |
| 46 | +++ |
| 47 | +++ |
| 48 | +++ |
| 49 | +++ |
| 50 | +++ |
| 51 | ++ |
| 52 | +++ |
| 53 | +++ |
| 54 | +++ |

TABLE 2-continued

Cell activity ($EC_{50}$) of Compounds 1-116

| # | EC50 |
|---|---|
| 55 | +++ |
| 56 | +++ |
| 57 | +++ |
| 58 | +++ |
| 59 | +++ |
| 60 | +++ |
| 61 | +++ |
| 62 | +++ |
| 63 | +++ |
| 64 | +++ |
| 65 | + |
| 66 | +++ |
| 67 | +++ |
| 68 | + |
| 69 | ++ |
| 70 | +++ |
| 71 | +++ |
| 72 | ++ |
| 73 | ++ |
| 74 | ++ |
| 75 | + |
| 76 | + |
| 77 | + |
| 78 | +++ |
| 79 | +++ |
| 80 | +++ |
| 81 | +++ |
| 82 | +++ |
| 83 | +++ |
| 84 | +++ |
| 85 | +++ |
| 86 | +++ |
| 87 | +++ |
| 88 | ++ |
| 89 | ++ |
| 90 | +++ |
| 91 | +++ |
| 92 | +++ |
| 93 | +++ |
| 94 | +++ |
| 95 | +++ |
| 96 | +++ |
| 97 | +++ |
| 98 | +++ |
| 99 | +++ |
| 100 | +++ |
| 101 | +++ |
| 102 | +++ |
| 103 | +++ |
| 104 | +++ |
| 105 | +++ |
| 106 | +++ |
| 107 | +++ |
| 108 | +++ |

TABLE 2-continued
| Cell activity ($EC_{50}$) of Compounds 1-116 | |
|---|---|
| # | EC50 |
| 109 | +++ |
| 110 | +++ |
| 111 | +++ |
| 112 | +++ |
| 113 | +++ |
| 114 | +++ |
| 115 | +++ |
| 116 | +++ |
TABLE 3
| Active Compounds 117-281: Structures | |
|---|---|
| 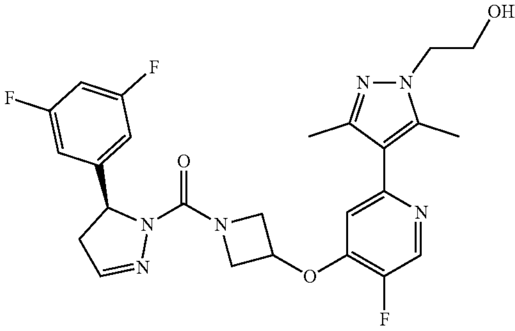 [SMILES: Cc1nn(CCO)c(C)c1-c1cc(OC2CN(C(=O)N3N=CC[C@H]3c3cc(F)cc(F)c3)C2)c(F)cn1] | 117 |
| 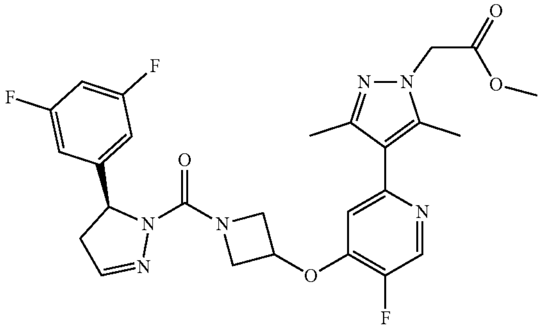 [SMILES: COC(=O)Cn1nc(C)c(-c2cc(OC3CN(C(=O)N4N=CC[C@H]4c4cc(F)cc(F)c4)C3)c(F)cn2)c1C] | 118 |
| 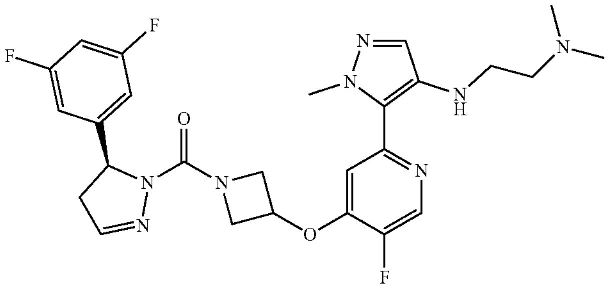 [SMILES: CN(C)CCNc1cnn(C)c1-c1cc(OC2CN(C(=O)N3N=CC[C@H]3c3cc(F)cc(F)c3)C2)c(F)cn1] | 119 |
| 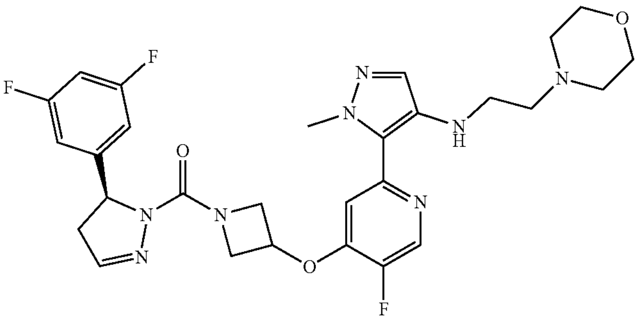 [SMILES: Cn1ncc(NCCN2CCOCC2)c1-c1cc(OC2CN(C(=O)N3N=CC[C@H]3c3cc(F)cc(F)c3)C2)c(F)cn1] | 120 |

TABLE 3-continued
| Active Compounds 117-281: Structures |
|---|
| 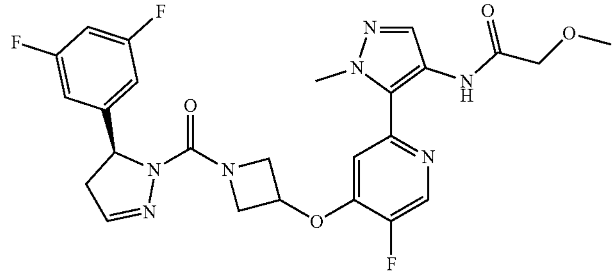 [SMILES: COCC(=O)Nc1cnn(C)c1-c1cc(OC2CN(C(=O)N3N=CC[C@H]3c3cc(F)cc(F)c3)C2)c(F)cn1] 121 |
| 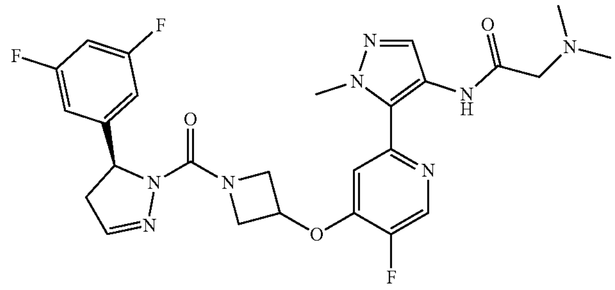 [SMILES: CN(C)CC(=O)Nc1cnn(C)c1-c1cc(OC2CN(C(=O)N3N=CC[C@H]3c3cc(F)cc(F)c3)C2)c(F)cn1] 122 |
| 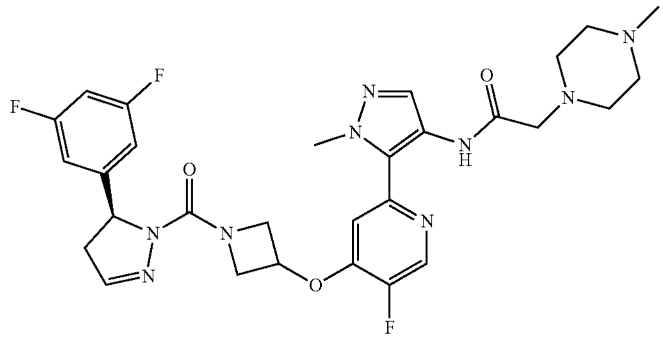 [SMILES: CN1CCN(CC(=O)Nc2cnn(C)c2-c2cc(OC3CN(C(=O)N4N=CC[C@H]4c4cc(F)cc(F)c4)C3)c(F)cn2)CC1] 123 |
| 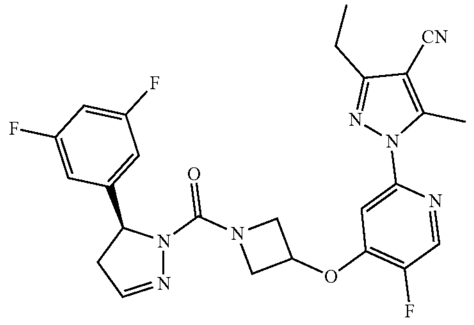 [SMILES: CCc1nn(-c2cc(OC3CN(C(=O)N4N=CC[C@H]4c4cc(F)cc(F)c4)C3)c(F)cn2)c(C)c1C#N] 124 |
| 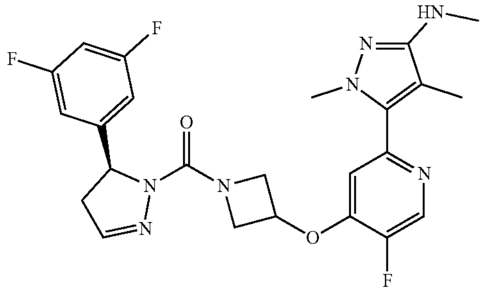 [SMILES: CNc1nn(C)c(-c2cc(OC3CN(C(=O)N4N=CC[C@H]4c4cc(F)cc(F)c4)C3)c(F)cn2)c1C] 125 |

TABLE 3-continued
| Active Compounds 117-281: Structures |
|---|
| 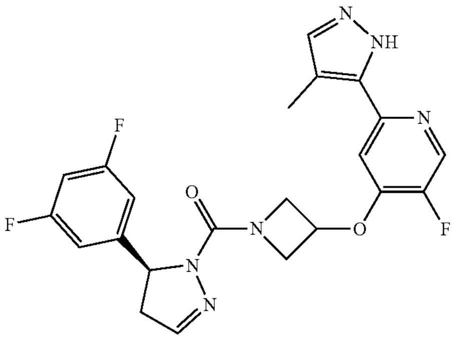 [SMILES: Cc1cn[nH]c1-c1cc(OC2CN(C(=O)N3N=CC[C@H]3c3cc(F)cc(F)c3)C2)c(F)cn1] 126 |
| 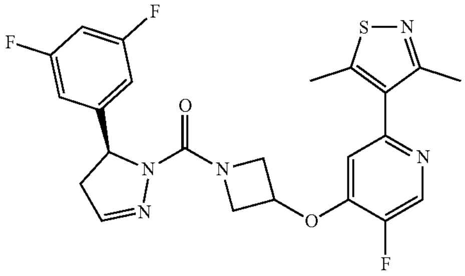 [SMILES: Cc1nsc(C)c1-c1cc(OC2CN(C(=O)N3N=CC[C@H]3c3cc(F)cc(F)c3)C2)c(F)cn1] 127 |
| 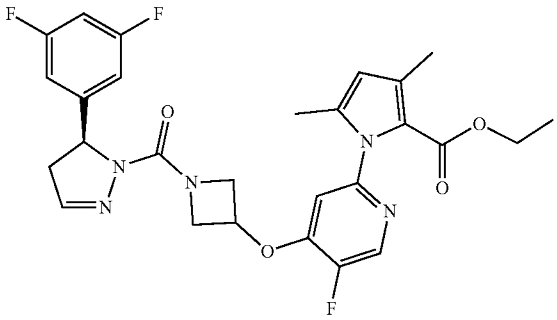 [SMILES: CCOC(=O)c1c(C)cc(C)n1-c1cc(OC2CN(C(=O)N3N=CC[C@H]3c3cc(F)cc(F)c3)C2)c(F)cn1] 128 |
| 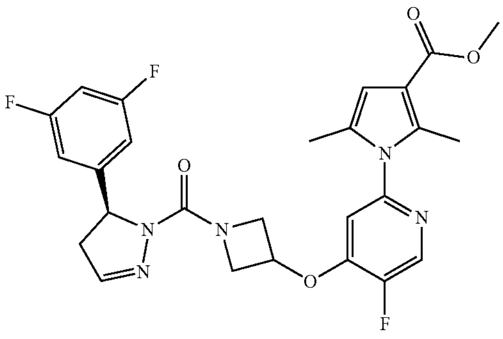 [SMILES: COC(=O)c1cc(C)n(-c2cc(OC3CN(C(=O)N4N=CC[C@H]4c4cc(F)cc(F)c4)C3)c(F)cn2)c1C] 129 |

TABLE 3-continued
| Active Compounds 117-281: Structures |
| --- |
| 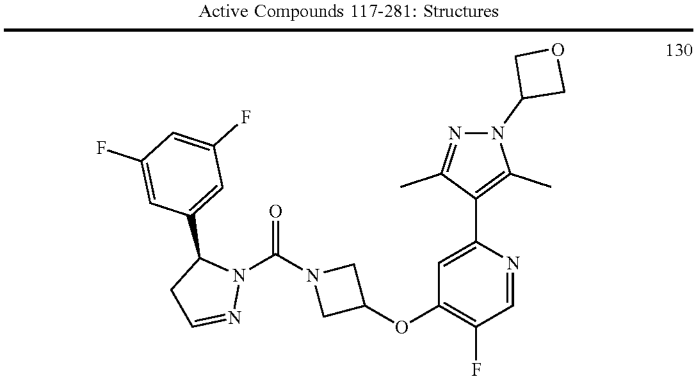 130 |
| 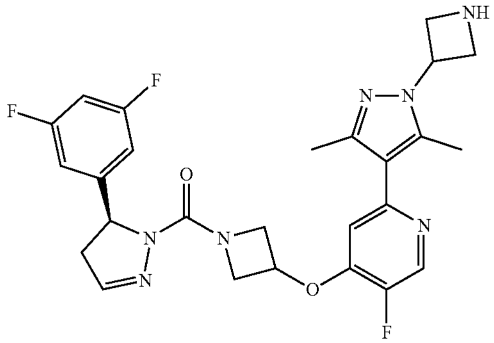 [SMILES: Cc1nn(C2CNC2)c(C)c1-c1cc(OC2CN(C(=O)N3N=CC[C@H]3c3cc(F)cc(F)c3)C2)c(F)cn1] 131 |
| 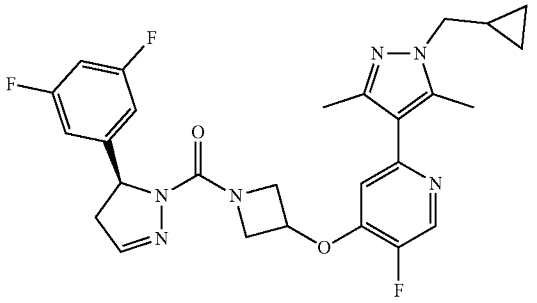 [SMILES: Cc1nn(CC2CC2)c(C)c1-c1cc(OC2CN(C(=O)N3N=CC[C@H]3c3cc(F)cc(F)c3)C2)c(F)cn1] 132 |
| 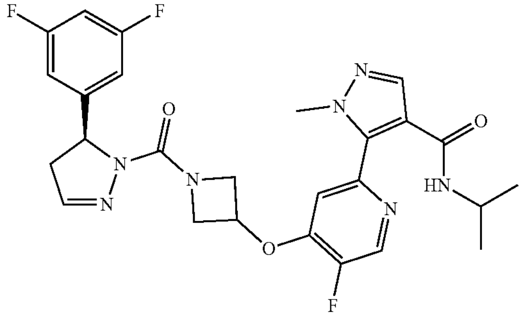 [SMILES: CC(C)NC(=O)c1cnn(C)c1-c1cc(OC2CN(C(=O)N3N=CC[C@H]3c3cc(F)cc(F)c3)C2)c(F)cn1] 133 |
| 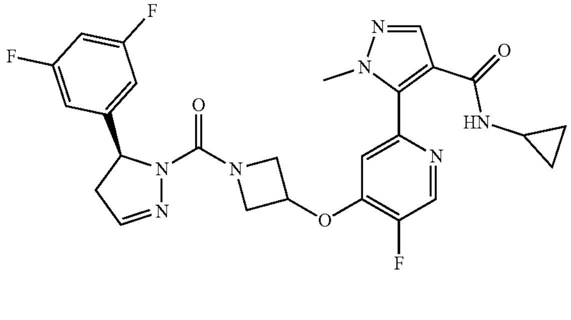 [SMILES: Cn1ncc(C(=O)NC2CC2)c1-c1cc(OC2CN(C(=O)N3N=CC[C@H]3c3cc(F)cc(F)c3)C2)c(F)cn1] 134 |

TABLE 3-continued
| Active Compounds 117-281: Structures |
| --- |
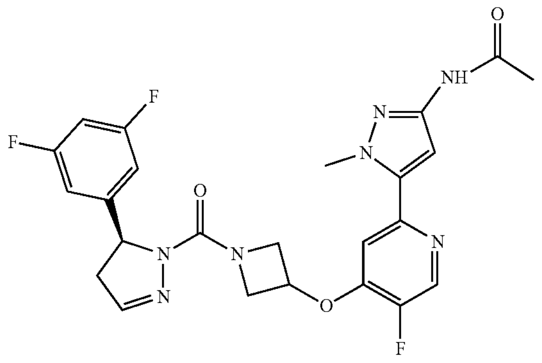 [SMILES: CC(=O)Nc1cc(-c2cc(OC3CN(C(=O)N4N=CC[C@H]4c4cc(F)cc(F)c4)C3)c(F)cn2)n(C)n1]
135
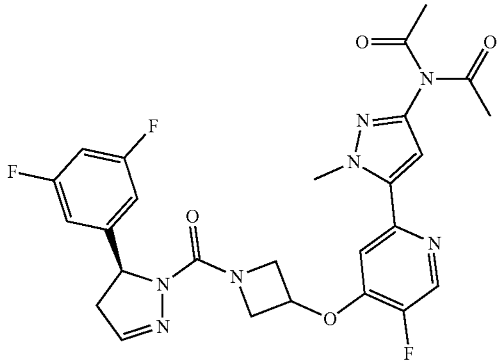 [SMILES: CC(=O)N(C(C)=O)c1cc(-c2cc(OC3CN(C(=O)N4N=CC[C@H]4c4cc(F)cc(F)c4)C3)c(F)cn2)n(C)n1]
136
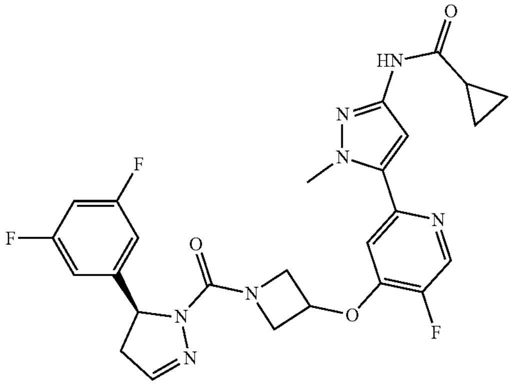 [SMILES: Cn1nc(NC(=O)C2CC2)cc1-c1cc(OC2CN(C(=O)N3N=CC[C@H]3c3cc(F)cc(F)c3)C2)c(F)cn1]
137
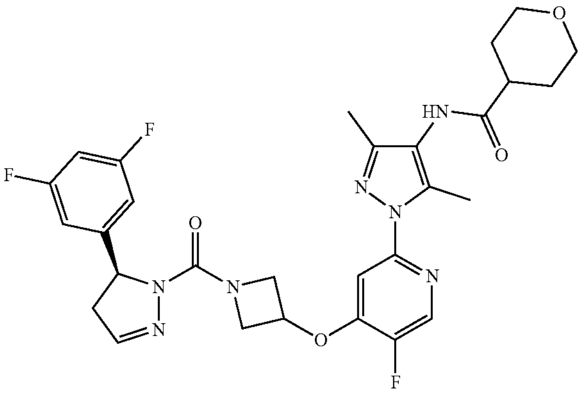 [SMILES: Cc1nn(-c2cc(OC3CN(C(=O)N4N=CC[C@H]4c4cc(F)cc(F)c4)C3)c(F)cn2)c(C)c1NC(=O)C1CCOCC1]
138

TABLE 3-continued
Active Compounds 117-281: Structures
139
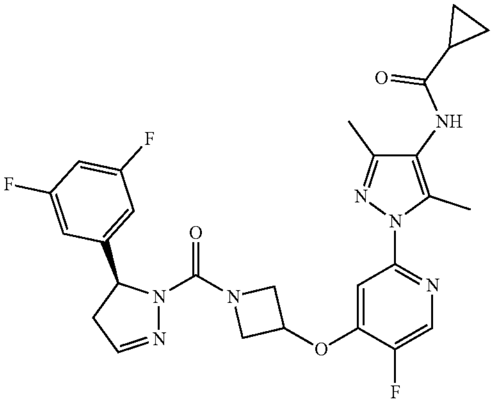 [SMILES: Cc1nn(-c2cc(OC3CN(C(=O)N4N=CC[C@H]4c4cc(F)cc(F)c4)C3)c(F)cn2)c(C)c1NC(=O)C1CC1]
140
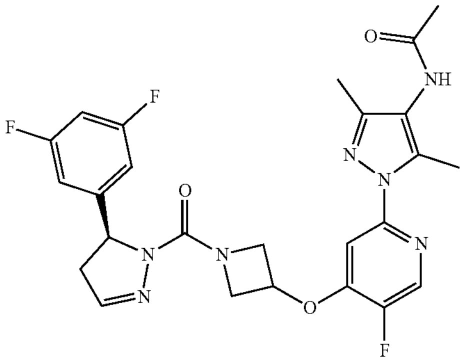 [SMILES: CC(=O)Nc1c(C)nn(-c2cc(OC3CN(C(=O)N4N=CC[C@H]4c4cc(F)cc(F)c4)C3)c(F)cn2)c1C]
141
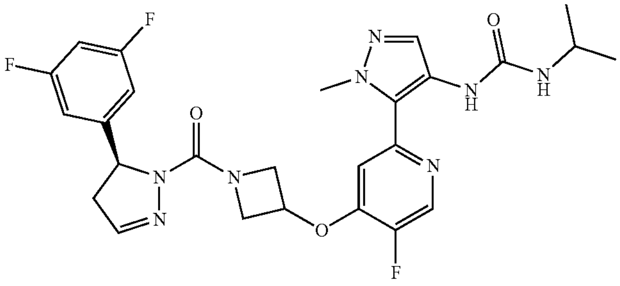 [SMILES: CC(C)NC(=O)Nc1cnn(C)c1-c1cc(OC2CN(C(=O)N3N=CC[C@H]3c3cc(F)cc(F)c3)C2)c(F)cn1]
142
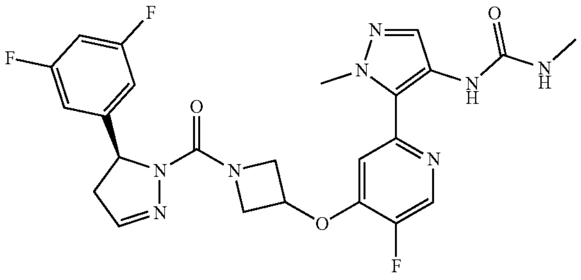 [SMILES: CNC(=O)Nc1cnn(C)c1-c1cc(OC2CN(C(=O)N3N=CC[C@H]3c3cc(F)cc(F)c3)C2)c(F)cn1]

TABLE 3-continued
| Active Compounds 117-281: Structures |
| --- |
143
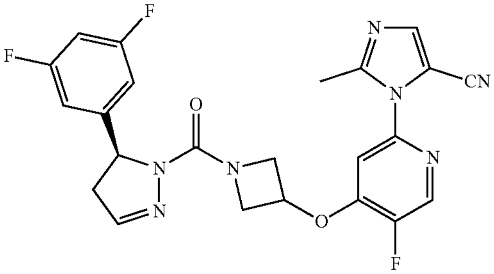 [SMILES: Cc1ncc(C#N)n1-c1cc(OC2CN(C(=O)N3N=CC[C@H]3c3cc(F)cc(F)c3)C2)c(F)cn1]
144
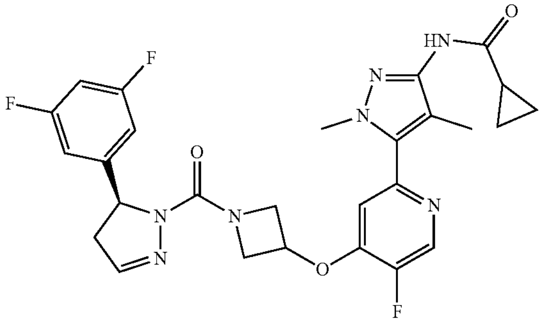 [SMILES: Cc1c(NC(=O)C2CC2)nn(C)c1-c1cc(OC2CN(C(=O)N3N=CC[C@H]3c3cc(F)cc(F)c3)C2)c(F)cn1]
145
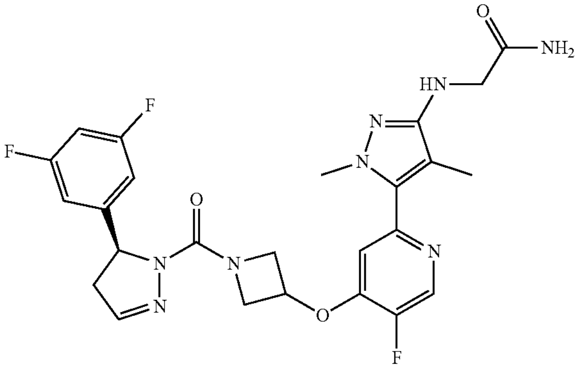 [SMILES: Cc1c(NCC(N)=O)nn(C)c1-c1cc(OC2CN(C(=O)N3N=CC[C@H]3c3cc(F)cc(F)c3)C2)c(F)cn1]
146
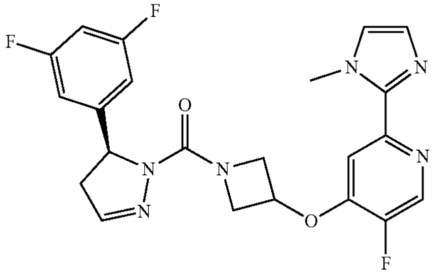 [SMILES: Cn1ccnc1-c1cc(OC2CN(C(=O)N3N=CC[C@H]3c3cc(F)cc(F)c3)C2)c(F)cn1]
147
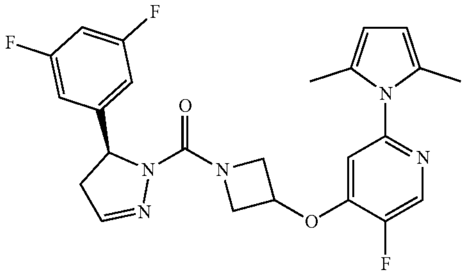 [SMILES: Cc1ccc(C)n1-c1cc(OC2CN(C(=O)N3N=CC[C@H]3c3cc(F)cc(F)c3)C2)c(F)cn1]

TABLE 3-continued
| Active Compounds 117-281: Structures |
|---|
| 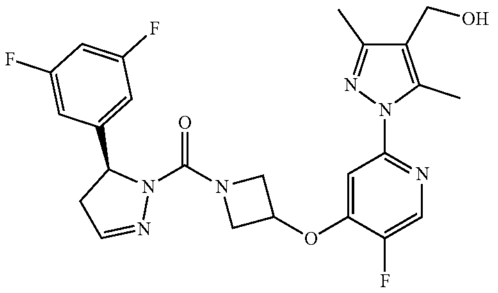 [SMILES: Cc1nn(-c2cc(OC3CN(C(=O)N4N=CC[C@H]4c4cc(F)cc(F)c4)C3)c(F)cn2)c(C)c1CO] 148 |
| 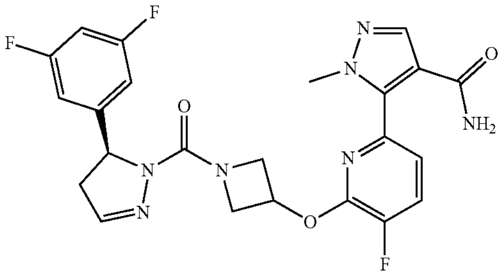 [SMILES: Cn1ncc(C(N)=O)c1-c1ccc(F)c(OC2CN(C(=O)N3N=CC[C@H]3c3cc(F)cc(F)c3)C2)n1] 149 |
| 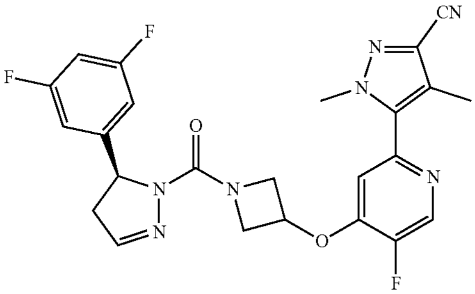 150 |
| 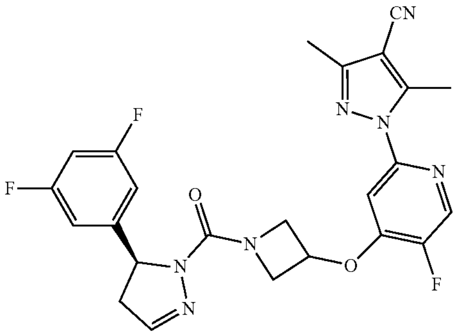 [SMILES: Cc1nn(-c2cc(OC3CN(C(=O)N4N=CC[C@H]4c4cc(F)cc(F)c4)C3)c(F)cn2)c(C)c1C#N] 151 |
| 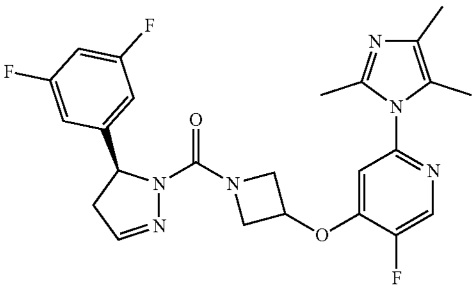 [SMILES: Cc1nc(C)n(-c2cc(OC3CN(C(=O)N4N=CC[C@H]4c4cc(F)cc(F)c4)C3)c(F)cn2)c1C] 152 |

TABLE 3-continued
| Active Compounds 117-281: Structures |
|---|
| 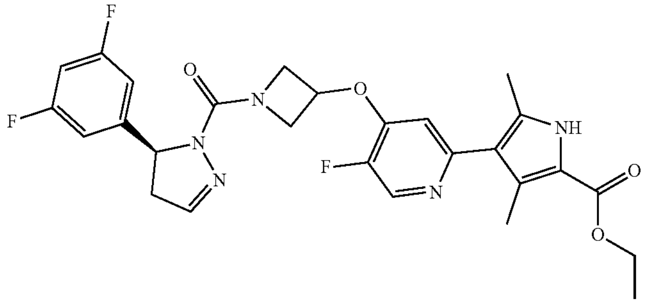 [SMILES: CCOC(=O)c1[nH]c(C)c(-c2cc(OC3CN(C(=O)N4N=CC[C@H]4c4cc(F)cc(F)c4)C3)c(F)cn2)c1C] 153 |
| 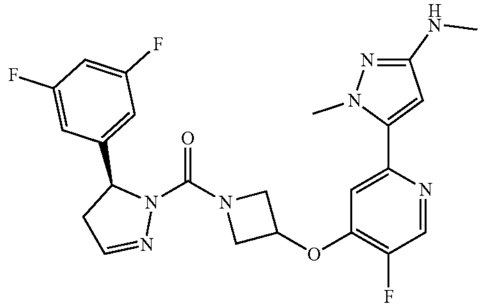 [SMILES: CNc1cc(-c2cc(OC3CN(C(=O)N4N=CC[C@H]4c4cc(F)cc(F)c4)C3)c(F)cn2)n(C)n1] 154 |
| 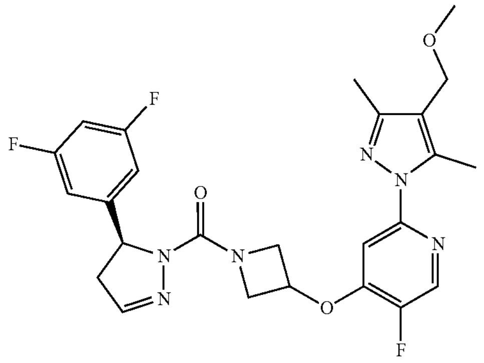 [SMILES: COCc1c(C)nn(-c2cc(OC3CN(C(=O)N4N=CC[C@H]4c4cc(F)cc(F)c4)C3)c(F)cn2)c1C] 155 |
| 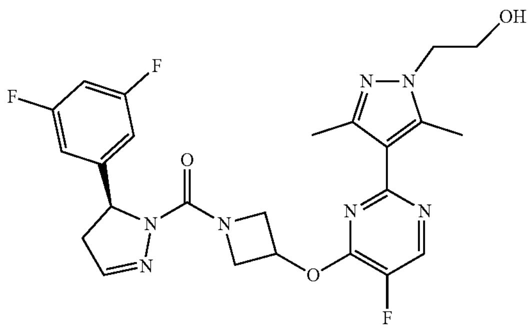 [SMILES: Cc1nn(CCO)c(C)c1-c1ncc(F)c(OC2CN(C(=O)N3N=CC[C@H]3c3cc(F)cc(F)c3)C2)n1] 156 |

TABLE 3-continued
| Active Compounds 117-281: Structures |
| --- |
| 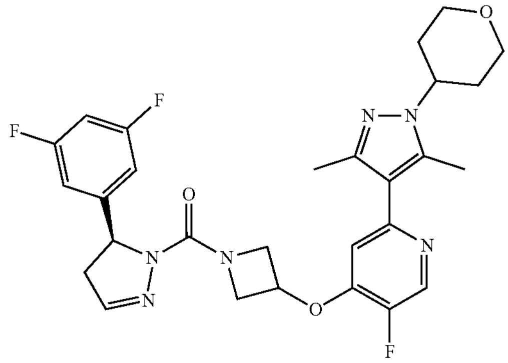 [SMILES: Cc1nn(C2CCOCC2)c(C)c1-c1cc(OC2CN(C(=O)N3N=CC[C@H]3c3cc(F)cc(F)c3)C2)c(F)cn1] 157 |
| 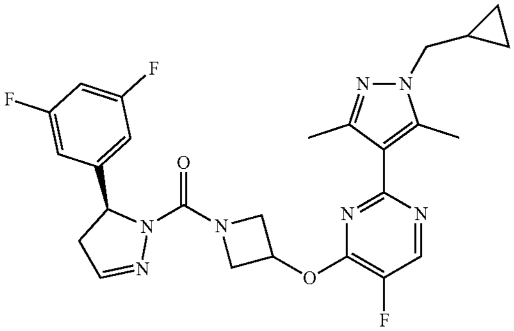 [SMILES: Cc1nn(CC2CC2)c(C)c1-c1ncc(F)c(OC2CN(C(=O)N3N=CC[C@H]3c3cc(F)cc(F)c3)C2)n1] 158 |
| 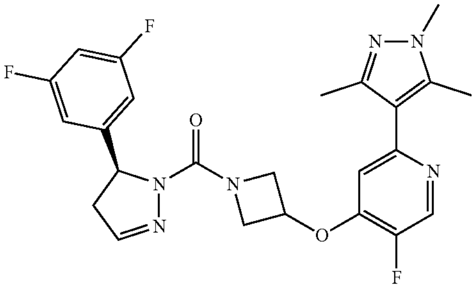 [SMILES: Cc1nn(C)c(C)c1-c1cc(OC2CN(C(=O)N3N=CC[C@H]3c3cc(F)cc(F)c3)C2)c(F)cn1] 159 |
| 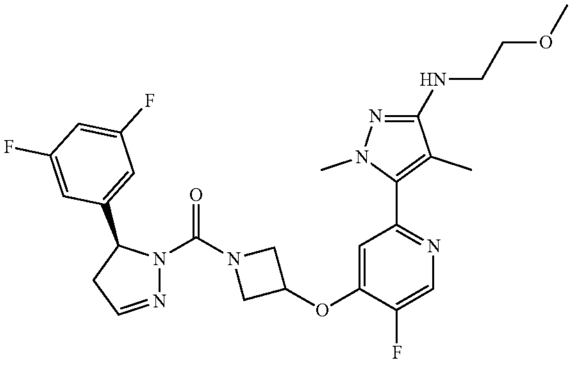 [SMILES: COCCNc1nn(C)c(-c2cc(OC3CN(C(=O)N4N=CC[C@H]4c4cc(F)cc(F)c4)C3)c(F)cn2)c1C] 160 |

TABLE 3-continued
| Active Compounds 117-281: Structures |
|---|
| 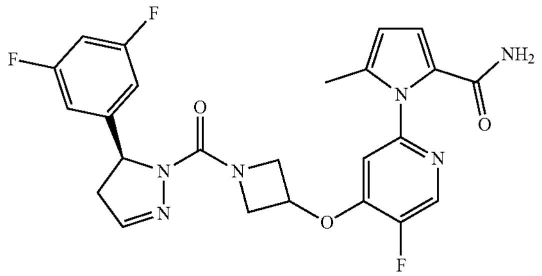 [SMILES: Cc1ccc(C(N)=O)n1-c1cc(OC2CN(C(=O)N3N=CC[C@H]3c3cc(F)cc(F)c3)C2)c(F)cn1] 161 |
| 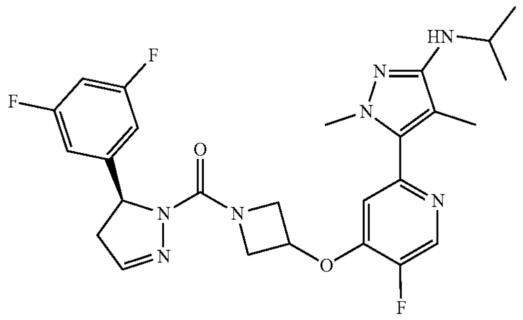 [SMILES: Cc1c(NC(C)C)nn(C)c1-c1cc(OC2CN(C(=O)N3N=CC[C@H]3c3cc(F)cc(F)c3)C2)c(F)cn1] 162 |
| 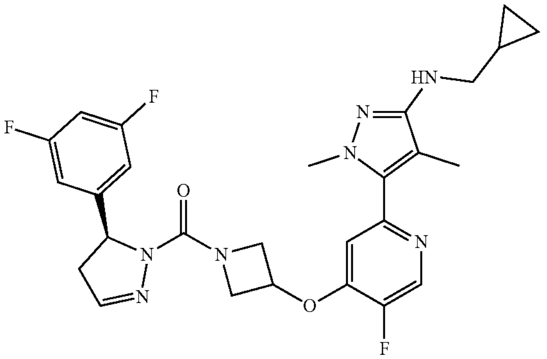 [SMILES: Cc1c(NCC2CC2)nn(C)c1-c1cc(OC2CN(C(=O)N3N=CC[C@H]3c3cc(F)cc(F)c3)C2)c(F)cn1] 163 |
| 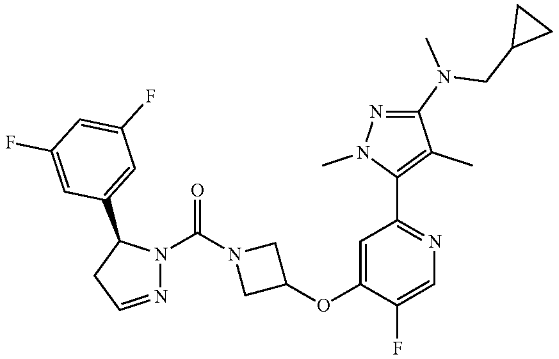 [SMILES: Cc1c(N(C)CC2CC2)nn(C)c1-c1cc(OC2CN(C(=O)N3N=CC[C@H]3c3cc(F)cc(F)c3)C2)c(F)cn1] 164 |

TABLE 3-continued
| Active Compounds 117-281: Structures |
|---|
| 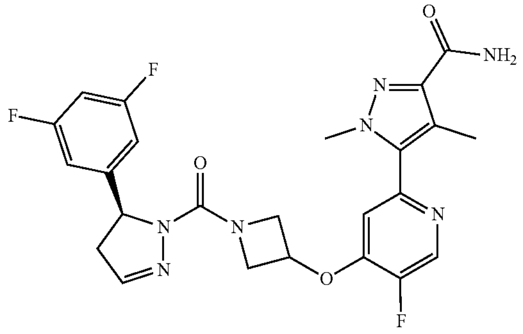 [SMILES: Cc1c(C(N)=O)nn(C)c1-c1cc(OC2CN(C(=O)N3N=CC[C@H]3c3cc(F)cc(F)c3)C2)c(F)cn1] 165 |
| 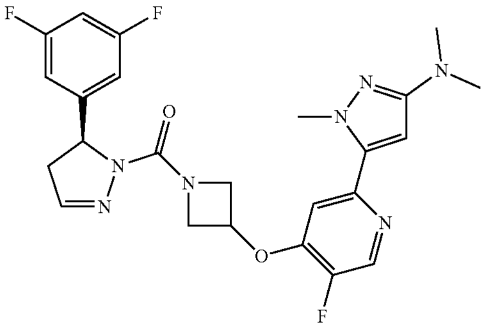 [SMILES: CN(C)c1cc(-c2cc(OC3CN(C(=O)N4N=CC[C@H]4c4cc(F)cc(F)c4)C3)c(F)cn2)n(C)n1] 166 |
| 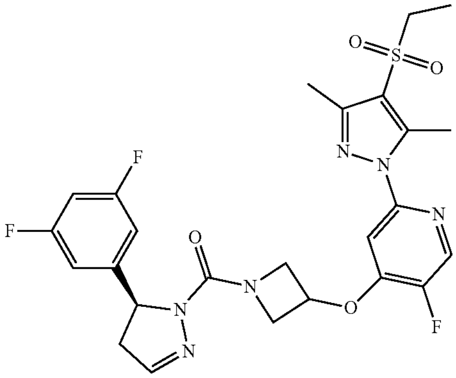 [SMILES: CCS(=O)(=O)c1c(C)nn(-c2cc(OC3CN(C(=O)N4N=CC[C@H]4c4cc(F)cc(F)c4)C3)c(F)cn2)c1C] 167 |
| 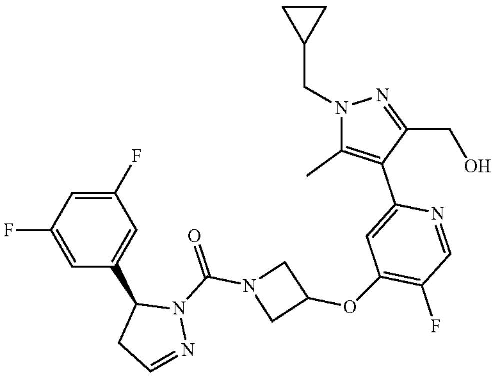 [SMILES: Cc1c(-c2cc(OC3CN(C(=O)N4N=CC[C@H]4c4cc(F)cc(F)c4)C3)c(F)cn2)c(CO)nn1CC1CC1] 168 |

TABLE 3-continued
| Active Compounds 117-281: Structures |
|---|
| 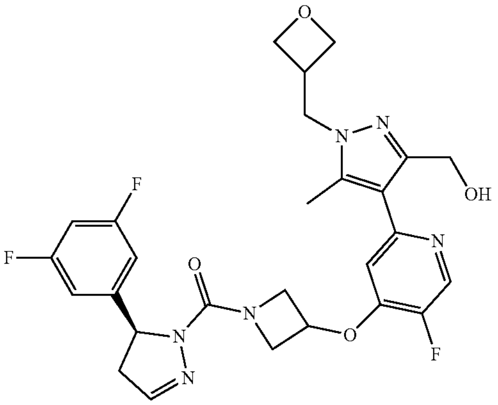 [SMILES: Cc1c(-c2cc(OC3CN(C(=O)N4N=CC[C@H]4c4cc(F)cc(F)c4)C3)c(F)cn2)c(CO)nn1CC1COC1] 169 |
| 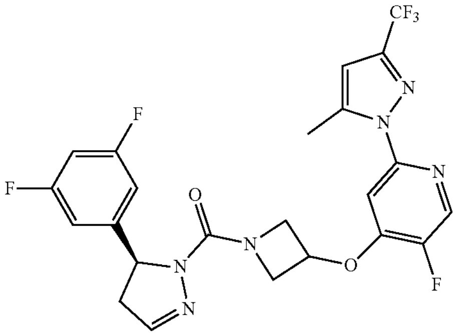 [SMILES: Cc1cc(C(F)(F)F)nn1-c1cc(OC2CN(C(=O)N3N=CC[C@H]3c3cc(F)cc(F)c3)C2)c(F)cn1] 170 |
| 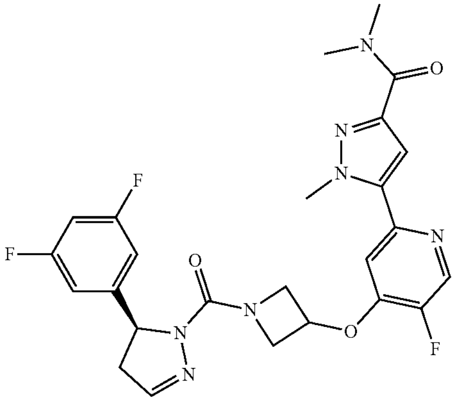 [SMILES: CN(C)C(=O)c1cc(-c2cc(OC3CN(C(=O)N4N=CC[C@H]4c4cc(F)cc(F)c4)C3)c(F)cn2)n(C)n1] 171 |
| 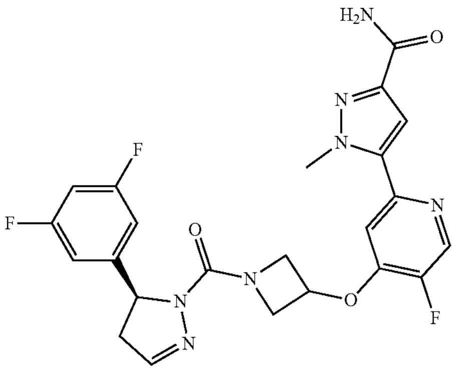 [SMILES: Cn1nc(C(N)=O)cc1-c1cc(OC2CN(C(=O)N3N=CC[C@H]3c3cc(F)cc(F)c3)C2)c(F)cn1] 172 |

TABLE 3-continued
| Active Compounds 117-281: Structures | |
|---|---|
| 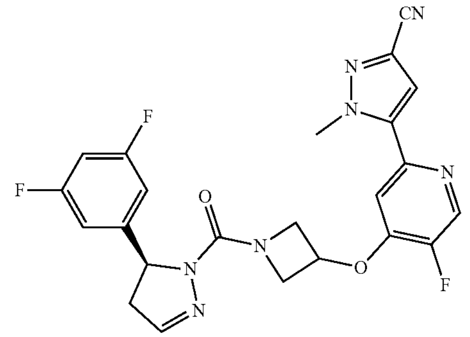 [SMILES: Cn1nc(C#N)cc1-c1cc(OC2CN(C(=O)N3N=CC[C@H]3c3cc(F)cc(F)c3)C2)c(F)cn1] | 173 |
| 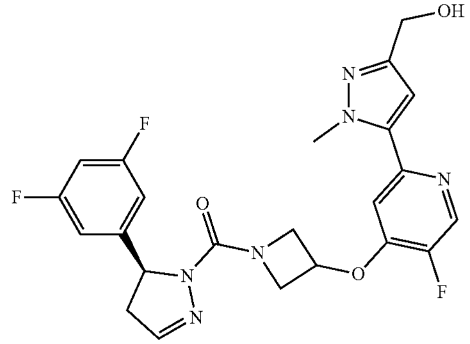 [SMILES: Cn1nc(CO)cc1-c1cc(OC2CN(C(=O)N3N=CC[C@H]3c3cc(F)cc(F)c3)C2)c(F)cn1] | 174 |
| 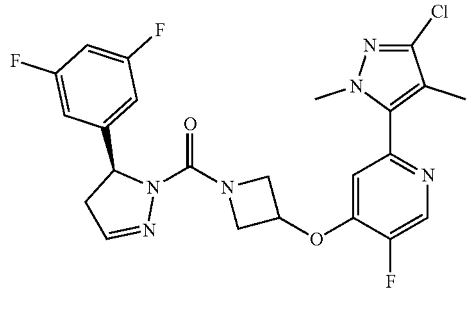 [SMILES: Cc1c(Cl)nn(C)c1-c1cc(OC2CN(C(=O)N3N=CC[C@H]3c3cc(F)cc(F)c3)C2)c(F)cn1] | 175 |
| 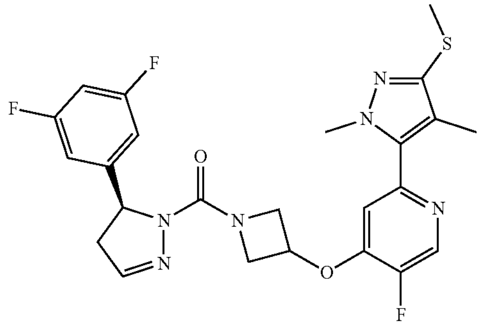 [SMILES: CSc1nn(C)c(-c2cc(OC3CN(C(=O)N4N=CC[C@H]4c4cc(F)cc(F)c4)C3)c(F)cn2)c1C] | 176 |

TABLE 3-continued
| Active Compounds 117-281: Structures |
| --- |
| 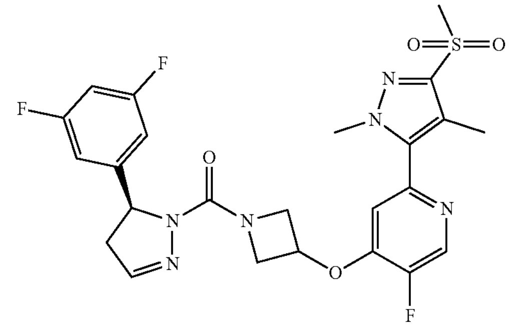 [SMILES: Cc1c(S(C)(=O)=O)nn(C)c1-c1cc(OC2CN(C(=O)N3N=CC[C@H]3c3cc(F)cc(F)c3)C2)c(F)cn1] 177 |
| 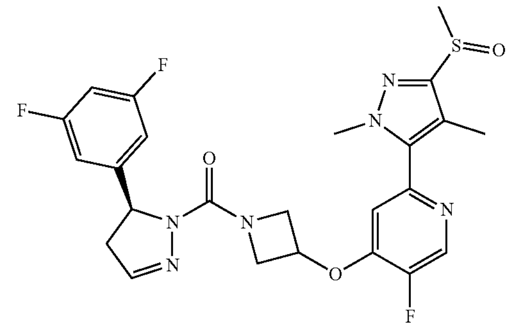 [SMILES: Cc1c(S(C)=O)nn(C)c1-c1cc(OC2CN(C(=O)N3N=CC[C@H]3c3cc(F)cc(F)c3)C2)c(F)cn1] 178 |
| 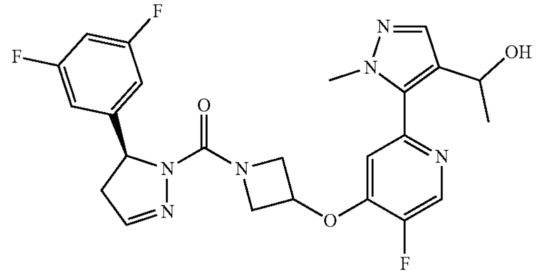 [SMILES: CC(O)c1cnn(C)c1-c1cc(OC2CN(C(=O)N3N=CC[C@H]3c3cc(F)cc(F)c3)C2)c(F)cn1] 179 |
| 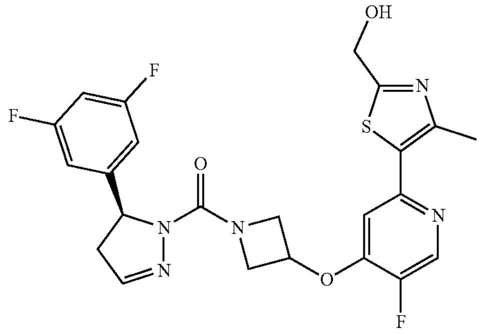 [SMILES: Cc1nc(CO)sc1-c1cc(OC2CN(C(=O)N3N=CC[C@H]3c3cc(F)cc(F)c3)C2)c(F)cn1] 180 |

TABLE 3-continued
| Active Compounds 117-281: Structures |
| --- |
| 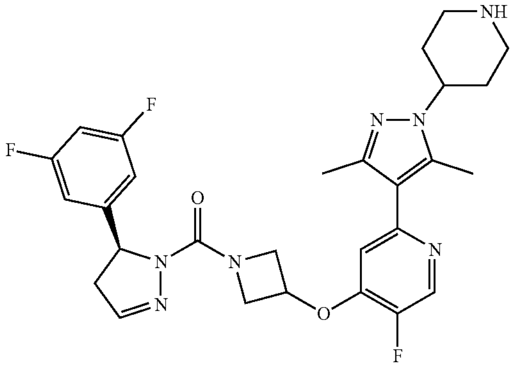 [SMILES: Cc1nn(C2CCNCC2)c(C)c1-c1cc(OC2CN(C(=O)N3N=CC[C@H]3c3cc(F)cc(F)c3)C2)c(F)cn1] 181 |
| 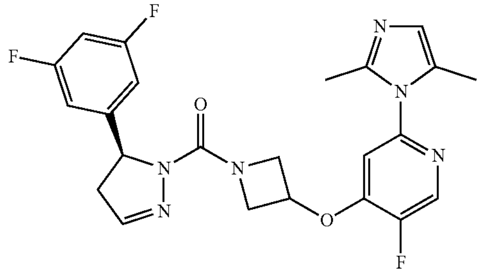 [SMILES: Cc1cnc(C)n1-c1cc(OC2CN(C(=O)N3N=CC[C@H]3c3cc(F)cc(F)c3)C2)c(F)cn1] 182 |
| 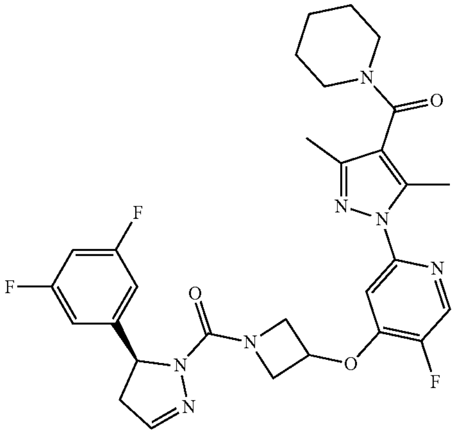 [SMILES: Cc1nn(-c2cc(OC3CN(C(=O)N4N=CC[C@H]4c4cc(F)cc(F)c4)C3)c(F)cn2)c(C)c1C(=O)N1CCCCC1] 183 |
| 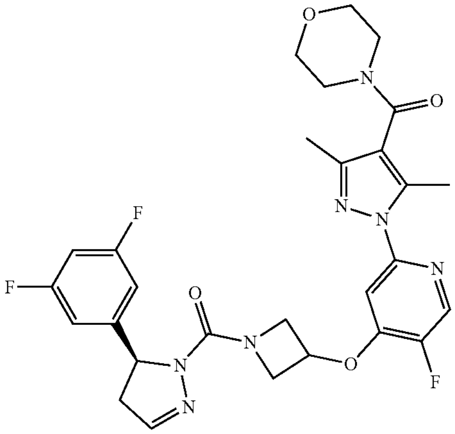 [SMILES: Cc1nn(-c2cc(OC3CN(C(=O)N4N=CC[C@H]4c4cc(F)cc(F)c4)C3)c(F)cn2)c(C)c1C(=O)N1CCOCC1] 184 |

TABLE 3-continued
Active Compounds 117-281: Structures
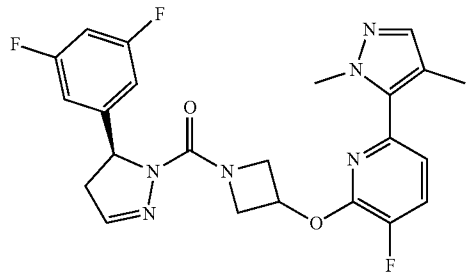
185
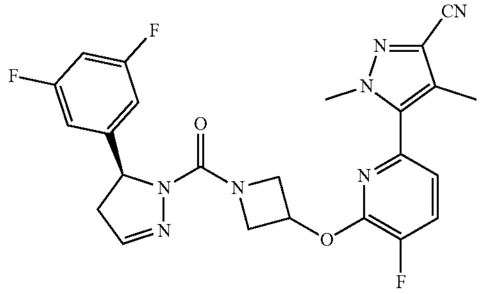 [SMILES: Cc1c(C#N)nn(C)c1-c1ccc(F)c(OC2CN(C(=O)N3N=CC[C@H]3c3cc(F)cc(F)c3)C2)n1]
186
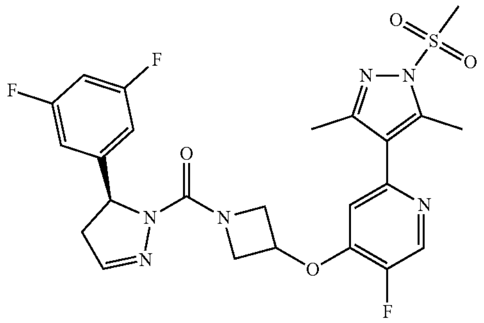 [SMILES: Cc1nn(S(C)(=O)=O)c(C)c1-c1cc(OC2CN(C(=O)N3N=CC[C@H]3c3cc(F)cc(F)c3)C2)c(F)cn1]
187
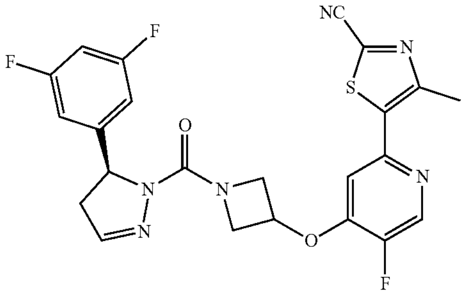
188
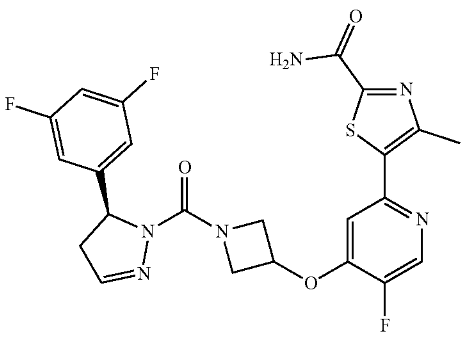 [SMILES: Cc1nc(C(N)=O)sc1-c1cc(OC2CN(C(=O)N3N=CC[C@H]3c3cc(F)cc(F)c3)C2)c(F)cn1]
189

TABLE 3-continued
| Active Compounds 117-281: Structures |
|---|
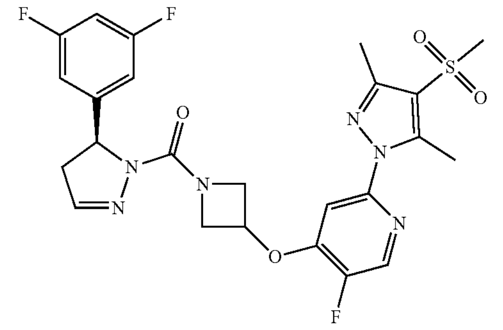 [SMILES: Cc1nn(-c2cc(OC3CN(C(=O)N4N=CC[C@H]4c4cc(F)cc(F)c4)C3)c(F)cn2)c(C)c1S(C)(=O)=O]
190
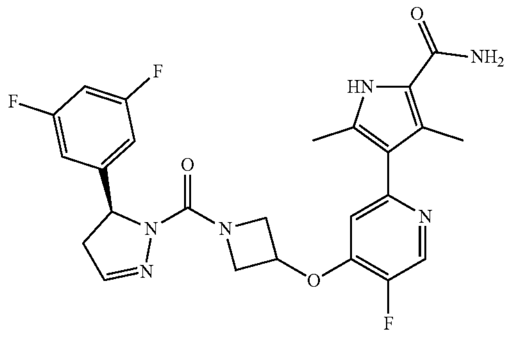 [SMILES: Cc1[nH]c(C(N)=O)c(C)c1-c1cc(OC2CN(C(=O)N3N=CC[C@H]3c3cc(F)cc(F)c3)C2)c(F)cn1]
191
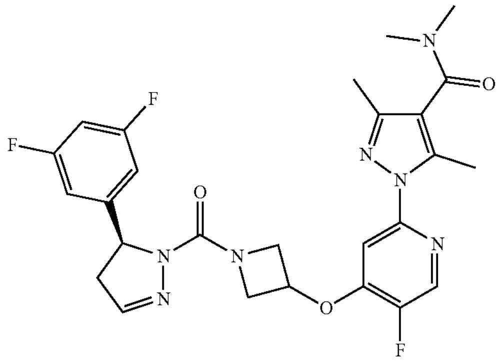 [SMILES: Cc1nn(-c2cc(OC3CN(C(=O)N4N=CC[C@H]4c4cc(F)cc(F)c4)C3)c(F)cn2)c(C)c1C(=O)N(C)C]
192
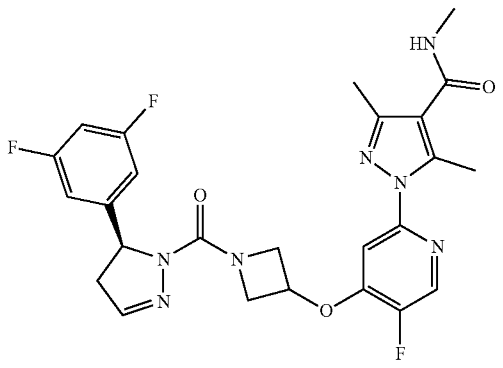 [SMILES: CNC(=O)c1c(C)nn(-c2cc(OC3CN(C(=O)N4N=CC[C@H]4c4cc(F)cc(F)c4)C3)c(F)cn2)c1C]
193

TABLE 3-continued
| Active Compounds 117-281: Structures |
| --- |
| 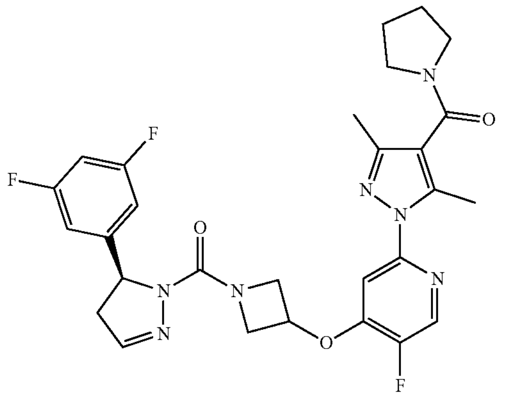 [SMILES: Cc1nn(-c2cc(OC3CN(C(=O)N4N=CC[C@H]4c4cc(F)cc(F)c4)C3)c(F)cn2)c(C)c1C(=O)N1CCCC1] 194 |
| 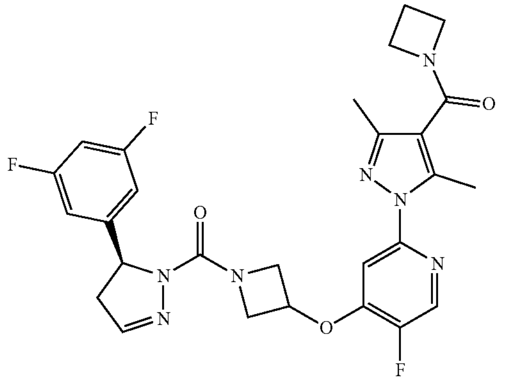 [SMILES: Cc1nn(-c2cc(OC3CN(C(=O)N4N=CC[C@H]4c4cc(F)cc(F)c4)C3)c(F)cn2)c(C)c1C(=O)N1CCC1] 195 |
| 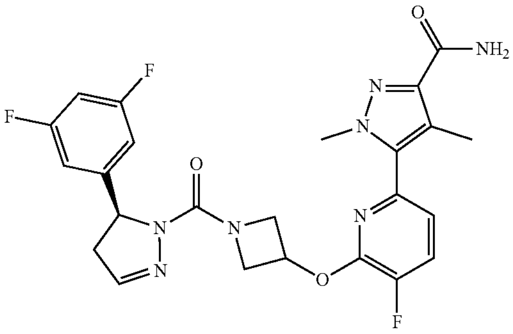 [SMILES: Cc1c(C(N)=O)nn(C)c1-c1ccc(F)c(OC2CN(C(=O)N3N=CC[C@H]3c3cc(F)cc(F)c3)C2)n1] 196 |
| 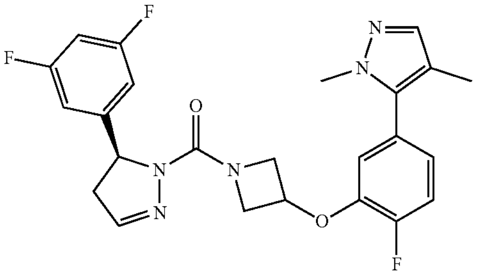 [SMILES: Cc1cnn(C)c1-c1ccc(F)c(OC2CN(C(=O)N3N=CC[C@H]3c3cc(F)cc(F)c3)C2)c1] 197 |

TABLE 3-continued
| Active Compounds 117-281: Structures |
| --- |
| 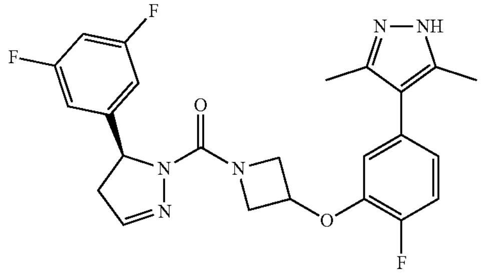 [SMILES: Cc1n[nH]c(C)c1-c1ccc(F)c(OC2CN(C(=O)N3N=CC[C@H]3c3cc(F)cc(F)c3)C2)c1] 198 |
| 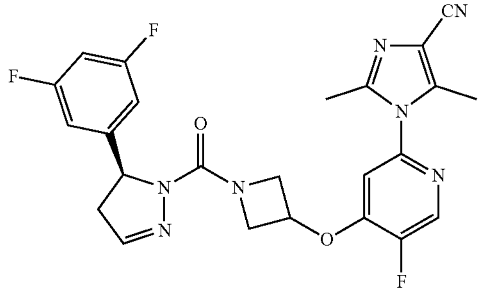 [SMILES: Cc1nc(C#N)c(C)n1-c1cc(OC2CN(C(=O)N3N=CC[C@H]3c3cc(F)cc(F)c3)C2)c(F)cn1] 199 |
| 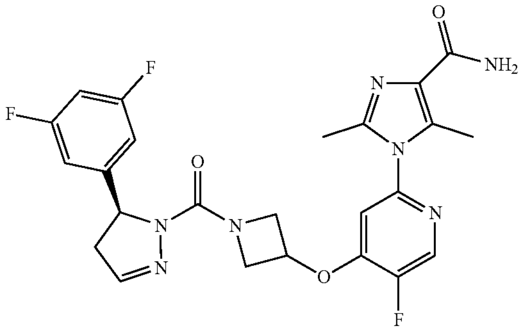 [SMILES: Cc1nc(C(N)=O)c(C)n1-c1cc(OC2CN(C(=O)N3N=CC[C@H]3c3cc(F)cc(F)c3)C2)c(F)cn1] 200 |
| 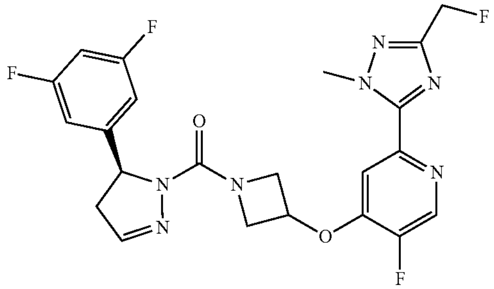 [SMILES: Cn1nc(CF)nc1-c1cc(OC2CN(C(=O)N3N=CC[C@H]3c3cc(F)cc(F)c3)C2)c(F)cn1] 201 |
| 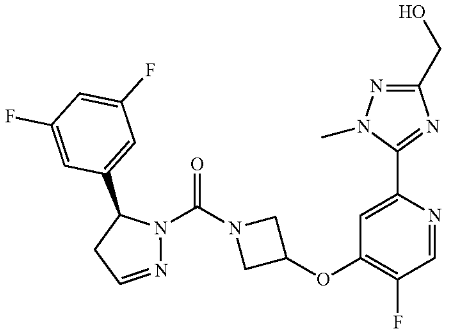 [SMILES: Cn1nc(CO)nc1-c1cc(OC2CN(C(=O)N3N=CC[C@H]3c3cc(F)cc(F)c3)C2)c(F)cn1] 202 |

TABLE 3-continued
| Active Compounds 117-281: Structures | |
|---|---|
| 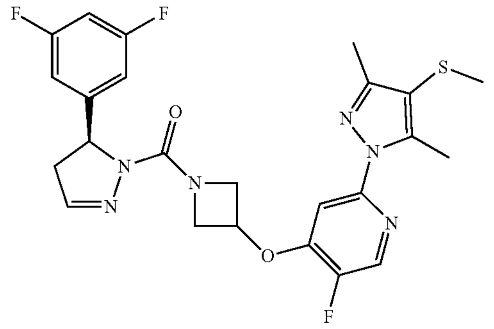 [SMILES: CSc1c(C)nn(-c2cc(OC3CN(C(=O)N4N=CC[C@H]4c4cc(F)cc(F)c4)C3)c(F)cn2)c1C] | 203 |
| 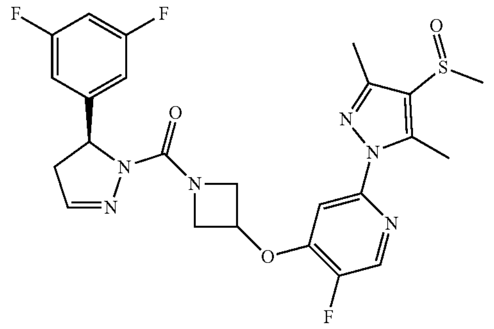 [SMILES: Cc1nn(-c2cc(OC3CN(C(=O)N4N=CC[C@H]4c4cc(F)cc(F)c4)C3)c(F)cn2)c(C)c1S(C)=O] | 204 |
| 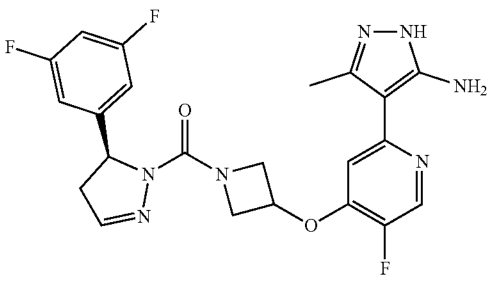 [SMILES: Cc1n[nH]c(N)c1-c1cc(OC2CN(C(=O)N3N=CC[C@H]3c3cc(F)cc(F)c3)C2)c(F)cn1] | 205 |
| 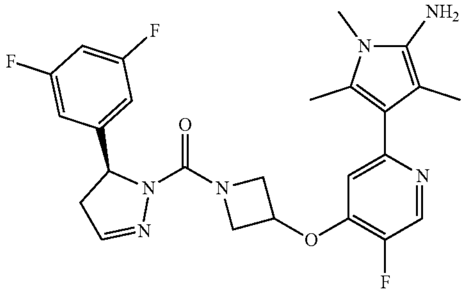 [SMILES: Cc1c(-c2cc(OC3CN(C(=O)N4N=CC[C@H]4c4cc(F)cc(F)c4)C3)c(F)cn2)c(C)n(C)c1N] | 206 |
| 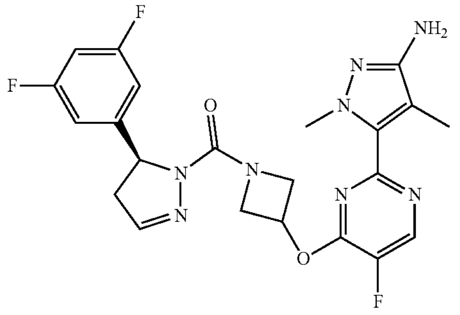 [SMILES: Cc1c(N)nn(C)c1-c1ncc(F)c(OC2CN(C(=O)N3N=CC[C@H]3c3cc(F)cc(F)c3)C2)n1] | 207 |

TABLE 3-continued
| Active Compounds 117-281: Structures |
| --- |
| 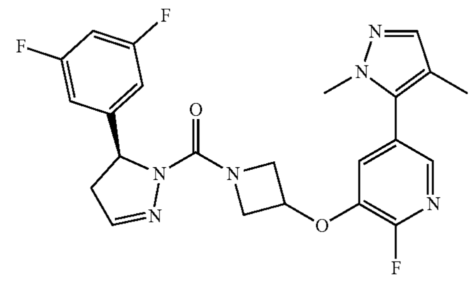 [SMILES: Cc1cnn(C)c1-c1cnc(F)c(OC2CN(C(=O)N3N=CC[C@H]3c3cc(F)cc(F)c3)C2)c1] 208 |
| 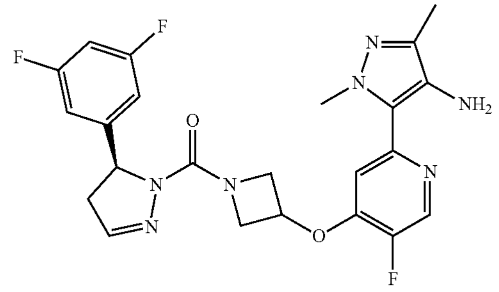 [SMILES: Cc1nn(C)c(-c2cc(OC3CN(C(=O)N4N=CC[C@H]4c4cc(F)cc(F)c4)C3)c(F)cn2)c1N] 209 |
| 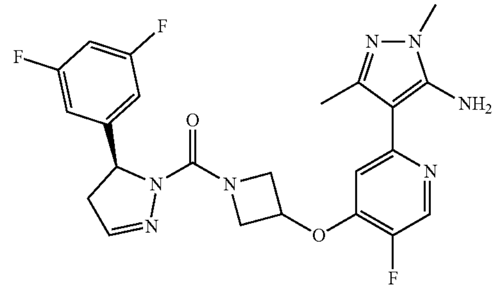 [SMILES: Cc1nn(C)c(N)c1-c1cc(OC2CN(C(=O)N3N=CC[C@H]3c3cc(F)cc(F)c3)C2)c(F)cn1] 210 |
| 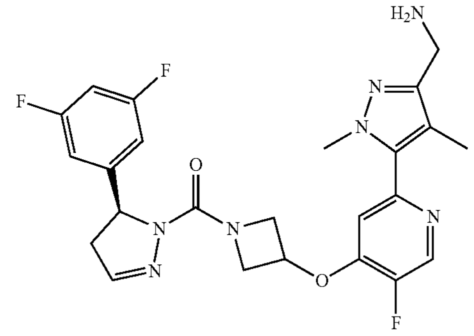 [SMILES: Cc1c(CN)nn(C)c1-c1cc(OC2CN(C(=O)N3N=CC[C@H]3c3cc(F)cc(F)c3)C2)c(F)cn1] 211 |
| 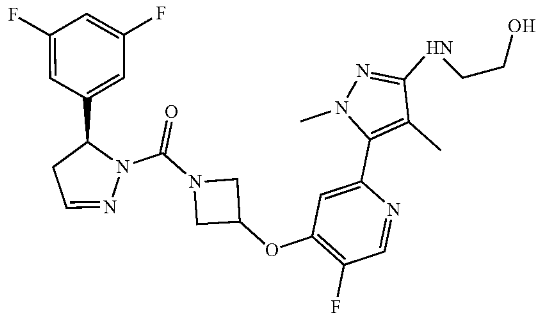 [SMILES: Cc1c(NCCO)nn(C)c1-c1cc(OC2CN(C(=O)N3N=CC[C@H]3c3cc(F)cc(F)c3)C2)c(F)cn1] 212 |

TABLE 3-continued
| Active Compounds 117-281: Structures |
|---|
| 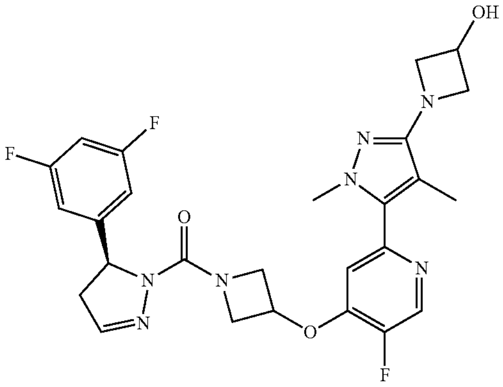 [SMILES: Cc1c(N2CC(O)C2)nn(C)c1-c1cc(OC2CN(C(=O)N3N=CC[C@H]3c3cc(F)cc(F)c3)C2)c(F)cn1] 213 |
| 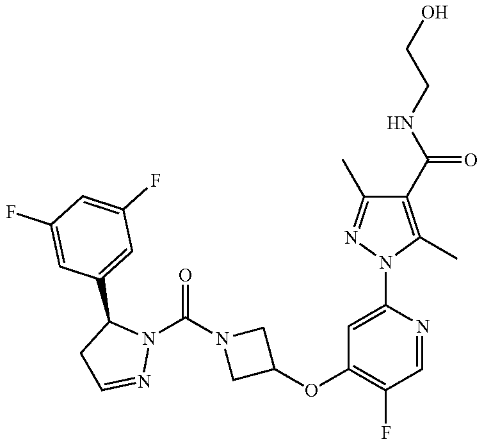 [SMILES: Cc1nn(-c2cc(OC3CN(C(=O)N4N=CC[C@H]4c4cc(F)cc(F)c4)C3)c(F)cn2)c(C)c1C(=O)NCCO] 214 |
| 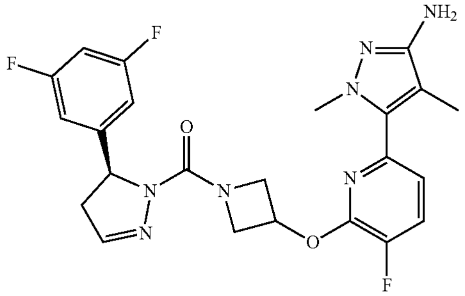 [SMILES: Cc1c(N)nn(C)c1-c1ccc(F)c(OC2CN(C(=O)N3N=CC[C@H]3c3cc(F)cc(F)c3)C2)n1] 215 |
| 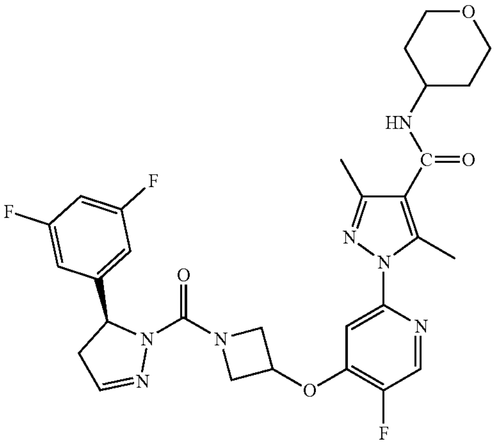 [SMILES: Cc1nn(-c2cc(OC3CN(C(=O)N4N=CC[C@H]4c4cc(F)cc(F)c4)C3)c(F)cn2)c(C)c1C(=O)NC1CCOCC1] 216 |

TABLE 3-continued
| Active Compounds 117-281: Structures | |
|---|---|
| 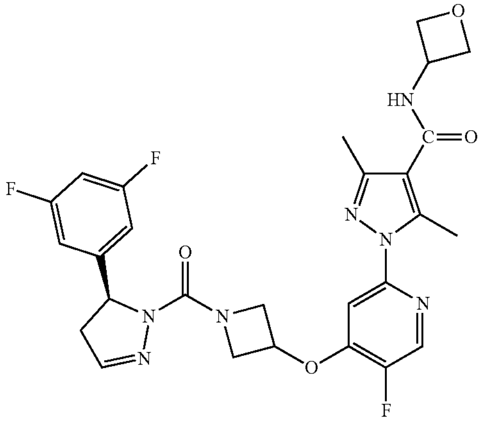 [SMILES: Cc1nn(-c2cc(OC3CN(C(=O)N4N=CC[C@H]4c4cc(F)cc(F)c4)C3)c(F)cn2)c(C)c1C(=O)NC1COC1] | 217 |
| 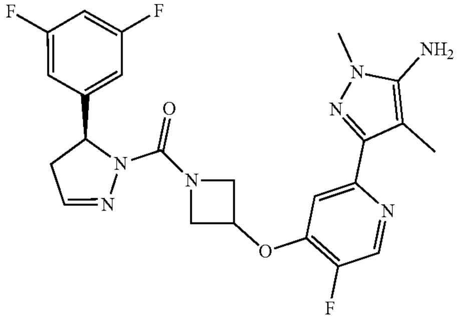 [SMILES: Cc1c(-c2cc(OC3CN(C(=O)N4N=CC[C@H]4c4cc(F)cc(F)c4)C3)c(F)cn2)nn(C)c1N] | 218 |
| 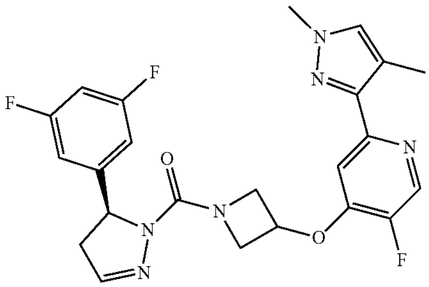 [SMILES: Cc1cn(C)nc1-c1cc(OC2CN(C(=O)N3N=CC[C@H]3c3cc(F)cc(F)c3)C2)c(F)cn1] | 219 |
| 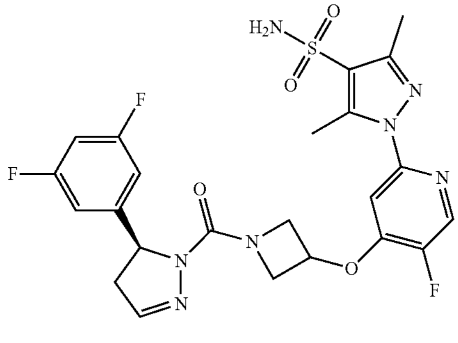 [SMILES: Cc1nn(-c2cc(OC3CN(C(=O)N4N=CC[C@H]4c4cc(F)cc(F)c4)C3)c(F)cn2)c(C)c1S(N)(=O)=O] | 220 |

TABLE 3-continued
| Active Compounds 117-281: Structures |
| --- |
| 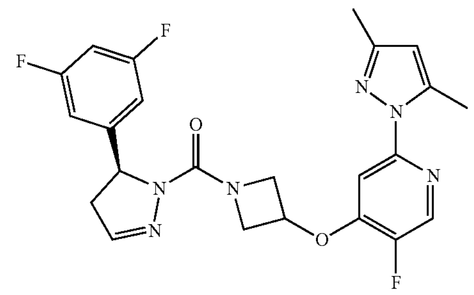 [SMILES: Cc1cc(C)n(-c2cc(OC3CN(C(=O)N4N=CC[C@H]4c4cc(F)cc(F)c4)C3)c(F)cn2)n1] 221 |
| 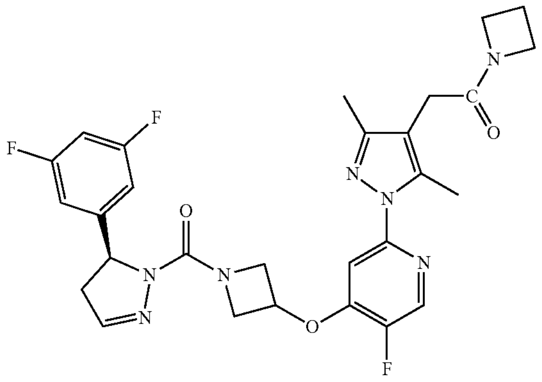 [SMILES: Cc1nn(-c2cc(OC3CN(C(=O)N4N=CC[C@H]4c4cc(F)cc(F)c4)C3)c(F)cn2)c(C)c1CC(=O)N1CCC1] 222 |
| 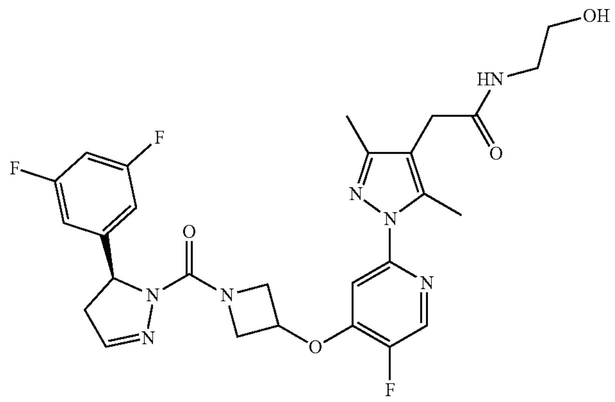 [SMILES: Cc1nn(-c2cc(OC3CN(C(=O)N4N=CC[C@H]4c4cc(F)cc(F)c4)C3)c(F)cn2)c(C)c1CC(=O)NCCO] 223 |
| 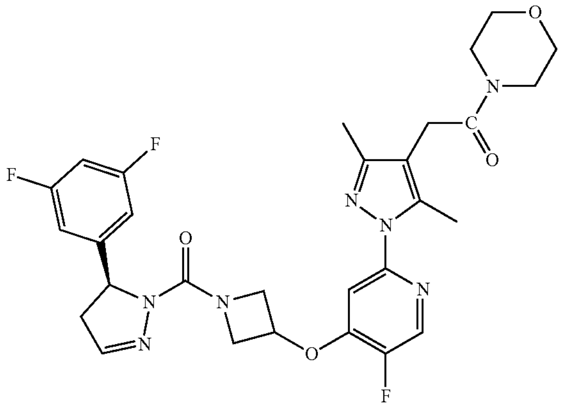 [SMILES: Cc1nn(-c2cc(OC3CN(C(=O)N4N=CC[C@H]4c4cc(F)cc(F)c4)C3)c(F)cn2)c(C)c1CC(=O)N1CCOCC1] 224 |

TABLE 3-continued
| Active Compounds 117-281: Structures |
| --- |
| 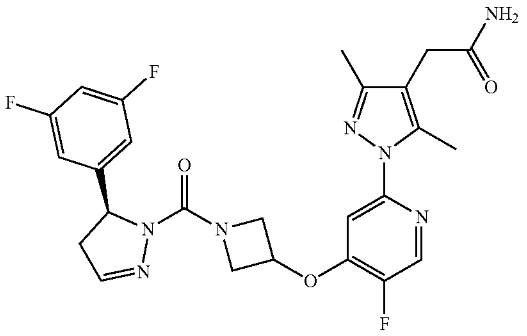 [SMILES: Cc1nn(-c2cc(OC3CN(C(=O)N4N=CC[C@H]4c4cc(F)cc(F)c4)C3)c(F)cn2)c(C)c1CC(N)=O] 225 |
| 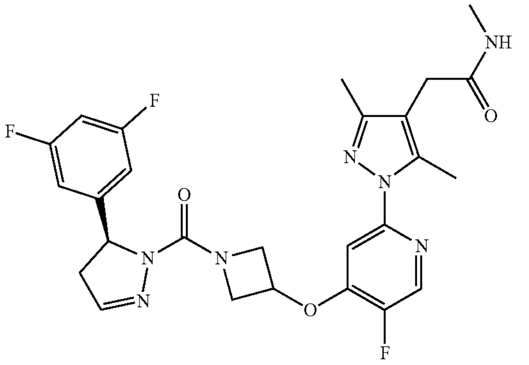 [SMILES: CNC(=O)Cc1c(C)nn(-c2cc(OC3CN(C(=O)N4N=CC[C@H]4c4cc(F)cc(F)c4)C3)c(F)cn2)c1C] 226 |
| 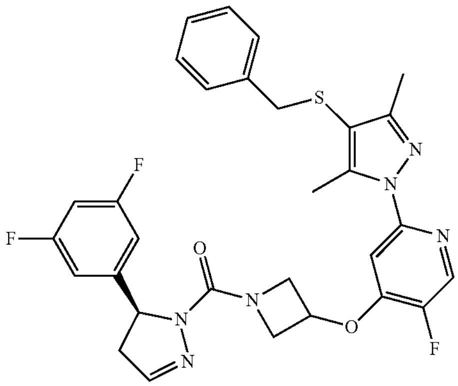 [SMILES: Cc1nn(-c2cc(OC3CN(C(=O)N4N=CC[C@H]4c4cc(F)cc(F)c4)C3)c(F)cn2)c(C)c1SCc1ccccc1] 227 |
| 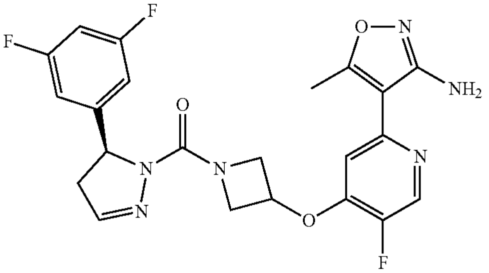 [SMILES: Cc1onc(N)c1-c1cc(OC2CN(C(=O)N3N=CC[C@H]3c3cc(F)cc(F)c3)C2)c(F)cn1] 228 |

TABLE 3-continued
| Active Compounds 117-281: Structures |
| --- |
| 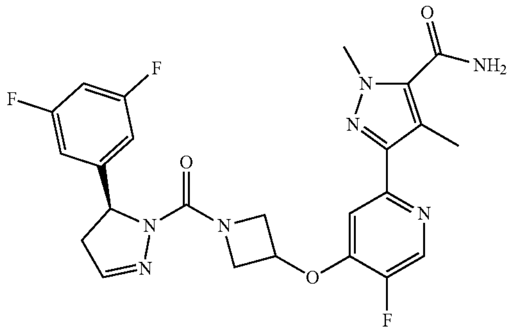 [SMILES: Cc1c(-c2cc(OC3CN(C(=O)N4N=CC[C@H]4c4cc(F)cc(F)c4)C3)c(F)cn2)nn(C)c1C(N)=O] 229 |
| 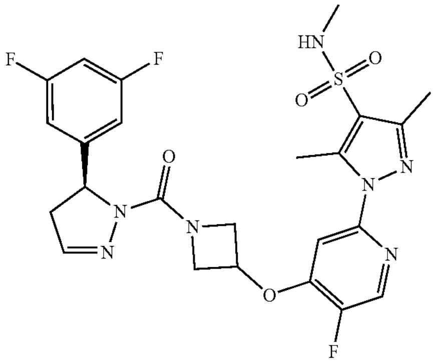 [SMILES: CNS(=O)(=O)c1c(C)nn(-c2cc(OC3CN(C(=O)N4N=CC[C@H]4c4cc(F)cc(F)c4)C3)c(F)cn2)c1C] 230 |
| 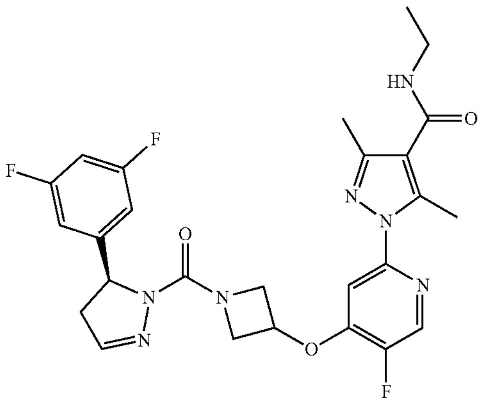 [SMILES: CCNC(=O)c1c(C)nn(-c2cc(OC3CN(C(=O)N4N=CC[C@H]4c4cc(F)cc(F)c4)C3)c(F)cn2)c1C] 231 |
| 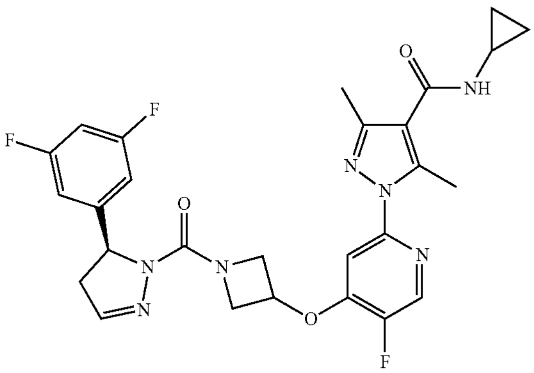 [SMILES: Cc1nn(-c2cc(OC3CN(C(=O)N4N=CC[C@H]4c4cc(F)cc(F)c4)C3)c(F)cn2)c(C)c1C(=O)NC1CC1] 232 |

TABLE 3-continued
Active Compounds 117-281: Structures
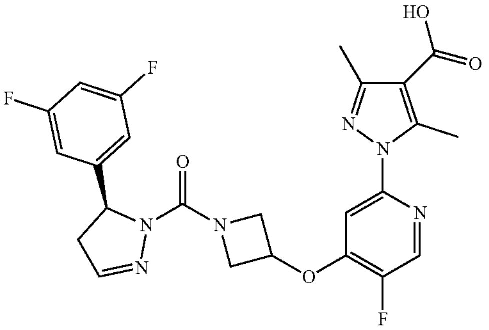 [SMILES: Cc1nn(-c2cc(OC3CN(C(=O)N4N=CC[C@H]4c4cc(F)cc(F)c4)C3)c(F)cn2)c(C)c1C(=O)O]
233
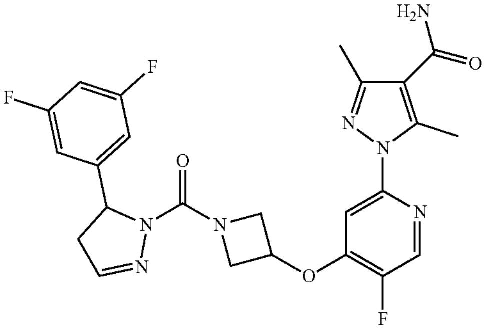 [SMILES: Cc1nn(-c2cc(OC3CN(C(=O)N4N=CCC4c4cc(F)cc(F)c4)C3)c(F)cn2)c(C)c1C(N)=O]
234
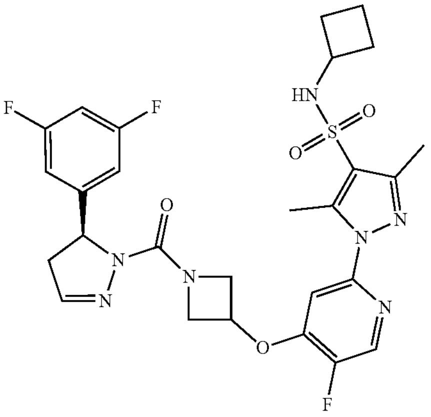 [SMILES: Cc1nn(-c2cc(OC3CN(C(=O)N4N=CC[C@H]4c4cc(F)cc(F)c4)C3)c(F)cn2)c(C)c1S(=O)(=O)NC1CCC1]
235
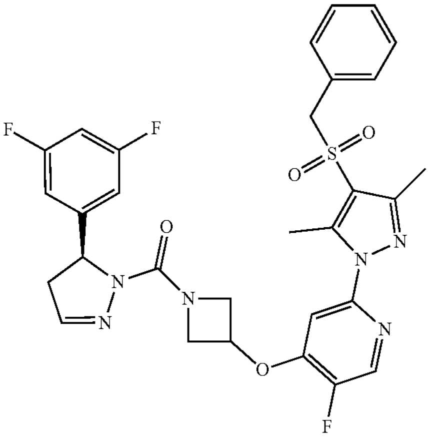 [SMILES: Cc1nn(-c2cc(OC3CN(C(=O)N4N=CC[C@H]4c4cc(F)cc(F)c4)C3)c(F)cn2)c(C)c1S(=O)(=O)Cc1ccccc1]
236

TABLE 3-continued
| Active Compounds 117-281: Structures |
| --- |
| 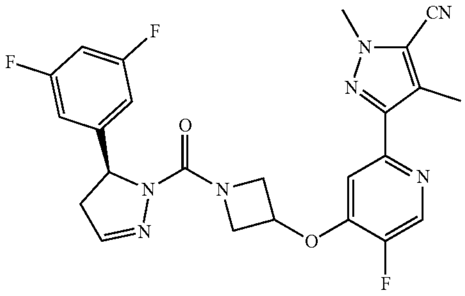 [SMILES: Cc1c(-c2cc(OC3CN(C(=O)N4N=CC[C@H]4c4cc(F)cc(F)c4)C3)c(F)cn2)nn(C)c1C#N] 237 |
| 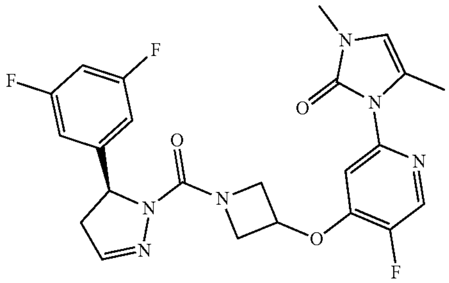 [SMILES: Cc1cn(C)c(=O)n1-c1cc(OC2CN(C(=O)N3N=CC[C@H]3c3cc(F)cc(F)c3)C2)c(F)cn1] 238 |
| 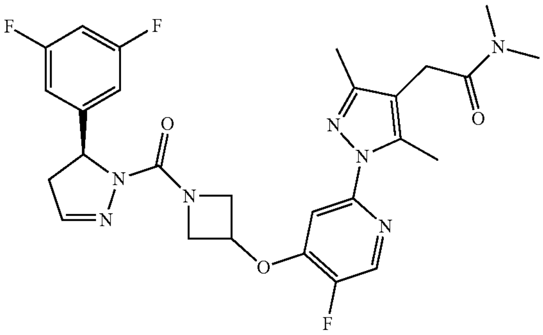 [SMILES: Cc1nn(-c2cc(OC3CN(C(=O)N4N=CC[C@H]4c4cc(F)cc(F)c4)C3)c(F)cn2)c(C)c1CC(=O)N(C)C] 239 |
| 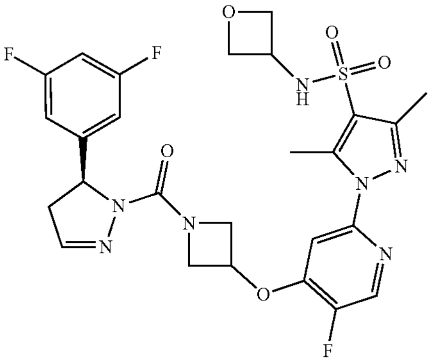 [SMILES: Cc1nn(-c2cc(OC3CN(C(=O)N4N=CC[C@H]4c4cc(F)cc(F)c4)C3)c(F)cn2)c(C)c1S(=O)(=O)NC1COC1] 240 |

TABLE 3-continued
| Active Compounds 117-281: Structures |
| --- |
| 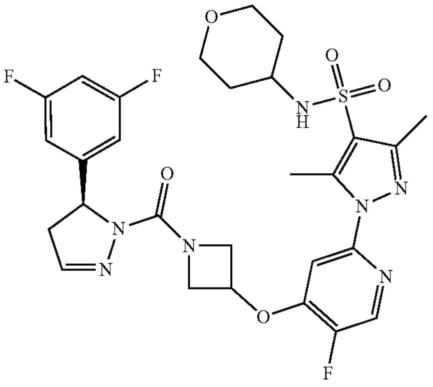 241 |
| 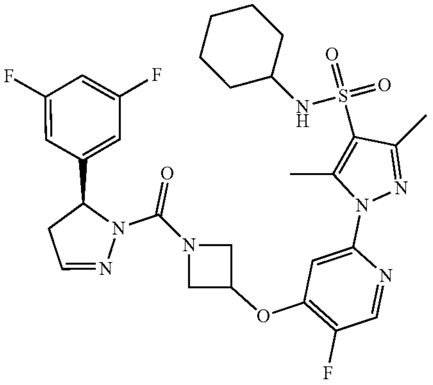 [SMILES: Cc1nn(-c2cc(OC3CN(C(=O)N4N=CC[C@H]4c4cc(F)cc(F)c4)C3)c(F)cn2)c(C)c1S(=O)(=O)NC1CCOCC1] 242 |
| 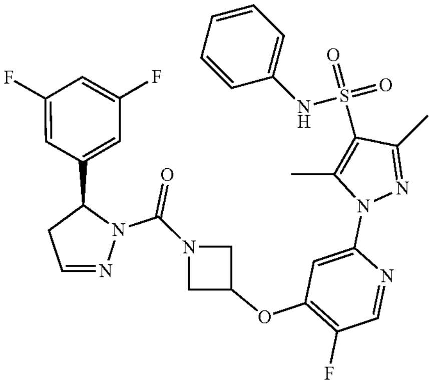 [SMILES: Cc1nn(-c2cc(OC3CN(C(=O)N4N=CC[C@H]4c4cc(F)cc(F)c4)C3)c(F)cn2)c(C)c1S(=O)(=O)Nc1ccccc1] 243 |
| 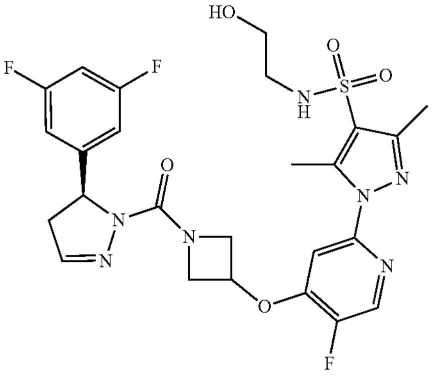 [SMILES: Cc1nn(-c2cc(OC3CN(C(=O)N4N=CC[C@H]4c4cc(F)cc(F)c4)C3)c(F)cn2)c(C)c1S(=O)(=O)NCCO] 244 |

TABLE 3-continued
| Active Compounds 117-281: Structures |
| --- |
| 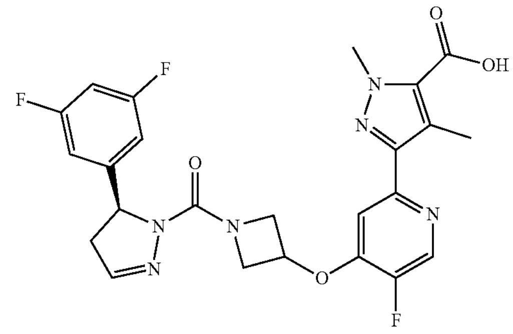 [SMILES: Cc1c(-c2cc(OC3CN(C(=O)N4N=CC[C@H]4c4cc(F)cc(F)c4)C3)c(F)cn2)nn(C)c1C(=O)O] 245 |
| 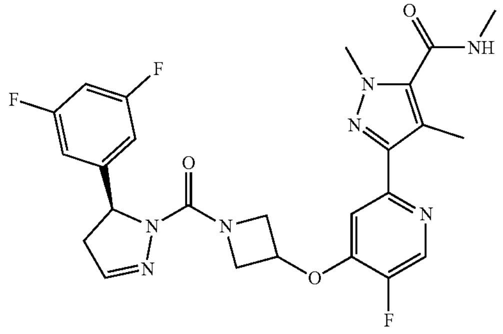 [SMILES: CNC(=O)c1c(C)c(-c2cc(OC3CN(C(=O)N4N=CC[C@H]4c4cc(F)cc(F)c4)C3)c(F)cn2)nn1C] 246 |
| 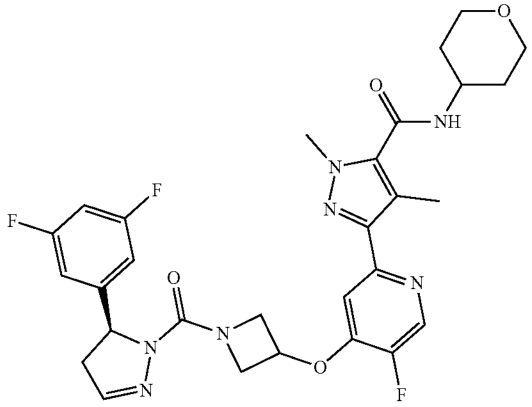 [SMILES: Cc1c(-c2cc(OC3CN(C(=O)N4N=CC[C@H]4c4cc(F)cc(F)c4)C3)c(F)cn2)nn(C)c1C(=O)NC1CCOCC1] 247 |
| 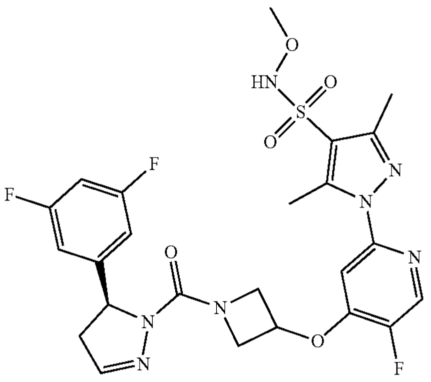 [SMILES: CONS(=O)(=O)c1c(C)nn(-c2cc(OC3CN(C(=O)N4N=CC[C@H]4c4cc(F)cc(F)c4)C3)c(F)cn2)c1C] 248 |

TABLE 3-continued
| Active Compounds 117-281: Structures |
| --- |
| 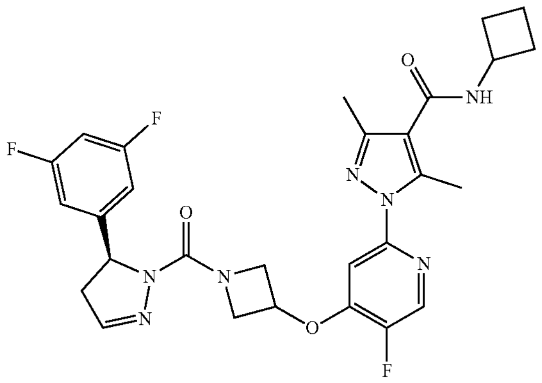 [SMILES: Cc1nn(-c2cc(OC3CN(C(=O)N4N=CC[C@H]4c4cc(F)cc(F)c4)C3)c(F)cn2)c(C)c1C(=O)NC1CCC1] 249 |
| 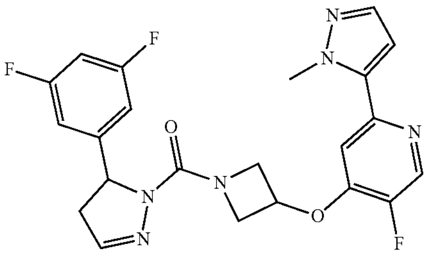 [SMILES: Cn1nccc1-c1cc(OC2CN(C(=O)N3N=CCC3c3cc(F)cc(F)c3)C2)c(F)cn1] 250 |
| 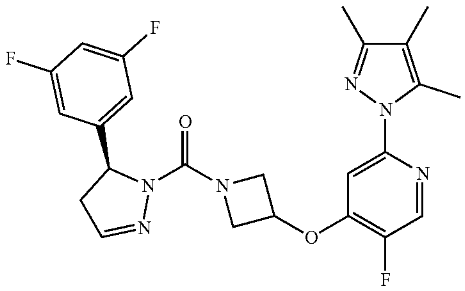 [SMILES: Cc1nn(-c2cc(OC3CN(C(=O)N4N=CC[C@H]4c4cc(F)cc(F)c4)C3)c(F)cn2)c(C)c1C] 251 |
| 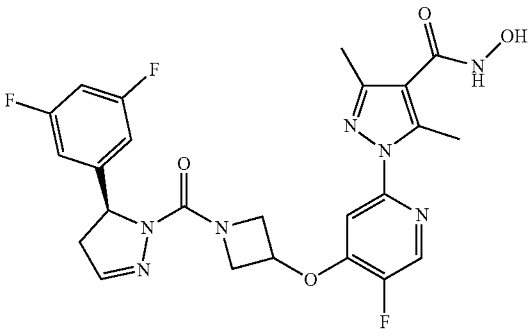 [SMILES: Cc1nn(-c2cc(OC3CN(C(=O)N4N=CC[C@H]4c4cc(F)cc(F)c4)C3)c(F)cn2)c(C)c1C(=O)NO] 252 |

TABLE 3-continued
| Active Compounds 117-281: Structures |
| --- |
| 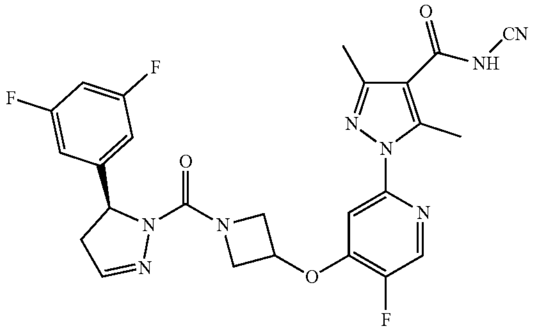 [SMILES: Cc1nn(-c2cc(OC3CN(C(=O)N4N=CC[C@H]4c4cc(F)cc(F)c4)C3)c(F)cn2)c(C)c1C(=O)NC#N] 253 |
| 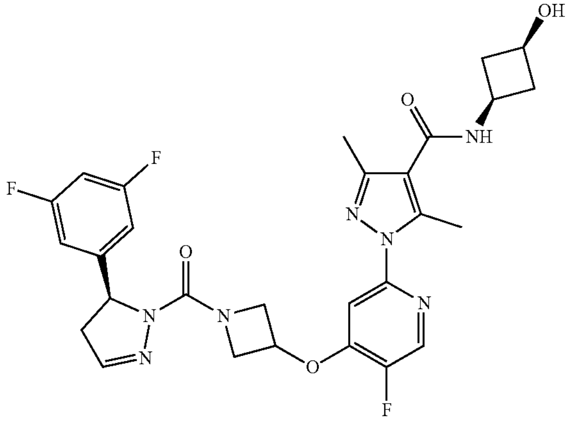 [SMILES: Cc1nn(-c2cc(OC3CN(C(=O)N4N=CC[C@H]4c4cc(F)cc(F)c4)C3)c(F)cn2)c(C)c1C(=O)N[C@H]1C[C@@H](O)C1] 254 |
| 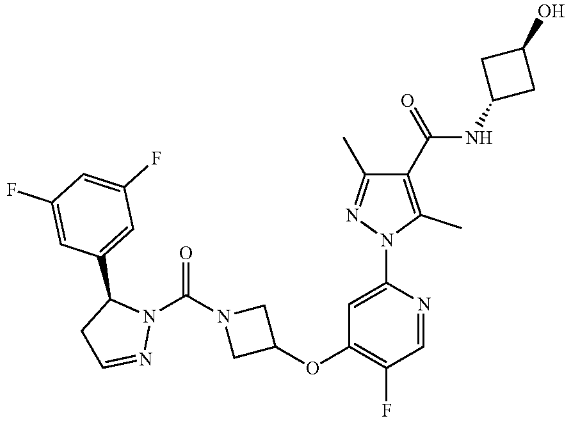 [SMILES: Cc1nn(-c2cc(OC3CN(C(=O)N4N=CC[C@H]4c4cc(F)cc(F)c4)C3)c(F)cn2)c(C)c1C(=O)N[C@H]1C[C@H](O)C1] 255 |
| 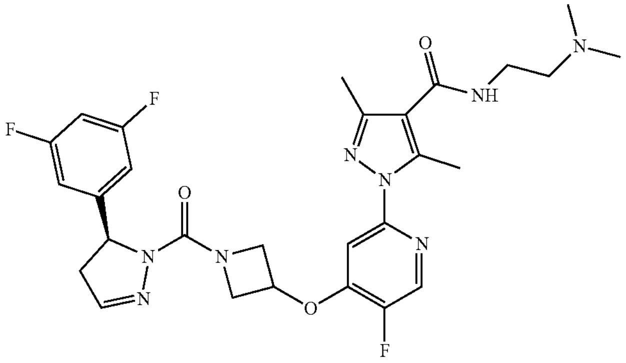 [SMILES: Cc1nn(-c2cc(OC3CN(C(=O)N4N=CC[C@H]4c4cc(F)cc(F)c4)C3)c(F)cn2)c(C)c1C(=O)NCCN(C)C] 256 |

TABLE 3-continued
| Active Compounds 117-281: Structures |
| --- |
| 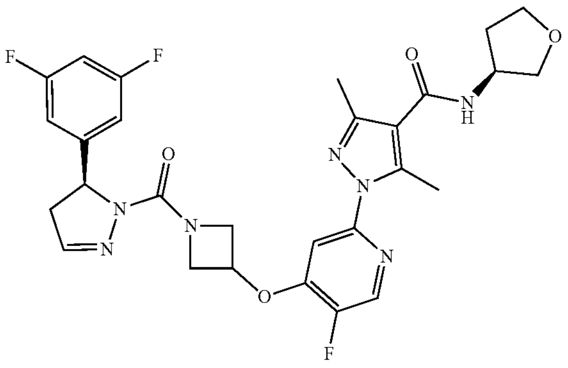 [SMILES: Cc1nn(-c2cc(OC3CN(C(=O)N4N=CC[C@H]4c4cc(F)cc(F)c4)C3)c(F)cn2)c(C)c1C(=O)N[C@H]1CCOC1] 257 |
| 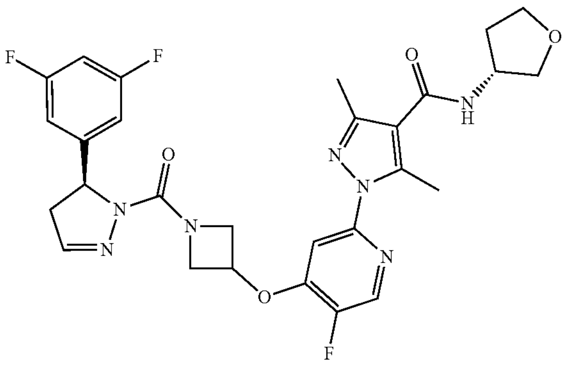 [SMILES: Cc1nn(-c2cc(OC3CN(C(=O)N4N=CC[C@H]4c4cc(F)cc(F)c4)C3)c(F)cn2)c(C)c1C(=O)N[C@@H]1CCOC1] 258 |
| 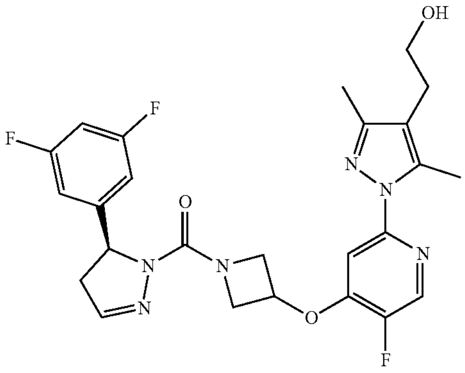 [SMILES: Cc1nn(-c2cc(OC3CN(C(=O)N4N=CC[C@H]4c4cc(F)cc(F)c4)C3)c(F)cn2)c(C)c1CCO] 259 |
| 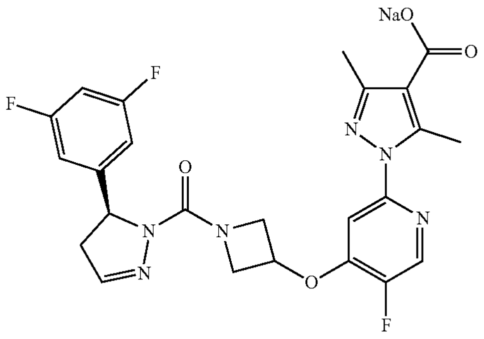 260 |

TABLE 3-continued
| Active Compounds 117-281: Structures | |
| --- | --- |
| 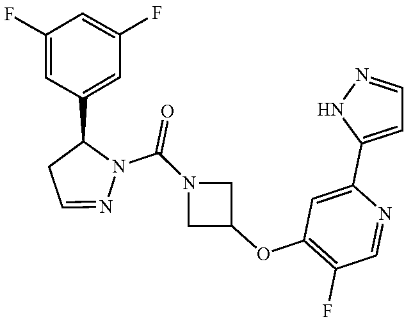 [SMILES: O=C(N1CC(Oc2cc(-c3ccn[nH]3)ncc2F)C1)N1N=CC[C@H]1c1cc(F)cc(F)c1] | 261 |
| 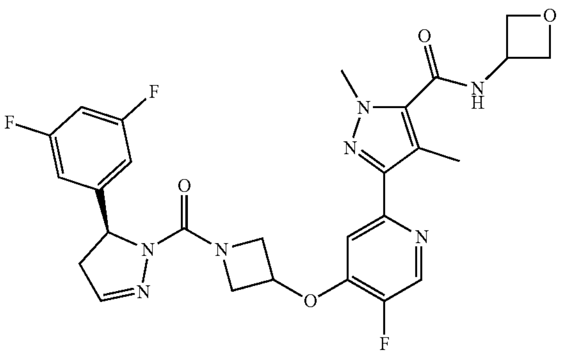 [SMILES: Cc1c(-c2cc(OC3CN(C(=O)N4N=CC[C@H]4c4cc(F)cc(F)c4)C3)c(F)cn2)nn(C)c1C(=O)NC1COC1] | 262 |
| 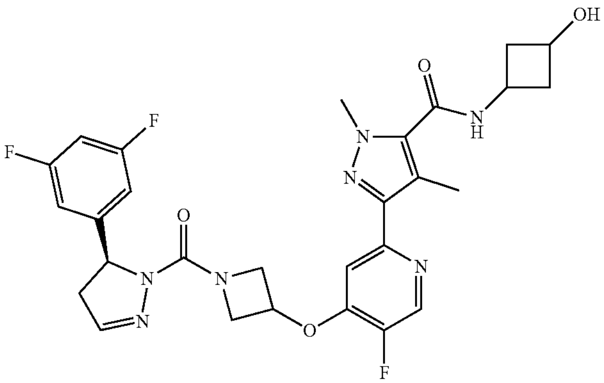 [SMILES: Cc1c(-c2cc(OC3CN(C(=O)N4N=CC[C@H]4c4cc(F)cc(F)c4)C3)c(F)cn2)nn(C)c1C(=O)NC1CC(O)C1] | 263 |
| 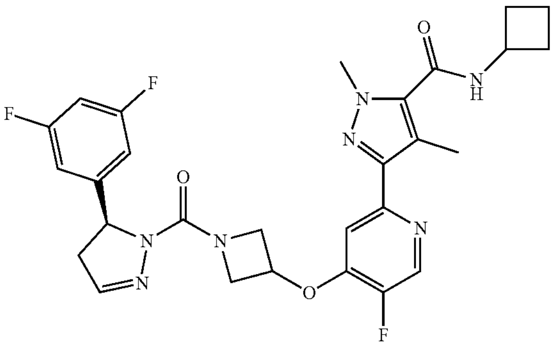 [SMILES: Cc1c(-c2cc(OC3CN(C(=O)N4N=CC[C@H]4c4cc(F)cc(F)c4)C3)c(F)cn2)nn(C)c1C(=O)NC1CCC1] | 264 |

TABLE 3-continued
Active Compounds 117-281: Structures
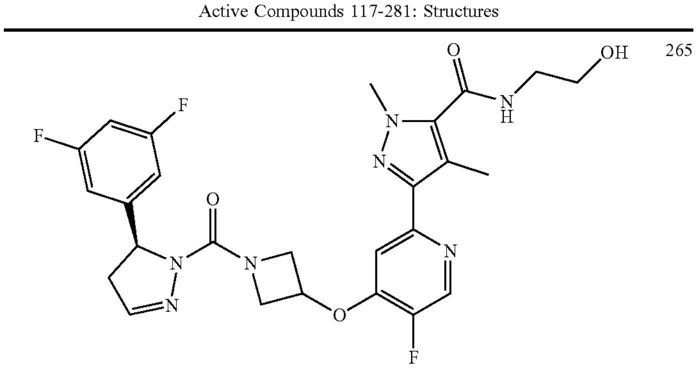
265
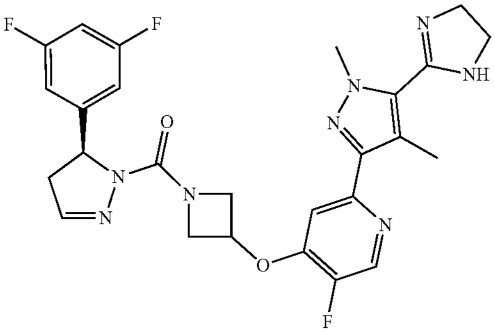 [SMILES: Cc1c(-c2cc(OC3CN(C(=O)N4N=CC[C@H]4c4cc(F)cc(F)c4)C3)c(F)cn2)nn(C)c1C1=NCCN1]
266
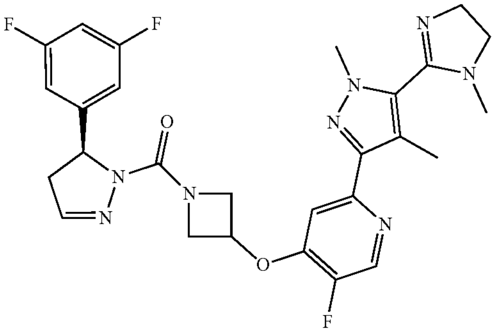 [SMILES: Cc1c(-c2cc(OC3CN(C(=O)N4N=CC[C@H]4c4cc(F)cc(F)c4)C3)c(F)cn2)nn(C)c1C1=NCCN1C]
267
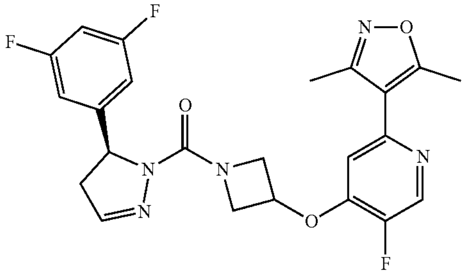 [SMILES: Cc1noc(C)c1-c1cc(OC2CN(C(=O)N3N=CC[C@H]3c3cc(F)cc(F)c3)C2)c(F)cn1]
268
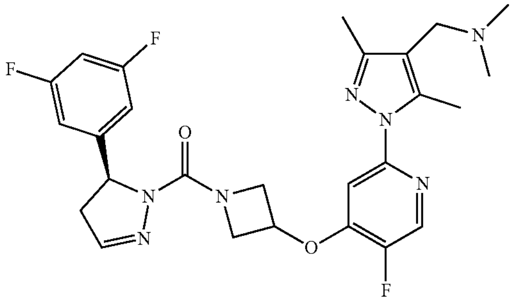 [SMILES: Cc1nn(-c2cc(OC3CN(C(=O)N4N=CC[C@H]4c4cc(F)cc(F)c4)C3)c(F)cn2)c(C)c1CN(C)C]
269

TABLE 3-continued
| Active Compounds 117-281: Structures |
| --- |
| 270<br>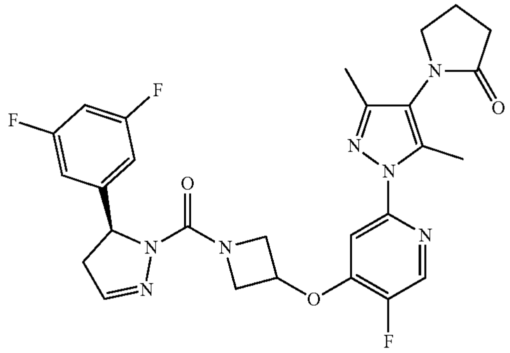 [SMILES: Cc1nn(-c2cc(OC3CN(C(=O)N4N=CC[C@H]4c4cc(F)cc(F)c4)C3)c(F)cn2)c(C)c1N1CCCC1=O] |
| 271<br>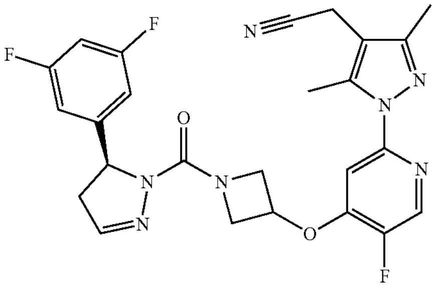 [SMILES: Cc1nn(-c2cc(OC3CN(C(=O)N4N=CC[C@H]4c4cc(F)cc(F)c4)C3)c(F)cn2)c(C)c1CC#N] |
| 272<br>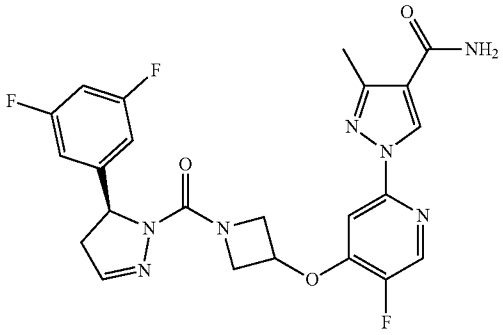 [SMILES: Cc1nn(-c2cc(OC3CN(C(=O)N4N=CC[C@H]4c4cc(F)cc(F)c4)C3)c(F)cn2)cc1C(N)=O] |
| 273<br>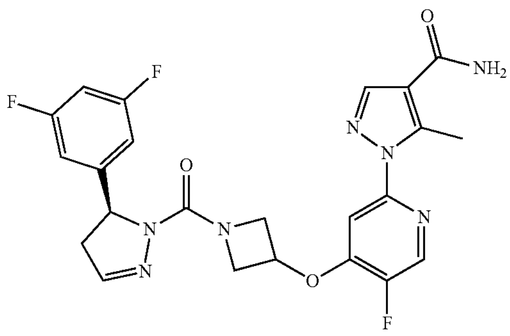 [SMILES: Cc1c(C(N)=O)cnn1-c1cc(OC2CN(C(=O)N3N=CC[C@H]3c3cc(F)cc(F)c3)C2)c(F)cn1] |

TABLE 3-continued
| Active Compounds 117-281: Structures |
| --- |
| 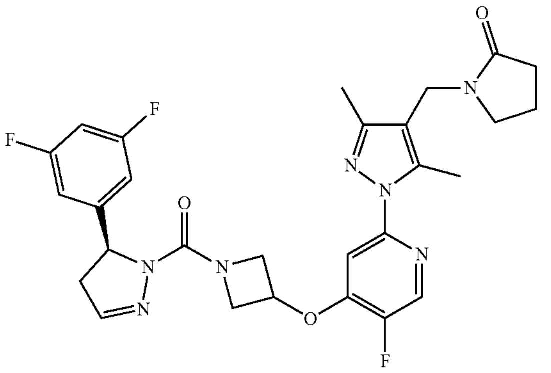 [SMILES: Cc1nn(-c2cc(OC3CN(C(=O)N4N=CC[C@H]4c4cc(F)cc(F)c4)C3)c(F)cn2)c(C)c1CN1CCCC1=O] 274 |
| 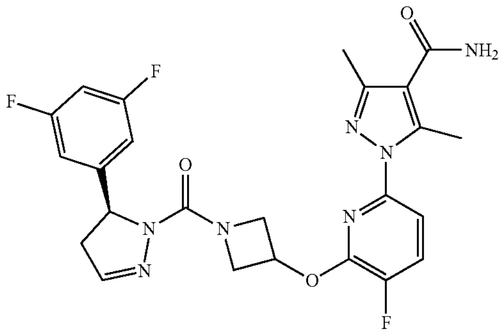 [SMILES: Cc1nn(-c2ccc(F)c(OC3CN(C(=O)N4N=CC[C@H]4c4cc(F)cc(F)c4)C3)n2)c(C)c1C(N)=O] 275 |
| 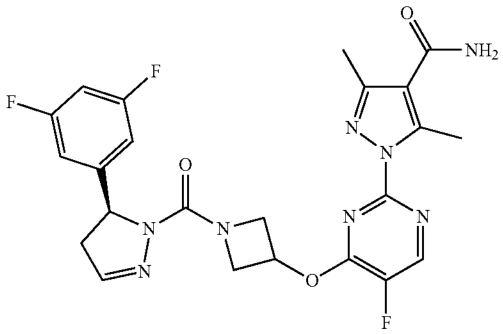 [SMILES: Cc1nn(-c2ncc(F)c(OC3CN(C(=O)N4N=CC[C@H]4c4cc(F)cc(F)c4)C3)n2)c(C)c1C(N)=O] 276 |
| 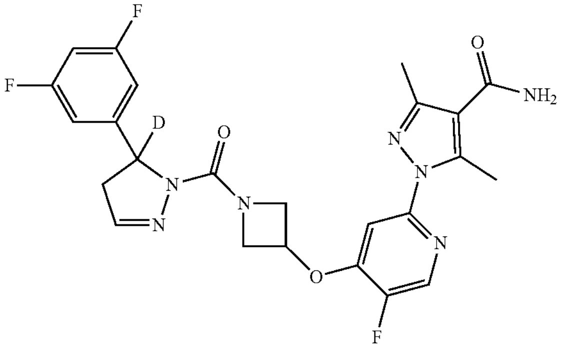 [SMILES: [2H]C1(c2cc(F)cc(F)c2)CC=NN1C(=O)N1CC(Oc2cc(-n3nc(C)c(C(N)=O)c3C)ncc2F)C1] 277 |

TABLE 3-continued
| Active Compounds 117-281: Structures | |
|---|---|
| 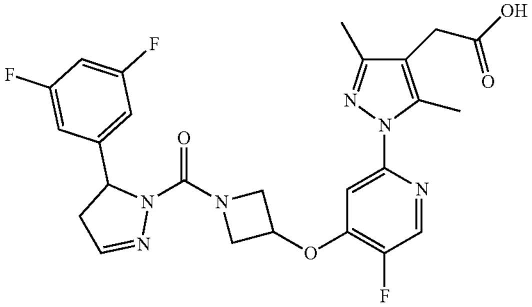 [SMILES: Cc1nn(-c2cc(OC3CN(C(=O)N4N=CCC4c4cc(F)cc(F)c4)C3)c(F)cn2)c(C)c1CC(=O)O] | 278 |
| 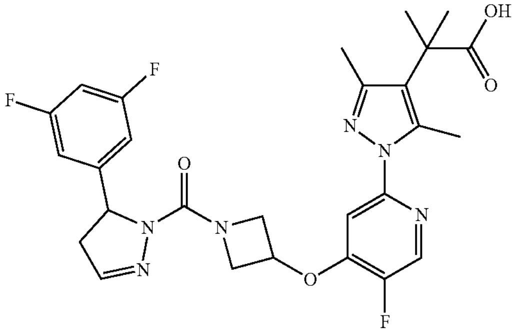 [SMILES: Cc1nn(-c2cc(OC3CN(C(=O)N4N=CCC4c4cc(F)cc(F)c4)C3)c(F)cn2)c(C)c1C(C)(C)C(=O)O] | 279 |
| 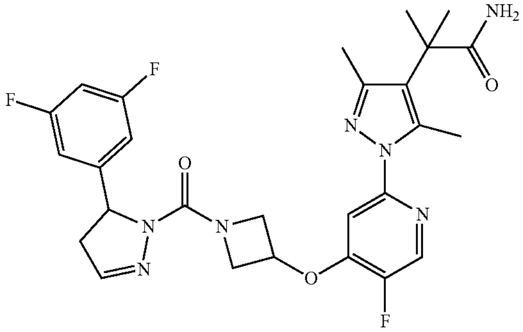 [SMILES: Cc1nn(-c2cc(OC3CN(C(=O)N4N=CCC4c4cc(F)cc(F)c4)C3)c(F)cn2)c(C)c1C(C)(C)C(N)=O] | 280 |
| 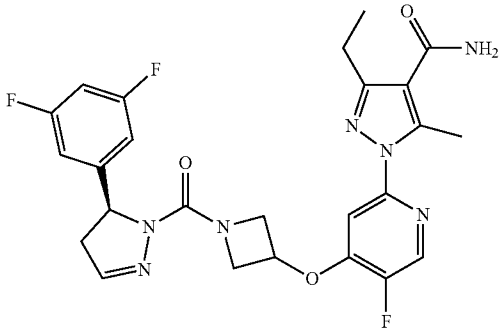 [SMILES: CCc1nn(-c2cc(OC3CN(C(=O)N4N=CC[C@H]4c4cc(F)cc(F)c4)C3)c(F)cn2)c(C)c1C(N)=O] | 281 |
TABLE 4
Cell activity ($EC_{50}$) of Compounds 117-281
| # | $EC_{50}$ | # | $EC_{50}$ | # | $EC_{50}$ | # | $EC_{50}$ |
|---|---|---|---|---|---|---|---|
| 117 | +++ | 118 | + | 119 | ++ | 120 | +++ |
| 121 | +++ | 122 | +++ | 123 | ++ | 124 | +++ |
| 125 | +++ | 126 | +++ | 127 | +++ | 128 | +++ |
| 129 | +++ | 130 | +++ | 131 | +++ | 132 | +++ |
TABLE 4-continued
Cell activity ($EC_{50}$) of Compounds 117-281
| # | $EC_{50}$ | # | $EC_{50}$ | # | $EC_{50}$ | # | $EC_{50}$ |
|---|---|---|---|---|---|---|---|
| 133 | +++ | 134 | +++ | 135 | +++ | 136 | +++ |
| 137 | +++ | 138 | +++ | 139 | +++ | 140 | +++ |
| 141 | +++ | 142 | +++ | 143 | +++ | 144 | +++ |
| 145 | +++ | 146 | +++ | 147 | +++ | 148 | +++ |

TABLE 4-continued

| Cell activity ($EC_{50}$) of Compounds 117-281 | | | | | | | |
|---|---|---|---|---|---|---|---|
| # | $EC_{50}$ | # | $EC_{50}$ | # | $EC_{50}$ | # | $EC_{50}$ |
| 149 | +++ | 150 | +++ | 151 | +++ | 152 | +++ |
| 153 | +++ | 154 | +++ | 155 | +++ | 156 | +++ |
| 157 | +++ | 158 | +++ | 159 | +++ | 160 | +++ |
| 161 | +++ | 162 | +++ | 163 | +++ | 164 | +++ |
| 165 | +++ | 166 | +++ | 167 | +++ | 168 | +++ |
| 169 | + | 170 | +++ | 171 | +++ | 172 | +++ |
| 173 | +++ | 174 | +++ | 175 | +++ | 176 | +++ |
| 177 | +++ | 178 | +++ | 179 | ++ | 180 | +++ |
| 181 | +++ | 182 | +++ | 183 | +++ | 184 | +++ |
| 185 | +++ | 186 | +++ | 187 | +++ | 188 | +++ |
| 189 | +++ | 190 | +++ | 191 | +++ | 192 | +++ |
| 193 | +++ | 194 | +++ | 195 | +++ | 196 | +++ |
| 197 | +++ | 198 | +++ | 199 | +++ | 200 | +++ |
| 201 | +++ | 202 | +++ | 203 | +++ | 204 | +++ |
| 205 | +++ | 206 | +++ | 207 | +++ | 208 | +++ |
| 209 | +++ | 210 | +++ | 211 | +++ | 212 | +++ |
| 213 | +++ | 214 | +++ | 215 | +++ | 216 | +++ |
| 217 | +++ | 218 | +++ | 219 | +++ | 220 | +++ |
| 221 | +++ | 222 | +++ | 223 | +++ | 224 | +++ |
| 225 | +++ | 226 | +++ | 227 | +++ | 228 | +++ |
| 229 | +++ | 230 | +++ | 231 | +++ | 232 | +++ |
| 233 | +++ | 234 | +++ | 235 | +++ | 236 | +++ |
| 237 | +++ | 238 | ++ | 239 | +++ | 240 | +++ |
| 241 | +++ | 242 | +++ | 243 | +++ | 244 | +++ |
| 245 | +++ | 246 | +++ | 247 | +++ | 248 | +++ |
| 249 | +++ | 250 | +++ | 251 | +++ | 252 | +++ |
| 253 | +++ | 254 | +++ | 255 | +++ | 256 | +++ |
| 257 | +++ | 258 | +++ | 259 | +++ | 260 | +++ |
| 261 | +++ | 262 | +++ | 263 | +++ | 264 | +++ |
| 265 | +++ | 266 | +++ | 267 | ++ | 268 | +++ |
| 269 | +++ | 270 | +++ | 271 | +++ | 272 | +++ |
| 273 | +++ | 274 | +++ | 275 | +++ | 276 | +++ |
| 277 | +++ | 278 | ++ | 279 | ++ | 280 | +++ |
| 281 | +++ | | | | | | |

EXAMPLES

Compound Preparation

(5-(3,5-difluorophenyl)-4,5-dihydro-1H-pyrazol-1-yl)(3-((3-fluoro-6-(1-methyl-1H-pyrazol-5-yl)pyridin-2-yl)oxy)azetidin-1-yl)methanone (1)

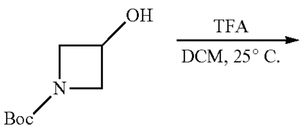

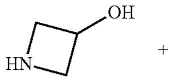

1-01

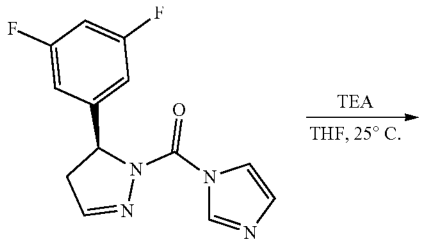

1-02

-continued

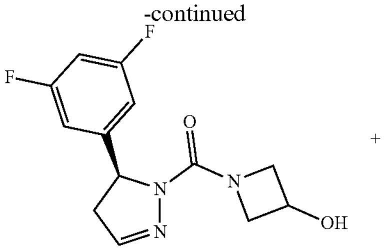

1-03

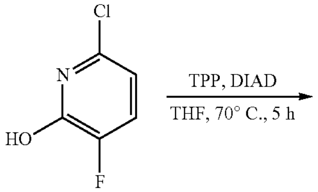

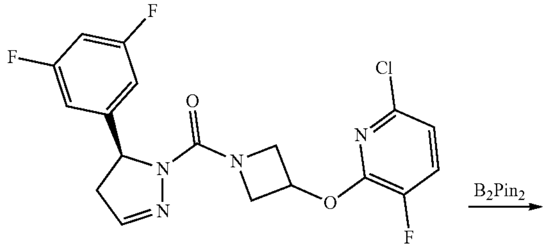

1-04

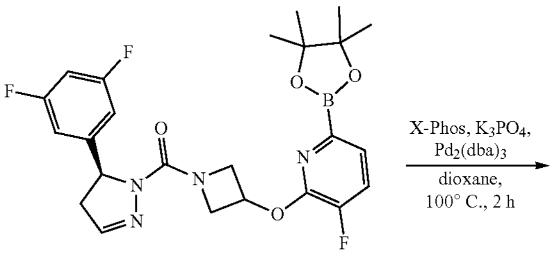

1-05

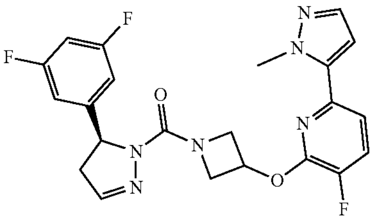

1

Step 1: tert-butyl 3-hydroxyazetidine-1-carboxylate (1.5 g, 8.66 mmol) was dissolved in 15 mL of DCM, trifluoroacetic acid (1.5 ml, 13.1 mmol) was added, the mixture was stirred at r.t. for 30 min. Concentrated to give the desired product 1-01, which was used for next step without further purification.

Step 2: 1-01 (633 mg, 8.66 mmol), 1-02 (2.39 g, 8.66 mmol) and TEA (1 mL) were dissolved in THE (15 mL) and stirred at 25° C. for 6 h. The mixture was extracted with EA, washed with brine, dried ($Na_2SO_4$), and concentrated in vacuo. Purification by silica gel chromatography to give the intermediate 1-03 (2.1 g, 87.5%) MS (m/z): 282.3 $[M+H]^+$.

Step 3: 6-chloro-3-fluoropyridin-2-ol (200 mg, 1.36 mmol) was dissolved in 3 ml of dry THF. DEAD (328 mg ml, 1.63 mmol), Compound 1-03 (400 mg, 1.423 mmol), $PPh_3$ (540 mg, 2.04 mmol) was added to the above solution at room temperature. The mixture was stirred for 12 hours at 25° C. The mixture was extracted with EA, washed with brine, dried ($Na_2SO_4$), and concentrated in vacuo. Purification by silica gel chromatography to give compound 1-04 (300 mg, 51%) as a white solid. Mass (m/z) 411.2 $[M+H]^+$.

Step 4: 1-04 (200 mg, 0.49 mmol), x-phos (46.3 mg, 0.098 mmol), bis(4,4,5,5-tetramethyl-1,3,2-dioxaborolan-2-yl) methane (534 mg, 2 mmol) and KOAc (150 mg, 1.5 mmol), $Pd_2(dba)_3$ (44.5 mg, 0.098 mmol) were placed in dioxane (3 mL). The mixture was stirred for 2 h at 100° C. under $N_2$, the mixture was extracted with DCM, washed with brine, dried ($Na_2SO_4$), and concentrated in vacuo. Purification by silica gel chromatography to give the intermediate 1-05 as a white solid. Mass (m/z): 503.2 $[M+H]^+$.

Step 5: 1-05 (100 mg, 0.24 mmol), 1-methyl-5-(4,4,5,5-tetramethyl-1,3,2-dioxaborolan-2-yl)-1H-pyrazole (101 mg, 0.48 mmol) X-Phos (11.42 mg, 0.028 mmol) and KOAc (70.56 mg, 0.96 mmol), $Pd_2(dba)_3$ (21.9 mg, 0.024 mmol), $K_3PO_4$ (5N, 1 mL) were placed in dioxane (3 mL). The mixture was stirred 100° C. for 2 h under $N_2$, the mixture was extracted with EA, washed with brine, dried ($Na_2SO_4$), and concentrated in vacuo. Purification by silica gel chromatography to give the titled compound 1 (20 mg, 20.3%) as a white solid. Mass (m/z) 457.2 $[M+H]^+$; $^1H$ NMR (400 MHz, Chloroform-d) δ 7.43 (d, J=0.0 Hz, 2H), 7.20 (dd, J=8.2, 2.8 Hz, 1H), 6.86-6.61 (m, 4H), 6.55-6.45 (m, 1H), 5.57-5.35 (m, 1H), 5.27 (dd, J=12.3, 6.5 Hz, 1H), 4.70-4.45 (m, 2H), 4.31 (dd, J=30.8, 9.7 Hz, 2H), 4.16 (s, 3H), 3.34 (dd, J=18.6, 12.2 Hz, 1H), 2.69 (dd, J=18.6, 6.4 Hz, 1H).

(S)-(5-(3,5-difluorophenyl)-4,5-dihydro-1H-pyrazol-1-yl)(3-((5-fluoro-2-(1-methyl-1H-pyrazol-5-yl)pyrimidin-4-yl)oxy)azetidin-1-yl)methanone (2)

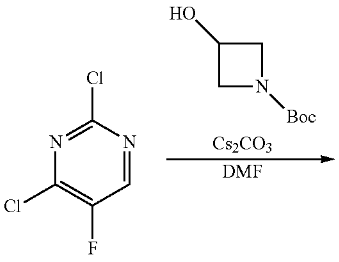

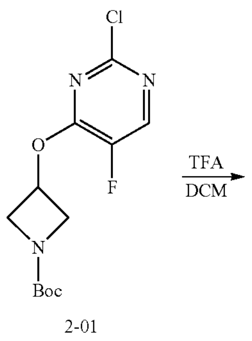

2-01

-continued

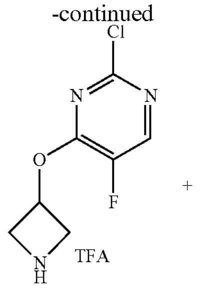

2-02

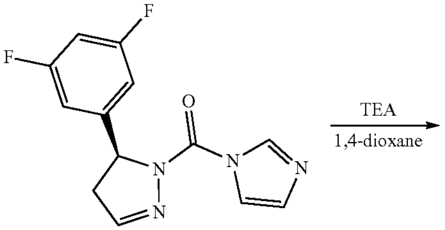

1-02

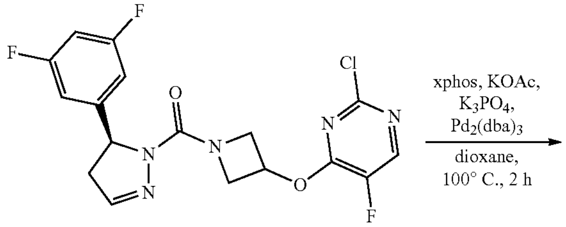

2-03

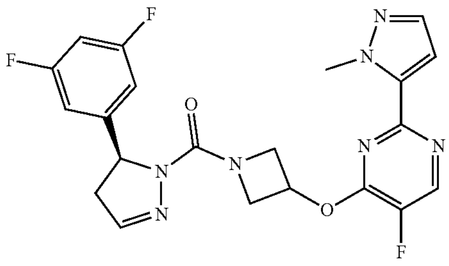

2

Step 1. 2,4-dichloro-5-fluoropyrimidine (5 g, 29.9 mmol) was added to a solution of $Cs_2CO_3$ (19.5 g, 59.9 mmol) in DMF (100 mL), and tert-butyl 3-hydroxyazetidine-1-carboxylate (5.7 g, 32.9 mmol) was added. The mixture was stirred at 100° C. for 2 hrs. The reaction mixture was then extracted by EtOAc/$H_2O$ (50 mL/50 mL) 3 times. The organic layer was combined, washed with brine, dried over $Na_2SO_4$, concentrated and further purified by silica gel column chromatography (PE/EA=5/1) to give tert-butyl 3-((2-chloro-5-fluoropyrimidin-4-yl)oxy)azetidine-1-carboxylate (2-01) 3.9 g as a colorless oil (43%). Mass (m/z) 304.1 $[M+H]^+$ Step 2. TFA (5 mL) was added to a solution of 2-01 (3.9 g, 12.9 mmol) in DCM (10 mL). the reaction mixture was stirred at room temperature for 0.5 hr. then the solvent was evaporated in vacuo to give 5.2 g of 4-(azetidin-3-yloxy)-2-chloro-5-fluoropyrimidine as a colorless oil (2-02) (crude). Mass (m/z) 204.1 $[M+H]^+$ Step 3. (S)-(5-(3,5-difluorophenyl)-4,5-dihydro-1H-pyrazol-1-yl)(1H-imidazol-1-yl)methanone (1-02) (3.23 g, 11.7 mmol) was added to a solution of 4-(azetidin-3-yloxy)-2- chloro-5-fluoropyrimidine (2-02) and TEA (3.55 g, 35.1 mmol) in 1,4-dioxane (30 mL). The reaction mixture was stirred at room temperature overnight. Then the solvent was evaporated in vacuo. The oil residue was purified by silica gel column chromatography (PE/EA=1/1) to give 4.35 g of (S)-(3-((2-chloro-5-fluoropyrimidin-4-yl)oxy)azetidin-1-yl)(5-(3,5-difluorophenyl)-4,5-dihydro-1H-pyrazol-1-yl)methanone as a yellow oil (2-03) (90%). Mass (ESI) m/z $[M+H]^+$:412.1.

Step 4: The titled compound 2 was prepared in 59.2% yield from 2-03 according to the procedure outlined for compound 1. Mass (m/z) 458.2 $[M+H]^+$; $^1H$ NMR (400 MHz, Chloroform-d) δ 8.42 (d, J=2.4 Hz, 1H), 7.51 (d, J=2.0 Hz, 11H), 6.94 (d, J=2.0 Hz, 11H), 6.79 (t, J=1.7 Hz, 1H), 6.77-6.74 (m, 2H), 6.69 (tt, J=8.9, 2.3 Hz, 1H), 5.53 (tt, J=6.6, 4.2 Hz, 1H), 5.28 (dd, J=12.2, 6.4 Hz, 1H), 4.69-4.58 (m, 2H), 4.37 (dd, J=10.7, 4.1 Hz, 1H), 4.30 (s, 4H), 3.36 (ddd, J=18.6, 12.2, 1.7 Hz, 1H), 2.70 (ddd, J=18.6, 6.4, 1.7 Hz, 1H).

(S)-(5-(3,5-difluorophenyl)-4,5-dihydro-1H-pyrazol-1-yl)(3-((5-fluoro-2-(1-methyl-1H-pyrazol-5-yl)pyridin-4-yl)oxy)azetidin-1-yl)methanone (3)

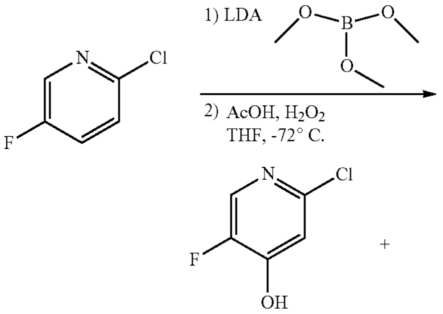

3-01

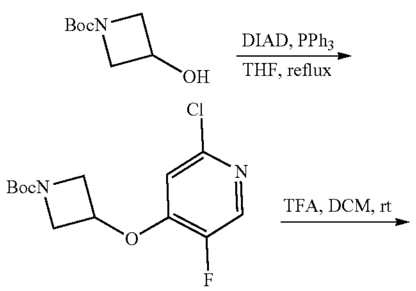

3-02

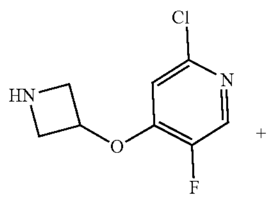

3-03

-continued

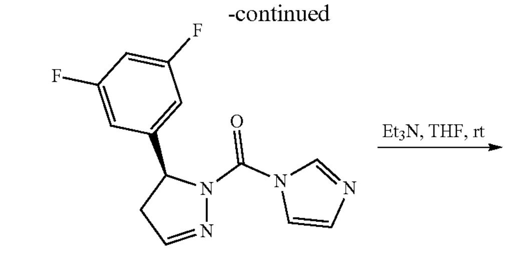

1-02

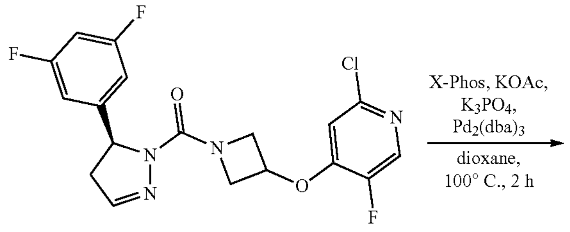

3-04

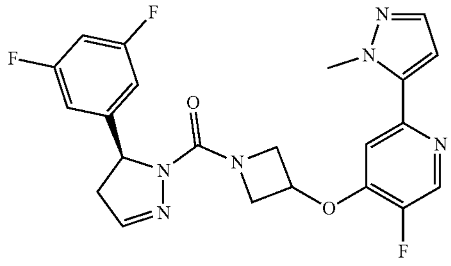

3

Step 1: Under a nitrogen atmosphere at −72° C. to a stirred solution of 2-chloro-5-fluoropyridine (25.0 g, 190 mmol) in tetrahydrofuran (250 mL) is added LDA (124 mL, 2M in tetrahydrofuran) dropwise over 30 min. The reaction mixture is stirred at −72° C. for 2 h. Afterwards a solution of trimethyl borate (39 g, 375 mmol) is added dropwise over 20 min. After addition, the reaction mixture is stirred at rt for another 2 h. The reaction mixture is cooled to 0° C. and acetic acid (32.5 mL) is added. The reaction mixture is stirred at 0° C. for 30 min. Hydrogen peroxide (58 mL, 30 percent solution) is added dropwise at 0° C. The reaction mixture is stirred at rt overnight. The reaction mixture is quenched with saturated aqueous $Na_2S_2O_4$. HCl (4M in dioxane) is added to the reaction mixture until the PH<7. After extraction with EA (300 mL×3), the combined organic phases are washed with water and brine, dried over anhydrous $Na_2SO_4$, filtered and concentrated under reduced pressure. The crude is beaten with DCM and filtered. The mother liquor was recrystallized twice with DCM to afford 15.2 g of the intermediate 3-01 (yield: 54%) white solid.

Step 2: $PPh_3$ (1.43 g, 5.4 mmol) in 50 ml dry THF was added DIAD (1.1 g, 5.4 mmol) at rt under nitrogen protection. 5 min later, 3-01 (670 mg, 4.5 mmol) was added to the above solution at room temperature. The mixture was stirred for 30 min at rt. Then tert-butyl 3-hydroxyazetidine-1-carboxylate (944 mg, 5.4 mmol) was added. The mixture was heated to reflux for 3 h. The resulting solution was added $H_2O$ and extracted with EA. The organic layers were washed with brine, dried over $Na_2SO_4$ and concentrated under vacuum. The crude product was purified by silica gel chromatography to afford of the intermediate 3-02 1.3 g (yield: 95%) white solid.

Step 3 and 4: The intermediate 3-04 was prepared from 3-02 according to the procedure from for 2-03.

Step 5: The title compound 3 was prepared from 3-04 according to the procedure from for 1.

Mass (m/z) 457.2 $[M+H]^+$ $^1$H NMR (400 MHz, Chloroform-d) δ 8.43 (d, J=2.8 Hz, 1H), 7.51 (d, J=2.0 Hz, 1H), 6.86 (d, J=6.5 Hz, 1H), 6.80 (s, 1H), 6.78, 6.66 (m, 3H), 6.47 (d, J=2.0 Hz, 1H), 5.28 (dd, J=12.2, 6.4 Hz, 1H), 5.13-5.04 (m, 1H), 4.67-4.52 (m, 2H), 4.32 (dd, J=29.1, 10.4 Hz, 2H), 4.17 (s, 3H), 3.36 (ddd, J=18.7, 12.2, 1.7 Hz, 1H), 2.71 (ddd, J=18.6, 6.4, 1.7 Hz, 1H).

(S)-(5-(3,5-difluorophenyl)-4,5-dihydro-1H-pyrazol-1-yl)(3-((2-(1-ethyl-1H-pyrazol-5-yl)-5-fluoropyridin-4-yl)oxy)azetidin-1-yl)methanone (4)

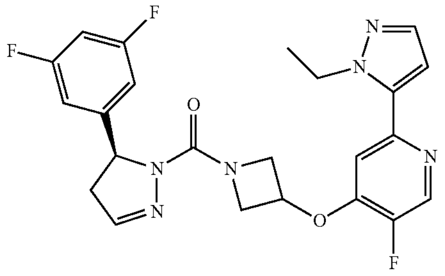 [SMILES: CCn1nccc1-c1cc(OC2CN(C(=O)N3N=CC[C@H]3c3cc(F)cc(F)c3)C2)c(F)cn1]

The titled compound 4 was prepared in a yield of 80.1% according to the procedure outlined for compound 3. Mass (m/z) 471.2 $[M+H]^+$; $^1$H NMR (400 MHz, Chloroform-d) δ 8.42 (dd, J=2.8, 0.6 Hz, 1H), 7.51 (dd, J=2.0, 0.6 Hz, 1H), 6.85 (d, J=6.5 Hz, 1H), 6.80-6.66 (m, 4H), 6.44 (dd, J=2.0, 0.6 Hz, 1H), 5.29-5.20 (m, 1H), 5.12-5.04 (m, 1H), 4.59 (q, J=7.2 Hz, 4H), 4.39-4.15 (m, 2H), 3.36 (ddd, J=18.7, 12.2, 1.7 Hz, 1H), 2.70 (ddd, J=18.7, 6.5, 1.7 Hz, 1H), 1.41 (t, J=7.2, 3H).

(S)-(5-(3,5-difluorophenyl)-4,5-dihydro-1H-pyrazol-1-yl)(3-((3-fluoro-6-(1-methyl-1H-imidazol-2-yl)pyridin-2-yl)oxy)azetidin-1-yl)methanone (5)

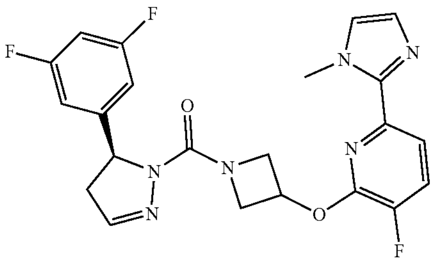 [SMILES: Cn1ccnc1-c1ccc(F)c(OC2CN(C(=O)N3N=CC[C@H]3c3cc(F)cc(F)c3)C2)n1]

The titled compound 5 was prepared in a yield of 18.6% according to the procedure outlined for compound 1. Mass (m/z) 457.2 $[M+H]^+$; 11H NMR (400 MHz, Chloroform-d) δ 7.98 (dd, J=8.1, 3.0 Hz, 1H), 7.64 (td, J=8.8, 2.8 Hz, 1H), 7.55 (s, 1H), 7.28-7.14 (d, 1H), 6.87-6.63 (m, 4H), 5.47-5.36 (m, 1H), 5.28-5.21 (m, 1H), 4.66-4.51 (m, 2H), 4.44-4.21 (m, 2H), 4.14 (s, 3H), 3.47-3.29 (m, 1H), 2.80-2.56 (m, 1H).

(S)-(5-(3,5-difluorophenyl)-4,5-dihydro-1H-pyrazol-1-yl)(3-((3-fluoro-6-(1-methyl-1H-imidazol-5-yl)pyridin-2-yl)oxy)azetidin-1-yl)methanone (6)

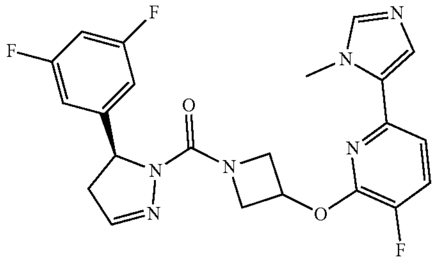 [SMILES: Cn1cncc1-c1ccc(F)c(OC2CN(C(=O)N3N=CC[C@H]3c3cc(F)cc(F)c3)C2)n1]

The titled compound 6 was prepared in a yield of 18.7% from 1-05 according to the procedure outlined for compound 1. Mass (m/z) 457.3 $[M+H]^+$; $^1$H NMR (400 MHz, Chloroform-d) δ 7.41-6.70 (m, 4H), 6.70-5.98 (m, 4H), 4.89 (d, J=16.0 Hz, 2H), 4.44-4.05 (m, 2H), 3.92 (d, J=37.8 Hz, 2H), 3.54 (s, 3H), 3.11-2.85 (m, 1H), 2.43-2.18 (m, 1H).

(S)-(5-(3,5-difluorophenyl)-4,5-dihydro-1H-pyrazol-1-yl)(3-((5-fluoro-2-(1-methyl-1H-imidazol-5-yl)pyridin-4-yl)oxy)azetidin-1-yl)methanone (7)

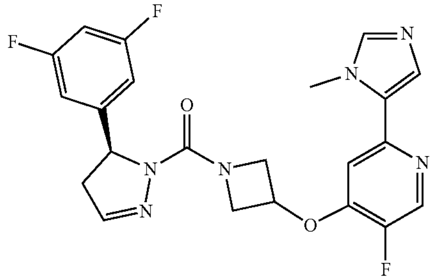 [SMILES: Cn1cncc1-c1cc(OC2CN(C(=O)N3N=CC[C@H]3c3cc(F)cc(F)c3)C2)c(F)cn1]

The titled compound 7 was prepared in a yield of 24.10% from 3-04 according to the procedure outlined for compound 3. Mass (m/z): 457.2 $[M+H]^+$, $^1$H NMR (400 MHz, Chloroform-d) δ 8.36 (dd, J=2.9, 1.0 Hz, 1H), 7.55 (s, 1H), 7.35 (s, 1H), 6.91-6.65 (m, 5H), 5.28-5.22 (m, 1H), 5.09-5.07 (m, 1H), 4.67-4.51 (s, 2H), 4.36-4.26 (dd, J=27.7, 9.7 Hz, 2H), 3.95 (s, 3H), 3.43-3.29 (m, 1H), 2.78-2.65 (m, 1H).

(S)-(5-(3,5-difluorophenyl)-4,5-dihydro-1H-pyrazol-1-yl)(3-((5-fluoro-2-(1-methyl-1H-imidazol-5-yl)pyrimidin-4-yl)oxy)azetidin-1-yl)methanone (8)

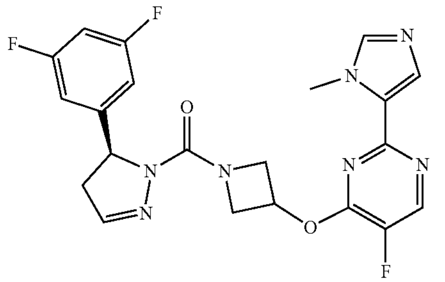 [SMILES: Cn1cncc1-c1ncc(F)c(OC2CN(C(=O)N3N=CC[C@H]3c3cc(F)cc(F)c3)C2)n1]

The titled compound 8 was prepared from 3-04 in a yield of 65.5% according to the procedure outlined for compound 2. Mass (m/z) 458.3 $[M+H]^+$; $^1H$ NMR (400 MHz, Chloroform-d) δ 8.74 (s, 1H), 8.43 (d, J=2.2 Hz, 1H), 7.98 (s, 1H), 6.89-6.59 (m, 4H), 5.51 (s, 1H), 5.29 (dd, J=12.3, 6.2 Hz, 1H), 4.64 (d, J=25.7 Hz, 2H), 4.42-4.12 (m, 5H), 3.37 (dd, J=18.7, 12.1 Hz, 11H), 2.72 (dd, J=18.6, 6.4 Hz, 11H).

(S)-(5-(3,5-difluorophenyl)-4,5-dihydro-1H-pyrazol-1-yl)(3-((5-fluoro-2-(4-methylthiazol-5-yl)pyrimidin-4-yl)oxy)azetidin-1-yl)methanone (9)

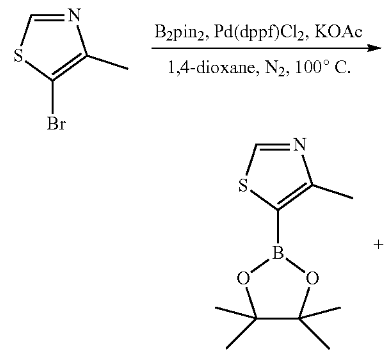

9-01

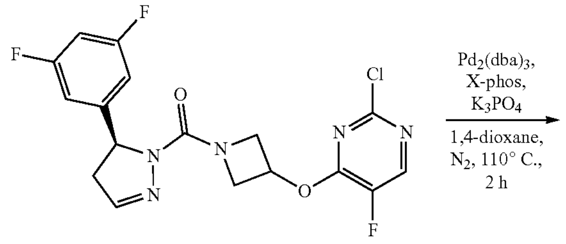

2-03

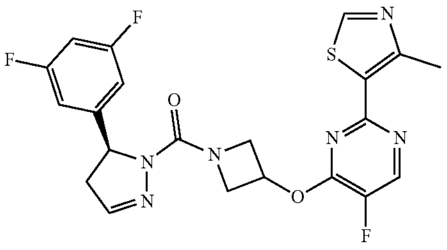

9

Step 1: 5-bromo-4-methylthiazole (89 mg, 0.5 mmol), $B_2pin_2$ (254 mg, 1.0 mmol), $Pd(dppf)Cl_2$ (36 mg, 0.05 mmol), KOAc (147 mg, 1.5 mmol) in 1,4-dioxane (2 mL) under $N_2$ and the reaction mixture was stirred at 100° C. for 3 hours. Concentrated to give the intermediate 9-01, which was used for next step without further purification. Mass (m/z): 226.2 $[M+H]^+$.

Step 2: Compound 2-03 (82 mg, 0.20 mmol), 4-methyl-5-(4,4,5,5-tetramethyl-1,3,2-dioxaborolan-2-yl)thiazole 9-01 (90 mg, 0.40 mmol), $Pd_2(dba)_3$ (18 mg, 0.02 mmol), X-phos (19 mg, 0.04 mmol) was added to a solution of $K_3PO_4$ (5N, 0.2 mL, 1.0 mmol) in 1,4-dioxane (2 mL) under N2 and the whole reaction mixture was stirred at 110° C. for 2 hours. After the mixture was concentrated and further purified by prep-HPLC to give the final compound 9 (9 mg, 9.5%) as a white solid. Mass (m/z) 475.2 $[M+H]^+$; $^1H$ NMR (400 MHz, Chloroform-d) δ 8.91 (s, 1H), 8.40 (d, J=2.3 Hz, 1H), 6.85-6.64 (m, 4H), 5.53 (s, 1H), 5.30 (d, J=0.4 Hz, 1H), 4.66 (s, 2H), 4.46-4.25 (m, 2H), 3.37 (dd, J=18.6, 11.5 Hz, 1H), 2.91 (s, 3H), 2.72 (dd, J=18.4, 5.3 Hz, 1H).

(S)-(5-(3,5-difluorophenyl)-4,5-dihydro-1H-pyrazol-1-yl)(3-((3-fluoro-6-(4-methylthiazol-5-yl)pyridin-2-yl)oxy)azetidin-1-yl)methanone (10)

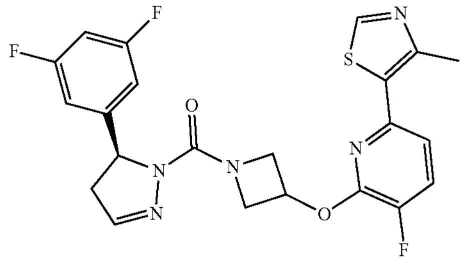 [SMILES: Cc1ncsc1-c1ccc(F)c(OC2CN(C(=O)N3N=CC[C@H]3c3cc(F)cc(F)c3)C2)n1]

The titled compound 10 was prepared from 1-05 according to the procedure outlined for compound 1. $^1H$ NMR (400 MHz, Chloroform-d) δ 8.67 (dd, J=8.7, 4.2 Hz, 1H), 7.48-7.34 (m, 1H), 7.20-7.07 (m, 1H), 6.84-6.56 (m, 4H), 5.50-5.35 (m, 1H), 5.30-5.20 (m, 1H), 4.77-4.48 (m, 2H), 4.43-4.17 (m, 2H), 3.44-3.16 (m, 1H), 2.68 (dd, J=8.8, 4.2 Hz, 3H), 2.13-1.91 (m, 1H). Mass (m/z): 474.2 $[M+H]^+$.

(S)-(5-(3,5-difluorophenyl)-4,5-dihydro-1H-pyrazol-1-yl)(3-((5-fluoro-2-(4-methylthiazol-5-yl)pyridin-4-yl)oxy)azetidin-1-yl)methanone (11)

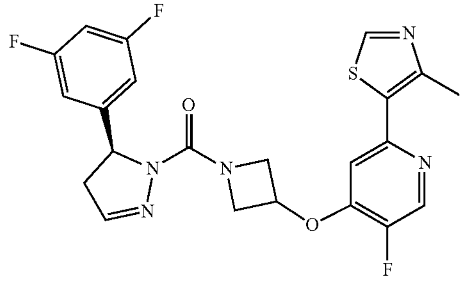 [SMILES: Cc1ncsc1-c1cc(OC2CN(C(=O)N3N=CC[C@H]3c3cc(F)cc(F)c3)C2)c(F)cn1]

The titled compound 11 was prepared from 3-04 in 42.2% yield according to the procedure outlined for compound 3. Mass (m/z) 474.2 $[M+H]^+$; $^1H$ NMR (400 MHz, Chloroform-d) δ 8.91 (s, 1H), 8.43 (dd, J=3.0, 1.7 Hz, 1H), 6.99-6.63 (m, 5H), 5.34-5.23 (m, 1H), 5.13 (s, 1H), 4.62 (s, 2H), 4.35 (dd, J=35.1, 10.3 Hz, 2H), 3.38 (dd, J=18.7, 12.1 Hz, 1H), 2.73 (s, 4H).

(S)-(5-(3,5-difluorophenyl)-4,5-dihydro-1H-pyrazol-1-yl)(3-((5-fluoro-2-(5-methylthiazol-4-yl)pyrimidin-4-yl)oxy)azetidin-1-yl)methanone (12)

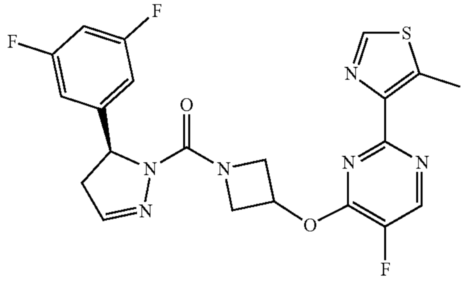 [SMILES: Cc1scnc1-c1ncc(F)c(OC2CN(C(=O)N3N=CC[C@H]3c3cc(F)cc(F)c3)C2)n1]

The titled compound 12 was prepared from 2-03 in 6.2% yield according to the procedure outlined for compound 2. $^{1}$H NMR (400 MHz, Chloroform-d) δ 8.98 (s, 1H), 8.51 (s, 1H), 6.75 (dd, J=23.2, 16.4 Hz, 4H), 5.76 (s, 1H), 5.37-5.24 (m, 1H), 4.65 (s, 2H), 4.41-4.23 (m, 2H), 3.39-3.32 (m, 1H), 2.89 (s, 3H), 2.70 (dd, J=18.5, 6.3 Hz, 1H); Mass (m/z) 475.2 $[M+H]^+$.

(S)-(5-(3,5-difluorophenyl)-4,5-dihydro-1H-pyrazol-1-yl)(3-((3-fluoro-6-(5-methylthiazol-4-yl)pyridin-2-yl)oxy)azetidin-1-yl)methanone (13)

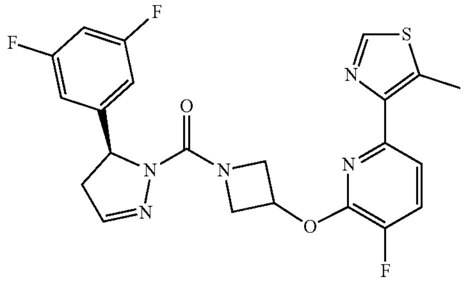 [SMILES: Cc1scnc1-c1ccc(F)c(OC2CN(C(=O)N3N=CC[C@H]3c3cc(F)cc(F)c3)C2)n1]

The titled compound 13 was prepared from 1-05 in 17.5% yield according to the procedure outlined for compound 1. $^{1}$H NMR (400 MHz, Chloroform-d) δ 8.58 (s, 1H), 7.78 (dd, J=8.3, 3.1 Hz, 1H), 7.45 (dd, J=9.8, 8.3 Hz, 1H), 6.83-6.66 (m, 4H), 5.52 (tt, J=6.6, 4.2 Hz, 1H), 5.28 (dd, J=12.2, 6.5 Hz, 1H), 4.59 (d, J=8.2 Hz, 2H), 4.32 (dd, J=38.5, 10.5 Hz, 2H), 3.35 (ddd, J=18.5, 12.2, 1.7 Hz, 1H), 2.84 (s, 3H), 2.69 (ddd, J=18.6, 6.5, 1.7 Hz, 1H). Mass (m/z) 474.2 $[M+H]^+$.

(S)-(5-(3,5-difluorophenyl)-4,5-dihydro-1H-pyrazol-1-yl)(3-((5-fluoro-2-(5-methylthiazol-4-yl)pyridin-4-yl)oxy)azetidin-1-yl)methanone (14)

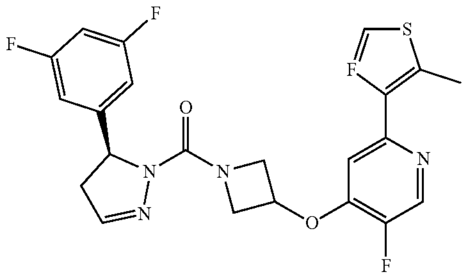

The titled compound 14 was prepared from 3-04 in 30.3% yield according to the procedure outlined for compound 3. $^{1}$H NMR (400 MHz, Chloroform-d) δ 8.59 (s, 1H), 8.41 (d, J=2.8 Hz, 1H), 7.51 (d, J=6.8 Hz, 1H), 6.80-6.63 (m, 4H), 5.28 (dd, J=12.2, 6.5 Hz, 1H), 5.15 (td, J=6.5, 3.3 Hz, 1H), 4.63 (s, 2H), 4.32 (dd, J=27.0, 10.6 Hz, 2H), 3.35 (ddd, J=18.6, 12.2, 1.7 Hz, 1H), 2.86 (s, 3H), 2.70 (ddd, J=18.6, 6.5, 1.7 Hz, 1H). Mass (m/z) 474.2 [M+H]+.

(S)-(5-(3,5-difluorophenyl)-4,5-dihydro-1H-pyrazol-1-yl)(3-((5-fluoro-2-(3-methylisothiazol-4-yl)pyrimidin-4-yl)oxy)azetidin-1-yl)methanone (15)

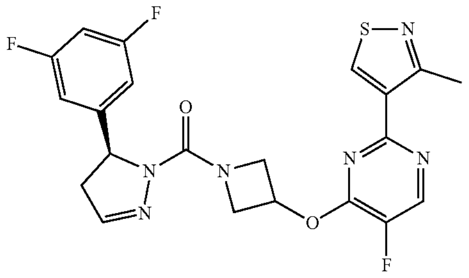

The titled compound 15 was prepared from 2-03 in 19.2% yield according to the procedure outlined for compound 2. $^{1}$H NMR (400 MHz, Chloroform-d) δ 9.30 (s, 1H), 8.43 (d, J=2.4 Hz, 1H), 6.86-6.65 (m, 4H), 5.56 (s, 1H), 5.30 (dd, J=11.9, 6.3 Hz, 1H), 4.66 (s, 2H), 4.46-4.25 (m, 2H), 3.40-3.29 (m, 1H), 2.85 (s, 3H), 2.72 (dd, J=18.7, 5.8 Hz, 1H). Mass (m/z) 475.2 [M+H]+.

(S)-(5-(3,5-difluorophenyl)-4,5-dihydro-1H-pyrazol-1-yl)(3-((3-fluoro-6-(3-methylisothiazol-4-yl)pyridin-2-yl)oxy)azetidin-1-yl)methanone (16)

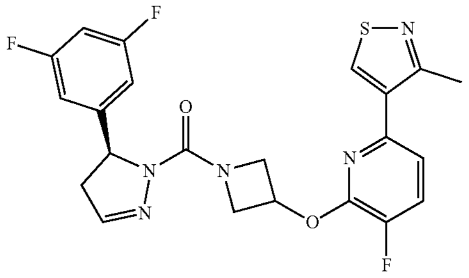 [SMILES: Cc1nscc1-c1ccc(F)c(OC2CN(C(=O)N3N=CC[C@H]3c3cc(F)cc(F)c3)C2)n1]

The titled compound 16 was prepared from 1-05 in 39.6% yield according to the procedure outlined for compound 1. $^{1}$H NMR (400 MHz, Chloroform-d) δ 8.32 (q, J=0.9 Hz, 1H), 7.77 (dd, J=8.2, 3.2 Hz, 1H), 7.47 (dd, J=9.8, 8.2 Hz, 1H), 6.80-6.64 (m, 4H), 5.51 (tt, J=6.6, 4.1 Hz, 1H), 5.28 (dd, J=12.2, 6.5 Hz, 1H), 4.59 (d, J=9.0 Hz, 2H), 4.31 (dd, J=36.4, 10.0 Hz, 2H), 3.34 (ddd, J=18.6, 12.2, 1.7 Hz, 1H), 2.69 (ddd, J=18.5, 6.6, 1.7 Hz, 1H), 2.60 (d, J=0.9 Hz, 3H). Mass (m/z) 474.2 [M+H]+.

(S)-(5-(3,5-difluorophenyl)-4,5-dihydro-1H-pyrazol-1-yl)(3-((5-fluoro-2-(3-methylisothiazol-4-yl)pyridin-4-yl)oxy)azetidin-1-yl)methanone (17)

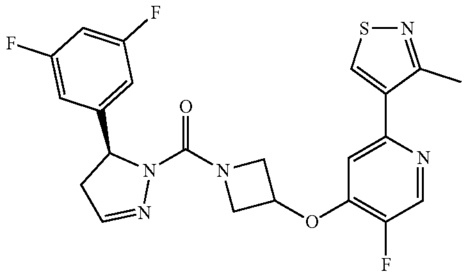 [SMILES: Cc1nscc1-c1cc(OC2CN(C(=O)N3N=CC[C@H]3c3cc(F)cc(F)c3)C2)c(F)cn1]

The titled compound 17 was prepared from 3-04 in 30.3% yield according to the procedure outlined for compound 3. $^{1}$H NMR (300 MHz, Chloroform-d) δ 8.77 (s, 1H), 8.44 (d, J=3.0 Hz, 1H), 6.90-6.52 (m, 5H), 5.28 (dd, J=12.1, 6.4 Hz, 1H), 5.10 (s, 1H), 4.60 (q, J=9.2, 8.8 Hz, 2H), 4.33 (dd, J=24.1, 8.3 Hz, 2H), 3.42-3.30 (m, 1H), 2.79-2.56 (m, 4H). Mass (m/z) 474.2 $[M+H]^+$.

(S)-(5-(3,5-difluorophenyl)-4,5-dihydro-1H-pyrazol-1-yl)(3-((5-fluoro-2-(4-methylisothiazol-3-yl)pyrimidin-4-yl)oxy)azetidin-1-yl)methanone (18)

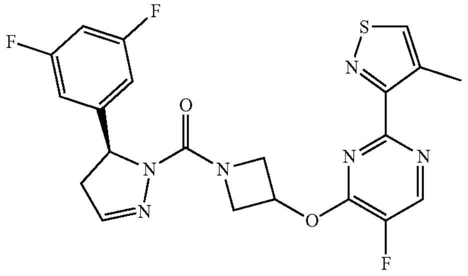 [SMILES: Cc1csnc1-c1ncc(F)c(OC2CN(C(=O)N3N=CC[C@H]3c3cc(F)cc(F)c3)C2)n1]

The titled compound 18 was prepared from 2-03 in 0.6% yield according to the procedure outlined for compound 2. $^{1}$H NMR (400 MHz, Chloroform-d) δ 8.62 (s, 1H), 8.42 (s, 1H), 6.83 (s, 1H), 6.77-6.51 (m, 3H), 5.65 (s, 1H), 5.32 (dt, J=12.2, 5.7 Hz, 1H), 4.67 (s, 2H), 4.38 (d, J=30.1 Hz, 2H), 3.38 (dd, J=18.6, 12.1 Hz, 1H), 2.81-2.66 (m, 1H), 2.62 (s, 3H).

Mass (m/z) 475.2 $[M+H]^+$.

(S)-(5-(3,5-difluorophenyl)-4,5-dihydro-1H-pyrazol-1-yl)(3-((2-(2,4-dimethylthiazol-5-yl)-5-fluoropyrimidin-4-yl)oxy)azetidin-1-yl)methanone (19)

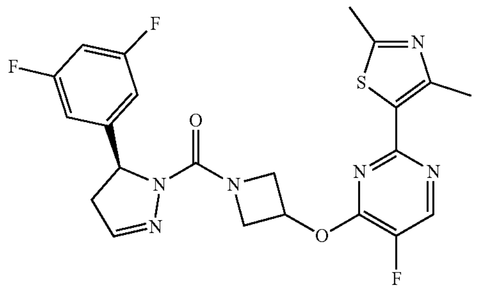 [SMILES: Cc1nc(C)c(-c2ncc(F)c(OC3CN(C(=O)N4N=CC[C@H]4c4cc(F)cc(F)c4)C3)n2)s1]

The titled compound 19 was prepared in 21.5% yield from 2-03 according to the procedure outlined for compound 2. $^{1}$H NMR (400 MHz, Chloroform-d) δ 8.35 (dd, J=2.5, 0.4 Hz, 1H), 6.83-6.67 (m, 4H), 5.54-5.48 (m, 1H), 5.28 (dd, J=12.2, 6.5 Hz, 1H), 4.64 (q, J=10.7 Hz, 2H), 4.41-4.24 (m, 2H), 3.36 (ddd, J=18.6, 12.2, 1.7 Hz, 1H), 2.80 (s, 3H), 2.75-2.66 (m, 4H). Mass (m/z) 489.2 $[M+H]^+$.

(S)-(5-(3,5-difluorophenyl)-4,5-dihydro-1H-pyrazol-1-yl)(3-((2-(3,5-dimethylisoxazol-4-yl)-5-fluoropyrimidin-4-yl)oxy)azetidin-1-yl)methanone (20)

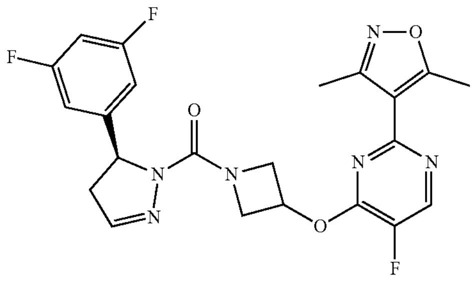 [SMILES: Cc1noc(C)c1-c1ncc(F)c(OC2CN(C(=O)N3N=CC[C@H]3c3cc(F)cc(F)c3)C2)n1]

The titled compound 20 was prepared in 33.5% yield from 2-03 according to the procedure outlined for compound 2. $^{1}$H NMR (400 MHz, Chloroform-d) δ 8.40 (d, J=2.5 Hz, 1H), 6.80 (t, J=1.7 Hz, 1H), 6.78-6.73 (m, 2H), 6.70 (tt, J=8.8, 2.3 Hz, 1H), 5.53 (tt, J=6.6, 4.0 Hz, 1H), 5.28 (dd, J=12.2, 6.4 Hz, 1H), 4.62 (q, J=11.3, 9.6 Hz, 2H), 4.38 (d, J=10.8 Hz, 1H), 4.29 (d, J=10.1 Hz, 1H), 3.36 (ddd, J=18.6, 12.2, 1.7 Hz, 1H), 2.74 (s, 3H), 2.73-2.67 (m, 1H), 2.56 (s, 3H). Mass (m/z) 473.2 $[M+H]^+$.

(S)-(5-(3,5-difluorophenyl)-4,5-dihydro-1H-pyrazol-1-yl)(3-((5-fluoro-2-(5-methylisoxazol-4-yl)pyrimidin-4-yl)oxy)azetidin-1-yl)methanone (21)

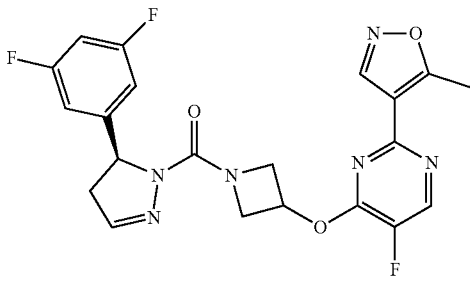 [SMILES: Cc1oncc1-c1ncc(F)c(OC2CN(C(=O)N3N=CC[C@H]3c3cc(F)cc(F)c3)C2)n1]

The titled compound 21 was prepared from 2-03 in 9.8% yield according to the procedure outlined for compound 2. $^{1}$H NMR (400 MHz, Chloroform-d) δ 8.71 (s, 1H), 8.37 (d, J=2.4 Hz, 1H), 6.83-6.66 (m, 4H), 5.56-5.49 (m, 1H), 5.28 (dd, J=12.1, 6.4 Hz, 1H), 4.65 (d, J=18.1 Hz, 2H), 4.33 (dd, J=33.0, 10.9 Hz, 2H), 3.36 (ddd, J=18.5, 12.3, 1.6 Hz, 1H), 2.81 (s, 3H), 2.71 (ddd, J=18.5, 6.4, 1.7 Hz, 1H). Mass (m/z) 459.2 $[M+H]^+$.

(S)-(5-(3,5-difluorophenyl)-4,5-dihydro-1H-pyrazol-1-yl)(3-((5-fluoro-2-(3-methylisoxazol-4-yl)pyrimidin-4-yl)oxy)azetidin-1-yl)methanone (22)

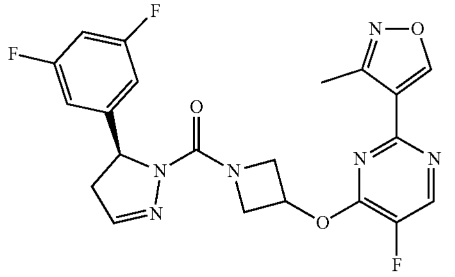 [SMILES: Cc1nocc1-c1ncc(F)c(OC2CN(C(=O)N3N=CC[C@H]3c3cc(F)cc(F)c3)C2)n1]

The titled compound 22 was prepared from 2-03 in 14.2% yield according to the procedure outlined for compound 2. $^1$H NMR (400 MHz, Chloroform-d) δ 8.95 (s, 1H), 8.37 (dd, J=2.4, 0.8 Hz, 1H), 6.82-6.65 (m, 4H), 5.52 (qd, J=6.6, 4.1 Hz, 1H), 5.28 (dd, J=12.2, 6.4 Hz, 1H), 4.63 (d, J=18.1 Hz, 2H), 4.33 (dd, J=33.3, 10.8 Hz, 2H), 3.36 (dd, J=18.6, 12.2 Hz, 1H), 2.71 (dd, J=18.8, 6.5 Hz, 1H), 2.63 (s, 3H). Mass (m/z) 459.2 [M+H]$^+$.

(S)-(5-(3,5-difluorophenyl)-4,5-dihydro-1H-pyrazol-1-yl)(3-((3-fluoro-6-(4-methylisothiazol-3-yl)pyridin-2-yl)oxy)azetidin-1-yl)methanone (23)

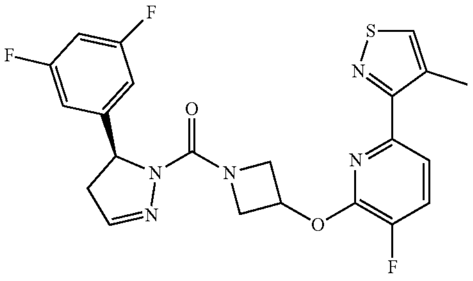 [SMILES: Cc1csnc1-c1ccc(F)c(OC2CN(C(=O)N3N=CC[C@H]3c3cc(F)cc(F)c3)C2)n1]

The titled compound 23 was prepared from 1-05 in 42.2% yield according to the procedure outlined for compound 1. $^1$H NMR (400 MHz, Chloroform-d) δ 8.74 (d, J=0.6 Hz, 1H), 7.43 (dd, J=9.7, 8.1 Hz, 1H), 7.13 (dd, J=8.1, 2.8 Hz, 1H), 6.81-6.64 (m, 4H), 5.47 (tt, J=6.6, 4.2 Hz, 1H), 5.28 (dd, J=12.2, 6.5 Hz, 1H), 4.60 (dd, J=17.7, 10.9 Hz, 2H), 4.38-4.23 (m, 2H), 3.34 (ddd, J=18.6, 12.2, 1.7 Hz, 1H), 2.76-2.63 (m, 4H). Mass (m/z) 474.2 [M+H]$^+$.

(S)-(5-(3,5-difluorophenyl)-4,5-dihydro-1H-pyrazol-1-yl)(3-((3-fluoro-6-(5-methyl-1,3,4-thiadiazol-2-yl)pyridin-2-yl)oxy)azetidin-1-yl)methanone (24)

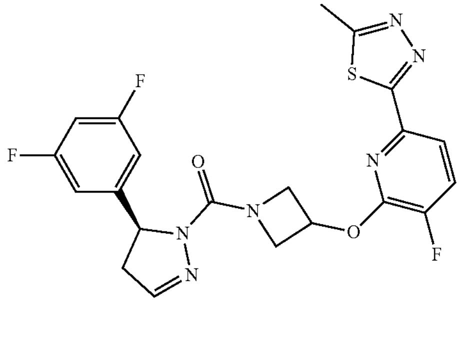 [SMILES: Cc1nnc(-c2ccc(F)c(OC3CN(C(=O)N4N=CC[C@H]4c4cc(F)cc(F)c4)C3)n2)s1]

The titled compound 24 was prepared from 1-05 in 4.7% yield according to the procedure outlined for compound 1. $^1$H NMR (400 MHz, Chloroform-d) δ 7.94 (dd, J=8.2, 3.1 Hz, 1H), 7.51 (dd, J=9.4, 8.2 Hz, 1H), 6.80-6.66 (m, 4H), 5.43 (ddd, J=11.2, 6.7, 4.4 Hz, 1H), 5.32-5.22 (m, 1H), 4.64 (d, J=10.3 Hz, 2H), 4.43-4.11 (m, 2H), 3.46-3.20 (m, 1H), 2.81 (s, 3H), 2.75-2.60 (m, 1H). Mass (m/z) 475.1 [M+H]$^+$ (S)-(5-(3,5-difluorophenyl)-4,5-dihydro-1H-pyrazol-1-yl)(3-((5-fluoro-2-(2-methylthiazol-5-yl)pyrimidin-4-yl)oxy)azetidin-1-yl)methanone (25)

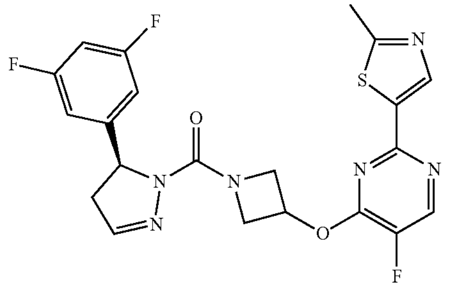 [SMILES: Cc1ncc(-c2ncc(F)c(OC3CN(C(=O)N4N=CC[C@H]4c4cc(F)cc(F)c4)C3)n2)s1]

The titled compound 25 was prepared in 23.2% yield from 2-03 according to the procedure outlined for compound 2. $^1$H NMR (400 MHz, Chloroform-d) δ 8.33 (d, J=2.5 Hz, 1H), 8.28 (s, 1H), 6.80-6.66 (m, 4H), 5.52 (tt, J=6.7, 4.3 Hz, 1H), 5.28 (dd, J=12.2, 6.5 Hz, 1H), 4.65 (dt, J=18.3, 8.4 Hz, 2H), 4.32 (ddd, J=32.0, 10.7, 4.4 Hz, 2H), 3.36 (ddd, J=18.6, 12.2, 1.7 Hz, 1H), 2.76 (s, 3H), 2.70 (ddd, J=18.6, 6.4, 1.7 Hz, 1H). Mass (m/z) 475.2 [M+H]$^+$.

(S)-(5-(3,5-difluorophenyl)-4,5-dihydro-1H-pyrazol-1-yl)(3-((5-fluoro-2-(2-methylthiazol-5-yl)pyridin-4-yl)oxy)azetidin-1-yl)methanone (26)

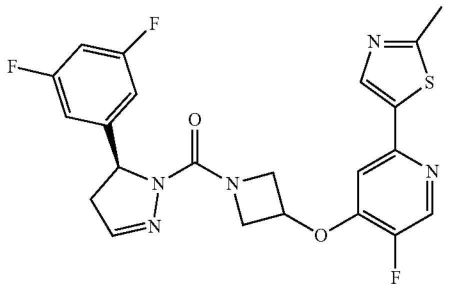 [SMILES: Cc1ncc(-c2cc(OC3CN(C(=O)N4N=CC[C@H]4c4cc(F)cc(F)c4)C3)c(F)cn2)s1]

The titled compound 26 was prepared from 3-04 in 17.1% yield according to the procedure outlined for compound 3. $^1$H NMR (300 MHz, Chloroform-d) δ 8.33 (d, J=3.0 Hz, 1H), 7.92 (s, 1H), 6.89 (d, J=6.4 Hz, 1H), 6.85-6.61 (m, 4H), 5.28 (dd, J=12.2, 6.4 Hz, 1H), 5.12 (ddd, J=10.6, 6.5, 4.0 Hz, 1H), 4.62 (q, J=9.3, 8.8 Hz, 2H), 4.32 (ddd, J=24.0, 10.5, 4.0 Hz, 2H), 3.41-3.30 (m, 1H), 2.79-2.63 (m, 4H). Mass (m/z) 474.2 [M+H]$^+$.

(5-(3,5-difluorophenyl)-4,5-dihydro-1H-pyrazol-1-yl)(3-((3-fluoro-6-(5-methyl-1,3,4-oxadiazol-2-yl)pyridin-2-yl)oxy)azetidin-1-yl)methanone (27)

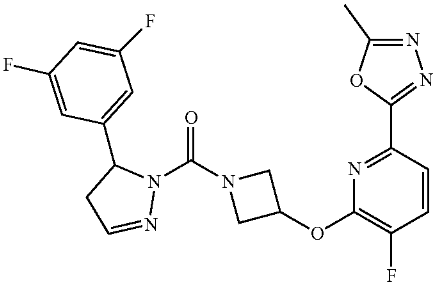 [SMILES: Cc1nnc(-c2ccc(F)c(OC3CN(C(=O)N4N=CCC4c4cc(F)cc(F)c4)C3)n2)o1]

The titled compound 27 was prepared from 1-05 in 4.5% yield according to the procedure outlined for compound 1. $^1$H NMR (400 MHz, Chloroform-d) δ 7.82 (dd, J=8.2, 3.0 Hz, 1H), 7.55-7.48 (m, 1H), 6.81-6.64 (m, 4H), 5.61-5.49 (m, 3.3 Hz, 1H), 5.29 (dd, J=12.3, 6.5 Hz, 1H), 476-4.54 (m, 2H), 4.37-4.23 (m, 2H), 3.42-3.28 (m, 1H), 2.73-2.66 (m, 1H), 2.64 (s, 3H). Mass (m/z) 459.2 [M+H]+

(S)-(5-(3,5-difluorophenyl)-4,5-dihydro-1H-pyrazol-1-yl)(3-((3-fluoro-6-(1-methyl-1H-1,2,4-triazol-5-yl)pyridin-2-yl)oxy)azetidin-1-yl)methanone (28)

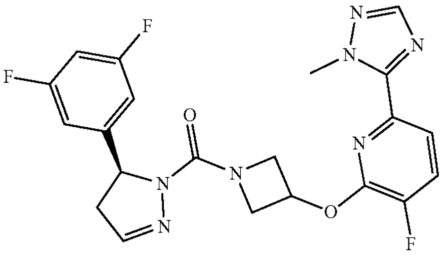 [SMILES: Cn1ncnc1-c1ccc(F)c(OC2CN(C(=O)N3N=CC[C@H]3c3cc(F)cc(F)c3)C2)n1]

The titled compound 28 was prepared from 1-05 in 23.5% yield according to the procedure outlined for compound 1. $^1$H NMR (400 MHz, Chloroform-d) δ 7.91-7.84 (m, 2H), 7.53 (dd, J=9.5, 8.2 Hz, 1H), 6.81-6.64 (m, 4H), 5.51-5.43 (m, 1H), 5.29-5.22 (m, 1H), 4.64-4.54 (d, J=9.7 Hz, 2H), 4.44-4.30 (m, 2H), 4.29 (s, 3H), 3.35 (ddd, J=18.6, 12.2, 1.7 Hz, 1H), 2.70 (ddd, J=18.6, 6.5, 1.7 Hz, 1H). Mass (m/z) 458.2 [M+H]$^+$ (S)-(5-(3,5-difluorophenyl)-4,5-dihydro-1H-pyrazol-1-yl)(3-((5-fluoro-2-(1-methyl-1H-1,2,4-triazol-5-yl)pyridin-4-yl)oxy)azetidin-1-yl)methanone (29)

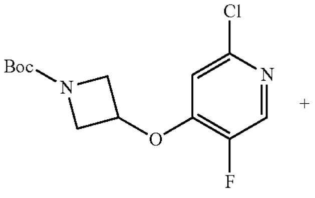

+

3-02

-continued

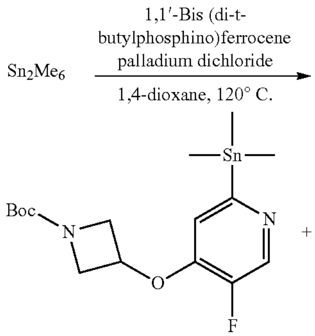

29-01

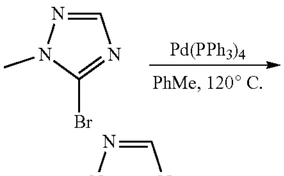

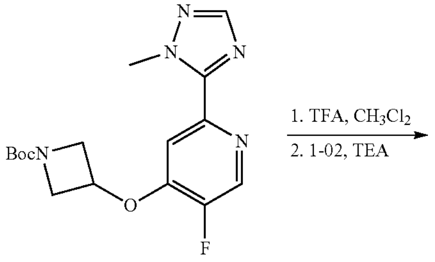

29-02

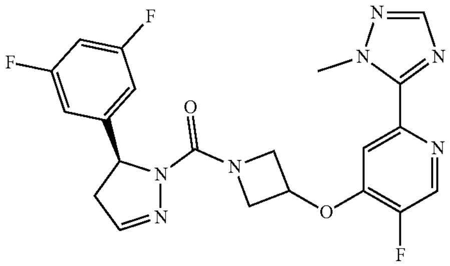

29

Step 1: compound 3-02 (1.04 g, 3.44 mmol), $Sn_2Me_3$ (1.7 g, 1.5 mmol), 1,1'-Bis (di-t-butylphosphino)ferrocene palladium dichloride (112 mg, 0.17 mmol) in 1,4-dioxane (15 mL) under $N_2$ and the whole reaction mixture was stirred at 120° C. for 3 hours. The black suspension was filtered through a plug of Celite and washed with EA (100 mL). Concentrated to give 29-01 (1.47 g, 99.3%) as a brown oil.

Step 2: 29-01 (320 mg, 0.74 mmol), 5-bromo-1-methyl-1H-1,2,4-triazole (61 mg, 0.38 mmol), $Pd(PPh_3)_4$ (58 mg, 0.05 mmol) in PhMe (5 mL) under $N_2$ and the whole reaction mixture was stirred at 120° C. for 15 hours. The mixture was extracted with EA, washed with brine, dried ($Na_2SO_4$), and concentrated in vacuo. Purification by silica gel chromatography to give 29-02 (110 mg) as a yellow solid.

Step 3: The titled compound 29 was prepared from 29-02 in 19.4% yield according to the procedure outlined for compound 2-03. Mass (m/z): 458.2 [M+H]$^+$. $^1$H NMR (400 MHz, Chloroform-d) δ 8.44 (d, J=2.5 Hz, 1H), 7.95 (s, 1H), 7.72 (d, J=6.5 Hz, 1H), 6.78 (d, J=1.6 Hz, 1H), 6.77-6.73 (m, 2H), 6.69 (tt, J=8.8, 2.3 Hz, 1H), 5.27 (dd, J=12.2, 6.4 Hz, 1H), 5.19 (s, 1H), 4.67 (s, 2H), 4.35 (s, 3H), 4.29 (d, J=13.5 Hz, 2H), 3.35 (ddd, J=18.6, 12.2, 1.7 Hz, 1H), 2.70 (ddd, J=18.6, 6.4, 1.7 Hz, 1H).

(S)-(5-(3,5-difluorophenyl)-4,5-dihydro-1H-pyrazol-1-yl)(3-((5-fluoro-2-(1-methyl-1H-1,2,4-triazol-5-yl)pyrimidin-4-yl)oxy)azetidin-1-yl)methanone (30)

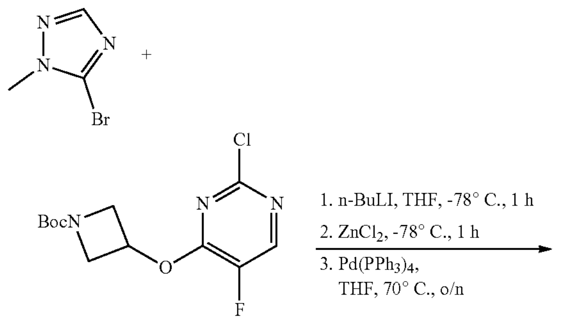

2-01

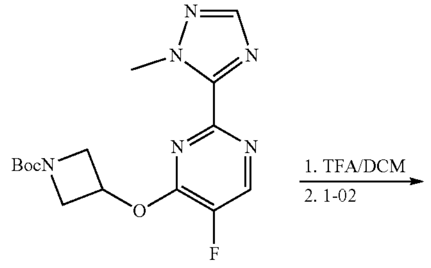

30-01

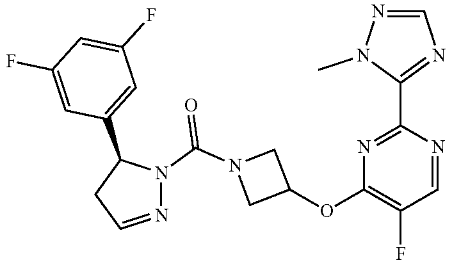

30

Step 1: To a solution of 5-bromo-1-methyl-1H-1,2,4-triazole (81 mg, 0.5 mmol) in THF (5 mL) was added n-BuLi (1.6 M, 0.38 mL, 0.6 mmol) under Ar at −78° C. The reaction was stirred at −78° C. for 1 h. Then $ZnCl_2$ (1M in THF, 0.6 mL, 0.6 mmol) was added to the reaction and stirred at −78° C. for another 0.5 h. The reaction mixture was allowed to warm to rt over 1 h at which time 2-01 (152 mg, 0.5 mmol) and $Pd(PPh_3)_4$ (115 mg, 0.1 mmol) in THF was added. The reaction mixture was stirred at 70° C. for 16 h. The reaction mixture was cooled to rt and diluted with water. The aqueous phase was extracted with EA. The combined organic extracts were washed with brine and dried over $Na_2SO_4$. The solvent was removed under vacuum and the crude product 30-01 was used to next step directly.

Step 2: To a solution of 30-01 (98 mg, 0.28 mmol) in DCM (5 mL) was added TFA (2 mL). The reaction was stirred at rt for 1 h. The solvent was removed under vacuum. To the resulting residue in THF (5 mL) was added TEA (3 mL) and (S)-(5-(3,5-difluorophenyl)-4,5-dihydro-1H-pyrazol-1-yl)(1H-imidazol-1-yl)methanone 1-02 (76 mg, 0.28 mmol). The reaction mixture was stirred at rt for 1 h. The reaction was cooled to rt and concentrated. The crude product was purified by Pre-TLC to give required product 30 (27 mg, 20.9%) as a white solid. Mass (m/z): 459.3 $[M+H]^+$. $^1H$ NMR (400 MHz, Chloroform-d) δ 8.55 (s, 1H), 8.01 (s, 1H), 6.84-6.65 (m, 4H), 5.69 (s, 1H), 5.27 (dd, J=12.1, 6.4 Hz, 1H), 4.66 (s, 2H), 4.32 (s, 5H), 3.45-3.22 (m, 2H), 2.70 (dd, J=18.5, 6.0 Hz, 1H).

(S)-(5-(3,5-difluorophenyl)-4,5-dihydro-1H-pyrazol-1-yl)(3-((5-fluoro-2-(4-methyl-4H-1,2,4-triazol-3-yl)pyridin-4-yl)oxy)azetidin-1-yl)methanone (31)

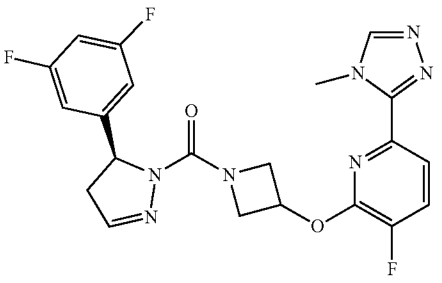 [SMILES: Cn1cnnc1-c1ccc(F)c(OC2CN(C(=O)N3N=CC[C@H]3c3cc(F)cc(F)c3)C2)n1]

The titled compound 31 was prepared from 1-05 according to the procedure outlined for compound 1. $^1H$ NMR (400 MHz, Chloroform-d) δ 7.92-7.86 (m, 2H), 7.55 (dd, J=9.5, 8.2 Hz, 1H), 6.85-6.65 (m, 4H), 5.53-5.42 (m, 1H), 5.31-5.25 (m, 1H), 4.63-4.54 (d, J=9.7 Hz, 2H), 4.46-4.33 (m, 2H), 4.29 (s, 3H), 3.36 (ddd, J=18.6, 12.2, 1.7 Hz, 1H), 2.72 (ddd, J=18.6, 6.5, 1.7 Hz, 1H). Mass (m/z) 458.2 $[M+H]^+$ (S)-(5-(3,5-difluorophenyl)-4,5-dihydro-1H-pyrazol-1-yl)(3-((5-fluoro-2-(1-methyl-1H-1,2,3-triazol-4-yl)pyridin-4-yl)oxy)azetidin-1-yl)methanone (32)

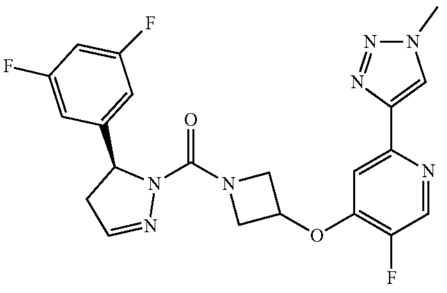 [SMILES: Cn1cc(-c2cc(OC3CN(C(=O)N4N=CC[C@H]4c4cc(F)cc(F)c4)C3)c(F)cn2)nn1]

The titled compound 32 was prepared from 29-01 in a yield of 42.9% according to the procedure outlined for compound 29. Mass (m/z): 458.2$[M+H]^+$. $^1H$ NMR (400 MHz, Chloroform-d) δ 8.42 (d, J=2.9 Hz, 11H), 8.20 (s, 11H), 7.30 (d, J=6.7 Hz, 11H), 6.82 (t, J=1.7 Hz, 11H), 6.80-6.68 (m, 3H), 5.36-5.26 (m, 11H), 5.19 (dt, J=6.5, 2.7 Hz, 11H), 4.68 (d, J=7.8 Hz, 2H), 4.36 (dd, J=32.6, 9.5 Hz, 2H), 4.27 (s, 3H), 3.39 (ddd, J=18.6, 12.2, 1.7 Hz, 1H), 2.74 (ddd, J=18.6, 6.5, 1.7 Hz, 1H).

(S)-(5-(3,5-difluorophenyl)-4,5-dihydro-1H-pyrazol-1-yl)(3-((5-fluoro-2-(2-methyl-2H-1,2,3-triazol-4-yl)pyridin-4-yl)oxy)azetidin-1-yl)methanone (33)

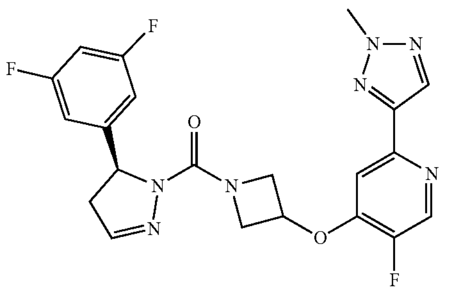 [SMILES: Cn1ncc(-c2cc(OC3CN(C(=O)N4N=CC[C@H]4c4cc(F)cc(F)c4)C3)c(F)cn2)n1]

The titled compound 33 was prepared from 29-01 in a yield of 38.2% according to the procedure outlined for compound 29. Mass (m/z): 458.1 $[M+H]^+$. $^1H$ NMR (400 MHz, Chloroform-d) δ 8.67 (d, J=3.8 Hz, 1H), 8.56 (s, 1H), 7.74 (d, J=7.0 Hz, 1H), 6.89-6.81 (m, 1H), 6.79-6.65 (m, 3H), 5.35-5.24 (m, 2H), 4.73 (s, 2H), 4.38 (dd, J=19.7, 10.8 Hz, 2H), 4.22 (s, 3H), 3.38 (ddd, J=18.7, 12.2, 1.7 Hz, 1H), 2.73 (ddd, J=18.6, 6.2, 1.7 Hz, 1H).

(S)-(5-(3,5-difluorophenyl)-4,5-dihydro-1H-pyrazol-1-yl)(3-((5-fluoro-2-(1-methyl-1H-1,2,3-triazol-5-yl)pyridin-4-yl)oxy)azetidin-1-yl)methanone (34)

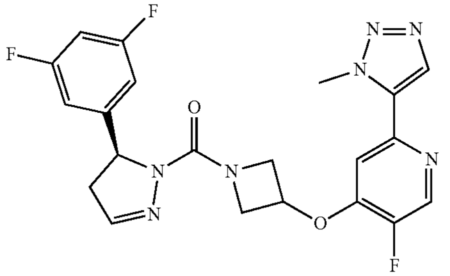 [SMILES: Cn1nncc1-c1cc(OC2CN(C(=O)N3N=CC[C@H]3c3cc(F)cc(F)c3)C2)c(F)cn1]

The titled compound 34 was prepared in 26.2% yield as white solid from 1-methyl-1H-1,2,3-triazole and 3-02 according to the procedure outlined for compound 30. Mass (m/z): 458.1 $[M+H]^+$. $^1H$ NMR (400 MHz, Chloroform-d) δ 8.46 (d, J=2.8 Hz, 1H), 8.02 (s, 1H), 6.98 (d, J=6.3 Hz, 1H), 6.80 (d, J=1.7 Hz, 1H), 6.78-6.66 (m, 3H), 5.28 (dd, J=12.1, 6.3 Hz, 1H), 5.16 (s, 1H), 4.64 (s, 2H), 4.37 (s, 3H), 4.35-4.23 (m, 2H), 3.46-3.30 (m, 11H), 2.71 (ddd, J=18.6, 6.4, 1.6 Hz, 11H).

(S)-(5-(3,5-difluorophenyl)-4,5-dihydro-1H-pyrazol-1-yl)(3-((2-(1,3-dimethyl-1H-pyrazol-5-yl)-5-fluoro-pyrimidin-4-yl)oxy)azetidin-1-yl)methanone (35)

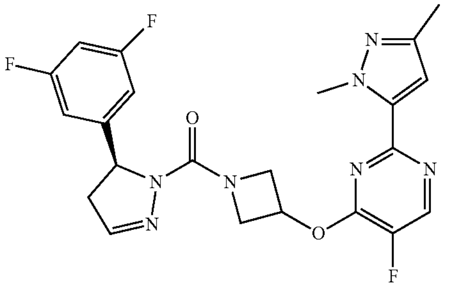 [SMILES: Cc1cc(-c2ncc(F)c(OC3CN(C(=O)N4N=CC[C@H]4c4cc(F)cc(F)c4)C3)n2)n(C)n1]

The titled compound 35 was prepared in 63.6% yield from 2-03 according to the procedure outlined for compound 2. $^1H$ NMR (400 MHz, Chloroform-d) δ 8.41 (d, J=2.4 Hz, 1H), 6.81-6.66 (m, 5H), 5.52 (tt, J=6.7, 4.2 Hz, 1H), 5.28 (dd, J=12.2, 6.5 Hz, 1H), 4.69-4.55 (m, 2H), 4.44-4.31 (m, 1H), 4.28 (s, 4H), 3.36 (ddd, J=18.6, 12.2, 1.7 Hz, 1H), 2.71 (ddd, J=18.6, 6.5, 1.7 Hz, 1H), 2.34 (s, 3H). Mass (m/z) 472.3 $[M+H]^+$.

(S)-(5-(3,5-difluorophenyl)-4,5-dihydro-1H-pyrazol-1-yl)(3-((2-(1,3-dimethyl-1H-pyrazol-5-yl)-5-fluoro-pyridin-4-yl)oxy)azetidin-1-yl)methanone (36)

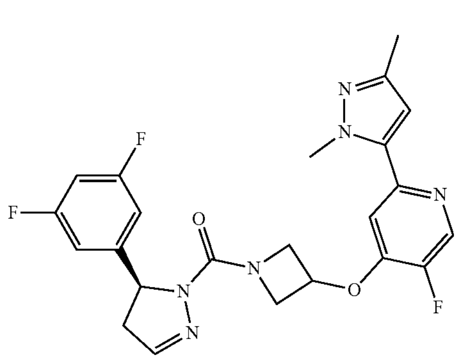 [SMILES: Cc1cc(-c2cc(OC3CN(C(=O)N4N=CC[C@H]4c4cc(F)cc(F)c4)C3)c(F)cn2)n(C)n1]

The titled compound 36 was prepared from 3-04 according to the procedure outlined for compound 3. Mass (m/z): 471.2 $[M+H]^+$. $^1H$ NMR (400 MHz, Chloroform-d) δ 8.43-8.40 (m, 1H), 6.86-6.65 (m, 5H), 6.28-6.22 (m, 1H), 5.32-5.24 (m, 1H), 5.12-5.04 (m, 1H), 4.67-4.54 (m, 2H), 4.41-4.32 (m, 1H), 4.31-4.23 (m, 1H), 4.11-4.06 (m, 3H), 3.42-3.31 (m, 1H), 2.77-2.67 (m, 1H), 2.33-2.27 (m, 3H).

(S)-(5-(3,5-difluorophenyl)-4,5-dihydro-1H-pyrazol-1-yl)(3-((2-(1,3-dimethyl-1H-pyrazol-4-yl)-5-fluoro-pyrimidin-4-yl)oxy)azetidin-1-yl)methanone (37)

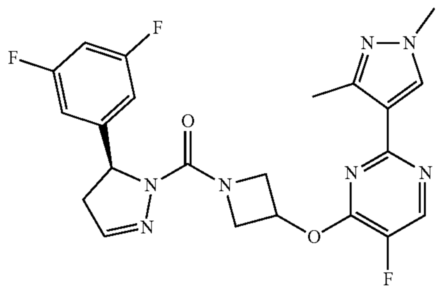 [SMILES: Cc1nn(C)cc1-c1ncc(F)c(OC2CN(C(=O)N3N=CC[C@H]3c3cc(F)cc(F)c3)C2)n1]

The titled compound 37 was prepared from 2-03 in 15.9% yield according to the procedure outlined for compound 2. $^1H$ NMR (400 MHz, Chloroform-d) δ 8.33 (d, J=2.7 Hz, 1H), 7.96 (s, 1H), 6.86-6.61 (m, 4H), 5.60-5.45 (m, 1H), 5.28 (dd, J=12.1, 6.4 Hz, 1H), 4.70-4.54 (m, 2H), 4.33 (dd, J=36.9, 10.4 Hz, 2H), 3.89 (s, 3H), 3.36 (dd, J=18.6, 12.1 Hz, 1H), 2.77-2.65 (m, 1H), 2.58 (s, 3H). Mass (m/z) 472.3 $[M+H]^+$.

(S)-(5-(3,5-difluorophenyl)-4,5-dihydro-1H-pyrazol-1-yl)(3-((2-(1,3-dimethyl-1H-pyrazol-4-yl)-5-fluoropyridin-4-yl)oxy)azetidin-1-yl)methanone (38)

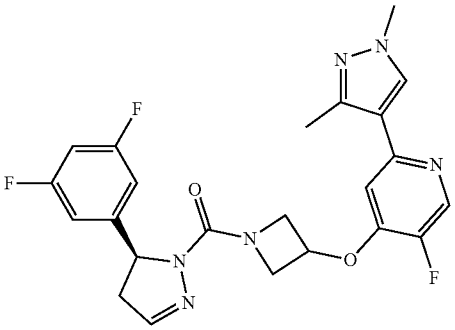 [SMILES: Cc1nn(C)cc1-c1cc(OC2CN(C(=O)N3N=CC[C@H]3c3cc(F)cc(F)c3)C2)c(F)cn1]

The titled compound 38 was prepared from 3-04 in a yield of 32% according to the procedure outlined for compound 3. Mass (m/z): 471.2[M+H]$^+$. $^1$H NMR (400 MHz, Chloroform-d) δ 8.35-8.32 (m, 1H), 7.74 (s, 1H), 6.82-6.65 (m, 5H), 5.27 (dd, J=12.3, 6.4 Hz, 1H), 5.11-5.04 (m, 1H), 4.65-4.52 (m, 2H), 4.41-4.33 (m, 1H), 4.32-4.23 (m, 1H), 3.87 (s, 3H), 3.42-3.31 (m, 1H), 2.76-2.66 (m, 1H), 2.47 (s, 3H).

(S)-(5-(3,5-difluorophenyl)-4,5-dihydro-1H-pyrazol-1-yl)(3-((5-fluoro-2-(1-methyl-1H-pyrazol-3-yl)pyrimidin-4-yl)oxy)azetidin-1-yl)methanone (39)

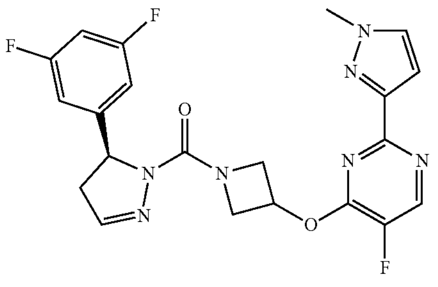 [SMILES: Cn1ccc(-c2ncc(F)c(OC3CN(C(=O)N4N=CC[C@H]4c4cc(F)cc(F)c4)C3)n2)n1]

The titled compound 39 was prepared in 47.4% yield from 3-04 according to the procedure outlined for compound 2. $^1$H NMR (400 MHz, Chloroform-d) δ 8.43 (d, J=2.5 Hz, 1H), 7.41 (d, J=2.3 Hz, 1H), 6.85 (d, J=2.3 Hz, 1H), 6.79 (t, J=1.7 Hz, 1H), 6.78-6.71 (m, 2H), 6.69 (ddd, J=8.9, 6.5, 2.3 Hz, 1H), 5.61 (tt, J=6.7, 4.3 Hz, 1H), 5.29 (dd, J=12.2, 6.4 Hz, 1H), 4.66 (t, J=10.0 Hz, 2H), 4.37 (d, J=9.9 Hz, 1H), 4.33-4.26 (m, 1H), 4.01 (s, 3H), 3.35 (ddd, J=18.6, 12.2, 1.7 Hz, 1H), 2.70 (ddd, J=18.6, 6.4, 1.8 Hz, 1H). Mass (m/z) 458.2 [M+H]$^+$.

(S)-(5-(3,5-difluorophenyl)-4,5-dihydro-1H-pyrazol-1-yl)(3-((2-(1,4-dimethyl-1H-imidazol-2-yl)-5-fluoropyridin-4-yl)oxy)azetidin-1-yl)methanone (40)

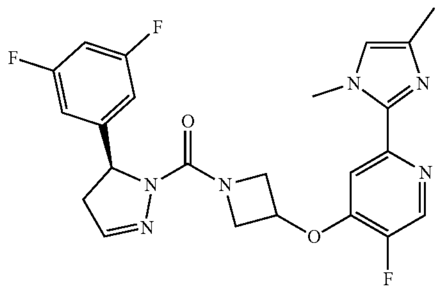 [SMILES: Cc1cn(C)c(-c2cc(OC3CN(C(=O)N4N=CC[C@H]4c4cc(F)cc(F)c4)C3)c(F)cn2)n1]

The titled compound 40 was prepared from 3-04 according to the procedure outlined for compound 3. Mass (m/z): 471.3[M+H]$^+$. $^1$H NMR (400 MHz, Chloroform-d) δ 8.31 (d, J=2.7 Hz, 1H), 7.57-7.49 (m, 1H), 6.81-6.73 (m, 3H), 6.72-6.65 (m, 2H), 5.27 (dd, J=12.2, 6.4 Hz, 1H), 5.21-5.15 (m, 1H), 4.70-4.57 (m, 2H), 4.36-4.22 (m, 2H), 4.01 (s, 3H), 3.34 (ddd, J=18.6, 12.2, 1.7 Hz, 1H), 2.69 (ddd, J=18.6, 6.5, 1.7 Hz, 1H), 2.26 (s, 3H).

(S)-(3-((2-(3-amino-1-methyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (41)

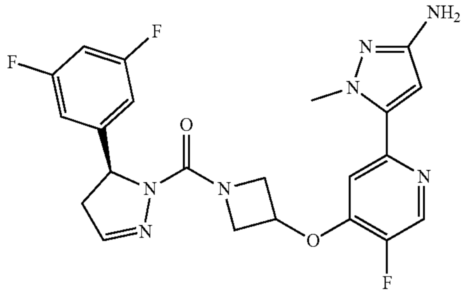 [SMILES: Cn1nc(N)cc1-c1cc(OC2CN(C(=O)N3N=CC[C@H]3c3cc(F)cc(F)c3)C2)c(F)cn1]

The titled compound 41 was prepared from 29-01 and 5-bromo-1-methyl-1H-pyrazol-3-amine according to the procedure outlined for compound 29. Mass (m/z): 472.3 [M+H]$^+$. $^1$H NMR (400 MHz, Chloroform-d) δ 8.40 (d, J=2.9 Hz, 1H), 6.84-6.65 (m, 5H), 5.82 (s, 1H), 5.27 (dd, J=12.2, 6.4 Hz, 1H), 5.12-5.02 (m, 1H), 4.66-4.51 (m, 2H), 4.40-4.22 (m, 2H), 3.97 (s, 3H), 3.36 (ddd, J=18.7, 12.2, 1.7 Hz, 1H), 2.71 (ddd, J=18.6, 6.4, 1.7 Hz, 1H).

(S)-(5-(3,5-difluorophenyl)-4,5-dihydro-1H-pyrazol-1-yl)(3-((2-(1,4-dimethyl-1H-pyrazol-5-yl)-5-fluoropyrimidin-4-yl)oxy)azetidin-1-yl)methanone (42)

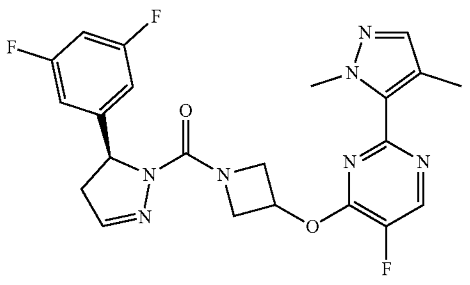 [SMILES: Cc1cnn(C)c1-c1ncc(F)c(OC2CN(C(=O)N3N=CC[C@H]3c3cc(F)cc(F)c3)C2)n1]

The titled compound 42 was prepared in 9.8% yield according to the procedure outlined for compound 2. $^1$H NMR (400 MHz, Chloroform-d) δ 8.47 (d, J=2.4 Hz, 1H), 7.40 (s, 1H), 6.81-6.67 (m, 4H), 5.56-5.50 (m, 1H), 5.27 (dd, J=12.2, 6.4 Hz, 1H), 4.63 (d, J=17.2 Hz, 2H), 4.33 (dd, J=33.8, 10.8 Hz, 2H), 4.21 (s, 3H), 3.36 (ddd, J=18.7, 12.1, 1.7 Hz, 1H), 2.71 (ddd, J=18.6, 6.5, 1.7 Hz, 1H), 2.33 (s, 3H). Mass (m/z) 472.3 [M+H]$^+$.

(S)-(5-(3,5-difluorophenyl)-4,5-dihydro-1H-pyrazol-1-yl)(3-((2-(1,4-dimethyl-1H-pyrazol-5-yl)-5-fluoropyridin-4-yl)oxy)azetidin-1-yl)methanone (43)

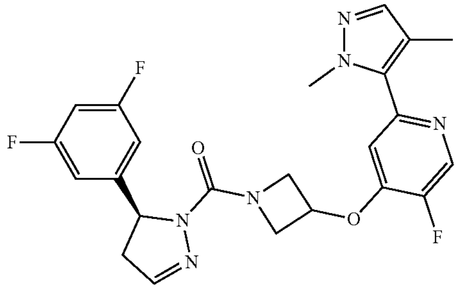 [SMILES: Cc1cnn(C)c1-c1cc(OC2CN(C(=O)N3N=CC[C@H]3c3cc(F)cc(F)c3)C2)c(F)cn1]

The titled compound 43 was prepared from 3-02 according to the procedure outlined for compound 3. Mass (m/z): 471.3[M+H]$^+$. $^1$H NMR (400 MHz, Chloroform-d) δ 8.52-8.47 (m, 1H), 7.36 (s, 1H), 6.83-6.65 (m, 5H), 5.27 (dd, J=12.2, 6.5 Hz, 1H), 5.10-5.03 (m, 1H), 4.66-4.52 (m, 2H), 4.44-4.33 (m, 1H), 4.33-4.24 (m, 1H), 3.96 (s, 3H), 3.43-3.30 (m, 1H), 2.76-2.67 (m, 1H), 2.12 (s, 3H).

(S)-(5-(3,5-difluorophenyl)-4,5-dihydro-1H-pyrazol-1-yl)(3-((6-(1,4-dimethyl-1H-imidazol-5-yl)-3-fluoropyridin-2-yl)oxy)azetidin-1-yl)methanone (44)

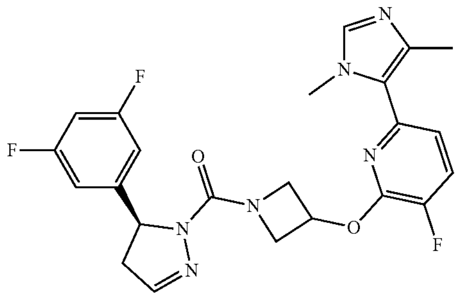 [SMILES: Cc1ncn(C)c1-c1ccc(F)c(OC2CN(C(=O)N3N=CC[C@H]3c3cc(F)cc(F)c3)C2)n1]

The titled compound 44 was prepared from 1-05 in a yield of 16.5% according to the procedure outlined for compound 1. $^1$H NMR (400 MHz, Chloroform-d) δ 9.01 (s, 1H), 7.94 (t, J=8.6 Hz, 1H), 7.47-7.35 (m, 1H), 7.22-6.99 (m, 4H), 5.80-5.72 (m, 1H), 5.67-5.61 (m, 1H), 5.01-4.88 (m, 2H), 4.69 (dd, J=25.3, 10.4 Hz, 2H), 4.28 (s, 3H), 3.74 (dd, J=18.4, 12.4 Hz, 1H), 3.08 (dd, J=18.6, 6.4 Hz, 1H), 2.84 (s, 3H). Mass (m/z) 471.2 [M+H]$^+$ (S)-(5-(3,5-difluorophenyl)-4,5-dihydro-1H-pyrazol-1-yl)(3-((2-(1,4-dimethyl-1H-imidazol-5-yl)-5-fluoropyridin-4-yl)oxy)azetidin-1-yl)methanone (45)

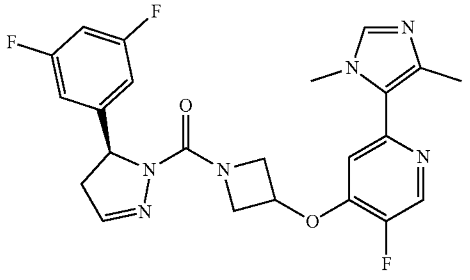 [SMILES: Cc1ncn(C)c1-c1cc(OC2CN(C(=O)N3N=CC[C@H]3c3cc(F)cc(F)c3)C2)c(F)cn1]

The titled compound 45 was prepared from 3-04 according to the procedure outlined for compound 3. LC-Mass (m/z): 471.3 [M+H]$^+$. $^1$H NMR (400 MHz, Chloroform-d) δ 8.43 (d, J=3.0 Hz, 1H), 7.50-7.42 (m, 1H), 6.82-6.66 (m, 5H), 5.27 (dd, J=12.2, 6.4 Hz, 1H), 5.10-5.03 (m, 1H), 4.65-4.51 (s, 2H), 4.41-4.24 (m, 2H), 3.77 (s, 3H), 3.36 (ddd, J=18.6, 12.2, 1.7 Hz, 1H), 2.71 (ddd, J=18.6, 6.5, 1.7 Hz, 1H), 2.35 (s, 3H).

(S)-(5-(3,5-difluorophenyl)-4,5-dihydro-1H-pyrazol-1-yl)(3-((2-(1,4-dimethyl-1H-1,2,3-triazol-5-yl)-5-fluoropyrimidin-4-yl)oxy)azetidin-1-yl)methanone (46)

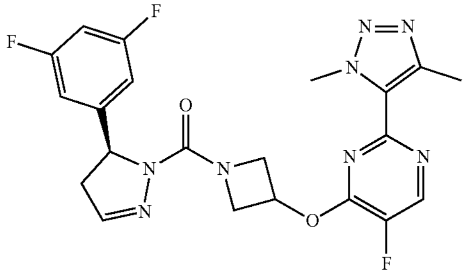 [SMILES: Cc1nnn(C)c1-c1ncc(F)c(OC2CN(C(=O)N3N=CC[C@H]3c3cc(F)cc(F)c3)C2)n1]

The titled compound 46 was prepared in 45.1% yield as white solid from 2-01 and 1,4-dimethyl-1H-1,2,3-triazole according to the procedure outlined for compound 30. Mass (m/z): 473.1 [M+H]$^+$. $^1$H NMR (400 MHz, Chloroform-d) δ 8.47 (d, J=2.3 Hz, 1H), 6.84-6.60 (m, 4H), 5.54 (tt, J=6.6, 4.0 Hz, 1H), 5.27 (dd, J=12.2, 6.5 Hz, 1H), 4.62 (dt, J=16.6, 9.0 Hz, 2H), 4.37 (s, 4H), 4.29 (dd, J=10.3, 3.6 Hz, 1H), 3.36 (ddd, J=18.6, 12.2, 1.7 Hz, 1H), 2.71 (ddd, J=18.6, 6.5, 1.7 Hz, 1H), 2.64 (s, 3H).

(S)-(5-(3,5-difluorophenyl)-4,5-dihydro-1H-pyrazol-1-yl)(3-((2-(1,4-dimethyl-1H-1,2,3-triazol-5-yl)-5-fluoropyridin-4-yl)oxy)azetidin-1-yl)methanone (47)

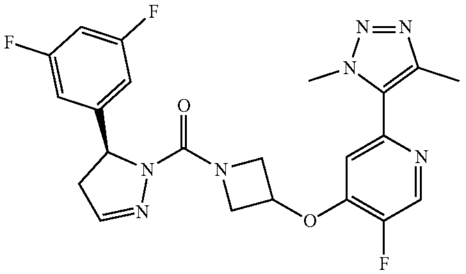 [SMILES: Cc1nnn(C)c1-c1cc(OC2CN(C(=O)N3N=CC[C@H]3c3cc(F)cc(F)c3)C2)c(F)cn1]

The titled compound 47 was prepared in 30.8% yield as white solid from 3-02 and 1,4-dimethyl-1H-1,2,3-triazole according to the procedure outlined for compound 30. Mass (m/z): 472.3 $[M+H]^+$. $^1H$ NMR (400 MHz, Chloroform-d) δ 8.50 (d, J=2.9 Hz, 1H), 6.80 (d, J=1.6 Hz, 1H), 6.79-6.66 (m, 4H), 5.27 (dd, J=12.1, 6.4 Hz, 1H), 5.09 (s, 1H), 4.60 (s, 2H), 4.37 (d, J=10.3 Hz, 1H), 4.29 (d, J=10.0 Hz, 1H), 4.18 (s, 3H), 3.37 (dd, J=18.6, 12.1 Hz, 1H), 2.76-2.67 (m, 1H), 2.45 (s, 3H).

(S)-5-(4-((1-(5-(3,5-difluorophenyl)-4,5-dihydro-1H-pyrazole-1-carbonyl)azetidin-3-yl)oxy)-5-fluoropyrimidin-2-yl)-1-methyl-1H-pyrazole-4-carbonitrile (48)

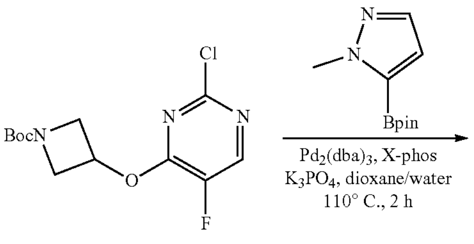

2-01

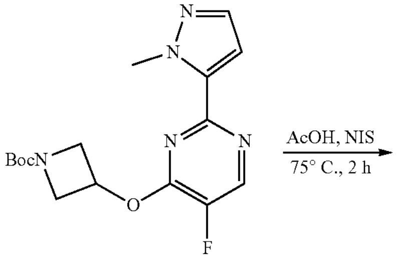

48-01

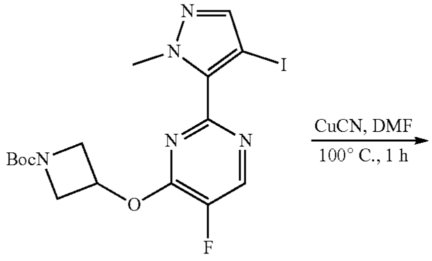

48-02

-continued

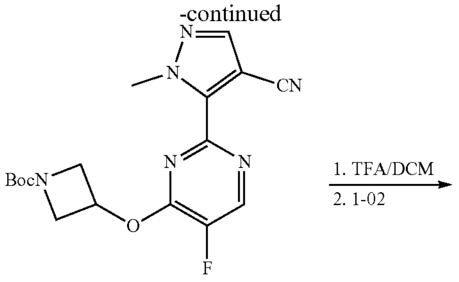

48-03

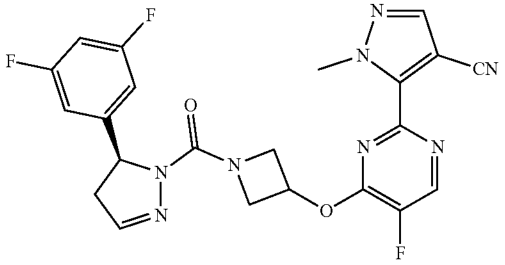

48

Step 1: A mixture of Compound 2-01 (1 g, 3.3 mmol), 1-methyl-5-(4,4,5,5-tetramethyl-1,3,2-dioxaborolan-2-yl)-1H-pyrazole (820 mg, 3.96 mmol), $Pd_2(dba)_3$ (310 mg, 0.33 mmol), X-Phos (320 mg, 0.66 mmol) and $K_3PO_4$ (3.5 g, 16.5 mmol) in dioxane (10 mL) and water (3 mL) was stirred under Ar at 110° C. for 2 h. The reaction mixture was cooled to rt and diluted with water. The aqueous phase was extracted with EA. The combined organic extracts were washed with brine and dried over $Na_2SO_4$. The solvent was removed under vacuum and the crude product 48-01 was used to next step directly.

Step 2: To a solution of 48-01 (1.3 g, 3.7 mmol) in AcOH (20 mL) was added NIS (1 g, 4.5 mmol). The reaction was stirred at 75° C. for 2 h. The reaction was quenched with water and extracted with EA. The combined organic extracts were washed with saturated aqueous $NaHCO_3$ and brine, dried over $Na_2SO_4$ and concentrated to give the crude product 48-02 which was used for next step directly.

Step 3: A mixture of Compound 48-02 (480 mg, 1.26 mmol) and CuCN (340 mg, 3.78 mmol) in DMF (10 mL) was stirred at 100° C. for 1 h. The reaction mixture was cooled to rt and diluted with water. The aqueous phase was extracted with EA. The combined organic extracts were washed with brine and dried over $Na_2SO_4$. The solvent was removed under vacuum and the crude product 48-03 was used to next step directly.

Step 4: To a solution of tert-butyl 3-((2-(4-cyano-1-methyl-1H-pyrazol-5-yl)-5-fluoropyrimidin-4-yl)oxy)azetidine-1-carboxylate 48-03 (200 mg, 0.53 mmol) in DCM (5 mL) was added TFA (2 mL). The reaction was stirred at rt for 1 h. The solvent was removed under vacuum. To the resulting residue in THE (5 mL) was added TEA (3 mL) and (S)-(5-(3,5-difluorophenyl)-4,5-dihydro-11H-pyrazol-1-yl)(1H-imidazol-1-yl)methanone (133 mg, 0.48 mmol), the reaction mixture was stirred at rt for 1 h. The reaction was cooled to rt and concentrated. The crude product was purified by Pre-TLC to give required product 48 (50 mg, 21.4%) as a white solid. MS (m/z): 483.3 $[M+H]^+$. $^1H$ NMR (300 MHz, Chloroform-d) δ 8.49 (d, J=2.3 Hz, 1H), 7.85 (s, 1H), 6.80-6.73 (m, 3H), 6.69 (tt, J=8.8, 2.2 Hz, 1H), 5.76 (tt, J=6.7, 3.6 Hz, 1H), 5.27 (dd, J=12.2, 6.4 Hz, 1H), 4.73 (s, 2H), 4.34 (s, 3H), 4.32-4.20 (m, 2H), 3.35 (ddd, J=18.5, 12.2, 1.7 Hz, 1H), 2.69 (ddd, J=18.5, 6.4, 1.7 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carbonitrile (49)

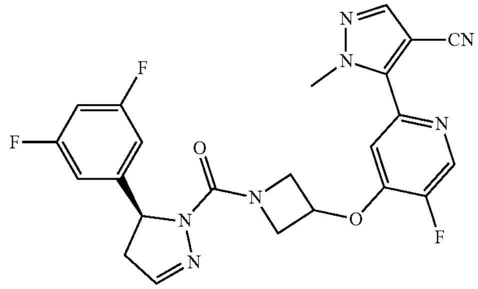 [SMILES: Cn1ncc(C#N)c1-c1cc(OC2CN(C(=O)N3N=CC[C@H]3c3cc(F)cc(F)c3)C2)c(F)cn1]

The title compound 49 was prepared in a yield of 62% (200 mg, 0.42 mmol) as a white solid from 3-02 according to the procedure for 48. Mass (m/z): 482.3 [M+H]$^+$; $^1$H NMR (400 MHz, Chloroform-d) δ 8.51 (d, J=2.7 Hz, 1H), 7.82 (s, 1H), 7.30 (d, J=6.4 Hz, 1H), 6.81-6.73 (m, 3H), 6.69 (tt, J=8.9, 2.4 Hz, 1H), 5.27 (dd, J=12.2, 6.4 Hz, 1H), 5.16-5.09 (m, 1H), 4.74-4.60 (m, 2H), 4.40-4.26 (m, 2H), 4.19 (s, 3H), 3.35 (ddd, J=18.6, 12.2, 1.7 Hz, 1H), 2.70 (ddd, J=18.6, 6.5, 1.7 Hz, 1H).

(S)-(5-(3,5-difluorophenyl)-4,5-dihydro-1H-pyrazol-1-yl)(3-((5-fluoro-2-(4-methoxy-1-methyl-1H-pyrazol-5-yl)pyridin-4-yl)oxy)azetidin-1-yl)methanone (50)

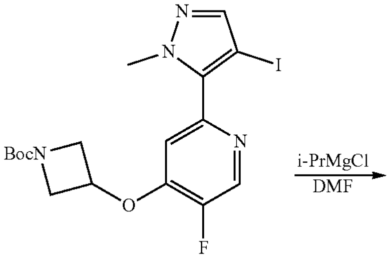

50-01

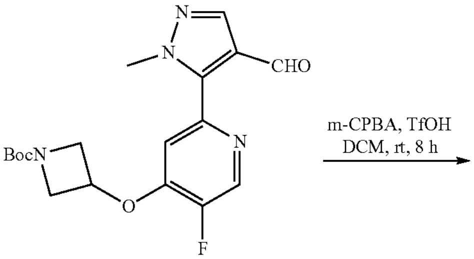

50-02

-continued

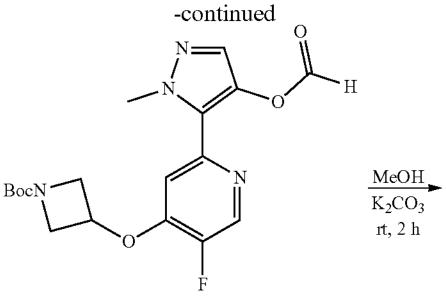

50-03

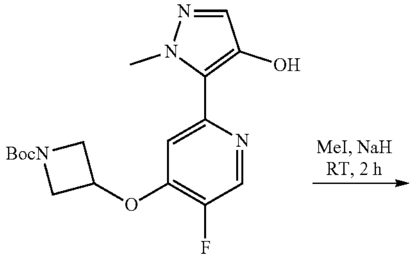

50-04

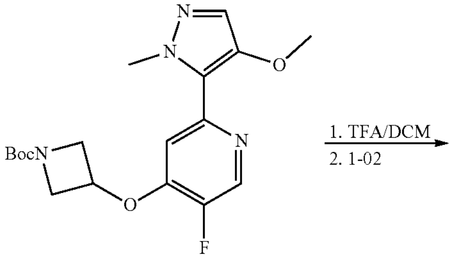

50-05

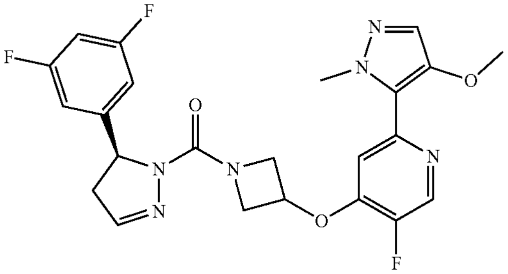

50

Step 1: To a solution of 50-01 (1 g, 2.1 mmol) in THE (5 mL) was added i-PrMgCl (2 M, 5.2 mL, 10.5 mmol) at 0° C. The reaction was stirred at 0° C. for 1 h then DMF (3 mL) was added. The reaction was stirred at RT for 2 h. The reaction was quenched with saturated $NH_4Cl$ and extracted with EA. The combined organic extracts were washed with brine and dried over $Na_2SO_4$. The solvent was removed under vacuum and the crude product 50-02 was used to next step directly.

Step 2: A mixture of 50-02 (800 mg, 2.1 mmol), TfOH (32 mg, 0.21 mmol) and m-CPBA (732 mg, 4.2 mmol) in DCM (20 mL) was stirred at RT for 6 h. The reaction mixture diluted with water. The aqueous phase was extracted with EA. The combined organic extracts were washed with brine and dried over $Na_2SO_4$. The solvent was removed under vacuum and the crude product 50-03 was used to next step directly.

Step 3: A mixture of 50-03 (300 mg, 0.83 mmol) and $K_2CO_3$ (344 mg, 3.5 mmol) in MeOH (20 mL) was stirred at RT for 2 h. The reaction mixture filtered and concentrated to give the crude product 50-04 was used to next step directly.

Step 4: To a solution of 50-04 (80 mg, 0.22 mmol) in THE (5 mL) was added NaH (17 mg, 0.43 mmol) at 0° C. The reaction was stirred at rt for 1 h then MeI (63 mg, 0.43 mmol) was added. The reaction was stirred at RT for 2 h. The reaction was quenched with saturated $NH_4Cl$ and extracted with EA. The combined organic extracts were washed with brine and dried over $Na_2SO_4$. The solvent was removed under vacuum and the crude product 50-05 was used to next step directly.

Step 5: To a solution of 50-05 (40 mg, 0.1 mmol) in DCM (5 mL) was added TFA (2 mL). The reaction was stirred at rt for 1 h. The solvent was removed under vacuum. To the resulting residue in THE (5 mL) was added TEA (3 mL) and 1-02 (26 mg, 0.09 mmol). The reaction mixture was stirred at rt for 1 h. The reaction was cooled to rt and concentrated. The crude product was purified by Pre-TLC to give required product 50 (14 mg, 27.4%) as a white solid. Mass (m/z): 487.2 $[M+H]^+$. $^1H$ NMR (400 MHz, Chloroform-d) δ 8.40 (d, J=2.9 Hz, 1H), 7.30 (s, 1H), 7.27-7.25 (m, 1H), 6.82-6.79 (m, 1H), 6.78-6.66 (m, 3H), 5.28 (dd, J=12.2, 6.4 Hz, 1H), 5.08 (ddd, J=10.5, 6.5, 4.1 Hz, 1H), 4.60 (d, J=7.9 Hz, 2H), 4.33 (dd, J=37.0, 10.8 Hz, 2H), 4.17 (s, 3H), 3.87 (s, 3H), 3.36 (ddd, J=18.6, 12.2, 1.7 Hz, 1H), 2.71 (ddd, J=18.6, 6.4, 1.7 Hz, 1H).

(S)-(5-(3,5-difluorophenyl)-4,5-dihydro-1H-pyrazol-1-yl)(3-((2-(4-(2-(dimethylamino)ethoxy)-1-methyl-1H-pyrazol-5-yl)-5-fluoropyridin-4-yl)oxy)azetidin-1-yl)methanone (51)

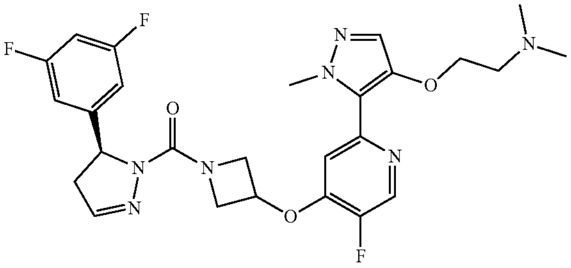 [SMILES: CN(C)CCOc1cnn(C)c1-c1cc(OC2CN(C(=O)N3N=CC[C@H]3c3cc(F)cc(F)c3)C2)c(F)cn1]

The titled compound 51 was prepared in 17.6% yield as white solid from 50-04 and 2-bromo-N,N-dimethylethan-1-amine according to the procedure outlined for compound 50. Mass (m/z): 544.1 $[M+H]^+$. $^1H$ NMR (400 MHz, Chloroform-d) δ 8.37 (d, J=2.8 Hz, 1H), 7.28 (s, 1H), 7.04 (d, J=6.5 Hz, 1H), 6.84 (s, 1H), 6.73-6.58 (m, 3H), 5.19 (dd, J=11.6, 6.1 Hz, 2H), 4.57 (s, 2H), 4.46 (s, 2H), 4.21 (s, 2H), 3.99 (s, 3H), 3.40-3.26 (m, 3H), 2.78 (s, 6H), 2.66 (dd, J=18.5, 6.0 Hz, 1H).

(S)-(5-(3,5-difluorophenyl)-4,5-dihydro-1H-pyrazol-1-yl)(3-((5-fluoro-2-(4-(2-methoxyethoxy)-1-methyl-1H-pyrazol-5-yl)pyridin-4-yl)oxy)azetidin-1-yl)methanone (52)

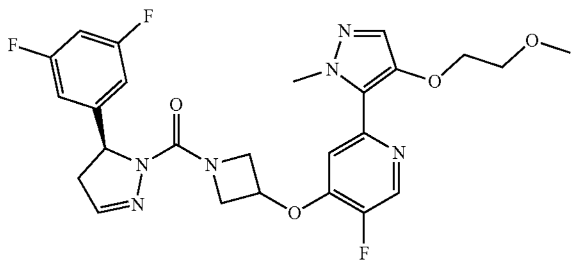 [SMILES: COCCOc1cnn(C)c1-c1cc(OC2CN(C(=O)N3N=CC[C@H]3c3cc(F)cc(F)c3)C2)c(F)cn1]

The titled compound 52 was prepared in 11.1% yield as white solid from 50-04 and 1-bromo-2-methoxyethane according to the procedure outlined for compound 50. Mass (m/z): 531.1 $[M+H]^+$. $^1H$ NMR (400 MHz, Chloroform-d) δ 8.41 (s, 1H), 7.43 (d, J=6.3 Hz, 1H), 7.35 (s, 1H), 6.80 (s, 1H), 6.77-6.66 (m, 3H), 5.35-5.25 (m, 1H), 5.10 (s, 1H), 4.64 (s, 2H), 4.33 (d, J=26.2 Hz, 2H), 4.23-4.13 (m, 5H), 3.73 (s, 2H), 3.40 (s, 3H), 3.38-3.32 (m, 1H), 2.71 (dd, J=18.5, 5.7 Hz, 1H).

(S)-(3-((2-(4-amino-1-methyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (53)

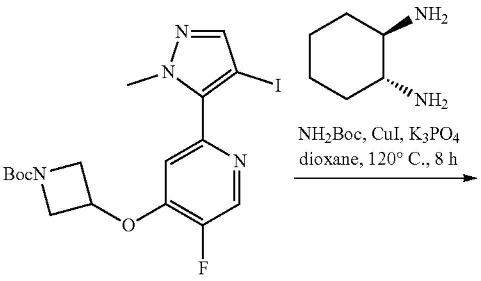

50-01

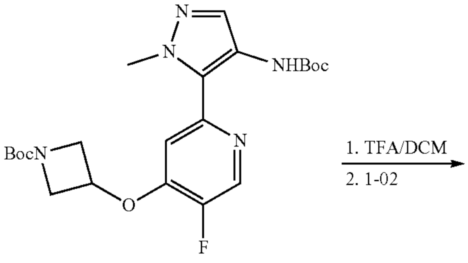

53-01

-continued

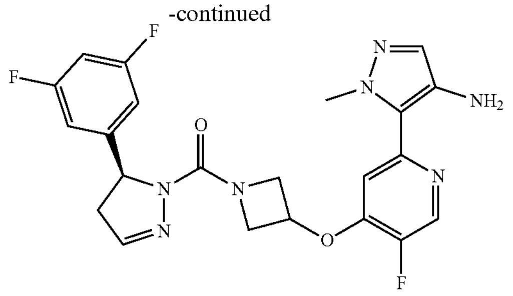

53

Step 1: A mixture of tert-butyl 3-((5-fluoro-2-(4-iodo-1-methyl-1H-pyrazol-5-yl)pyridin-4-yl)oxy)azetidine-1-carboxylate 50-01 (500 mg, 1.05 mmol), (1R,2R)-cyclohexane-1,2-diamine (240 mg, 2.1 mmol), $NH_2Boc$ (182 mg, 1.58 mmol), CuI (19 mg, 0.105 mmol) and $K_3PO_4$ (445 mg, 2.1 mmol) in dioxane (10 mL) was stirred under Ar at 120° C. for 8 h. The reaction mixture was cooled to rt and diluted with water. The aqueous phase was extracted with EA. The combined organic extracts were washed with brine and dried over $Na_2SO_4$. The solvent was removed under vacuum and the crude product 53-01 was used to next step directly.

Step 2: The titled compound 53 was prepared in 57.3% yield as white solid from 53-01 according to the procedure outlined for compound 50 from 50-05. Mass (m/z): 472.1 $[M+H]^+$. $^1H$ NMR (400 MHz, Chloroform-d) δ 8.45 (d, J=2.8 Hz, 1H), 7.27 (s, 1H), 7.06 (d, J=6.4 Hz, 1H), 6.79 (s, 1H), 6.69 (t, J=6.9 Hz, 3H), 5.14 (s, 2H), 4.72 (d, J=8.0 Hz, 1H), 4.63 (s, 1H), 4.38 (s, 1H), 4.25 (s, 1H), 3.99 (s, 3H), 3.34 (dd, J=18.6, 12.0 Hz, 1H), 2.67 (dd, J=18.4, 6.4 Hz, 1H).

(S)-(5-(3,5-difluorophenyl)-4,5-dihydro-1H-pyrazol-1-yl)(3-((5-fluoro-2-(1-methyl-4-(methylamino)-1H-pyrazol-5-yl)pyridin-4-yl)oxy)azetidin-1-yl)methanone (54)

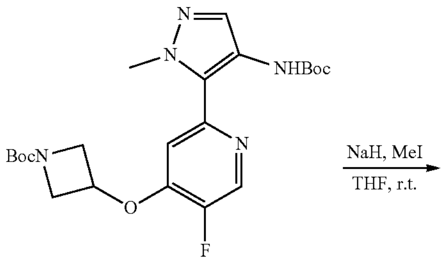

50-01

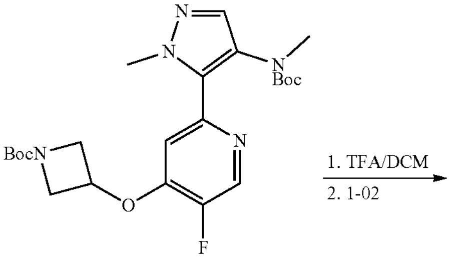

54-01

-continued

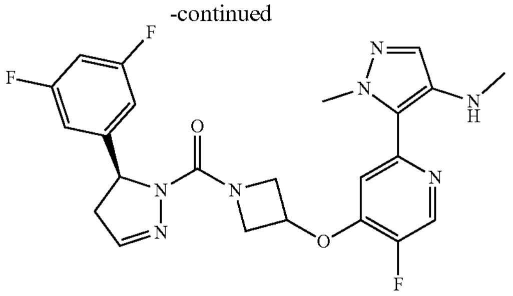

54

The titled compound 54 was prepared in 42.6% yield as white solid from 50-01 and Iodomethane according to the procedure outlined for compound 50. Mass (m/z): 486.2 $[M+H]^+$. $^1H$ NMR (400 MHz, Chloroform-d) δ 8.43 (d, J=3.0 Hz, 1H), 7.25 (s, 1H), 6.65 (d, J=6.5 Hz, 1H), 6.82-6.79 (m, 1H), 6.77-6.65 (m, 3H), 5.26 (dd, J=12.2, 6.4 Hz, 1H), 5.15-5.05 (m, 1H), 4.62 (t, J=8.7 Hz, 2H), 4.32 (dd, J=35.5, 9.6 Hz, 2H), 4.00 (s, 3H), 3.36 (ddd, J=18.6, 12.2, 1.7 Hz, 1H), 2.83 (s, 3H), 2.71 (ddd, J=18.6, 6.4, 1.7 Hz, 1H).

(S)-(5-(3,5-difluorophenyl)-4,5-dihydro-1H-pyrazol-1-yl)(3-((2-(4-(dimethylamino)-1-methyl-1H-pyrazol-5-yl)-5-fluoropyridin-4-yl)oxy)azetidin-1-yl)methanone (55)

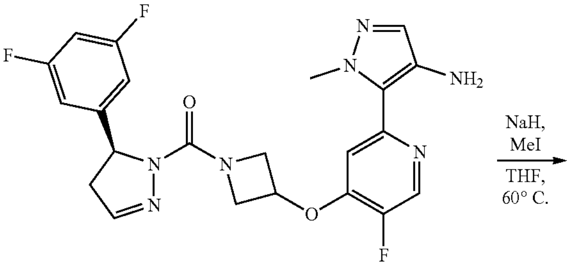

53

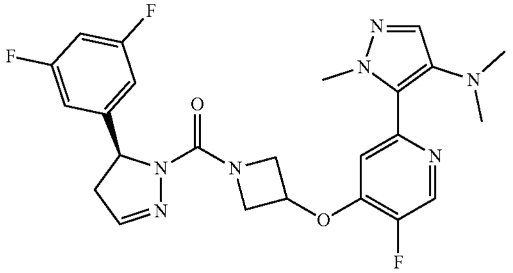

55

To a solution of 53 (64 mg, 0.14 mmol) in THE (5 mL) was added NaH (11 mg, 0.27 mmol) at 0° C. The reaction was stirred at rt for 1 h then MeI (77 mg, 0.54 mmol) was added. The reaction was stirred at rt for 16 h. The reaction was quenched with saturated $NH_4Cl$ and extracted with EA. The combined organic extracts were washed with brine and dried over $Na_2SO_4$. The solvent was removed under vacuum. The crude product was purified by Pre-TLC to give required product 55 (20 mg, 29.5%) as a white solid. Mass (m/z): 500.2 $[M+H]^+$. $^1H$ NMR (400 MHz, Chloroform-d) δ

8.43 (s, 1H), 7.62 (s, 1H), 6.79 (s, 1H), 6.77-6.66 (m, 4H), 5.27 (dd, J=12.2, 6.4 Hz, 1H), 5.07 (s, 1H), 4.61 (s, 2H), 4.43-4.22 (m, 2H), 4.05 (s, 3H), 3.46-3.30 (m, 1H), 2.70 (dd, J=18.6, 6.4 Hz, 1H), 1.31-1.18 (m, 6H).

(S)-(5-(3,5-difluorophenyl)-4,5-dihydro-1H-pyrazol-1-yl)(3-((5-fluoro-2-(4-((2-methoxyethyl)amino)-1-methyl-1H-pyrazol-5-yl)pyridin-4-yl)oxy)azetidin-1-yl)methanone (56)

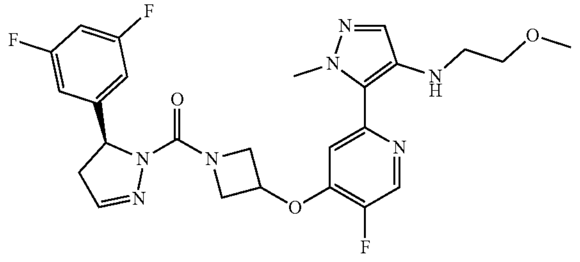 [SMILES: COCCNc1cnn(C)c1-c1cc(OC2CN(C(=O)N3N=CC[C@H]3c3cc(F)cc(F)c3)C2)c(F)cn1]

The titled compound 56 was prepared in 41.6% yield as white solid from 53-01 and 1-bromo-2-methoxyethane according to the procedure outlined for compound 50-04 to 50. Mass (m/z): 530.1 $[M+H]^+$. $^1H$ NMR (400 MHz, Chloroform-d) δ 8.46 (d, J=2.6 Hz, 1H), 7.75 (s, 1H), 7.07 (d, J=6.1 Hz, 1H), 6.82 (s, 1H), 6.78-6.65 (m, 4H), 5.29 (dd, J=12.1, 6.0 Hz, 1H), 5.20 (s, 1H), 4.63 (s, 2H), 4.42-4.26 (m, 2H), 4.08 (s, 3H), 3.64 (s, 2H), 3.42 (s, 2H), 3.40-3.36 (m, 1H), 3.34 (s, 3H), 2.72 (dd, J=18.7, 5.9 Hz, 1H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)acetamide 57)

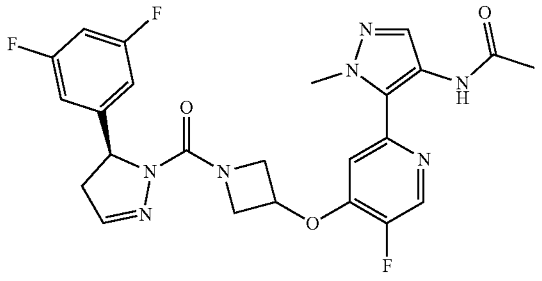 [SMILES: CC(=O)Nc1cnn(C)c1-c1cc(OC2CN(C(=O)N3N=CC[C@H]3c3cc(F)cc(F)c3)C2)c(F)cn1]

The titled compound 57 was prepared in 28.2% yield as white solid from 50-01 and Acetamide according to the procedure outlined for compound 53. Mass (m/z): 514.1 $[M+H]^+$. $^1H$ NMR (400 MHz, Chloroform-d) δ 8.99 (s, 1H), 8.48 (s, 1H), 8.11 (s, 1H), 6.87 (d, J=6.3 Hz, 1H), 6.79 (s, 1H), 6.77-6.65 (m, 3H), 5.26 (dd, J=12.2, 6.4 Hz, 1H), 5.08 (s, 1H), 4.60 (s, 2H), 4.32 (dd, J=31.1, 9.6 Hz, 2H), 4.01 (s, 3H), 3.36 (dd, J=18.6, 11.9 Hz, 1H), 2.71 (dd, J=18.6, 6.1 Hz, 1H), 2.14 (s, 3H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)propionamide (58)

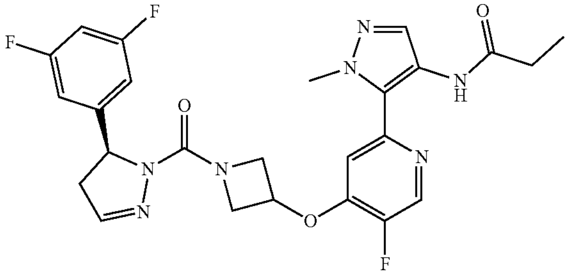 [SMILES: CCC(=O)Nc1cnn(C)c1-c1cc(OC2CN(C(=O)N3N=CC[C@H]3c3cc(F)cc(F)c3)C2)c(F)cn1]

The titled compound 58 was prepared in 39.9% yield as white solid from 50-01 according to the procedure outlined for compound 53. Mass (m/z): 528.1 $[M+H]^+$. $^1H$ NMR (400 MHz, Chloroform-d) δ 9.23 (s, 1H), 8.48 (d, J=3.0 Hz, 1H), 8.21 (s, 1H), 6.87 (d, J=6.4 Hz, 1H), 6.82-6.78 (m, 1H), 6.78-6.62 (m, 3H), 5.27 (dd, J=12.2, 6.4 Hz, 1H), 5.09 (d, J=3.7 Hz, 1H), 4.62 (d, J=15.9 Hz, 2H), 4.33 (dd, J=31.3, 9.8 Hz, 2H), 4.04 (s, 3H), 3.36 (ddd, J=18.6, 12.2, 1.7 Hz, 1H), 2.72 (ddd, J=18.6, 6.4, 1.7 Hz, 1H), 2.40 (q, J=7.6 Hz, 2H), 1.24 (t, J=7.6 Hz, 4H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)isobutyramide (59)

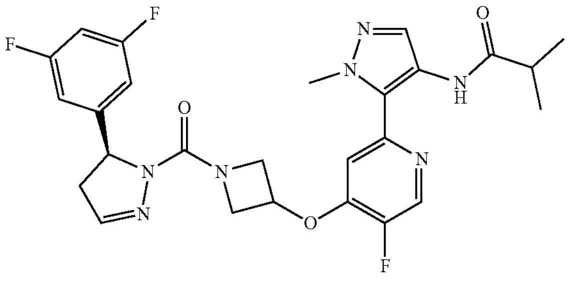 [SMILES: CC(C)C(=O)Nc1cnn(C)c1-c1cc(OC2CN(C(=O)N3N=CC[C@H]3c3cc(F)cc(F)c3)C2)c(F)cn1]

The titled compound 59 was prepared in 42.2% yield as white solid from 50-01 according to the procedure outlined for compound 53. Mass (m/z): 542.3 $[M+H]^+$. $^1H$ NMR (400 MHz, Chloroform-d) δ 9.49 (s, 1H), 8.48 (d, J=3.0 Hz, 1H), 8.25 (s, 1H), 6.87 (d, J=6.4 Hz, 1H), 6.83-6.79 (m, 1H), 6.79-6.65 (m, 3H), 5.27 (dd, J=12.2, 6.4 Hz, 1H), 5.18-5.07 (m, 1H), 4.70-4.53 (m, 2H), 4.33 (dd, J=33.2, 9.7 Hz, 2H), 4.05 (s, 3H), 3.37 (ddd, J=18.7, 12.2, 1.7 Hz, 1H), 2.72 (ddd, J=18.6, 6.5, 1.7 Hz, 1H), 2.55 (p, J=6.9 Hz, 1H), 1.25 (d, J=6.9 Hz, 6H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)-3-methylbutanamide (60)

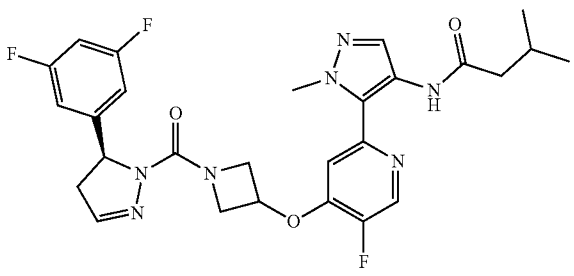 [SMILES: CC(C)CC(=O)Nc1cnn(C)c1-c1cc(OC2CN(C(=O)N3N=CC[C@H]3c3cc(F)cc(F)c3)C2)c(F)cn1]

The titled compound 60 was prepared in 26.4% yield as white solid from 50-01 according to the procedure outlined for compound 53. Mass (m/z): 556.1 $[M+H]^+$. $^1H$ NMR (400 MHz, Chloroform-d) δ 9.19 (s, 1H), 8.49 (d, J=3.0 Hz, 1H), 8.22 (s, 1H), 6.87 (d, J=6.4 Hz, 1H), 6.82-6.78 (m, 1H), 6.78-6.65 (m, 3H), 5.27 (dd, J=12.2, 6.4 Hz, 1H), 5.10 (s, 1H), 4.60 (s, 2H), 4.33 (dd, J=31.4, 10.4 Hz, 2H), 4.04 (s, 3H), 3.37 (ddd, J=18.6, 12.2, 1.7 Hz, 1H), 2.72 (ddd, J=18.7, 6.4, 1.7 Hz, 1H), 2.25-2.16 (m, 3H), 0.99 (d, J=6.3 Hz, 7H).

(S)-2-((5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)amino)-N-methylacetamide (61)

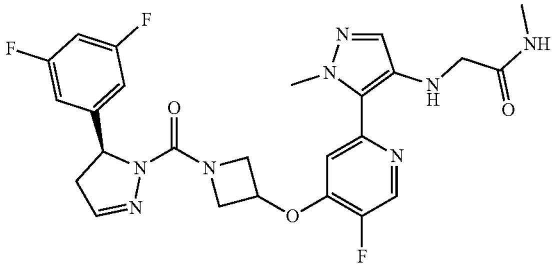 [SMILES: CNC(=O)CNc1cnn(C)c1-c1cc(OC2CN(C(=O)N3N=CC[C@H]3c3cc(F)cc(F)c3)C2)c(F)cn1]

The titled compound 61 was prepared in 20.4% yield as white solid from 53-01 and 2-bromo-N-methylacetamide according to the procedure outlined for compound 50-04 to 50. Mass (m/z): 543.1 $[M+H]^+$. $^1H$ NMR (400 MHz, Chloroform-d) δ 8.52 (d, J=2.8 Hz, 1H), 7.67 (s, 1H), 6.98 (d, J=6.6 Hz, 1H), 6.81 (d, J=2.1 Hz, 1H), 6.78-6.66 (m, 4H), 5.28 (dd, J=12.1, 6.2 Hz, 1H), 5.02 (s, 1H), 4.56 (d, J=32.7 Hz, 2H), 4.32 (dd, J=23.3, 10.4 Hz, 2H), 4.08 (d, J=3.7 Hz, 3H), 4.01-3.93 (m, 2H), 3.42-3.30 (m, 1H), 2.95 (d, J=5.0 Hz, 3H), 2.74-2.66 (m, 1H).

(S)-2-((5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)amino)-1-morpholinoethan-1-one (62)

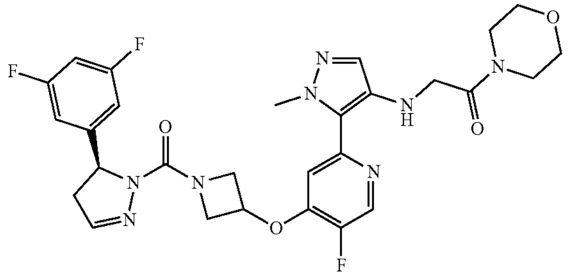 [SMILES: Cn1ncc(NCC(=O)N2CCOCC2)c1-c1cc(OC2CN(C(=O)N3N=CC[C@H]3c3cc(F)cc(F)c3)C2)c(F)cn1]

The titled compound 62 was prepared in 10.7% yield as white solid from 53-01 according to the procedure outlined for compound 50-04 to 50. Mass (m/z): 599.2 $[M+H]^+$. $^1H$ NMR (400 MHz, Chloroform-d) δ 8.45 (d, J=2.9 Hz, 1H), 8.23 (s, 1H), 7.66 (s, 1H), 7.37 (d, J=6.9 Hz, 1H), 6.83-6.80 (m, 1H), 6.76-6.66 (m, 3H), 5.27 (ddd, J=12.4, 6.5, 3.2 Hz, 1H), 5.11 (td, J=6.6, 3.4 Hz, 1H), 4.59 (s, 2H), 4.35-4.22 (m, 2H), 4.15 (s, 3H), 3.81 (t, J=4.9 Hz, 2H), 3.73 (dq, J=4.9, 3.0, 2.6 Hz, 4H), 3.69-3.59 (m, 4H), 3.35 (ddd, J=18.6, 12.2, 1.7 Hz, 1H), 2.69 (ddd, J=18.6, 6.4, 1.7 Hz, 1H).

(S)-2-((5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)amino)-N,N-dimethylacetamide (63)

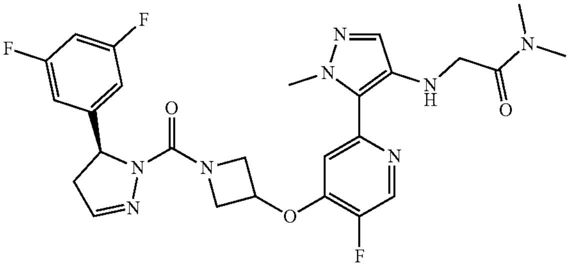 [SMILES: CN(C)C(=O)CNc1cnn(C)c1-c1cc(OC2CN(C(=O)N3N=CC[C@H]3c3cc(F)cc(F)c3)C2)c(F)cn1]

The titled compound 63 was prepared in 1.7% yield as white solid from 53-01 according to the procedure outlined for compound 50-04 to 50. Mass (m/z): 557.1 $[M+H]^+$. $^1H$ NMR (400 MHz, Chloroform-d) δ 8.44 (d, J=2.9 Hz, 1H), 8.26 (d, J=7.5 Hz, OH), 7.52 (s, 1H), 6.82-6.66 (m, 4H), 5.35 (s, 1H), 5.27 (s, 1H), 5.11 (s, 1H), 4.60 (s, 2H), 4.31 (s, 2H), 4.12 (d, J=43.2 Hz, 3H), 3.50 (s, 1H), 3.21 (d, J=6.7 Hz, 1H), 3.10-2.99 (m, 3H), 2.71 (s, 1H), 2.28-2.15 (m, 1H), 2.02 (d, J=10.1 Hz, 2H).

methyl (S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carboxylate (64)

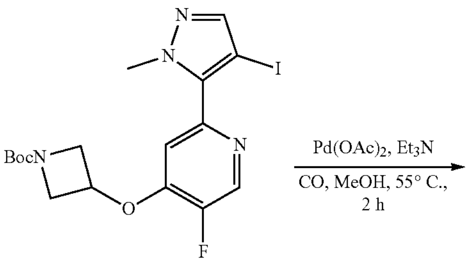

50-01

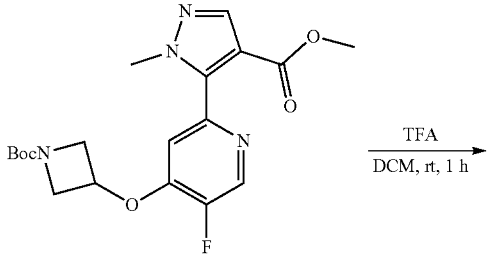

64-01

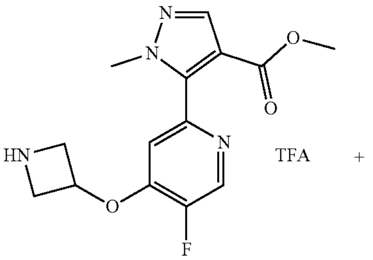

64-02

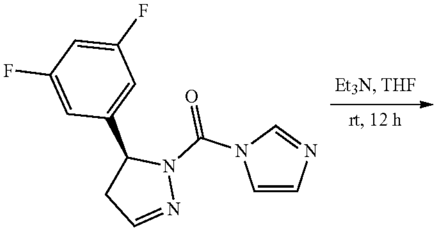

1-02

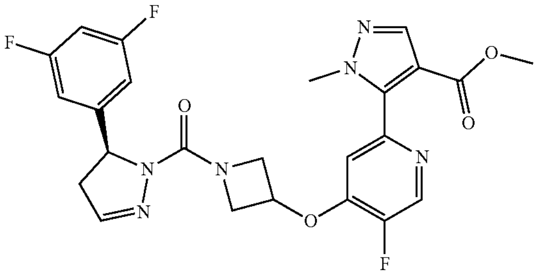

64

Step 1: Compound 50-01 (3.7 g, crude) was dissolved in 40 ml $CH_3OH$. $Pd(OAc)_2$ (0.35 g, 1.56 mmol), $Et_3N$ (2.37 g, 23.4 mmol) were added to the above solution at room temperature. The reaction was degassed with CO and stirred for 2 h at 55° C. The resulting solution was filtered and concentrated in vacuum. The crude product was purified by silica gel chromatography to afford 2.6 g yellow solid. (Two-step yield: 70%) Mass (m/z): 407.3 $[M+H]^+$.

Step 2-3: The titled compound 64 was prepared in 66% yield from 64-01 according to the procedure outlined for compound 50-05 to 50. Mass (m/z): 515.3$[M+H]^+$; $^1H$ NMR (400 MHz, Chloroform-d) δ 8.48 (d, J=2.8 Hz, 1H), 7.95 (s, 1H), 7.20 (d, J=6.7 Hz, 1H), 6.80-6.73 (m, 3H), 6.69 (tt, J=8.8, 2.3 Hz, 1H), 5.27 (dd, J=12.2, 6.4 Hz, 1H), 5.13-5.05 (m, 1H), 4.66-4.54 (m, 2H), 4.42-4.24 (m, 2H), 3.65 (s, 3H), 3.77 (s, 3H), 3.36 (ddd, J=18.6, 12.2, 1.7 Hz, 1H), 2.70 (ddd, J=18.6, 6.5, 1.8 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carboxylic acid (65)

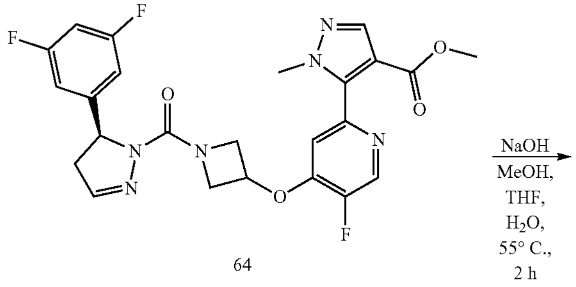

64

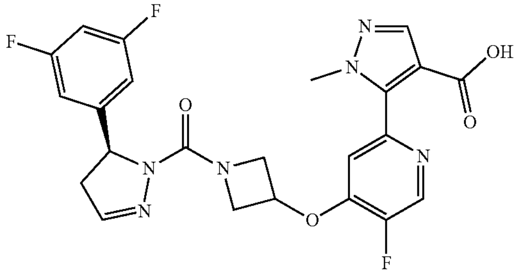

65

Compound 64 (540 mg, 1.05 mmol) was dissolved in 20 ml $CH_3OH$ and 10 ml THF. Then NaOH (1M, 4.2 ml, 4.2 mmol) was added at room temperature. The mixture was stirred for 2 h at 55° C. The PH of the resulting solution was adjusted to 4-5. Then added $H_2O$ and extracted with EA. The organic layers were concentrated under vacuum. The crude product was purified by silica gel chromatography to give the desired compound 65 (250 mg, yield: 48%) as a light yellow solid. Mass (m/z): 501.3 $[M+H]^+$; $^1H$ NMR (400 MHz, Chloroform-d) δ 8.48 (d, J=2.8 Hz, 1H), 8.03 (s, 1H), 7.10 (d, J=6.5 Hz, 1H), 6.82-6.65 (m, 4H), 5.27 (dd, J=12.1, 6.3 Hz, 1H), 5.08-5.00 (m, 1H), 4.66-4.52 (m, 2H), 4.43-4.22 (m, 2H), 3.95 (s, 3H), 3.41-3.28 (m, 1H), 2.75-2.65 (m, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carboxamide (66)

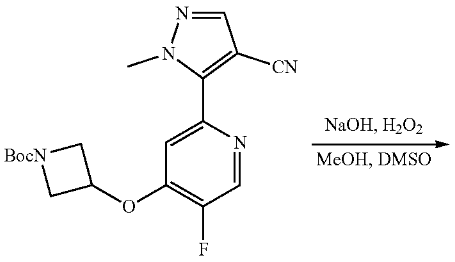

66-01

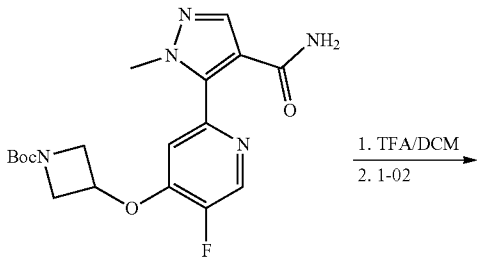

66-02

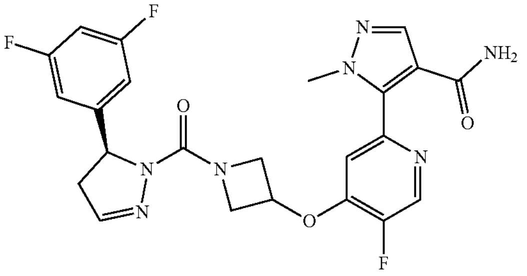

66

Step 1: To a solution of 66-01 (200 mg, 0.54 mmol) in MeOH (5 mL) and DMSO (5 mL) was added 15% NaOH (3 mL) and 3% $H_2O_2$ (5 mL). The reaction was stirred at rt for 1 h. The reaction mixture was diluted with water. The aqueous phase was extracted with EA. The combined organic extracts were washed with brine and dried over $Na_2SO_4$. The solvent was removed under vacuum and the crude product 66-02 was used to next step directly.

Step 2: The titled compound 66 was prepared in 31.2% yield as white solid from Compound 66-02 according to the procedure outlined for compound 50-05 to 50. Mass (m/z): 500.3 $[M+H]^+$. $^1H$ NMR (400 MHz, Chloroform-d) δ 8.47 (s, 1H), 7.90 (s, 1H), 7.04 (s, 1H), 6.66 (d, J=1.6 Hz, 1H), 6.79-6.73 (m, 2H), 6.69 (tt, J=8.8, 2.3 Hz, 1H), 5.30 (dd, J=12.2, 6.3 Hz, 1H), 5.05 (s, 1H), 4.61 (s, 2H), 4.34 (d, J=35.3 Hz, 2H), 3.65 (s, 3H), 3.43-3.30 (m, 1H), 2.71 (ddd, J=18.7, 6.4, 1.6 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N,1-dimethyl-1H-pyrazole-4-carboxamide (67)

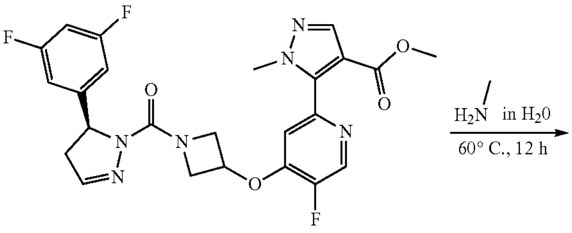

64

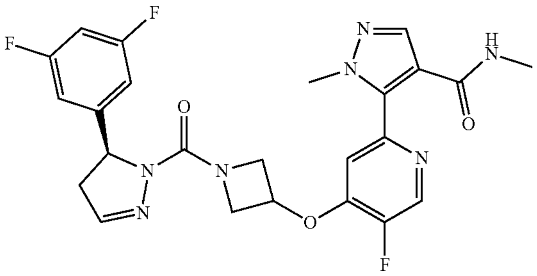

67

Compound 64 (60 mg, 0.12 mmol) in aqueous solution of methylamine was stirred at 60° C. for 12 h. The resulting solution was added EA and washed by brine, dried over $MgSO_4$, concentrated in vacuum. The crude product was purified by Prep-HPLC to afford 20 mg (yield: 33%) white solid. Mass (m/z): 514.3$[M+H]^+$; $^1H$ NMR (400 MHz, Chloroform-d) δ 8.52-8.48 (m, 1H), 7.84 (s, 1H), 7.25-7.21 (m, 1H), 6.80 (s, 1H), 6.78-6.61 (m, 3H), 5.28 (dd, J=12.1, 6.3 Hz, 1H), 5.20-5.08 (m, 1H), 4.71-4.55 (m, 2H), 4.42-4.24 (m, 2H), 3.93 (s, 3H), 3.42-3.31 (m, 1H), 2.88 (d, J=3.9 Hz, 3H), 2.76-2.66 (m, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N,N,1-trimethyl-1H-pyrazole-4-carboxamide (68)

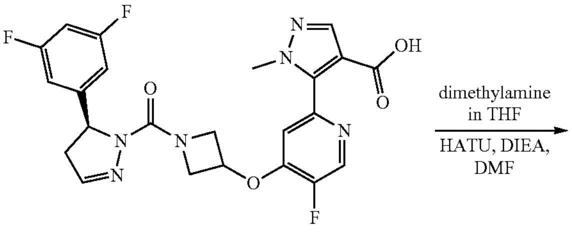

65

-continued

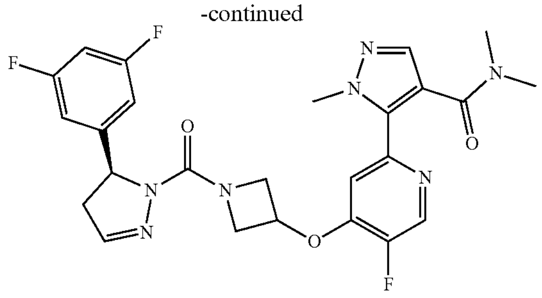

68

Compound 65 (50 mg, 0.1 mmol) was dissolved in 10 ml DMF. HATU (57 mg, 0.15 mmol), DIEA (39 mg, 0.3 mmol) were added to the above solution at room temperature. The reaction was stirred for 15 min at rt. Then dimethylamine in THE was added. The reaction was stirred for 1 hour at rt. The resulting solution was added $H_2O$ and extracted by EA. The combined organic layers were washed by brine, dried over $MgSO_4$, concentrated in vacuum. The crude product was purified by silica gel chromatography to afford 18.6 mg (yield: 35%) white solid. Mass (m/z): 528.3 $[M+H]^+$; $^1H$ NMR (400 MHz, Chloroform-d) δ 8.45 (d, J=2.8 Hz, 1H), 7.54 (s, 1H), 7.35 (d, J=6.7 Hz, 1H), 6.79-6.65 (m, 4H), 5.27 (dd, J=12.2, 6.4 Hz, 1H), 5.09-4.99 (m, 1H), 4.75-4.57 (m, 2H), 4.26 (t, J=11.5 Hz, 2H), 4.04 (s, 3H), 3.35 (ddd, J=18.6, 12.1, 1.7 Hz, 1H), 3.04 (s, 3H), 2.84 (s, 3H), 2.69 (ddd, J=18.6, 6.5, 1.7 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N-(2-(dimethylamino)ethyl)-1-methyl-1H-pyrazole-4-carboxamide (69)

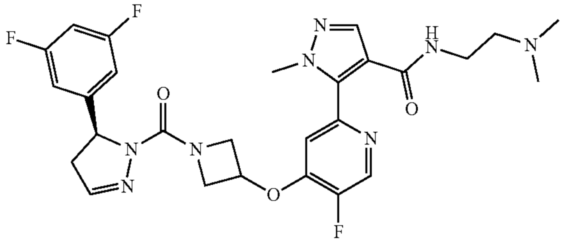 [SMILES: CN(C)CCNC(=O)c1cnn(C)c1-c1cc(OC2CN(C(=O)N3N=CC[C@H]3c3cc(F)cc(F)c3)C2)c(F)cn1]

The title compound 69 was prepared in a yield of 46% (26 mg, 0.05 mmol) as a white solid from Compound 65 (50 mg, 0.1 mmol) according to the procedure for Compound 68. Mass (m/z): 571.4 $[M+H]^+$; $^1H$ NMR (400 MHz, Chloroform-d) δ 8.51 (d, J=2.9 Hz, 1H), 7.92-7.83 (m, 2H), 6.84-6.81 (m, 1H), 6.78-6.66 (m, 3H), 5.26 (dd, J=12.1, 6.2 Hz, 1H), 5.14-5.07 (m, 1H), 4.69-4.59 (m, 2H), 4.43-4.23 (m, 2H), 3.86 (s, 3H), 3.78-3.63 (m, 2H), 3.37 (ddd, J=18.6, 12.1, 1.6 Hz, 1H), 3.27 (s, 2H), 2.89 (s, 6H), 2.71 (ddd, J=18.6, 6.2, 1.8 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N-isobutyl-1-methyl-1H-pyrazole-4-carboxamide (70)

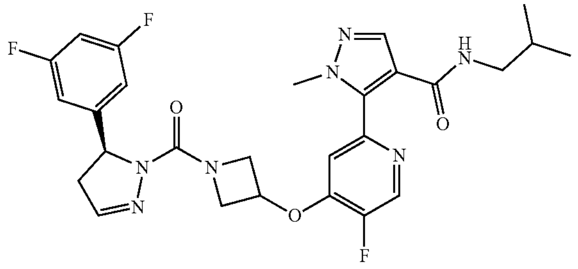 [SMILES: CC(C)CNC(=O)c1cnn(C)c1-c1cc(OC2CN(C(=O)N3N=CC[C@H]3c3cc(F)cc(F)c3)C2)c(F)cn1]

The title compound 70 was prepared in a yield of 27% (15.2 mg, 0.03 mmol) as a white solid from Compound 65 (50 mg, 0.1 mmol) according to the procedure for Compound 68. Mass (m/z): 556.4 $[M+H]^+$; $^1H$ NMR (400 MHz, Chloroform-d) δ 8.46 (d, J=2.8 Hz, 1H), 7.83 (s, 1H), 7.19 (d, J=6.6 Hz, 1H), 6.81-6.64 (m, 4H), 5.26 (dd, J=12.2, 6.4 Hz, 1H), 5.15-5.07 (m, 1H), 4.69-4.52 (m, 2H), 4.39-4.22 (m, 2H), 3.90 (s, 3H), 3.35 (ddd, J=18.6, 12.2, 1.7 Hz, 1H), 3.21-3.09 (m, 2H), 2.70 (ddd, J=18.6, 6.4, 1.8 Hz, 1H), 1.79-1.73 (m, 1H), 0.88 (d, J=6.7 Hz, 6H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N-ethyl-1-methyl-1H-pyrazole-4-carboxamide (71)

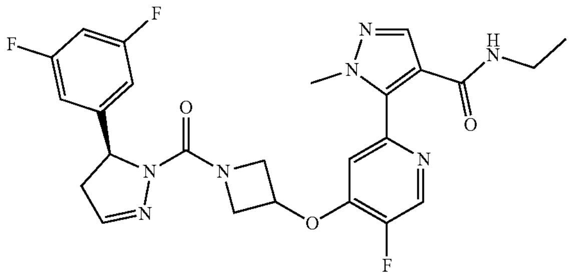 [SMILES: CCNC(=O)c1cnn(C)c1-c1cc(OC2CN(C(=O)N3N=CC[C@H]3c3cc(F)cc(F)c3)C2)c(F)cn1]

The title compound 71 was prepared in a yield of 29% (15.2 mg, 0.03 mmol) as a white solid from Compound 65 (50 mg, 0.1 mmol) according to the procedure for Compound 68. Mass (m/z): 528.3 $[M+H]^+$; $^1H$ NMR (400 MHz, Chloroform-d) δ 8.46 (d, J=2.8 Hz, 1H), 7.80 (s, 1H), 6.82-6.63 (m, 4H), 6.55-6.48 (m, 1H), 5.26 (dd, J=12.2, 6.4 Hz, 1H), 5.15-5.07 (m, 1H), 4.68-4.53 (m, 2H), 4.38-4.22 (m, 2H), 3.91 (s, 3H), 3.43-3.27 (m, 3H), 2.69 (ddd, J=18.6, 6.4, 1.7 Hz, 1H), 1.14 (t, J=7.2 Hz, 3H).

(S)-azetidin-1-yl(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)methanone (72)

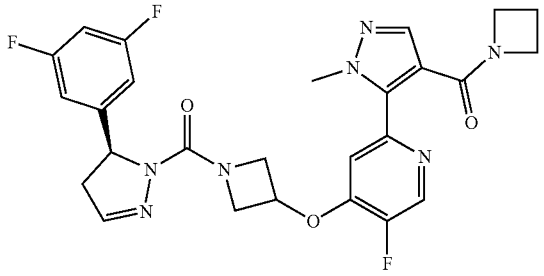 [SMILES: Cn1ncc(C(=O)N2CCC2)c1-c1cc(OC2CN(C(=O)N3N=CC[C@H]3c3cc(F)cc(F)c3)C2)c(F)cn1]

The title compound 72 was prepared in a yield of 21% (11.5 mg, 0.02 mmol) as a white solid from Compound 65 (50 mg, 0.1 mmol) according to the procedure for Compound 68. Mass (m/z): 540.3[M+H]$^+$; $^1$H NMR (400 MHz, Chloroform-d) δ 8.44 (d, J=2.8 Hz, 1H), 7.62 (s, 1H), 7.51 (d, J=6.8 Hz, 1H), 6.79-6.64 (m, 4H), 5.26 (dd, J=12.2, 6.4 Hz, 1H), 5.16-5.08 (m, 1H), 4.70-4.56 (m, 2H), 4.37-4.22 (m, 2H), 4.15-4.05 (m, 4H), 3.97 (s, 3H), 3.34 (ddd, J=18.5, 12.2, 1.7 Hz, 1H), 2.68 (ddd, J=18.6, 6.5, 1.7 Hz, 1H), 2.32-2.19 (m, 2H).

(S)-(5-(3,5-difluorophenyl)-4,5-dihydro-1H-pyrazol-1-yl)(3-((5-fluoro-2-(4-(3-hydroxyazetidine-1-carbonyl)-1-methyl-1H-pyrazol-5-yl)pyridin-4-yl)oxy)azetidin-1-yl)methanone (73)

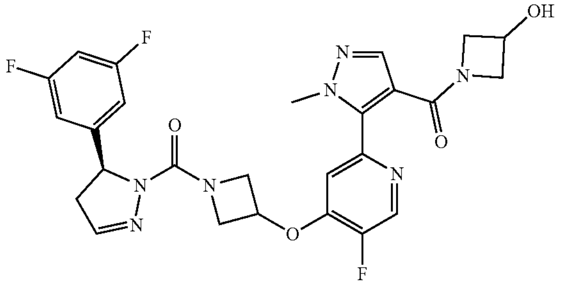 [SMILES: Cn1ncc(C(=O)N2CC(O)C2)c1-c1cc(OC2CN(C(=O)N3N=CC[C@H]3c3cc(F)cc(F)c3)C2)c(F)cn1]

The title compound 73 was prepared in a yield of 59% (33 mg, 0.06 mmol) as a white solid from Compound 65 (50 mg, 0.1 mmol) according to the procedure for Compound 68. Mass (m/z): 556.3 [M+H]$^+$; $^1$H NMR (400 MHz, Chloroform-d) δ 8.44 (d, J=2.6 Hz, 1H), 7.60 (s, 1H), 7.37 (d, J=6.6 Hz, 1H), 6.81-6.64 (m, 4H), 5.25 (dd, J=12.1, 6.3 Hz, 1H), 5.10 (s, 1H), 4.68-4.48 (m, 3H), 4.38-4.16 (m, 4H), 3.96 (s, 3H), 3.92-3.76 (m, 2H), 3.34 (ddd, J=18.5, 12.2, 1.8 Hz, 1H), 2.68 (ddd, J=18.6, 6.3, 1.7 Hz, 1H).

(S)-(5-(3,5-difluorophenyl)-4,5-dihydro-1H-pyrazol-1-yl)(3-((5-fluoro-2-(4-(3-methoxyazetidine-1-carbonyl)-1-methyl-1H-pyrazol-5-yl)pyridin-4-yl)oxy)azetidin-1-yl)methanone (74)

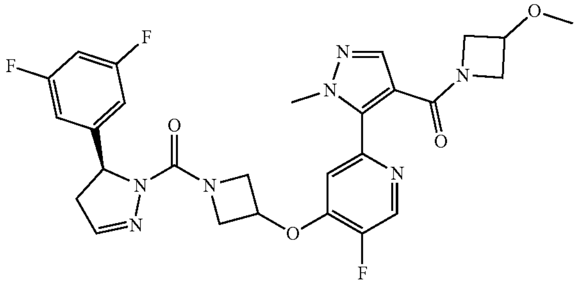 [SMILES: COC1CN(C(=O)c2cnn(C)c2-c2cc(OC3CN(C(=O)N4N=CC[C@H]4c4cc(F)cc(F)c4)C3)c(F)cn2)C1]

The title compound 74 was prepared in a yield of 81% (46 mg, 0.08 mmol) as a white solid from Compound 65 (50 mg, 0.1 mmol) according to the procedure for Compound 68. Mass (m/z): 570.3[M+H]$^+$; $^1$H NMR (400 MHz, Chloroform-d) δ 8.47 (d, J=2.8 Hz, 1H), 7.63 (s, 1H), 7.48 (d, J=6.7 Hz, 1H), 6.81-6.64 (m, 4H), 5.27 (dd, J=12.1, 6.4 Hz, 1H), 5.14 (s, 1H), 4.70-4.55 (m, 2H), 4.38-4.12 (m, 5H), 3.99 (s, 3H), 3.97-3.91 (m, 2H), 3.35 (ddd, J=18.6, 12.3, 1.6 Hz, 1H), 3.26 (s, 3H), 2.69 (ddd, J=18.5, 6.5, 1.6 Hz, 1H).

(S)-(5-(3,5-difluorophenyl)-4,5-dihydro-1H-pyrazol-1-yl)(3-((5-fluoro-2-(1-methyl-4-(pyrrolidine-1-carbonyl)-1H-pyrazol-5-yl)pyridin-4-yl)oxy)azetidin-1-yl)methanone (75)

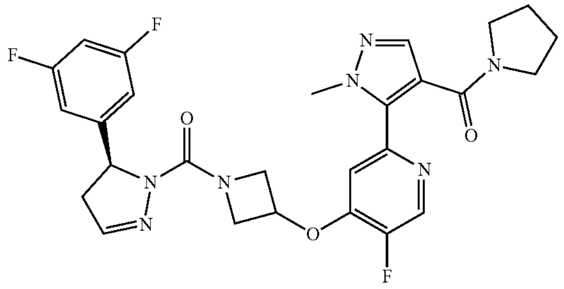 [SMILES: Cn1ncc(C(=O)N2CCCC2)c1-c1cc(OC2CN(C(=O)N3N=CC[C@H]3c3cc(F)cc(F)c3)C2)c(F)cn1]

The title compound 75 was prepared in a yield of 78% (43 mg, 0.08 mmol) as a white solid from Compound 65 (50 mg, 0.1 mmol) according to the procedure for Compound 68. Mass (m/z): 554.3 [M+H]$^+$; $^1$H NMR (400 MHz, Chloroform-d) δ 8.44 (d, J=2.7 Hz, 1H), 7.61 (s, 1H), 7.46 (d, J=6.8 Hz, 1H), 6.78-6.64 (m, 4H), 5.26 (dd, J=12.2, 6.4 Hz, 1H), 5.11-5.02 (m, 1H), 4.72-4.55 (m, 2H), 4.25 (t, J=12.9 Hz, 2H), 4.01 (s, 3H), 3.54 (t, J=6.9 Hz, 2H), 3.34 (ddd, J=18.6, 12.2, 1.7 Hz, 1H), 3.25 (t, J=6.5 Hz, 2H), 2.68 (ddd, J=18.6, 6.5, 1.7 Hz, 1H), 1.92-1.74 (m, 4H).

(S)-(5-(3,5-difluorophenyl)-4,5-dihydro-1H-pyrazol-1-yl)(3-((5-fluoro-2-(1-methyl-4-(piperidine-1-carbonyl)-1H-pyrazol-5-yl)pyridin-4-yl)oxy)azetidin-1-yl)methanone (76)

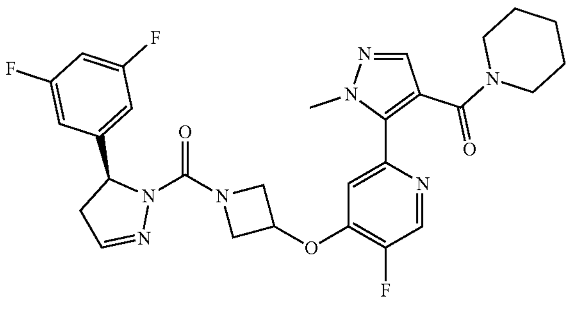 [SMILES: Cn1ncc(C(=O)N2CCCCC2)c1-c1cc(OC2CN(C(=O)N3N=CC[C@H]3c3cc(F)cc(F)c3)C2)c(F)cn1]

The title compound 76 was prepared in a yield of 75% (43 mg, 0.08 mmol) as a white solid from Compound 65 (50 mg, 0.1 mmol) according to the procedure for Compound 68. Mass (m/z): 568.3 $[M+H]^+$; $^1H$ NMR (400 MHz, Chloroform-d) δ 8.45 (d, J=2.8 Hz, 1H), 7.52 (s, 1H), 7.32 (d, J=6.7 Hz, 1H), 6.78-6.66 (m, 4H), 5.27 (dd, J=12.2, 6.4 Hz, 1H), 5.06-4.97 (m, 1H), 4.74-4.57 (m, 2H), 4.26 (t, J=12.1 Hz, 2H), 4.05 (s, 3H), 3.65 (s, 2H), 3.35 (ddd, J=18.6, 12.2, 1.6 Hz, 1H), 3.20 (s, 2H), 2.69 (ddd, J=18.6, 6.5, 1.7 Hz, 1H), 1.62-1.50 (m, 4H), 1.32-1.20 (m, 2H).

(S)-(5-(3,5-difluorophenyl)-4,5-dihydro-1H-pyrazol-1-yl)(3-((5-fluoro-2-(1-methyl-4-(morpholine-4-carbonyl)-1H-pyrazol-5-yl)pyridin-4-yl)oxy)azetidin-1-yl)methanone (77)

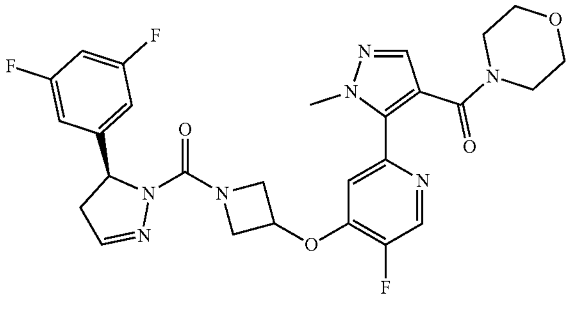

The title compound 77 was prepared in a yield of 36% (20.3 mg, 0.04 mmol) as a white solid from Compound 65 (50 mg, 0.1 mmol) according to the procedure for Compound 68. Mass (m/z): 570.3 $[M+H]^+$; $^1H$ NMR (400 MHz, Chloroform-d) δ 8.47 (d, J=2.8 Hz, 1H), 7.53 (s, 1H), 7.32 (d, J=6.6 Hz, 1H), 6.79-6.65 (m, 4H), 5.27 (dd, J=12.2, 6.4 Hz, 1H), 5.04 (s, 1H), 4.72-4.57 (m, 2H), 4.27 (t, J=13.5 Hz, 2H), 4.03 (s, 3H), 3.83-3.20 (m, 9H), 2.70 (ddd, J=18.6, 6.4, 1.7 Hz, 1H).

(S)-(5-(3,5-difluorophenyl)-4,5-dihydro-1H-pyrazol-1-yl)(3-((5-fluoro-2-(4-(hydroxymethyl)-1-methyl-1H-pyrazol-5-yl)pyridin-4-yl)oxy)azetidin-1-yl)methanone (78)

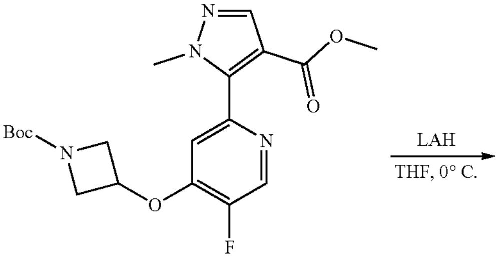

64-01

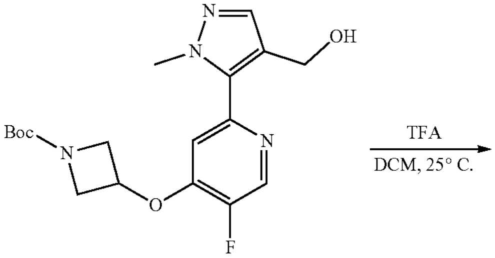

78-01

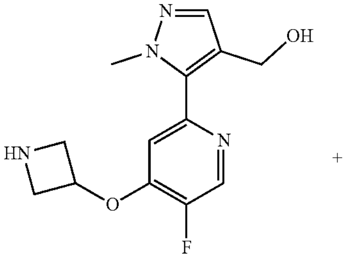

78-02

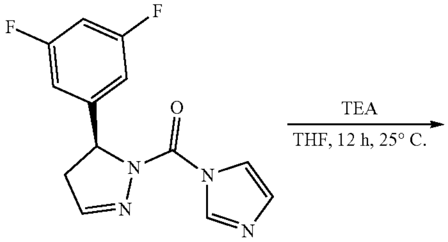

1-02

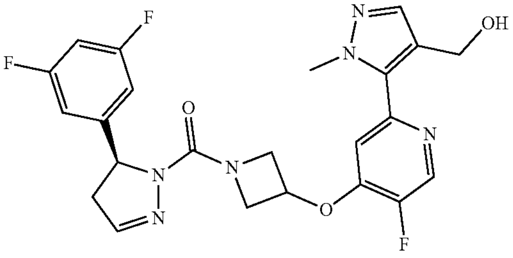

78

Step 1: 64-01 (2 g, 4.92 mmol) was dissolved in 20 ml of dry THF, $AlLiH_4$ (1M, 5 mL) was added to the above solution at 0° C., the mixture was stirred for 10 min at 0° C. water was added and extracted with EA, washed with brine, dried ($Na_2SO_4$), and concentrated to dryness to give the intermediate 78-01. MS (m/z): 379.2 [M+H]$^+$.

Step 2-3: The title compound 78 was prepared in a yield of 42.9% (55 mg) as a white solid from Compound 78-01 (100 mg, 0.27 mmol) according to the procedure for Compound 50-05 to 50. Mass (m/z): 469.1 [M+H]$^+$. $^1$H NMR (400 MHz, Chloroform-d) δ 8.50 (d, J=2.9 Hz, 1H), 7.54 (s, 1H), 7.25 (d, J=6.7 Hz, 1H), 6.84-6.64 (m, 4H), 5.35-5.23 (m, 1H), 5.12 (ddd, J=10.3, 6.5, 3.9 Hz, 1H), 4.70-4.60 (m, 2H), 4.48 (s, 2H), 4.35 (dd, J=32.1, 10.3 Hz, 2H), 4.08 (s, 3H), 3.38 (ddd, J=18.7, 12.2, 1.7 Hz, 1H), 2.73 (ddd, J=18.6, 6.4, 1.8 Hz, 1H).

(S)-(5-(3,5-difluorophenyl)-4,5-dihydro-1H-pyrazol-1-yl)(3-((2-(4-((dimethylamino)methyl)-1-methyl-1H-pyrazol-5-yl)-5-fluoropyridin-4-yl)oxy)azetidin-1-yl)methanone (79)

+

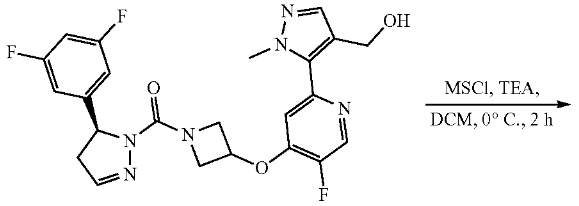

78

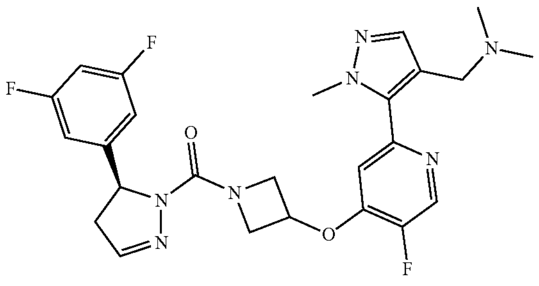

79

Compound 78 (54 mg, 0.11 mmol) was dissolved in 10 ml of dry DCM, TEA (0.1 mL) was added to the above solution at 0° C., the mixture was stirred for 30 min at 0° C. Then Dimethylamine (5 mg, 0.11 mmol) was added, the mixture was stirred for 1.5 h, water was added and extracted with EA, Purification by silica gel chromatography to give the titled compound 79 (21 mg, 46.2%) as a white solid. Mass (m/z): 514.2 [M+H]$^+$. $^1$H NMR (400 MHz, Chloroform-d) δ 8.58 (s, 1H), 7.69 (s, 1H), 6.90 (d, J=6.3 Hz, 1H), 6.84 (d, J=1.7 Hz, 1H), 6.80-6.69 (m, 3H), 5.30 (dd, J=12.1, 6.3 Hz, 1H), 5.25-5.17 (m, 1H), 4.70-4.57 (m, 2H), 4.43-4.26 (m, 2H), 4.20 (s, 2H), 3.96 (s, 3H), 3.45-3.40 (m, 1H), 2.78 (s, 6H), 2.74-2.70 (m, 1H).

(S)-(5-(3,5-difluorophenyl)-4,5-dihydro-1H-pyrazol-1-yl)(3-((5-fluoro-2-(4-(methoxymethyl)-1-methyl-1H-pyrazol-5-yl)pyridin-4-yl)oxy)azetidin-1-yl)methanone (80)

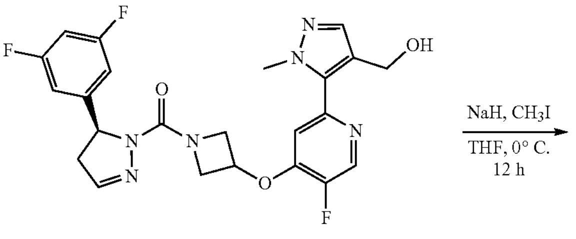

78

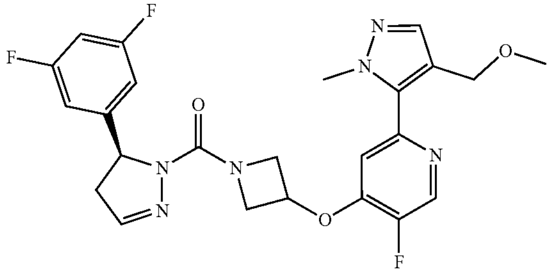

80

Compound 78 (80 mg, 0.16 mmol) was dissolved in 10 ml of dry THF, NaH (1M, 5 mL) was added to the above solution at 0° C., the mixture was stirred for 30 min at 0° C. Then $CH_3I$ (1 g, 6.78 mmol) was added, the mixture was stirred for 10 min water was added and extracted with EA, Purification by silica gel chromatography to give the titled compound 80 (50 mg, 60%) as a white solid. Mass (m/z): 501.2 [M+H]$^+$. $^1$H NMR (400 MHz, Chloroform-d) δ 8.48 (d, J=2.9 Hz, 11H), 7.53 (s, 11H), 7.31 (d, J=6.8 Hz, 1H), 6.83-6.64 (m, 4H), 5.27 (dd, J=12.2, 6.4 Hz, 1H), 5.03 (ddd, J=10.2, 6.4, 3.9 Hz, 1H), 4.69-4.53 (m, 2H), 4.41-4.27 (m, 2H), 4.27 (s, 2H), 4.07 (s, 3H), 3.40 (s, 3H), 3.38-3.30 (m, 1H), 2.70 (ddd, J=18.6, 6.4, 1.7 Hz, 1H).

(S)-(5-(3,5-difluorophenyl)-4,5-dihydro-1H-pyrazol-1-yl)(3-((5-fluoro-2-(4-fluoro-1-methyl-1H-pyrazol-5-yl)pyridin-4-yl)oxy)azetidin-1-yl)methanone (81)

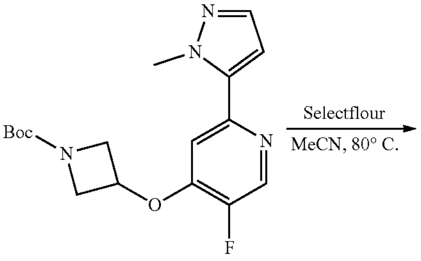

81-01

-continued

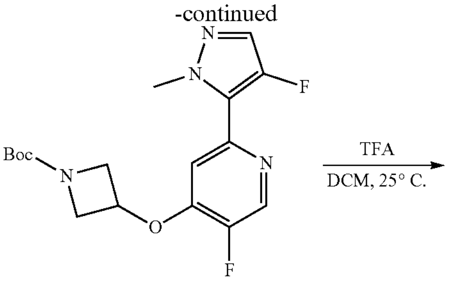

81-02

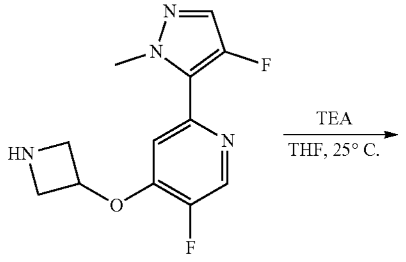

81-03

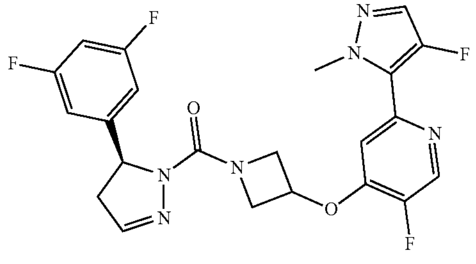

81

Step 1: 81-01 (1.1 g, 3.16 mmol) was dissolved in 15 ml of dry MeCN, Selectfluor (1.18 g, 3.16 mmol) was added to the above solution at 0° C., the mixture was stirred for 3 h at 80° C. Water was added and extracted with EA, Purification by silica gel chromatography to give the compound 81-02 (320 mg, 27.6%). Mass (m/z): 367.2 $[M+H]^+$.

Step 2-3: The title compound 81 was prepared in a yield of 26.9% from Compound 81-02 according to the procedure for Compound 50-05 to 50. $^1H$ NMR (300 MHz, Chloroform-d) δ 8.44 (d, J=2.8 Hz, 1H), 7.39 (d, J=4.4 Hz, 1H), 6.99 (d, J=6.6 Hz, 1H), 6.83-6.65 (m, 4H), 5.28 (dd, J=12.2, 6.4 Hz, 1H), 5.10 (ddd, J=10.4, 6.5, 4.0 Hz, 1H), 4.68-4.53 (m, 2H), 4.32 (ddd, J=24.3, 10.7, 4.0 Hz, 2H), 4.16 (s, 3H), 3.36 (ddd, J=18.6, 12.2, 1.7 Hz, 1H), 2.71 (ddd, J=18.6, 6.5, 1.7 Hz, 1H). Mass (m/z): 475.1 $[M+H]^+$ (S)-(5-(3,5-difluorophenyl)-4,5-dihydro-1H-pyrazol-1-yl)(3-((5-fluoro-2-(4-fluoro-1-methyl-1H-pyrazol-5-yl)pyrimidin-4-yl)oxy)azetidin-1-yl)methanone (82)

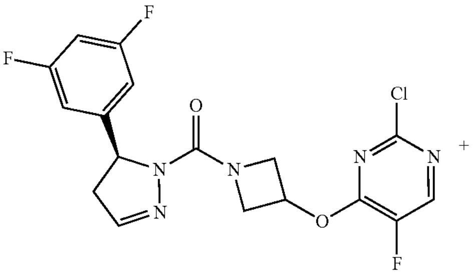

2-03

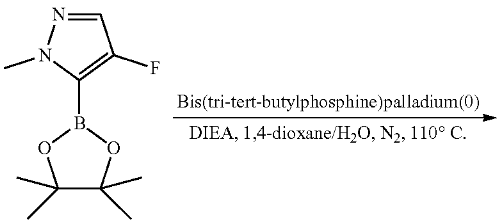

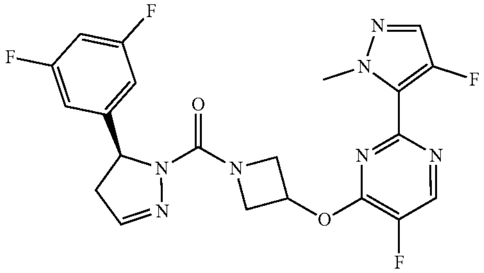

82

Compound 2-03 (82 mg, 0.2 mmol), 4-fluoro-1-methyl-5-(4,4,5,5-tetramethyl-1,3,2-dioxaborolan-2-yl)-1H-pyrazole (90 mg, 0.4 mmol), Bis(tri-tert-butylphosphine)palladium(0) (21 mg, 0.04 mmol), DIEA (155 mg, 1.2 mmol) in 1,4-dioxane (2 mL) and $H_2O$ (0.2 mL) under $N_2$ and the whole reaction mixture was stirred at 100° C. for 2 hours. After the mixture was concentrated and further purified by prep-HPLC to give the title compound 82 (25 mg, 26.3%) as a white solid. $^1H$ NMR (400 MHz, Chloroform-d) δ 8.45 (s, 1H), 7.51-7.33 (m, 1H), 6.74 (t, J=18.9 Hz, 4H), 5.52 (s, 1H), 5.29 (s, 1H), 4.63 (s, 2H), 4.24 (d, J=31.7 Hz, 5H), 3.35 (t, J=15.4 Hz, 1H), 2.70 (d, J=18.4 Hz, 1H). Mass (m/z) 476.2 $[M+H]^+$.

(S)-(3-((2-(4-chloro-1-methyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (83)

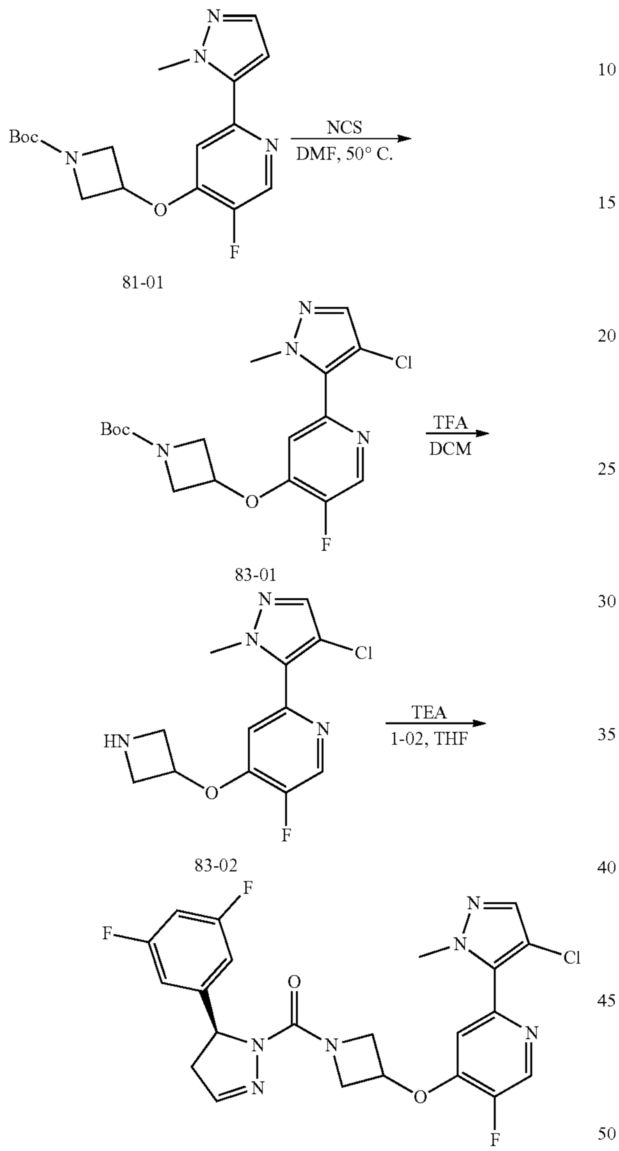

83

Step 1: 81-01 (600 mg, 1.72 mmol) was dissolved in 10 ml of dry DMF, NCS (230 mg, 1.72 mmol) was added to the above solution at 0° C., the mixture was stirred for 12 h at 50° C. water was added and extracted with EA, Purification by silica gel chromatography to give the intermediate 83-01 (360 mg, 54%). Mass (m/z): 383.1 $[M+H]^+$.

Step 2-3: The title compound 83 was prepared in a yield of 26.6% from Compound 83-01 according to the procedure for Compound 50-05 to 50. $^1$H NMR (300 MHz, DMSO-$d_6$) δ 8.68 (d, J=3.1 Hz, 1H), 7.67 (s, 1H), 7.28 (d, J=6.8 Hz, 1H), 7.09 (tt, J=9.3, 2.3 Hz, 1H), 7.01 (s, 1H), 6.92-6.86 (m, 2H), 5.31-5.17 (m, 2H), 4.60-4.45 (m, 2H), 4.14-4.00 (m, J=10.7 Hz, 2H), 3.90 (s, 3H), 3.43-3.35 (m, 1H), 2.68-2.58 (m, 1H). Mass (m/z) 491.1 $[M+H]^+$ (S)-(3-((2-(4-chloro-1-methyl-1H-pyrazol-5-yl)-5-fluoropyrimidin-4-yl)oxy)azetidin-1-yl)(5-(3,5-difluorophenyl)-4,5-dihydro-1H-pyrazol-1-yl)methanone (84)

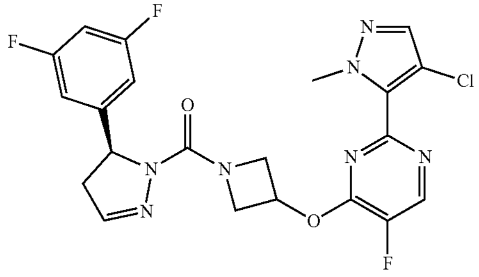

The titled compound 84 was prepared from 2-03 in 15.2% yield according to the procedure outlined for compound 2. $^1$H NMR (400 MHz, Chloroform-d) δ 8.51-8.47 (m, 1H), 7.55-7.48 (m, 1H), 6.82-6.66 (m, 4H), 5.63-5.55 (m, 1H), 5.28 (dd, J=12.1, 6.3 Hz, 1H), 4.65 (s, 2H), 4.33 (dd, J=27.2, 8.7 Hz, 2H), 4.18 (s, 3H), 3.36 (dd, J=18.6, 12.1 Hz, 1H), 2.70 (dd, J=18.6, 6.3 Hz, 1H). Mass (m/z) 492.2 $[M+H]^+$.

(S)-(5-(3,5-difluorophenyl)-4,5-dihydro-1H-pyrazol-1-yl)(3-((5-fluoro-2-(3-methyl-1H-pyrazol-4-yl)pyridin-4-yl)oxy)azetidin-1-yl)methanone (85)

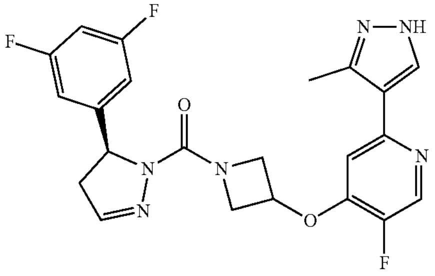 [SMILES: Cc1n[nH]cc1-c1cc(OC2CN(C(=O)N3N=CC[C@H]3c3cc(F)cc(F)c3)C2)c(F)cn1]

The titled compound 85 was prepared from 3-04 in 28.0% yield according to the procedure outlined for compound 3. $^1$H NMR (300 MHz, Chloroform-d) δ 8.36 (d, J=3.0 Hz, 1H), 7.86 (s, 1H), 6.87-6.63 (m, 5H), 5.28 (dd, J=12.1, 6.4 Hz, 1H), 5.10 (q, J=5.3, 4.0 Hz, 1H), 4.60 (q, J=8.7, 8.2 Hz, 2H), 4.40-4.25 (m, 2H), 3.36 (ddd, J=18.6, 12.2, 1.7 Hz, 1H), 2.77-2.67 (m, 1H), 2.65 (d, J=11.5 Hz, 3H). Mass (m/z) 457.3 $[M+H]^+$.

(S)-(5-(3,5-difluorophenyl)-4,5-dihydro-1H-pyrazol-1-yl)(3-((5-fluoro-2-(1-(2-methoxyethyl)-3-methyl-1H-pyrazol-4-yl)pyridin-4-yl)oxy)azetidin-1-yl)methanone (86)

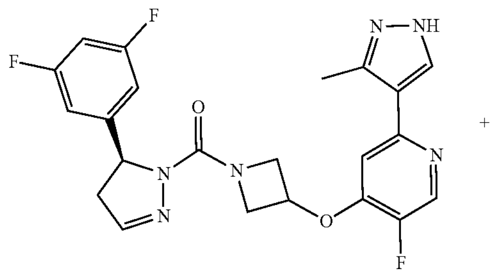

85

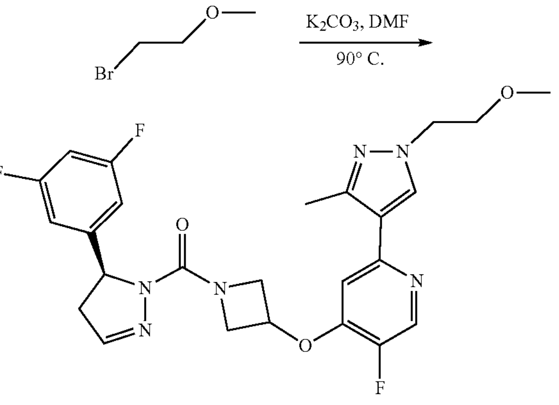

86

Compound 85 (70 mg, 0.15 mmol), 1-bromo-2-methoxyethane (107 mg, 0.75 mmol), $K_2CO_3$ (207 mg, 1.50 mmol) were placed in DMF (3 mL). The mixture was stirred 90° C. for overnight. Concentrated. Purification by prep-HPLC to give the titled compound 86 (19 mg, 24.10%) as a white solid. $^1$H NMR (300 MHz, Chloroform-d) δ 8.35 (t, J=3.1 Hz, 1H), 7.77 (d, J=29.8 Hz, 1H), 6.84-6.64 (m, 5H), 5.27 (dd, J=12.2, 6.5 Hz, 1H), 5.08 (dq, J=6.5, 3.4 Hz, 1H), 4.59 (q, J=8.1 Hz, 2H), 4.40-4.20 (m, 4H), 3.76 (q, J=5.2 Hz, 2H), 3.42-3.29 (m, 4H), 2.71 (ddd, J=18.6, 6.6, 1.7 Hz, 1H), 2.53 (d, J=29.8 Hz, 3H). Mass (m/z) 515.3 [M+H]$^+$.

(S)-(5-(3,5-difluorophenyl)-4,5-dihydro-1H-pyrazol-1-yl)(3-((5-fluoro-2-(1H-pyrazol-5-yl)pyrimidin-4-yl)oxy)azetidin-1-yl)methanone (87)

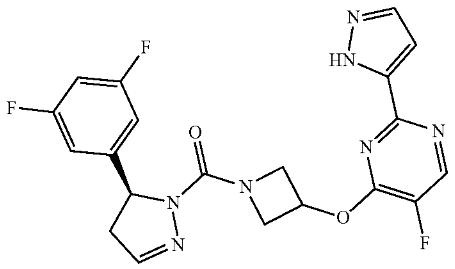 [SMILES: O=C(N1CC(Oc2nc(-c3ccn[nH]3)ncc2F)C1)N1N=CC[C@H]1c1cc(F)cc(F)c1]

The titled compound 87 was prepared from 2-03 in a yield of 13.0% according to the procedure outlined for compound 2. $^1$H NMR (400 MHz, Chloroform-d) δ 8.40 (d, J=2.5 Hz, 1H), 7.66 (d, J=2.0 Hz, 1H), 6.93 (d, J=1.9 Hz, 1H), 6.87-6.56 (m, 4H), 5.57 (tt, J=6.7, 4.3 Hz, 1H), 5.29 (dd, J=12.2, 6.5 Hz, 1H), 4.66 (m, 2H), 4.34 (ddd, J=32.8, 10.7, 4.3 Hz, 2H), 3.36 (ddd, J=18.6, 12.2, 1.7 Hz, 1H), 2.70 (ddd, J=18.6, 6.5, 1.7 Hz, 1H). Mass (m/z) 444.2 [M+H]$^+$, (S)-2-(5-(4-((1-(5-(3,5-difluorophenyl)-4,5-dihydro-1H-pyrazole-1-carbonyl)azetidin-3-yl)oxy)-5-fluoropyrimidin-2-yl)-1H-pyrazol-1-yl)acetamide (88) and (S)-2-(3-(4-((1-(5-(3,5-difluorophenyl)-4,5-dihydro-1H-pyrazole-1-carbonyl)azetidin-3-yl)oxy)-5-fluoropyrimidin-2-yl)-1H-pyrazol-1-yl)acetamide (89)

88

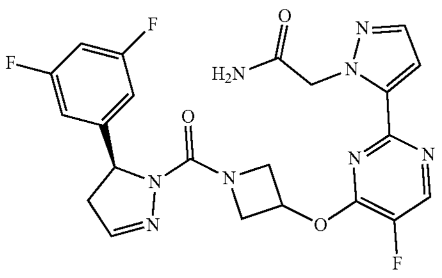

89

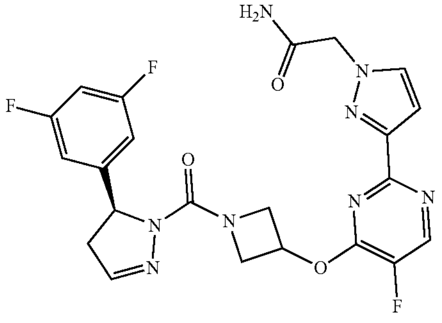

The titled compound 88 and 89 was prepared in a yield of 2.9% (1.1 mg) and 10.1% (3.8 mg) according to the procedure outlined for compound 86. 88: $^1$H NMR (400 MHz, Chloroform-d) δ 8.43 (d, J=2.3 Hz, 1H), 7.67 (d, J=2.0 Hz, 1H), 7.05 (d, J=2.0 Hz, 1H), 6.82 (d, J=1.8 Hz, 1H), 6.78-6.67 (m, 3H), 6.03 (s, 1H), 5.82 (s, 1H), 5.58 (s, 1H), 5.48 (s, 2H), 5.30 (dd, J=12.0, 6.3 Hz, 1H), 4.69 (s, 2H), 4.33 (dd, J=23.8, 10.6 Hz, 2H), 3.40-3.33 (m, 1H), 2.75-2.70 (m, 1H). Mass (m/z) 501.3 [M+H]$^+$. 89: $^1$H NMR (400 MHz, Chloroform-d) δ 8.47 (s, 1H), 7.57 (s, 1H), 6.96 (s, 1H), 6.81-6.67 (m, 4H), 6.23 (s, 1H), 5.60 (ddd, J=11.8, 7.2, 4.9 Hz, 2H), 5.29 (dd, J=12.2, 6.5 Hz, 1H), 4.92 (s, 2H), 4.68 (d, J=17.7 Hz, 2H), 4.35 (dd, J=35.2, 10.7 Hz, 2H), 3.36 (ddd, J=18.5, 12.2, 1.6 Hz, 1H), 2.71 (ddd, J=18.6, 6.4, 1.7 Hz, 1H).

Mass (m/z) 501.3 [M+H]$^+$.

(S)-(5-(3,5-difluorophenyl)-4,5-dihydro-1H-pyrazol-1-yl)(3-((5-fluoro-2-(5-methyl-1H-pyrazol-4-yl)pyrimidin-4-yl)oxy)azetidin-1-yl)methanone (90)

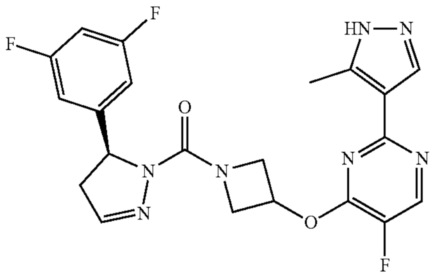 [SMILES: Cc1[nH]ncc1-c1ncc(F)c(OC2CN(C(=O)N3N=CC[C@H]3c3cc(F)cc(F)c3)C2)n1]

The titled compound 90 was prepared from 2-03 in a yield of 27% (30 mg) according to the procedure outlined for compound 2. $^1$H NMR (400 MHz, Chloroform-d) δ 8.32 (d, J=2.6 Hz, 1H), 8.13 (s, 1H), 6.79 (t, J=1.7 Hz, 1H), 6.77-6.57 (m, 3H), 5.58-5.49 (m, 1H), 5.33-5.25 (m, 1H), 4.66 (d, J=16.6 Hz, 2H), 4.33 (dd, J=34.3, 10.5 Hz, 2H), 3.35 (ddd, J=18.6, 12.2, 1.7 Hz, 1H), 2.69 (ddd, J=18.6, 6.5, 1.7 Hz, 1H), 2.64 (s, 3H). Mass (m/z) 458.2 [M+H]$^+$.

(S)-(5-(3,5-difluorophenyl)-4,5-dihydro-1H-pyrazol-1-yl)(3-((2-(3,5-dimethyl-1H-pyrazol-4-yl)-5-fluoropyrimidin-4-yl)oxy)azetidin-1-yl)methanone (91)

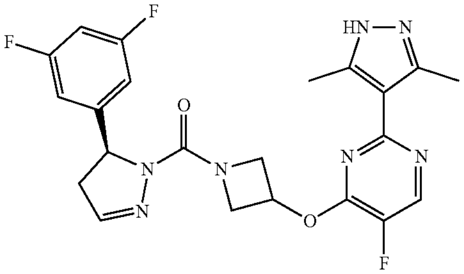 [SMILES: Cc1n[nH]c(C)c1-c1ncc(F)c(OC2CN(C(=O)N3N=CC[C@H]3c3cc(F)cc(F)c3)C2)n1]

The titled compound 91 was prepared from 2-03 in a yield of 34.6% according to the procedure outlined for compound 2. $^1$H NMR (400 MHz, Chloroform-d) δ 8.37 (d, J=2.6 Hz, 1H), 6.78 (t, J=1.7 Hz, 1H), 6.77-6.61 (m, 3H), 5.58-5.50 (m, 1H), 5.30-5.25 (m, 1H), 4.61 (q, J=10.1, 8.8 Hz, 2H), 4.32 (dd, J=35.8, 10.3 Hz, 2H), 3.35 (ddd, J=18.6, 12.2, 1.7 Hz, 1H), 2.70 (ddd, J=18.6, 6.5, 1.7 Hz, 1H), 2.61 (s, 6H). Mass (m/z) 472.3 [M+H]$^+$.

(S)-(5-(3,5-difluorophenyl)-4,5-dihydro-1H-pyrazol-1-yl)(3-((2-(3,5-dimethyl-1H-pyrazol-4-yl)-5-fluoropyridin-4-yl)oxy)azetidin-1-yl)methanone (92)

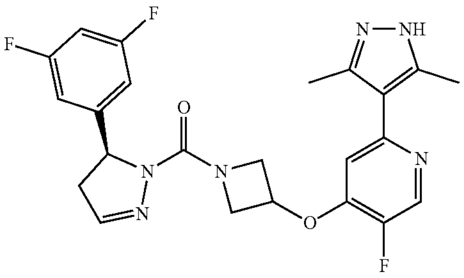

The titled compound 92 was prepared from 3-04 in 31.9% yield according to the procedure outlined for compound 3. $^1$H NMR (400 MHz, Chloroform-d) δ 8.41 (d, J=3.1 Hz, 1H), 6.83-6.67 (m, 4H), 6.62 (d, J=6.6 Hz, 11H), 5.27 (dd, J=12.2, 6.5 Hz, 11H), 5.09-5.01 (m, 11H), 4.58 (d, J=8.2 Hz, 2H), 4.33 (dd, J=36.9, 10.3 Hz, 2H), 3.36 (ddd, J=18.6, 12.2, 1.7 Hz, 1H), 2.71 (ddd, J=18.6, 6.5, 1.7 Hz, 1H), 2.41 (s, 6H). Mass (m/z) 471.2 [M+H]$^+$.

(S)-(5-(3,5-difluorophenyl)-4,5-dihydro-1H-pyrazol-1-yl)(3-((5-fluoro-2-(1-(2-methoxyethyl)-3,5-dimethyl-1H-pyrazol-4-yl)pyridin-4-yl)oxy)azetidin-1-yl)methanone (93)

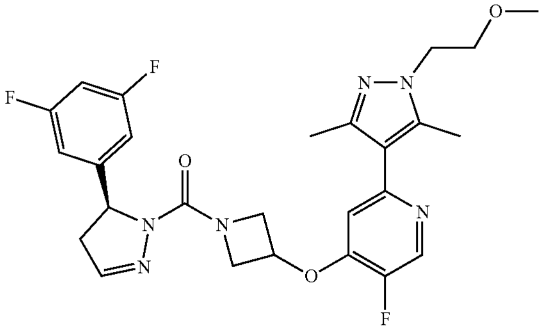 [SMILES: COCCn1nc(C)c(-c2cc(OC3CN(C(=O)N4N=CC[C@H]4c4cc(F)cc(F)c4)C3)c(F)cn2)c1C]

The titled compound 93 was prepared in 29.6% yield from 92 according to the procedure outlined for compound 86. $^1$H NMR (400 MHz, DMSO-$d_6$) δ 8.50 (d, J=3.0 Hz, 1H), 7.12 (tt, J=9.3, 2.4 Hz, 1H), 7.03 (d, J=1.7 Hz, 1H), 6.93 (qd, J=6.6, 3.3 Hz, 2H), 6.84 (d, J=6.8 Hz, 1H), 5.31-5.20 (m, 2H), 4.54 (s, 2H), 4.16 (t, J=5.4 Hz, 2H), 4.09 (s, 2H), 3.65 (t, J=5.4 Hz, 2H), 3.44-3.37 (m, 1H), 3.23 (s, 3H), 2.65 (ddd, J=18.7, 6.7, 1.8 Hz, 1H), 2.35 (s, 3H), 2.24 (s, 3H). Mass (m/z) 529.4 [M+H]$^+$.

(S)-2-(4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-1-yl)acetamide (94)

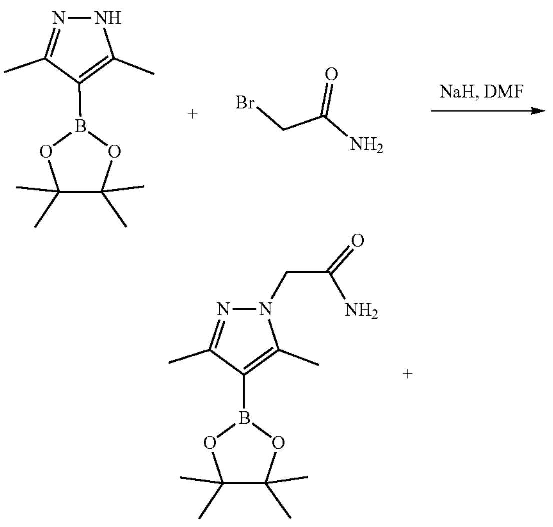

94-01

-continued

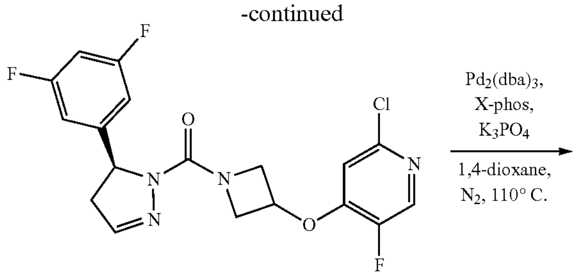

3-04

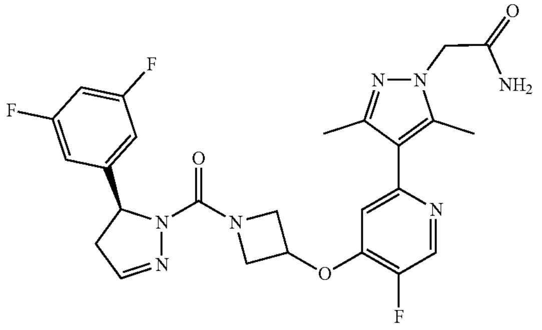

94

Step 1: 3,5-dimethyl-4-(4,4,5,5-tetramethyl-1,3,2-dioxaborolan-2-yl)-1H-pyrazole (222 mg, 1.0 mmol), 2-bromoacetamide (276 mg, 2.0 mmol), NaH (60%, 120 mg, 3.0 mmol) were placed in DMF (5 mL). The mixture was stirred 25° C. for 45 min, and then the reaction liquid was poured into water. The mixture was extracted with EA, washed with brine, dried ($Na_2SO_4$), and concentrated in vacuo. Purification by prep-HPLC to give the intermediate compound 94-01 (215 mg, 77.0%) as a white solid.

Step 2: The titled compound 94 was prepared in 36.5% yield (73 mg) according to the procedure outlined for compound 3. $^1$H NMR (400 MHz, Chloroform-d) δ 8.42 (d, J=3.0 Hz, 1H), 6.83-6.65 (m, 4H), 6.59 (d, J=6.5 Hz, 1H), 6.09 (s, 1H), 5.60 (s, 1H), 5.27 (dd, J=12.2, 6.5 Hz, 1H), 5.05 (td, J=6.5, 3.3 Hz, 1H), 4.72 (s, 2H), 4.56 (d, J=14.8 Hz, 2H), 4.33 (dd, J=34.3, 10.6 Hz, 2H), 3.36 (ddd, J=18.6, 12.2, 1.7 Hz, 1H), 2.71 (ddd, J=18.6, 6.5, 1.7 Hz, 1H), 2.36 (d, J=16.6 Hz, 6H). Mass (m/z) 528.3 [M+H]$^+$.

(S)-2-(4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-1-yl)-N,N-dimethylacetamide (95)

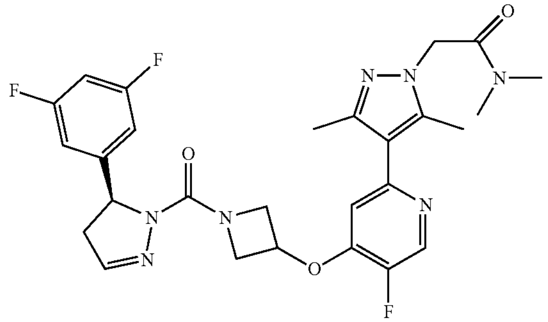 [SMILES: Cc1nn(CC(=O)N(C)C)c(C)c1-c1cc(OC2CN(C(=O)N3N=CC[C@H]3c3cc(F)cc(F)c3)C2)c(F)cn1]

The titled compound 95 was prepared from compound 92 in 45.6% yield according to the procedure outlined for compound 86. $^1$H NMR (400 MHz, Chloroform-d) δ 8.75 (d, J=3.6 Hz, 1H), 6.83 (d, J=1.7 Hz, 1H), 6.79-6.66 (m, 4H), 5.28 (dd, J=12.1, 6.3 Hz, 1H), 5.12 (s, 1H), 5.03 (s, 2H), 4.64 (s, 2H), 4.36 (dd, J=27.1, 10.5 Hz, 2H), 3.38 (dd, J=18.6, 12.1 Hz, 1H), 3.12 (s, 3H), 3.01 (s, 3H), 2.77-2.68 (m, 1H), 2.31 (s, 6H). Mass (m/z) 556.4 [M+H]$^+$.

(S)-2-(4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-1-yl)-1-morpholinoethan-1-one (96)

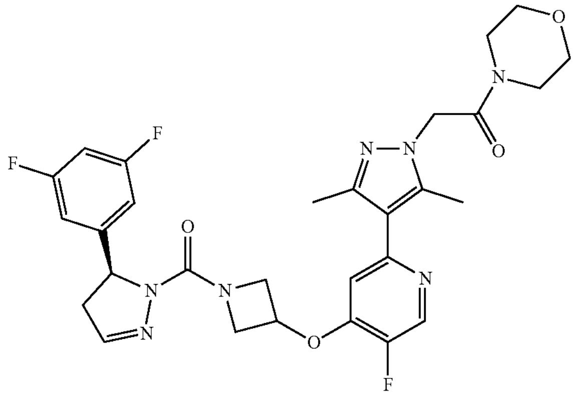 [SMILES: Cc1nn(CC(=O)N2CCOCC2)c(C)c1-c1cc(OC2CN(C(=O)N3N=CC[C@H]3c3cc(F)cc(F)c3)C2)c(F)cn1]

The titled compound 96 was prepared from compound 92 in 35.8% yield according to the procedure outlined for compound 86. $^1$H NMR (400 MHz, Chloroform-d) δ 8.41 (d, J=3.0 Hz, 1H), 6.82-6.58 (m, 5H), 5.27 (dd, J=12.2, 6.4 Hz, 1H), 5.04 (s, 1H), 4.91 (s, 2H), 4.58 (s, 2H), 4.32 (dd, J=29.2, 9.5 Hz, 2H), 3.71 (d, J=4.6 Hz, 4H), 3.62 (dd, J=12.8, 4.9 Hz, 4H), 3.36 (ddd, J=18.6, 12.2, 1.6 Hz, 1H), 2.71 (ddd, J=18.7, 6.5, 1.7 Hz, 1H), 2.38 (s, 3H), 2.32 (s, 3H). Mass (m/z) 598.4 [M+H]$^+$.

(S)-2-(4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-1-yl)-N-methylacetamide (97)

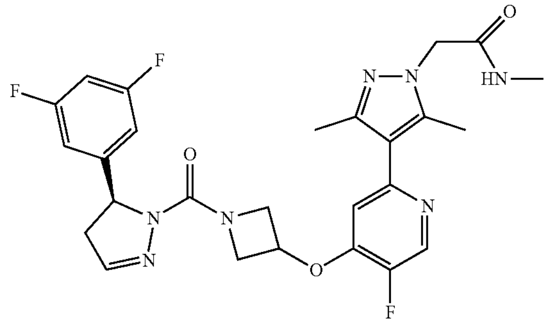 [SMILES: CNC(=O)Cn1nc(C)c(-c2cc(OC3CN(C(=O)N4N=CC[C@H]4c4cc(F)cc(F)c4)C3)c(F)cn2)c1C]

The titled compound 97 was prepared from compound 92 in 26.3% yield (30 mg) according to the procedure outlined for compound 86. $^1$H NMR (400 MHz, Chloroform-d) δ 8.66 (d, J=3.8 Hz, 1H), 6.85 (d, J=1.7 Hz, 1H), 6.82-6.66 (m, 4H), 6.48 (d, J=5.1 Hz, 1H), 5.30 (dd, J=12.1, 6.3 Hz, 1H), 5.19 (tt, J=6.5, 3.8 Hz, 1H), 4.82 (s, 2H), 4.66 (s, 2H), 4.39 (dd, J=30.1, 10.5 Hz, 2H), 3.40 (ddd, J=18.7, 12.1, 1.7 Hz, 1H), 2.83 (d, J=4.7 Hz, 3H), 2.76 (ddd, J=18.7, 6.3, 1.8 Hz, 1H), 2.32 (d, J=8.6 Hz, 6H). Mass (m/z) 542.3 $[M+H]^+$.

(S)-2-(4-(4-((1-(5-(3,5-difluorophenyl)-4,5-dihydro-1H-pyrazole-1-carbonyl)azetidin-3-yl)oxy)-5-fluoro-pyrimidin-2-yl)-3,5-dimethyl-1H-pyrazol-1-yl)-N-methylacetamide (98)

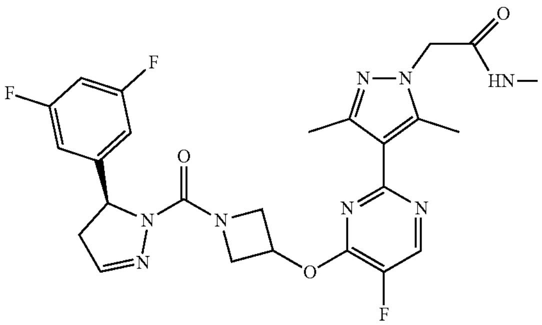 [SMILES: CNC(=O)Cn1nc(C)c(-c2ncc(F)c(OC3CN(C(=O)N4N=CC[C@H]4c4cc(F)cc(F)c4)C3)n2)c1C]

The titled compound 98 was prepared from compound 91 in 6.1% yield according to the procedure outlined for compound 86. $^1$H NMR (400 MHz, Chloroform-d) δ 8.32 (d, J=2.5 Hz, 1H), 6.77-6.59 (m, 4H), 6.08 (s, 1H), 5.45 (td, J=6.5, 3.2 Hz, 1H), 5.21 (dd, J=12.2, 6.4 Hz, 1H), 4.70 (s, 2H), 4.55 (s, 2H), 4.26 (dd, J=31.8, 10.4 Hz, 2H), 3.36-3.22 (m, 1H), 2.74 (d, J=4.8 Hz, 3H), 2.64 (ddd, J=18.6, 6.5, 1.7 Hz, 1H), 2.51 (d, J=20.5 Hz, 6H). Mass (m/z) 543.3 $[M+H]^+$.

(S)-2-(4-(4-((1-(5-(3,5-difluorophenyl)-4,5-dihydro-1H-pyrazole-1-carbonyl)azetidin-3-yl)oxy)-5-fluoro-pyrimidin-2-yl)-3,5-dimethyl-1H-pyrazol-1-yl)acet-amide (99)

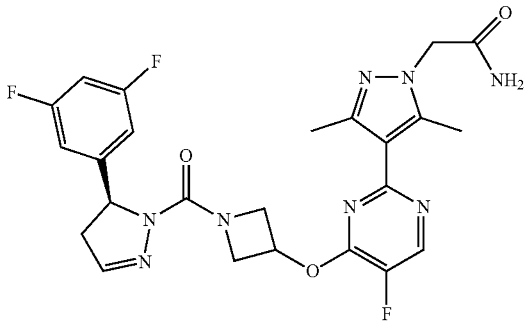 [SMILES: Cc1nn(CC(N)=O)c(C)c1-c1ncc(F)c(OC2CN(C(=O)N3N=CC[C@H]3c3cc(F)cc(F)c3)C2)n1]

The titled compound 99 was prepared from compound 91 in 22.5% yield according to the procedure outlined for compound 86. $^1$H NMR (400 MHz, Chloroform-d) δ 8.42 (dd, J=2.6, 1.1 Hz, 1H), 6.87-6.68 (m, 4H), 6.35 (s, 1H), 5.81 (s, 1H), 5.55 (s, 1H), 5.31 (dd, J=12.2, 6.3 Hz, 1H), 4.86 (s, 2H), 4.65 (s, 2H), 4.37 (d, J=32.3 Hz, 2H), 3.39 (dd, J=18.7, 12.2 Hz, 1H), 2.74 (dd, J=18.8, 6.3 Hz, 1H), 2.62 (dt, J=33.5, 2.0 Hz, 6H). Mass (m/z) 529.3 $[M+H]^+$.

(S)-2-(4-(4-((1-(5-(3,5-difluorophenyl)-4,5-dihydro-1H-pyrazole-1-carbonyl)azetidin-3-yl)oxy)-5-fluoro-pyrimidin-2-yl)-3,5-dimethyl-1H-pyrazol-1-yl)-N,N-dimethylacetamide (100)

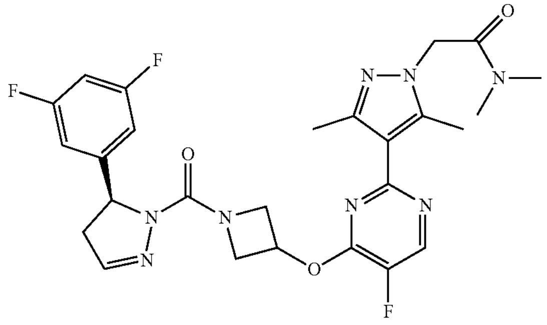

The titled compound 100 was prepared from compound 91 in 8.5% yield according to the procedure outlined for compound 86. $^1$H NMR (400 MHz, Chloroform-d) δ 8.27 (d, J=2.6 Hz, 1H), 6.73-6.65 (m, 3H), 6.61 (tt, J=8.8, 2.3 Hz, 11H), 5.44 (td, J=6.6, 3.4 Hz, 11H), 5.19 (dd, J=12.2, 6.5 Hz, 1H), 4.86 (s, 2H), 4.52 (d, J=8.9 Hz, 2H), 4.23 (dd, J=30.7, 10.8 Hz, 2H), 3.27 (ddd, J=18.6, 12.2, 1.7 Hz, 1H), 3.03 (s, 3H), 2.91 (s, 3H), 2.62 (ddd, J=18.5, 6.5, 1.7 Hz, 1H), 2.48 (d, J=21.3 Hz, 6H). Mass (m/z) 557.4 $[M+H]^+$.

(S)-(3-((2-(3-amino-1,4-dimethyl-11H-pyrazol-5-yl)-5-fluoropyridin-4-yl)oxy)azetidin-1-yl)(5-(3,5-dif-luorophenyl)-4,5-dihydro-1H-pyrazol-1-yl)metha-none (101)

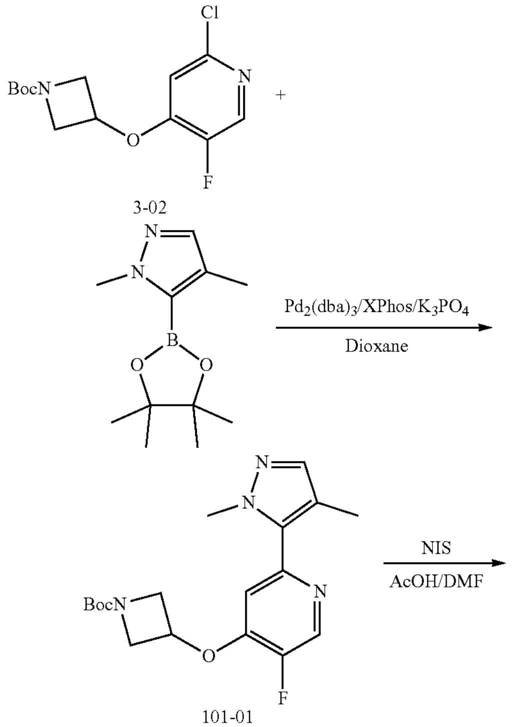

-continued

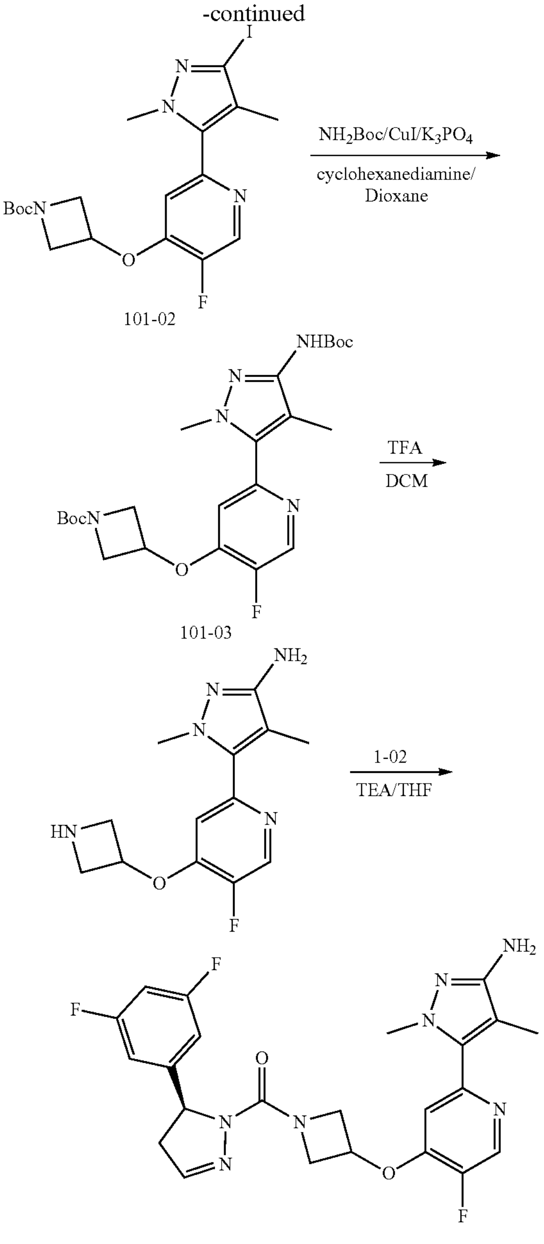

101-02

101-03

101

Step 1: Compound 3-02 (2.0 g, 6.62 mmoL), 1,4-dimethyl-5-(4,4,5,5-tetramethyl-1,3,2-dioxaborolan-2-yl)-1H-pyrazole (2.2 g, 9.93 mmol), $Pd_2(dba)_3$ (605 mg, 0.66 mmol), XPhos (314 mg, 0.66 mmol) and 5N $K_3PO_4$ (4 mL, 19.9 mmol) were dissolved in dioxane (30 mL) under $N_2$ (g) atmosphere. The mixture was stirred at 100° C. for 15 hours. Concentrated and purified by flash chromatography (PE/EA=1/1) to give yellow oil 1.1 g. Yield: 45.8%

Step 2: The intermediate 101-01 (800 mg, 2.21 mmol) was dissolved in AcOH (5 mL) and DMF (2 mL). Then NIS (994 mg, 4.42 mmoL) was added. The mixture was stirred at 80° C. for 4 hours. EA (50 mL) was added. $H_2O$ (20 mL) and $NaHCO_3$ (20 mL) washed. Then purified by flash chromatography (PE/EA=1/1) to give 300 mg of 101-02 as brown oil. Yield: 27.8%

Step 3: 101-02 (360 mg, 0.74 mmoL), tert-butyl carbamate (173 mg, 1.48 mmol), CuI (141 mg, 0.74 mmol), Cyclohexanediamine (253 mg, 2.22 mmol) and $K_3PO_4$ (471 mg, 22.2 mmol) were dissolved in dioxane (15 mL) under $N_2$ (g) atmosphere. The mixture was stirred at 100° C. for hours. Concentrated and purified by TLC-chromatography (DCM/MeOH=30/1) to give 70 mg of 101-03 as yellow solid. Yield: 18.6%.

Step 4-5: The titled compound 101 was prepared from compound 101-03 (20 mg, 0.04 mmol) according to the procedure outlined for compound 50-05 to 50. $^1$H NMR (400 MHz, Chloroform-d) δ 8.48 (d, J=2.9 Hz, 1H), 6.84-6.79 (m, 1H), 6.78-6.56 (m, 4H), 5.27 (dd, J=12.2, 6.4 Hz, 1H), 5.11-5.01 (m, 1H), 4.61 (d, J=16.4 Hz, 2H), 4.32 (dd, J=31.4, 10.7 Hz, 2H), 3.78 (s, 3H), 3.36 (ddd, J=18.7, 12.2, 1.7 Hz, 1H), 2.71 (ddd, J=18.6, 6.5, 1.8 Hz, 1H), 1.95 (s, 3H). Mass (m/z) 486.2 $[M+H]^+$.

(S)-(5-(3,5-difluorophenyl)-4,5-dihydro-1H-pyrazol-1-yl)(3-((5-fluoro-2-(2-methyl-1H-pyrrol-1-yl)pyrimidin-4-yl)oxy)azetidin-1-yl)methanone (102)

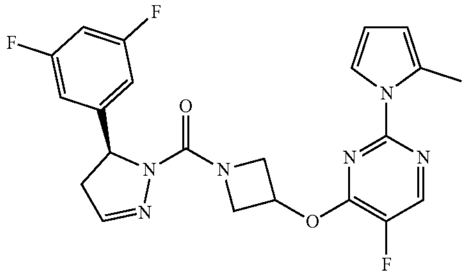

Compound 2-03 (60 mg, 0.144 mmol), 2-methyl-1H-pyrrole (24 mg, 0.29 mmol), NaOtBu (18 mg, 0.18 mmol), $Pd_2(dba)_3$ (12 mg, 0.012 mmol) and X-Phos (6 mg, 0.012 mmol) were added to DMF (3 mL) under $N_2$ atmosphere. The mixture was stirred at 90° C. overnight. The mixture was concentrated and purified by TLC (PE/EA=2/1) to give white solid 17 mg. yield: 21.9%. $^1$H NMR (400 MHz, Chloroform-d) δ 8.27 (d, J=2.2 Hz, 1H), 7.55 (dd, J=3.3, 1.9 Hz, 1H), 6.82-6.73 (m, 3H), 6.73-6.66 (m, 1H), 6.16 (t, J=3.3 Hz, 1H), 6.03-5.99 (m, 1H), 5.53-5.46 (m, 1H), 5.28 (dd, J=12.2, 6.5 Hz, 1H), 4.69-4.56 (m, 2H), 4.41-4.23 (m, 2H), 3.35 (ddd, J=18.6, 12.2, 1.7 Hz, 1H), 2.70 (ddd, J=18.6, 6.5, 1.7 Hz, 1H), 2.59 (s, 3H). Mass (m/z) 457.3 $[M+H]^+$.

(S)-(5-(3,5-difluorophenyl)-4,5-dihydro-1H-pyrazol-1-yl)(3-((2-(3,5-dimethyl-1H-1,2,4-triazol-1-yl)-5-fluoropyrimidin-4-yl)oxy)azetidin-1-yl)methanone (103)

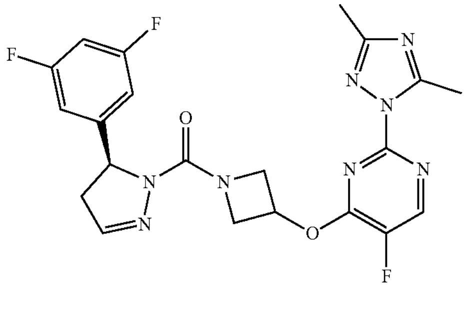 [SMILES: Cc1nc(C)n(-c2ncc(F)c(OC3CN(C(=O)N4N=CC[C@H]4c4cc(F)cc(F)c4)C3)n2)n1]

The titled compound 103 was prepared from 2-03 in 1.0% yield according to the procedure outlined for compound 102. $^{1}$H NMR (400 MHz, Chloroform-d) δ 8.48 (s, 1H), 6.82 (t, J=2.0 Hz, 1H), 6.77-6.56 (m, 4H), 5.62-5.52 (m, 1H), 5.29 (dd, J=12.2, 6.2 Hz, 1H), 4.72-4.57 (m, 2H), 4.36 (dd, J=27.7, 11.0 Hz, 2H), 3.38 (ddd, J=18.6, 12.1, 1.7 Hz, 1H), 2.91 (s, 3H), 2.73 (ddd, J=18.6, 6.1, 1.7 Hz, 3H), 2.57-2.41 (m, 3H). Mass (m/z) 473.3[M+H]$^{+}$.

(S)-(5-(3,5-difluorophenyl)-4,5-dihydro-1H-pyrazol-1-yl)(3-((2-(3,5-dimethyl-1H-1,2,4-triazol-1-yl)-5-fluoropyridin-4-yl)oxy)azetidin-1-yl)methanone (104)

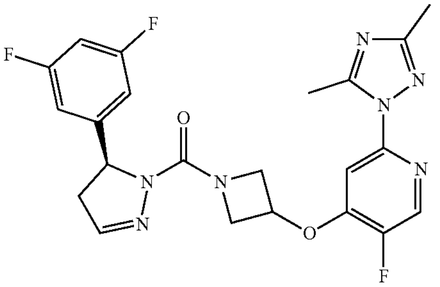 [SMILES: Cc1nc(C)n(-c2cc(OC3CN(C(=O)N4N=CC[C@H]4c4cc(F)cc(F)c4)C3)c(F)cn2)n1]

The titled compound 104 was prepared from 3-04 in 48.1% yield according to the procedure outlined for compound 102. $^{1}$H NMR (400 MHz, Chloroform-d) δ 8.22 (d, J=2.4 Hz, 1H), 7.22 (d, J=6.1 Hz, 1H), 6.80 (t, J=1.7 Hz, 1H), 6.78-6.58 (m, 3H), 5.28 (dd, J=12.2, 6.4 Hz, 1H), 5.19-5.10 (m, 1H), 4.71-4.59 (m, 2H), 4.32 (dd, J=31.3, 10.0 Hz, 2H), 3.36 (ddd, J=18.7, 12.2, 1.8 Hz, 1H), 2.84 (s, 3H), 2.71 (ddd, J=18.6, 6.4, 1.7 Hz, 1H), 2.43 (s, 3H). Mass (m/z) 472.2 [M+H]$^{+}$.

(S)-(5-(3,5-difluorophenyl)-4,5-dihydro-1H-pyrazol-1-yl)(3-((5-fluoro-2-(2-methyl-1H-imidazol-1-yl) pyrimidin-4-yl)oxy)azetidin-1-yl)methanone (105)

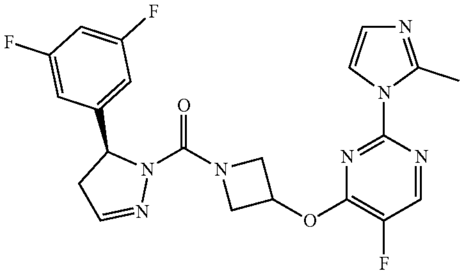 [SMILES: Cc1nccn1-c1ncc(F)c(OC2CN(C(=O)N3N=CC[C@H]3c3cc(F)cc(F)c3)C2)n1]

The titled compound 105 was prepared from 2-03 in 18.2% yield according to the procedure outlined for compound 102. $^{1}$H NMR (400 MHz, Chloroform-d) δ 8.46 (d, J=1.7 Hz, 1H), 7.89 (s, 1H), 7.37 (s, 1H), 6.83-6.78 (m, 1H), 6.78-6.62 (m, 3H), 5.55-5.49 (m, 1H), 5.27 (dd, J=12.1, 6.4 Hz, 1H), 4.66 (dd, J=19.8, 11.1 Hz, 2H), 4.35 (dd, J=22.3, 10.7 Hz, 2H), 3.37 (ddd, J=18.6, 12.1, 1.7 Hz, 1H), 3.08 (s, 3H), 2.72 (ddd, J=18.6, 6.3, 1.7 Hz, 1H). Mass (m/z) 458.2 [M+H]$^{+}$.

(S)-1-(4-((1-(5-(3,5-difluorophenyl)-4,5-dihydro-1H-pyrazole-1-carbonyl)azetidin-3-yl)oxy)-5-fluoropyrimidin-2-yl)-1H-pyrrole-2-carbonitrile (106)

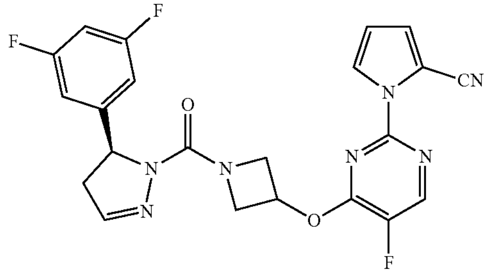 [SMILES: N#Cc1cccn1-c1ncc(F)c(OC2CN(C(=O)N3N=CC[C@H]3c3cc(F)cc(F)c3)C2)n1]

The titled compound 106 was prepared from 2-03 in 29.8% yield according to the procedure outlined for compound 102. $^{1}$H NMR (400 MHz, Chloroform-d) δ 8.32 (d, J=2.1 Hz, 1H), 7.88 (dd, J=3.1, 1.7 Hz, 1H), 7.06 (dd, J=3.7, 1.7 Hz, 1H), 6.86-6.73 (m, 3H), 6.72-6.65 (m, 1H), 6.36 (dd, J=3.7, 3.2 Hz, 1H), 5.77-5.70 (m, 1H), 5.28 (dd, J=12.2, 6.3 Hz, 1H), 4.82-4.67 (m, 2H), 4.30 (t, J=13.0 Hz, 2H), 3.35 (ddd, J=18.6, 12.2, 1.7 Hz, 1H), 2.69 (ddd, J=18.6, 6.3, 1.7 Hz, 1H). Mass (m/z) 468.3 [M+H]$^{+}$.

(S)-1-(4-((1-(5-(3,5-difluorophenyl)-4,5-dihydro-1H-pyrazole-1-carbonyl)azetidin-3-yl)oxy)-5-fluoropyrimidin-2-yl)-1H-pyrrole-2-carboxamide (107)

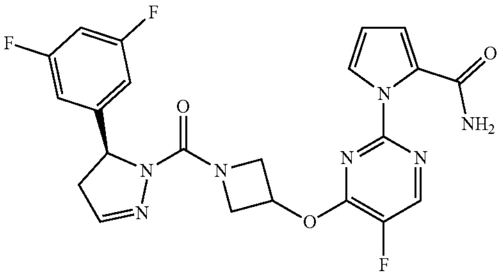 [SMILES: NC(=O)c1cccn1-c1ncc(F)c(OC2CN(C(=O)N3N=CC[C@H]3c3cc(F)cc(F)c3)C2)n1]

The titled compound 107 was prepared from compound 106 in 10.3% yield according to the procedure outlined for compound 66-02. $^{1}$H NMR (400 MHz, Chloroform-d) δ 8.31 (s, 1H), 7.55 (s, 1H), 6.91-6.62 (m, 5H), 6.27 (t, J=3.3 Hz, 1H), 5.50-5.49 (m, 1H), 5.33-5.23 (m, 1H), 4.70-4.56 (m, 2H), 4.42-4.25 (m, 2H), 3.44-3.29 (m, 1H), 2.76-2.65 (m, 1H). Mass (m/z) 486.2 [M+H]$^{+}$.

(S)-(5-(3,5-difluorophenyl)-4,5-dihydro-1H-pyrazol-1-yl)(3-((2-(3,5-dimethyl-4-nitro-1H-pyrazol-1-yl)-5-fluoropyridin-4-yl)oxy)azetidin-1-yl)methanone (108)

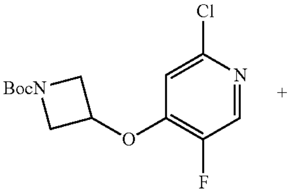

3-02

-continued

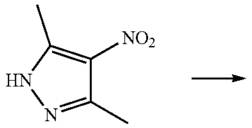

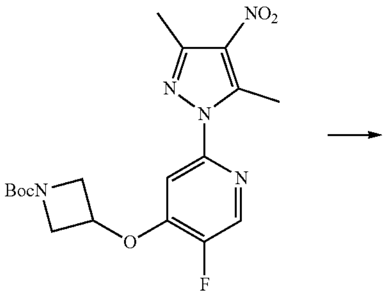

108-01

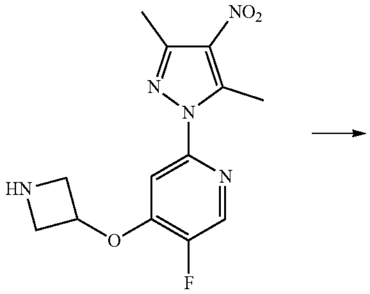

108-02

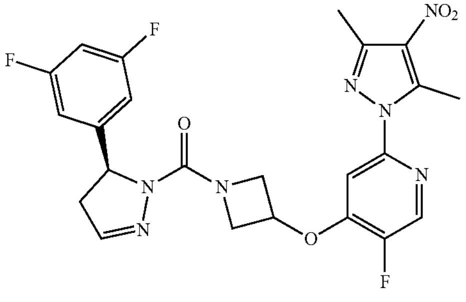

108

Step 1: To a mixture of tert-butyl 3-((2-chloro-5-fluoropyridin-4-yl)oxy)azetidine-1-carboxylate 3-02 (300 mg, 0.99 mmol), 3,5-dimethyl-4-nitro-1H-pyrazole (280 mg, 1.98 mmol) and (1S,2S)-cyclohexane-1,2-diamine (338 mg, 2.97 mmol) were added anhydrous DMF (4.0 mL). This mixture was purged with argon for 5 minutes and copper(I) iodide (56 mg, 0.297 mmol) and $K_3PO_4$ (629 mg, 2.97 mmol) were added. The reaction mixture was heated at 140° C. for 24 hours and then purification by column chromatography to give compound 108-01 as yellow oil. (yield: 28.3%, 210 mg).

Step 2-3: The titled compound 108 was prepared from compound 108-01 according to the procedure outlined for compound 50-05 to 50. $^1$H NMR (400 MHz, Chloroform-d) δ 8.25 (d, J=2.4 Hz, 1H), 7.18 (d, J=6.1 Hz, 1H), 6.85-6.78 (m, 1H), 6.78-6.58 (m, 3H), 5.34-5.22 (m, 1H), 5.19-5.12 (m, 1H), 4.71-4.57 (m, 2H), 4.33 (dd, J=33.7, 10.0 Hz, 2H), 3.37 (ddd, J=18.6, 12.2, 1.7 Hz, 1H), 2.97 (s, 3H), 2.71 (ddd, J=18.6, 6.4, 1.7 Hz, 1H), 2.58 (s, 3H). Mass (m/z) 516.2 $[M+H]^+$.

(S)-(3-((2-(4-amino-3,5-dimethyl-11H-pyrazol-1-yl)-5-fluoropyridin-4-yl)oxy)azetidin-1-yl)(5-(3,5-difluorophenyl)-4,5-dihydro-1H-pyrazol-1-yl)methanone (109)

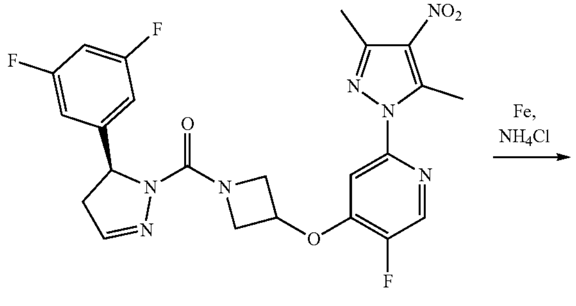

108

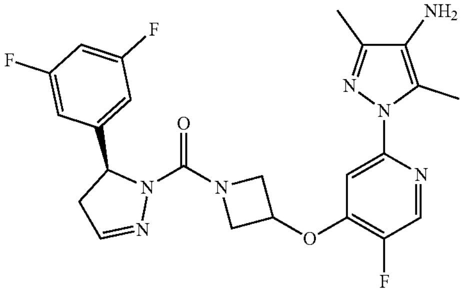

109

Compound 108 (45 mg, 0.087 mmol), Fe (24 mg, 0.44 mmol) and $NH_4Cl$ (24 mg, 0.44 mmol) were dissolved in EtOH (2 mL) and $H_2O$ (2 mL). The mixture was stirred at 80° C. for 2 hrs. The mixture was reduced pressure and purified by prep-TLC to give the title compound 109 as white solid. 42 mg, yield: 89.4%. $^1$H NMR (400 MHz, Chloroform-d) δ 8.11 (d, J=2.5 Hz, 1H), 7.17 (d, J=6.2 Hz, 1H), 6.78 (t, J=1.7 Hz, 1H), 6.77-6.41 (m, 3H), 5.27 (dd, J=12.2, 6.4 Hz, 1H), 5.19-5.05 (m, 1H), 4.69-4.56 (m, 2H), 4.31 (dd, J=31.0, 10.4 Hz, 2H), 3.35 (ddd, J=18.6, 12.2, 1.7 Hz, 1H), 2.70 (ddd, J=18.6, 6.4, 1.7 Hz, 1H), 2.52 (s, 3H), 2.25 (s, 3H). Mass (m/z) 486.2$[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxamide (110)

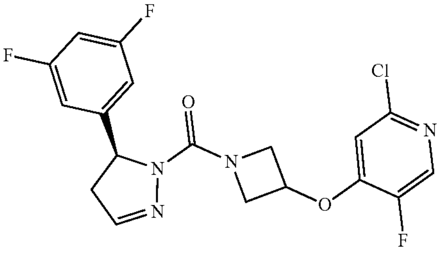

+

3-04

-continued

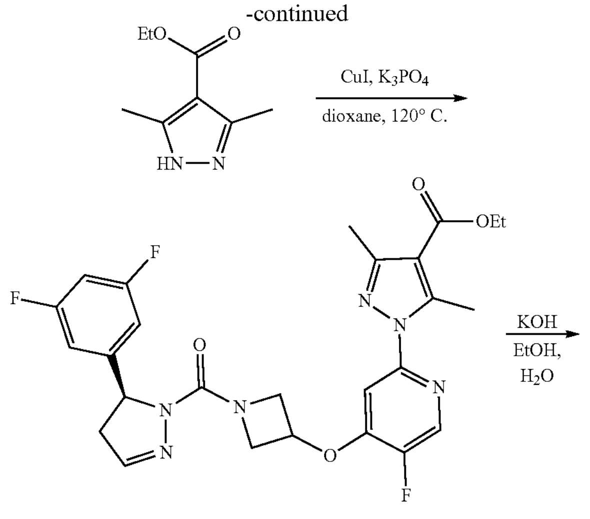

110-01

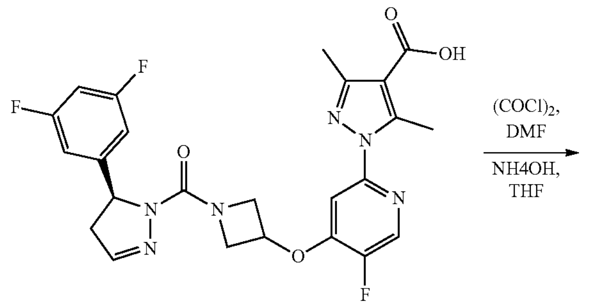

110-02

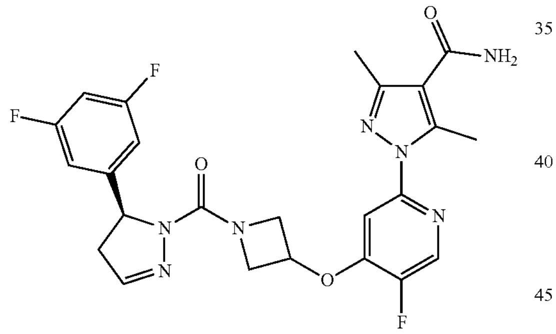

110

Step 1: 3-04 (2 g, 4.87 mmol), ethyl 3,5-dimethyl-1H-pyrazole-4-carboxylate (900 mg, 5.36 mmol), CuI (4.3 g, 9.74 mmol) and $K_3PO_4$ (3.1 g, 14.61 mmol), (1S, 2S)—$N^1$, $N^2$-dimethylcyclohexane-1,2-diamine (1.38 g, 9.74 mmol) were placed in dioxane (50 mL). The mixture was stirred for 12 h at 120° C. under $N_2$. The mixture was extracted with DCM, washed with brine, dried ($Na_2SO_4$), and concentrated in vacuo. Purification by silica gel chromatography to give the intermediate compound 110-01 (800 mg, 30.2%) as a white solid. Mass (m/z): 453.2 $[M+H]^+$.

Step 2: Compound 110-01 (700 mg, 1.55 mmol), and KOH (200 mg, 3.57 mmol) were placed in EtOH (3 mL) and $H_2O$ (3 ml). The mixture was stirred for 12 h at 55° C., then adjust pH to 7, extracted with EA, washed with brine, dried ($Na_2SO_4$), and concentrated in vacuo. Purification by silica gel chromatography to give the compound 110-02 (compound 233) (520 mg, 65%) as a white solid. Mass (m/z): 515.2 $[M+H]^+$.

Step 3: 110-02 (250 mg, 0.48 mmol), DMF (0.01 ml) were placed in THE (5 mL). Then Oxalyl chloride (0.2 ml) was added to the mixture. The mixture was stirred for 30 min at 25° C., then $NH_4OH$ (10 ml, 30%), stirred 30 min at 25° C. The mixture was extracted with EA, washed with brine, dried ($Na_2SO_4$), and concentrated in vacuo. Purification by silica gel chromatography to give the titled compound 110 (18 mg, 24.2%) as a white solid. $^1H$ NMR (400 MHz, Chloroform-d) δ 8.14 (s, 1H), 7.10 (d, J=6.1 Hz, 1H), 6.75-6.59 (m, 4H), 5.56 (s, 2H), 5.21 (dd, J=12.2, 6.4 Hz, 1H), 5.11-5.05 (m, 1H), 4.64-4.47 (m, 2H), 4.25 (dd, J=33.0, 10.6 Hz, 2H), 3.29 (ddd, J=18.7, 12.2, 1.7 Hz, 1H), 2.75 (s, 3H), δ 2.64 (ddd, J=18.6, 6.5, 1.7 Hz, 1H), 2.41 (s, 3H). Mass (m/z): 515.2 $[M+H]^+$ 5-(6-((1-(5-(3,5-difluorophenyl)-4,5-dihydro-1H-pyrazole-1-carbonyl)azetidin-3-yl)oxy)-5-fluoropyridin-2-yl)-1-methyl-11H-pyrazole-4-carbonitrile (111)

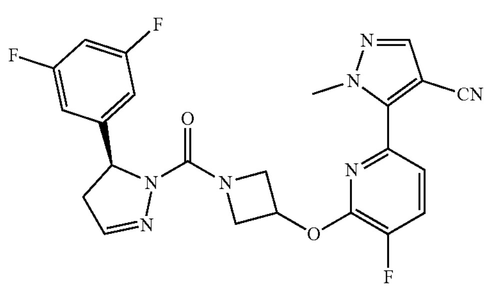

The titled compound 111 was prepared in 11.1% yield from 1-05 according to the procedure outlined for compound 1. $^1H$ NMR (400 MHz, Chloroform-d) δ 7.85-7.77 (m, 1H), 7.60-7.43 (m, 2H), 6.80-6.62 (m, 4H), 5.49-5.39 (m, 1H), 5.32-5.21 (m, 1H), 4.67-4.49 (m, 2H), 4.4-4.20 (m, 2H), 4.08 (s, 3H), 3.40-3.27 (m, 1H), 2.75-2.61 (m, 1H). Mass (m/z) 482.2$[M+H]^+$ (S)-(5-(3,5-difluorophenyl)-4,5-dihydro-1H-pyrazol-1-yl)(3-(5-(1,4-dimethyl-1H-pyrazol-5-yl)-2-fluorophenoxy)azetidin-1-yl)methanone (112)

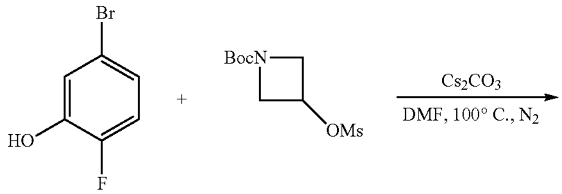

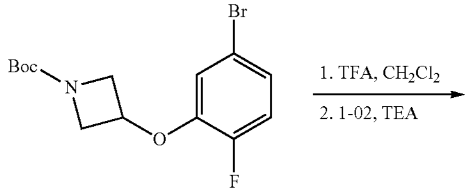

112-01

-continued

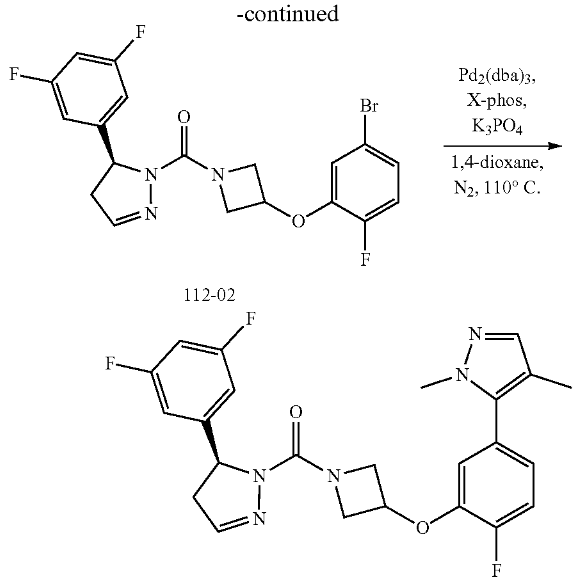

112-02

112

Step 1: 5-bromo-2-fluorophenol (0.96 g, 5.0 mmol), 6-tert-butyl 3-((methylsulfonyl)oxy)azetidine-1-carboxylate (1.3 g, 5.25 mmol), $Cs_2CO_3$ (2.4 g, 7.5 mmol) were placed in DMF (20 mL). The mixture was stirred 100° C. for 2 hours, water was added and extracted with EA, washed with brine, dried ($Na_2SO_4$), and concentrated to dryness to give the intermediate 112-01 (1.4 g, 82.5%) as a white solid. Mass (m/z): 290.1 $[M-56+H]^+$.

Step 2: The intermediate compound 112-02 was prepared in 86.1% yield from 112-01 according to the procedure outlined for compound 50-5 to 50. Mass (m/z): 246.0 $[M+H]^+$.

Step 3: The titled compound 112 was prepared in 41.5% yield from 112-02 according to the procedure outlined for compound 3. $^1$H NMR (400 MHz, Chloroform-d) δ 7.37 (s, 11H), 7.21 (dd, J=11.0, 8.3 Hz, 11H), 6.89 (ddd, J=8.3, 4.3, 2.0 Hz, 1H), 6.80-6.73 (m, 3H), 6.69 (tt, J=8.9, 2.4 Hz, 1H), 6.62 (dd, J=7.9, 2.0 Hz, 1H), 5.27 (dd, J=12.2, 6.5 Hz, 1H), 4.97 (td, J=6.3, 3.2 Hz, 1H), 4.54 (d, J=6.6 Hz, 2H), 4.30 (dd, J=26.0, 9.8 Hz, 2H), 3.74 (s, 3H), 3.35 (ddd, J=18.6, 12.2, 1.8 Hz, 1H), 2.70 (ddd, J=18.6, 6.5, 1.7 Hz, 1H), 1.98 (s, 3H). Mass (m/z): 470.3 $[M+H]^+$.

(S)-(5-(3,5-difluorophenyl)-4,5-dihydro-1H-pyrazol-1-yl)(3-(5-(3,5-dimethyl-1H-pyrazol-4-yl)-2-fluorophenoxy)azetidin-1-yl)methanone (113)

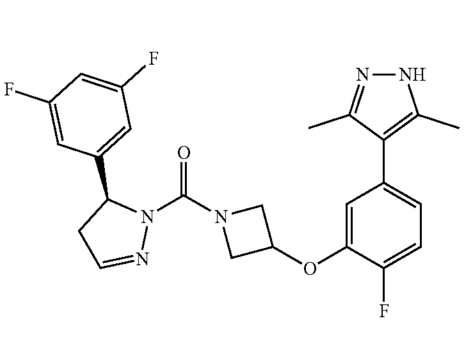 [SMILES: Cc1n[nH]c(C)c1-c1ccc(F)c(OC2CN(C(=O)N3N=CC[C@H]3c3cc(F)cc(F)c3)C2)c1]

The titled compound 113 was prepared in 35.1% yield from 112-02 according to the procedure outlined for compound 3. $^1$H NMR (400 MHz, Chloroform-d) δ 7.13 (dd, J=11.2, 8.4 Hz, 1H), 6.85-6.64 (m, 5H), 6.58 (dd, J=8.0, 2.1 Hz, 1H), 5.27 (dd, J=12.2, 6.5 Hz, 1H), 4.97 (td, J=6.4, 3.2 Hz, 1H), 4.60-4.47 (m, 2H), 4.31 (dd, J=31.5, 10.1 Hz, 2H), 3.38-3.29 (m, 1H), 2.69 (ddd, J=18.6, 6.5, 1.8 Hz, 1H), 2.26 (s, 6H). Mass (m/z): 470.3 $[M+H]^+$.

(S)-(5-(3,5-difluorophenyl)-4,5-dihydro-1H-pyrazol-1-yl)(3-((5-fluoro-2-(1-(2-hydroxyethyl)-3,5-dimethyl-1H-pyrazol-4-yl)pyridin-4-yl)oxy)azetidin-1-yl)methanone (117)

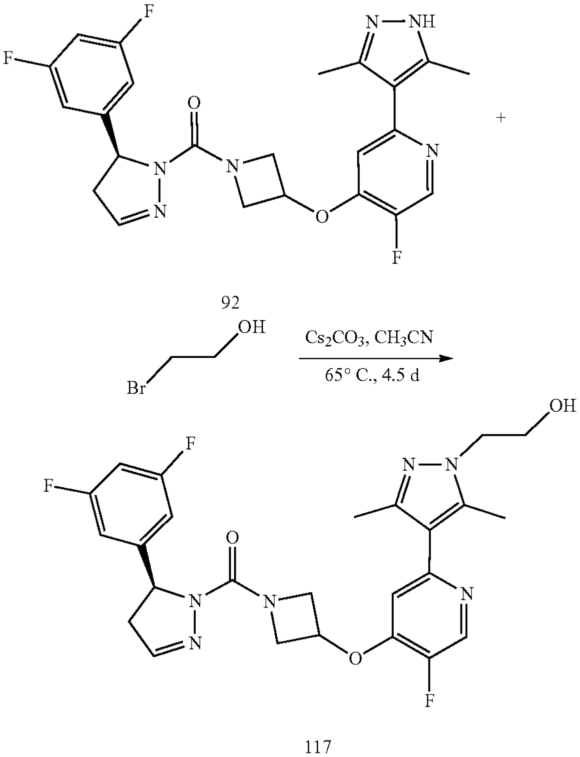

92

117

Compound 92 (99 mg, 0.21 mmol), 2-bromoethan-1-ol (250 mg, 0.42 mmol), $Cs_2CO_3$ (342 mg, 1.05 mmol) were placed in $CH_3CN$ (5 mL). The mixture was stirred at 65° C. for 4.5 d, and then the reaction liquid was poured into water. The mixture was extracted with EA, washed with brine, dried ($Na_2SO_4$), and concentrated in vacuo. Purification by prep-HPLC to give the titled compound 117 (29 mg, 26.8%) as a white solid. Mass (m/z) 515.3 $[M+H]^+$. $^1$H NMR (400 MHz, Chloroform-d) δ 8.69 (d, J=3.8 Hz, 1H), 6.83 (d, J=1.8 Hz, 1H), 6.79-6.63 (m, 4H), 5.28 (dd, J=12.1, 6.2 Hz, 1H), 5.16 (s, 1H), 4.76-4.55 (m, 2H), 4.50-4.20 (m, 4H), 3.99 (d, J=8.7 Hz, 2H), 3.38 (ddd, J=18.7, 12.1, 1.6 Hz, 1H), 2.73 (ddd, J=18.7, 6.3, 1.8 Hz, 1H), 2.33 (dd, J=22.7, 9.5 Hz, 6H).

methyl (S)-2-(4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-1-yl) acetate (118)

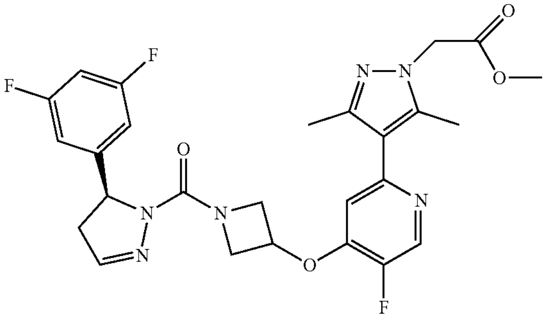 [SMILES: COC(=O)Cn1nc(C)c(-c2cc(OC3CN(C(=O)N4N=CC[C@H]4c4cc(F)cc(F)c4)C3)c(F)cn2)c1C]

The titled compound 118 was prepared in 34.6% yield from compound 92 according to the procedure outlined for compound 86. $^1$H NMR (400 MHz, Chloroform-d) δ 8.59 (d, J=3.2 Hz, 1H), 7.01-6.64 (m, 5H), 5.16 (d, J=7.8 Hz, 1H), 4.88 (s, 2H), 4.81 (d, J=7.8 Hz, 1H), 4.46 (t, J=7.8 Hz, 2H), 4.20 (d, J=9.1 Hz, 2H), 3.80 (s, 3H), 3.04 (dd, J=16.8, 6.1 Hz, 1H), 2.91 (dd, J=16.8, 5.2 Hz, 1H), 2.32 (d, J=4.6 Hz, 6H). Mass (m/z) 543.3 [M+H]$^+$.

(S)-(5-(3,5-difluorophenyl)-4,5-dihydro-1H-pyrazol-1-yl)(3-((2-(4-((2-(dimethylamino)ethyl)amino)-1-methyl-1H-pyrazol-5-yl)-5-fluoropyridin-4-yl)oxy) azetidin-1-yl)methanone (119)

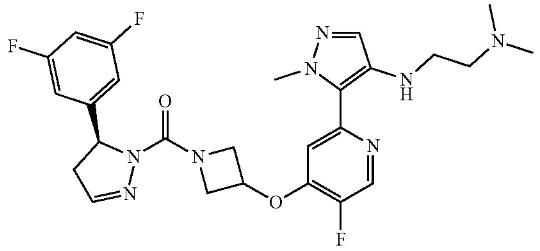

The titled compound 119 was prepared in 16.8% yield from compound 53 according to the procedure outlined for compound 50. Mass (m/z) 543.2 [M+H]$^+$. $^1$H NMR (400 MHz, Chloroform-d) δ 8.43 (d, J=2.9 Hz, 11H), 7.24 (s, 11H), 7.10 (d, J=6.5 Hz, 11H), 6.79 (s, 11H), 6.76-6.65 (m, 3H), 5.51 (s, 1H), 5.25 (dd, J=12.2, 6.4 Hz, 1H), 4.63 (s, 2H), 4.35-4.21 (m, 2H), 3.97 (s, 3H), 3.52 (d, J=5.6 Hz, 2H), 3.34 (dd, J=18.6, 12.3 Hz, 1H), 3.26 (s, 2H), 2.84 (s, 6H), 2.71-2.65 (m, 1H).

(S)-(5-(3,5-difluorophenyl)-4,5-dihydro-1H-pyrazol-1-yl)(3-((5-fluoro-2-(1-methyl-4-((2-morpholinoethyl)amino)-1H-pyrazol-5-yl)pyridin-4-yl)oxy)azetidin-1-yl)methanone (120)

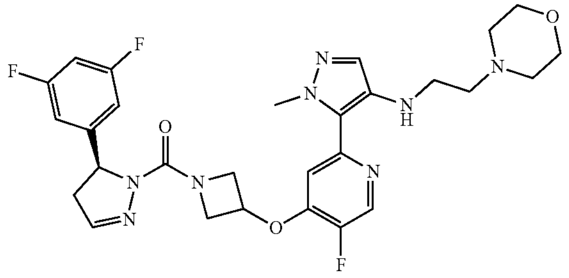 [SMILES: Cn1ncc(NCCN2CCOCC2)c1-c1cc(OC2CN(C(=O)N3N=CC[C@H]3c3cc(F)cc(F)c3)C2)c(F)cn1]

The titled compound 120 was prepared in 19.8% yield from compound 53 according to the procedure outlined for compound 50. Mass (m/z) 585.1 [M+H]$^+$. $^1$H NMR (400 MHz, Chloroform-d) δ 8.44 (d, J=2.9 Hz, 1H), 7.20 (s, 1H), 6.95 (d, J=6.5 Hz, 1H), 6.79 (d, J=1.8 Hz, 1H), 6.78-6.66 (m, 3H), 5.27 (dd, J=12.2, 6.4 Hz, 1H), 5.10 (s, 1H), 4.60 (s, 2H), 4.32 (dd, J=33.6, 10.4 Hz, 2H), 4.00 (s, 3H), 3.70 (s, 4H), 3.36 (ddd, J=18.7, 12.2, 1.7 Hz, 1H), 3.17 (s, 2H), 2.76-2.62 (m, 3H), 2.52 (s, 4H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)-2-methoxyacetamide (121)

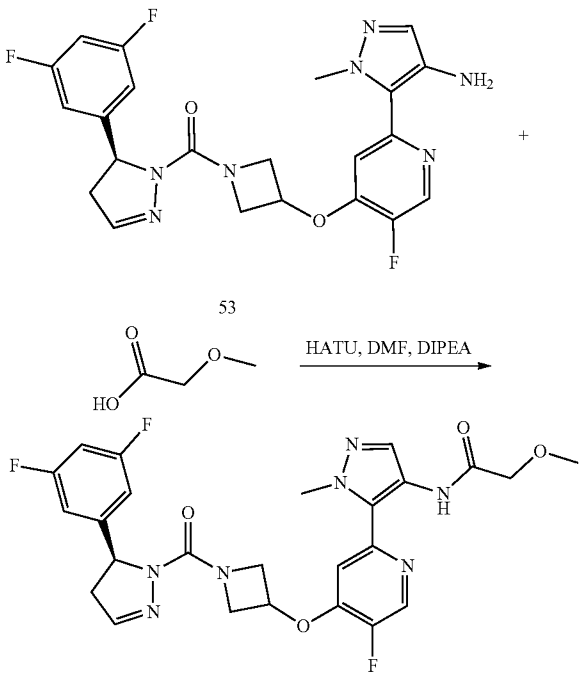

53

121

Compound 53 (200 mg, 0.42 mmol), 2-methoxyacetic acid (76 mg, 0.84 mmol), DIPEA (110 mg, 0.84 mmol), HATU (160 mg, 0.42 mmol) were dissolved in DMF (5 mL)

and stirred at 25° C. for 10 mins. The mixture was extracted with EA, washed with brine, dried ($Na_2SO_4$), and concentrated in vacuo. Purification by prep-HPLC gave the titled compound 121 (54 mg, 23.5%) as a white solid. Mass (m/z) 544.1 $[M+H]^+$. $^1H$ NMR (400 MHz, Chloroform-d) δ 9.77 (s, 1H), 8.51 (d, J=2.8 Hz, 1H), 8.20 (s, 1H), 6.90 (d, J=6.4 Hz, 1H), 6.82 (d, J=1.7 Hz, 1H), 6.79-6.69 (m, 31H), 5.30 (dd, J=12.2, 6.4 Hz, 11H), 5.10 (td, J=6.5, 3.3 Hz, 1H), 4.70-4.55 (m, 2H), 4.35 (dd, J=30.2, 10.3 Hz, 2H), 4.07 (s, 3H), 4.05 (s, 2H), 3.51 (s, 3H), 3.39 (ddd, J=18.6, 12.2, 1.7 Hz, 1H), 2.74 (ddd, J=18.6, 6.4, 1.7 Hz, 1H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)-2-(dimethylamino)acetamide (122)

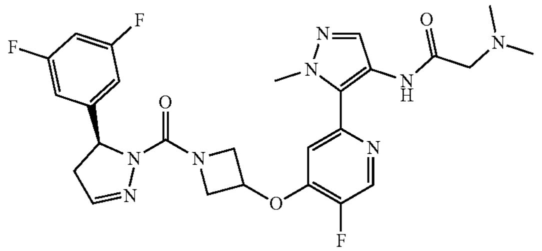

The titled compound 122 was prepared in 25.8% yield from compound 53 according to the procedure outlined for compound 121. Mass (m/z) 557.1 $[M+H]^+$. $^1H$ NMR (400 MHz, Chloroform-d) δ 10.27 (s, 1H), 8.49 (d, J=2.9 Hz, 1H), 8.01 (s, 1H), 6.90 (d, J=6.4 Hz, 1H), 6.81 (d, J=1.7 Hz, 1H), 6.78-6.66 (m, 3H), 5.30-5.23 (m, 1H), 5.17 (s, 1H), 4.59 (s, 2H), 4.32 (dd, J=31.6, 10.5 Hz, 2H), 3.98 (s, 5H), 3.46-3.29 (m, 1H), 2.97 (s, 6H), 2.70 (ddd, J=18.5, 6.3, 1.7 Hz, 1H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)-2-(4-methylpiperazin-1-yl)acetamide (123)

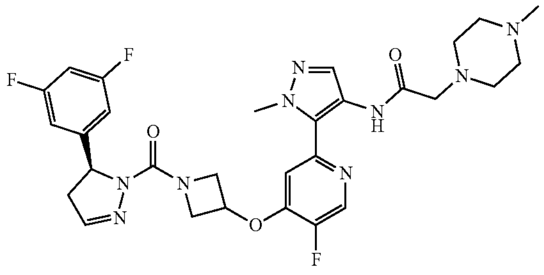 [SMILES: CN1CCN(CC(=O)Nc2cnn(C)c2-c2cc(OC3CN(C(=O)N4N=CC[C@H]4c4cc(F)cc(F)c4)C3)c(F)cn2)CC1]

The titled compound 123 was prepared in 24.3% yield from compound 53 according to the procedure outlined for compound 121. Mass (m/z) 612.3 $[M+H^+]$. $^1H$ NMR (400 MHz, Chloroform-d) δ 9.92 (s, 1H), 8.46 (d, J=2.9 Hz, 11H), 8.13 (s, 11H), 6.92 (d, J=6.4 Hz, 11H), 6.88-6.81 (m, 1H), 6.79-6.65 (m, 3H), 5.27 (dd, J=12.1, 6.3 Hz, 1H), 5.12 (q, J=6.0, 4.9 Hz, 1H), 4.62 (d, J=9.9 Hz, 2H), 4.33 (dd, J=29.8, 10.6 Hz, 2H), 4.02 (s, 3H), 3.58 (s, 2H), 3.43-3.32 (m, 3H), 3.04 (s, 6H), 2.86 (s, 3H), 2.73 (ddd, J=18.7, 6.3, 1.8 Hz, 1H).

(S)-1-(4-((1-(5-(3,5-difluorophenyl)-4,5-dihydro-1H-pyrazole-1-carbonyl)azetidin-3-yl)oxy)-5-fluoropyridin-2-yl)-3-ethyl-5-methyl-1H-pyrazole-4-carbonitrile (124)

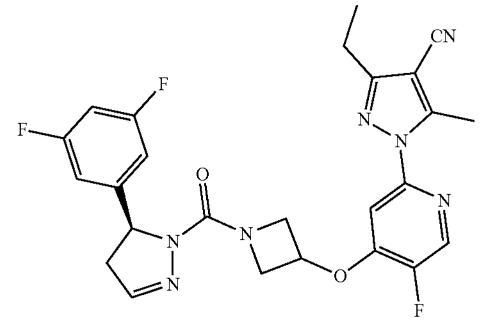 [SMILES: CCc1nn(-c2cc(OC3CN(C(=O)N4N=CC[C@H]4c4cc(F)cc(F)c4)C3)c(F)cn2)c(C)c1C#N]

The titled compound 124 was prepared in a yield of 23.1% according to the procedure outlined for compound 110. $^1H$ NMR (400 MHz, Chloroform-d) δ 8.18 (d, J=2.3 Hz, 1H), 7.23 (s, 1H), 6.81-6.65 (m, 4H), 5.27 (dd, J=12.2, 6.4 Hz, 1H), 5.14 (dt, J=6.4, 2.7 Hz, 1H), 4.62 (d, J=6.5 Hz, 2H), 4.31 (dd, J=36.7, 10.6 Hz, 2H), 3.35 (ddd, J=18.7, 12.2, 1.7 Hz, 1H), 2.80-2.67 (m, 6H), 1.33 (t, J=7.6 Hz, 3H). Mass (m/z) 510.1 $[M+H]^+$.

(S)-(5-(3,5-difluorophenyl)-4,5-dihydro-1H-pyrazol-1-yl)(3-((2-(1,4-dimethyl-3-(methylamino)-1H-pyrazol-5-yl)-5-fluoropyridin-4-yl)oxy)azetidin-1-yl)methanone (125)

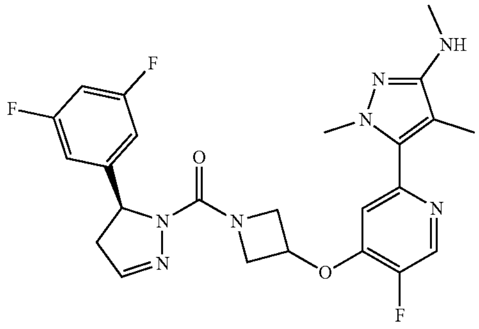 [SMILES: CNc1nn(C)c(-c2cc(OC3CN(C(=O)N4N=CC[C@H]4c4cc(F)cc(F)c4)C3)c(F)cn2)c1C]

The titled compound 125 was prepared from compound 101-03 according to the procedure outlined for compound 56. Mass (m/z) 500.2 $[M+H]^+$.

(S)-(5-(3,5-difluorophenyl)-4,5-dihydro-1H-pyrazol-1-yl)(3-((5-fluoro-2-(4-methyl-1H-pyrazol-5-yl)pyridin-4-yl)oxy)azetidin-1-yl)methanone (126)

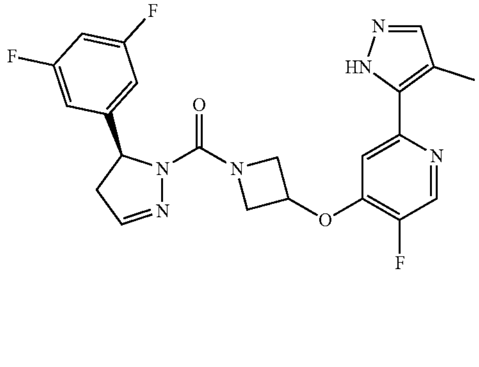 [SMILES: Cc1cn[nH]c1-c1cc(OC2CN(C(=O)N3N=CC[C@H]3c3cc(F)cc(F)c3)C2)c(F)cn1]

The titled compound 126 was prepared from 29-01 in a yield of 1.2% according to the procedure outlined for compound 29. Mass (m/z) 456.4 $[M+H]^+$. $^1H$ NMR (400 MHz, DMSO-$d_6$) δ 8.51 (d, J=2.8 Hz, 1H), 7.56 (s, 1H), 7.33 (d, J=6.8 Hz, 1H), 7.17-7.08 (m, 1H), 7.03 (d, J=1.6 Hz, 1H), 6.97-6.90 (m, 2H), 5.30-5.21 (m, 2H), 4.59-4.51 (m, 2H), 4.15-4.05 (m, 2H), 3.41-3.35 (m, 1H), 2.70-2.65-2.56 (m, 1H), 2.31 (s, 3H).

(S)-(5-(3,5-difluorophenyl)-4,5-dihydro-1H-pyrazol-1-yl)(3-((2-(3,5-dimethylisothiazol-4-yl)-5-fluoropyridin-4-yl)oxy)azetidin-1-yl)methanone (127)

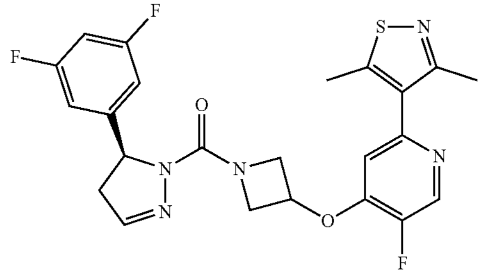 [SMILES: Cc1nsc(C)c1-c1cc(OC2CN(C(=O)N3N=CC[C@H]3c3cc(F)cc(F)c3)C2)c(F)cn1]

The titled compound 127 was prepared from 29-01 in a yield of 4.7% according to the procedure outlined for compound 29. Mass (m/z) 488.3 $[M+H]^+$. $^1H$ NMR (400 MHz, Chloroform-d) δ 8.54 (d, J=3.1 Hz, 1H), 6.81 (d, J=1.7 Hz, 1H), 6.79-6.66 (m, 3H), 6.62 (d, J=6.5 Hz, 1H), 5.28 (dd, J=12.2, 6.4 Hz, 1H), 5.08 (s, 1H), 4.59 (s, 2H), 4.34 (dd, J=27.8, 10.3 Hz, 2H), 3.37 (dd, J=18.7, 12.2 Hz, 1H), 2.72 (dd, J=18.7, 6.3 Hz, 2H), 2.47 (s, 3H), 2.41 (s, 3H).

Ethyl (S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrrole-2-carboxylate (128)

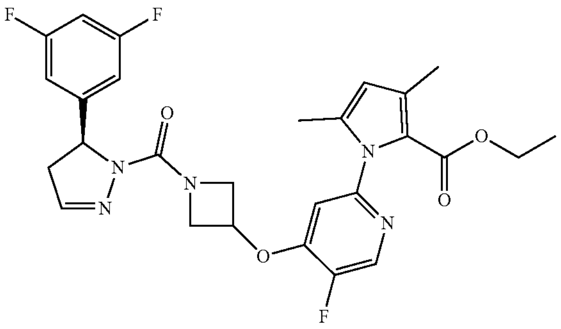 [SMILES: CCOC(=O)c1c(C)cc(C)n1-c1cc(OC2CN(C(=O)N3N=CC[C@H]3c3cc(F)cc(F)c3)C2)c(F)cn1]

The titled compound 128 was prepared from compound 3-04 in a yield of 12.0% according to the procedure outlined for compound 108. Mass (m/z) 542.2 $[M+H]^+$; $^1H$ NMR (400 MHz, $CDCl_3$) δ 8.23 (d, J=2.7 Hz, 1H), 6.75-6.56 (m, 4H), 6.44 (d, J=6.0 Hz, 1H), 5.84 (s, 1H), 5.20 (dd, J=12.2, 6.4 Hz, 1H), 4.93 (td, J=6.4, 3.3 Hz, 1H), 4.47 (s, 2H), 4.22 (dd, J=25.3, 10.2 Hz, 2H), 4.03 (q, J=7.1 Hz, 2H), 3.29 (ddd, J=18.6, 12.2, 1.7 Hz, 1H), 2.73-2.39 (m, 2H), 2.28 (s, 3H), 1.09 (t, J=7.1 Hz, 3H).

methyl (S)-1-(4-((1-(5-(3,5-difluorophenyl)-4,5-dihydro-1H-pyrazole-1-carbonyl)azetidin-3-yl)oxy)-5-fluoropyridin-2-yl)-2,5-dimethyl-1H-pyrrole-3-carboxylate (129)

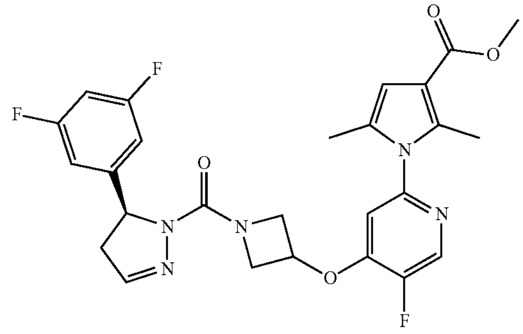 [SMILES: COC(=O)c1cc(C)n(-c2cc(OC3CN(C(=O)N4N=CC[C@H]4c4cc(F)cc(F)c4)C3)c(F)cn2)c1C]

The titled compound 129 was prepared from compound 3-04 in a yield of 11.5% according to the procedure outlined for compound 108. Mass (m/z) 528.2 $[M+H]^+$; $^1H$ NMR (400 MHz, $CDCl_3$) δ 8.32 (d, J=2.7 Hz, 1H), 6.78-6.51 (m, 4H), 6.45 (d, J=6.0 Hz, 1H), 6.27 (d, J=1.1 Hz, 1H), 5.20 (ddd, J=12.2, 6.5, 3.0 Hz, 1H), 5.00-4.84 (m, 1H), 4.59-4.40 (m, 2H), 4.33-4.13 (m, 2H), 3.74 (s, 3H), 3.30 (ddd, J=18.6, 12.2, 1.7 Hz, 1H), 2.70-2.58 (m, 1H), 2.28 (s, 3H), 1.97 (d, J=1.0 Hz, 3H).

(S)-(5-(3,5-difluorophenyl)-4,5-dihydro-1H-pyrazol-1-yl)(3-((2-(3,5-dimethyl-1-(oxetan-3-yl)-1H-pyrazol-4-yl)-5-fluoropyridin-4-yl)oxy)azetidin-1-yl)methanone (130)

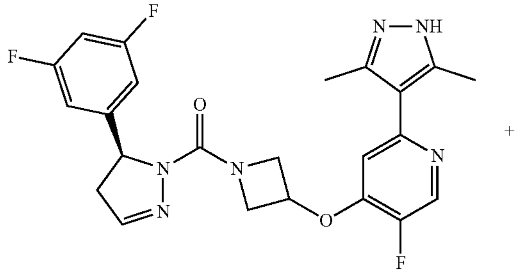

92

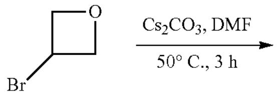

-continued

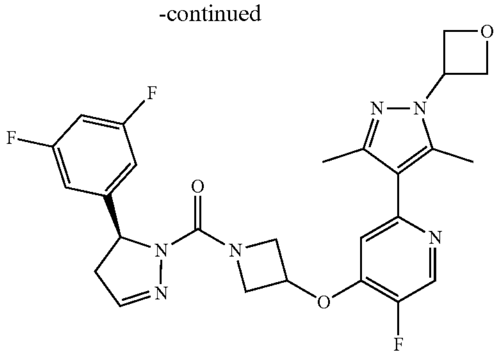

130

Compound 92 (94 mg, 0.2 mmol), 3-bromooxetane (55 mg, 0.4 mmol), $Cs_2CO_3$ (261 mg, 0.8 mmol) were placed in DMF (4 mL). The mixture was stirred 50° C. for 3 hours, and then the reaction liquid was poured into water. The mixture was extracted with EA, washed with brine, dried ($Na_2SO_4$), and concentrated in vacuo. Purification by prep-HPLC to give the titled compound 130 (20 mg, 19.0%) as a white solid.

$^1H$ NMR (400 MHz, Chloroform-d) δ 8.43 (d, J=3.1 Hz, 1H), 6.82-6.65 (m, 4H), 6.59 (d, J=6.6 Hz, 1H), 5.40 (p, J=7.1 Hz, 1H), 5.25 (dt, J=22.5, 6.4 Hz, 3H), 5.05 (s, 1H), 4.97 (dd, J=7.6, 6.4 Hz, 2H), 4.58 (s, 2H), 4.33 (dd, J=35.0, 10.4 Hz, 2H), 3.36 (ddd, J=18.7, 12.2, 1.7 Hz, 1H), 2.71 (ddd, J=18.6, 6.5, 1.8 Hz, 1H), 2.35 (d, J=13.0 Hz, 6H). Mass (m/z) 527.3 $[M+H]^+$.

(S)-(3-((2-(1-(azetidin-3-yl)-3,5-dimethyl-11H-pyrazol-4-yl)-5-fluoropyridin-4-yl)oxy)azetidin-1-yl)(5-(3,5-difluorophenyl)-4,5-dihydro-1H-pyrazol-1-yl) methanone (131)

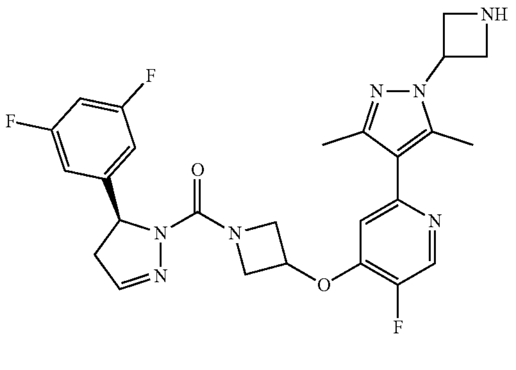 [SMILES: Cc1nn(C2CNC2)c(C)c1-c1cc(OC2CN(C(=O)N3N=CC[C@H]3c3cc(F)cc(F)c3)C2)c(F)cn1]

The titled compound 131 was prepared from compound 92 in a yield of 57.1% according to the procedure outlined for compound 130. $^1H$ NMR (400 MHz, Chloroform-d) δ 8.51 (d, J=3.2 Hz, 1H), 6.85-6.58 (m, 5H), 5.41-5.22 (m, 2H), 5.09 (tt, J=6.6, 3.8 Hz, 1H), 4.74-4.21 (m, 8H), 3.36 (ddd, J=18.7, 12.1, 1.6 Hz, 11H), 2.70 (ddd, J=18.6, 6.4, 1.7 Hz, 1H), 2.40-2.21 (m, 6H). Mass (m/z) 526.3 $[M+H]^+$.

(S)-(3-((2-(1-(cyclopropylmethyl)-3,5-dimethyl-1H-pyrazol-4-yl)-5-fluoropyridin-4-yl)oxy)azetidin-1-yl)(5-(3,5-difluorophenyl)-4,5-dihydro-1H-pyrazol-1-yl)methanone (132)

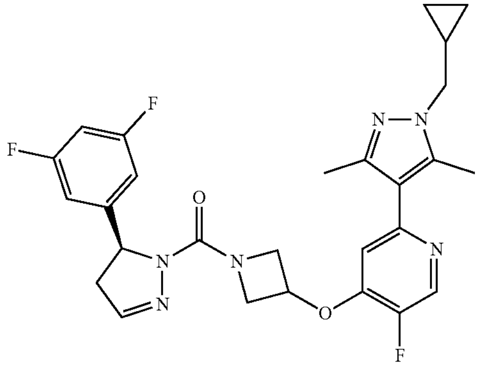 [SMILES: Cc1nn(CC2CC2)c(C)c1-c1cc(OC2CN(C(=O)N3N=CC[C@H]3c3cc(F)cc(F)c3)C2)c(F)cn1]

The titled compound 132 was prepared from compound 92 in a yield of 29.5% according to the procedure outlined for compound 130. $^1H$ NMR (400 MHz, Chloroform-d) δ 8.40 (d, J=3.0 Hz, 1H), 6.83-6.65 (m, 4H), 6.59 (d, J=6.6 Hz, 1H), 5.27 (dd, J=12.2, 6.5 Hz, 1H), 5.04 (td, J=6.5, 3.3 Hz, 1H), 4.59 (t, J=9.4 Hz, 2H), 4.32 (dd, J=35.0, 10.2 Hz, 2H), 3.92 (d, J=6.8 Hz, 2H), 3.36 (ddd, J=18.6, 12.2, 1.7 Hz, 1H), 2.71 (ddd, J=18.6, 6.5, 1.8 Hz, 1H), 2.36 (d, J=26.0 Hz, 6H), 1.26 (dddt, J=8.1, 6.4, 3.2, 1.6 Hz, 1H), 0.63-0.53 (m, 2H), 0.38 (dt, J=6.2, 4.8 Hz, 2H). Mass (m/z) 525.3 $[M+H]^+$.

(S)-5-(4-((1-(5-(3,5-difluorophenyl)-4,5-dihydro-1H-pyrazole-1-carbonyl)azetidin-3-yl)oxy)-5-fluoropyridin-2-yl)-N-isopropyl-1-methyl-1H-pyrazole-4-carboxamide (133)

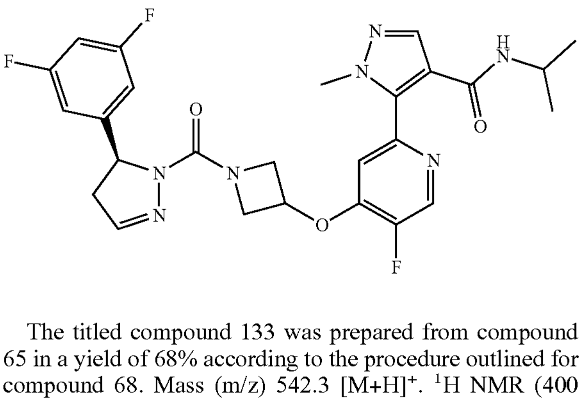

The titled compound 133 was prepared from compound 65 in a yield of 68% according to the procedure outlined for compound 68. Mass (m/z) 542.3 $[M+H]^+$. $^1H$ NMR (400 MHz, Chloroform-d) δ 8.46 (d, J=2.8 Hz, 1H), 7.79 (s, 1H), 7.23 (d, J=6.7 Hz, 1H), 6.80-6.64 (m, 4H), 6.38 (d, J=7.7 Hz, 1H), 5.27 (dd, J=12.2, 6.4 Hz, 1H), 5.15-5.07 (m, 1H), 4.69-4.54 (m, 2H), 4.38-4.24 (m, 2H), 4.17-4.04 (m, 1H), 3.91 (s, 3H), 3.35 (ddd, J=18.6, 12.2, 1.7 Hz, 1H), 2.70 (ddd, J=18.6, 6.4, 1.8 Hz, 1H), 1.15 (d, J=6.6 Hz, 6H).

(S)—N-cyclopropyl-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carboxamide (134)

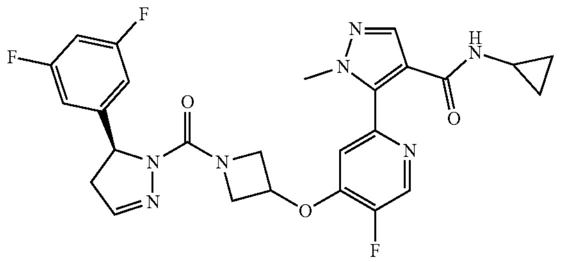 [SMILES: Cn1ncc(C(=O)NC2CC2)c1-c1cc(OC2CN(C(=O)N3N=CC[C@H]3c3cc(F)cc(F)c3)C2)c(F)cn1]

The titled compound 134 was prepared from compound 65 in a yield of 69% according to the procedure outlined for compound 68. Mass (m/z) 540.3 $[M+H]^+$. $^1H$ NMR (400 MHz, Chloroform-d) δ 8.46 (d, J=2.8 Hz, 1H), 7.78 (s, 1H), 7.24 (d, J=6.7 Hz, 1H), 6.88-6.61 (m, 4H), 5.27 (dd, J=12.2, 6.4 Hz, 1H), 5.20-5.07 (m, 1H), 4.70-4.53 (m, 2H), 4.41-4.25 (m, 2H), 3.90 (s, 3H), 3.35 (ddd, J=18.6, 12.2, 1.7 Hz, 1H), 2.77 (dq, J=7.2, 3.5 Hz, 1H), 2.70 (ddd, J=18.6, 6.5, 1.7 Hz, 1H), 0.84-0.74 (m, 2H), 0.57-0.44 (m, 2H).

S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-3-yl)acetamide (135)

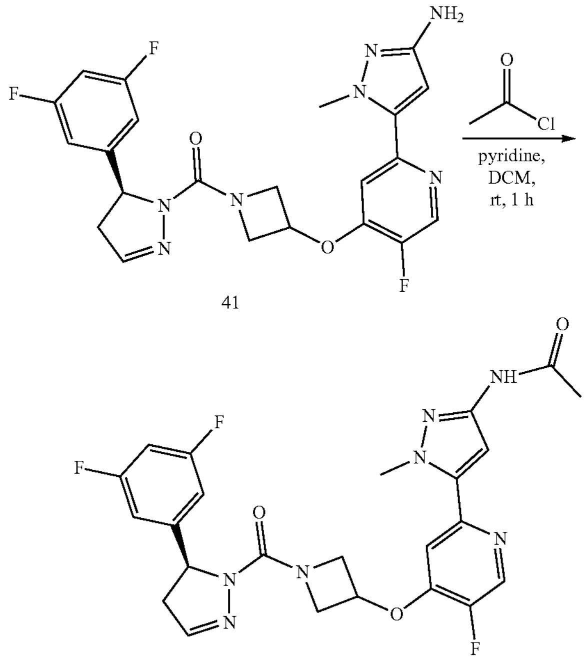

41

135

Compound 41 (57 mg, 0.12 mmol), acetyl chloride and pyridine were placed in DCM (5 mL). The mixture was stirred at room temperature for 1 h. Added $H_2O$ and DCM, the combined organic layers were washed by saturated $NaHCO_3$ solution and 1N HCl solution. Concentrated in vacuo and purification by silica gel plate to give the titled compound 135 (5 mg, 8%) as a white solid. Mass (m/z) 514.3$[M+H]^+$. $^1H$ NMR (400 MHz, Chloroform-d) δ 8.40 (d, J=2.7 Hz, 1H), 6.96-6.88 (m, 2H), 6.82-6.65 (m, 4H), 5.28 (dd, J=12.2, 6.5 Hz, 1H), 5.12-5.04 (m, 1H), 4.66-4.53 (m, 2H), 4.37-4.23 (m, 2H), 4.06 (s, 3H), 3.35 (ddd, J=18.6, 12.2, 1.7 Hz, 1H), 2.70 (ddd, J=18.6, 6.5, 1.8 Hz, 1H), 2.17 (s, 3H).

(S)—N-acetyl-N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-3-yl)acetamide (136)

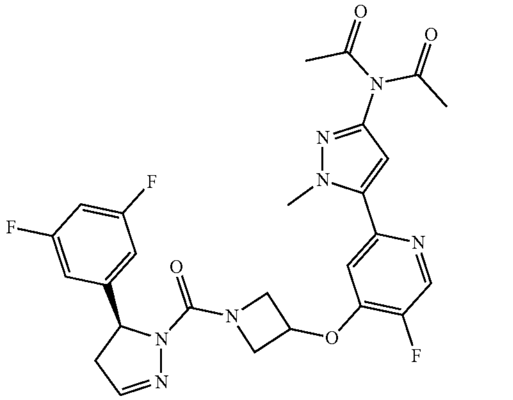 [SMILES: CC(=O)N(C(C)=O)c1cc(-c2cc(OC3CN(C(=O)N4N=CC[C@H]4c4cc(F)cc(F)c4)C3)c(F)cn2)n(C)n1]

The title compound 136 was prepared in a yield of 10% as a white solid from compound 41 according to the procedure outlined for compound 135. Mass (m/z) 556.3 $[M+H]^+$. $^1H$ NMR (400 MHz, Chloroform-d) δ 8.44 (d, J=2.8 Hz, 1H), 6.87 (d, J=6.4 Hz, 1H), 6.80 (t, J=1.7 Hz, 1H), 6.78-6.64 (m, 3H), 6.39 (s, 1H), 5.27 (dd, J=12.2, 6.4 Hz, 1H), 5.10-5.02 (m, 1H), 4.68-4.52 (m, 2H), 4.40-4.23 (m, 2H), 4.16 (s, 3H), 3.36 (ddd, J=18.6, 12.2, 1.7 Hz, 1H), 2.71 (ddd, J=18.7, 6.5, 1.8 Hz, 1H), 2.36 (s, 6H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-3-yl)cyclopropanecarboxamide (137)

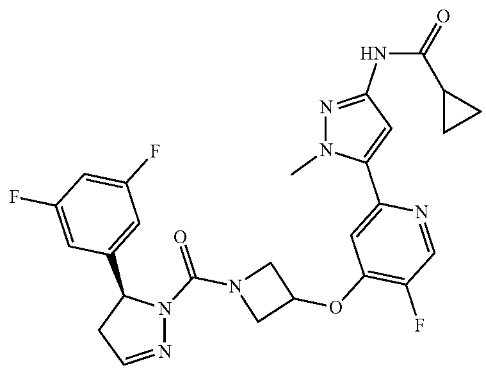 [SMILES: Cn1nc(NC(=O)C2CC2)cc1-c1cc(OC2CN(C(=O)N3N=CC[C@H]3c3cc(F)cc(F)c3)C2)c(F)cn1]

The title compound 137 was prepared in a yield of 14% as a white solid from compound 41 according to the procedure outlined for compound 135. Mass (m/z) 540.3[M+H]$^+$. $^1$H NMR (400 MHz, Chloroform-d) δ 8.40 (d, J=2.7 Hz, 1H), 8.26 (s, 1H), 6.93 (s, 1H), 6.88 (d, J=6.4 Hz, 1H), 6.82-6.65 (m, 4H), 5.27 (dd, J=12.2, 6.4 Hz, 1H), 5.08-4.98 (m, 1H), 4.71-4.52 (m, 2H), 4.35-4.21 (m, 2H), 4.07 (s, 3H), 3.35 (ddd, J=18.6, 12.2, 1.7 Hz, 1H), 2.70 (ddd, J=18.6, 6.5, 1.8 Hz, 1H), 1.57-1.47 (m, 1H), 1.14-1.06 (m, 2H), 0.91-0.83 (m, 2H).

(S)—N-(4-((1-(5-(3,5-difluorophenyl)-4,5-dihydro-1H-pyrazole-1-carbonyl)azetidin-3-yl)oxy)-5-fluoropyridin-2-yl)tetrahydro-2H-pyran-4-carboxamide 138)

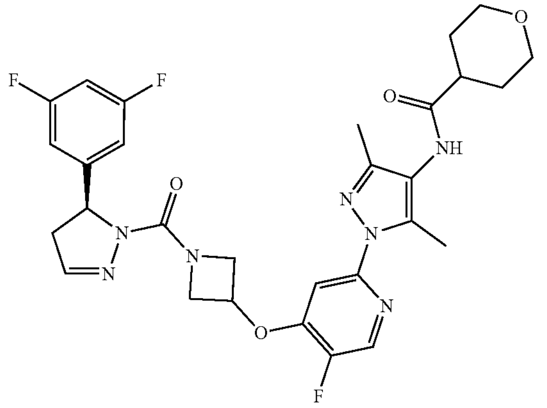 [SMILES: Cc1nn(-c2cc(OC3CN(C(=O)N4N=CC[C@H]4c4cc(F)cc(F)c4)C3)c(F)cn2)c(C)c1NC(=O)C1CCOCC1]

The title compound 138 was prepared in a yield of 19.5% as a white solid from compound 109 according to the procedure outlined for compound 135. Mass (m/z) 598.4 [M+H]$^+$. $^1$H NMR (400 MHz, Chloroform-d) δ 8.14 (d, J=2.4 Hz, 1H), 7.20 (d, J=6.2 Hz, 1H), 6.80 (d, J=1.7 Hz, 1H), 6.78-6.74 (m, 2H), 6.73-6.67 (m, 1H), 5.32-5.25 (m, 1H), 5.14 (d, J=6.3 Hz, 1H), 4.69-4.52 (m, 2H), 4.41-4.22 (m, 4H), 4.09 (dd, J=11.0, 7.4 Hz, 2H), 3.49 (td, J=11.3, 3.2 Hz, 2H), 3.44-3.27 (m, 2H), 2.76-2.66 (m, 1H), 2.64-2.52 (m, 1H), 2.46 (s, 3H), 2.18 (s, 3H), 2.08-1.84 (m, 4H).

(S)—N-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl) cyclopropanecarboxamide (139)

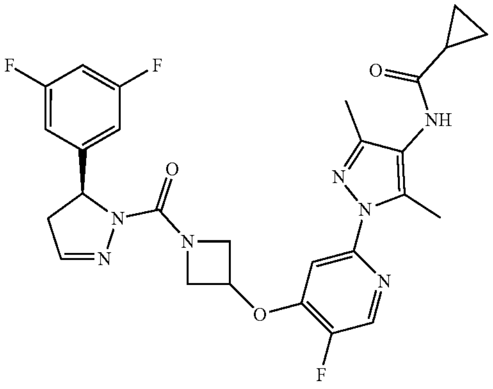 [SMILES: Cc1nn(-c2cc(OC3CN(C(=O)N4N=CC[C@H]4c4cc(F)cc(F)c4)C3)c(F)cn2)c(C)c1NC(=O)C1CC1]

The title compound 139 was prepared in a yield of 30% as a white solid from compound 109 according to the procedure outlined for compound 135. $^1$H NMR (400 MHz, Chloroform-d) δ 8.18 (dd, J=10.3, 2.4 Hz, 1H), 7.21 (d, J=6.2 Hz, 1H), 6.82 (d, J=1.8 Hz, 1H), 6.80-6.76 (m, 2H), 6.73-6.68 (m, 1H), 5.34-5.26 (m, 1H), 5.22-5.3 (m, 1H), 4.70-4.60 (m, 2H), 4.34 (d, J=28.2 Hz, 2H), 3.37 (dd, J=18.8, 12.3 Hz, 1H), 2.78-2.69 (m, 1H), 2.51 (s, 3H), 2.23 (s, 3H), 1.37-1.34 (m, 2H), 1.10 (ddd, J=10.0, 5.9, 3.6 Hz, 2H), 0.89 (dq, J=7.2, 4.0 Hz, 2H), 0.81-0.75 (m, 1H). Mass (m/z) 554.3 [M+H]$^+$.

(S)—N-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl) acetamide (140)

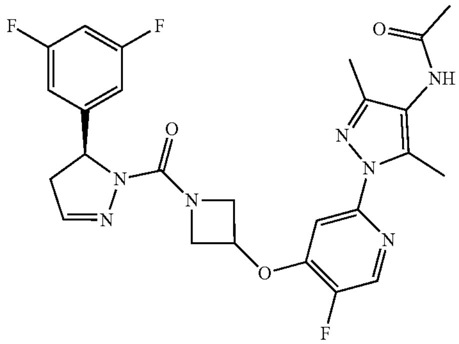 [SMILES: CC(=O)Nc1c(C)nn(-c2cc(OC3CN(C(=O)N4N=CC[C@H]4c4cc(F)cc(F)c4)C3)c(F)cn2)c1C]

The title compound 140 was prepared in a yield of 19.8% as a white solid from compound 109 according to the procedure outlined for compound 135. $^1$H NMR (400 MHz, Chloroform-d) δ 8.14 (d, J=2.4 Hz, 11H), 7.19 (d, J=6.2 Hz, 11H), 6.79 (d, J=1.6 Hz, 11H), 6.75 (dt, J=6.4, 2.1 Hz, 2H), 6.71-6.66 (m, 1H), 5.27 (ddd, J=12.1, 6.4, 3.2 Hz, 1H), 5.20-5.09 (m, 1H), 4.71-4.53 (s, 2H), 4.40-4.24 (m, 2H), 3.42-3.30 (m, 1H), 2.74-2.65 (m, 1H), 2.48 (s, 3H), 2.20 (s, 6H). Mass (m/z) 528.3 [M+H]$^+$.

(S)-1-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazol-4-yl)-3-isopropylurea (141)

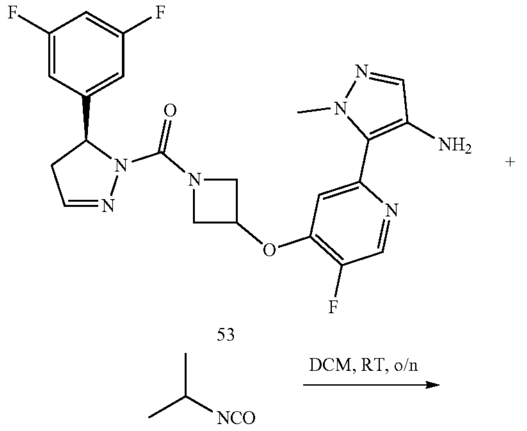

53

-continued

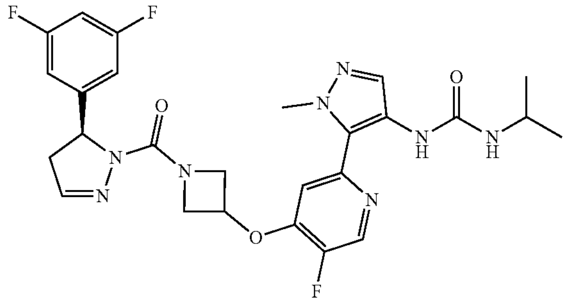

141

A mixture of compound 53 (50 mg, 0.11 mmol) and 2-isocyanatopropane (18 mg, 0.22 mmol) in DCM (5 mL) reacted under $N_2$ and the whole reaction mixture was stirred at rt for 16 h. The reaction mixture was concentrated. The crude product was purified by Pre-TLC to give required product 141 (27 mg, 45.7%) as a white solid. Mass (m/z) 557.1 $[M+H]^+$. $^1H$ NMR (400 MHz, Chloroform-d) δ 8.45 (d, J=2.9 Hz, 1H), 7.68 (s, 1H), 7.05 (d, J=6.5 Hz, 1H), 6.79 (d, J=1.7 Hz, 1H), 6.76-6.66 (m, 3H), 5.26 (dd, J=12.2, 6.4 Hz, 1H), 5.15 (s, 1H), 4.62 (s, 2H), 4.30 (dd, J=21.6, 10.7 Hz, 2H), 4.05 (s, 3H), 3.93-3.84 (m, 1H), 3.36 (ddd, J=18.7, 12.2, 1.7 Hz, 1H), 2.70 (ddd, J=18.6, 6.4, 1.7 Hz, 1H), 1.09 (d, J=6.5 Hz, 6H).

(S)-1-(5-(4-((1-(5-(3,5-difluorophenyl)-4,5-dihydro-1H-pyrazole-1-carbonyl)azetidin-3-yl)oxy)-5-fluoropyridin-2-yl)-1-methyl-11H-pyrazol-4-yl)-3-methylurea (142)

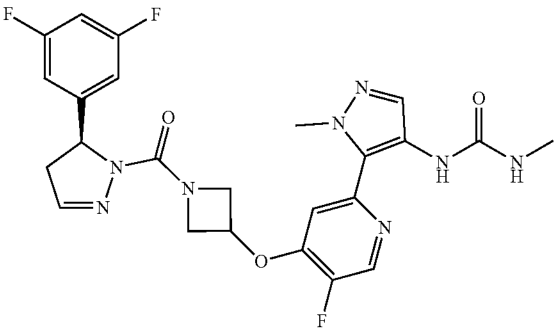 [SMILES: CNC(=O)Nc1cnn(C)c1-c1cc(OC2CN(C(=O)N3N=CC[C@H]3c3cc(F)cc(F)c3)C2)c(F)cn1]

The title compound 142 was prepared in a yield of 37.5% as a white solid from compound 53 according to the procedure outlined for compound 141. Mass (m/z) 529.1 $[M+H]^+$. $^1H$ NMR (400 MHz, Chloroform-d) δ 8.44 (d, J=2.8 Hz, 1H), 7.68 (s, 1H), 6.97 (d, J=6.6 Hz, 1H), 6.79 (d, J=1.6 Hz, 1H), 6.77-6.64 (m, 3H), 5.26 (dd, J=12.1, 6.4 Hz, 1H), 5.07 (s, 1H), 4.73 (s, 1H), 4.59 (s, 2H), 4.28 (dd, J=21.1, 10.4 Hz, 2H), 4.05 (s, 3H), 3.35 (dd, J=18.6, 12.2 Hz, 1H), 2.78 (s, 3H), 2.75-2.64 (m, 1H).

(S)-1-(4-((1-(5-(3,5-difluorophenyl)-4,5-dihydro-1H-pyrazole-1-carbonyl)azetidin-3-yl)oxy)-5-fluoropyridin-2-yl)-2-methyl-1H-imidazole-5-carbonitrile (143)

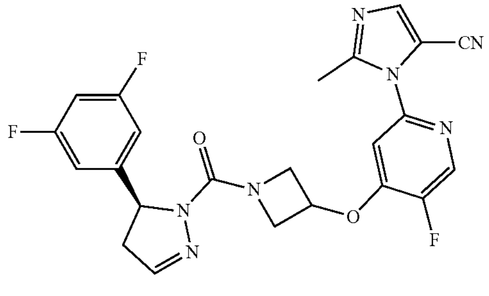 [SMILES: Cc1ncc(C#N)n1-c1cc(OC2CN(C(=O)N3N=CC[C@H]3c3cc(F)cc(F)c3)C2)c(F)cn1]

The title compound 143 was prepared in a yield of 8.6% as a white solid from compound 3-04 according to the procedure outlined for compound 110. Mass (m/z) 482.2 $[M+H]^+$. $^1H$ NMR (400 MHz, $CDCl_3$) δ 8.34 (d, J=2.6 Hz, 1H), 7.72 (s, 1H), 6.88-6.48 (m, 5H), 5.27 (dd, J=12.2, 6.4 Hz, 1H), 5.10 (d, J=3.8 Hz, 1H), 4.62 (dd, J=18.8, 10.9 Hz, 2H), 4.33 (dd, J=27.3, 10.3 Hz, 2H), 3.37 (ddd, J=18.7, 12.2, 1.7 Hz, 1H), 2.76-2.66 (m, 1H), 2.54 (s, 3H).

(S)—N-(5-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazol-3-yl) cyclopropanecarboxamide (144)

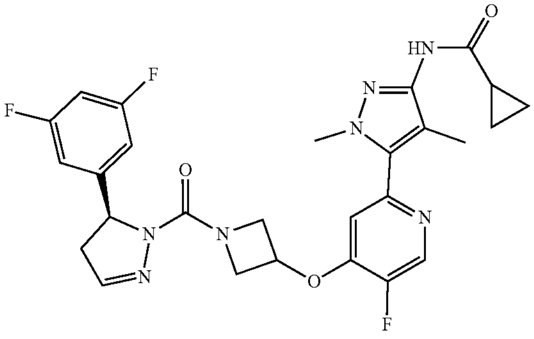 [SMILES: Cc1c(NC(=O)C2CC2)nn(C)c1-c1cc(OC2CN(C(=O)N3N=CC[C@H]3c3cc(F)cc(F)c3)C2)c(F)cn1]

The title compound 144 was prepared in a yield of 12.5% as a brown solid from compound 101 according to the procedure outlined for compound 135. $^1H$ NMR (400 MHz, Chloroform-d) δ 8.48 (d, J=2.8 Hz, 1H), 6.89-6.52 (m, 5H), 5.26 (dd, J=12.2, 6.5 Hz, 1H), 5.09-4.97 (m, 1H), 4.66-4.48 (m, 2H), 4.41-4.24 (m, 2H), 3.90 (s, 3H), 3.36 (ddd, J=18.7, 12.2, 1.7 Hz, 1H), 3.18-3.08 (m, 1H), 2.71 (ddd, J=18.6, 6.5, 1.7 Hz, 1H), 2.00 (s, 3H), 1.38 (t, J=7.3 Hz, 2H), 1.13-1.06 (m, 2H). Mass (m/z) 554.3 $[M+H]^+$.

(S)-2-((5-(4-((1-(5-(3,5-difluorophenyl)-4,5-dihydro-1H-pyrazole-1-carbonyl)azetidin-3-yl)oxy)-5-fluoro-pyridin-2-yl)-1,4-dimethyl-1H-pyrazol-3-yl)amino) acetamide (145)

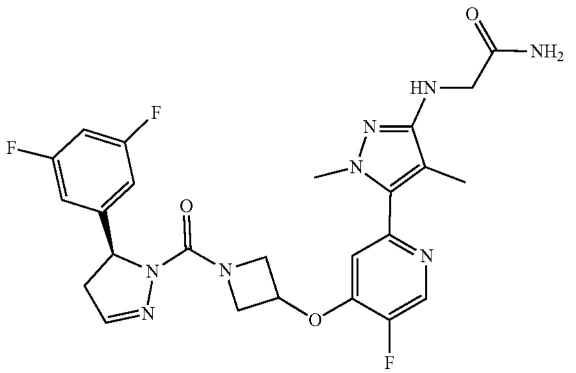 [SMILES: Cc1c(NCC(N)=O)nn(C)c1-c1cc(OC2CN(C(=O)N3N=CC[C@H]3c3cc(F)cc(F)c3)C2)c(F)cn1]

The title compound 145 was prepared in a yield of 82.1% as a white solid from compound 101 according to the procedure outlined for compound 56. $^1$H NMR (400 MHz, Chloroform-d) δ 8.59-8.44 (m, 1H), 6.80 (t, J=1.5 Hz, 1H), 6.78-6.53 (m, 4H), 5.26 (dd, J=12.1, 6.4 Hz, 1H), 5.13-4.99 (m, 1H), 4.59 (s, 2H), 4.39-4.25 (m, 2H), 4.14-4.01 (m, 2H), 3.92-3.73 (m, 3H), 3.36 (dd, J=18.6, 12.2 Hz, 1H), 2.71 (ddd, J=18.7, 6.5, 1.7 Hz, 1H), 2.05-1.90 (m, 3H). Mass (m/z) 543.3 $[M+H]^+$.

(S)-(5-(3,5-difluorophenyl)-4,5-dihydro-1H-pyrazol-1-yl)(3-((5-fluoro-2-(1-methyl-1H-imidazol-2-yl) pyridin-4-yl)oxy)azetidin-1-yl)methanone (146)

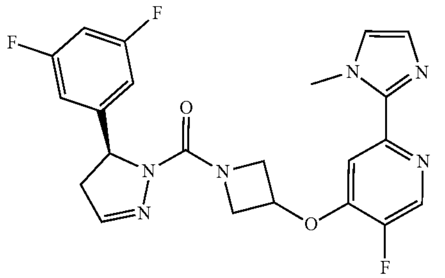 [SMILES: Cn1ccnc1-c1cc(OC2CN(C(=O)N3N=CC[C@H]3c3cc(F)cc(F)c3)C2)c(F)cn1]

The title compound 146 was prepared in a yield of 34.5% as a white solid from compound 3-02 according to the procedure outlined for compound 30. Mass (m/z) 457.3 $[M+H]^+$. $^1$H NMR (400 MHz, Chloroform-d) δ 8.33 (d, J=2.7 Hz, 1H), 7.59 (d, J=6.8 Hz, 1H), 7.09 (d, J=1.1 Hz, 1H), 6.96 (s, 1H), 6.82-6.60 (m, 4H), 5.32-5.25 (m, 1H), 5.21-5.10 (m, 1H), 4.65 (s, 2H), 4.29 (t, J=12.3 Hz, 2H), 4.08 (s, 3H), 3.34 (ddd, J=18.6, 12.2, 1.7 Hz, 1H), 2.68 (ddd, J=18.6, 6.5, 1.7 Hz, 1H).

(S)-(5-(3,5-difluorophenyl)-4,5-dihydro-1H-pyrazol-1-yl)(3-((2-(2,5-dimethyl-1H-pyrrol-1-yl)-5-fluoro-pyridin-4-yl)oxy)azetidin-1-yl)methanone (147)

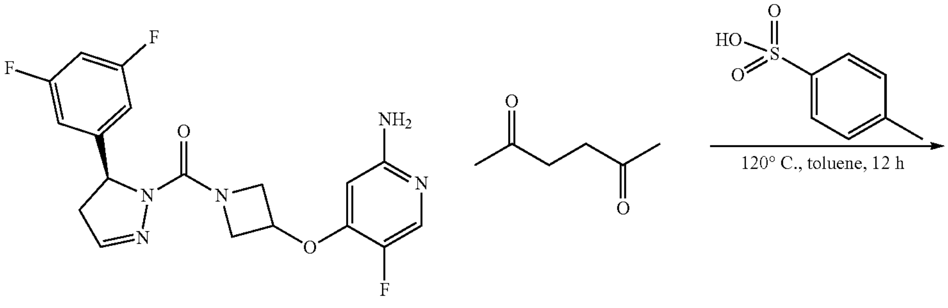

147-01

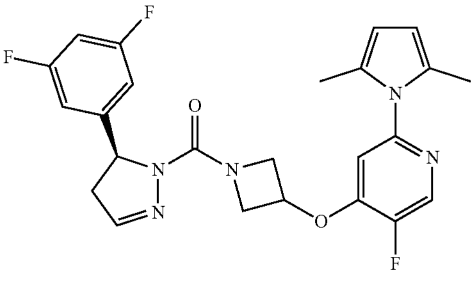

147

Compound 147-01 (100 mg, 0.25 mmol) was dissolved in 3 mL of toluene, hexane-2,5-dione (115 mg, 1 mmol) and 4-methylbenzenesulfonic acid (20 mg, 0.025 mmol) and the mixture was stirred at 120° C. for 12 h. Concentrated and purification by prep-HPLC to give the titled compound 147 (50 mg, 48.2%) as a white solid. $^1$H NMR (400 MHz, Chloroform-d) δ 8.37 (d, J=2.7 Hz, 11H), 6.82 (t, J=1.7 Hz, 11H), 6.78 (dd, J=4.8, 3.3 Hz, 2H), 6.76-6.69 (m, 1H), 6.54 (d, J=6.0 Hz, 1H), 5.91 (s, 2H), 5.29 (dd, J=12.2, 6.5 Hz, 1H), 5.03 (td, J=6.4, 3.2 Hz, 1H), 4.66-4.53 (m, 2H), 4.33 (dd, J=23.3, 10.4 Hz, 2H), 3.39 (ddd, J=18.7, 12.2, 1.7 Hz, 1H), 2.74 (ddd, J=18.7, 6.5, 1.8 Hz, 1H), 2.13 (s, 6H). Mass (m/z) 470.3 [M+H]$^+$.

(S)-(5-(3,5-difluorophenyl)-4,5-dihydro-1H-pyrazol-1-yl)(3-((5-fluoro-2-(4-(hydroxymethyl)-3,5-dimethyl-1H-pyrazol-1-yl)pyridin-4-yl)oxy)azetidin-1-yl)methanone (148)

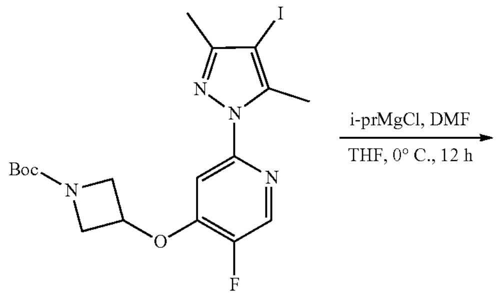

148-01

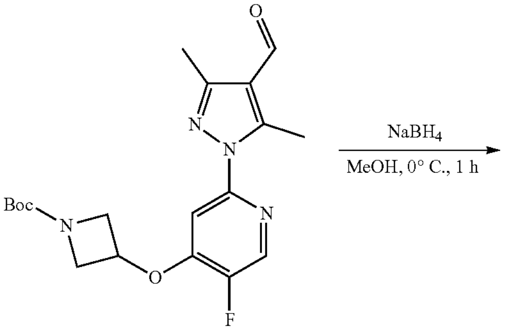

148-02

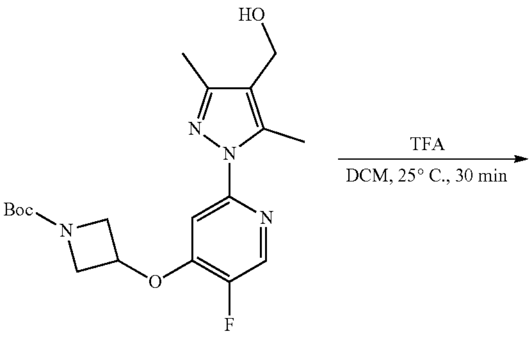

148-03

-continued

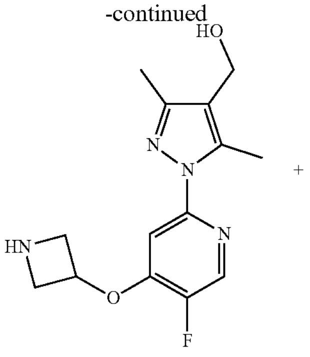

148-04

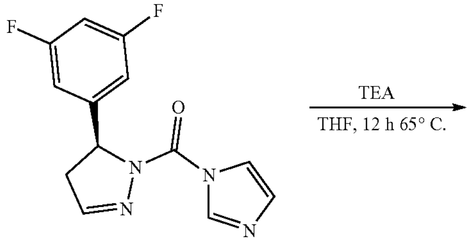

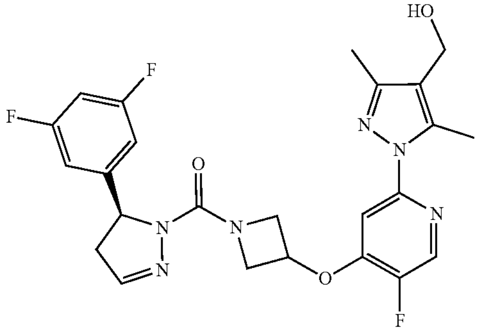

148

Step 1: Compound 148-01 (500 mg, 1.02 mmol) were dissolved in THE (10 mL), i-prMgCl (250 ul, 2M, 2.52 mmol) was added at 0° C., stirred at 0° C. for 1 h. DMF (1 mL) was added and the reaction mixture was stirred at rt for 12 h. The mixture was extracted with EA, washed with brine, dried ($Na_2SO_4$), and concentrated in vacuo. Purification by silica gel chromatography to give the compound 148-02 (96 mg, 25.1%). MS (m/z) 391.2 [M+H]$^+$.

Step 2: Compound 148-02 (96 mg, 0.25 mmol), were dissolved in MeOH (2 mL) and $NaBH_4$ (20 mg, 0.51 mmol) was added, stirred at 0° C. for 1 h. The mixture was extracted with EA, washed with brine, dried ($Na_2SO_4$), and concentrated in vacuo. Purification by silica gel chromatography to give the compound 148-03 (76 mg, 79.1%). MS (m/z) 393.3 [M+H]$^+$.

The title compound 148 was prepared in a yield of 10.2% as a white solid from compound 148-03 according to the procedure outlined for compound 1-03. $^1$H NMR (400 MHz, Chloroform-d) δ 8.16 (d, J=2.5 Hz, 1H), 7.21 (dd, J=6.2, 2.6 Hz, 1H), 6.80-6.66 (m, 4H), 5.27 (dd, J=12.2, 6.4 Hz, 1H), 5.21-5.12 (m, 1H), 4.670-4.56 (m, 2H), 4.54 (m, 2H), 4.31 (dd, J=30.7, 10.2 Hz, 3H), 3.35 (ddd, J=18.6, 12.2, 1.7 Hz, 1H), 2.76-2.67 (m, 1H), 2.61 (s, 3H), 2.34 (s, 3H). Mass (m/z) 501.2 [M+H]$^+$.

(S)-5-(6-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-4-carboxamide (149)

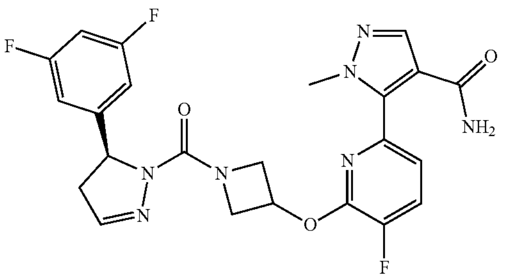 [SMILES: Cn1ncc(C(N)=O)c1-c1ccc(F)c(OC2CN(C(=O)N3N=CC[C@H]3c3cc(F)cc(F)c3)C2)n1]

The title compound 149 was prepared in a yield of 82% as a pale green solid from compound 111 according to the procedure outlined for compound 66. Mass (m/z) 500.2 $[M+H]^+$. $^1H$ NMR (400 MHz, Chloroform-d) δ 7.86 (s, 1H), 7.54-7.48 (m, 1H), 7.30 (dd, J=8.1, 3.0 Hz, 1H), 6.81-6.72 (m, 3H), 6.71-6.64 (m, 1H), 5.44-5.34 (m, 1H), 5.26 (dd, J=12.2, 6.5 Hz, 1H), 4.67-4.47 (m, 2H), 4.38-4.20 (m, 2H), 3.84 (s, 3H), 3.34 (ddd, J=18.6, 12.2, 1.7 Hz, 1H), 2.69 (ddd, J=18.6, 6.5, 1.7 Hz, 1H).

(S)-5-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-3-carbonitrile (150)

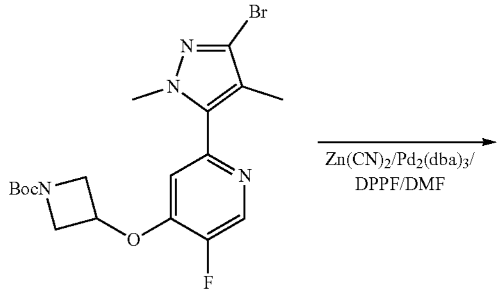

212-01

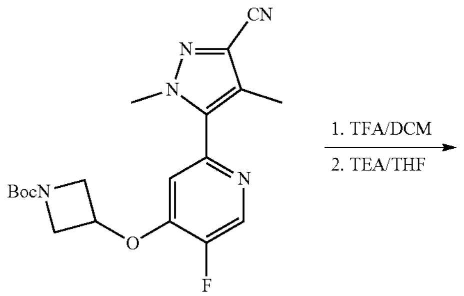

150-01

-continued

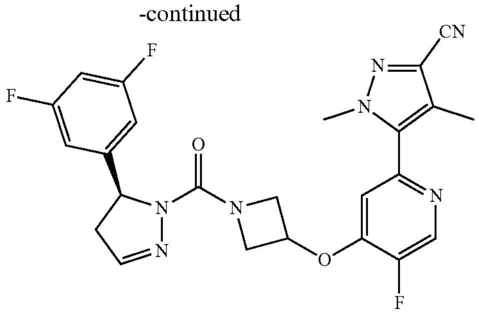

150

Step 1: Compound 212-01 (500 mg, 1.14 mmol), $Zn(CN)_2$ (147 mg, 1.25 mmol), $Pd_2(dba)_3$ (104 mg, 0.11 mmol), DPPF (61 mg, 0.11 mmol) and Zn (19 mg, 0.29 mmol) were dissolved in DMF (5 mL). The mixture was stirred at 140° C. for 4 hrs under $N_2$ (g) atmosphere. Concentrated and purified by silica gel chromatography (PE/EA=2/1) gave the compound 150-01 (280 mg, 63.6%) as yellow oil. Mass (m/z) 388.2 $[M+H]^+$.

The title compound 150 was prepared in a yield of 96.2% as a white solid from compound 150-01 according to the procedure outlined for compound 1-03. $^1H$ NMR (400 MHz, Chloroform-d) δ 8.51 (d, J=2.9 Hz, 1H), 6.81 (t, J=1.7 Hz, 1H), 6.78-6.58 (m, 4H), 5.27 (dd, J=12.2, 6.4 Hz, 1H), 5.14-5.04 (m, 1H), 4.68-4.51 (m, 2H), 4.33 (dd, J=30.0, 10.5 Hz, 2H), 4.01 (s, 3H), 3.37 (ddd, J=18.6, 12.2, 1.7 Hz, 1H), 2.72 (ddd, J=18.7, 6.4, 1.7 Hz, 1H), 2.23 (s, 3H). Mass (m/z) 496.3 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carbonitrile (151)

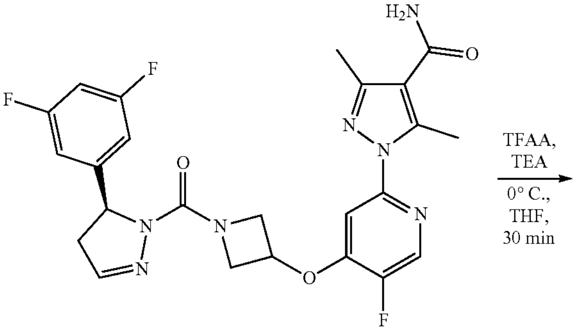

110

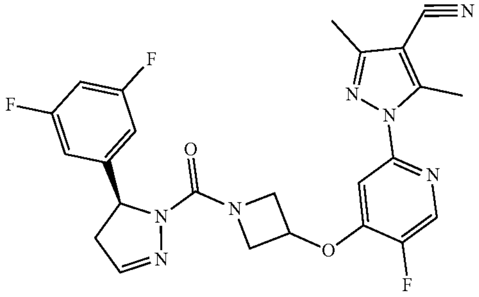

151

Compound 110 (20 mg, 0.04 mmol) was dissolved in 1 mL of THF, TEA (0.1 mL), TFAA (0.1 mL) was added at 0° C., the mixture was stirred at 0° C. for 30 min, quenched by ice-water. Concentrated and purification by prep-HPLC to give the titled compound 151 (8 mg, 40%) as a white solid. $^1$H NMR (400 MHz, Chloroform-d) δ 8.42-8.12 (m, 1H), 7.78-7.47 (m, 1H), 6.94-6.60 (m, 4H), 5.38-5.11 (m, 2H), 4.64 (s, 2H), 4.28 (dd, J=29.6, 10.6 Hz, 2H), 3.53-3.30 (m, 1H), 3.27-2.90 (m, 1H), 2.76 (s, 3H), 2.30 (s, 3H). Mass (m/z) 496.2 $[M+H]^+$.

(S)-(5-(3,5-difluorophenyl)-4,5-dihydro-1H-pyrazol-1-yl)(3-((5-fluoro-2-(2,4,5-trimethyl-11H-imidazol-1-yl)pyridin-4-yl)oxy)azetidin-1-yl)methanone (152)

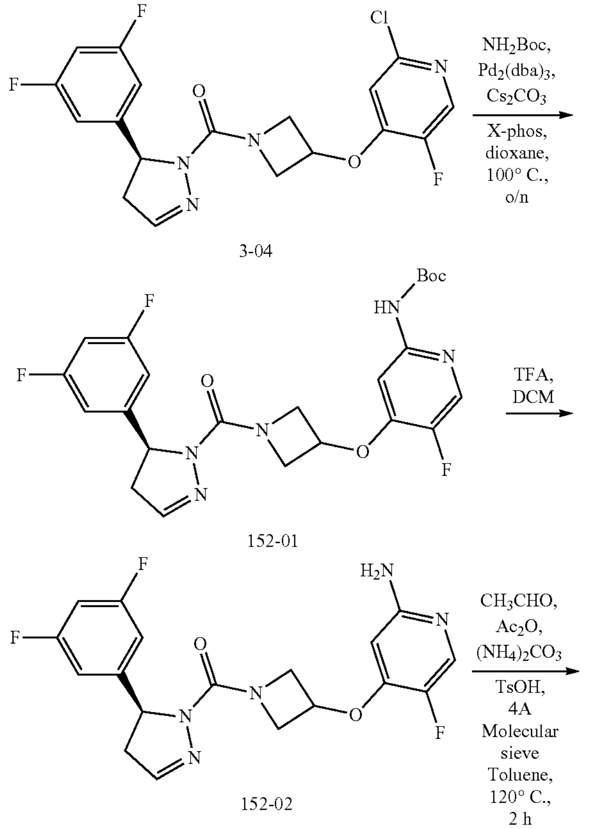

3-04

152-01

152-02

-continued

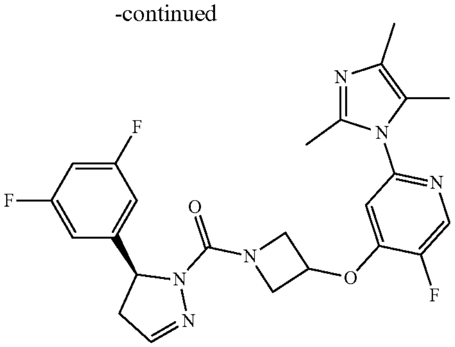

152

Step 1: Compound 3-04 (960 mg, 2.3 mmol), $NH_2Boc$ (1.08 g, 9.37 mmol), $Pd_2(dba)_3$ (214 mg, 0.23 mmol), $Cs_2CO_3$ (2.3 g, 7.02 mmol) and X-phos (111 mg, 0.23 mmol) were placed in dioxane (10 mL). The mixture was stirred 100° C. for overnight under $N_2$, the mixture was extracted with EA, washed with brine, dried ($Na_2SO_4$), and concentrated in vacuo. Purification by column chromatography on silica gel eluting with (PE:EA=1:2) to give the titled compound 152-01 (500 mg, 43%). Mass (m/z) 492.4 $[M+H]^+$;

Step 2: Compound 152-01 (1.3 g, 2.60 mmol) was dissolved in 15 mL of DCM, trifluoroacetic acid (1.5 ml, 13.1 mmol) was added, the mixture was stirred at room temperature for 30 min. Concentrated to give the desired product 152-02, which was used for next step without further purification. Mass (m/z) 392.4 $[M+H]^+$.

Step 3: Compound 152-02 (50 mg, 0.13 mmol), $CH_3CHO$ (5.6 mg, 0.13 mmol), $Ac_2O$ (50 mg, 0.13 mmol) and p-toluenesulfonic acid (2 mg, 0.012 mmol) (bound with 4 A Molecular sieve) in Toluene. The mixture was stirred 120° C. for 2 h under $N_2$ and concentrated. Purification by prep-HPLC to give the titled compound 152 (10 mg, 16%). Mass (m/z) 485.4 $[M+H]^+$. $^1$H NMR (300 MHz, DMSO-$d_6$) δ 8.66 (d, J=2.8 Hz, 1H), 7.44 (d, J=6.2 Hz, 11H), 7.10 (t, J=9.4 Hz, 11H), 7.02 (s, 11H), 6.94-6.68 (m, 2H), 5.36-5.13 (m, 2H), 4.54 (s, 1H), 4.09 (d, J=7.0 Hz, 2H), 3.42-3.29 (m, 1H), 2.65 (dd, J=18.6, 6.3 Hz, 1H), 2.45 (s, 6'H), 1.99 (s, 3H).

Ethyl (S)-4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrrole-2-carboxylate (153)

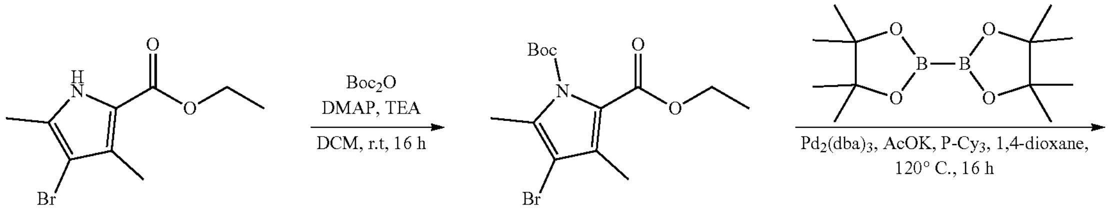

153-01

153-02

-continued

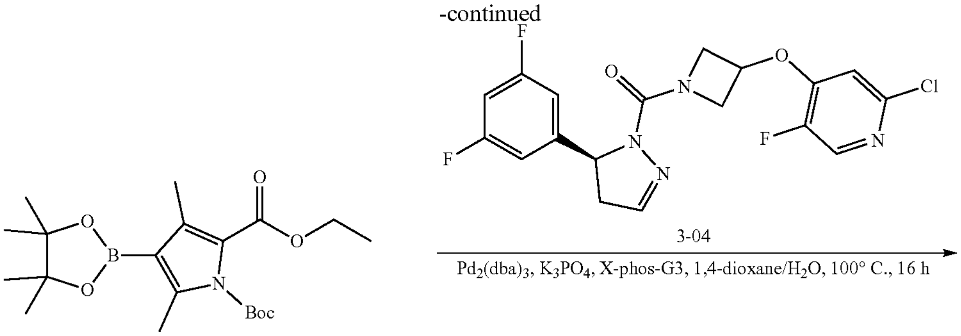

153-03

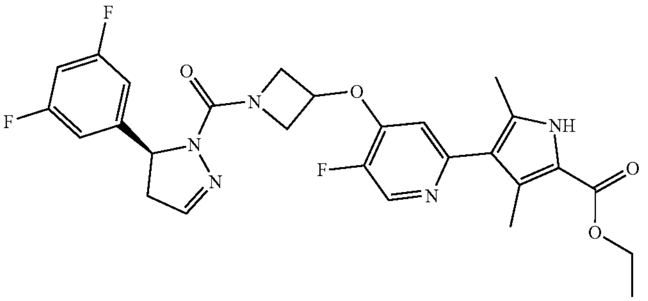

153

Step 1: Compound 153-01 (3 g, 12.195 mmol), $Boc_2O$ (3.19 g, 14.616 mmol), DMAP (0.297 g, 2.43 mmol) and TEA (1 ml) were dissolved in 30 mL DCM. Let it stir at room temperature for 16 h. The solvent was evaporated to dryness and purified by column chromatography (PE/EA=10/1) to give compound 153-02 (4.2 g, 99.5%) as colorless oil. Mass (m/z) 347.3 $[M+H]^+$.

Step 2: Compound 153-02 (212 mg, 0.613 mmol), $Pd_2(dba)_3$ (56 mg, 0.061 mmol), 4,4,4',4',5,5,5',5'-octamethyl-2,2'-bi(1,3,2-dioxaborolane) (466.8 mg, 1.838 mmol), AcOK (172.4 mg, 1.838 mmol) and $P\text{-}Cy_3$ (34.3 mg, 0.123 mmol) were mixed in 4 mL 1,4-dioxane. Let it stir at 120° C. for 16 h under $N_2$. The solvent was evaporated to dryness and purified by prep-TLC (PE/EA=5/1) to give compound 153-03 (110 mg, 45.7%) as light-yellow oil. Mass (m/z) 394.3 $[M+H]^+$.

Step 3: Compound 3-04 (100 mg, 0.244 mmol), compound 153-03 (110 mg, 0.28 mmol), X-Phos-$G_3$ (20.6 mg, 0.024 mmol), $Pd_2(dba)_3$ (22.3 mg, 0.023 mmol), $K_3PO_4$ (517 mg, 2.439 mmol) were placed in 5 mL 1,4-dioxane/$H_2O$ (v/v=4/1). The mixture was stirred at 100° C. for 16 h under $N_2$. The solvent was evaporated to dryness and purified by prep-TLC (PE/EA=1/2) to give 8 mg white solid, Yield: 5.24%. Mass (m/z) 542.4 $[M+H]^+$. $^1H$ NMR (400 MHz, $CDCl_3$) δ 8.78 (brs, 1H), 8.42 (d, J=3.2 Hz, 1H), 6.79 (t, J=1.2 Hz, 1H), 6.77-6.73 (m, 2H), 6.72-6.66 (m, 1H), 6.56 (d, J=6.8 Hz, 1H), 5.27 (dd, J=12.0, 6.4 Hz, 1H), 5.07-4.99 (m, 1H), 4.63-4.51 (m, 2H), 4.40-4.23 (m, 4H), 3.36 (ddd, J=18.4, 12.0, 1.6 Hz, 1H), 2.71 (ddd, J=18.4, 6.4, 1.6 Hz, 1H), 2.37 (s, 3H), 2.36 (s, 3H), 1.37 (t, J=7.2 Hz, 3H).

(S)-3-fluoro-5-(1-(3-((5-fluoro-2-(1-methyl-3-(methylamino)-1H-pyrazol-5-yl)pyridin-4-yl)oxy)azetidine-1-carbonyl)-4,5-dihydro-1H-pyrazol-5-yl)benzonitrile (154)

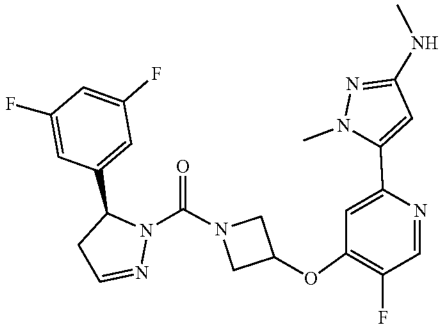 [SMILES: CNc1cc(-c2cc(OC3CN(C(=O)N4N=CC[C@H]4c4cc(F)cc(F)c4)C3)c(F)cn2)n(C)n1]

The title compound 154 was prepared in a yield of 8% as a white solid from compound 41 according to the procedure outlined for compound 56. Mass (m/z) 486.3$[M+H]^+$. $^1H$ NMR (400 MHz, Chloroform-d) δ 8.47 (d, J=2.8 Hz, 1H), 6.94 (d, J=6.3 Hz, 1H), 6.83-6.80 (m, 1H), 6.78-6.67 (m, 3H), 5.74 (s, 1H), 5.29 (dd, J=12.2, 6.4 Hz, 1H), 5.18-5.09 (m, 1H), 4.62 (s, 3H), 4.33 (dd, J=32.4, 10.5 Hz, 3H), 4.05 (s, 3H), 3.44-3.31 (m, 1H), 2.91 (s, 3H), 2.73 (ddd, J=18.7, 6.3, 1.8 Hz, 1H).

(S)-(5-(3,5-difluorophenyl)-4,5-dihydro-1H-pyrazol-1-yl)(3-((5-fluoro-2-(4-(methoxymethyl)-3,5-dimethyl-1H-pyrazol-1-yl)pyridin-4-yl)oxy)azetidin-1-yl)methanone (155)

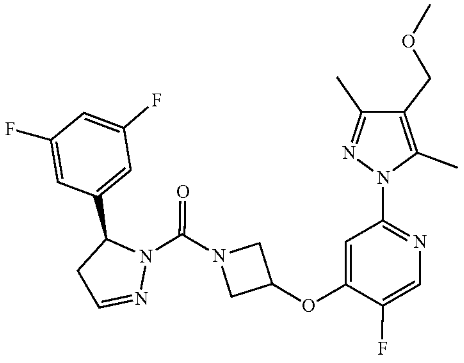 [SMILES: COCc1c(C)nn(-c2cc(OC3CN(C(=O)N4N=CC[C@H]4c4cc(F)cc(F)c4)C3)c(F)cn2)c1C]

The title compound 155 was prepared in a yield of 40% as a white solid from compound 148 according to the procedure outlined for compound 50. $^1$H NMR (400 MHz, Chloroform-d) δ 7.90 (s, 1H), 6.94 (s, 1H), 6.62-6.37 (m, 4H), 5.05-4.87 (m, 2H), 4.50-4.23 (m, 2H), 4.10-3.88 (m, 4H), 3.20-310 (m, 1H), 3.10-3.01 (m, 3H), 2.85 (s, 3H), 2.44 (d, J=18.9 Hz, 1H), 2.31 (m, 3H). Mass (m/z) 515.3 [M+H]$^+$.

(S)-(5-(3,5-difluorophenyl)-4,5-dihydro-1H-pyrazol-1-yl)(3-((5-fluoro-2-(1-(2-hydroxyethyl)-3,5-dimethyl-1H-pyrazol-4-yl)pyrimidin-4-yl)oxy)azetidin-1-yl)methanone (156)

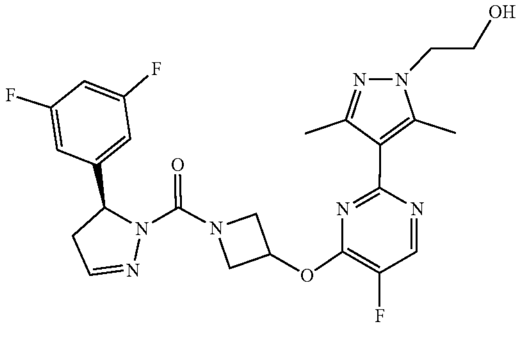 [SMILES: Cc1nn(CCO)c(C)c1-c1ncc(F)c(OC2CN(C(=O)N3N=CC[C@H]3c3cc(F)cc(F)c3)C2)n1]

The title compound 156 was prepared in a yield of 8.7% as a white solid from compound 91 according to the procedure outlined for compound 86. $^1$H NMR (400 MHz, Chloroform-d) δ 8.30 (d, J=2.6 Hz, 1H), 6.76-6.58 (m, 4H), 5.50-5.41 (m, 1H), 5.21 (dd, J=12.2, 6.4 Hz, 1H), 4.54 (s, 2H), 4.25 (dd, J=34.6, 10.7 Hz, 2H), 4.12 (t, J=4.8 Hz, 2H), 3.96 (t, J=4.8 Hz, 2H), 3.34-3.22 (m, 1H), 2.63 (ddd, J=18.7, 6.5, 1.7 Hz, 1H), 2.55 (s, 3H), 2.47 (s, 3H). Mass (m/z) 516.3 [M+H]$^+$.

(S)-(5-(3,5-difluorophenyl)-4,5-dihydro-1H-pyrazol-1-yl)(3-((2-(3,5-dimethyl-1-(tetrahydro-2H-pyran-4-yl)-1H-pyrazol-4-yl)-5-fluoropyridin-4-yl)oxy)azetidin-1-yl)methanone (157)

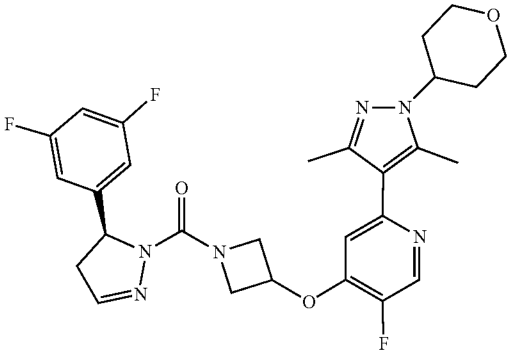 [SMILES: Cc1nn(C2CCOCC2)c(C)c1-c1cc(OC2CN(C(=O)N3N=CC[C@H]3c3cc(F)cc(F)c3)C2)c(F)cn1]

The title compound 157 was prepared in a yield of 21.6% as a white solid from compound 92 according to the procedure outlined for compound 86. $^1$H NMR (400 MHz, Chloroform-d) δ 8.78 (s, 1H), 6.83 (d, J=1.7 Hz, 1H), 6.80-6.64 (m, 4H), 5.28 (dd, J=12.1, 6.3 Hz, 1H), 5.15 (s, 1H), 4.64 (s, 2H), 4.37 (dd, J=34.8, 10.1 Hz, 2H), 4.28-4.19 (m, 1H), 4.14 (dd, J=11.7, 4.3 Hz, 2H), 3.54 (t, J=11.9 Hz, 2H), 3.45-3.33 (m, 1H), 2.79-2.69 (m, 1H), 2.34 (d, J=30.9 Hz, 8H), 1.85 (d, J=12.9 Hz, 2H). Mass (m/z) 555.4 [M+H]$^+$.

(S)-(3-((2-(1-(cyclopropylmethyl)-3,5-dimethyl-1H-pyrazol-4-yl)-5-fluoropyrimidin-4-yl)oxy)azetidin-1-yl)(5-(3,5-difluorophenyl)-4,5-dihydro-1H-pyrazol-1-yl)methanone (158)

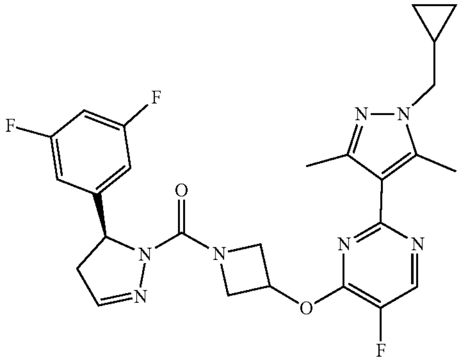 [SMILES: Cc1nn(CC2CC2)c(C)c1-c1ncc(F)c(OC2CN(C(=O)N3N=CC[C@H]3c3cc(F)cc(F)c3)C2)n1]

The title compound 158 was prepared in a yield of 24.7% as a white solid from compound 91 according to the procedure outlined for compound 86. $^1$H NMR (400 MHz, Chloroform-d) δ 8.36 (d, J=2.6 Hz, 1H), 6.83-6.65 (m, 4H), 5.53 (s, 1H), 5.29 (s, 1H), 4.61 (s, 2H), 4.33 (d, J=27.3 Hz, 2H), 3.98 (d, J=6.8 Hz, 2H), 3.35 (dd, J=18.6, 12.1 Hz, 1H), 2.77-2.49 (m, 7H), 1.26 (s, 1H), 0.58 (dd, J=7.7, 5.2 Hz, 2H), 0.41 (t, J=5.0 Hz, 2H). Mass (m/z) 526.3 [M+H]$^+$.

(S)-(5-(3,5-difluorophenyl)-4,5-dihydro-1H-pyrazol-1-yl)(3-((5-fluoro-2-(1,3,5-trimethyl-1H-pyrazol-4-yl)pyridin-4-yl)oxy)azetidin-1-yl)methanone (159)

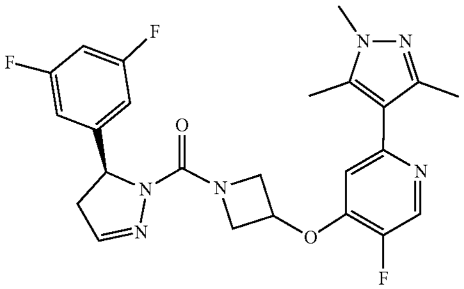 [SMILES: Cc1nn(C)c(C)c1-c1cc(OC2CN(C(=O)N3N=CC[C@H]3c3cc(F)cc(F)c3)C2)c(F)cn1]

The title compound 159 was prepared in a yield of 30.5% as a white solid from compound 3-04 according to the procedure outlined for compound 3. $^1$H NMR (400 MHz, Chloroform-d) δ 8.40 (d, J=3.1 Hz, 1H), 6.81-6.65 (m, 4H), 6.57 (d, J=6.6 Hz, 1H), 5.27 (dd, J=12.2, 6.5 Hz, 1H), 5.04 (ddd, J=7.8, 6.4, 3.9 Hz, 1H), 4.58 (t, J=10.0 Hz, 2H), 4.32 (dd, J=35.2, 10.2 Hz, 2H), 3.76 (s, 3H), 3.36 (ddd, J=18.6, 12.2, 1.7 Hz, 1H), 2.71 (ddd, J=18.6, 6.5, 1.7 Hz, 1H), 2.35 (d, J=22.7 Hz, 6H). Mass (m/z) 485.3 [M+H]$^+$.

(S)-(5-(3,5-difluorophenyl)-4,5-dihydro-1H-pyrazol-1-yl)(3-((5-fluoro-2-(3-((2-methoxyethyl)amino)-1,4-dimethyl-1H-pyrazol-5-yl)pyridin-4-yl)oxy)azetidin-1-yl)methanone (160)

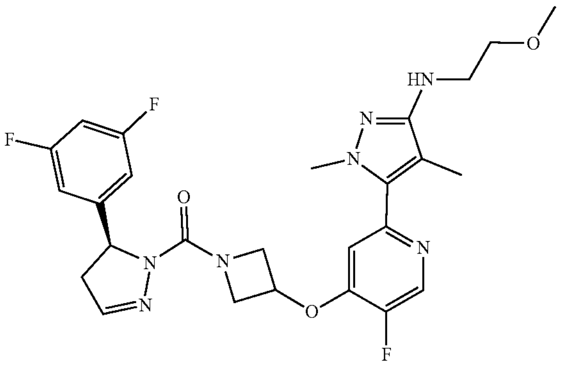 [SMILES: COCCNc1nn(C)c(-c2cc(OC3CN(C(=O)N4N=CC[C@H]4c4cc(F)cc(F)c4)C3)c(F)cn2)c1C]

The title compound 160 was prepared in a yield of 36.8% as a white solid from compound 101-03 according to the procedure outlined for compound 56. $^1$H NMR (400 MHz, Chloroform-d) δ 8.54 (d, J=2.9 Hz, 1H), 6.91-6.60 (m, 5H), 5.28 (dd, J=12.1, 6.3 Hz, 1H), 5.13-5.05 (m, 1H), 4.71-4.54 (m, 2H), 4.33 (dd, J=23.8, 10.5 Hz, 2H), 3.80 (s, 3H), 3.62 (t, J=4.6 Hz, 2H), 3.55 (t, J=4.7 Hz, 2H), 3.40 (s, 3H), 3.39-3.31 (m, 1H), 2.72 (dd, J=18.6, 6.2 Hz, 1H), 1.95 (s, 3H). Mass (m/z) 544.4 [M+H]$^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-5-methyl-1H-pyrrole-2-carboxamide (161)

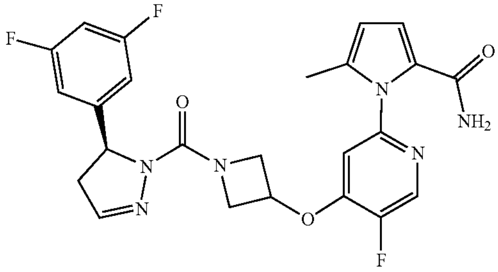 [SMILES: Cc1ccc(C(N)=O)n1-c1cc(OC2CN(C(=O)N3N=CC[C@H]3c3cc(F)cc(F)c3)C2)c(F)cn1]

The titled compound 161 was prepared in 19.2% yield according to the procedure outlined for compound 66-02. $^1$H NMR (400 MHz, Chloroform-d) δ 8.30 (d, J=2.7 Hz, 1H), 6.79 (d, J=1.7 Hz, 1H), 6.77-6.65 (m, 3H), 6.10 (d, J=2.8 Hz, 1H), 6.04 (d, J=4.0 Hz, 1H), 5.75 (s, 1H), 5.33-5.21 (m, 1H), 5.08-5.00 (m, 1H), 4.62-4.49 (m, 2H), 4.42-4.19 (m, 2H), 3.41-3.30 (m, 1H), 2.77-2.63 (m, 1H), 2.08 (s, 3H). Mass (m/z) 499.3 [M+H]$^+$.

(S)-(5-(3,5-difluorophenyl)-4,5-dihydro-1H-pyrazol-1-yl)(3-((5-fluoro-2-(3-(isopropylamino)-1,4-dimethyl-1H-pyrazol-5-yl)pyridin-4-yl)oxy)azetidin-1-yl)methanone (162)

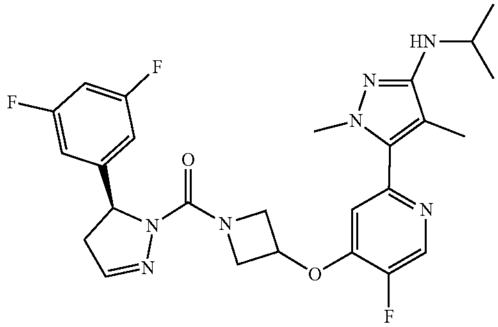 [SMILES: Cc1c(NC(C)C)nn(C)c1-c1cc(OC2CN(C(=O)N3N=CC[C@H]3c3cc(F)cc(F)c3)C2)c(F)cn1]

The title compound 162 was prepared in a yield of 42.8% as a white solid from compound 101-03 according to the procedure outlined for compound 56. $^1$H NMR (400 MHz, Chloroform-d) δ 8.52 (d, J=2.8 Hz, 1H), 6.81 (t, J=1.6 Hz, 1H), 6.78-6.55 (m, 4H), 5.28 (dd, J=12.1, 6.3 Hz, 1H), 5.14-5.02 (m, 1H), 4.71-4.52 (m, 2H), 4.32 (dd, J=21.1, 10.1 Hz, 2H), 3.92-3.84 (m, 1H), 3.82 (s, 3H), 3.44-3.28 (m, 1H), 2.76-2.67 (m, 1H), 1.99 (s, 3H), 1.43-1.18 (m, 6H). Mass (m/z) 528.4 [M+H]$^+$.

(S)-(3-((2-(3-((cyclopropylmethyl)amino)-1,4-dimethyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (163)

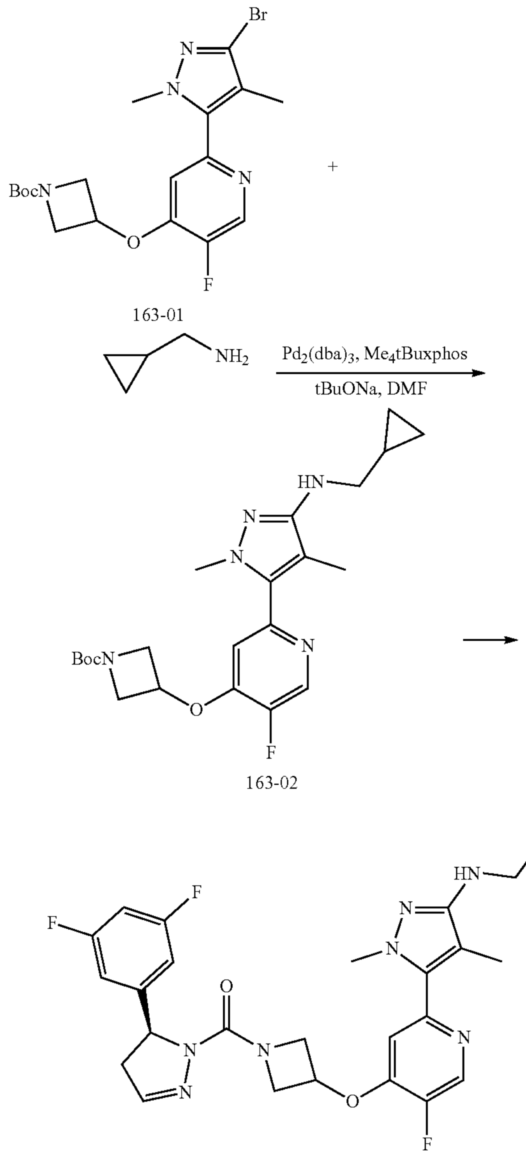

163-01

163-02

163

Step 1: Compound 163-01 (150 mg, 0.34 mmol), cyclopropylmethanamine (48.4 mg, 0.68 mmol), $Pd_2(dba)_3$ (27 mg, 0.03 mmol), $Me_4$tBuPhos (16 mg, 0.03 mmol) and NaOtBu (65 mg, 0.68 mmol) were dissolved in DMF (3 mL). The mixture was stirred at 90° C. for 2 hrs under $N_2$ atmosphere. Concentrated and purified by prep-TLC to give compound 163-02 (70 mg, 42.2%) as yellow oil.

The title compound 163 was prepared in a yield of 42.1% as a white solid from compound 163-02 according to the procedure outlined for compound 1-03. $^1$H NMR (400 MHz, Chloroform-d) δ 8.48 (d, J=2.9 Hz, 1H), 6.80 (t, J=1.7 Hz, 1H), 6.78-6.57 (m, 4H), 5.27 (dd, J=12.2, 6.5 Hz, 1H), 5.09-5.01 (m, 1H), 4.67-4.51 (m, 2H), 4.32 (dd, J=31.8, 10.5 Hz, 2H), 3.77 (s, 3H), 3.36 (ddd, J=18.6, 12.2, 1.7 Hz, 1H), 3.13 (d, J=7.0 Hz, 2H), 2.71 (ddd, J=18.6, 6.5, 1.7 Hz, 1H), 1.95 (s, 3H), 1.18-1.09 (m, 1H), 0.58-0.49 (m, 2H), 0.29-0.20 (m, 2H). Mass (m/z) 539.2 [M+H]$^+$.

(S)-(3-((2-(3-((cyclopropylmethyl)(methyl)amino)-1,4-dimethyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (164)

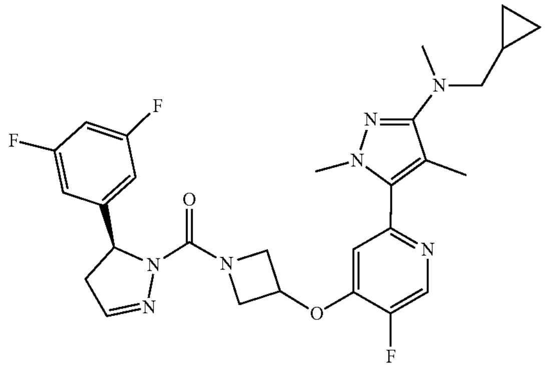 [SMILES: Cc1c(N(C)CC2CC2)nn(C)c1-c1cc(OC2CN(C(=O)N3N=CC[C@H]3c3cc(F)cc(F)c3)C2)c(F)cn1]

The title compound 164 was prepared in a yield of 16.7% as a white solid from compound 163 according to the procedure outlined for compound 56. $^1$H NMR (400 MHz, Chloroform-d) δ 8.51 (d, J=2.7 Hz, 1H), 6.82 (s, 1H), 6.69 (d, J=25.6 Hz, 4H), 5.30 (s, 1H), 5.07 (s, 1H), 4.63 (d, J=25.8 Hz, 2H), 4.33 (s, 2H), 3.89 (s, 3H), 3.39 (d, J=7.1 Hz, 2H), 3.36-3.29 (m, 1H), 3.26 (s, 2H), 2.73 (s, 1H), 2.19 (s, 3H), 1.05 (s, 1H), 0.62 (d, J=7.9 Hz, 2H), 0.35 (s, 2H). Mass (m/z) 554.4 [M+H]$^+$.

(S)-5-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-3-carboxamide (165)

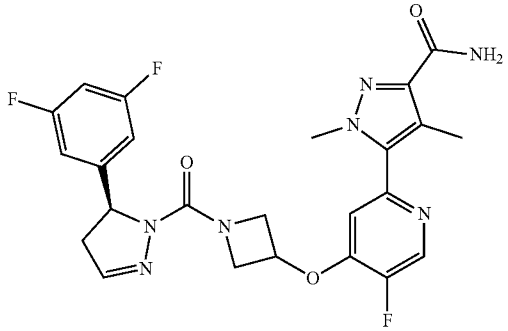 [SMILES: Cc1c(C(N)=O)nn(C)c1-c1cc(OC2CN(C(=O)N3N=CC[C@H]3c3cc(F)cc(F)c3)C2)c(F)cn1]

The title compound 165 was prepared in a yield of 96.10% as a white solid from compound 150 according to the procedure outlined for compound 66. $^1$H NMR (400 MHz, Chloroform-d) δ 8.51 (d, J=2.9 Hz, 1H), 6.87-6.78 (m, 2H), 6.78-6.55 (m, 4H), 5.46 (s, 1H), 5.27 (dd, J=12.2, 6.4 Hz, 1H), 5.11-5.04 (m, 1H), 4.60 (dd, J=19.7, 10.9 Hz, 2H), 4.33 (dd, J=25.1, 10.3 Hz, 2H), 3.95 (s, 3H), 3.36 (ddd, J=18.6, 12.2, 1.7 Hz, 1H), 2.71 (ddd, J=18.6, 6.4, 1.7 Hz, 1H), 2.37 (s, 3H). Mass (m/z) 514.2 [M+H]$^+$.

(S)-(5-(3,5-difluorophenyl)-4,5-dihydro-1H-pyrazol-1-yl)(3-((2-(3-(dimethylamino)-1-methyl-1H-pyrazol-5-yl)-5-fluoropyridin-4-yl)oxy)azetidin-1-yl) methanone (166)

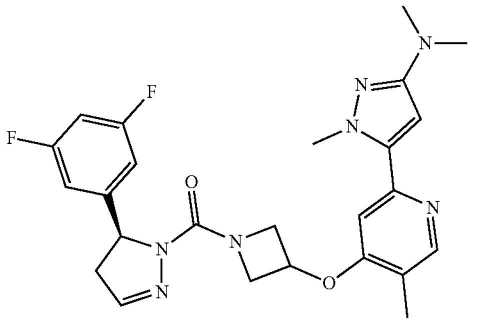 [SMILES: Cc1cnc(-c2cc(N(C)C)nn2C)cc1OC1CN(C(=O)N2N=CC[C@H]2c2cc(F)cc(F)c2)C1]

The title compound 166 was prepared in a yield of 48% as a white solid from compound 41 according to the procedure outlined for compound 56. Mass (m/z) 500.3 $[M+H]^+$. $^1H$ NMR (301 MHz, Chloroform-d) δ 8.46-8.39 (m, 1H), 6.90-6.62 (m, 5H), 5.95 (s, 1H), 5.28 (dd, J=12.3, 6.4 Hz, 1H), 5.15-5.04 (m, 1H), 4.69-4.53 (m, 2H), 4.41-4.22 (m, 2H), 4.04 (s, 3H), 3.45-3.29 (m, 1H), 2.98 (s, 6H), 2.79-2.64 (m, 1H).

(S)-(5-(3,5-difluorophenyl)-4,5-dihydro-1H-pyrazol-1-yl)(3-((2-(4-(ethylsulfonyl)-3,5-dimethyl-1H-pyrazol-1-yl)-5-fluoropyridin-4-yl)oxy)azetidin-1-yl) methanone (167)

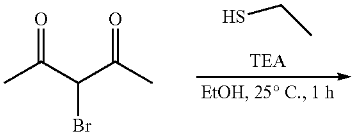

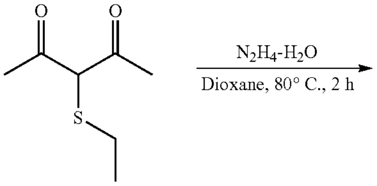

167-01

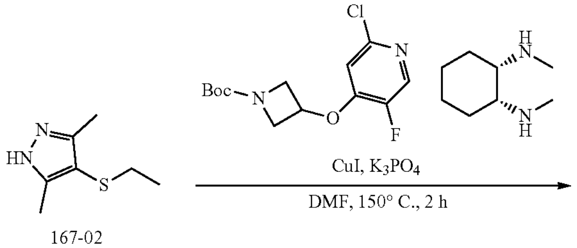

167-02

-continued

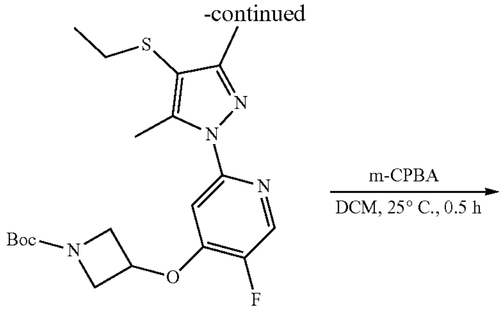

167-03

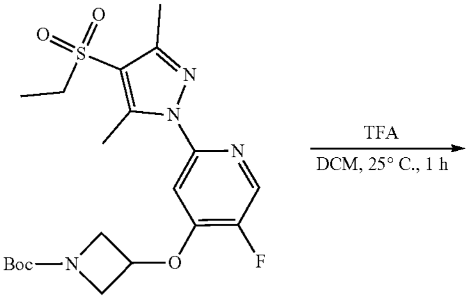

167-04

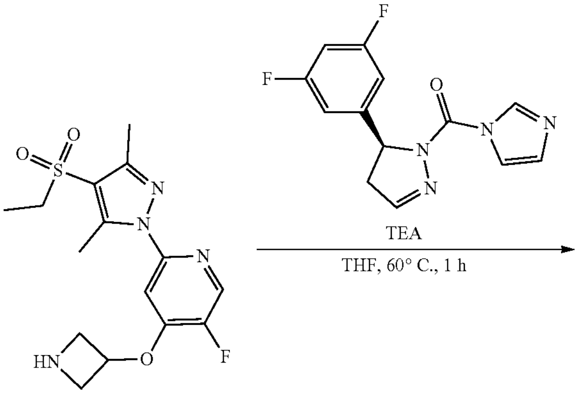

167-05

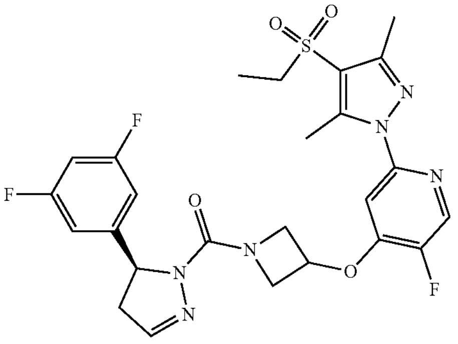

167

Step 1: 3-bromopentane-2,4-dione (1.0 g, 5.65 mmol), ethanethiol (700 mg, 11.29 mmol), TEA (1.1 g, 1.89 mmol) in EtOH (10 mL) under $N_2$ and the whole reaction mixture was stirred at 25° C. for 1 hour. The mixture was concentrated in vacuo to give compound 167-01 (1.5 g) as a yellow oil and used into next step reaction without purification. MS (m/z) 161.2 $[M+H]^+$.

Step 2: Compound 167-01 (1.5 g, crude), $N_2H4$-$H_2O$ (5 mL) were in dioxane (10 mL) under $N_2$ and the whole reaction mixture was stirred at 80° C. for 2 hours. The mixture was extracted with EA, washed with brine, dried ($Na_2SO_4$), and concentrated in vacuo. Purification by silica gel chromatography to give compound 167-02 (100 mg) as a yellow oil. MS (m/z) 157.2 $[M+H]^+$.

Step 3: Compound 167-02 (100 mg, 0.64 mmol), tert-butyl 3-((2-chloro-5-fluoropyridin-4-yl)oxy)azetidine-1-carboxylate (386 mg, 1.27 mmol), (1R,2S)—N1,N2-dimethylcyclohexane-1,2-diamine (273 mg, 1.92 mmol), CuI (365 mg, 1.92 mmol) and $K_3PO_4$ (407 mg, 1.92 mmol) were in DMF (10 mL) under $N_2$ and the whole reaction mixture was stirred at 150° C. for 2 hours. The mixture was extracted with EA, washed with brine, dried ($Na_2SO_4$), and concentrated in vacuo. Purification by silica gel chromatography to give compound 167-03 (200 mg) as a yellow oil. MS (m/z) 423.5 $[M+H]^+$.

Step 4: Compound 167-03 (200 mg, 0.47 mmol), m-CPBA (200 mg, 1.16 mmol) were in DCM (10 mL) under $N_2$ and the whole reaction mixture was stirred at 25° C. for 0.5 hours. The mixture was extracted with EA, washed with brine, dried ($Na_2SO_4$), and concentrated in vacuo to give compound 167-04 (300 mg, crude) as a yellow oil and used into next step reaction without purification. MS (m/z) 455.5 $[M+H]^+$.

Step 5: Compound 167-04 (300 mg, crude), TFA (2 mL) were dissolved in DCM (5 mL) and stirred at 25° C. for 1 h. The mixture was concentrated in vacuo to give compound 167-05 (400 mg, crude) as a yellow oil and used into next step reaction without purification. MS (m/z): 355.4 $[M+H]^+$.

Step 6: Compound 167-05 (400 mg, crude), (S)-(5-(3,5-difluorophenyl)-4,5-dihydro-11H-pyrazol-1-yl)(11H-imidazol-1-yl)methanone (80 mg, 0.28 mmol) and TEA (3 mL) were in THF (5 mL) under $N_2$ and the whole reaction mixture was stirred at 60° C. for 1 hour. The mixture was extracted with EA, washed with brine, dried ($Na_2SO_4$), and concentrated in vacuo. Purification by silica gel chromatography to give compound 167 (2.0 mg, 1.2%) as a grey solid. Mass (m/z): 563.5 $[M+H]^+$ (S)-(3-((2-(1-(cyclopropylmethyl)-3-(hydroxymethyl)-5-methyl-1H-pyrazol-4-yl)-5-fluoropyridin-4-yl)oxy)azetidin-1-yl)(5-(3,5-difluorophenyl)-4,5-dihydro-1H-pyrazol-1-yl)methanone (168)

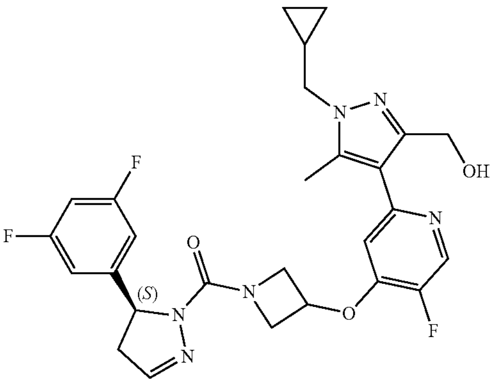

The titled compound 168 was prepared from 169-04 in a yield of 2.0% according to the procedure outlined for compound 169. Mass (m/z): 541.5 $[M+H]^+$. $^1H$ NMR (300 MHz, DMSO-$d_6$) δ 8.50 (d, J=3.2 Hz, 1H), 7.32 (d, J=7.2 Hz, 11H), 7.10 (tt, J=9.6, 2.4 Hz, 11H), 7.02 (d, J=1.6 Hz, 1H), 6.96-6.86 (m, 2H), 5.23 (m, 2H), 4.59-4.50 (m, 2H), 4.48-4.41 (m, 2H), 4.11-4.05 (m, 2H), 3.94 (d, J=6.8 Hz, 2H), 3.39 (dd, J=18.8, 12.0 Hz, 1H), 2.74-2.54 (m, 1H), 2.47 (s, 3H), 1.30-1.23 (m, 1H), 0.56-0.45 (m, 2H), 0.42-0.32 (m, 2H).

(S)-(5-(3,5-difluorophenyl)-4,5-dihydro-1H-pyrazol-1-yl)(3-((5-fluoro-2-(3-(hydroxymethyl)-5-methyl-1-(oxetan-3-ylmethyl)-1H-pyrazol-4-yl)pyridin-4-yl)oxy)azetidin-1-yl)methanone (169)

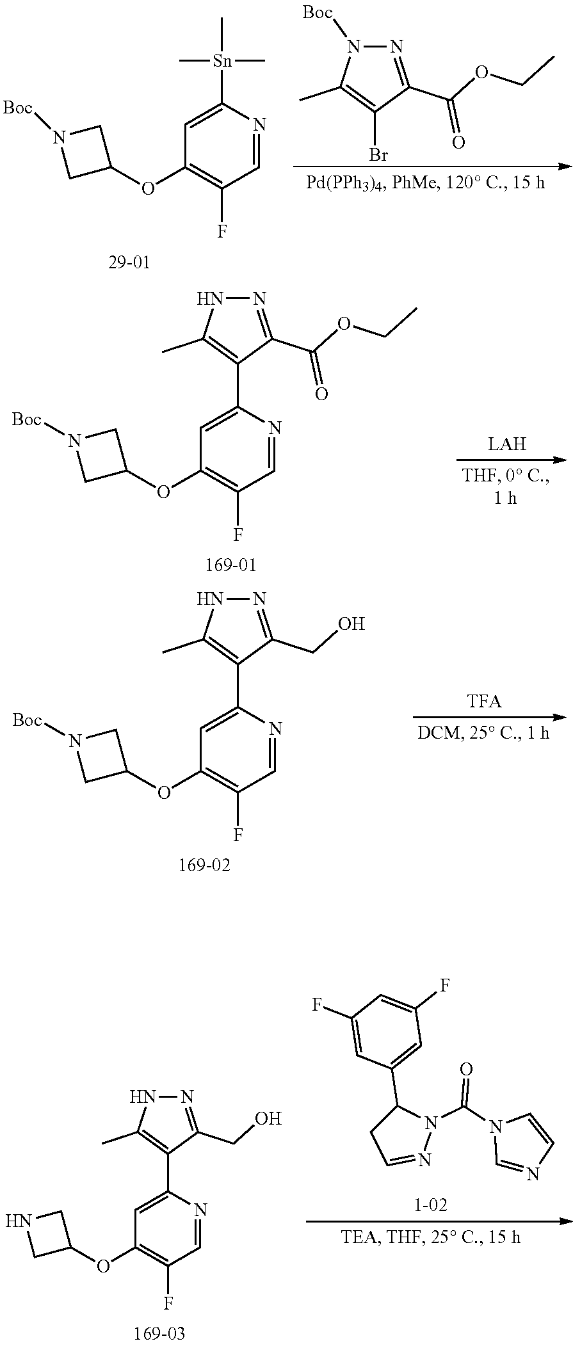

-continued

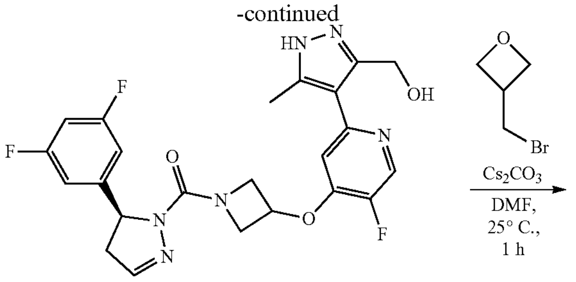

169-04

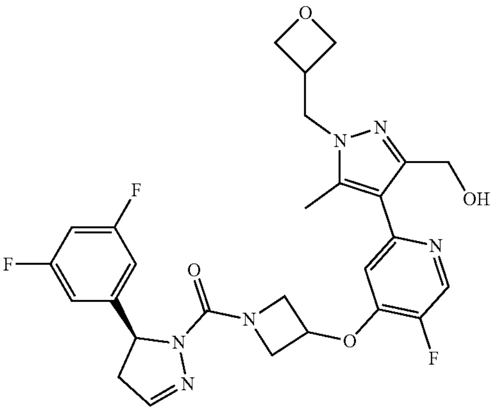

169

Step 1: Compound 29-01 (7.0 g, crude), 1-(tert-butyl) 3-ethyl 4-bromo-5-methyl-1H-pyrazole-1,3-dicarboxylate (5.0 g, 15.06 mmol), $Pd(PPh_3)_4$ (1.70 g, 1.47 mmol) in PhMe (50 mL) under $N_2$ and the whole reaction mixture was stirred at 120° C. for 15 hours. The mixture was extracted with EA, washed with brine, dried ($Na_2SO_4$), and concentrated in vacuo. Purification by silica gel chromatography to give 169-01 (1.0 g) as a yellow solid. MS (m/z): 421.4 $[M+H]^+$.

Step 2: 169-01 (600 mg, 1.42 mmol), LAH (7.0 mL, 1 mol/L, 5.00 mmol), in THE (5 mL) under $N_2$ and the whole reaction mixture was stirred at 0° C. for 1 hour. The mixture was extracted with EA, washed with brine, dried ($Na_2SO_4$), and concentrated in vacuo. Purification by silica gel chromatography to give 169-02 (300 mg) as a yellow oil. MS (m/z): 379.4 $[M+H]^+$.

Step 3: 169-02 (300 mg, 0.79 mmol), TFA (3 mL), in DCM (6 mL) under $N_2$ and the whole reaction mixture was stirred at 25° C. for 1 hour. The mixture was concentrated in vacuo and used into next step reaction without purification. MS (m/z): 279.4 $[M+H]^+$.

Step 4: 169-03 (500 mg, crude), 1-02 (400 mg, 1.45 mmol) and TEA (1 mL) in THE (5 mL) under $N_2$ and the whole reaction mixture was stirred at 25° C. for 15 hours. The mixture was extracted with EA, washed with brine, dried ($Na_2SO_4$), and concentrated in vacuo. Purification by silica gel chromatography to give 169-04 (200 mg) as a yellow oil. MS (m/z): 487.4 $[M+H]^+$.

Step 5: 169-04 (70 mg, 0.14 mmol), $Cs_2CO_3$ (100 mg, 0.30 mmol) and 3-(bromomethyl)oxetane (50 mg, 0.33 mmol) were dissolved in DMF (5 mL) and stirred at 25° C. for 1 h. The mixture was extracted with EA, washed with brine, dried ($Na_2SO_4$), and concentrated in vacuo. Purification by silica gel chromatography to give the 169 (1.7 mg, 2.0%) as a yellow oil. MS (m/z): 557.5 $[M+H]^+$. $^1H$ NMR (300 MHz, DMSO-$d_6$) δ 8.63 (d, J=3.2 Hz, 1H), 7.16-7.07 (m, 2H), 7.02 (d, J=1.6 Hz, 1H), 6.94-6.87 (m, 2H), 5.75 (s, 1H), 5.29-5.20 (m, 2H), 4.77 (s, 2H), 4.73-4.31 (m, 6H), 4.15-4.05 (m, 2H), 3.63 (d, J=5.6 Hz, 2H), 3.49-3.33 (m, 2H), 2.74-2.60 (m, 1H), 2.56 (s, 3H).

(S)-(5-(3,5-difluorophenyl)-4,5-dihydro-1H-pyrazol-1-yl)(3-((5-fluoro-2-(5-methyl-3-(trifluoromethyl)-1H-pyrazol-1-yl)pyridin-4-yl)oxy)azetidin-1-yl)methanone (170)

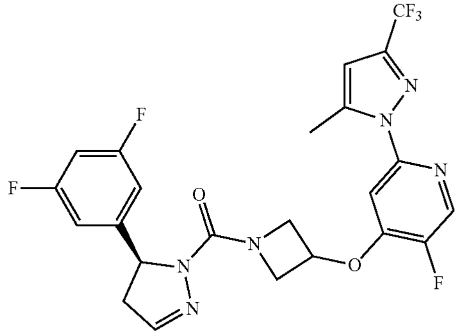 [SMILES: Cc1cc(C(F)(F)F)nn1-c1cc(OC2CN(C(=O)N3N=CC[C@H]3c3cc(F)cc(F)c3)C2)c(F)cn1]

The titled compound 170 was prepared from 3-04 in a yield of 4.0% according to the procedure outlined for compound 102. Mass (m/z): 525.4 $[M+H]^+$. $^1H$ NMR (300 MHz, DMSO-$d_6$) δ 8.51 (d, J=2.8 Hz, 1H), 7.30 (d, J=6.0 Hz, 11H), 7.10 (tt, J=9.6, 2.4 Hz, 11H), 7.02 (d, J=1.6 Hz, 11H), 6.96-6.86 (m, 2H), 6.81 (s, 1H), 5.35 (dd, J=6.4, 3.2 Hz, 1H), 5.24 (dd, J=12.0, 6.4 Hz, 1H), 4.55-4.50 (m, 2H), 4.12-4.07 (m, 2H), 3.48-3.35 (m, 1H), 2.74-2.57 (m, 1H), 2.54 (d, J=0.8 Hz, 3H).

(S)-5-(4-((1-(5-(3,5-difluorophenyl)-4,5-dihydro-1H-pyrazole-1-carbonyl)azetidin-3-yl)oxy)-5-fluoropyridin-2-yl)-N,N,1-trimethyl-11H-pyrazole-3-carboxamide (171)

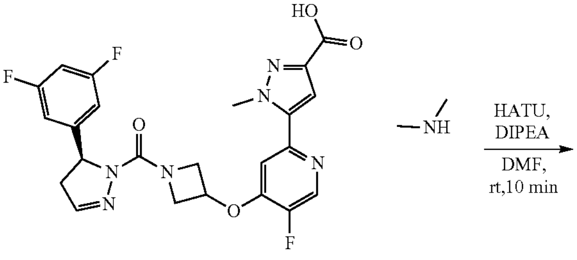

171-01

-continued

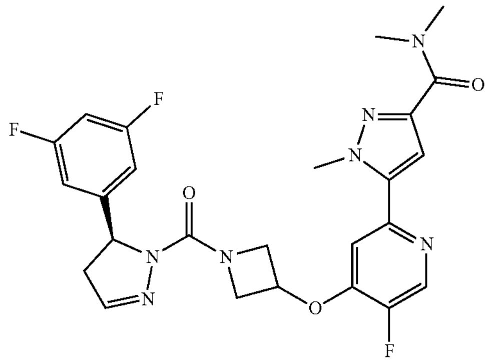

171

Compound 171-01 was prepared in a yield of 34.0% according to the procedure outlined for compound 2.

Compound 171-01 (100 mg, 0.2 mmol), dimethylamine (16 mg, 0.40 mmol), DIPEA (100 mg), HATU (188 mg, 0.5 mmol) were dissolved in DMF (5 mL) and stirred at 25° C. for 10 mins. The mixture was extracted with EA, washed with brine, dried ($Na_2SO_4$), and concentrated in vacuo. Purification by prep-HPLC to give the titled compound 171 (20 mg, 19.0%) as a white solid. $^{1}$H NMR (400 MHz, Chloroform-d) δ 8.45 (d, J=2.7 Hz, 1H), 6.98-6.90 (m, 2H), 6.86-6.68 (m, 4H), 5.30 (dd, J=12.2, 6.4 Hz, 1H), 5.13-5.05 (m, 1H), 4.72-4.54 (m, 3H), 4.46-4.25 (m, 2H), 4.21 (s, 3H), 3.43 (s, 3H), 3.41-3.32 (m, 1H), 3.15 (s, 3H), 2.73 (dd, J=18.7, 6.5 Hz, 1H). Mass (m/z) 528.3 ($M+H^+$).

(S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-1H-pyrazole-3-carboxamide (172)

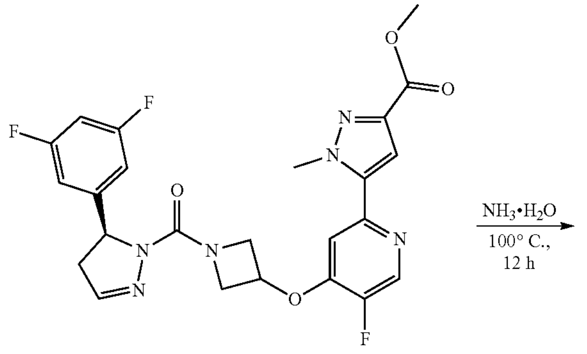

172-01

-continued

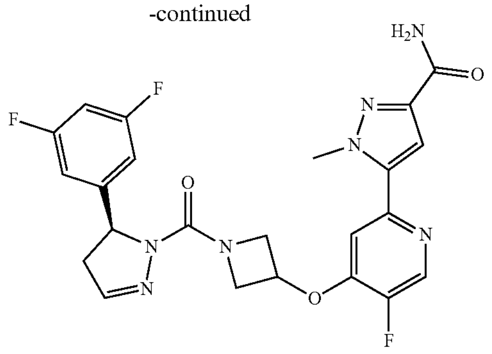

172

Compound 172-01 (200 mg, 0.4 mmol), $NH_3$ in MeOH (2 mL) stirred at 100° C. for 12 h. The mixture was extracted with EA, washed with brine, dried ($Na_2SO_4$), and concentrated in vacuo. Purification by prep-HPLC to give the titled compound 172 (34 mg, 16.9%) as a white solid. $^{1}$H NMR (400 MHz, Chloroform-d) δ 8.36 (d, J=2.7 Hz, 1H), 6.98 (s, 1H), 6.84-6.62 (m, 5H), 5.21 (dd, J=12.2, 6.4 Hz, 1H), 5.05-4.05 (m, 1H), 4.63-4.43 (m, 2H), 4.29-4.20 (m, 2H), 4.14 (s, 3H), 3.30 (dd, J=18.6, 12.2 Hz, 1H), 2.65 (dd, J=18.7, 6.3 Hz, 1H). Mass (m/z) 500.2 $[M+H]^+$.

(S)-5-(4-((1-(5-(3,5-difluorophenyl)-4,5-dihydro-1H-pyrazole-1-carbonyl)azetidin-3-yl)oxy)-5-fluoropyridin-2-yl)-1-methyl-11H-pyrazole-3-carbonitrile (173)

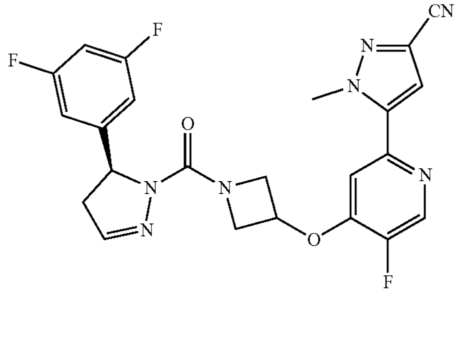 [SMILES: Cn1nc(C#N)cc1-c1cc(OC2CN(C(=O)N3N=CC[C@H]3c3cc(F)cc(F)c3)C2)c(F)cn1]

The titled compound 173 was prepared from 3-04 in a yield of 16.2% according to the procedure outlined for compound 3. H NMR (400 MHz, Chloroform-d) δ 8.46 (d, J=2.8 Hz, 1H), 6.94-6.66 (m, 6H), 5.29 (dd, J=12.0, 6.2 Hz, 1H), 5.11 (s, 1H), 4.68-4.56 (m, 2H), 4.32 (dd, J=26.8, 10.6 Hz, 2H), 4.21 (d, J=3.6 Hz, 3H), 3.45-3.33 (m, 1H), 2.72 (dd, J=18.6, 6.4 Hz, 1H). Mass (m/z) 482.7 $[M+H]^+$.

(S)-(5-(3,5-difluorophenyl)-4,5-dihydro-1H-pyrazol-1-yl)(3-((5-fluoro-2-(3-(hydroxymethyl)-1-methyl-1H-pyrazol-5-yl)pyridin-4-yl)oxy)azetidin-1-yl)methanone (174)

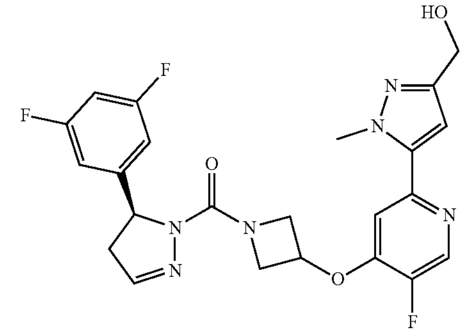 [SMILES: Cn1nc(CO)cc1-c1cc(OC2CN(C(=O)N3N=CC[C@H]3c3cc(F)cc(F)c3)C2)c(F)cn1]

The titled compound 174 was prepared from 3-04 in a yield of 10.2% according to the procedure outlined for compound 3. $^1$H NMR (301 MHz, Chloroform-d) δ 8.46 (d, J=2.7 Hz, 1H), 6.99-6.47 (m, 6H), 5.28 (dd, J=12.1, 6.3 Hz, 1H), 5.16-5.02 (m, 1H), 4.70-4.50 (m, 2H), 4.62 (s, 2H), 4.44-4.25 (m, 2H), 4.19 (s, 3H), 3.37 (dd, J=18.8, 12.2 Hz, 1H), 2.72 (dd, J=18.2, 6.3 Hz, 1H). Mass (m/z) 487.2 $[M+H]^+$.

(S)-(3-((2-(3-chloro-1,4-dimethyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (175)

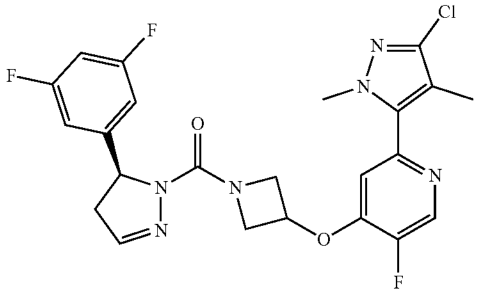 [SMILES: Cc1c(Cl)nn(C)c1-c1cc(OC2CN(C(=O)N3N=CC[C@H]3c3cc(F)cc(F)c3)C2)c(F)cn1]

The titled compound 175 was prepared from 3-02 in a yield of 47.2% according to the procedure outlined for compound 101-02. $^1$H NMR (400 MHz, Chloroform-d) δ 8.49 (d, J=2.9 Hz, 1H), 6.80 (t, J=1.7 Hz, 1H), 6.78-6.57 (m, 4H), 5.26 (dd, J=12.1, 6.4 Hz, 1H), 5.06 (td, J=6.4, 3.2 Hz, 1H), 4.58 (dt, J=16.3, 8.6 Hz, 2H), 4.41-4.22 (m, 2H), 3.89 (s, 3H), 3.36 (ddd, J=18.6, 12.2, 1.7 Hz, 1H), 2.71 (ddd, J=18.6, 6.4, 1.8 Hz, 1H), 2.05 (s, 3H). Mass (m/z): 505.2 $[M+H]^+$.

(S)-(5-(3,5-difluorophenyl)-4,5-dihydro-1H-pyrazol-1-yl)(3-((2-(1,4-dimethyl-3-(methylthio)-1H-pyrazol-5-yl)-5-fluoropyridin-4-yl)oxy)azetidin-1-yl)methanone (176)

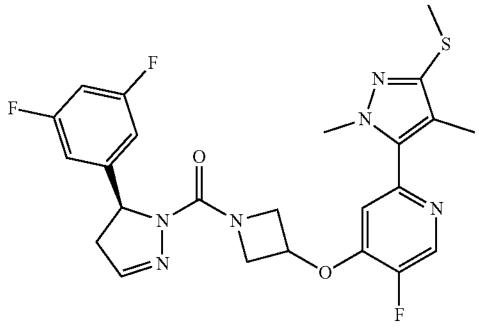 [SMILES: CSc1nn(C)c(-c2cc(OC3CN(C(=O)N4N=CC[C@H]4c4cc(F)cc(F)c4)C3)c(F)cn2)c1C]

The titled compound 176 was prepared according to the procedure outlined for compound 163. $^1$H NMR (400 MHz, Chloroform-d) δ 8.52 (d, J=3.0 Hz, 1H), 6.82 (d, J=1.7 Hz, 1H), 6.79-6.64 (m, 4H), 5.31-5.25 (m, 1H), 5.07 (d, J=3.6 Hz, 1H), 4.60 (s, 2H), 4.34 (dd, J=29.7, 10.6 Hz, 2H), 3.92 (s, 3H), 3.43-3.31 (m, 1H), 2.76-2.70 (m, 1H), 2.47 (s, 3H), 2.08 (s, 3H). Mass (m/z): 517.2$[M+H]^+$.

(5-(3,5-difluorophenyl)-4,5-dihydro-1H-pyrazol-1-yl)(3-((2-(1,4-dimethyl-3-(methylsulfonyl)-1H-pyrazol-5-yl)-5-fluoropyridin-4-yl)oxy)azetidin-1-yl)methanone (177) and (5-(3,5-difluorophenyl)-4,5-dihydro-1H-pyrazol-1-yl)(3-((2-(1,4-dimethyl-3-(methylsulfinyl)-1H-pyrazol-5-yl)-5-fluoropyridin-4-yl)oxy)azetidin-1-yl)methanone (178)

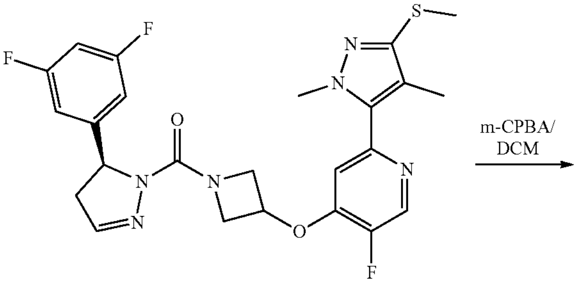

176

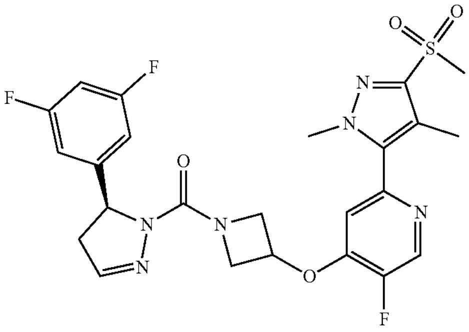

+

177

-continued

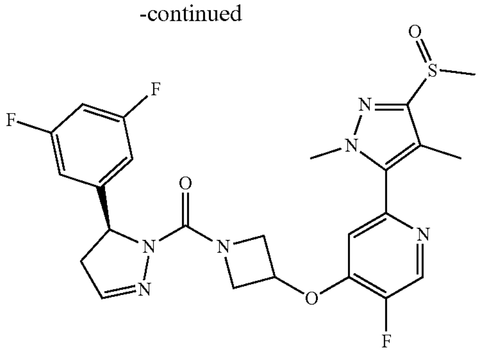

178

Compound 176 (20 mg, 0.04 mmol) and m-CPBA (3.3 mg, 0.02 mmol) were dissolved in DCM (2 mL). The mixture was stirred at r.t. for 90 min. Concentrated and purified by prep-TLC to give compound 177 (10 mg) and compound 178 (0.7 mg) as white solid.

compound 177: $^1$H NMR (301 MHz, Chloroform-d) δ 8.53 (d, J=3.0 Hz, 1H), 8.07 (s, 1H), 7.97 (d, J=7.7 Hz, 1H), 7.58 (d, J=8.0 Hz, 1H), 6.85-6.64 (m, 3H), 5.28 (dd, J=12.2, 6.4 Hz, 1H), 5.13-5.03 (m, 1H), 4.70-5.51 (m, 2H), 4.40-4.19 (m, 2H), 3.98 (s, 3H), 3.37 (ddd, J=18.6, 12.2, 1.7 Hz, 1H), 3.21 (s, 3H), 2.72 (ddd, J=18.8, 6.6, 1.8 Hz, 1H), 2.32 (s, 3H). Mass (m/z): 548.3[M+H]$^+$ compound 178: Mass (m/z): 533.3[M+H]$^+$ ((S)-5-(3,5-difluorophenyl)-4,5-dihydro-1H-pyrazol-1-yl)(3-((5-fluoro-2-(4-(1-hydroxyethyl)-1-methyl-1H-pyrazol-5-yl)pyridin-4-yl)oxy)azetidin-1-yl)methanone (179)

To a solution of compound 179-01 (100 mg, 0.17 mmol) in THE (2 mL) was added isopropylmagnesium chloride lithium chloride complex solution (0.15 mL, 0.20 mmol) at 0° C. The reaction mixture was stirred for 30 min before cooling to −78° C. and addition of N-methoxy-N-methyl-acetamide (53 mg, 0.51 mmol). The solution was stirred at −78° C. for 1 h before removing the cold bath and warming to ambient temperature. The solution was diluted with EtOAc and quenched via the addition of 1N HCl. The layers were separated and the aqueous was extracted with EtOAc. The combined organics layer was washed with brine, dried over $Na_2SO_4$, filtered, and concentrated. The crude residue was taken up in MeOH and cooled to 0° C. before addition of $NaBH_4$ (19 mg, 0.51 mmol). The reaction was stirred while warming to ambient temperature and quenched when LCMS showed disappearance of starting material. This solution was then diluted with 1N HCl and EtOAc. The layers were separated and the aqueous was extracted with EtOAc. The combined organic layer was washed with brine, dried over $Na_2SO_4$, filtered, and concentrated. The crude product was purified by Pre-HPLC to give required product 179 (6 mg, 7%) as a white solid. Mass (m/z) 501.3 [M+H$^+$]. $^1$H NMR (400 MHz, Chloroform-d) δ 8.46 (d, J=2.7 Hz, 1H), 7.58 (s, 1H), 6.88 (d, J=6.3 Hz, 1H), 6.76-6.68 (m, 3H), 6.51 (s, 1H), 5.31 (d, J=5.2 Hz, 1H), 5.19-5.04 (m, 1H), 4.63 (s, 2H), 4.45-4.26 (m, 2H), 4.19 (s, 3H), 3.98 (dt, J=27.4, 6.0 Hz, 1H), 3.02-2.93 (m, 3H), 1.29 (dd, J=6.2, 4.2 Hz, 3H).

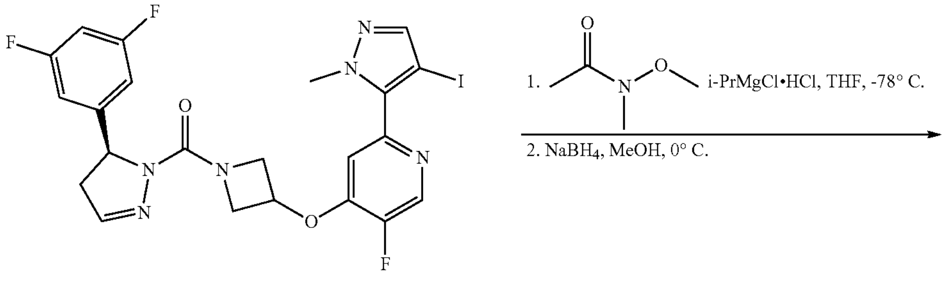

179-01

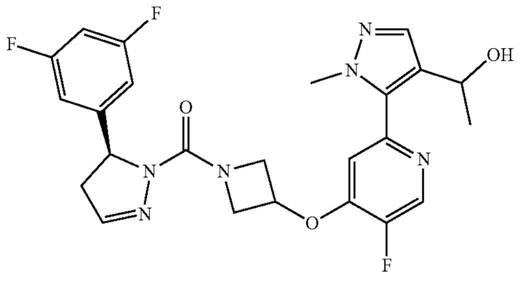

179

(S)-(5-(3,5-difluorophenyl)-4,5-dihydro-1H-pyrazol-1-yl)(3-((5-fluoro-2-(2-(hydroxymethyl)-4-methylthiazol-5-yl)pyridin-4-yl)oxy)azetidin-1-yl)methanone (180)

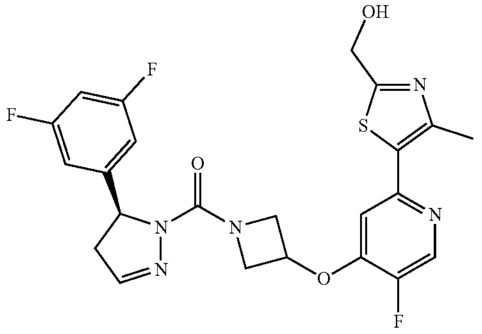 [SMILES: Cc1nc(CO)sc1-c1cc(OC2CN(C(=O)N3N=CC[C@H]3c3cc(F)cc(F)c3)C2)c(F)cn1]

The titled compound 180 was prepared from 3-04 in a yield of 28% according to the procedure outlined for compound 2. Mass (m/z) 504.2 $[M+H]^+$. $^1H$ NMR (300 MHz, Chloroform-d) δ 8.39 (d, J=2.8 Hz, 1H), 7.01-6.55 (m, 5H), 5.27 (dd, J=12.1, 6.1 Hz, 1H), 5.10 (s, 1H), 4.93 (s, 2H), 4.61 (s, 2H), 4.34 (d, J=27.3 Hz, 2H), 3.37 (dd, J=18.4, 11.8 Hz, 1H), 2.74 (d, J=5.9 Hz, 1H), 2.66 (d, J=9.9 Hz, 3H).

(S)-(5-(3,5-difluorophenyl)-4,5-dihydro-1H-pyrazol-1-yl)(3-((2-(3,5-dimethyl-1-(piperidin-4-yl)-1H-pyrazol-4-yl)-5-fluoropyridin-4-yl)oxy)azetidin-1-yl methanone (181)

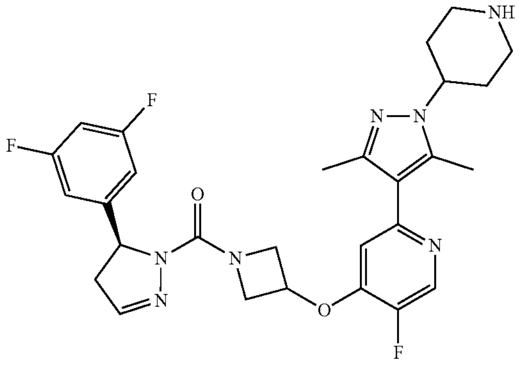 [SMILES: Cc1nn(C2CCNCC2)c(C)c1-c1cc(OC2CN(C(=O)N3N=CC[C@H]3c3cc(F)cc(F)c3)C2)c(F)cn1]

The titled compound 181 was prepared from 92 in a yield of 23.6% according to the procedure outlined for compound 86. $^1H$ NMR (400 MHz, Chloroform-d) δ 9.69 (s, 1H), 9.14 (s, 1H), 8.65 (s, 1H), 6.86-6.64 (m, 4H), 5.28 (dd, J=12.1, 6.3 Hz, 1H), 5.14 (s, 1H), 4.98 (s, 1H), 4.63 (s, 2H), 4.37 (d, J=31.5 Hz, 3H), 3.72 (s, 2H), 3.38 (dd, J=18.6, 12.2 Hz, 1H), 3.21 (s, 2H), 2.73 (dd, J=18.7, 6.3 Hz, 1H), 2.30 (d, J=31.0 Hz, 8H). Mass (m/z) 554.4$[M+H]^+$.

(S)-(5-(3,5-difluorophenyl)-4,5-dihydro-1H-pyrazol-1-yl)(3-((2-(2,5-dimethyl-1H-imidazol-1-yl)-5-fluoropyridin-4-yl)oxy)azetidin-1-yl)methanone (182)

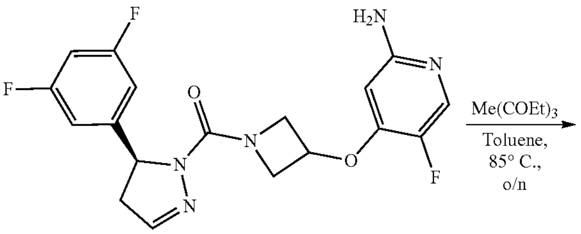

147-01

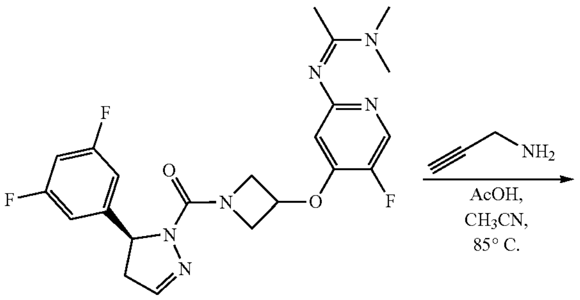

182-01

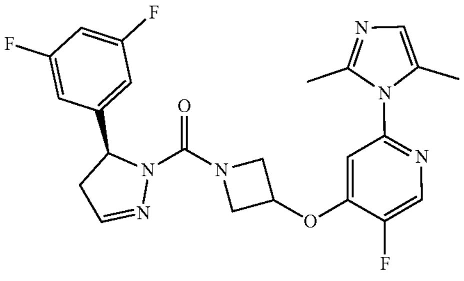

182

Step 1: Compound 147-01 (100 mg, 0.26 mmol) and N,N-dimethylacetamide dimethylacetal (170 mg, 1.28 mmol) mixed in toluene, and the reaction mixture was heated to 85° C. while stirring and was kept at this temperature overnight. The mixture was cooled to room temperature to give the desired product 182-01 in 90% purity. Mass (m/z) 461.4 $[M+H]^+$.

Step 2: Compound 182-01 (50 mg, 5.4 mmol) in 50 ml dry MeCN was added prop-2-yn-1-amine (8 mg, 0.15 mmol) and AcOH (20 mg, 0.33 mmol) to 0° C. The mixture reaction was stirred at 80° C. for overnight and was cooled to room temperature. After the mixture was concentrated and further purified by prep-HPLC to give the final compound 182 (20 mg, 40%) as a white solid. Mass (m/z) 470.2 $[M+H]^+$; $^1H$ NMR (301 MHz, $CDCl_3$) δ 8.41 (d, J=2.0 Hz, 1H), 7.07 (d, J=19.1 Hz, 2H), 6.85-6.58 (m, 4H), 5.34-5.02 (m, 2H), 4.64 (s, 2H), 4.30 (s, 2H), 3.35 (dd, J=18.4, 12.0 Hz, 1H), 2.69 (dd, J=18.5, 5.3 Hz, 1H), 2.53 (s, 3H), 2.07 (d, J=32.8 Hz, 3H).

(S)-(5-(3,5-difluorophenyl)-4,5-dihydro-1H-pyrazol-1-yl)(3-((2-(3,5-dimethyl-4-(piperidine-1-carbonyl)-1H-pyrazol-1-yl)-5-fluoropyridin-4-yl)oxy)azetidin-1-yl)methanone (183)

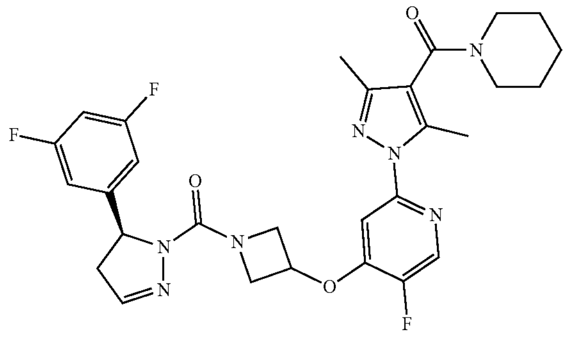 [SMILES: Cc1nn(-c2cc(OC3CN(C(=O)N4N=CC[C@H]4c4cc(F)cc(F)c4)C3)c(F)cn2)c(C)c1C(=O)N1CCCCC1]

The titled compound 183 was prepared from 110-02 in a yield of 14.8% according to the procedure outlined for compound 68. $^1$H NMR (400 MHz, Chloroform-d) δ 8.10 (s, 1H), 7.12 (s, 1H), 6.76-6.57 (dd, J=23.8, 17.0 Hz, 4H), 5.21 (dd, J=12.0, 6.3 Hz, 1H), 5.014-5.02 (m, 1H), 4.64-4.50 (m, 2H), 4.25 (dd, J=29.1, 9.9 Hz, 2H), 3.75-3.54 (m, 2H), 3.39-3.20 (m, 3H), 2.64 (dd, J=18.6, 6.2 Hz, 1H), 2.51 (s, 3H), 2.21 (s, 3H), 1.56 (s, 6H). Mass (m/z) 582.3 [M+H]$^+$.

(S)-(5-(3,5-difluorophenyl)-4,5-dihydro-1H-pyrazol-1-yl)(3-((2-(3,5-dimethyl-4-(morpholine-4-carbonyl)-1H-pyrazol-1-yl)-5-fluoropyridin-4-yl)oxy) azetidin-1-yl)methanone (184

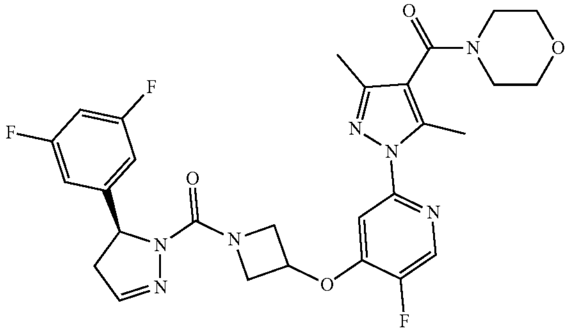 [SMILES: Cc1nn(-c2cc(OC3CN(C(=O)N4N=CC[C@H]4c4cc(F)cc(F)c4)C3)c(F)cn2)c(C)c1C(=O)N1CCOCC1]

The titled compound 184 was prepared from 110-02 in a yield of 14.9% according to the procedure outlined for compound 68. $^1$H NMR (400 MHz, Chloroform-d) δ 8.19 (s, 1H), 7.22 (d, J=6.1 Hz, 1H), 6.85-6.69 (m, 4H), 5.30 (dd, J=12.2, 6.4 Hz, 1H), 5.18 (s, 1H), 4.65 (s, 2H), 4.34 (dd, J=31.0, 10.5 Hz, 2H), 3.62 (d, J=94.6 Hz, 8H), 3.38 (dd, J=18.5, 12.2 Hz, 1H), 2.73 (dd, J=18.6, 6.5 Hz, 1H), 2.61 (s, 3H), 2.32 (s, 3H). Mass (m/z) 584.3 [M+H]$^+$.

(S)-(5-(3,5-difluorophenyl)-4,5-dihydro-1H-pyrazol-1-yl)(3-((6-(1,4-dimethyl-1H-pyrazol-5-yl)-3-fluoropyridin-2-yl)oxy)azetidin-1-yl)methanone (185)

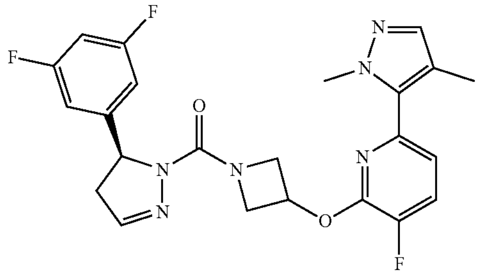 [SMILES: Cc1cnn(C)c1-c1ccc(F)c(OC2CN(C(=O)N3N=CC[C@H]3c3cc(F)cc(F)c3)C2)n1]

The titled compound 185 was prepared from 1-04 in a yield of 47% according to the procedure outlined for compound 2. Mass (m/z): 471.3[M+H]$^+$. $^1$H NMR (300 MHz, Chloroform-d) δ 7.52-7.42 (m, 1H), 7.37 (s, 1H), 7.01 (dd, J=8.1, 2.9 Hz, 1H), 6.85-6.73 (m, 3H), 6.68 (tt, J=8.8, 2.4 Hz, 1H), 5.49-5.36 (m, 1H), 5.27 (dd, J=12.2, 6.5 Hz, 1H), 4.69-4.45 (m, 1H), 4.40-4.21 (m, 2H), 3.96 (s, 3H), 3.34 (ddd, J=18.6, 12.2, 1.7 Hz, 1H), 2.69 (ddd, J=18.6, 6.5, 1.7 Hz, 1H), 2.12 (s, 3H).

(S)-5-(6-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-3-carbonitrile (186)

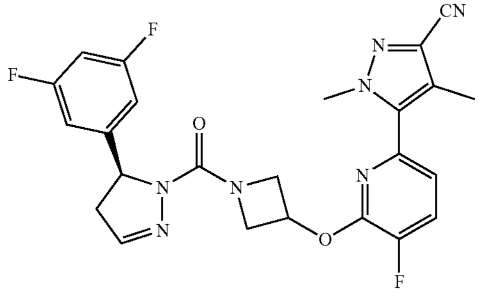 [SMILES: Cc1c(C#N)nn(C)c1-c1ccc(F)c(OC2CN(C(=O)N3N=CC[C@H]3c3cc(F)cc(F)c3)C2)n1]

The titled compound 186 was prepared in a yield of 51% according to the procedure outlined for compound 150. Mass (m/z): 496.3[M+H]$^+$. $^1$H NMR (400 MHz, Chloroform-d) δ 7.52 (dd, J=9.4, 8.0 Hz, 1H), 7.02 (dd, J=8.0, 2.8 Hz, 1H), 6.81-6.72 (m, 3H), 6.69 (tt, J=8.8, 2.2 Hz, 1H), 5.44-5.35 (m, 1H), 5.27 (dd, J=12.1, 6.4 Hz, 1H), 4.68-4.49 (m, 2H), 4.38-4.21 (m, 2H), 3.99 (s, 3H), 3.42-3.29 (m, 1H), 2.70 (ddd, J=18.6, 6.4, 1.7 Hz, 1H), 2.23 (s, 3H).

(S)-(5-(3,5-difluorophenyl)-4,5-dihydro-1H-pyrazol-1-yl)(3-((2-(3,5-dimethyl-1-(methylsulfonyl)-1H-pyrazol-4-yl)-5-fluoropyridin-4-yl)oxy)azetidin-1-yl) methanone (187)

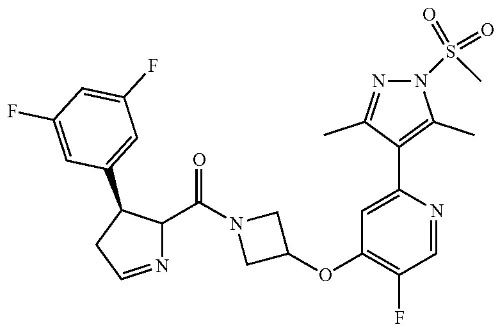 [SMILES: Cc1nn(S(C)(=O)=O)c(C)c1-c1cc(OC2CN(C(=O)C3N=CC[C@H]3c3cc(F)cc(F)c3)C2)c(F)cn1]

The titled compound 187 was prepared from compound 92 in a yield of 33.2% according to the procedure outlined for compound 86. $^{1}$H NMR (400 MHz, Chloroform-d) δ 8.48 (d, J=3.0 Hz, 1H), 6.80 (d, J=1.7 Hz, 1H), 6.78-6.65 (m, 3H), 6.60 (d, J=6.5 Hz, 1H), 5.27 (dd, J=12.2, 6.4 Hz, 1H), 5.07 (tt, J=6.7, 4.0 Hz, 1H), 4.64-4.52 (m, 2H), 4.40-4.25 (m, 2H), 3.41-3.34 (m, 1H), 3.33 (s, 3H), 2.73-2.67 (m, 1H), 2.56 (s, 3H), 2.32 (s, 3H). Mass (m/z) 549.3 $[M+H]^+$.

(S)-5-(4-((1-(5-(3,5-difluorophenyl)-4,5-dihydro-1H-pyrazole-1-carbonyl)azetidin-3-yl)oxy)-5-fluoropyridin-2-yl)-4-methylthiazole-2-carbonitrile (188)

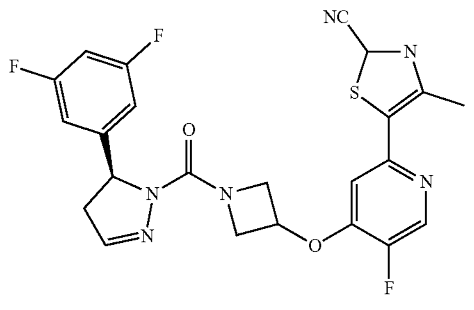 [SMILES: CC1=C(c2cc(OC3CN(C(=O)N4N=CC[C@H]4c4cc(F)cc(F)c4)C3)c(F)cn2)SC(C#N)N1]

The titled compound 188 was prepared from compound 3-02 in a yield of 11% according to the procedure outlined for compound 48. Mass (m/z) 499.1 $[M+H]^+$. $^{1}$H NMR (300 MHz, Chloroform-d) δ 8.42 (d, J=2.9 Hz, 1H), 6.96 (d, J=6.2 Hz, 1H), 6.88-6.63 (m, 4H), 5.28 (dd, J=12.1, 6.4 Hz, 1H), 5.12 (s, 1H), 4.62 (d, J=8.5 Hz, 2H), 4.35 (dd, J=27.0, 10.6 Hz, 2H), 3.38 (dd, J=18.7, 12.2 Hz, 1H), 2.77-2.68 (m, 4H).

(S)-5-(4-((1-(5-(3,5-difluorophenyl)-4,5-dihydro-1H-pyrazole-1-carbonyl)azetidin-3-yl)oxy)-5-fluoropyridin-2-yl)-4-methylthiazole-2-carboxamide (189)

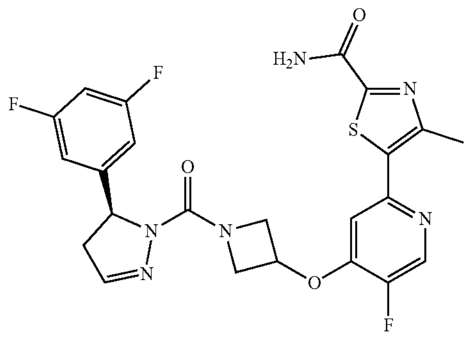 [SMILES: Cc1nc(C(N)=O)sc1-c1cc(OC2CN(C(=O)N3N=CC[C@H]3c3cc(F)cc(F)c3)C2)c(F)cn1]

The titled compound 189 was prepared from compound 188 in a yield of 7.9% according to the procedure outlined for compound 66. Mass (m/z) 517.2 $[M+H]^+$. $^{1}$H NMR (300 MHz, Chloroform-d) δ 8.43 (d, J=2.9 Hz, 1H), 7.14 (s, 1H), 6.88 (d, J=6.3 Hz, 1H), 6.84-6.64 (m, 4H), 5.77 (s, 1H), 5.28 (dd, J=12.1, 6.3 Hz, 1H), 5.10 (s, 1H), 4.72-4.50 (m, 2H), 4.46-4.22 (m, 2H), 3.37 (dd, J=18.6, 12.1 Hz, 1H), 2.79-2.69 (m, 1H), 2.66 (s, 3H).

(S)-(5-(3,5-difluorophenyl)-4,5-dihydro-1H-pyrazol-1-yl)(3-((2-(3,5-dimethyl-4-(methylsulfonyl)-1H-pyrazol-1-yl)-5-fluoropyridin-4-yl)oxy)azetidin-1-yl) methanone (190)

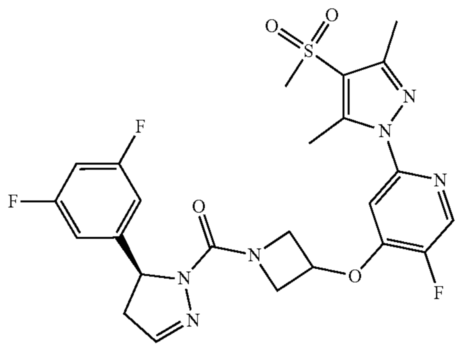 [SMILES: Cc1nn(-c2cc(OC3CN(C(=O)N4N=CC[C@H]4c4cc(F)cc(F)c4)C3)c(F)cn2)c(C)c1S(C)(=O)=O]

The titled compound 190 was prepared from compound 3-02 in a yield of 5.0% according to the procedure outlined for compound 167. Mass (m/z): 549.5 $[M+H]^+$. $^{1}$H NMR (400 MHz, Chloroform-d) δ 8.16 (d, J=2.4 Hz, 1H), 7.09 (d, J=6.0 Hz, 1H), 6.73 (t, J=1.6 Hz, 1H), 6.71-6.75 (m, 2H), 6.63 (tt, J=8.8, 2.4 Hz, 1H), 5.21 (dd, J=12.0, 6.4 Hz, 1H), 5.08 (ddd, J=10.4, 6.4, 4.0 Hz, 1H), 4.60-4.55 (m, 2H), 4.29-4.23 (m, 2H), 3.30 (ddd, J=18.4, 12.0, 1.6 Hz, 1H), 3.01 (s, 3H), 2.78 (s, 3H), 2.64 (ddd, J=18.4, 6.4, 1.6 Hz, 1H), 2.43 (s, 3H).

(S)-4-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrrole-2-carboxamide (191)

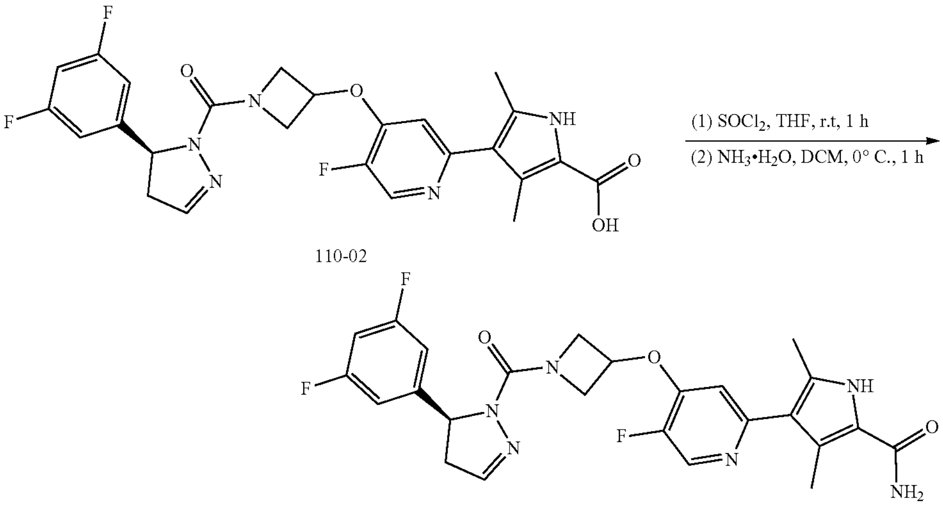

110-02

191

Compound 110-02 (50 mg, 0.097 mmol) was dissolved in 2 mL THF. 0.1 mL $SOCl_2$ was added. Let it stir at r.t for 1 h. The solvent was evaporated to dryness. It was used for next step without further purification. The above residue was dissolved in 2 mL DCM. It was added dropwise to the solution of ammonia solution (0.5 ml) in 2 mL DCM at 0° C. Let it stir at 0° C. for 30 min. The organic layer was separated and evaporated to dryness and purified by prep-TLC (PE/EA=1/3) to give compound 191 (5 mg, 10%) as white solid. Mass (m/z) 513.4 $[M+H]^+$. $^1H$ NMR (400 MHz, $CDCl_3$) δ 9.85 (brs, 1H), 8.71 (s, 1H), 6.81 (s, 1H), 6.77-6.70 (m, 2H), 6.69-6.60 (m, 2H), 6.00 (brs, 2H), 5.27 (dd, J=11.6, 6.4 Hz, 1H), 5.17-5.10 (m, 1H), 4.68-4.53 (m, 2H), 4.45-4.26 (m, 2H), 3.37 (ddd, J=18.4, 12.0, 1.6 Hz, 1H), 2.72 (ddd, J=18.4, 6.4, 1.6 Hz, 1H), 2.29 (s, 6H).

(S)-1-(4-((1-(5-(3,5-difluorophenyl)-4,5-dihydro-1H-pyrazole-1-carbonyl)azetidin-3-yl)oxy)-5-fluoropyridin-2-yl)-N,N,3,5-tetramethyl-1H-pyrazole-4-carboxamide (192)

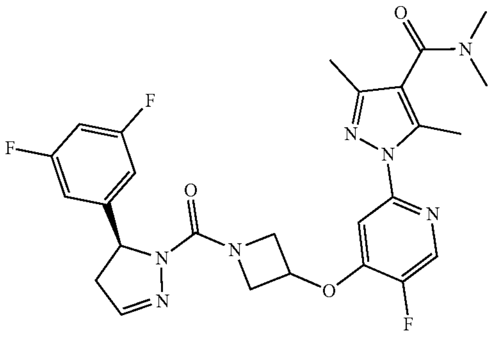 [SMILES: Cc1nn(-c2cc(OC3CN(C(=O)N4N=CC[C@H]4c4cc(F)cc(F)c4)C3)c(F)cn2)c(C)c1C(=O)N(C)C]

The titled compound 192 was prepared from compound 191 in a yield of 16.4% according to the procedure outlined for compound 68. $^1H$ NMR (400 MHz, Chloroform-d) δ 8.19 (d, J=2.5 Hz, 1H), 7.21 (d, J=6.1 Hz, 1H), 6.82 (t, J=1.7 Hz, 1H), 6.78 (dt, J=6.5, 2.2 Hz, 2H), 6.72 (tt, J=8.8, 2.3 Hz, 1H), 5.30 (dd, J=12.2, 6.5 Hz, 1H), 5.17 (td, J=6.5, 3.2 Hz, 1H), 4.71-4.58 (m, 2H), 4.34 (dd, J=30.3, 10.4 Hz, 2H), 3.38 (ddd, J=18.6, 12.2, 1.7 Hz, 1H), 3.14 (s, 3H), 3.04 (s, 3H), 2.73 (ddd, J=18.6, 6.5, 1.7 Hz, 1H), 2.59 (s, 3H), 2.31 (s, 3H). Mass (m/z) 542.3 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-N,3,5-trimethyl-1H-pyrazole-4-carboxamide (193)

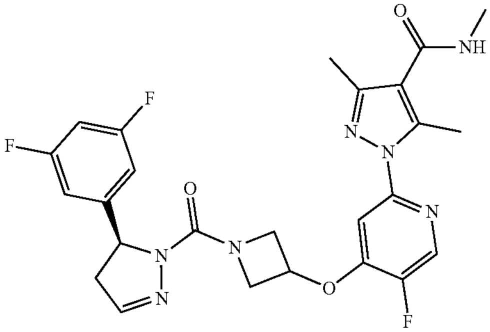 [SMILES: CNC(=O)c1c(C)nn(-c2cc(OC3CN(C(=O)N4N=CC[C@H]4c4cc(F)cc(F)c4)C3)c(F)cn2)c1C]

The titled compound 193 was prepared from compound 191 in a yield of 15.2% according to the procedure outlined for compound 68. $^1H$ NMR (400 MHz, Chloroform-d) δ 8.22 (s, 1H), 7.20 (s, 1H), 6.82-6.67 (m, 4H), 5.61 (s, 1H), 5.30 (dd, J=12.2, 6.4 Hz, 1H), 5.19 (s, 1H), 4.65 (s, 2H), 4.35 (d, J=32.9 Hz, 2H), 3.38 (dd, J=18.0, 12.4 Hz, 1H), 3.02 (d, J=3.7 Hz, 3H), 2.79 (s, 2H), 2.73 (dd, J=17.9, 6.5 Hz, 1H), 2.47 (s, 3H). Mass (m/z) 528.3 $[M+H]^+$.

(S)-(5-(3,5-difluorophenyl)-4,5-dihydro-1H-pyrazol-1-yl)(3-((2-(3,5-dimethyl-4-(pyrrolidine-1-carbonyl)-1H-pyrazol-1-yl)-5-fluoropyridin-4-yl)oxy)azetidin-1-yl)methanone (194)

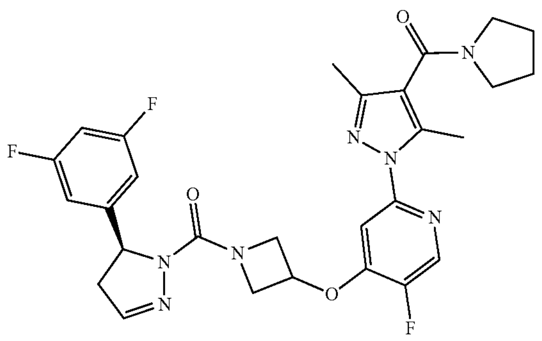 [SMILES: Cc1nn(-c2cc(OC3CN(C(=O)N4N=CC[C@H]4c4cc(F)cc(F)c4)C3)c(F)cn2)c(C)c1C(=O)N1CCCC1]

The titled compound 194 was prepared from compound 191 in a yield of 21.2% according to the procedure outlined for compound 68. $^1H$ NMR (400 MHz, Chloroform-d) δ 8.18 (s, 1H), 7.21 (s, 1H), 6.82 (s, 1H), 6.79-6.64 (m, 3H), 5.27 (s, 1H), 5.18 (s, 1H), 4.67 (s, 2H), 3.67 (s, 2H), 3.35 (d, J=18.6 Hz, 3H), 2.78-2.67 (m, 2H), 2.57 (s, 4H), 2.32 (s, 3H), 1.97 (d, J=26.7 Hz, 4H). Mass (m/z) 568.1 $[M+H]^+$.

(S)-azetidin-1-yl(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)methanone (195)

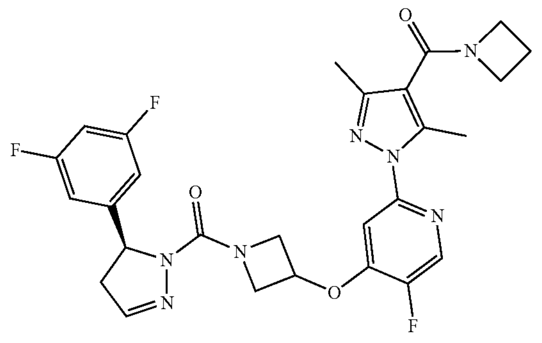 [SMILES: Cc1nn(-c2cc(OC3CN(C(=O)N4N=CC[C@H]4c4cc(F)cc(F)c4)C3)c(F)cn2)c(C)c1C(=O)N1CCC1]

The titled compound 195 was prepared from compound 191 in a yield of 2.9% according to the procedure outlined for compound 68. $^1H$ NMR (400 MHz, Chloroform-d) δ 8.10 (d, J=2.4 Hz, 1H), 7.13 (d, J=6.3 Hz, 1H), 6.74-6.60 (m, 4H), 5.21 (dd, J=12.2, 6.4 Hz, 1H), 5.13-5.03 (m, 1H), 4.65-4.48 (m, 2H), 4.25 (dd, J=29.0, 10.2 Hz, 2H), 3.60 (t, J=6.8 Hz, 2H), 3.37-3.26 (m, 3H), 2.64 (dd, J=18.8, 6.5 Hz, 2H), 2.51 (s, 3H), 2.24 (s, 3H), 1.97-1.84 (m, 2H). Mass (m/z) 554.3 $[M+H]^+$.

(S)-5-(6-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-3-carboxamide (196)

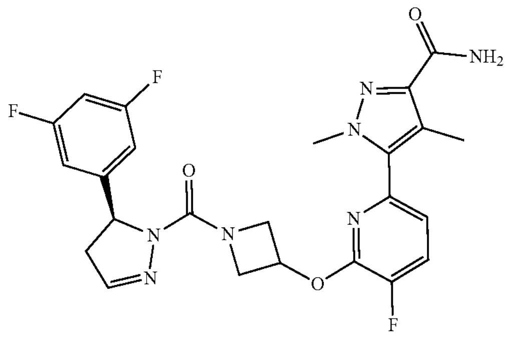 [SMILES: Cc1c(C(N)=O)nn(C)c1-c1ccc(F)c(OC2CN(C(=O)N3N=CC[C@H]3c3cc(F)cc(F)c3)C2)n1]

The titled compound 196 was prepared from compound 186 in a yield of 46% according to the procedure outlined for compound 66. Mass (m/z): 514.3$[M+H]^+$. $^1H$ NMR (400 MHz, Chloroform-d) δ 7.50 (dd, J=9.5, 8.0 Hz, 1H), 7.02 (dd, J=8.0, 2.9 Hz, 1H), 6.86 (s, 1H), 6.80-6.72 (m, 3H), 6.68 (tt, J=8.9, 2.3 Hz, 1H), 5.73 (s, 1H), 5.45-5.37 (m, 1H), 5.27 (dd, J=12.2, 6.5 Hz, 1H), 4.66-4.48 (m, 2H), 4.39-4.22 (m, 2H), 3.92 (s, 3H), 3.35 (ddd, J=18.6, 12.2, 1.7 Hz, 1H), 2.69 (ddd, J=18.6, 6.5, 1.7 Hz, 1H), 2.36 (s, 3H).

(S)-(5-(3,5-difluorophenyl)-4,5-dihydro-1H-pyrazol-1-yl)(3-(5-(1,4-dimethyl-1H-pyrazol-5-yl)-2-fluorophenoxy)azetidin-1-yl)methanone (197)

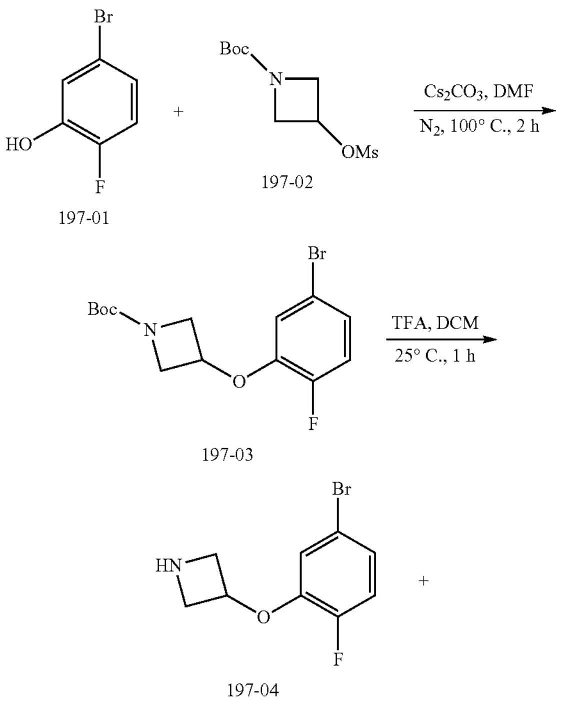

-continued

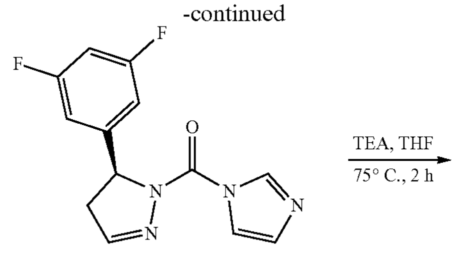

1-02

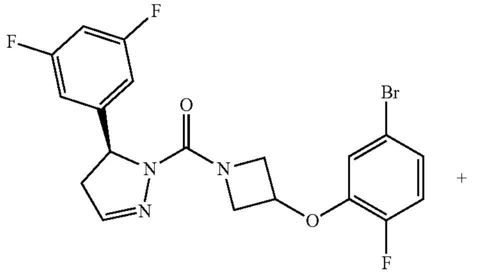

197-05

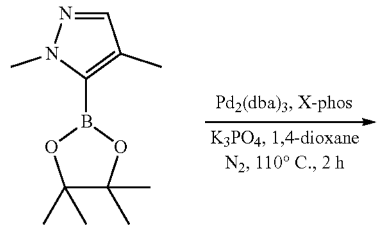

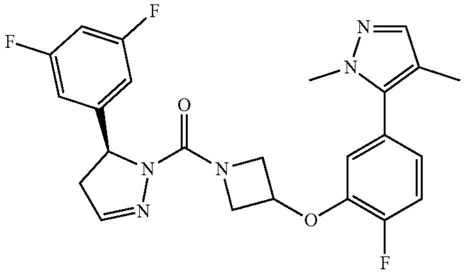

197

Step 1: Compound 197-01 (955 mg, 5.0 mmol), compound 197-02 (1320 mg, 5.25 mmol), $Cs_2CO_3$ (2445 mg, 7.5 mmol), in DMF (20 mL) under $N_2$ and the whole reaction mixture was stirred at 100° C. for 2 hours. After the mixture was concentrated and further purification by silica gel chromatography to give compound 197-03 (1.43 g, 82.5%) as a white solid.

Mass (m/z) 290.1 [M+H−56]$^+$.

Step 2: Compound 197-03 (710 mg, 2.05 mmol) was dissolved in 10 mL of DCM, trifluoroacetic acid (2337 mg, 20.5 mmol) was added, the mixture was stirred at 25° C. for 1 hour. Concentrated to give the desired product compound 197-04, which was used for next step without further purification.

Step 3: Compound 197-04, compound 1-05 (510 mg, 1.845 mmol) and TEA (5 mL) were dissolved in THF (10 mL) and stirred at 75° C. for 2 h. The mixture was extracted with EA, washed with brine, dried ($Na_2SO_4$), and concentrated in vacuo. Purification by silica gel chromatography to give compound 197-05 (720 mg, 86.1%) as a yellow solid. Mass (m/z) 454.0 [M+H]$^+$.

Step 4: Compound 197-05 (91 mg, 0.2 mmol), 1,4-dimethyl-5-(4,4,5,5-tetramethyl-1,3,2-dioxaborolan-2-yl)-1H-pyrazole (54 mg, 0.24 mmol), $Pd_2(dba)_3$ (19 mg, 0.02 mmol), X-phos (19 mg, 0.04 mmol) was added to a solution of $K_3PO_4$ (5N, 0.2 mL, 1.0 mmol) in 1,4-dioxane (2 mL) under $N_2$ and the whole reaction mixture was stirred at 110° C. for 2 hours. After the mixture was concentrated and further purification by prep-HPLC to give compound 197 (39 mg, 41.5%) as a white solid. $^1$H NMR (400 MHz, Chloroform-d) δ 7.37 (s, 1H), 7.21 (dd, J=11.0, 8.3 Hz, 1H), 6.89 (ddd, J=8.3, 4.3, 2.0 Hz, 1H), 6.80-6.73 (m, 3H), 6.69 (tt, J=8.9, 2.4 Hz, 1H), 6.62 (dd, J=7.9, 2.0 Hz, 1H), 5.27 (dd, J=12.2, 6.5 Hz, 1H), 4.97 (td, J=6.3, 3.2 Hz, 1H), 4.54 (d, J=6.6 Hz, 2H), 4.30 (dd, J=26.0, 9.8 Hz, 2H), 3.74 (s, 3H), 3.35 (ddd, J=18.6, 12.2, 1.8 Hz, 1H), 2.70 (ddd, J=18.6, 6.5, 1.7 Hz, 1H), 1.98 (s, 3H). Mass (m/z) 470.3 [M+H]$^+$.

(S)-(5-(3,5-difluorophenyl)-4,5-dihydro-1H-pyrazol-1-yl)(3-(5-(3,5-dimethyl-1H-pyrazol-4-yl)-2-fluorophenoxy)azetidin-1-yl)methanone (198)

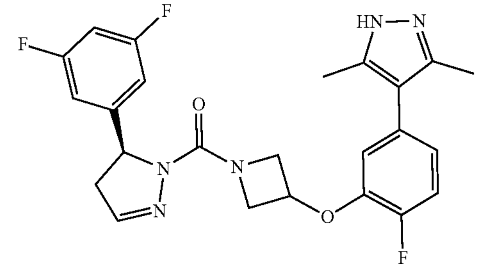 [SMILES: Cc1n[nH]c(C)c1-c1ccc(F)c(OC2CN(C(=O)N3N=CC[C@H]3c3cc(F)cc(F)c3)C2)c1]

The titled compound 198 was prepared from compound 197-05 in a yield of 35.1% according to the procedure outlined for compound 197. $^1$H NMR (400 MHz, Chloroform-d) δ 7.13 (dd, J=11.2, 8.4 Hz, 1H), 6.85-6.64 (m, 5H), 6.58 (dd, J=8.0, 2.1 Hz, 1H), 5.27 (dd, J=12.2, 6.5 Hz, 1H), 4.97 (td, J=6.4, 3.2 Hz, 1H), 4.60-4.47 (m, 2H), 4.31 (dd, J=31.5, 10.1 Hz, 2H), 3.38-3.29 (m, 1H), 2.69 (ddd, J=18.6, 6.5, 1.8 Hz, 1H), 2.26 (s, 6H). Mass (m/z) 470.3 [M+H]$^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-2,5-dimethyl-1H-imidazole-4-carbonitrile (199)

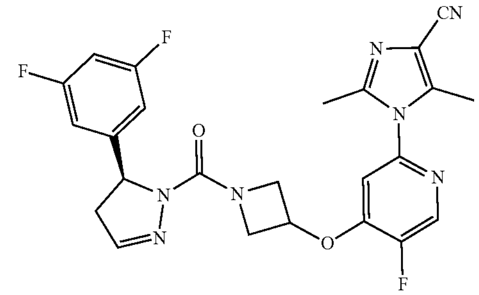 [SMILES: Cc1nc(C#N)c(C)n1-c1cc(OC2CN(C(=O)N3N=CC[C@H]3c3cc(F)cc(F)c3)C2)c(F)cn1]

The titled compound 199 was prepared from compound 182 in a yield of 16% according to the procedure outlined for compound 150. Mass (m/z) 496.4 [M+H]$^+$. $^1$H NMR (400 MHz, $CDCl_3$) δ 8.34 (d, J=2.6 Hz, 1H), 6.75 (s, 1H), 6.71-6.53 (m, 4H), 5.20 (dd, J=12.2, 6.4 Hz, 1H), 5.04 (s, 1H), 4.56 (s, 2H), 4.31-4.15 (m, 2H), 3.30 (dd, J=18.7, 12.3 Hz, 1H), 2.65 (dd, J=18.7, 6.4 Hz, 1H), 2.25 (s, 3H), 2.19 (s, 3H).

(S)-1-(4-((1-(5-(3,5-difluorophenyl)-4,5-dihydro-1H-pyrazole-1-carbonyl)azetidin-3-yl)oxy)-5-fluoropyridin-2-yl)-2,5-dimethyl-1H-imidazole-4-carboxamide (200)

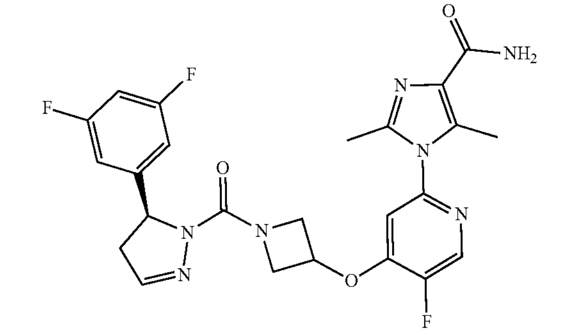 [SMILES: Cc1nc(C(N)=O)c(C)n1-c1cc(OC2CN(C(=O)N3N=CC[C@H]3c3cc(F)cc(F)c3)C2)c(F)cn1]

The titled compound 200 was prepared from compound 199 in a yield of 62% according to the procedure outlined for compound 66. Mass (m/z) 514.4 $[M+H]^+$. $^1H$ NMR (400 MHz, $CDCl_3$) δ 8.34 (d, J=2.7 Hz, 1H), 6.92 (brs, 1H), 6.74 (t, J=1.6 Hz, 1H), 6.70-6.58 (m, 3H), 6.47 (d, J=5.9 Hz, 1H), 5.23-5.16 (m, 1H), 5.03-4.96 (m, 1H), 4.61-4.42 (m, 2H), 4.25 (dd, J=16.9, 10.6 Hz, 2H), 3.30 (ddd, J=18.7, 12.2, 1.7 Hz, 1H), 2.65 (ddd, J=18.7, 6.4, 1.7 Hz, 1H), 2.35 (s, 3H), 2.18 (s, 3H).

(S)-(5-(3,5-difluorophenyl)-4,5-dihydro-1H-pyrazol-1-yl)(3-((5-fluoro-2-(3-(fluoromethyl)-1-methyl-1H-1,2,4-triazol-5-yl)pyridin-4-yl)oxy)azetidin-1-yl)methanone (201)

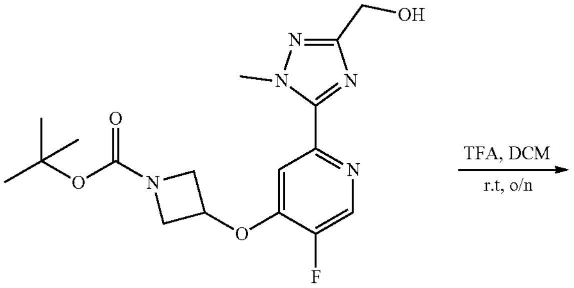

202

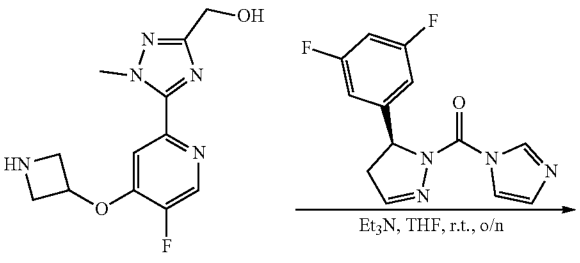

201-01

-continued

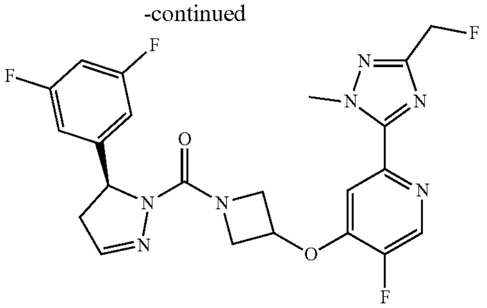

201

Step 1: TFA (1 mL) was added to a solution of compound 202 (100 mg, 0.26 mmol) in DCM (3 mL). The reaction mixture was stirred at room temperature for 0.5 hr. Then the solvent was evaporated in vacuo to give compound 201 as a colorless oil. Mass (m/z) 280.1 $[M+H]^+$.

Step 2: Compound 201-01 was added to a solution of (S)-(5-(3,5-difluorophenyl)-4,5-dihydro-11H-pyrazol-1-yl)(1H-imidazol-1-yl)methanone (87 mg, 0.31 mmol) and TEA (80 mg, 0.79 mmol) in THE (2 mL). The reaction mixture was stirred at room temperature overnight. Then the solvent was evaporated in vacuo. The oil residue was purified by prep-HPLC to give compound 201 (20 mg, 15%) as a white solid. Mass (m/z) 490.1 $[M+H]^+$. $^1H$ NMR (400 MHz, $CDCl_3$) δ 8.37 (d, J=2.3 Hz, 1H), 7.57 (d, J=6.7 Hz, 1H), 6.76-6.57 (m, 4H), 5.44 (s, 1H), 5.32 (s, 1H), 5.21 (dd, J=12.2, 6.3 Hz, 1H), 5.10 (td, J=6.4, 3.3 Hz, 1H), 4.60 (s, 2H), 4.27 (d, J=0.7 Hz, 3H), 4.22 (d, J=11.0 Hz, 2H), 3.29 (ddd, J=18.6, 12.2, 1.6 Hz, 1H), 2.64 (ddd, J=18.6, 6.4, 1.7 Hz, 1H).

(S)-(5-(3,5-difluorophenyl)-4,5-dihydro-1H-pyrazol-1-yl)(3-((5-fluoro-2-(3-(hydroxymethyl)-1-methyl-1H-1,2,4-triazol-5-yl)pyridin-4-yl)oxy)azetidin-1-yl)methanone (202)

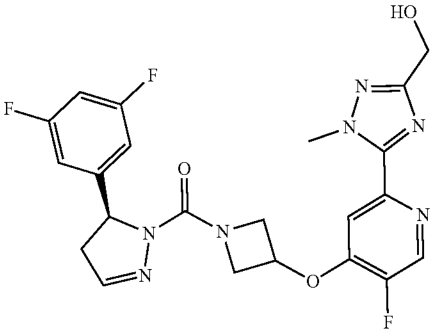 [SMILES: Cn1nc(CO)nc1-c1cc(OC2CN(C(=O)N3N=CC[C@H]3c3cc(F)cc(F)c3)C2)c(F)cn1]

The titled compound 202 was prepared from compound 3-02 in a yield of 24.7% according to the procedure outlined for compound 30. Mass (m/z) 488.1 $[M+H]^+$. $^1H$ NMR (301 MHz, Chloroform-d) δ 8.42 (d, J=2.6 Hz, 1H), 7.59 (d, J=6.7 Hz, 1H), 6.83-6.64 (m, 4H), 5.27 (dd, J=12.2, 6.4 Hz, 1H), 5.16 (d, J=4.4 Hz, 1H), 4.78 (s, 2H), 4.66 (s, 2H), 4.30 (s, 5H), 3.45-3.27 (m, 1H), 2.79-2.62 (m, 1H).

(S)-(5-(3,5-difluorophenyl)-4,5-dihydro-1H-pyrazol-1-yl)(3-((2-(3,5-dimethyl-4-(methylthio)-1H-pyrazol-1-yl)-5-fluoropyridin-4-yl)oxy)azetidin-1-yl)methanone (203)

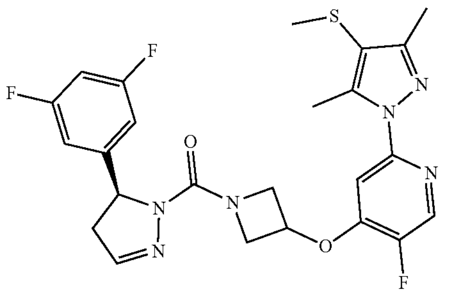 [SMILES: CSc1c(C)nn(-c2cc(OC3CN(C(=O)N4N=CC[C@H]4c4cc(F)cc(F)c4)C3)c(F)cn2)c1C]

The titled compound 203 was prepared from compound 3-02 in a yield of 32.0% according to the procedure outlined for compound 167. Mass (m/z) 517.5 $[M+H]^+$. $^1H$ NMR (400 MHz, Chloroform-d) δ 8.19-8.13 (m, 1H), 7.21 (d, J=6.0 Hz, 1H), 6.79 (t, J=1.6 Hz, 1H), 6.77-6.73 (m, 2H), 6.70 (tt, J=8.8, 2.4 Hz, 1H), 5.28 (dd, J=12.0, 6.4 Hz, 1H), 5.15 (td, J=6.4, 3.2 Hz, 1H), 4.68-4.57 (m, 2H), 4.39-4.24 (m, 2H), 3.36 (ddd, J=18.4, 12.0, 1.6 Hz, 1H), 2.75-2.70 (m, 1H), 2.69 (s, 3H), 2.36 (s, 3H), 2.18 (s, 3H).

((S)-5-(3,5-difluorophenyl)-4,5-dihydro-1H-pyrazol-1-yl)(3-((2-(3,5-dimethyl-4-(methylsulfinyl)-1H-pyrazol-1-yl)-5-fluoropyridin-4-yl)oxy)azetidin-1-yl)methanone (204)

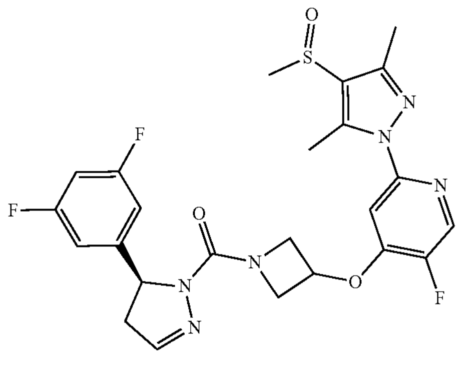 [SMILES: Cc1nn(-c2cc(OC3CN(C(=O)N4N=CC[C@H]4c4cc(F)cc(F)c4)C3)c(F)cn2)c(C)c1S(C)=O]

The titled compound 204 was prepared from compound 203 in a yield of 32.0% according to the procedure outlined for compound 167. Mass (m/z) 533.5 $[M+H]^+$.

$^1H$ NMR (400 MHz, Chloroform-d) δ 8.19 (d, J=2.4 Hz, 1H), 7.19 (d, J=6.0 Hz, 1H), 6.80 (t, J=1.6 Hz, 1H), 6.78-6.73 (m, 2H), 6.73-6.67 (m, 11H), 5.28 (dd, J=12.0, 6.4 Hz, 11H), 5.15 (ddd, J=10.4, 6.4, 4.0 Hz, 1H), 4.70-4.57 (m, 2H), 4.41-4.24 (m, 2H), 3.41-3.31 (m, 1H), 2.93 (s, 3H), 2.75 (s, 3H), 2.73-2.65 (m, 1H), 2.52 (s, 3H).

(S)-(3-((2-(5-amino-3-methyl-1H-pyrazol-4-yl)-5-fluoropyridin-4-yl)oxy)azetidin-1-yl)(5-(3,5-difluorophenyl)-4,5-dihydro-1H-pyrazol-1-yl)methanone (205)

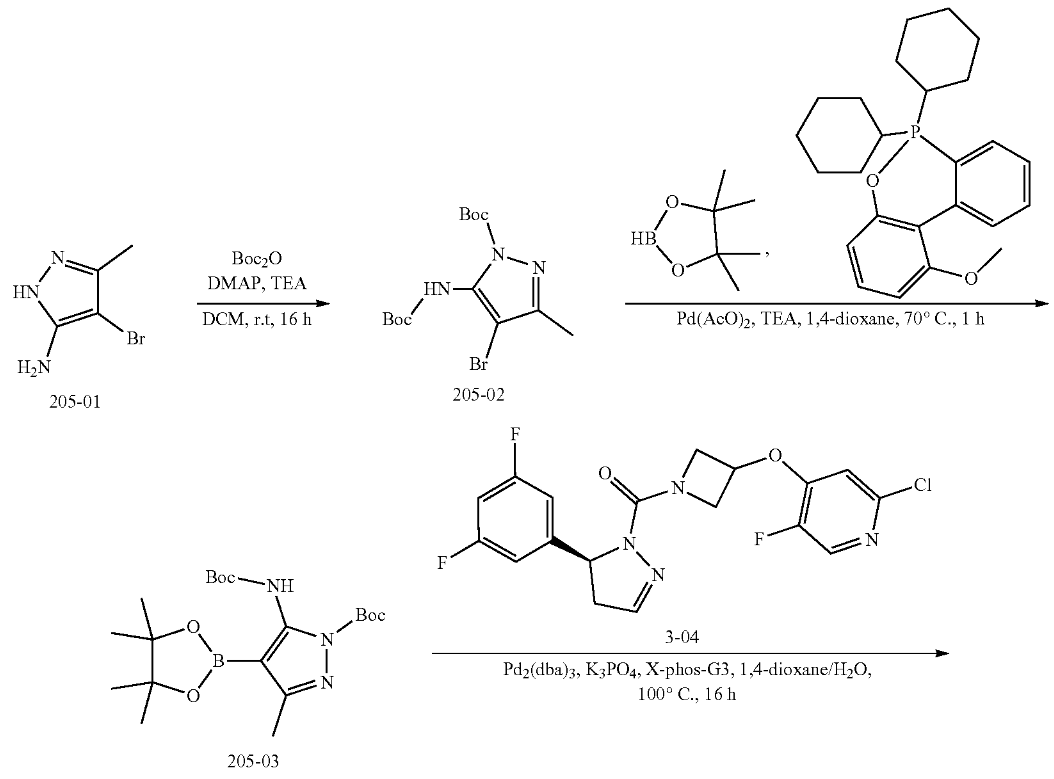

-continued

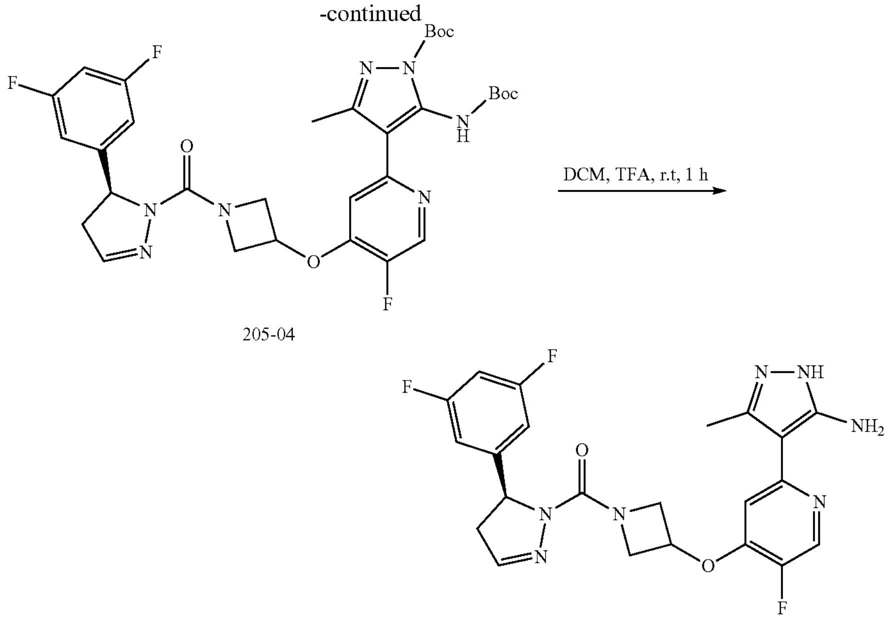

205-04

205

Step 1: Compound 205-01 (1 g, 5.68 mmol), $Boc_2O$ (4.96 g, 22.75 mmol), DMAP (0.139 g, 1.14 mmol) and TEA (2 ml) were dissolved in 15 mL DCM. Let it stir at room temperature for 16 h. The solvent was evaporated to dryness and purified by prep-TLC (PE/EA=3/1) to give compound 205-02 (430 mg, 20.1%) as a white solid. Mass (m/z) 377.3 $[M+H]^+$.

Step 2: Compound 205-02 (430 mg, 1.144 mmol), dicyclohexyl(2',6'-dimethoxy-[1,1'-biphenyl]-2-yl)phosphane (55.7 mg, 0.136 mmol), $Pd(AcO)_2$ (15.2 mg, 0.068 mmol) were mixed in 8 mL 1,4-dioxane. TEA (411 mg, 4.07 mmol) was added. 4,4,5,5-tetramethyl-1,3,2-dioxaborolane (694 mg, 5.42 mmol) was added slowly to the reaction. Let it stir at 70° C. for 1 h. The solvent was evaporated to dryness and purified by prep-TLC (PE/EA=3.5/1) to give compound 205-03 (210 mg, 43.5%) as light-yellow oil. Mass (m/z) 424.3 $[M+H]^+$.

Step 3: Compound 205-03 (190 mg, 0.463 mmol), tert-butyl 5-((tert-butoxycarbonyl)amino)-3-methyl-4-(4,4,5,5-tetramethyl-1,3,2-dioxaborolan-2-yl)-1H-pyrazole-1-carboxylate (210 mg, 0.506 mmol), X-Phos-$G_3$ (39 mg, 0.043 mmol), $Pd_2(dba)_3$ (39 mg, 0.043 mmol), $K_3PO_4$ (982 mg, 4.63 mmol) were mixed in 8 mL 1,4-dioxane/$H_2O$ (v/v=4/1). The mixture was stirred at 100° C. for 16 h under $N_2$. The solvent was evaporated to dryness and purified by prep-TLC (PE/EA=1/3) to give compound 205-04 (40 mg, 12.9%) as light-yellow solid. Mass (m/z) 673.4 $[M+H]^+$.

Step 4: Compound 205-04 (40 mg, 0.06 mmol) was dissolved in 2 mL DCM, 2 mL DCM/TFA (1/1) was added. Let it stir at r.t for 1 h. The solvent was evaporated to dryness and purified by prep-TLC (DCM/MeOH=12/1) to give compound 205 (9.8 mg, 34.6%) as light-yellow oil. Mass (m/z) 473.4 $[M+H]^+$. $^1H$ NMR (400 MHz, $CDCl_3$) δ 8.31 (d, J=2.8 Hz, 1H), 6.80 (t, J=1.6 Hz, 1H), 6.79-6.73 (m, 2H), 6.73-6.65 (m, 1H), 6.64 (d, J=6.4 Hz, 1H), 5.27 (dd, J=12.0, 6.4 Hz, 1H), 5.11-5.01 (m, 1H), 4.65-4.51 (m, 2H), 4.42-4.33 (m, 1H), 4.30-4.23 (m, 1H), 3.36 (ddd, J=18.4, 12.0, 1.6 Hz, 1H), 2.71 (ddd, J=18.4, 6.4, 1.6 Hz, 1H), 2.49 (s, 3H).

(S)-(3-((2-(5-amino-1,2,4-trimethyl-1H-pyrrol-3-yl)-5-fluoropyridin-4-yl)oxy)azetidin-1-yl)(5-(3,5-difluorophenyl)-4,5-dihydro-1H-pyrazol-1-yl)methanone (206)

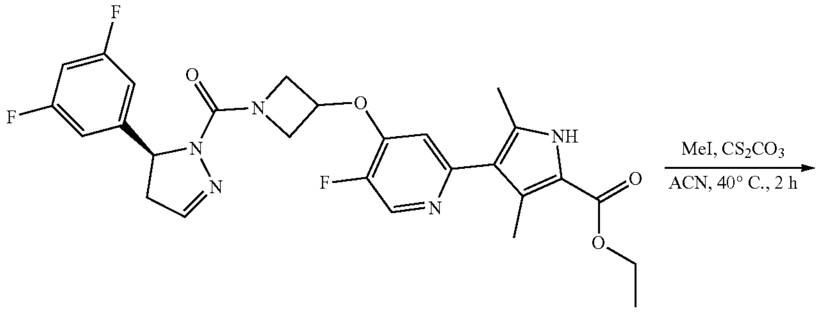

110-01

-continued

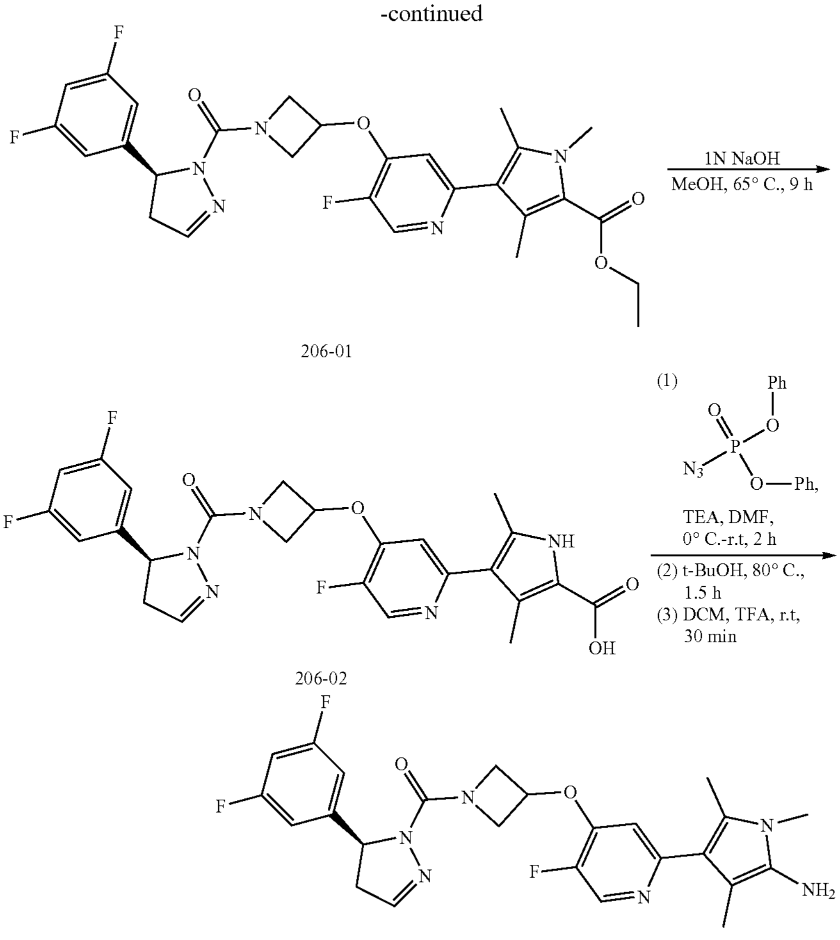

206-01

206-02

206

Step 1: Compound 110-01 (260 mg, 0.48 mmol) and $Cs_2CO_3$ (623.6 mg, 1.92 mmol) were mixed in 8 mL CAN. Mel (170.3 mg, 1.2 mmol) was added. Let it stir at 40° C. for 2 h. The solvent was evaporated to dryness and purified by column chromatography (PE/EA=1/3) to give compound 206-01 (190 mg, 71.2%) as light-yellow oil. Mass (m/z) 556.4 $[M+H]^+$.

Step 2: Compound 206-01 (190 mg, 0.34 mmol) was dissolved in 5 mL MeOH. 2 mL THE was added. 4 mL 1N NaOH was added. Let it stir at 65° C. for 9 h. The solvent was evaporated to dryness and acidified with 1N HCl to PH=6. It was extracted with EA (15 mlx3). The organic layer was evaporated to dryness and purified by column chromatography (PE/EA=1/3) to give compound 206-02 (60 mg, 34.2%). Mass (m/z) 514.3 $[M+H]^+$.

Step 3: Compound 206-02 (60 mg, 0.114 mmol) and TEA (11.5 mg, 0.114 mmol) were dissolved in 1 mL DMF. Diphenyl phosphorazidate (282.2 mg, 0.102 mmol) was added to the mixture at 0° C. Let it stir at r.t under dark for 2 h. Then it was added to 2 mL t-BuOH solution. Let it stir at 80° C. for 1.5 h. The solvent was evaporated to dryness and water was added. It was extracted with EA (15 mlx3). The organic layer was evaporated to dryness and purified by column chromatography (PE/EA=1/3) to give 5 mg tert-butyl (S)-(4-(4-((1-(5-(3,5-difluorophenyl)-4,5-dihydro-1H-pyrazole-1-carbonyl)azetidin-3-yl)oxy)-5-fluoropyridin-2-yl)-1,3,5-trimethyl-1H-pyrrol-2-yl)carbamate as light-yellow solid. Yield: 8.2%. Mass (m/z) 599.4 $[M+H]^+$. The above residue was dissolved in 2 mL DCM. It was added dropwise to the solution of ammonia solution (0.5 ml) in 2 mL DCM at 0° C. Let it stir at 0° C. for 30 min. The organic layer was separated and evaporated to dryness and purified by prep-TLC (DCM/MeOH=8/1) to give compound 206 (2 mg, 48%) as white solid. Mass (m/z) 499.4 $[M+H]^+$.

(S)-(3-((2-(3-amino-1,4-dimethyl-1H-pyrazol-5-yl)-5-fluoropyrimidin-4-yl)oxy)azetidin-1-yl)(5-(3,5-difluorophenyl)-4,5-dihydro-1H-pyrazol-1-yl)methanone (207)

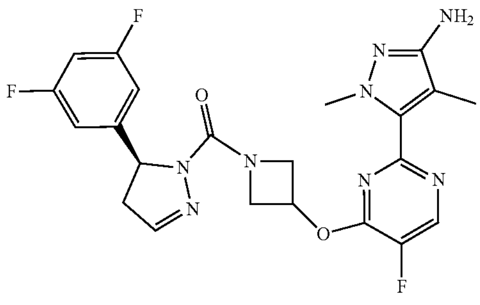 [SMILES: Cc1c(N)nn(C)c1-c1ncc(F)c(OC2CN(C(=O)N3N=CC[C@H]3c3cc(F)cc(F)c3)C2)n1]

The titled compound 207 was prepared in a yield of 44% according to the procedure outlined for compound 1-03.

Mass (m/z) 487.1 [M+H]$^+$. $^1$H NMR (400 MHz, $CDCl_3$) δ 8.44 (d, J=2.2 Hz, 1H), 6.78-6.56 (m, 4H), 5.69 (brs, 2H), 5.43 (ddd, J=10.5, 6.6, 4.0 Hz, 1H), 5.21 (dd, J=12.1, 6.3 Hz, 1H), 4.62-4.46 (m, 2H), 4.27 (dd, J=28.6, 7.7 Hz, 2H), 3.98 (s, 3H), 3.30 (ddd, J=18.6, 12.2, 1.5 Hz, 1H), 2.65 (ddd, J=18.7, 6.3, 1.6 Hz, 1H), 2.09 (s, 3H).

(S)-(5-(3,5-difluorophenyl)-4,5-dihydro-1H-pyrazol-1-yl)(3-((5-(1,4-dimethyl-1H-pyrazol-5-yl)-2-fluoropyridin-3-yl)oxy)azetidin-1-yl)methanone (208)

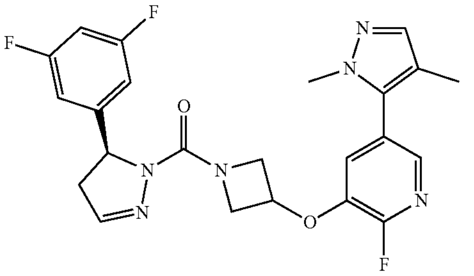 [SMILES: Cc1cnn(C)c1-c1cnc(F)c(OC2CN(C(=O)N3N=CC[C@H]3c3cc(F)cc(F)c3)C2)c1]

The titled compound 208 was prepared in 26.1% yield according to the procedure outlined for compound 197. $^1$H NMR (301 MHz, Chloroform-d) δ 7.77 (s, 1H), 7.44 (s, 1H), 6.97 (d, J=9.3 Hz, 1H), 6.85-6.61 (m, 4H), 5.27 (dd, J=12.1, 6.4 Hz, 1H), 5.01 (s, 1H), 4.57 (d, J=10.5 Hz, 2H), 4.32 (dt, J=21.5, 6.6 Hz, 2H), 3.80 (s, 3H), 3.37 (ddd, J=18.6, 12.1, 1.6 Hz, 1H), 2.71 (ddd, J=18.7, 6.5, 1.7 Hz, 1H), 2.02 (s, 3H). Mass (m/z) 471.3 [M+H]$^+$.

(S)-(3-((2-(4-amino-1,3-dimethyl-1H-pyrazol-5-yl)-5-fluoropyridin-4-yl)oxy)azetidin-1-yl)(5-(3,5-difluorophenyl)-4,5-dihydro-1H-pyrazol-1-yl)methanone (209)

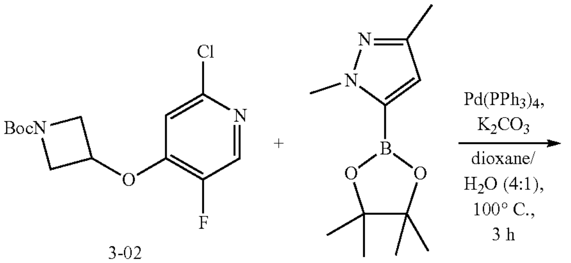

3-02

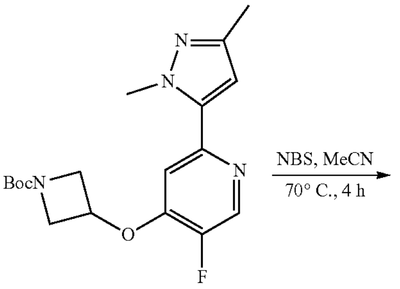

209-01

-continued

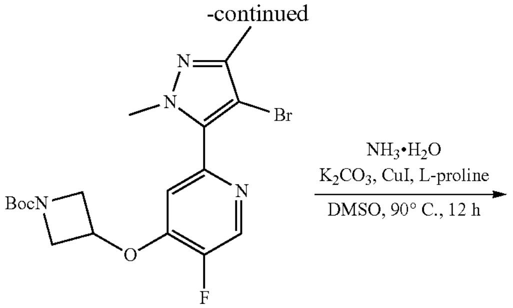

209-02

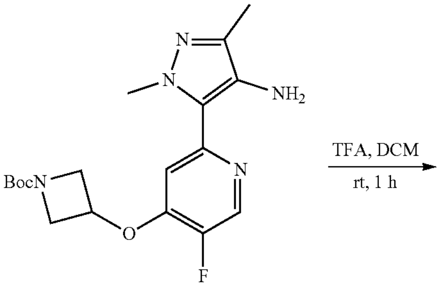

209-03

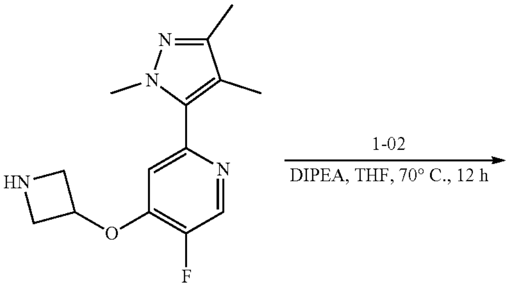

209-04

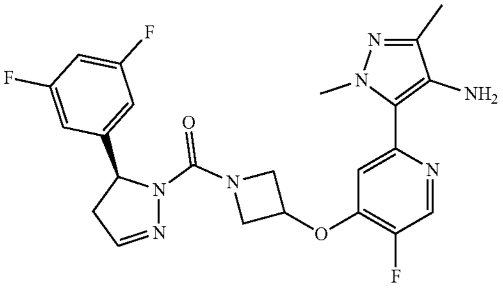

209

Step 1: To a solution of compound 3-02 (1 g, 3.3 mmol) in dioxane/$H_2O$ (4:1, 50 mL) was added 1,3-dimethyl-5-(4,4,5,5-tetramethyl-1,3,2-dioxaborolan-2-yl)-1H-pyrazole (807 mg, 3.63 mmol), $Pd(PPh_3)_4$ (573 mg, 495.5 umol) and $K_2CO_3$ (1.37 g, 9.91 mmol) under Ar. The reaction mixture was stirred at 100° C. for 3 h. The crude mixture was purified by column chromatography on silica gel to give compound 209-01 (0.9 g, 75%) as a white solid. Mass (m/z) 363.3 [M+H]$^+$.

Step 2: To a solution of compound 209-01 (900 mg, 2.48 mmol) in MeCN (50 mL) was added NBS (884 mg, 4.97 mmol). The reaction mixture was stirred at 70° C. for 4 h. The crude mixture was purified by column chromatography on silica gel to give compound 209-02 (1 g, 91%) as a white solid. Mass (m/z) 442.2 [M+H]$^+$.

Step 3: To a solution of compound 209-02 (1 g, 2.27 mmol) in DMSO (20 mL) was added $NH_3 \cdot H_2O$ (950 mg, 6.8 mmol), $K_2CO_3$ (375 mg, 2.72 mmol), CuI (648 mg, 3.4 mmol) and L-proline (392 mg, 3.4 mmol) under Ar. The reaction mixture was stirred at 90° C. for 12 h. The crude mixture was purified by column chromatography on silica gel to give compound 209-03 (180 mg, 21%) as a light-yellow solid. Mass (m/z) 378.1 $[M+H]^+$.

Step 4: To a solution of compound (120 mg, 317.95 umol) in DCM (2 mL) was added TFA (2 mL). The reaction mixture was stirred at rt for 1 h. The solvent was concentrated under vacuum. The crude compound 209-04 was used to next step directly MS (m/z) 278.1 $[M+H]^+$.

Step 5: To a solution of compound 209-04 (40 mg, 144.8 umol) in THE (5 mL) was added compound 1-02 (44 mg, 159.3 umol) and DIPEA (95 mg, 724 umol). The reaction mixture was stirred at 70° C. for 12 h. The crude mixture was purified by Pre-HPLC to give compound 209 (14 mg, 21%) as a white solid. Mass (m/z) 485.1 $[M+H]^+$.

(S)-(3-((2-(5-amino-1,3-dimethyl-11H-pyrazol-4-yl)-5-fluoropyridin-4-yl)oxy)azetidin-1-yl)(5-(3,5-difluorophenyl)-4,5-dihydro-1H-pyrazol-1-yl)methanone (210)

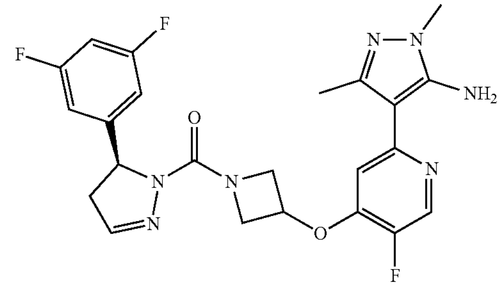 [SMILES: Cc1nn(C)c(N)c1-c1cc(OC2CN(C(=O)N3N=CC[C@H]3c3cc(F)cc(F)c3)C2)c(F)cn1]

The titled compound 210 was prepared as white solid in 41.4% yield from compound 3-04 according to the procedure outlined for compound 3. Mass (m/z) 486.4 $[M+H]^+$. $^1H$ NMR (400 MHz, $CDCl_3$) δ 8.31 (d, J=2.8 Hz, 1H), 6.80 (t, J=1.6 Hz, 1H), 6.79-6.64 (m, 4H), 5.27 (dd, J=12.0, 6.4 Hz, 11H), 5.11-5.01 (m, 11H), 4.65-4.51 (m, 2H), 4.42-4.33 (m, 11H), 4.30-4.23 (m, 1H), 3.80 (s, 3H), 3.36 (ddd, J=18.4, 12.0, 1.6 Hz, 1H), 2.71 (ddd, J=18.4, 6.4, 1.6 Hz, 1H), 2.54 (s, 3H).

(S)-(3-((2-(3-(aminomethyl)-1,4-dimethyl-11H-pyrazol-5-yl)-5-fluoropyridin-4-yl)oxy)azetidin-1-yl)(5-(3,5-difluorophenyl)-4,5-dihydro-1H-pyrazol-1-yl) methanone (211)

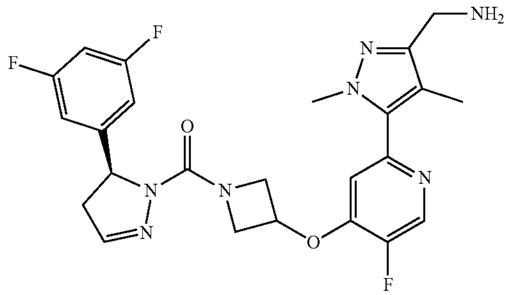 [SMILES: Cc1c(CN)nn(C)c1-c1cc(OC2CN(C(=O)N3N=CC[C@H]3c3cc(F)cc(F)c3)C2)c(F)cn1]

The title compound 211 was prepared in a yield of 16% (13 mg, 0.03 mmol) as a white solid according to the procedure for compound 30. Mass (m/z) 500.3 $[M+H]^+$. $^1H$ NMR (400 MHz, Chloroform-d) δ 8.48 (d, J=2.9 Hz, 1H), 6.81-6.78 (m, 1H), 6.78-6.65 (m, 4H), 5.26 (dd, J=12.2, 6.4 Hz, 1H), 5.10-5.02 (m, 1H), 4.67-4.50 (m, 2H), 4.42-4.22 (m, 2H), 3.99-3.77 (m, 5H), 3.36 (ddd, J=18.6, 12.2, 1.7 Hz, 1H), 2.71 (ddd, J=18.7, 6.4, 1.7 Hz, 1H), 2.19-2.10 (m, 2H), 2.08 (s, 3H).

(S)-(5-(3,5-difluorophenyl)-4,5-dihydro-1H-pyrazol-1-yl)(3-((5-fluoro-2-(3-((2-hydroxyethyl)amino)-1,4-dimethyl-1H-pyrazol-5-yl)pyridin-4-yl)oxy)azetidin-1-yl)methanone (212)

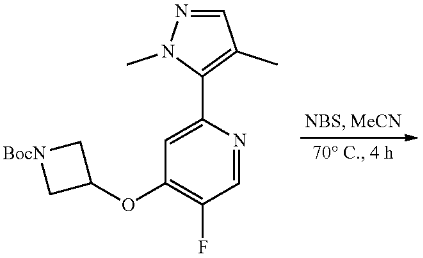

101-01

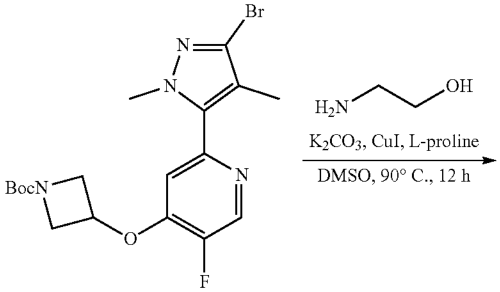

212-01

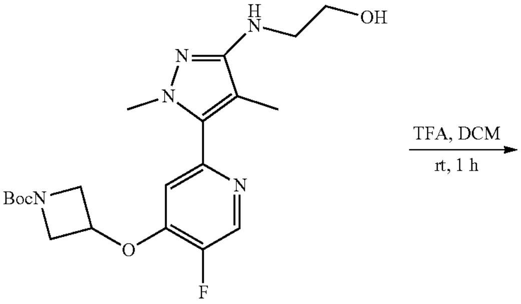

212-02

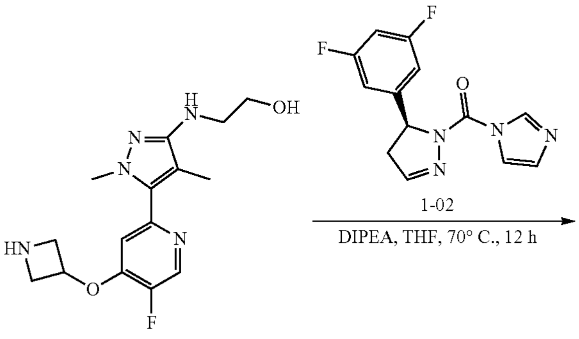

212-03

-continued

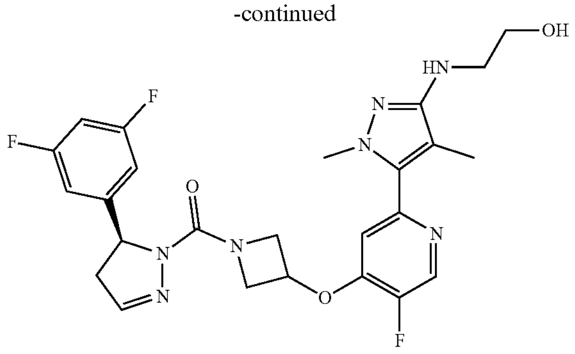

212

Step 1: To a solution of compound 101-01 (5 g, 13.8 mmol) in MeCN (50 mL) was added NBS (2.7 g, 15.2 mmol). The reaction mixture was stirred at 70° C. for 12 h. The crude mixture was purified by column chromatography on silica gel to give compound to give compound 212-01 (5.2 g, yield 85%) as a white solid. Mass (m/z) 441.1 $[M+H]^+$.

Step 2: To a solution of compound 212-01 (400 mg, 906.4 umol) in DMSO (10 mL) was added 2-aminoethan-1-ol (85 mg, 1.36 mmol), $K_2CO_3$ (375 mg, 2.72 mmol), CuI (180 mg, 906.4 umol) and L-proline (110 mg, 906.4 umol) under Ar. The reaction mixture was stirred at 90° C. for 12 h. The crude mixture was purified by column chromatography on silica gel to give compound 212-02 (100 mg, 26%) as a white solid. Mass (m/z) 422.1 $[M+H]^+$.

Step 3: To a solution of compound 212-02 (100 mg, 237.3 umol) in DCM (3 mL) was added TFA (3 mL). The reaction mixture was stirred at rt for 1 h. The solvent was concentrated under vacuum. The crude compound 212-03 was used to next step directly MS (m/z) 322.1 $[M+H]^+$.

Step 4: To a solution of compound 212-03 (70 mg, 253.4 umol) in THE (7 mL) was added compound 1-02 (82 mg, 253.4 umol) and DIPEA (165 mg, 1.27 mmol). The reaction mixture was stirred at 70° C. for 12 h. The crude mixture was purified by Pre-HPLC to give compound 212 (33 mg, 24%) as a white solid. MS (m/z) 530.1 $[M+H]^+$. $^1H$ NMR (400 MHz, DMSO-$d_6$) δ 8.66 (d, J=3.0 Hz, 1H), 7.17-7.06 (m, 2H), 7.03 (d, J=1.7 Hz, 1H), 6.96-6.85 (m, 2H), 5.33-5.19 (m, 2H), 4.61 (d, J=36.7 Hz, 4H), 3.71 (s, 3H), 3.61 (t, J=5.8 Hz, 2H), 3.40 (ddd, J=18.7, 12.2, 1.7 Hz, 1H), 3.27 (t, J=5.8 Hz, 2H), 2.66 (ddd, J=18.7, 6.6, 1.8 Hz, 1H), 1.94 (s, 3H).

(S)-(5-(3,5-difluorophenyl)-4,5-dihydro-1H-pyrazol-1-yl)(3-((5-fluoro-2-(3-(3-hydroxyazetidin-1-yl)-1,4-dimethyl-1H-pyrazol-5-yl)pyridin-4-yl)oxy)azetidin-1-yl)methanone (213)

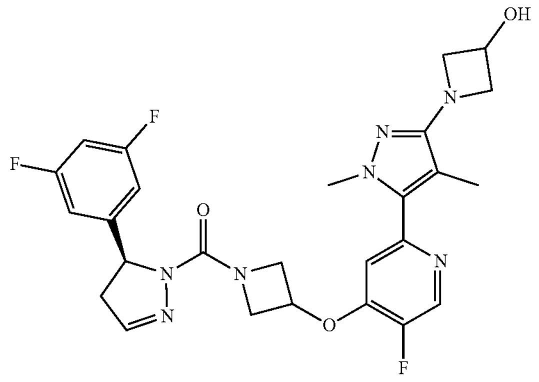 [SMILES: Cc1c(N2CC(O)C2)nn(C)c1-c1cc(OC2CN(C(=O)N3N=CC[C@H]3c3cc(F)cc(F)c3)C2)c(F)cn1]

The titled compound 213 was prepared from compound 212-01 in a yield of 27.0% according to the procedure outlined for compound 212. MS (m/z) 542.1 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-N-(2-hydroxyethyl)-3,5-dimethyl-1H-pyrazole-4-carboxamide (214)

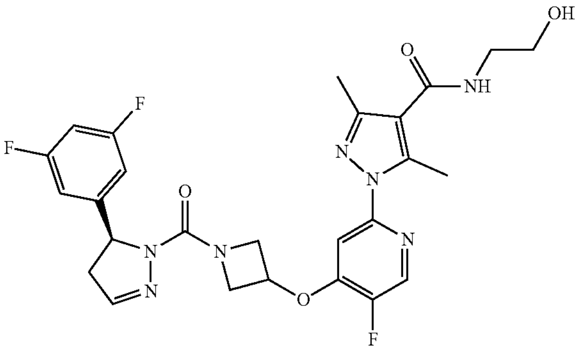 [SMILES: Cc1nn(-c2cc(OC3CN(C(=O)N4N=CC[C@H]4c4cc(F)cc(F)c4)C3)c(F)cn2)c(C)c1C(=O)NCCO]

The titled compound 214 was prepared from compound 110-02 in a yield of 7.5% according to the procedure outlined for compound 68. $^1H$ NMR (400 MHz, DMSO-$d_6$) δ 8.53 (d, J=2.7 Hz, 1H), 7.85 (t, J=5.7 Hz, 1H), 7.32 (d, J=6.3 Hz, 1H), 7.20 (tt, J=9.4, 2.4 Hz, 1H), 7.13-7.09 (m, 1H), 7.05-6.98 (m, 2H), 5.45-5.38 (m, 1H), 5.33 (dd, J=12.2, 6.6 Hz, 1H), 4.80 (t, J=5.4 Hz, 1H), 4.61 (s, 2H), 4.17 (s, 2H), 3.58 (q, J=6.0 Hz, 2H), 3.53-3.44 (m, 1H), 3.40-3.35 (m, 2H), 2.78-2.69 (m, 1H), 2.67 (s, 3H), 2.39 (s, 3H). Mass (m/z) 558.4 $[M+H]^+$.

(S)-(3-((6-(3-amino-1,4-dimethyl-1H-pyrazol-5-yl)-3-fluoropyridin-2-yl)oxy)azetidin-1-yl)(5-(3,5-difluorophenyl)-4,5-dihydro-1H-pyrazol-1-yl)methanone (215)

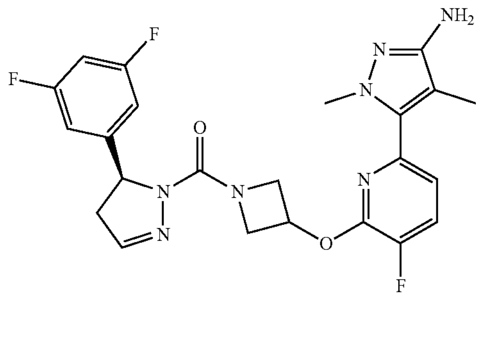 [SMILES: Cc1c(N)nn(C)c1-c1ccc(F)c(OC2CN(C(=O)N3N=CC[C@H]3c3cc(F)cc(F)c3)C2)n1]

The title compound 215 was prepared in a yield of 47% (43 mg, 0.09 mmol) as a white solid according to the procedure for 207. Mass (m/z) 486.3 $[M+H]^+$. $^1H$ NMR (400 MHz, Chloroform-d) δ 7.55-7.48 (m, 1H), 7.07-7.01 (m, 1H), 6.81-6.73 (m, 3H), 6.72-6.65 (m, 1H), 5.43-5.34 (m, 1H), 5.27 (dd, J=12.1, 6.5 Hz, 1H), 4.67-4.49 (m, 2H), 4.39-4.22 (m, 2H), 3.84 (s, 3H), 3.40-3.28 (m, 1H), 2.74-2.64 (m, 1H), 2.49-2.14 (m, 2H), 1.97 (s, 3H).

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-N-(tetrahydro-2H-pyran-4-yl)-1H-pyrazole-4-carboxamide (216)

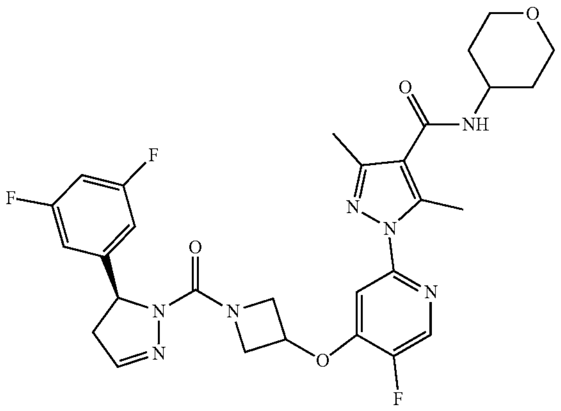 [SMILES: Cc1nn(-c2cc(OC3CN(C(=O)N4N=CC[C@H]4c4cc(F)cc(F)c4)C3)c(F)cn2)c(C)c1C(=O)NC1CCOCC1]

The titled compound 216 was prepared in 7.5% yield according to the procedure outlined for compound 214. $^1H$ NMR (400 MHz, Chloroform-d) δ 8.20 (d, J=2.4 Hz, 1H), 7.16 (d, J=6.1 Hz, 1H), 6.82-6.79 (m, 1H), 6.75 (dt, J=6.6, 2.1 Hz, 2H), 6.70 (tt, J=8.9, 2.3 Hz, 1H), 5.50 (d, J=7.9 Hz, 1H), 5.28 (dd, J=12.2, 6.4 Hz, 1H), 5.15 (td, J=6.4, 3.3 Hz, 1H), 4.72-4.56 (m, 2H), 4.32 (dd, J=32.7, 9.4 Hz, 2H), 4.20 (dp, J=11.5, 4.2, 3.7 Hz, 1H), 4.00 (ddd, J=11.4, 5.4, 2.9 Hz, 2H), 3.54 (td, J=11.7, 2.2 Hz, 2H), 3.36 (ddd, J=18.6, 12.2, 1.7 Hz, 1H), 2.71 (ddd, J=18.6, 6.5, 1.7 Hz, 1H), 2.03 (d, J=13.0 Hz, 2H), 1.59-1.48 (m, 2H). Mass (m/z) 598.4 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-N-(oxetan-3-yl)-1H-pyrazole-4-carboxamide (217)

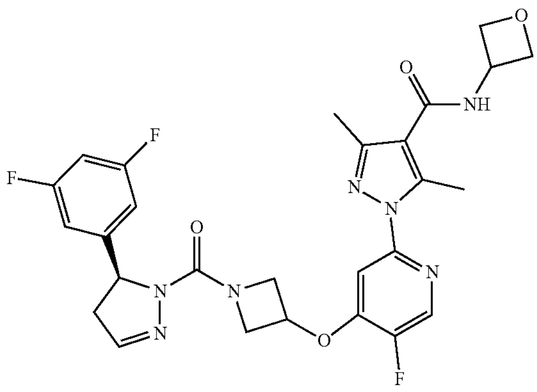 [SMILES: Cc1nn(-c2cc(OC3CN(C(=O)N4N=CC[C@H]4c4cc(F)cc(F)c4)C3)c(F)cn2)c(C)c1C(=O)NC1COC1]

The titled compound 217 was prepared in 7.5% yield according to the procedure outlined for compound 214. $^1H$ NMR (301 MHz, Chloroform-d) δ 8.20 (d, J=2.5 Hz, 1H), 7.16 (d, J=6.1 Hz, 1H), 6.85-6.62 (m, 4H), 6.09 (d, J=7.4 Hz, 1H), 5.30-5.12 (m, 2H), 5.03 (t, J=7.0 Hz, 2H), 4.61 (dt, J=13.0, 7.7 Hz, 4H), 4.45-4.21 (m, 3H), 3.36 (ddd, J=18.6, 12.2, 1.7 Hz, 1H), 2.78 (s, 3H), 2.71 (ddd, J=18.6, 6.4, 1.7 Hz, 1H), 2.47 (s, 3H). Mass (m/z) 570.4 $[M+H]^+$.

(S)-(3-((2-(5-amino-1,4-dimethyl-1H-pyrazol-3-yl)-5-fluoropyridin-4-yl)oxy)azetidin-1-yl)(5-(3,5-difluorophenyl)-4,5-dihydro-1H-pyrazol-1-yl)methanone (218)

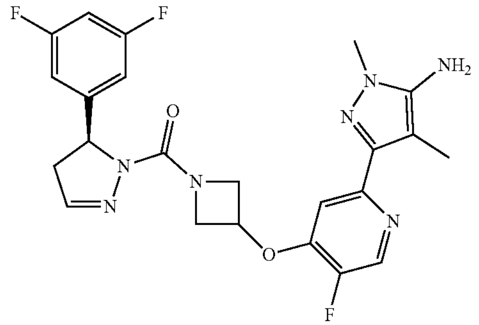 [SMILES: Cc1c(-c2cc(OC3CN(C(=O)N4N=CC[C@H]4c4cc(F)cc(F)c4)C3)c(F)cn2)nn(C)c1N]

The titled compound 218 was prepared in a 9% yield according to the procedure outlined for compound 209. Mass (m/z) 486.1 $[M+H]^+$.

(S)-(5-(3,5-difluorophenyl)-4,5-dihydro-1H-pyrazol-1-yl)(3-((2-(1,4-dimethyl-1H-pyrazol-3-yl)-5-fluoro-pyridin-4-yl)oxy)azetidin-1-yl)methanone (219)

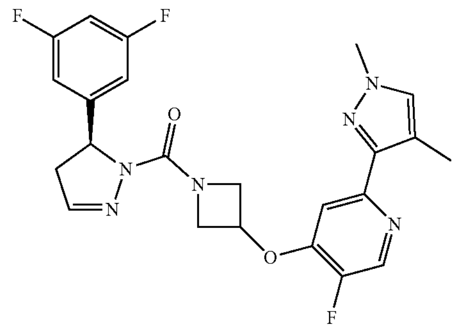 [SMILES: Cc1cn(C)nc1-c1cc(OC2CN(C(=O)N3N=CC[C@H]3c3cc(F)cc(F)c3)C2)c(F)cn1]

The titled compound 219 was prepared in a 37% yield from compound 3-02 according to the procedure outlined for compound 101-01. Mass (m/z) 471.1 [M+H]+.

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-sulfonamide (220)

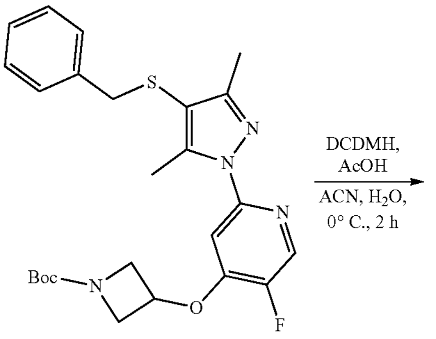

227-01

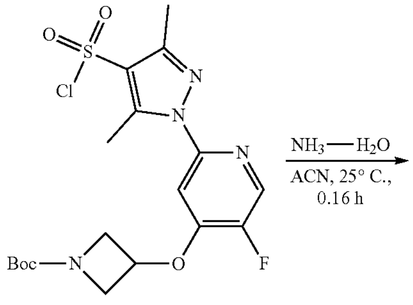

220-01

-continued

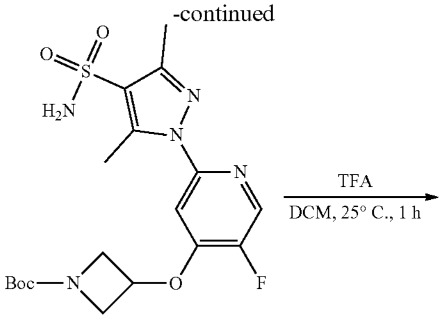

220-02

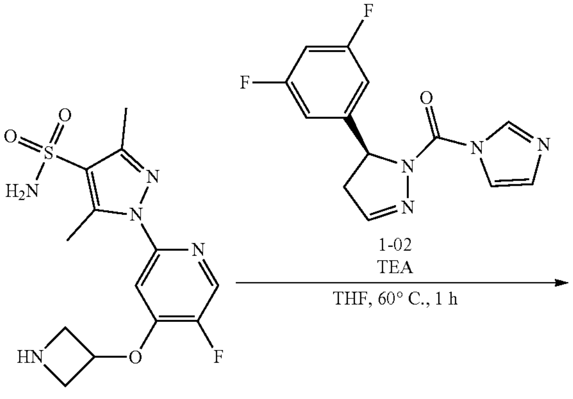

220-03

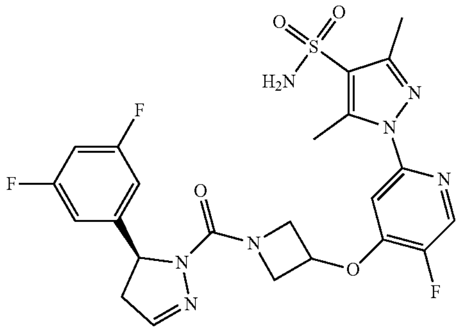

220

Step 1: 227-01 (300 mg, 0.62 mmol), DCDMH (300 mg, 1.52 mmol), AcOH (1.4 mL), $H_2O$ (0.6 mL) were in CAN (20 mL) under $N_2$ and the whole reaction mixture was stirred at 0° C. for 2 hours. The mixture was concentrated in vacuo to give 220-01 (500 mg, crude) as a brown oil and used into next step reaction without purification. Mass (m/z) 461.4 [M+H]+.

Step 2: 220-01 (500 mg, crude) and $NH_3$—$H_2O$ (3 mL, 30 w %) were in ACN (5 mL) under $N_2$ and the whole reaction mixture was stirred at 25° C. for 0.16 hours. The mixture was extracted with EA, washed with brine, dried ($Na_2SO_4$), and concentrated in vacuo. Purification by silica gel chromatography to give 220-02 (150 mg, crude) as a yellow oil. Mass (m/z) 442.4 [M+H]+.

Step 3: 220-02 (150 mg, crude) and TFA (3 mL) were in DCM (5 mL) under $N_2$ and the whole reaction mixture was stirred at 25° C. for 1 hour. The mixture was extracted with EA, washed with brine, dried ($Na_2SO_4$), and concentrated in vacuo to give 220-03 (200 mg, crude) as a brown oil and used into next step reaction without purification. Mass (m/z) 342.4 [M+H]+.

Step 4: 220-03 (200 mg, crude), TEA (3 mL), 1-02 (50 mg, 0.18 mmol) were in THE (20 mL) under $N_2$ and the whole reaction mixture was stirred at 60° C. for 1 hour. The mixture was extracted with EA, washed with brine, dried ($Na_2SO_4$), and concentrated in vacuo. Purification by silica gel chromatography gave 220 (12.3 mg, 13.5%) as a light yellow solid. Mass (m/z) 550.4 $[M+H]^+$. $^1$H NMR (400 MHz, DMSO-$d_6$) δ 8.49 (d, J=2.4 Hz, 1H), 7.32 (s, 2H), 7.26 (d, J=6.4 Hz, 1H), 7.12 (tt, J=9.2, 2.4 Hz, 1H), 7.06-7.00 (m, 1H), 6.98-6.88 (m, 2H), 5.32 (tt, J=6.8, 3.6 Hz, 1H), 5.24 (dd, J=12.0, 6.4 Hz, 1H), 4.59-4.47 (m, 2H), 4.15-4.00 (m, 2H), 3.46-3.36 (m, 1H), 2.67 (dd, J=6.4, 1.8 Hz, 1H), 2.63 (s, 3H), 2.38 (s, 3H).

(S)-(5-(3,5-difluorophenyl)-4,5-dihydro-1H-pyrazol-1-yl)(3-((2-(3,5-dimethyl-1H-pyrazol-1-yl)-5-fluoropyridin-4-yl)oxy)azetidin-1-yl)methanone (221)

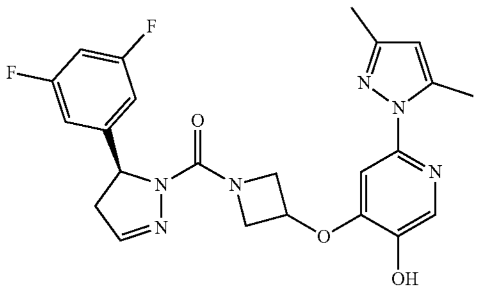 [SMILES: Cc1cc(C)n(-c2cc(OC3CN(C(=O)N4N=CC[C@H]4c4cc(F)cc(F)c4)C3)c(O)cn2)n1]

The titled compound 221 was prepared in 15.2% yield according to the procedure outlined for compound 110. $^1$H NMR (400 MHz, Chloroform-d) δ 8.15 (d, J=2.5 Hz, 1H), 7.22 (d, J=6.2 Hz, 1H), 6.85-6.63 (m, 4H), 5.98 (s, 1H), 5.28 (dd, J=12.2, 6.4 Hz, 1H), 5.20-5.13 (m, 1H), 4.71-4.56 (m, 2H), 4.41-4.24 (m, 2H), 3.36 (ddd, J=18.6, 12.1, 1.7 Hz, 1H), 2.70 (ddd, J=18.7, 6.5, 1.8 Hz, 1H), 2.59 (s, 3H), 2.28 (s, 3H). Mass (m/z) 471.3 $[M+H]^+$.

(S)-1-(azetidin-1-yl)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)ethan-1-one (222)

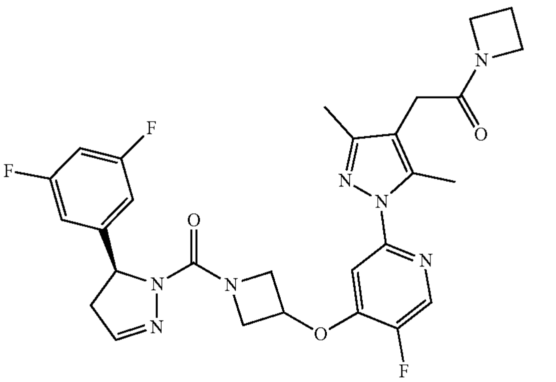 [SMILES: Cc1nn(-c2cc(OC3CN(C(=O)N4N=CC[C@H]4c4cc(F)cc(F)c4)C3)c(F)cn2)c(C)c1CC(=O)N1CCC1]

The titled compound 222 was prepared in 41.2% yield according to the procedure outlined for compound 68. $^1$H NMR (400 MHz, Chloroform-d) δ 8.16 (d, J=2.5 Hz, 1H), 7.19 (d, J=6.1 Hz, 1H), 6.82-6.66 (m, 4H), 5.28 (dd, J=12.2, 6.4 Hz, 1H), 5.20-5.10 (m, 1H), 4.72-4.57 (d, J=9.9 Hz, 2H), 4.31 (dd, J=26.8, 9.9 Hz, 2H), 4.16 (t, J=7.6 Hz, 2H), 4.06 (t, J=7.8 Hz, 2H), 3.36 (ddd, J=18.6, 12.2, 1.7 Hz, 1H), 3.24 (s, 2H), 2.70 (ddd, J=18.6, 6.4, 1.7 Hz, 1H), 2.54 (s, 3H), 2.34-2.23 (m, 5H). Mass (m/z) 568.4 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)-N-(2-hydroxyethyl)acetamide (223)

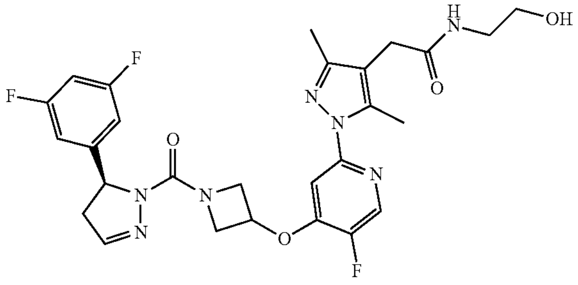 [SMILES: Cc1nn(-c2cc(OC3CN(C(=O)N4N=CC[C@H]4c4cc(F)cc(F)c4)C3)c(F)cn2)c(C)c1CC(=O)NCCO]

The titled compound 223 was prepared in 38.5% yield according to the procedure outlined for compound 68. $^1$H NMR (400 MHz, Chloroform-d) δ 8.16 (d, J=2.3 Hz, 1H), 7.21 (d, J=6.1 Hz, 1H), 6.84-6.64 (m, 4H), 6.00 (s, 1H), 5.27 (dd, J=12.2, 6.4 Hz, 1H), 5.19-5.11 (m, 1H), 4.671-4.56 (m, 2H), 4.32 (dd, J=31.4, 10.4 Hz, 2H), 3.68 (dd, J=5.5, 4.3 Hz, 2H), 3.46-3.31 (m, 5H), 2.70 (ddd, J=18.6, 6.5, 1.7 Hz, 1H), 2.55 (s, 3H), 2.24 (s, 3H). Mass (m/z) 572.4 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)-1-morpholinoethan-1-one (224)

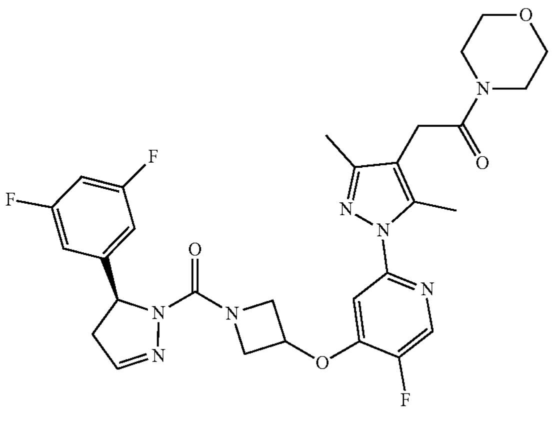 [SMILES: Cc1nn(-c2cc(OC3CN(C(=O)N4N=CC[C@H]4c4cc(F)cc(F)c4)C3)c(F)cn2)c(C)c1CC(=O)N1CCOCC1]

The titled compound 224 was prepared in 42.8% yield according to the procedure outlined for compound 68. $^1$H NMR (400 MHz, Chloroform-d) δ 8.15 (d, J=2.5 Hz, 1H), 7.21 (d, J=6.2 Hz, 1H), 6.82-6.65 (m, 4H), 5.28 (dd, J=12.2, 6.4 Hz, 11H), 5.16 (td, J=6.4, 3.2 Hz, 1H), 4.70-4.57 (m, 2H), 4.31 (dd, J=28.1, 10.3 Hz, 2H), 3.72-3.61 (m, 6H), 3.53 (t, J=4.8 Hz, 2H), 3.45 (s, 2H), 3.36 (ddd, J=18.6, 12.2, 1.7 Hz, 1H), 2.70 (ddd, J=18.6, 6.5, 1.7 Hz, 1H), 2.53 (s, 3H), 2.24 (s, 3H). Mass (m/z) 598.4 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoro-pyridin-2-yl)-3,5-dimethyl-1H-pyrazol-4-yl)acetamide (225)

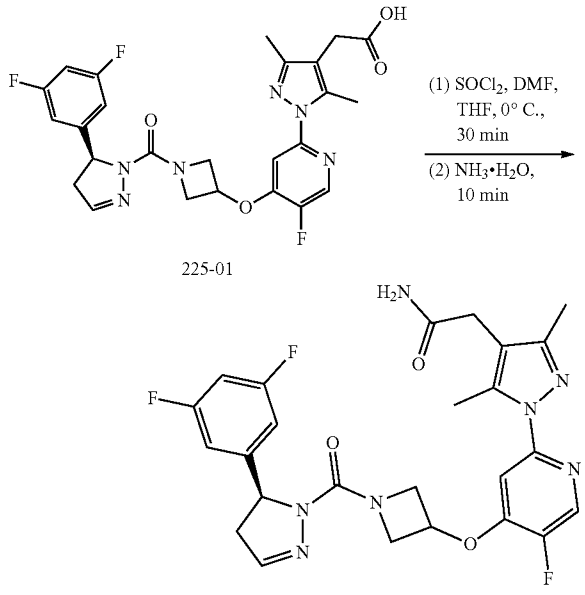

225-01

225

Step 1: 225-01 (100 mg, 0.29 mmol) were dissolved in THE (1 mL) and DMF (1 drop), $SOCl_2$ (0.05 ml) was added to the above solution at 0° C., the mixture was stirred for 30 min, then the mixture was drop into $NH_3$—$H_2O$ (2 mL), the mixture was stirred for 10 min, quenched by ice-water. Concentrated and purification by prep-HPLC to give the titled compound 225 (41 mg, 41.2%) as a white solid. $^1H$ NMR (400 MHz, Chloroform-d) δ 8.17 (d, J=2.4 Hz, 1H), 7.22 (d, J=6.2 Hz, 1H), 6.81-6.67 (m, 4H), 5.54 (s, 1H), 5.36 (s, 1H), 5.28 (dd, J=12.2, 6.4 Hz, 1H), 5.16 (td, J=6.5, 3.3 Hz, 1H), 4.70-4.56 (m, 2H), 4.32 (dd, J=31.0, 10.3 Hz, 2H), 3.42-3.28 (m, 3H), 2.71 (ddd, J=18.6, 6.5, 1.8 Hz, 1H), 2.57 (s, 3H), 2.27 (s, 3H). Mass (m/z) 528.3 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoro-pyridin-2-yl)-3,5-dimethyl-1H-pyrazol-4-yl)-N-methylacetamide (226)

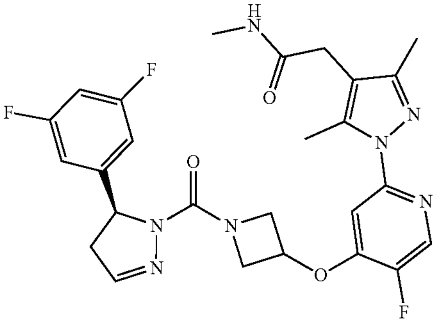 [SMILES: CNC(=O)Cc1c(C)nn(-c2cc(OC3CN(C(=O)N4N=CC[C@H]4c4cc(F)cc(F)c4)C3)c(F)cn2)c1C]

The titled compound 226 was prepared in 21.4% yield according to the procedure outlined for compound 225. $^1H$ NMR (400 MHz, Chloroform-d) δ 8.17 (d, J=2.4 Hz, 1H), 7.22 (d, J=6.1 Hz, 1H), 6.81-6.79 (m, 1H), 6.75 (dt, J=6.4, 2.1 Hz, 2H), 6.70 (tt, J=8.8, 2.3 Hz, 1H), 5.56 (s, 1H), 5.28 (dd, J=12.2, 6.4 Hz, 1H), 5.21-5.12 (m, 1H), 4.70-4.57 (m, 2H), 4.32 (dd, J=30.7, 10.4 Hz, 2H), 3.44-3.32 (m, 3H), 2.79 (d, J=4.6 Hz, 3H), 2.71 (ddd, J=18.7, 6.4, 1.7 Hz, 1H), 2.54 (s, 3H), 2.24 (s, 3H). Mass (m/z) 542.3 $[M+H]^+$.

(S)-(3-((2-(4-(benzylthio)-3,5-dimethyl-1H-pyrazol-1-yl)-5-fluoropyridin-4-yl)oxy)azetidin-1-yl)(5-(3,5-difluorophenyl)-4,5-dihydro-1H-pyrazol-1-yl)methanone (227)

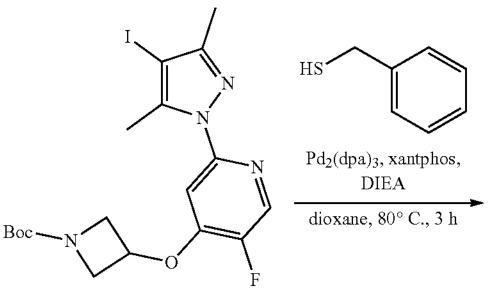

148-01

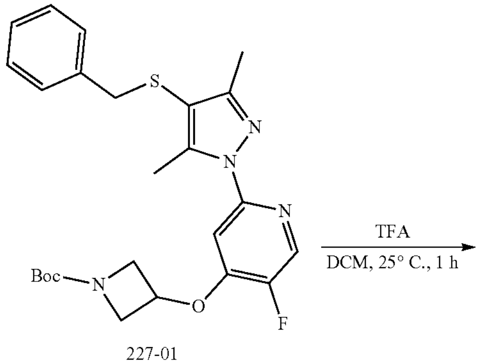

227-01

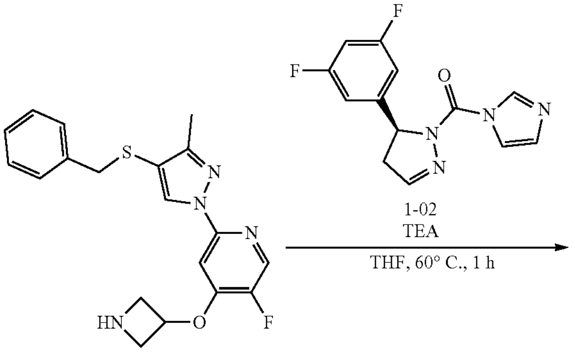

227-02

-continued

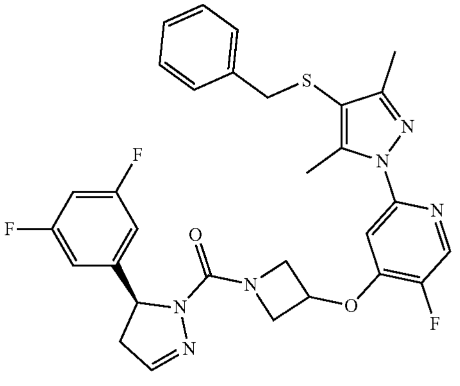

227

Step 1: Compound 148-01 (1.8 g, 3.68 mmol), phenylmethanethiol (680 mg, 5.48 mmol), $Pd_2(dba)_3$ (675 mg, 0.74 mmol), xantphos (852 mg, 1.47 mmol) and DIEA (951 mg, 7.37 mmol) were in dioxane (30 mL) under $N_2$ and the whole reaction mixture was stirred at 80° C. for 3 hours. The mixture was concentrated in vacuo. Purification by silica gel chromatography to give 227-01 (850 mg, 47.0%) as a brown oil. Mass (m/z) 485.6 $[M+H]^+$.

Step 2: 227-01 (80 mg, 0.16 mmol) and TFA (3 mL) were in DCM (5 mL) under $N_2$ and the whole reaction mixture was stirred at 25° C. for 2 hours. The mixture was extracted with EA, washed with brine, dried ($Na_2SO_4$), and concentrated in vacuo to give 227-02 (150 mg, crude) as a yellow oil and used into next step reaction without purification. Mass (m/z) 385.5 $[M+H]^+$.

Step 3: 227-02 (150 mg, crude), TEA (1 mL), 1-02 (45 mg, 0.16 mmol) were in THF (5 mL) under $N_2$ and the whole reaction mixture was stirred at 60° C. for 1 hour. The mixture was extracted with EA, washed with brine, dried ($Na_2SO_4$), and concentrated in vacuo. Purification by silica gel chromatography to give 227 (13.0 mg, 13.5%) as a white solid. Mass (m/z) 593.4 $[M+H]^+$. $^1H$ NMR (400 MHz, Chloroform-d) δ 8.14 (d, J=2.4 Hz, 1H), 7.24-7.18 (m, 4H), 7.06 (dt, J=6.4, 2.2 Hz, 2H), 6.81-6.73 (m, 3H), 6.70 (tt, J=8.8, 2.4 Hz, 1H), 5.28 (dd, J=12.0, 6.4 Hz, 1H), 5.15 (ddd, J=10.4, 6.4, 4.0 Hz, 1H), 4.68-4.55 (m, 2H), 4.39-4.22 (m, 2H), 3.67 (s, 2H), 3.36 (ddd, J=18.4, 12.0, 1.6 Hz, 1H), 2.70 (ddd, J=18.4, 6.4, 1.6 Hz, 1H), 2.37 (s, 3H), 2.09 (s, 3H).

(S)-(3-((2-(3-amino-5-methylisoxazol-4-yl)-5-fluoropyridin-4-yl)oxy)azetidin-1-yl)(5-(3,5-difluorophenyl)-4,5-dihydro-1H-pyrazol-1-yl)methanone (228)

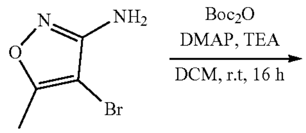

228-01

-continued

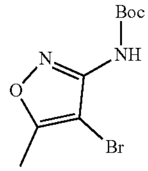

228-02

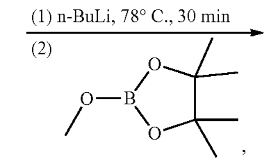

r.t, 2 h

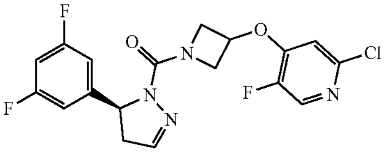

3-04

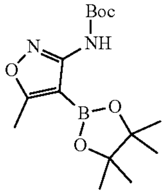

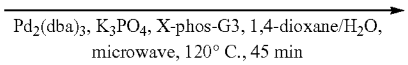

228-03

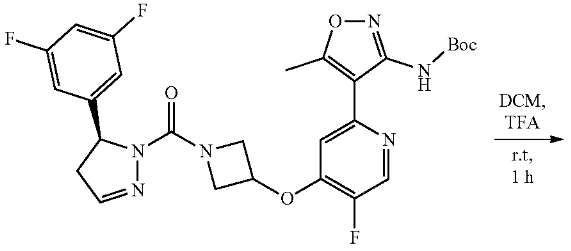

228-04

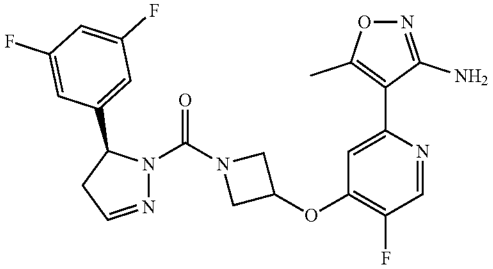

228

Step 1: Compound 228-01 (1.77 g, 10 mmol), $Boc_2O$ (2.616 g, 12 mmol), DMAP (0.122 g, 1 mmol) and TEA (0.4 ml) were dissolved in 20 mL DCM. Let it stir at room temperature for 16 h. The solvent was evaporated to dryness and purified by prep-TLC (PE/EA=6/1) to give compound 228-02 (1.2 g, 43.3%) as white solid. Mass (m/z) 278.3 $[M+H]^+$.

Step 2: Compound 228-02 (715 mg, 2.58 mmol) was dissolved in 15 mL of THF. n-BuLi (2.42 mL, 3.87 mmol) was added slowly at −78° C. Let it stir at −78° C. for 30 min. Then 2-methoxy-4,4,5,5-tetramethyl-1,3,2-dioxaborolane (960 mg, 5.16 mmol) was added. Let it stir at −78° C. for 1 h. Water was added to quench the reaction. The solvent was evaporated to dryness and used for next step without further purification.

Step 3: Compound 228-03 (250 mg, 0.61 mmol), tert-butyl (5-methyl-4-(4,4,5,5-tetramethyl-1,3,2-dioxaborolan-2-yl)isoxazol-3-yl)carbamate (750 mg, crude), X-Phos-$G_3$ (101.5 mg, 0.12 mmol), $Pd_2(dba)_3$ (109.8 mg, 0.12 mmol), $K_3PO_4$ (1.272 g, 6.1 mmol) were mixed in 12 mL 1,4- dioxane/$H_2O$ (v/v=4/1). The mixture was stirred at 120° C. for 45 min under microwave. The solvent was evaporated to dryness and purified by column chromatography (EA) to give compound 228-04 (80 mg, 22.9%) as brown oil. Mass (m/z) 573.4 $[M+H]^+$.

Step 4: Compound 228-04 (80 mg, 0.14 mmol) was dissolved in 3 mL of DCM. 2 mL of DCM/TFA (1/1) was added. Let it stir at r.t. for 1 h. The solvent was evaporated to dryness and purified by prep-HPLC to give compound 228 (40 mg, 60.6%) as white solid. Mass (m/z) 473.4 $[M+H]^+$. $^1H$ NMR (400 MHz, $CDCl_3$) δ 8.37 (s, 1H), 6.81 (t, J=1.2 Hz, 1H), 6.78-6.71 (m, 2H), 6.69 (m, 2H), 5.28 (dd, J=12.0, 6.4 Hz, 1H), 5.13-5.02 (m, 1H), 4.66-4.51 (m, 2H), 4.43-4.34 (m, 1H), 4.32-4.25 (m, 1H), 3.37 (ddd, J=18.4, 12.0, 1.6 Hz, 1H), 2.72 (ddd, J=18.4, 6.4, 1.6 Hz, 1H), 2.54 (s, 3H).

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-5-carboxamide (229)

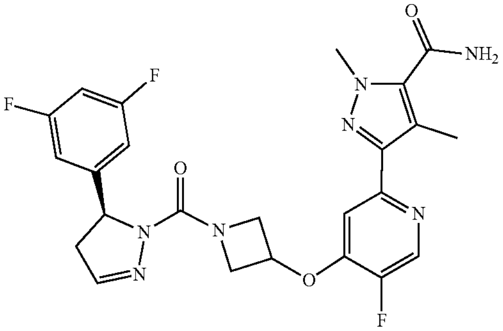 [SMILES: Cc1c(-c2cc(OC3CN(C(=O)N4N=CC[C@H]4c4cc(F)cc(F)c4)C3)c(F)cn2)nn(C)c1C(N)=O]

The titled compound 229 was prepared in 9% yield according to the procedure outlined for compound 66 as a white solid. MS (m/z) 514.1 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-N,3,5-trimethyl-1H-pyrazole-4-sulfonamide (230)

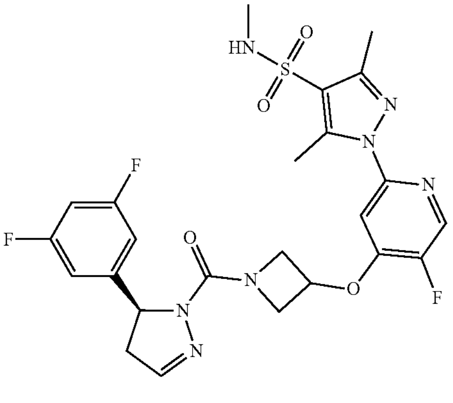 [SMILES: CNS(=O)(=O)c1c(C)nn(-c2cc(OC3CN(C(=O)N4N=CC[C@H]4c4cc(F)cc(F)c4)C3)c(F)cn2)c1C]

The titled compound 230 was prepared from 220-01 in a yield of 19.8% according to the procedure outlined for compound 220. Mass (m/z) 564.4 $[M+H]^+$. $^1H$ NMR (400 MHz, DMSO-$d_6$) δ 8.50 (d, J=2.4 Hz, 1H), 7.36 (q, J=5.2 Hz, 11H), 7.29 (d, J=6.4 Hz, 11H), 7.12 (tt, J=9.2, 2.4 Hz, 1H), 7.03 (t, J=1.6 Hz, 1H), 6.96-6.87 (m, 2H), 5.32 (dq, J=6.4, 3.6 Hz, 1H), 5.24 (dd, J=12.0, 6.4 Hz, 1H), 4.60-4.43 (m, 2H), 4.16-4.40 (m, 2H), 3.45-3.36 (m, 1H), 2.67 (dd, J=6.4, 1.6 Hz, 1H), 2.63 (s, 3H), 2.44 (d, J=5.2 Hz, 3H), 2.37 (s, 3H).

(S)-1-(4-((1-(5-(3,5-difluorophenyl)-4,5-dihydro-1H-pyrazole-1-carbonyl)azetidin-3-yl)oxy)-5-fluoropyridin-2-yl)-N-ethyl-3,5-dimethyl-1H-pyrazole-4-carboxamide (231)

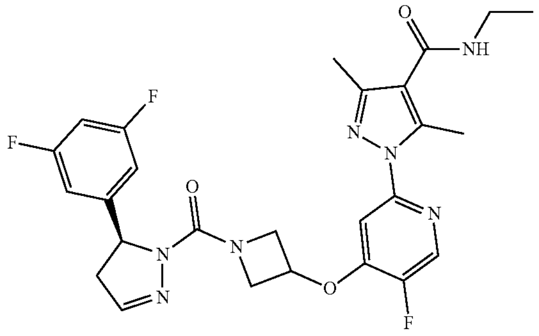 [SMILES: CCNC(=O)c1c(C)nn(-c2cc(OC3CN(C(=O)N4N=CC[C@H]4c4cc(F)cc(F)c4)C3)c(F)cn2)c1C]

The titled compound 231 was prepared in 32.4% yield according to the procedure outlined for compound 225. $^1H$ NMR (400 MHz, Chloroform-d) δ 8.20 (d, J=2.4 Hz, 1H), 7.34 (t, J=1.5 Hz, 1H), 7.29-7.24 (m, 1H), 7.20 (dt, J=9.2, 2.0 Hz, 1H), 7.16 (d, J=6.1 Hz, 1H), 6.83 (t, J=1.7 Hz, 1H), 5.56 (s, 1H), 5.31 (dd, J=12.2, 6.7 Hz, 1H), 5.15 (td, J=6.5, 3.4 Hz, 1H), 4.63 (s, 2H), 4.33 (d, J=29.5 Hz, 2H), 3.55-3.36 (m, 3H), 2.76 (s, 3H), 2.70 (ddd, J=18.6, 6.7, 1.7 Hz, 1H), 2.43 (s, 3H), 1.25 (t, J=7.3 Hz, 3H). Mass (m/z) 542.3 $[M+H]^+$.

(S)—N-cyclopropyl-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxamide (232)

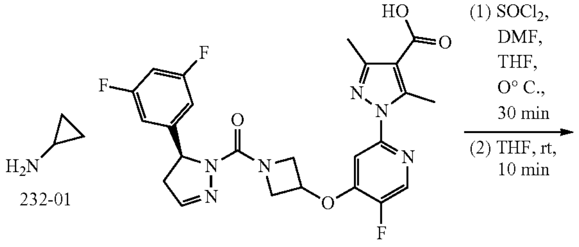

232-01

110-2

-continued
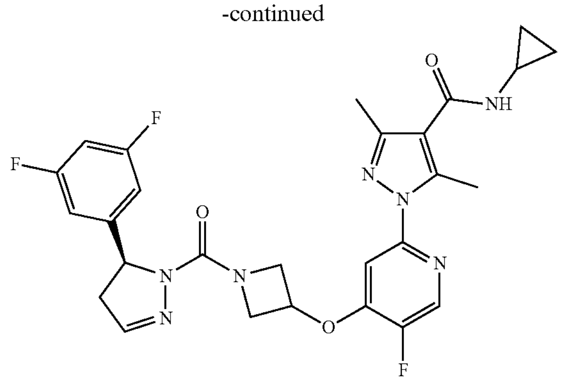
232
The titled compound 232 was prepared according to the procedure outlined for compound 225. $^1$H NMR (400 MHz, Chloroform-d) δ 8.20 (d, J=2.5 Hz, 11H), 7.34 (t, J=1.5 Hz, 11H), 7.3-7.23 (m, 11H), 7.2-7.19 (m, 11H), 7.15 (d, J=6.1 Hz, 11H), 6.86-6.78 (m, 11H), 5.73 (s, 11H), 5.31 (dd, J=12.2, 6.7 Hz, 1H), 5.15 (td, J=6.4, 3.3 Hz, 1H), 4.70-4.54 (m, 2H), 4.33 (d, J=31.4 Hz, 2H), 3.40 (ddd, J=18.7, 12.2, 1.7 Hz, 1H), 2.87 (dd, J=7.2, 3.9 Hz, 1H), 2.75 (s, 3H), 2.75-2.63 (m, 1H), 2.41 (s, 3H), 0.89 (q, J=6.3 Hz, 2H), 0.64-0.56 (m, 2H). Mass (m/z) 554.4 $[M+H]^+$.
(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxylic acid (233)
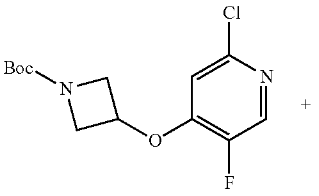
3-02
+
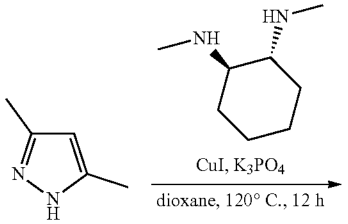
233-01
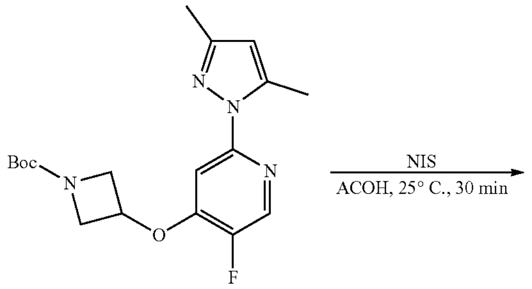
233-02
-continued
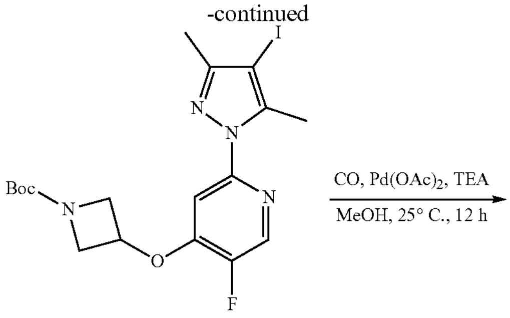
233-03
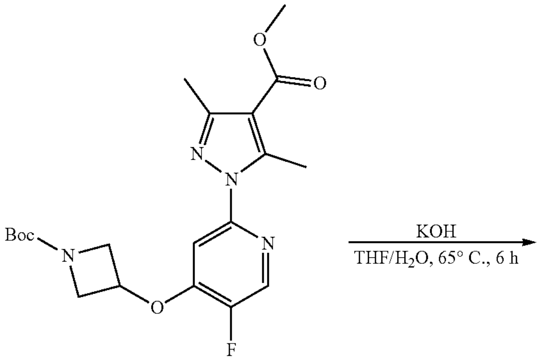
233-04
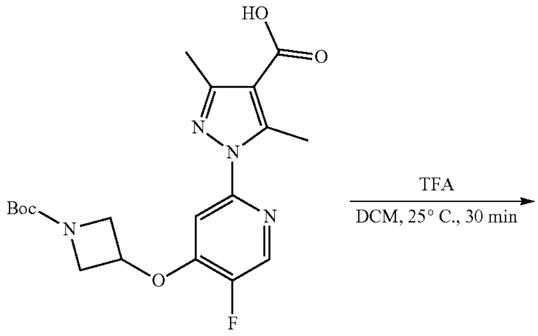
233-05
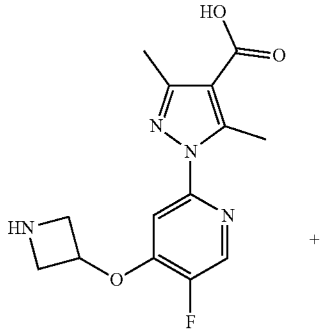
233-06
+
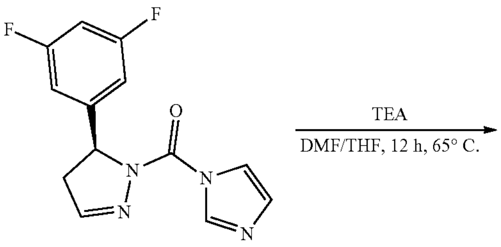
1-02

-continued

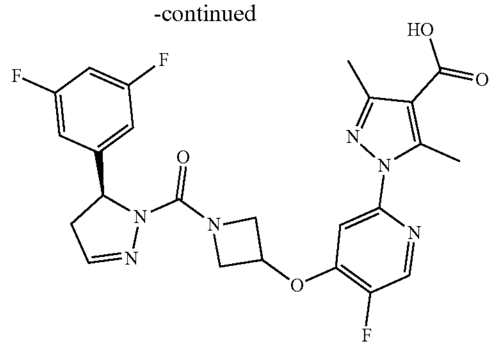

233

Step 1: 3-02 (8.5 g, 28.15 mmol) and 233-01 (2.76 g, 42.23 mmol) were dissolved in 200 ml of dry dioxane, CuI (10.7 g, 56.3 mmol), $K_3PO_4$ (12 g, 56.3 mmol), and (1R, 2R)—N1,N2-dimethylcyclohexane-1,2-diamine (7.9 g, 56.3 mmol) was added to the above solution, the mixture was stirred for 12 h at 120° C. Water was added and the reaction mixture was extracted with EA, washed with brine, dried ($Na_2SO_4$), and concentrated in vacuo. Purification of the concentrate by silica gel chromatography gave the compound 233-02 (6 g, 58.8%). Mass (m/z) 363.2 $[M+H]^+$.

Step 2: 233-02 (6 g, 16.57 mmol) was dissolved in 60 mL of acetic acid, NIS (3.7 g, 16.57 mmol) was added, and the mixture was stirred at r.t. for 30 min. Water was added and the reaction mixture was extracted with EA, washed with brine, dried ($Na_2SO_4$), and concentrated in vacuo. Purification of the concentrate by silica gel chromatography gave the compound 233-03 (3.85 g, 47.6%). Mass (m/z) 489.2 $[M+H]^+$.

Step 3: 233-03 (3.8 g, 7.89 mmol) and $Pd(OAc)_2$ (176 mg, 0.789 mmol) were dissolved in MeOH (150 mL), and the reaction mixture was stirred at 25° C. under CO (1 atm) for 12 h. The mixture was extracted with EA, washed with brine, dried ($Na_2SO_4$), and concentrated in vacuo to give the compound 233-04 (2.9 g, crude). Mass (m/z) 388.1 $[M+H]^+$.

Step 4: 233-04 (1.2 g, 3.9 mmol) was dissolved in EtOH (10 mL), KOH (5 mL, 2M) was added, and the reaction mixture was stirred at 65° C. for 12 h. Water was added and the reaction mixture was extracted with EA, washed with brine, dried ($Na_2SO_4$), and concentrated in vacuo. Purification of the concentrate by silica gel chromatography gave the compound 233-05 (800 mg, 69.6%).

Step 5: 233-05 (800 mg, 1.97 mmol) was dissolved in 10 mL of DCM, trifluoroacetic acid (1 mL) was added, and the mixture was stirred at r.t. for 30 min. The reaction mixture was concentrated to give the desired product 233-06, which was used for next step without further purification.

Step 6: 233-06 (crude), 1-02 (545 mg, 1.97 mmol) and TEA (1 mL) were dissolved in THE (30 mL) and DMF (5 mL) and stirred at 65° C. for 6 h. The mixture was extracted with EA, washed with brine, dried ($Na_2SO_4$), and concentrated in vacuo. Purification of the concentrate by silica gel chromatography gave the titled compound. $^1H$ NMR (400 MHz, Chloroform-d) δ 8.23 (d, J=2.4 Hz, 1H), 7.18 (d, J=6.1 Hz, 1H), 6.83-6.68 (m, 4H), 5.28 (dd, J=12.1, 6.5 Hz, 1H), 5.16 (s, 1H), 4.64 (s, 2H), 4.33 (dd, J=31.2, 10.5 Hz, 2H), 3.36 (dd, J=18.4, 12.0 Hz, 1H), 2.88 (s, 3H), 2.71 (dd, J=18.7, 6.9 Hz, 1H), 2.51 (s, 3H).

1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxamide (234)

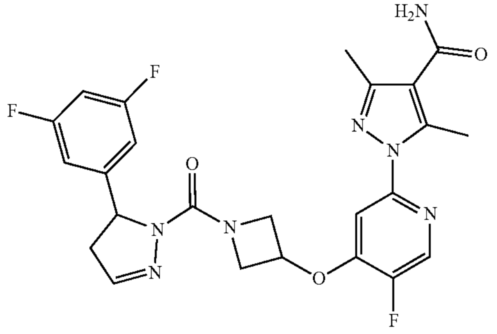 [SMILES: Cc1nn(-c2cc(OC3CN(C(=O)N4N=CCC4c4cc(F)cc(F)c4)C3)c(F)cn2)c(C)c1C(N)=O]

The titled compound 234 was prepared in a 63.2% yield according to the procedure outlined for compound 110. $^1H$ NMR (400 MHz, Chloroform-d) δ 8.23 (d, J=2.4 Hz, 1H), 7.18 (d, J=6.1 Hz, 1H), 6.81-6.79 (m, 1H), 6.77-6.74 (m, 2H), 6.70 (ddd, J=8.8, 6.5, 2.3 Hz, 1H), 5.28 (dd, J=12.2, 6.4 Hz, 1H), 5.19-5.13 (m, 1H), 4.70-4.56 (m, 2H), 4.39-4.29 (m, 2H), 3.36 (ddd, J=18.6, 12.2, 1.7 Hz, 2H), 2.88 (s, 3H), 2.71 (ddd, J=18.6, 6.4, 1.7 Hz, 2H), 2.51 (s, 3H). Mass (m/z) 514.3 $[M+H]^+$.

(S)—N-cyclobutyl-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-sulfonamide (235)

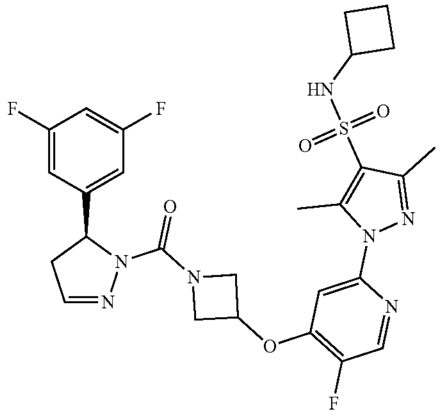 [SMILES: Cc1nn(-c2cc(OC3CN(C(=O)N4N=CC[C@H]4c4cc(F)cc(F)c4)C3)c(F)cn2)c(C)c1S(=O)(=O)NC1CCC1]

The titled compound 235 was prepared from 220-01 in a yield of 3.4% according to the procedure outlined for compound 220. Mass (m/z) 604.3 $[M+H]^+$.

(S)-(3-((2-(4-(benzylsulfonyl)-3,5-dimethyl-1H-pyrazol-1-yl)-5-fluoropyridin-4-yl)oxy)azetidin-1-yl)(5-(3,5-difluorophenyl)-4,5-dihydro-1H-pyrazol-1-yl)methanone (236)

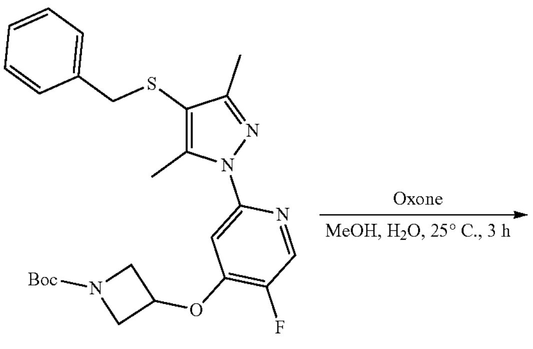

227-01

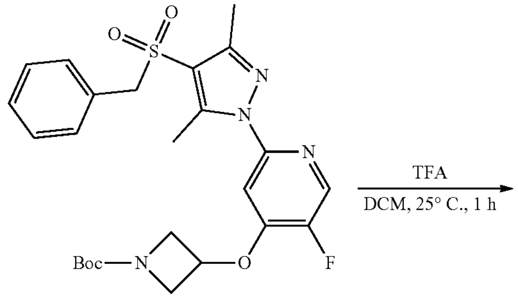

236-01

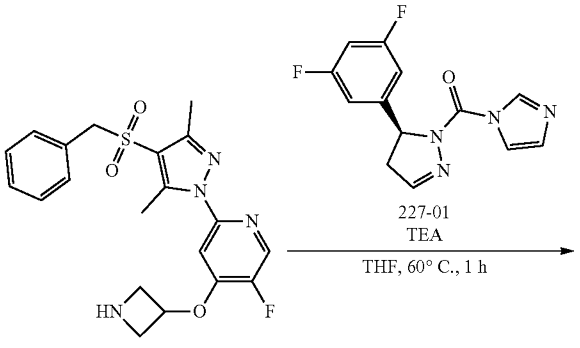

236-02

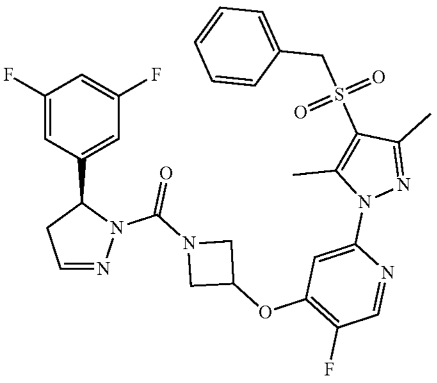

236

Step 1: 227-01 (100 mg, 0.20 mmol), Oxone (300 mg, 0.49 mmol) were in MeOH (5 mL) and $H_2O$ (3 mL) under $N_2$ and the whole reaction mixture was stirred at 25° C. for 3 hours. The mixture was concentrated in vacuo. Purification by silica gel chromatography to give 236-01 (70 mg, 66.0%) as a grey solid. Mass (m/z) 517.3 $[M+H]^+$.

Step 2: 236-01 (70 mg, 0.14 mmol) and TFA (3 mL) were in DCM (5 mL) under $N_2$ and the whole reaction mixture was stirred at 25° C. for 1 hour. The mixture was extracted with EA, washed with brine, dried ($Na_2SO_4$), and concentrated in vacuo to give 236-02 (100 mg, crude) as a yellow oil and used into next step reaction without purification. Mass (m/z) 417.4 $[M+H]^+$.

Step 3: 236-02 (100 mg, crude), TEA (1 mL), 1-02 (30 mg, 0.16 mmol) were in THE (5 mL) under $N_2$ and the whole reaction mixture was stirred at 60° C. for 1 hour. The mixture was extracted with EA, washed with brine, dried ($Na_2SO_4$), and concentrated in vacuo. Purification by silica gel chromatography to give 236 (20.0 mg, 29.8%) as a white solid. Mass (m/z) 625.4 $[M+H]^+$.

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-5-carbonitrile (237)

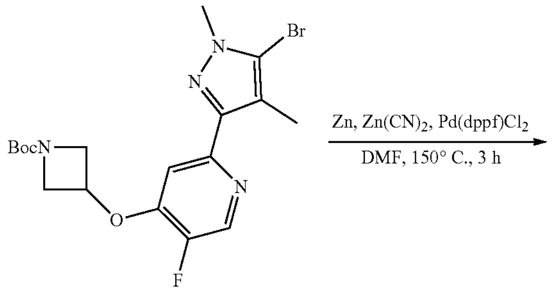

237-01

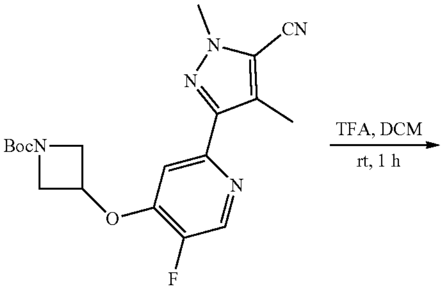

237-02

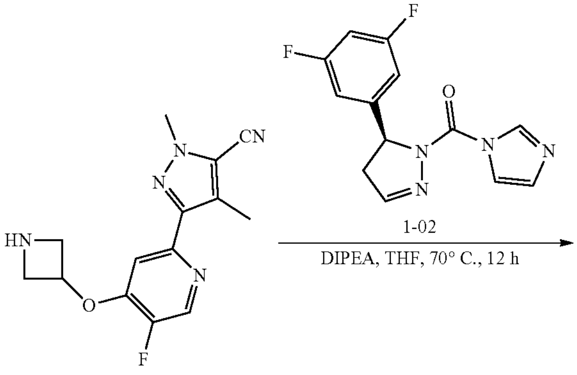

237-03

-continued

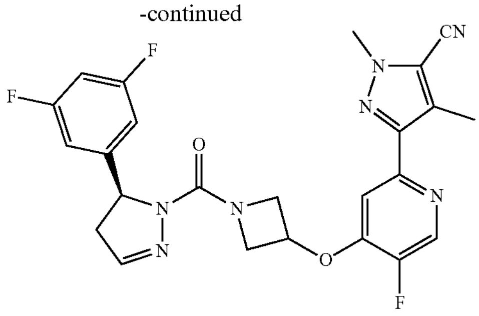

237

Step 1: To a solution of compound 237-01 (360 mg, 815.8 umol) in DMF (4 mL) was added Zn (160 mg, 2.54 umol), $Zn(CN)_2$ (192 mg, 1.63 mmol) and $Pd(dppf)Cl_2$ (60 mg, 81.6 umol) under Ar. The reaction mixture was stirred at 150° C. for 3 h. The crude mixture was purified by column chromatography on silica gel to give compound 237-02 (80 mg, 25%) as a white solid. Mass (m/z) 388.1 $[M+H]^+$.

Step 2: To a solution of compound 237-02 (80 mg, 206.5 umol) in DCM (3 mL) was added TFA (3 mL). The reaction mixture was stirred at rt for 1 h. The solvent was concentrated under vacuum. The crude compound 237-03 was used to next step directly Mass (m/z) 288.1 $[M+H]^+$.

Step 3: To a solution of compound 237-03 (50 mg, 181 umol) in THE (4 mL) was added compound 1-02 (52 mg, 181 umol) and DIPEA (94 mg, 724.0 umol). The reaction mixture was stirred at 70° C. for 12 h. The crude mixture was purified by Pre-HPLC to give compound 237 (68 mg, 76%) as a white solid. Mass (m/z) 496.1 $[M+H]^+$. $^1H$ NMR (400 MHz, $CDCl_3$) δ 8.38 (d, J=2.8 Hz, 1H), 7.28-7.26 (m, 1H), 6.80 (t, J=1.7 Hz, 1H), 6.77-6.67 (m, 2H), 5.28 (dd, J=12.2, 6.4 Hz, 1H), 5.13 (td, J=6.4, 3.3 Hz, 1H), 4.71-4.54 (m, 2H), 4.43-4.21 (m, 2H), 4.04 (s, 3H), 3.36 (ddd, J=18.6, 12.2, 1.7 Hz, 1H), 2.71 (ddd, J=18.6, 6.5, 1.8 Hz, 1H), 2.51 (s, 3H).

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1,3-dihydro-2H-imidazol-2-one (238)

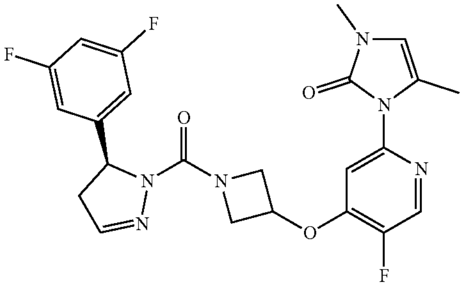 [SMILES: Cc1cn(C)c(=O)n1-c1cc(OC2CN(C(=O)N3N=CC[C@H]3c3cc(F)cc(F)c3)C2)c(F)cn1]

The titled compound 238 was prepared from compound 3-02 in a yield of 18.0% according to the procedure outlined for compound 167-03. Mass (m/z) 487.1 $[M+H]^+$. $^1H$ NMR (400 MHz, Chloroform-d) δ 8.22 (d, J=2.6 Hz, 1H), 7.22 (d, J=6.2 Hz, 1H), 6.82-6.65 (m, 4H), 6.04 (d, J=1.4 Hz, 1H), 5.28 (dd, J=12.2, 6.4 Hz, 1H), 5.11 (td, J=6.4, 3.2 Hz, 1H), 4.62 (s, 2H), 4.31 (t, J=14.9 Hz, 2H), 3.44-3.30 (m, 1H), 3.27 (s, 3H), 2.69 (ddd, J=18.6, 6.4, 1.8 Hz, 1H), 2.20 (d, J=1.4 Hz, 3H).

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)-N,N-dimethylacetamide (239)

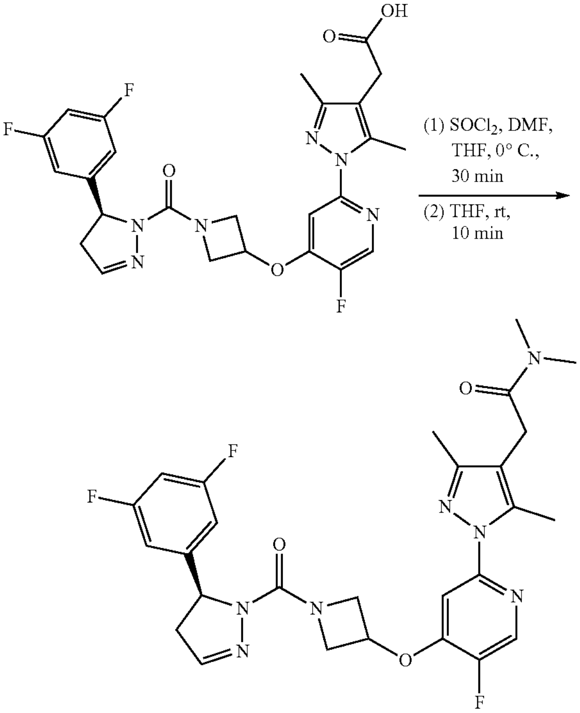

The titled compound 239 was prepared in 10.6% yield according to the procedure outlined for compound 225. $^1H$ NMR (400 MHz, Chloroform-d) δ 8.16 (s, 1H), 7.19 (d, J=6.1 Hz, 1H), 6.80 (s, 1H), 6.77-6.73 (m, 2H), 6.73-6.66 (m, 1H), 5.28 (dd, J=12.1, 6.4 Hz, 1H), 5.15 (s, 1H), 4.6-4.55 (s, 2H), 4.31 (dd, J=26.0, 10.4 Hz, 2H), 3.46 (s, 2H), 3.36 (dd, J=18.4, 12.3 Hz, 1H), 3.10 (s, 3H), 2.99 (s, 3H), 2.70 (dd, J=19.3, 7.2 Hz, 1H), 2.51 (s, 3H), 2.24 (s, 3H). Mass (m/z) 556.4 $[M+H]^+$.

(S)—N-cyclobutyl-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-sulfonamide (240)

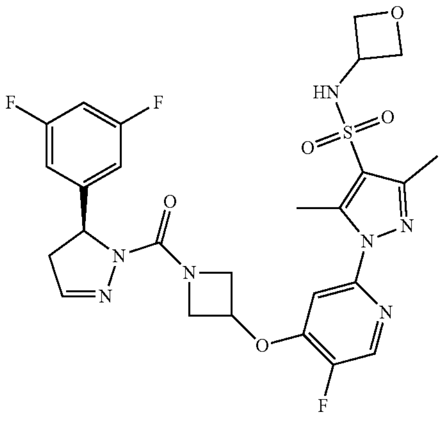 [SMILES: Cc1nn(-c2cc(OC3CN(C(=O)N4N=CC[C@H]4c4cc(F)cc(F)c4)C3)c(F)cn2)c(C)c1S(=O)(=O)NC1COC1]

The titled compound 240 was prepared from 220-01 in a yield of 14.3% according to the procedure outlined for compound 220. Mass (m/z) 606.4 $[M+H]^+$. $^1$H NMR (400 MHz, DMSO-$d_6$) δ 8.50 (d, J=2.4 Hz, 1H), 8.47 (d, J=6.4 Hz, 11H), 7.28 (d, J=6.0 Hz, 11H), 7.12 (tt, J=9.2, 2.4 Hz, 1H), 7.06-7.00 (m, 1H), 6.96-6.89 (m, 2H), 5.36-5.29 (m, 1H), 5.24 (dd, J=12.0, 6.4 Hz, 1H), 4.60-4.46 (m, 4H), 4.39-4.29 (m, 3H), 4.13-4.02 (m, 2H), 3.43-3.36 (m, 1H), 2.70-2.65 (m, 1H), 2.63 (s, 3H), 2.37 (s, 3H).

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-N-(tetrahydro-2H-pyran-4-yl)-1H-pyrazole-4-sulfonamide (241)

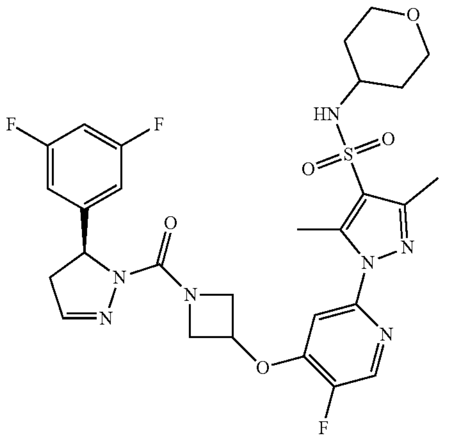 [SMILES: Cc1nn(-c2cc(OC3CN(C(=O)N4N=CC[C@H]4c4cc(F)cc(F)c4)C3)c(F)cn2)c(C)c1S(=O)(=O)NC1CCOCC1]

The titled compound 241 was prepared from 220-01 in a yield of 19.0% according to the procedure outlined for compound 220. Mass (m/z) 634.2 $[M+H]^+$. $^1$H NMR (400 MHz, DMSO-$d_6$) δ 8.49 (d, J=2.4 Hz, 1H), 7.77 (d, J=7.6 Hz, 1H), 7.29 (d, J=6.0 Hz, 1H), 7.16-7.07 (m, 1H), 7.03 (d, J=1.6 Hz, 1H), 6.96-6.89 (m, 2H), 5.36-5.30 (m, 1H), 5.24 (dd, J=12.0, 6.4 Hz, 1H), 4.61-4.40 (m, 2H), 4.19-3.97 (m, 2H), 3.75 (d, J=11.6 Hz, 2H), 3.46-3.36 (m, 1H), 3.31-3.22 (m, 2H), 3.18 (d, J=6.4 Hz, 1H), 2.66 (s, 3H), 2.65-2.61 (m, 1H), 2.38 (s, 3H), 1.57 (d, J=12.0 Hz, 2H), 1.48-1.34 (m, 2H).

(S)—N-cyclohexyl-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-sulfonamide (242)

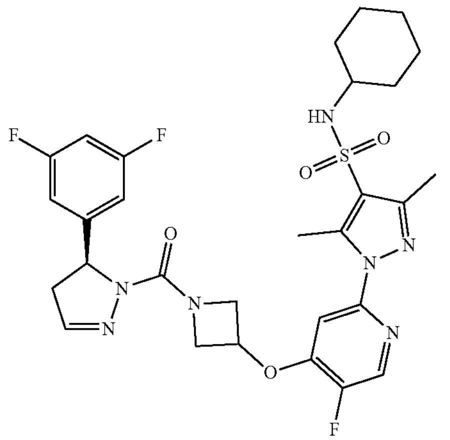 [SMILES: Cc1nn(-c2cc(OC3CN(C(=O)N4N=CC[C@H]4c4cc(F)cc(F)c4)C3)c(F)cn2)c(C)c1S(=O)(=O)NC1CCCCC1]

The titled compound 242 was prepared from 220-01 in a yield of 12.6% according to the procedure outlined for compound 220. Mass (m/z) 632.4 $[M+H]^+$. $^1$H NMR (400 MHz, DMSO-$d_6$) δ 8.48 (d, J=2.8 Hz, 1H), 7.62 (d, J=7.6 Hz, 1H), 7.29 (d, J=6.4 Hz, 1H), 7.17-7.06 (m, 1H), 7.05-7.00 (m, 1H), 6.96-6.89 (m, 2H), 5.37-5.29 (m, 1H), 5.24 (dd, J=12.0, 6.4 Hz, 1H), 4.60-4.44 (m, 2H), 4.16-3.99 (m, 2H), 3.44-3.37 (m, 1H), 2.98-2.86 (m, 1H), 2.69-2.66 (m, 1H), 2.65 (s, 3H), 2.37 (s, 3H), 1.66-1.55 (m, 4H), 1.50-1.42 (m, 1H), 1.20-1.11 (m, 4H), 1.07-1.02 (m, 1H).

(S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-N-phenyl-1H-pyrazole-4-sulfonamide (243)

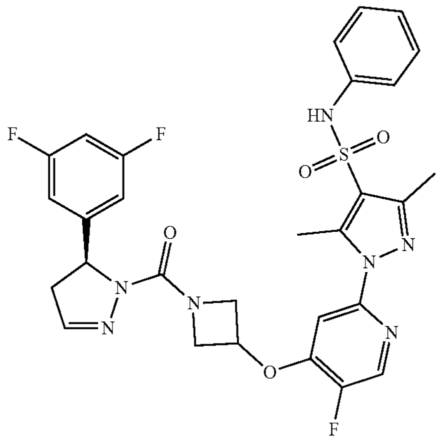 [SMILES: Cc1nn(-c2cc(OC3CN(C(=O)N4N=CC[C@H]4c4cc(F)cc(F)c4)C3)c(F)cn2)c(C)c1S(=O)(=O)Nc1ccccc1]

The titled compound 243 was prepared from 220-01 in a yield of 16.1% according to the procedure outlined for compound 220. Mass (m/z) 626.4 $[M+H]^+$. $^1$H NMR (400 MHz, DMSO-$d_6$) δ 10.23 (brs, 1H), 8.45 (d, J=2.4 Hz, 1H), 7.31-7.20 (m, 3H), 7.15-7.00 (m, 5H), 6.94-6.88 (m, 2H), 5.32-5.26 (m, 1H), 5.23 (dd, J=12.0, 6.4 Hz, 1H), 4.60-4.44 (m, 2H), 4.16-3.99 (m, 2H), 3.44-3.35 (m, 1H), 2.68-2.58 (m, 1H), 2.55 (s, 3H), 2.28 (s, 3H).

(S)-1-(4-((1-(5-(3,5-difluorophenyl)-4,5-dihydro-1H-pyrazole-1-carbonyl)azetidin-3-yl)oxy)-5-fluoropyridin-2-yl)-N-(2-hydroxyethyl)-3,5-dimethyl-1H-pyrazole-4-sulfonamide (244)

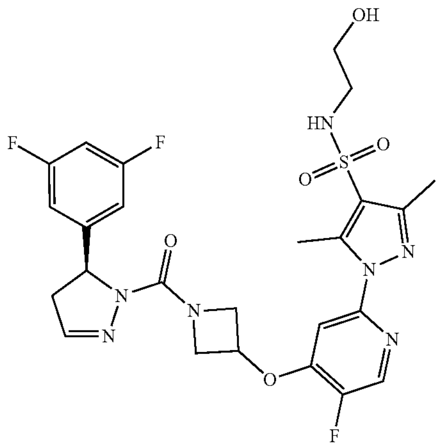 [SMILES: Cc1nn(-c2cc(OC3CN(C(=O)N4N=CC[C@H]4c4cc(F)cc(F)c4)C3)c(F)cn2)c(C)c1S(=O)(=O)NCCO]

The titled compound 244 was prepared from 220-01 in a yield of 14.6% according to the procedure outlined for compound 220. Mass (m/z) 594.3 $[M+H]^+$. $^1H$ NMR (400 MHz, DMSO-$d_6$) δ 8.49 (d, J=2.4 Hz, 1H), 7.53 (t, J=6.0 Hz, 1H), 7.29 (d, J=6.4 Hz, 1H), 7.12 (tt, J=9.2, 2.4 Hz, 1H), 7.06-7.00 (m, 1H), 6.97-6.89 (m, 2H), 5.32 (dd, J=6.4, 3.2 Hz, 11H), 5.24 (dd, J=12.0, 6.4 Hz, 11H), 4.70 (t, J=5.6 Hz, 11H), 4.61-4.45 (m, 2H), 4.14-4.00 (m, 2H), 3.46-3.36 (m, 3H), 2.83 (q, J=6.4 Hz, 2H), 2.69-2.66 (m, 1H), 2.63 (s, 3H), 2.37 (s, 3H).

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-5-carboxylic acid (245)

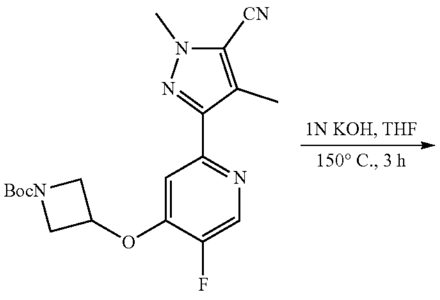

237-02

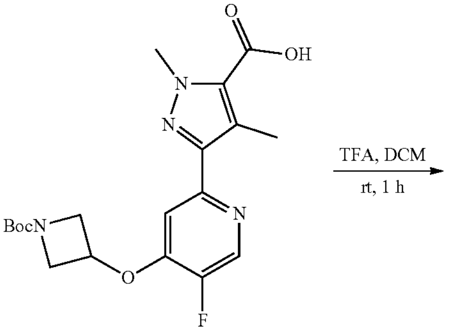

245-01

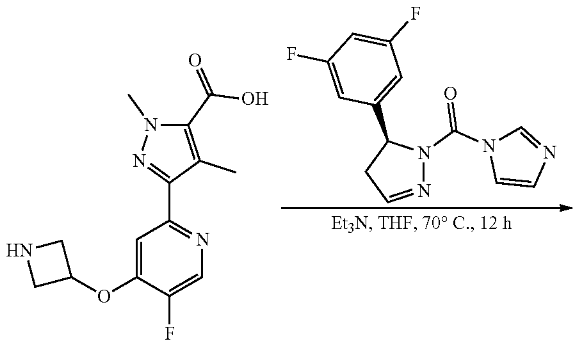

245-02

-continued

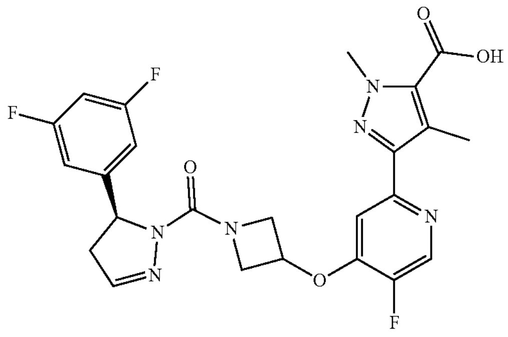

245

Step 1: To a solution of compound 237-02 (1.2 g, 3.1 mmol) in THF (20 mL) was added 1 N KOH (20 mL). The reaction mixture was stirred at 150° C. for 3 h. The crude mixture was purified by column chromatography on silica gel to give compound 245-01 (400 mg, 32%) was obtained as a white solid. Mass (m/z) 407.1 $[M+H]^+$.

Step 2: To a solution of compound 245-01 (400 mg, 984.2 umol) in DCM (6 mL) was added TFA (6 mL). The reaction mixture was stirred at rt for 1 h. The solvent was concentrated under vacuum. The crude compound 245-02 was used to next step directly Mass (m/z) 307.1 $[M+H]^+$.

Step 3: To a solution of compound 245-02 (235 mg, 848.9 umol) in THF (5 mL) was added compound 1-02 (260 mg, 848.9 umol) and $Et_3N$ (430 mg, 4.24 mmol). The reaction mixture was stirred at 70° C. for 12 h. The crude mixture was purified by Pre-HPLC to give compound 245 (220 mg, 50%) was obtained as a white solid Mass (m/z) 515.1 $[M+H]^+$.

(S)-3-(4-((1-(5-(3,5-difluorophenyl)-4,5-dihydro-1H-pyrazole-1-carbonyl)azetidin-3-yl)oxy)-5-fluoropyridin-2-yl)-N,1,4-trimethyl-1H-pyrazole-5-carboxamide (246)

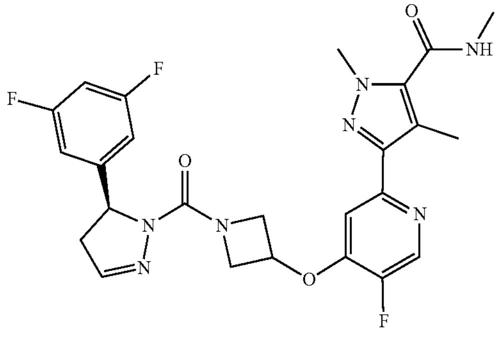 [SMILES: CNC(=O)c1c(C)c(-c2cc(OC3CN(C(=O)N4N=CC[C@H]4c4cc(F)cc(F)c4)C3)c(F)cn2)nn1C]

The titled compound 246 was prepared from 245 in a yield of 54% according to the procedure outlined for compound 68. Mass (m/z) 528.1 $[M+H]^+$. $^1H$ NMR (400 MHz, $CDCl_3$) δ 8.38 (d, J=2.8 Hz, 1H), 7.28-7.26 (m, 1H), 6.80 (t, J=1.7 Hz, 1H), 6.77-6.67 (m, 2H), 5.24-5.19 (m, 2H), 4.59-4.51 (m, 2H), 4.20-4.05 (m, 2H), 3.90 (s, 3H), 3.36 (ddd, J=18.6, 12.2, 1.7 Hz, 1H), 2.71 (ddd, J=18.6, 6.5, 1.8 Hz, 1H), 2.82 (s, 3H), 2.35 (s, 3H).

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-N-(tetrahydro-2H-pyran-4-yl)-1H-pyrazole-5-carboxamide (247)

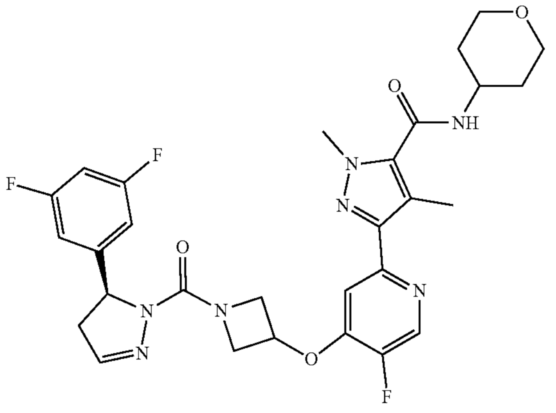 [SMILES: Cc1c(-c2cc(OC3CN(C(=O)N4N=CC[C@H]4c4cc(F)cc(F)c4)C3)c(F)cn2)nn(C)c1C(=O)NC1CCOCC1]

The titled compound 247 was prepared from 245 in a yield of 27% according to the procedure outlined for compound 68. Mass (m/z) 598.1 $[M+H]^+$. $^1H$ NMR (400 MHz, $CDCl_3$) δ 8.37 (d, J=2.8 Hz, 1H), 7.31-7.18 (m, 1H), 6.83-6.62 (m, 4H), 5.82-5.80 (m, 1H), 5.28 (dd, J=12.2, 6.4 Hz, 1H), 5.14 (td, J=6.5, 3.4 Hz, 1H), 4.66-4.58 (m, 2H), 4.42-4.31 (m, 1H), 4.31-4.14 (m, 3H), 4.08 (s, 3H), 4.01 (dt, J=11.9, 3.5 Hz, 2H), 3.55 (td, J=11.7, 2.2 Hz, 2H), 3.36 (ddd, J=18.6, 12.2, 1.7 Hz, 1H), 2.75-2.66 (m, 1H), 2.51 (s, 3H), 2.13-1.97 (m, 2H), 1.70-1.53 (m, 2H).

(S)-1-(4-((1-(5-(3,5-difluorophenyl)-4,5-dihydro-1H-pyrazole-1-carbonyl)azetidin-3-yl)oxy)-5-fluoropyridin-2-yl)-N-methoxy-3,5-dimethyl-1H-pyrazole-4-sulfonamide (248)

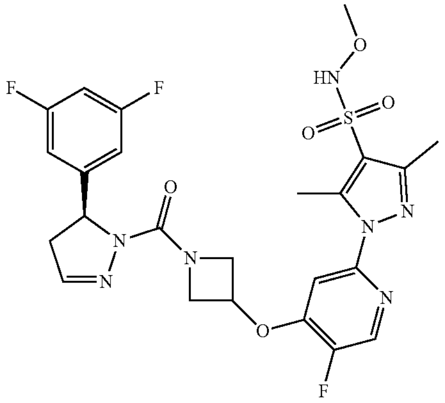 [SMILES: CONS(=O)(=O)c1c(C)nn(-c2cc(OC3CN(C(=O)N4N=CC[C@H]4c4cc(F)cc(F)c4)C3)c(F)cn2)c1C]

The titled compound 248 was prepared from 220-01 in a yield of 10.4% according to the procedure outlined for compound 220. Mass (m/z) 580.4 $[M+H]^+$. $^1H$ NMR (400 MHz, Chloroform-d) δ 8.23 (d, J=2.4 Hz, 1H), 7.17 (d, J=6.0 Hz, 1H), 7.00 (s, 1H), 6.80 (t, J=1.6 Hz, 1H), 6.78-6.65 (m, 3H), 5.28 (dd, J=12.0, 6.4 Hz, 1H), 5.15 (ddd, J=10.4, 6.4, 4.0 Hz, 1H), 4.70-4.56 (m, 2H), 4.40-4.23 (m, 2H), 3.81 (s, 3H), 3.36 (ddd, J=18.4, 12.0, 1.6 Hz, 1H), 2.83 (s, 3H), 2.79-2.65 (m, 1H), 2.47 (s, 3H).

(S)—N-cyclobutyl-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxamide (249)

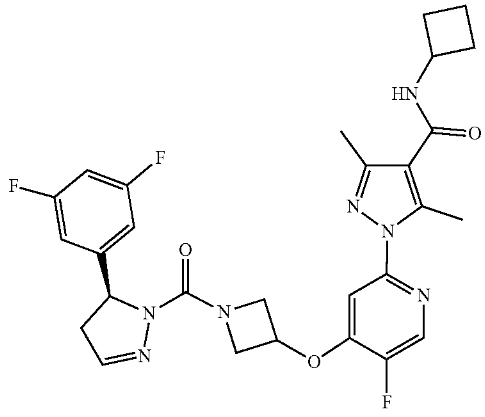 [SMILES: Cc1nn(-c2cc(OC3CN(C(=O)N4N=CC[C@H]4c4cc(F)cc(F)c4)C3)c(F)cn2)c(C)c1C(=O)NC1CCC1]

The titled compound 249 was prepared from 245 in a yield of 39.2% according to the procedure outlined for compound 68. $^1H$ NMR (400 MHz, Chloroform-d) δ 8.20 (d, J=2.5 Hz, 1H), 7.15 (d, J=6.1 Hz, 1H), 6.81-6.78 (m, 1H), 6.75 (dt, J=6.5, 2.1 Hz, 2H), 6.70 (tt, J=8.8, 2.3 Hz, 1H), 5.71 (d, J=7.9 Hz, 1H), 5.28 (dd, J=12.2, 6.4 Hz, 1H), 5.14 (dd, J=8.8, 5.0 Hz, 1H), 4.70-4.51 (m, 3H), 4.32 (dd, J=32.7, 10.3 Hz, 2H), 3.36 (ddd, J=18.7, 12.2, 1.7 Hz, 1H), 2.76 (s, 3H), 2.71 (ddd, J=18.7, 6.5, 1.8 Hz, 1H), 2.44 (s, 3H), 2.50-2.40 (m, 2H), 1.92 (dt, J=11.0, 8.8 Hz, 2H), 1.84-1.71 (m, 2H). Mass (m/z) 568.4 $[M+H]^+$.

(5-(3,5-difluorophenyl)-4,5-dihydro-1H-pyrazol-1-yl)(3-((5-fluoro-2-(1-methyl-1H-pyrazol-5-yl)pyridin-4-yl)oxy)azetidin-1-yl)methanone (250)

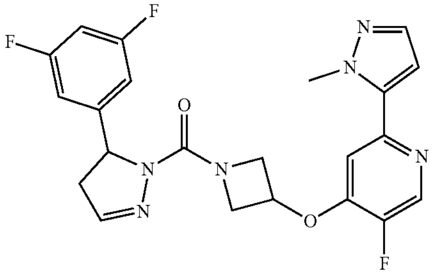 [SMILES: Cn1nccc1-c1cc(OC2CN(C(=O)N3N=CCC3c3cc(F)cc(F)c3)C2)c(F)cn1]

The titled compound 250 was prepared according to the procedure outlined for compound 3. $^1H$ NMR (400 MHz, Chloroform-d) δ 8.44 (d, J=2.9 Hz, 1H), 7.52 (d, J=2.0 Hz, 1H), 6.87 (d, J=6.4 Hz, 1H), 6.81 (t, J=1.7 Hz, 1H), 6.75 (dt, J=6.4, 2.1 Hz, 2H), 6.70 (tt, J=8.8, 2.3 Hz, 1H), 6.48 (d, J=2.0 Hz, 1H), 5.28 (dd, J=12.2, 6.4 Hz, 1H), 5.015-5.04 (m, 1H), 4.66-4.53 (m, 2H), 4.41-4.25 (m, 2H), 4.17 (s, 3H), 3.37 (ddd, J=18.7, 12.2, 1.7 Hz, 1H), 2.72 (ddd, J=18.6, 6.4, 1.8 Hz, 1H). Mass (m/z) 457.2 $[M+H]^+$.

(S)-(5-(3,5-difluorophenyl)-4,5-dihydro-1H-pyrazol-1-yl)(3-((5-fluoro-2-(3,4,5-trimethyl-1H-pyrazol-1-yl)pyridin-4-yl)oxy)azetidin-1-yl)methanone (251)

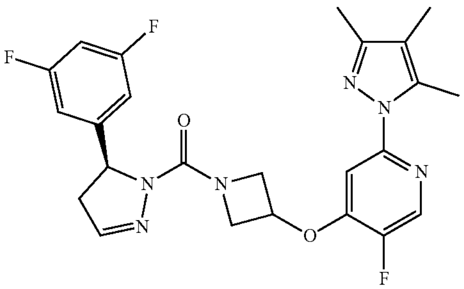 [SMILES: Cc1nn(-c2cc(OC3CN(C(=O)N4N=CC[C@H]4c4cc(F)cc(F)c4)C3)c(F)cn2)c(C)c1C]

The titled compound 251 was prepared from 3-04 in a yield of 10.2% according to the procedure outlined for compound 167-03. $^1$H NMR (400 MHz, Chloroform-d) δ 8.14 (d, J=2.5 Hz, 1H), 7.18 (d, J=6.2 Hz, 1H), 6.79 (d, J=1.7 Hz, 1H), 6.75 (dt, J=6.5, 2.0 Hz, 2H), 6.70 (td, J=8.9, 4.4 Hz, 1H), 5.28 (dd, J=12.2, 6.4 Hz, 1H), 5.15 (td, J=6.4, 3.3 Hz, 1H), 4.69-4.55 (m, 2H), 4.31 (dd, J=30.7, 10.5 Hz, 2H), 3.35 (ddd, J=18.7, 12.2, 1.7 Hz, 1H), 2.70 (ddd, J=18.7, 6.5, 1.8 Hz, 1H), 2.50 (s, 3H), 2.23 (s, 3H), 1.95 (s, 3H). Mass (m/z) 485.3 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-N-hydroxy-3,5-dimethyl-1H-pyrazole-4-carboxamide (252)

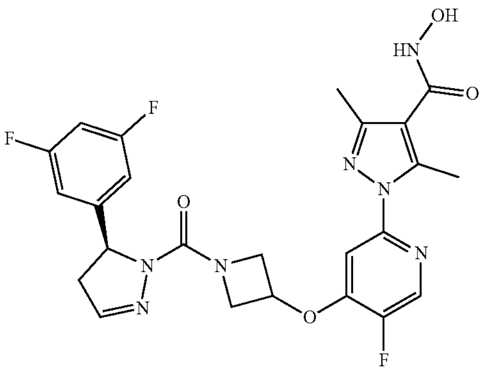 [SMILES: Cc1nn(-c2cc(OC3CN(C(=O)N4N=CC[C@H]4c4cc(F)cc(F)c4)C3)c(F)cn2)c(C)c1C(=O)NO]

The titled compound 252 was prepared in 15% yield according to the procedure outlined for compound 225. $^1$H NMR (400 MHz, Chloroform-d) δ 8.20 (d, J=2.4 Hz, 1H), 7.17 (d, J=6.1 Hz, 1H), 6.79 (d, J=1.8 Hz, 1H), 6.77-6.74 (m, 2H), 6.73-6.67 (m, 1H), 5.28 (dd, J=12.2, 6.4 Hz, 1H), 5.20-5.09 (m, 2H), 4.71-4.53 (m, 3H), 4.32 (dd, J=32.1, 10.4 Hz, 3H), 3.42-3.32 (m, 1H), 2.79 (s, 3H), 2.78-2.68 (m, 1H), 2.44 (s, 3H). Mass (m/z) 530.2 $[M+H]^+$.

(S)—N-cyano-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxamide (253)

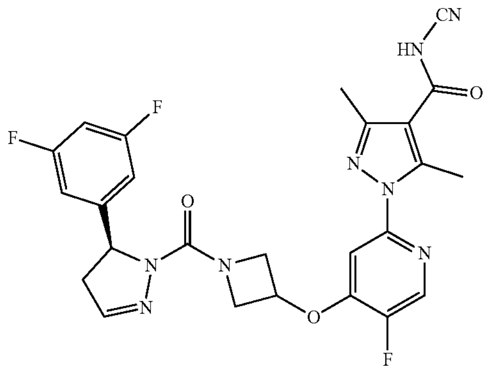 [SMILES: Cc1nn(-c2cc(OC3CN(C(=O)N4N=CC[C@H]4c4cc(F)cc(F)c4)C3)c(F)cn2)c(C)c1C(=O)NC#N]

The titled compound 253 was prepared in 10.2% yield according to the procedure outlined for compound 225. $^1$H NMR (400 MHz, Chloroform-d) δ 8.22 (d, J=2.4 Hz, 1H), 7.37 (s, 1H) 7.15 (d, J=6.1 Hz, 1H), 6.81 (t, J=1.7 Hz, 1H), 6.78-6.74 (m, 2H), 6.74-6.68 (m, 1H), 5.28 (dd, J=12.2, 6.4 Hz, 1H), 5.18-5.09 (d, J=4.1 Hz, 2H), 4.69-4.56 (s, 2H), 4.40-4.23 (m, 2H), 3.37 (ddd, J=18.6, 12.2, 1.7 Hz, 1H), 2.82 (s, 3H), 2.76-2.68 (m, 1H), 2.49 (s, 3H). Mass (m/z) 539.3 $[M+H]^+$.

1-(4-((1-((S)-5-(3,5-difluorophenyl)-4,5-dihydro-1H-pyrazole-1-carbonyl)azetidin-3-yl)oxy)-5-fluoropyridin-2-yl)-N-((1s,3s)-3-hydroxycyclobutyl)-3,5-dimethyl-1H-pyrazole-4-carboxamide (254)

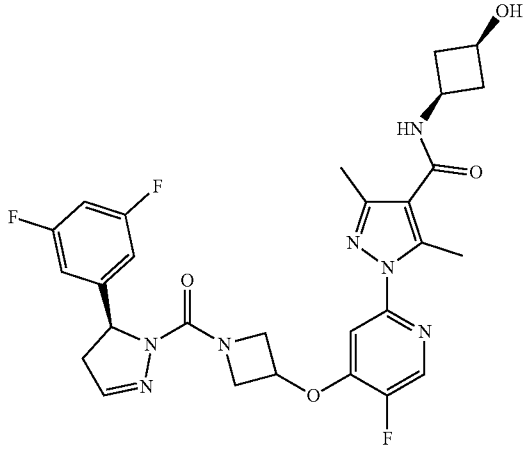 [SMILES: Cc1nn(-c2cc(OC3CN(C(=O)N4N=CC[C@H]4c4cc(F)cc(F)c4)C3)c(F)cn2)c(C)c1C(=O)N[C@H]1C[C@@H](O)C1]

The titled compound 254 was prepared in 37.8% yield according to the procedure outlined for compound 225. $^1$H NMR (400 MHz, Chloroform-d) δ 8.20 (s, 1H), 7.15 (d, J=6.1 Hz, 1H), 6.81-6.79 (m, 1H), 6.77-6.73 (m, 2H), 6.73-6.66 (m, 1H), 5.72 (d, J=7.6 Hz, 1H), 5.28 (dd, J=12.2, 6.4 Hz, 1H), 5.14 (td, J=6.5, 3.4 Hz, 1H), 4.63 (s, 2H), 4.32 (dd, J=33.4, 9.1 Hz, 2H), 4.15 (dq, J=14.8, 7.8, 7.3 Hz, 2H), 3.36 (ddd, J=18.6, 12.2, 1.7 Hz, 1H), 2.91 (dtd, J=9.8, 6.9, 3.0 Hz, 2H), 2.76 (s, 2H), 2.71 (ddd, J=18.6, 6.5, 1.7 Hz, 2H), 2.44 (s, 3H), 1.98-1.86 (m, 2H). Mass (m/z) 584.4 $[M+H]^+$.

1-(4-((1-((S)-5-(3,5-difluorophenyl)-4,5-dihydro-1H-pyrazole-1-carbonyl)azetidin-3-yl)oxy)-5-fluoropyridin-2-yl)-N-((1r,3r)-3-hydroxycyclobutyl)-3,5-dimethyl-1H-pyrazole-4-carboxamide (255)

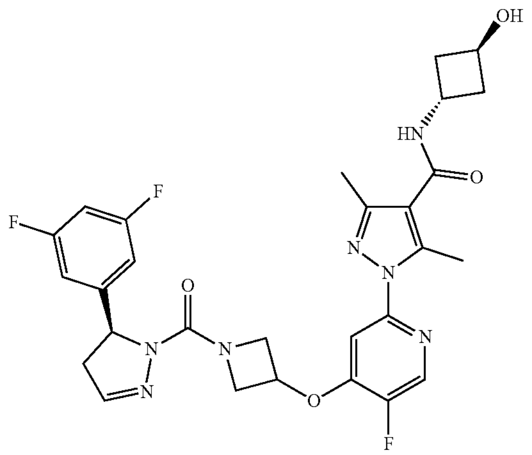 [SMILES: Cc1nn(-c2cc(OC3CN(C(=O)N4N=CC[C@H]4c4cc(F)cc(F)c4)C3)c(F)cn2)c(C)c1C(=O)N[C@H]1C[C@H](O)C1]

The titled compound 255 was prepared in 54.3% yield according to the procedure outlined for compound 225. $^1$H NMR (400 MHz, Chloroform-d) δ 8.20 (d, J=2.4 Hz, 1H), 7.15 (d, J=6.1 Hz, 1H), 6.81-6.79 (m, 1H), 6.78-6.73 (m, 2H), 6.70 (tt, J=8.8, 2.4 Hz, 1H), 5.73 (d, J=6.5 Hz, 1H), 5.28 (dd, J=12.2, 6.4 Hz, 1H), 5.15 (ddd, J=10.3, 6.5, 4.0 Hz, 1H), 4.69-4.55 (m, 4H), 4.32 (dd, J=33.4, 10.2 Hz, 2H), 3.36 (ddd, J=18.6, 12.2, 1.7 Hz, 2H), 2.76 (s, 2H), 2.71 (ddd, J=18.6, 6.4, 1.8 Hz, 2H), 2.53-2.45 (m, 2H), 2.44 (s, 3H), 2.38-2.30 (m, 2H). Mass (m/z) 584.4 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-N-(2-(dimethylamino)ethyl)-3,5-dimethyl-1H-pyrazole-4-carboxamide (256)

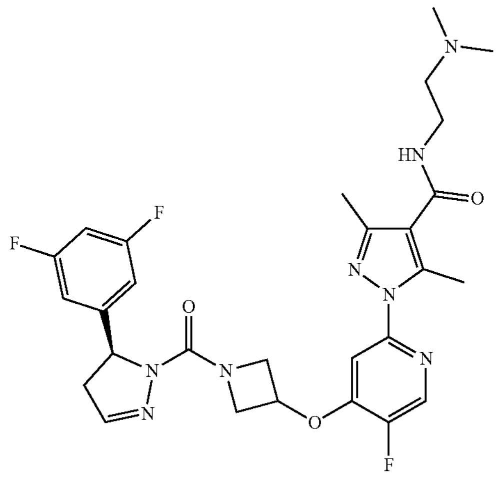 [SMILES: Cc1nn(-c2cc(OC3CN(C(=O)N4N=CC[C@H]4c4cc(F)cc(F)c4)C3)c(F)cn2)c(C)c1C(=O)NCCN(C)C]

The titled compound 256 was prepared in 160% yield according to the procedure outlined for compound 225. $^1$H NMR (400 MHz, Chloroform-d) δ 8.21 (d, J=2.4 Hz, 1H), 7.33 (s, 1H), 7.11 (d, J=6.1 Hz, 1H), 6.79 (t, J=1.7 Hz, 1H), 6.75 (dt, J=6.4, 2.1 Hz, 2H), 6.70 (tt, J=8.8, 2.3 Hz, 1H), 5.28 (dd, J=12.2, 6.3 Hz, 1H), 5.14 (dq, J=6.7, 4.0, 3.4 Hz, 1H), 4.72-4.53 (m, 2H), 4.32 (dd, J=26.5, 10.7 Hz, 2H), 3.87 (d, J=5.4 Hz, 2H), 3.41-3.30 (m, 3H), 2.92 (s, 6H), 2.74 (s, 3H), 2.72-2.66 (m, 1H), 2.45 (s, 3H). Mass (mi/z) 585.4 $[M+H]^+$.

1-(4-((1-((S)-5-(3,5-difluorophenyl)-4,5-dihydro-1H-pyrazole-1-carbonyl)azetidin-3-yl)oxy)-5-fluoropyridin-2-yl)-3,5-dimethyl-N—((S)-tetrahydrofuran-3-yl)-1H-pyrazole-4-carboxamide (257)

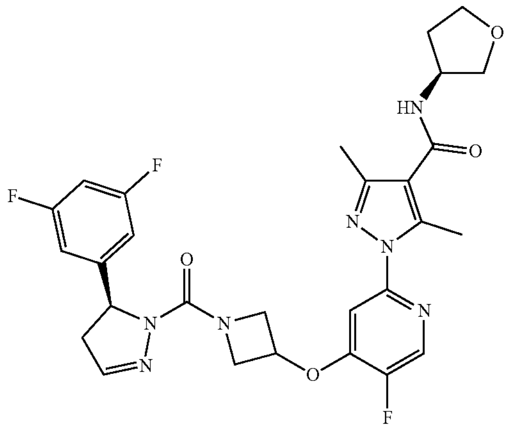 [SMILES: Cc1nn(-c2cc(OC3CN(C(=O)N4N=CC[C@H]4c4cc(F)cc(F)c4)C3)c(F)cn2)c(C)c1C(=O)N[C@H]1CCOC1]

The titled compound 257 was prepared in 39.8% yield according to the procedure outlined for compound 225. $^1$H NMR (400 MHz, Chloroform-d) δ 8.20 (d, J=2.5 Hz, 1H), 7.15 (d, J=6.1 Hz, 1H), 6.83-6.66 (m, 4H), 5.78 (d, J=7.6 Hz, 1H), 5.28 (dd, J=12.1, 6.4 Hz, 1H), 5.14 (td, J=6.5, 3.3 Hz, 1H), 4.78-4.56 (m, 3H), 4.32 (dd, J=32.6, 10.6 Hz, 2H), 4.07-3.74 (m, 4H), 3.36 (ddd, J=18.7, 12.2, 1.7 Hz, 1H), 2.76 (s, 3H), 2.71 (ddd, J=18.6, 6.5, 1.8 Hz, 1H), 2.43 (s, 3H), 2.42-2.32 (m, 1H), 1.96-1.86 (m, 1H). Mass (m/z) 584.4 $[M+H]^+$.

1-(4-((1-((S)-5-(3,5-difluorophenyl)-4,5-dihydro-1H-pyrazole-1-carbonyl)azetidin-3-yl)oxy)-5-fluoropyridin-2-yl)-3,5-dimethyl-N—((R)-tetrahydrofuran-3-yl)-1H-pyrazole-4-carboxamide (258)

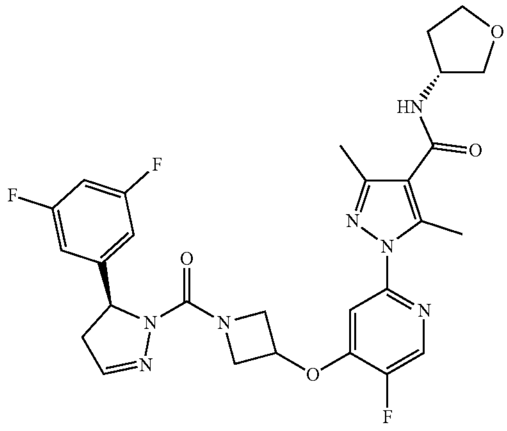 [SMILES: Cc1nn(-c2cc(OC3CN(C(=O)N4N=CC[C@H]4c4cc(F)cc(F)c4)C3)c(F)cn2)c(C)c1C(=O)N[C@@H]1CCOC1]

The titled compound 258 was prepared in 45.4% yield according to the procedure outlined for compound 225. $^1$H NMR (400 MHz, Chloroform-d) δ 8.20 (d, J=2.4 Hz, 1H), 7.15 (d, J=6.1 Hz, 1H), 6.86-6.66 (m, 4H), 5.81 (d, J=7.5 Hz, 1H), 5.28 (dd, J=12.2, 6.4 Hz, 1H), 5.15 (tt, J=6.4, 4.0 Hz, 1H), 4.81-4.54 (m, 3H), 4.32 (dd, J=32.2, 10.3 Hz, 2H), 4.07-3.72 (m, 4H), 3.36 (ddd, J=18.7, 12.2, 1.7 Hz, 1H), 2.76 (s, 3H), 2.71 (ddd, J=18.6, 6.5, 1.7 Hz, 1H), 2.43 (s, 3H), 2.36 (ddt, J=13.2, 8.6, 7.1 Hz, 1H), 1.91 (dddd, J=13.2, 8.0, 5.4, 3.1 Hz, 1H). Mass (m/z) 584.4 [M+H]$^+$.

(S)-(5-(3,5-difluorophenyl)-4,5-dihydro-1H-pyrazol-1-yl)(3-((5-fluoro-2-(4-(2-hydroxyethyl)-3,5-dimethyl-1H-pyrazol-1-yl)pyridin-4-yl)oxy)azetidin-1-yl)methanone (259)

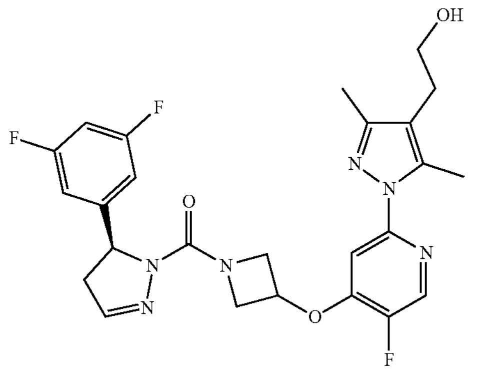 [SMILES: Cc1nn(-c2cc(OC3CN(C(=O)N4N=CC[C@H]4c4cc(F)cc(F)c4)C3)c(F)cn2)c(C)c1CCO]

The titled compound 259 was prepared in 28.9% yield according to the procedure outlined for compound 202. $^1$H NMR (400 MHz, Chloroform-d) δ 8.15 (d, J=2.5 Hz, 1H), 7.19 (d, J=6.2 Hz, 1H), 6.81-6.64 (m, 4H), 5.32-5.25 (m, 1H), 5.15 (td, J=6.5, 3.3 Hz, 1H), 4.71-4.56 (m, 3H), 4.31 (dd, J=31.4, 10.3 Hz, 2H), 3.72 (t, J=6.7 Hz, 2H), 3.36 (ddd, J=18.6, 12.2, 1.7 Hz, 1H), 2.76-2.66 (m, 3H), 2.55 (s, 3H), 2.27 (s, 2H). Mass (m/z) 514.30 [M+H]$^+$ (S)-1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazole-4-carboxylate_ (260)

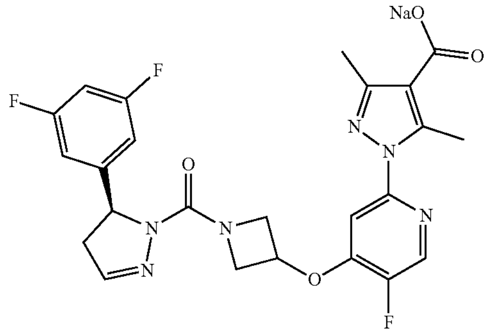

The titled compound 260 was prepared from compound 233. Mass (m/z) 537.2 [M+H]$^+$ (S)-(5-(3,5-difluorophenyl)-4,5-dihydro-1H-pyrazol-1-yl)(3-((5-fluoro-2-(1H-pyrazol-5-yl)pyridin-4-yl)oxy)azetidin-1-yl)methanone (261)

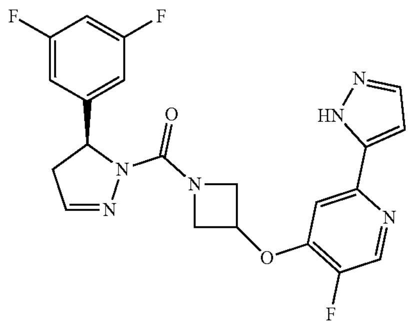 [SMILES: O=C(N1CC(Oc2cc(-c3ccn[nH]3)ncc2F)C1)N1N=CC[C@H]1c1cc(F)cc(F)c1]

The titled compound 261 was prepared from 3-04 in a yield of 3.4% according to the procedure outlined for compound 3. Mass (m/z) 443.4 [M+H]$^+$. $^1$H NMR (400 MHz, DMSO-$d_6$) δ 13.06 (brs, 1H), 8.47 (s, 1H), 7.82 (s, 1H), 7.39 (d, J=0.8 Hz, 1H), 7.14-7.08 (m, 1H), 7.03 (t, J=1.6 Hz, 1H), 6.98-6.86 (m, 2H), 6.78 (s, 1H), 5.37-5.27 (m, 1H), 5.25 (dd, J=12.0, 6.4 Hz, 1H), 4.68-4.43 (m, 2H), 4.17-3.97 (m, 2H), 3.39 (ddd, J=18.4, 12.0, 1.6 Hz, 1H), 2.64 (ddd, J=18.4, 6.4, 1.6 Hz, 1H).

(S)-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-N-(oxetan-3-yl)-1H-pyrazole-5-carboxamide (262)

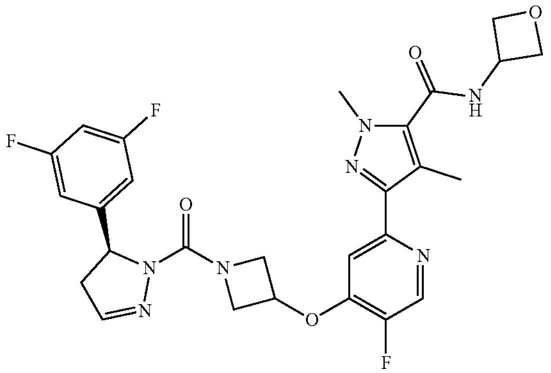 [SMILES: Cc1c(-c2cc(OC3CN(C(=O)N4N=CC[C@H]4c4cc(F)cc(F)c4)C3)c(F)cn2)nn(C)c1C(=O)NC1COC1]

The titled compound 262 was prepared from 245 in a yield of 30% according to the procedure outlined for compound 68. Mass (m/z) 570.1 [M+H]$^+$.

(S)-3-(4-((1-(5-(3,5-difluorophenyl)-4,5-dihydro-1H-pyrazole-1-carbonyl)azetidin-3-yl)oxy)-5-fluoropyridin-2-yl)-N-(3-hydroxycyclobutyl)-1,4-dimethyl-1H-pyrazole-5-carboxamide (263)

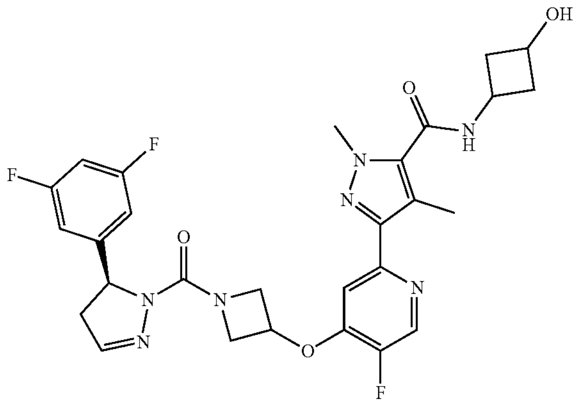 [SMILES: Cc1c(-c2cc(OC3CN(C(=O)N4N=CC[C@H]4c4cc(F)cc(F)c4)C3)c(F)cn2)nn(C)c1C(=O)NC1CC(O)C1]

The titled compound 263 was prepared from 245 in a yield of 31% according to the procedure outlined for compound 68. Mass (m/z) 584.1 $[M+H]^+$.

(S)—N-cyclobutyl-3-(4-((1-(5-(3,5-difluorophenyl)-4,5-dihydro-1H-pyrazole-1-carbonyl)azetidin-3-yl)oxy)-5-fluoropyridin-2-yl)-1,4-dimethyl-1H-pyrazole-5-carboxamide (264)

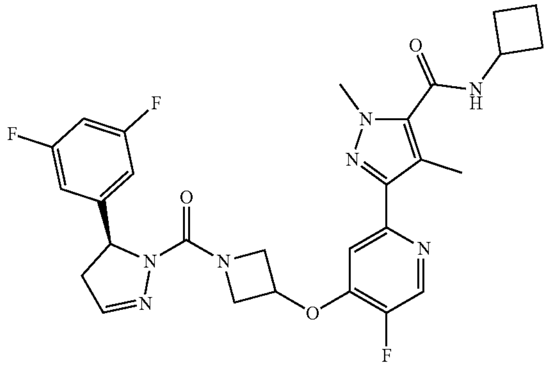 [SMILES: Cc1c(-c2cc(OC3CN(C(=O)N4N=CC[C@H]4c4cc(F)cc(F)c4)C3)c(F)cn2)nn(C)c1C(=O)NC1CCC1]

The titled compound 264 was prepared from 245 in a yield of 29% according to the procedure outlined for compound 68. Mass (m/z) 568.1 $[M+H]^+$.

(S)-3-(4-((1-(5-(3,5-difluorophenyl)-4,5-dihydro-1H-pyrazole-1-carbonyl)azetidin-3-yl)oxy)-5-fluoropyridin-2-yl)-N-(2-hydroxyethyl)-1,4-dimethyl-1H-pyrazole-5-carboxamide (265)

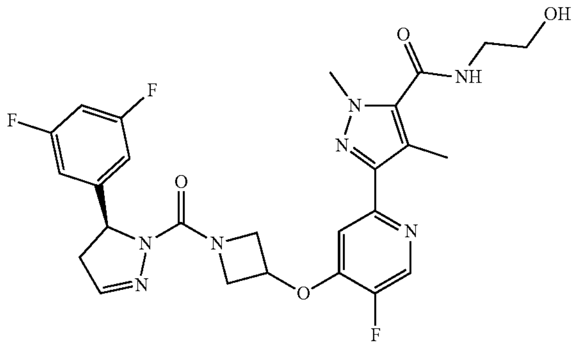 [SMILES: Cc1c(-c2cc(OC3CN(C(=O)N4N=CC[C@H]4c4cc(F)cc(F)c4)C3)c(F)cn2)nn(C)c1C(=O)NCCO]

The titled compound 265 was prepared from 245 in a yield of 22% according to the procedure outlined for compound 68. Mass (m/z) 558.1 $[M+H]^+$. $^1H$ NMR (400 MHz, $CDCl_3$) δ 8.38 (d, J=2.8 Hz, 1H), 7.24 (d, J=6.8 Hz, 1H), 6.86-6.59 (m, 4H), 6.40 (m, 1H), 5.28 (dd, J=12.2, 6.4 Hz, 1H), 5.14 (td, J=6.4, 3.3 Hz, 1H), 4.62 (d, J=9.7 Hz, 2H), 4.32 (dd, J=32.8, 10.3 Hz, 2H), 4.10 (s, 3H), 3.91-3.80 (m, 2H), 3.65 (q, J=5.3 Hz, 2H), 3.36 (ddd, J=18.6, 12.2, 1.7 Hz, 1H), 2.70 (ddd, J=18.6, 6.5, 1.8 Hz, 1H), 2.54 (s, 3H).

(S)-(5-(3,5-difluorophenyl)-4,5-dihydro-1H-pyrazol-1-yl)(3-((2-(5-(4,5-dihydro-1H-imidazol-2-yl)-1,4-dimethyl-1H-pyrazol-3-yl)-5-fluoropyridin-4-yl)oxy)azetidin-1-yl)methanone (266)

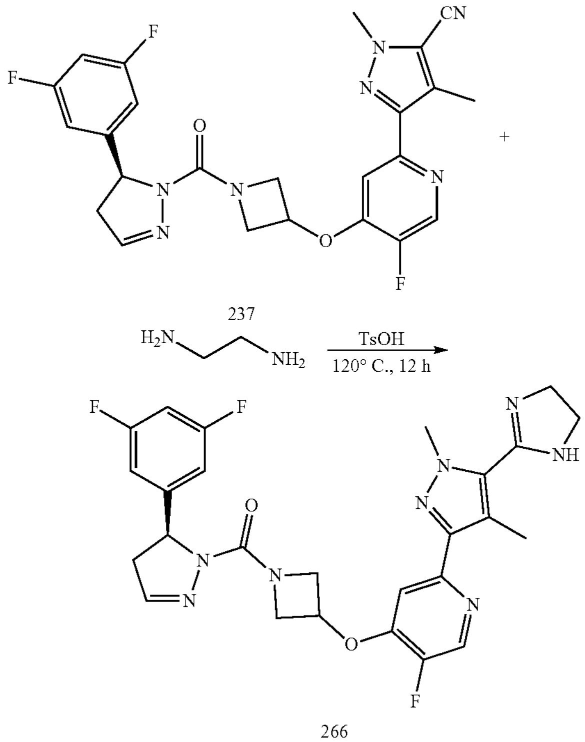

266

To a solution of compound 237 (30 mg, 60.6 umol) in ethane-1,2-diamine (2 mL) was added TsOH (105 mg, 605.5 umol). The reaction mixture was stirred at 120° C. for 12 h. The crude mixture was purified by Pre-HPLC to give compound 266 (4 mg, 12%) as a white solid MS (m/z) 539.1 $[M+H]^+$.

(S)-(5-(3,5-difluorophenyl)-4,5-dihydro-1H-pyrazol-1-yl)(3-((2-(1,4-dimethyl-5-(1-methyl-4,5-dihydro-1H-imidazol-2-yl)-1H-pyrazol-3-yl)-5-fluoropyridin-4-yl)oxy)azetidin-1-yl)methanone (267)

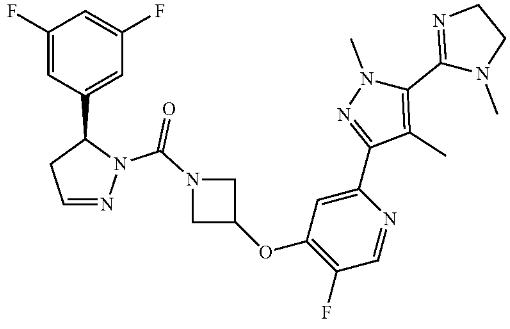 [SMILES: Cc1c(-c2cc(OC3CN(C(=O)N4N=CC[C@H]4c4cc(F)cc(F)c4)C3)c(F)cn2)nn(C)c1C1=NCCN1C]

The titled compound 267 was prepared from 237 in a yield of 8% according to the procedure outlined for compound 266. Mass (m/z) 553.1 $[M+H]^+$.

(S)-(5-(3,5-difluorophenyl)-4,5-dihydro-1H-pyrazol-1-yl)(3-((2-(3,5-dimethylisoxazol-4-yl)-5-fluoropyridin-4-yl)oxy)azetidin-1-yl)methanone (268)

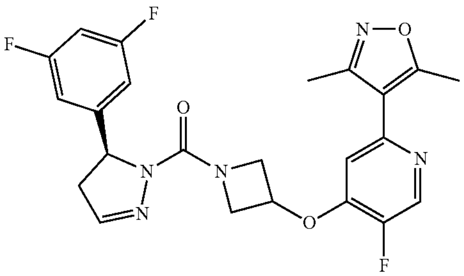 [SMILES: Cc1noc(C)c1-c1cc(OC2CN(C(=O)N3N=CC[C@H]3c3cc(F)cc(F)c3)C2)c(F)cn1]

The titled compound 268 was prepared from 3-02 in a yield of 20.2% according to the procedure outlined for compound 3. MS (m/z) 472.4 $[M+H]^+$. $^1$H NMR (400 MHz, DMSO-$d_6$) δ 8.54 (d, J=3.0 Hz, 1H), 7.08 (tt, J=9.3, 2.4 Hz, 1H), 7.01-6.98 (m, 2H), 6.91-6.86 (m, 2H), 5.28-5.17 (m, 2H), 4.52 (s, 2H), 4.07 (d, J=14.5 Hz, 2H), 3.36 (ddd, J=18.4, 12.0, 1.6 Hz, 1H), 2.62 (ddd, J=18.7, 6.6, 1.7 Hz, 1H), 2.50 (s, 3H), 2.31 (s, 3H).

(S)-(5-(3,5-difluorophenyl)-4,5-dihydro-1H-pyrazol-1-yl)(3-((2-(4-((dimethylamino)methyl)-3,5-dimethyl-1H-pyrazol-1-yl)-5-fluoropyridin-4-yl)oxy)azetidin-1-yl)methanone (269)

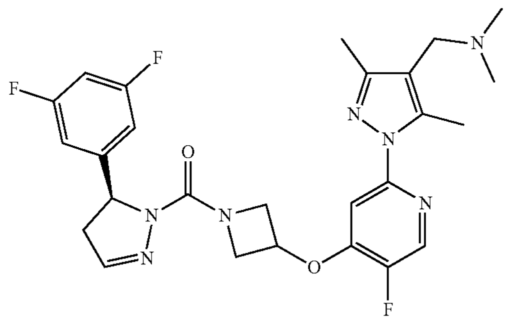 [SMILES: Cc1nn(-c2cc(OC3CN(C(=O)N4N=CC[C@H]4c4cc(F)cc(F)c4)C3)c(F)cn2)c(C)c1CN(C)C]

The titled compound 269 was prepared in a yield of 16.8% according to the procedure outlined for compound 110. $^1$H NMR (400 MHz, DMSO-$d_6$) δ 8.37 (d, J=2.7 Hz, 11H), 7.25 (d, J=6.3 Hz, 11H), 7.10 (tt, J=9.3, 2.4 Hz, 1H), 7.02 (d, J=1.7 Hz, 1H), 6.96-6.88 (m, 2H), 5.32 (tt, J=6.5, 3.6 Hz, 1H), 5.25 (dd, J=12.1, 6.6 Hz, 1H), 4.52 (s, 2H), 4.08 (s, 2H), 3.39 (ddd, J=18.7, 12.1, 1.8 Hz, 1H), 3.18 (s, 2H), 2.62 (dd, J=6.5, 1.8 Hz, 1H), 2.52 (s, 3H) 2.19 (s, 3H), 2.12 (s, 6H). Mass (m/z) 528.2 $[M+H]^+$.

(S)-1-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)pyrrolidin-2-one (270)

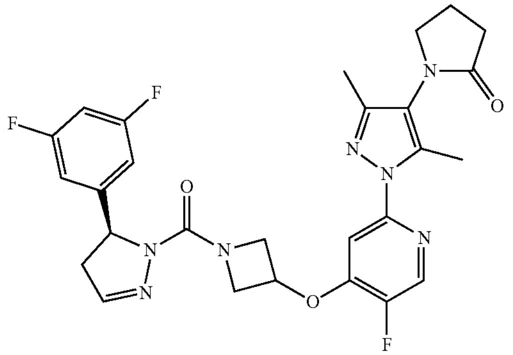 [SMILES: Cc1nn(-c2cc(OC3CN(C(=O)N4N=CC[C@H]4c4cc(F)cc(F)c4)C3)c(F)cn2)c(C)c1N1CCCC1=O]

The titled compound 270 was prepared in a yield of 20.10% according to the procedure outlined for compound 110. $^1$H NMR (400 MHz, DMSO-$d_6$) δ 8.40 (d, J=2.6 Hz, 1H), 7.25 (d, J=6.3 Hz, 1H), 7.10 (tt, J=9.2, 2.3 Hz, 1H), 7.03 (d, J=1.7 Hz, 1H), 6.93 (qd, J=6.6, 3.3 Hz, 2H), 5.34 (tt, J=6.6, 3.6 Hz, 1H), 5.25 (dd, J=12.1, 6.6 Hz, 1H), 4.53 (s, 2H), 4.09 (s, 2H), 3.59 (t, J=6.9 Hz, 2H), 3.39 (ddd, J=18.8, 12.2, 1.8 Hz, 1H), 2.62 (dd, J=6.7, 1.8 Hz, 1H), 2.42 (t, J=8.0 Hz, 2H), 2.37 (s, 3H), 2.12 (d, J=6.7 Hz, 5H). Mass (m/z) 554.2 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)acetonitrile (271)

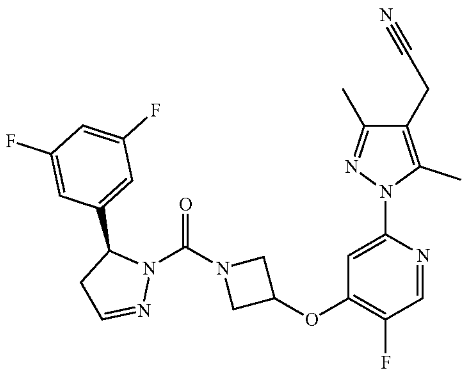 [SMILES: Cc1nn(-c2cc(OC3CN(C(=O)N4N=CC[C@H]4c4cc(F)cc(F)c4)C3)c(F)cn2)c(C)c1CC#N]

The titled compound 271 was prepared in a yield of 35.4% according to the procedure outlined for compound 110. $^1$H NMR (400 MHz, Chloroform-d) δ 8.15 (d, J=2.4 Hz, 1H), 7.19 (d, J=6.1 Hz, 1H), 6.82-6.63 (m, 4H), 5.30-5.23 (m, 1H), 5.15 (s, 1H), 4.62 (s, 2H), 4.31 (dd, J=31.6, 10.2 Hz, 2H), 3.47 (s, 2H), 3.41-3.30 (m, 1H), 2.74-2.66 (m, 1H), 2.59 (s, 3H), 2.31 (s, 3H). Mass (m/z) 510.3 $[M+H]^+$ (S)-1-(4-((1-(5-(3,5-difluorophenyl)-4,5-dihydro-1H-pyrazole-1-carbonyl)azetidin-3-yl)oxy)-5-fluoropyridin-2-yl)-3-methyl-11H-pyrazole-4-carboxamide (272)

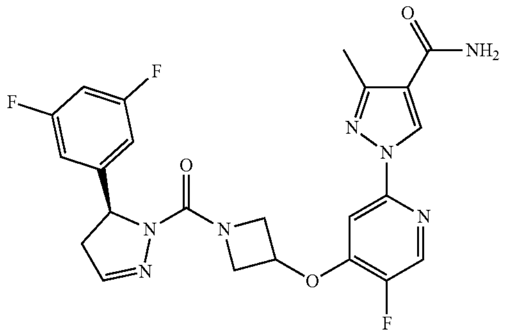 [SMILES: Cc1nn(-c2cc(OC3CN(C(=O)N4N=CC[C@H]4c4cc(F)cc(F)c4)C3)c(F)cn2)cc1C(N)=O]

The titled compound 272 was prepared in a yield of 73.2% according to the procedure outlined for compound 110. $^1$H NMR (400 MHz, Chloroform-d) δ 8.74 (s, 1H), 8.14 (d, J=2.5 Hz, 1H), 7.30 (d, J=6.1 Hz, 1H), 6.85-6.63 (m, 4H), 5.63 (s, 2H), 5.27 (dd, J=12.1, 6.4 Hz, 1H), 5.20-5.22 (m, 1H), 4.72-4.58 (m, 2H), 4.32 (dd, J=30.4, 9.4 Hz, 2H), 3.35 (ddd, J=18.6, 12.2, 1.7 Hz, 1H), 2.70 (ddd, J=18.6, 6.4, 1.7 Hz, 1H), 2.55 (s, 3H). Mass (m/z) 500.30 $[M+H]^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-5-methyl-1H-pyrazole-4-carboxamide (273)

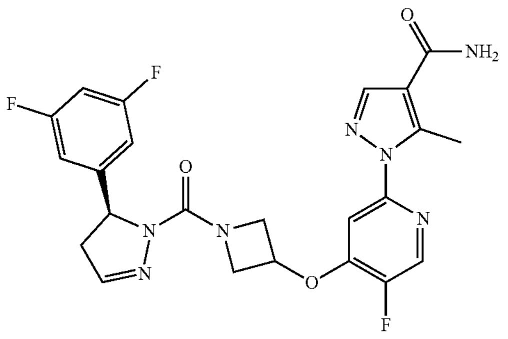 [SMILES: Cc1c(C(N)=O)cnn1-c1cc(OC2CN(C(=O)N3N=CC[C@H]3c3cc(F)cc(F)c3)C2)c(F)cn1]

The titled compound 273 was prepared in a yield of 21.2% according to the procedure outlined for compound 110. $^1$H NMR (400 MHz, Chloroform-d) δ 8.23 (d, J=2.4 Hz, 1H), 7.79 (s, 1H), 7.17 (d, J=6.1 Hz, 1H), 6.82-6.65 (m, 4H), 5.61 (m, 2H), 5.27 (dd, J=12.6, 6.8 Hz, 1H), 5.18-5.08 (m, 1H), 4.62 (m, 2H), 4.31 (dd, J=28.8, 10.4 Hz, 2H), 3.35 (ddd, J=18.6, 12.1, 1.7 Hz, 1H), 2.89 (s, 3H), 2.70 (ddd, J=18.7, 6.4, 1.7 Hz, 1H). Mass (m/z) 500.30 $[M+H]^+$ (S)-1-((1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-11H-pyrazol-4-yl)methyl)pyrrolidin-2-one (274)

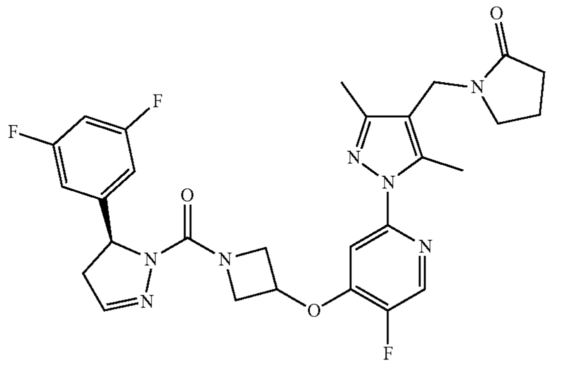 [SMILES: Cc1nn(-c2cc(OC3CN(C(=O)N4N=CC[C@H]4c4cc(F)cc(F)c4)C3)c(F)cn2)c(C)c1CN1CCCC1=O]

The titled compound 274 was prepared in a yield of 28.1% according to the procedure outlined for compound 110. $^1$H NMR (400 MHz, Chloroform-d) δ 8.15 (d, J=2.4 Hz, 1H), 7.18 (d, J=6.2 Hz, 1H), 6.82-6.62 (m, 4H), 5.31-5.23 (m, 1H), 5.148-5.10 (m, 1H), 4.69-4.54 (m, 2H), 4.39-4.22 (m, 2H), 4.32 (s, 2H), 3.35 (ddd, J=18.6, 12.2, 1.7 Hz, 1H), 3.23 (t, J=7.1 Hz, 2H), 2.69 (ddd, J=18.6, 6.4, 1.7 Hz, 1H), 2.57 (s, 3H), 2.41 (t, J=8.1 Hz, 2H), 2.26 (s, 3H), 1.96 (p, J=7.6 Hz, 2H). Mass (m/z) 568.40 $[M+H]^+$ (S)-1-(4-((1-(5-(3,5-difluorophenyl)-4,5-dihydro-1H-pyrazole-1-carbonyl)azetidin-3-yl)oxy)-5-fluoropyrimidin-2-yl)-3,5-dimethyl-1H-pyrazole-4-carboxamide (275)

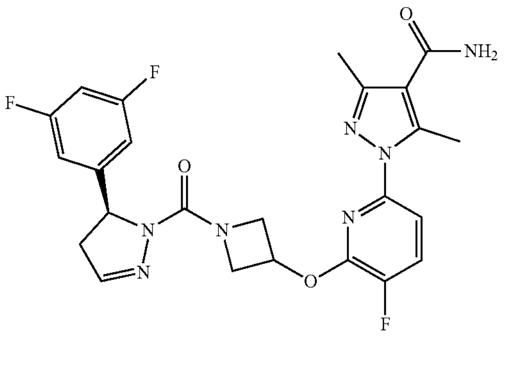 [SMILES: Cc1nn(-c2ccc(F)c(OC3CN(C(=O)N4N=CC[C@H]4c4cc(F)cc(F)c4)C3)n2)c(C)c1C(N)=O]

The titled compound 275 was prepared in a yield of 58.2% according to the procedure outlined for compound 110. $^1$H NMR (400 MHz, Chloroform-d) δ 7.53 (dd, J=9.1, 8.4 Hz, 1H), 7.37 (dd, J=8.4, 2.7 Hz, 1H), 6.79-6.74 (m, 3H), 6.72-6.65 (m, 1H), 5.69 (s, 2H), 5.40-5.34 (m, 1H), 5.27 (dd, J=12.2, 6.5 Hz, 1H), 4.65-4.52 (m, 2H), 4.38-4.22 (m, 2H), 3.34 (ddd, J=18.6, 12.2, 1.7 Hz, 1H), 2.77 (s, 3H), 2.69 (ddd, J=18.6, 6.5, 1.7 Hz, 1H), 2.48 (s, 3H). Mass (m/z) 514.3 $[M+H]^+$ (S)-1-(4-((1-(5-(3,5-difluorophenyl)-4,5-dihydro-1H-pyrazole-1-carbonyl)azetidin-3-yl)oxy)-5-fluoropyrimidin-2-yl)-3,5-dimethyl-1H-pyrazole-4-carboxamide (276)

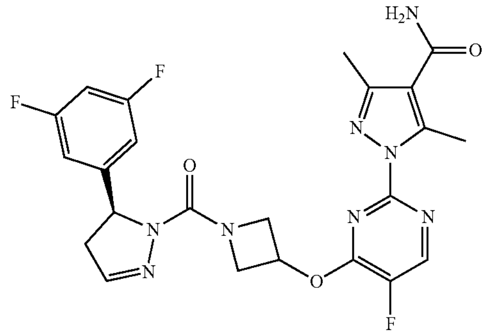 [SMILES: Cc1nn(-c2ncc(F)c(OC3CN(C(=O)N4N=CC[C@H]4c4cc(F)cc(F)c4)C3)n2)c(C)c1C(N)=O]

The titled compound 276 was prepared in a yield of 82.3% according to the procedure outlined for compound 110. $^1$H NMR (400 MHz, Chloroform-d) δ 8.46 (s, 1H), 6.84-6.64 (m, 4H), 5.62 (s, 2H), 5.52 (tt, J=6.6, 4.0 Hz, 1H), 5.26 (dd, J=12.2, 6.4 Hz, 1H), 4.70-4.55 (m, 2H), 4.31 (dd, J=28.4, 10.5 Hz, 2H), 3.35 (ddd, J=18.6, 12.2, 1.7 Hz, 1H), 2. 2.84 (s, 3H), 2.70 (ddd, J=18.6, 6.5, 1.7 Hz, 1H), 2.52 (s, 3H). Mass (m/z) 515.4 $[M+H]^+$.

1-(4-((1-(5-(3,5-difluorophenyl)-4,5-dihydro-1H-pyrazole-1-carbonyl-5-d)azetidin-3-yl)oxy)-5-fluoropyridin-2-yl)-3,5-dimethyl-1H-pyrazole-4-carboxamide (277)

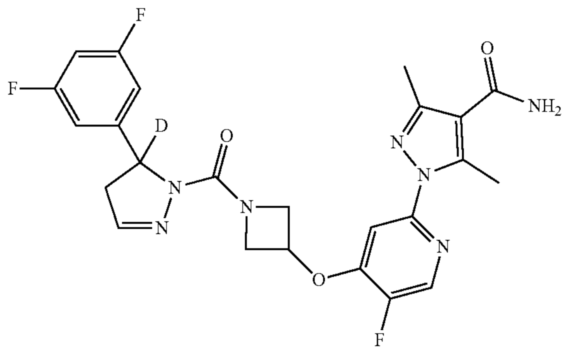 [SMILES: [2H]C1(c2cc(F)cc(F)c2)CC=NN1C(=O)N1CC(Oc2cc(-n3nc(C)c(C(N)=O)c3C)ncc2F)C1]

The titled compound 277 was prepared in a yield of 26% according to the procedure outlined for compound 110. Mass (m/z) 515.1 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)acetic acid (278)

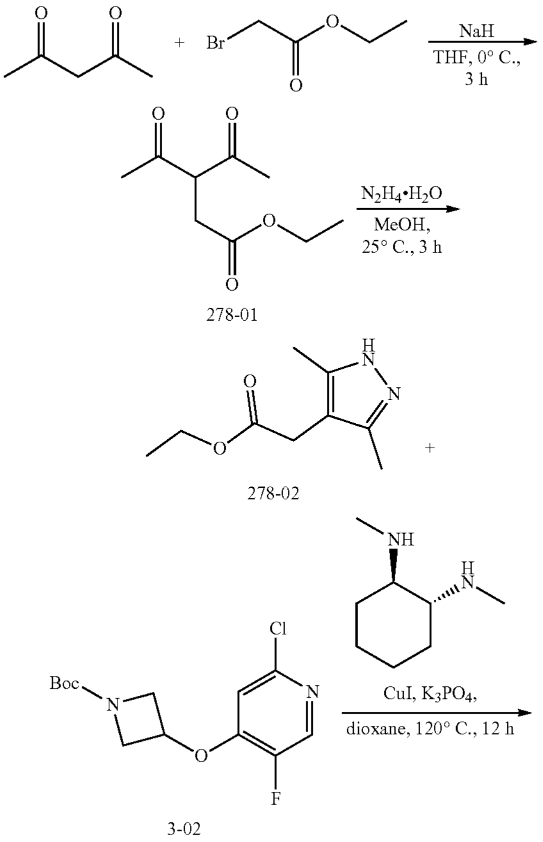

-continued

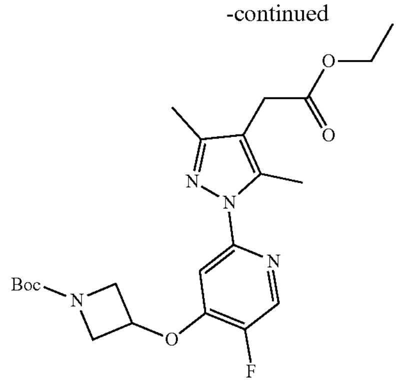

278-03

TFA, $CH_2Cl_2$

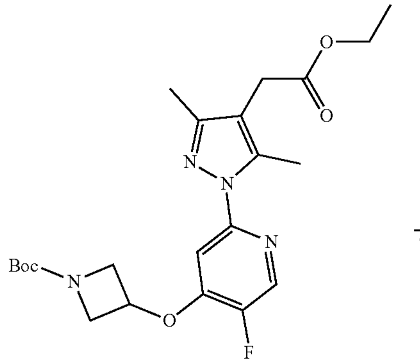

278-04

1-02, TEA

THF, DCM

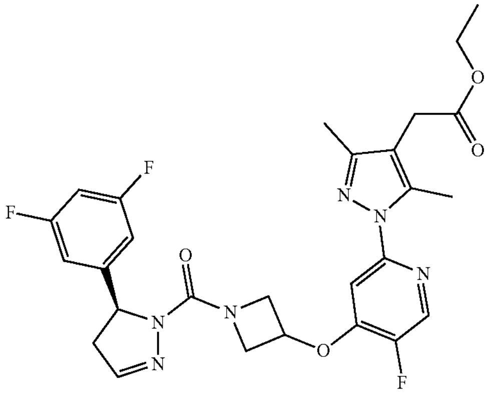

278-05

KOH

EtOH, $H_2O$,

65° C., 30 min

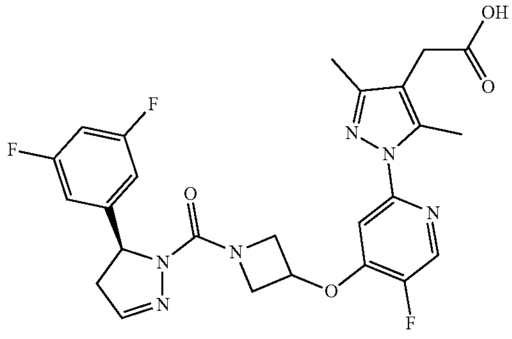

278

Step 1: Pentane-2,4-dione (10 g, 100 mmol) was dissolved in 100 ml of dry THF, NaH (3.6 g, 150 mmol) was added to the above solution at 0° C., the mixture was stirred for 1 h. Then ethyl 2-bromoacetate (16.7 g, 100 mmol) was added to the above solution, the mixture was stirred for 3 h. The mixture was added water and extracted with EA, washed with brine, dried ($Na_2SO_4$), and concentrated in vacuo. Purification by silica gel chromatography gave compound 278-01 (15 g, 80.6%) as a yellow oil. Mass (m/z) 186.2 $[M+H]^+$.

Step 2: 278-01 (15 g, 80.6 mmol), $N_2H4$-$H_2O$ (4 g, 120 mmol) were placed in MeOH (200 mL). The mixture was stirred rt for 3 h, was added water and extracted with DCM, washed with brine, dried ($Na_2SO_4$), and concentrated in vacuo. Purification by silica gel chromatography to give the titled compound 278-02 (10 g, 79.4%) as a yellow oil. Mass (m/z) 183.2 $[M+H]^+$.

Step 3: 278-02 (10 g, 33.1 mmol) and 3-02 (10 g, 54 mmol) was dissolved in 200 mL of dry dioxane, CuI (10.7 g, 56.3 mmol), $K_3PO_4$ (12 g, 56.3 mmol) and (1R,2R)—N1,N2-dimethylcyclohexane-1,2-diamine (7.9 g, 56.3 mmol) was added to the above solution, the mixture was stirred for 12 h at 120° C. Water was added and extracted with EA, washed with brine, dried ($Na_2SO_4$), and concentrated in vacuo. Purification by silica gel chromatography gave the compound 278-03 (6 g, 40.5%). Mass (m/z) 449.2 $[M+H]^+$.

Step 4: 278-03 (1 g, 2.23 mmol) was dissolved in 10 mL of DCM, trifluoroacetic acid (1 mL) was added, the mixture was stirred at r.t. for 30 min. Concentrated to give the desired product 278-04, which was used for next step without further purification.

Step 5: 278-04 (crude), 1-02 (616 mg, 2.23 mmol) and TEA (1 mL) were dissolved in THE (30 mL) DMF (5 mL) and stirred at 65° C. for 6 h. The mixture was extracted with EA, washed with brine, dried ($Na_2SO_4$), and concentrated in vacuo. Purification by silica gel chromatography to give the titled compound 278-05 (600 mg, 49.5%). Mass (m/z) 556.4 $[M+H]^+$.

Step 6: 278-05 (600 mg, 1.08 mmol), were dissolved in EtOH (10 mL), KOH (5 mL, 2M) was added, stirred at 65° C. for 12 h. Water and was added and extracted with EA, washed with brine, dried ($Na_2SO_4$), and concentrated in vacuo. purification by prep-HPLC to give the titled compound 278 (300 mg, 52.6%). $^1H$ NMR (400 MHz, DMSO-$d_6$) δ 8.35 (d, J=2.6 Hz, 11H), 7.19 (d, J=6.3 Hz, 11H), 7.08 (tt, J=9.3, 2.4 Hz, 11H), 7.00-6.99 (m, 1H), 6.92-6.87 (m, 2H), 5.29 (tt, J=6.5, 3.5 Hz, 1H), 5.21 (dd, J=12.1, 6.6 Hz, 1H), 4.49 (s, 2H), 4.05 (s, 2H), 3.42-3.35 (m, 1H), 3.33 (s, 2H), 2.66-2.57 (m, 1H), 2.42 (s, 3H), 2.12 (s, 3H). Mass (m/z) 528.4 $[M+H]^+$.

(S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)-2-methylpropanoic acid (279)

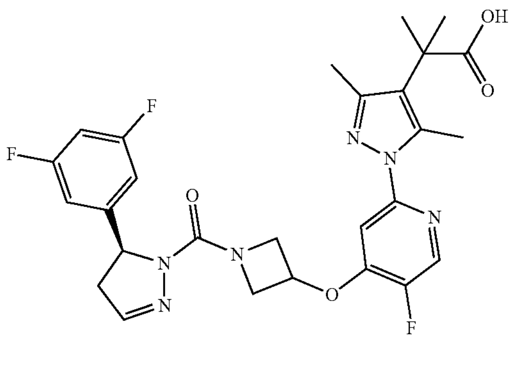 [SMILES: Cc1nn(-c2cc(OC3CN(C(=O)N4N=CC[C@H]4c4cc(F)cc(F)c4)C3)c(F)cn2)c(C)c1C(C)(C)C(=O)O]

The titled compound 279 was prepared in a yield of 15.8% according to the procedure outlined for compound 110. $^1$H NMR (400 MHz, DMSO-$d_6$) δ 8.37 (d, J=2.7 Hz, 11H), 7.15 (d, J=6.3 Hz, 11H), 7.08 (tt, J=9.3, 2.4 Hz, 1H), 7.01-6.99 (m, 1H), 6.93-6.83 (m, 2H), 5.28 (dq, J=6.4, 3.3, 2.9 Hz, 1H), 5.21 (dd, J=12.1, 6.6 Hz, 1H), 4.48 (s, 2H), 4.04 (s, 2H), 3.35-3.20 (m, 1H), 2.65-2.58 (m, 1H), 2.35 (s, 3H), 2.21 (s, 3H), 1.45 (s, 6H). Mass (m/z) 557.4 [M+H]$^+$ (S)-2-(1-(4-((1-(5-(3,5-difluorophenyl)-4,5-dihydro-1H-pyrazole-1-carbonyl)azetidin-3-yl)oxy)-5-fluoropyridin-2-yl)-3,5-dimethyl-1H-pyrazol-4-yl)-2-methylpropanamide (280)

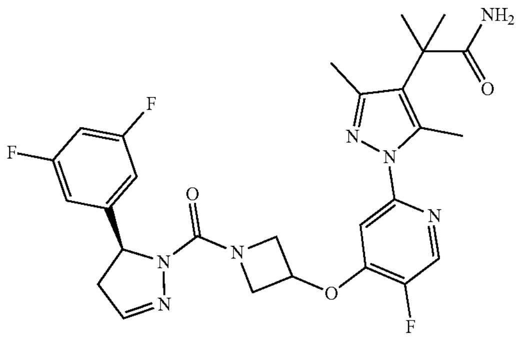 [SMILES: Cc1nn(-c2cc(OC3CN(C(=O)N4N=CC[C@H]4c4cc(F)cc(F)c4)C3)c(F)cn2)c(C)c1C(C)(C)C(N)=O]

The titled compound 280 was prepared in a yield of 16.3% according to the procedure outlined for compound 68. $^1$H NMR (400 MHz, Chloroform-d) δ 8.17 (d, J=2.5 Hz, 1H), 7.10 (d, J=6.1 Hz, 1H), 6.84-6.63 (m, 4H), 5.59 (s, 1H), 5.32 (s, 1H), 5.26 (dd, J=12.2, 6.5 Hz, 1H), 5.14 (tt, J=6.4, 4.0 Hz, 1H), 4.61 (s, 2H), 4.30 (dd, J=32.0, 10.2 Hz, 2H), 3.35 (ddd, J=18.6, 12.2, 1.7 Hz, 1H), 2.69 (ddd, J=18.6, 6.5, 1.8 Hz, 1H), 2.51 (s, 3H), 2.35 (s, 3H), 1.58 (s, 6H). Mass (m/z) 556.4 [M+H]$^+$.

(S)-1-(4-((1-(5-(3,5-difluorophenyl)-4,5-dihydro-1H-pyrazole-1-carbonyl)azetidin-3-yl)oxy)-5-fluoropyridin-2-yl)-3-ethyl-5-methyl-1H-pyrazole-4-carboxamide (281)

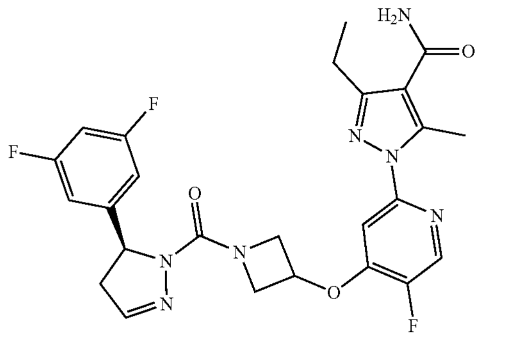 [SMILES: CCc1nn(-c2cc(OC3CN(C(=O)N4N=CC[C@H]4c4cc(F)cc(F)c4)C3)c(F)cn2)c(C)c1C(N)=O]

The titled compound 281 was prepared in a yield of 25.2% according to the procedure outlined for compound 110. $^1$H NMR (400 MHz, Chloroform-d) δ 8.20 (s, 1H), 7.17 (d, J=6.0 Hz, 1H), 6.84-6.65 (m, 4H), 5.58 (s, 2H), 5.26 (dd, J=12.2, 6.4 Hz, 1H), 5.14 (td, J=6.4, 3.3 Hz, 1H), 4.61 (s, 2H), 4.31 (dd, J=34.9, 9.8 Hz, 2H), 3.35 (ddd, J=18.6, 12.2, 1.7 Hz, 1H), 2.85 (q, J=7.5 Hz, 2H), 2.78 (s, 3H), 2.70 (ddd, J=18.6, 6.4, 1.7 Hz, 1H), 1.31 (t, J=7.5 Hz, 3H). Mass (m/z) 510.1 [M+H]$^+$.

Protocol for HT29 Cells 0FBS Assay In Vitro

1. Materials

Cell line: HT-29 (ATCC® HTB-38™)

Culture medium: McCOY's 5 A, Gibco, Cat No. 16600-082

FBS, Gibco, Cat No. 10099-141C

Trypsin: Gibco, Cat No. 25200-056

DMSO: Sigma, Cat No. 67-68-5, 1 L

Assay plate: Corning #3903

Compound dilution plate: Corning #3357

Inducers: TNFα, GenScript, Cat No. ZO1001-50,

SmacM, Cat. No., HY-15989, MedChemExpress (MCE)

Z_VAD FMK, TargetMol, T6013

Cell Titer-Glo® Luminescent Cell Viability Assay Kit: Promega, Cat No. G7573

EnVision: PerkinElmer, 2105-0010

2. Cell Seeding of HT-29 Cells

1) HT-29 cells were checked every day to make sure they are healthy and growing as expected. They were split sub-culturing when were approximately 80% confluent.
2) First pre-warm the culture medium of McCOY's 5 A medium (Gibco, Cat No. 16600-082) with 10% FBS (Gibco, Cat No. 10099-141C) in 37° C. water bath for at least 30 min.
3) Growing cells to desired level of confluency 80% in a T75 flask, aspirate the medium, and wash with warm PBS two times.
4) Add 2-3 ml fresh warm trypsin (Gibco, Cat No. 25200-056) solution. Transfer the flask to a 37° C. incubator.
5) After 5 minutes, tap the side of the flask, and examine the flask under a microscope for lifting. If necessary, return the cells to the incubator for an additional 5-10 minutes, with occasional tapping, until lifting is complete.
6) Quickly neutralize the trypsin reaction by adding 6-9 ml cell culture medium, then transfer the cells to sterile 15 ml conical tubes. Pellet the cells by centrifugation at 300×g for 7 minutes, then decant the supernatant.
7) Resuspend the cells in fresh cell culture medium. Do cell counting with hemocytometer.
8) Seed 100 μl of 5,000 cells into each well of the sterile 96-well cell culture plate (Corning 3903) and culture overnight at 37° C. with 5% C02.

3. Compounds Titration and Treatment of HT-29 Cells

1) All batches of compounds (CPDs) (e.g., compound 1-281) were dissolved in DMSO (Dimethyl sulfoxide) as 20 mM stock solution.
2) Take 3 ul 20 mM stock solution of CPDs to 27 ul DMSO and mix well, continue the titration ratio of 1:3 (20 ul CPDs+40 ul DMSO), e.g., to give solutions of CPDS at 6.6 mM, 2.2 mM, etc., till the 10 points end.
3) Take out assay plates with HT-29 cells from incubator, remove all culture medium then wash 1 time with 1×PBS, and change fresh McCOY's 5 A medium of FBS free with a cocktail of TNF-α (10 ng/ml), the SMAC mimetic (6 uM) and zVAD-FMK (10 μM) to stimulate the HT-29 cells to increase pRIPK1 levels and necroptosis.
4) Add 0.5 μL of the diluted compound to the corresponding 96-well assay plates.
5) Incubate the assay plates for 20 hours at 37° C. with 5% C02.

4. Performing Cell Viability Detection of HT-29 Cells after Treated with Compounds 1) The CellTiter-Glo® Luminescent Cell Viability Assay was employed to detect the ATP levels of viable HT-29 cells.
2) Equilibrate the CellTiter-Glo® buffer and the lyophilized substrate to room temperature prior to use.
3) Resuspend the CellTiter-Glo® substrate with CellTiter-Glo® buffer, mix by gently vortexing to obtain a homogeneous solution.
4) Pipette 20 μl the enzyme/substrate mixture by multichannel pipette into the 96-well assay plates from step 5) under the Compounds titration and treatment stage.
5) Place the plates on an orbital shaker and mix the contents for 3 minutes to induce cell lysis.
6) Then allow the plates to incubate at room temperature for 10 minutes to stabilize luminescent signal.
7) Read and record luminescence signal with EnVision.
8) The geometric mean $EC_{50}$ of the compounds were calculated from points response dose with duplicate. RIP1 inhibitory activity of compounds 1-281 is summarized in Tables 2 and 4. In Tables 2 and 4, activity is provided as follows: +++=0.1 nM≤EC50<100 nM; ++=100 nM≤EC50<1000 nM; +=1000 nM≤EC50<10000 nM.

The invention claimed is:

1. A compound of formula I:

I

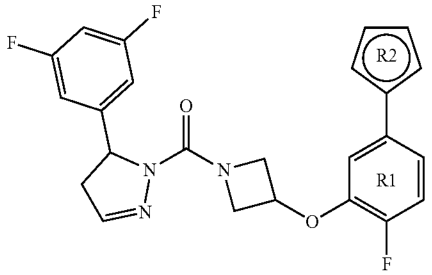

R1 is a 1-F substituted 6-membered aryl, or a 1-F substituted 6-membered heteroaryl comprising 1 or 2 N heteroatoms; and R2 is a 5-membered heteroaryl comprising 1, 2 or 3 N heteroatoms, or 1 or 2 N heteroatoms and an O or S heteroatom, wherein the 5-membered heteroaryl of R2 is substituted with 0-3 substituents independently selected from halogen, —R', —OR', ═O, —NR'R", —SR', —OC(O)R', —C(O)R', —CO2R', —CONR'R", —OC(O)NR'R", —NR"C(O)R', —NR'—C(O)NR"R"', —NR'—SO2NR"', —NR"CO2R', —S(O)R', —SO2R', —SO2NR'R", —NR"SO2R, —CN, —NO2, —CH(Ph) 2, perfluoro(C1-C4)alkoxy, and perfluoro(C1-C4)alkyl, wherein R', R" and R"' each independently refer to hydrogen, unsubstituted C1-C8 alkyl, unsubstituted C1-C8 heteroalkyl, C1-C8 alkyl substituted with one to three halogens, C1-C8 heteroalkyl substituted with one to three halogens, unsubstituted C6-C14 aryl, C6-C14 aryl substituted with one to three halogens or unsubstituted aryl-(C1-C4)alkyl groups, and wherein when R' and R" are attached to the same nitrogen atom, they are optionally combined with the nitrogen atom to form a 5-, 6- or 7-membered ring;

or a salt, hydrate or stereoisomer thereof.

2. The compound, salt, hydrate, or stereoisomer of claim 1 wherein:

R1 comprises N2, N4 or N2/N4;

R2 comprises N1, N1/N2, N2/N3, N3/N4, N2/N5; N2/N4, S2/N4, N2/S4, S3/N4, N2/S3, N3/O4, N2/N3/S5, N2/N3/O5, N2/N3/N5 or N2/N3/N4; or any combination of the foregoing substituents.

3. The compound, salt, hydrate, or stereoisomer of claim 1, wherein the compound has one of the following structural formula II(1):

II(1)

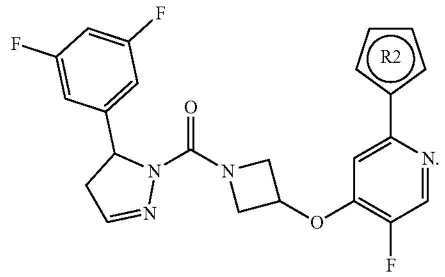

4. The compound, salt, hydrate, or stereoisomer of claim 1, wherein the compound has one of the following structural formula II(2):

II(2)

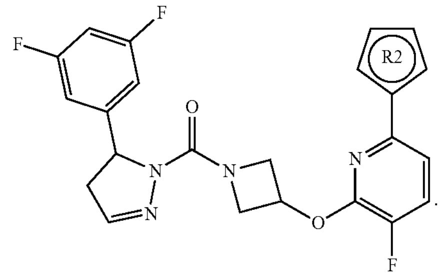

5. The compound, salt, hydrate, or stereoisomer of claim 1, wherein the compound has one of the following structural formula II(3):

II(3)

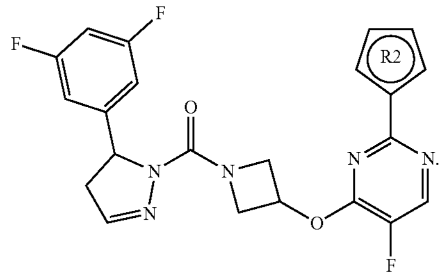

6. The compound, salt, hydrate, or stereoisomer of claim 1, wherein the compound has one of the following structural formula II(4):

II(4)

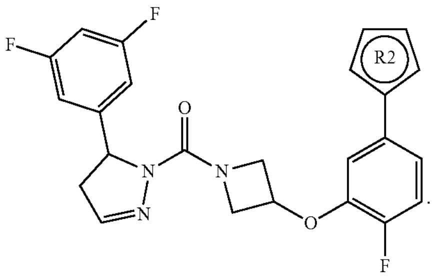

7. The compound, salt, hydrate, or stereoisomer of claim 1, wherein the compound has one of the following structural formula II(5):

II(5)

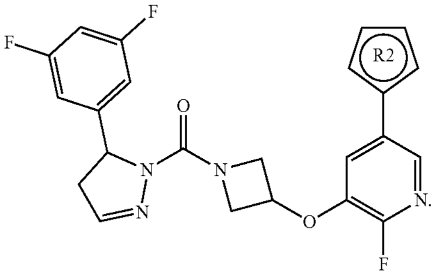

8. The compound, salt, hydrate, or stereoisomer of claim 1, wherein R2 is

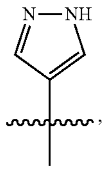,
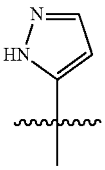,
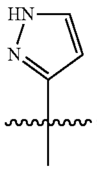,
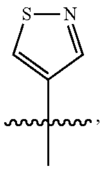,
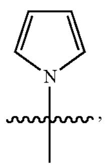,
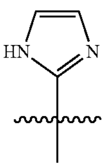,
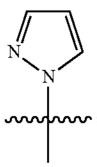,
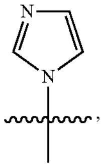,
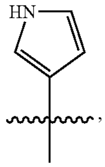,
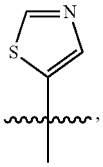,
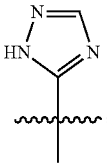,
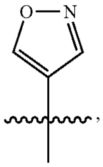,
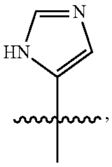,
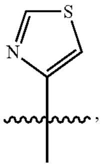,
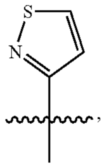,
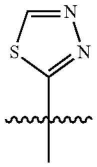,
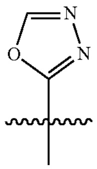,
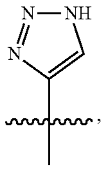,
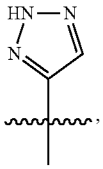, -continued

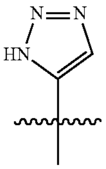, or 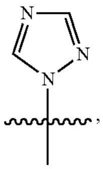, substituted with the 0-3 substituents of claim 1.

9. The compound, salt, hydrate, or stereoisomer of claim 1, wherein the compound has one of the following structural formula III(1):

III(1)

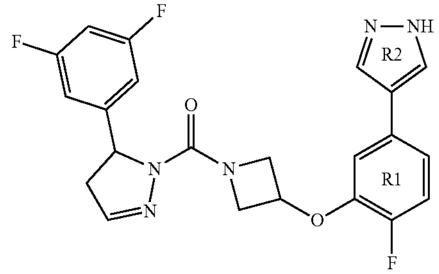

wherein R1 is a 1-F substituted 6-membered aryl, or a 1-F substituted 6-membered heteroaryl comprising 1 or 2 N heteroatoms; and wherein R2 is a 5-membered heteroaryl as set forth in structural formula III(1), substituted with the 0-3 substituents of claim 1.

10. The compound, salt, hydrate, or stereoisomer of claim 1, wherein the compound has one of the following structural formula III(2):

III(2)

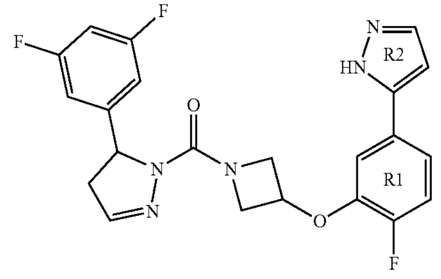

wherein R1 is a 1-F substituted 6-membered aryl, or a 1-F substituted 6-membered heteroaryl comprising 1 or 2 N heteroatoms; and wherein R2 is a 5-membered heteroaryl as set forth in structural formula III(2), substituted with the 0-3 substituents of claim 1.

11. The compound, salt, hydrate, or stereoisomer of claim 1, wherein the compound has one of the following structural formula III(3):

III(3)

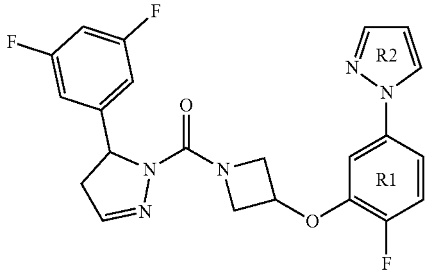

wherein R1 is a 1-F substituted 6-membered aryl, or a substituted 6-membered heteroaryl comprising 1 or 2 N heteroatoms; and wherein R2 is a 5-membered heteroaryl as set forth in structural formula III(3), substituted with the 0-3 substituents of claim 1.

12. The compound, salt, hydrate, or stereoisomer of claim 1, wherein the compound has one of the following structural formulae IV(1)-IV(5):

IV(1)

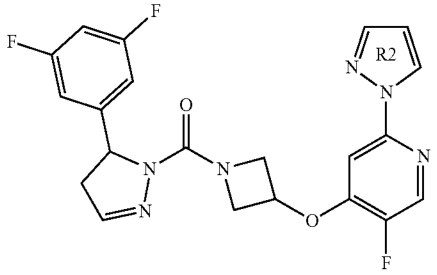

IV(2)

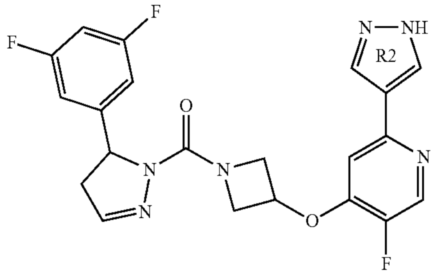

IV(3)

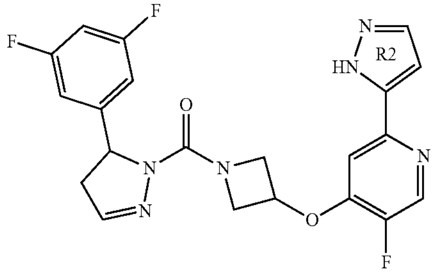

-continued

IV(4)

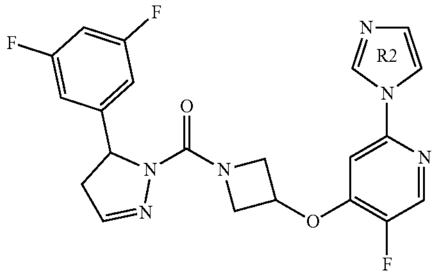

IV(5)

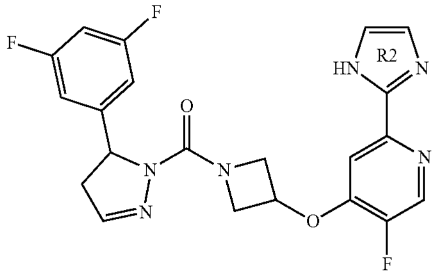

wherein R2 is a 5-membered heteroaryl as set forth in structural formulae IV(1)-IV(5), substituted with the 0-3 substituents of claim 1.

13. The compound, salt, hydrate, or stereoisomer of claim 1, wherein the compound has one of the following structural formulae IV(6)-IV(10):

IV(6)

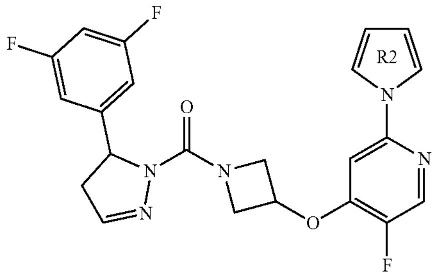

IV(7)

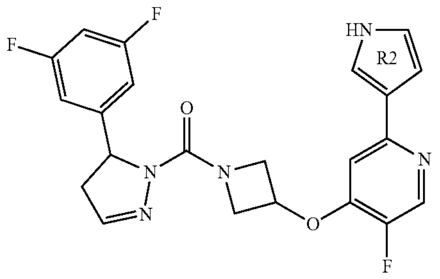

IV(8)

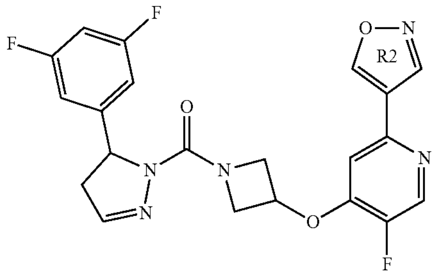

-continued

IV(9)

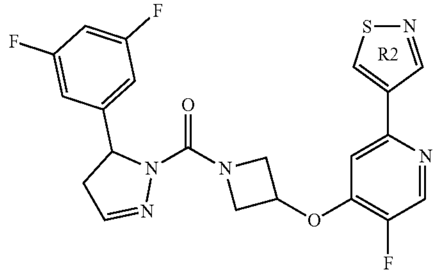

IV(10)

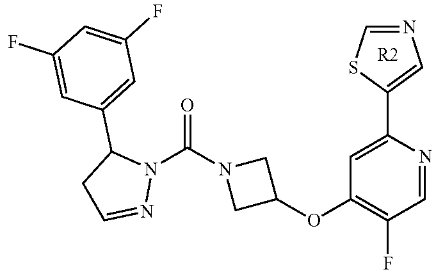

wherein R2 is a 5-membered heteroaryl as set forth in structural formulae IV(6)-IV(10), substituted with the 0-3 substituents of claim 1.

14. The compound, salt, hydrate, or stereoisomer of claim 1, wherein the compound has one of the following structural formulae IV(11)-IV(15):

IV(11)

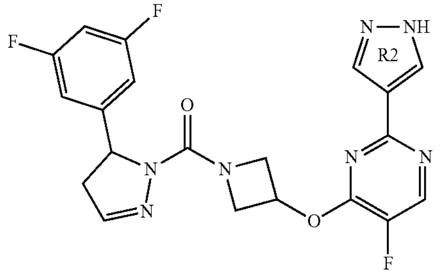

IV(12)

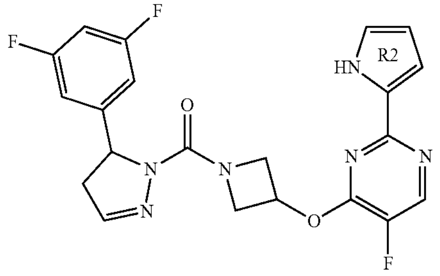

IV(13)

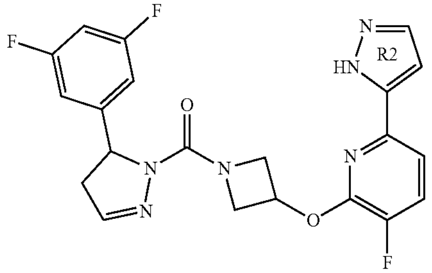

-continued

IV(14)

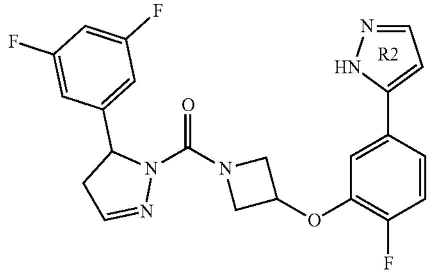

IV(15)

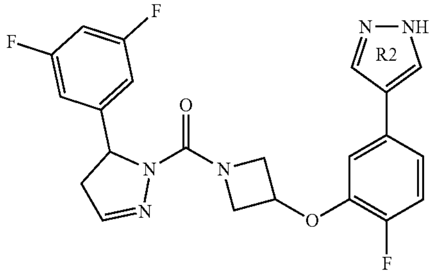

wherein R2 is a 5-membered heteroaryl as set forth in structural formulae IV(11)-IV(15), substituted with the 0-3 substituents of claim 1.

15. A compound of formula I:

I

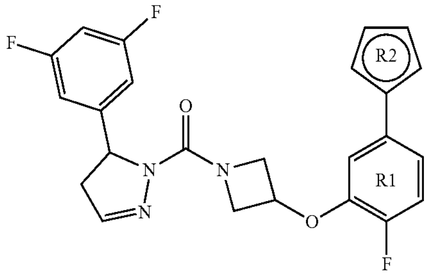

or a salt, hydrate or stereoisomer thereof;

wherein R1 is a 1-F substituted 6-membered aryl, or a 1-F substituted 6-membered heteroaryl comprising 1 or 2 N heteroatoms; and R2 is a 5-membered heteroaryl comprising 1, 2 or 3 N heteroatoms, or 1 or 2 N heteroatoms and an O or S heteroatom, wherein R2 is substituted with 0-3 $R^a$, wherein $R^a$, for each occurrence, is independently selected from:

halogen, cyano, $C_1$-$C_6$ alkyl, $C_3$-$C_6$ cycloalkyl, 3- to 6-membered heterocyclyl, $C_2$-$C_6$ alkenyl, $C_1$-$C_6$ alkoxy, —C(═O)($C_1$-$C_6$ alkyl), —C(═O)($C_3$-$C_6$ cycloalkyl), —C(═O)(3- to 6-membered heterocyclyl), ═O, —$NO_2$, —C(═O)$OR^s$, —C(═O)$NR^pR^q$, —$NR^pR^q$, —$NR^p$C(═O)$R^s$, —$NR^p$C(═O)$OR^s$, —$NR^p$C(═O)$NR^qR^r$, —$NR^p$S(═O)$_w$$R^s$, —$OR^s$, —OC(═O)$R^s$, —OC(═O)$OR^s$, —OC(═O)$NR^pR^q$, —S(═O)$_w$$R^s$, and —S(═O)$_w$$NR^pR^q$; wherein the $C_1$-$C_6$ alkyl, $C_3$-$C_6$ cycloalkyl, 3- to 6-membered heterocyclyl, $C_2$-$C_6$ alkenyl, and $C_1$-$C_6$ alkoxy of $R^a$, the $C_1$-$C_6$ alkyl of —C(═O)($C_1$-$C_6$ alkyl), the $C_3$-$C_6$ cycloalkyl of —C(═O)($C_3$-$C_6$ cycloalkyl), and the 3- to 6-membered heterocyclyl of —C(═O)(3- to 6-membered heterocyclyl) are each optionally substituted with 1 to 3 groups selected from halogen, cyano, =O, —C(=O)$R^s$, —C(=O)O$R^s$, —C(=O)N$R^pR^q$, —N$R^pR^q$, —N$R^p$C(=O)$R^s$, —N$R^p$C(=O)O$R^s$, —N$R^p$C(=O)N$R^qR^r$, —N$R^p$S(=O)$_w R^s$, —O$R^s$, —OC(=O)$R^s$, —OC(=O)O$R^s$, —OC(=O)N$R^pR^q$, —S(=O)$_w R^s$, —S(=O)$_w$N$R^pR^q$, $C_3$-$C_6$ cycloalkyl, and 3- to 6-membered heterocyclyl; wherein $R^p$, $R^q$, $R^r$, and $R^s$, for each occurrence, are each independently selected from hydrogen, OH, $NH_2$, $C_1$-$C_4$ alkyl, $C_3$-$C_6$ cycloalkyl, and 3- to 6-membered heterocyclyl; wherein the $C_1$-$C_4$ alkyl, $C_3$-$C_6$ cycloalkyl, and 3- to 6-membered heterocyclyl of any one of $R^p$, $R^q$, $R^r$, and $R^s$ are optionally substituted with 1 to 3 groups selected from halogen, cyano, —OH, $C_1$-$C_6$ alkyl, —O($C_1$-$C_6$ alkyl), —C(=O)N($C_1$-$C_6$ alkyl)($C_1$-$C_6$ alkyl), —C(=O)NH ($C_1$-$C_6$ alkyl), —C(=O)(3- to 6-membered heterocyclyl), —C(=O)($C_3$-$C_6$ cycloalkyl), $C_3$-$C_6$ cycloalkyl, phenyl, and 3- to 6-membered heterocyclyl; and wherein w is an integer selected from 0, 1, and 2.

16. The compound, salt, hydrate or stereoisomer of claim 15, wherein R2 is substituted with 1-3 $R^a$, wherein $R^a$, for each occurrence, is independently selected from: halogen; cyano; 4- to 6-membered heterocyclyl optionally substituted with oxo; —C(=O)($C_1$-$C_6$ alkyl); —C(=O)($C_3$-$C_6$ cycloalkyl); —C(=O)(4- to 6-membered heterocyclyl); 3- to 4-membered cycloalkyl;

—C(=O)O$R^s$, wherein $R^s$ is H or $C_1$-$C_3$ alkyl;

$C_1$-$C_3$ alkyl, optionally substituted with OH, $NH_2$, cyano, halogen, $C_1$-$C_3$ alkoxyl, 3- to 4-membered cycloalkyl, 4- to 6-membered heterocyclyl, —C(=O)OH, —C(=O)(4- to 6-membered heterocyclyl), —C(=O) NH$(CH_2)_2$OH, or —C(=O)$NH_2$;

—C(=O)N$R^pR^q$, wherein $R^p$ and $R^q$ each are independently selected from H; OH; CN; 4- to 6-membered heterocyclyl; $C_1$-$C_3$ alkyl optionally substituted with OH; and 3- to 4-membered cycloalkyl optionally substituted with OH;

—N$R^pR^q$, wherein $R^p$ and $R^q$ each are independently selected from H, OH, —C(=O)$CH_3$, and $C_1$-$C_3$ alkyl optionally substituted with OH, 3- to 4-membered cycloalkyl, or 6-membered heterocyclyl;

—N$R^p$C(=O)N$R^qR^r$, wherein $R^p$, $R^q$ and $R^r$ each are independently selected from H and $C_1$-$C_3$ alkyl;

—N$R^p$C(=O)$R^s$, wherein $R^p$ is selected from H and $C_1$-$C_3$ alkyl, and $R^s$ is selected from $C_1$-$C_3$ alkyl and 3- to 4-membered cycloalkyl;

—S(=O)$_w R^s$, wherein $R^s$ is selected from $C_1$-$C_3$ alkyl optionally substituted with phenyl or $NH_2$, and wherein w is 0 or 2; and —S(=O)$_w$N$R^pR^q$, wherein $R^p$ and $R^q$ each are independently selected from H, 3- to 6-membered cycloalkyl, 4- to 6-membered heterocyclyl, and $C_1$-$C_3$ alkyl optionally substituted with OH, $C_1$-$C_3$ alkoxyl, or phenyl, and wherein w is 2.

17. The compound, salt, hydrate, or stereoisomer of claim 15, wherein R2 is substituted with 1-3 $R^a$, wherein $R^a$, for each occurrence, is independently selected from methyl, ethyl, —$NH_2$, —CN, —$OCH_3$, —O$(CH_2)_2$N$(CH_3)_2$, —$NHCH_3$, —O$(CH_2)_2$$OCH_3$, —N$(CH_3)_2$, —NH$(CH_2)$ $OCH_3$, —NHC(=O)$CH_3$, —NHC(=O)$CH_2CH_3$, —NHC (=O)CH$(CH_3)_2$, —NHC(=O)$CH_2$CH$(CH_3)_2$, —NHC$H_2$C (=O)NHC$H_3$, —NHC$H_2$C(=O)NHC$H_3$,

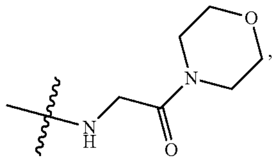 [SMILES: *NCC(=O)N1CCOCC1]

—NHC$H_2$C(=O)N$(CH_3)_2$, —C(=O)$OCH_3$, —C(=O) OH, —C(=O)$CH_3$, —C(=O)$NH_2$, —C(=O)NHC$H_3$, —C(=O)NH$(CH_2)_2$N$(CH_3)_2$, —C(=O)NHC$H_2$N$(CH_3)_2$, —C(=O)NHC$H_2CH_3$,

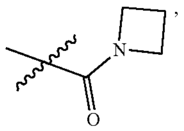

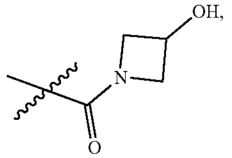

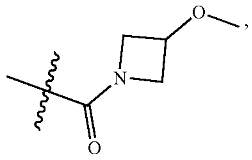

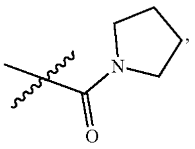

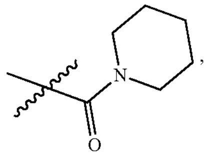

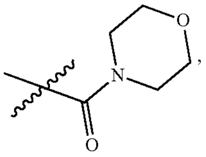

—$CH_2$OH, —$CH_2$N$(CH_3)_2$, —$CH_2OCH_3$, —F, —Cl, —$(CH_2)_2OCH_3$, —$CH_2$C(=O)$NH_2$, —$CH_2$C(=O)N$(CH_3)$ 2,

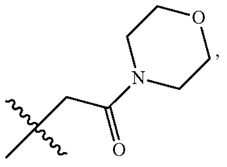 [SMILES: *CC(=O)N1CCOCC1]

—$CH_2$C(=O)NHC$H_3$, —$NO_2$, —$(CH_2)_2$OH, —$CH_2$C (=O)$OCH_3$, —NH$(CH_2)_2$N$(CH_3)_2$,

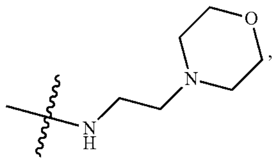 [SMILES: *NCCN1CCOCC1]

—NHC(=O)$CH_2OCH_3$, —NHC(=O)$CH_2$N$(CH_3)_2$,

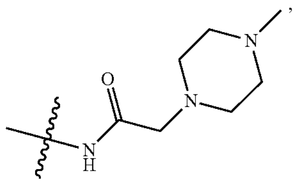 [SMILES: *NC(=O)CN1CCN(C)CC1]
—$NHCH_3$, —$C(=O)OCH_2CH_3$,
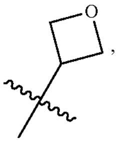
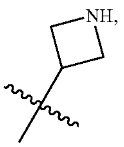
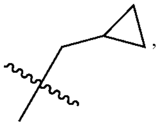
—$C(=O)NHCH(CH_3)_2$,
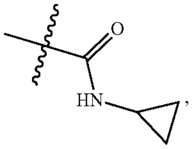 [SMILES: *C(=O)NC1CC1]
—$N(C(=O)CH_3)_2$,
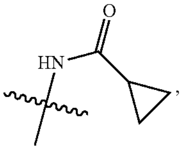
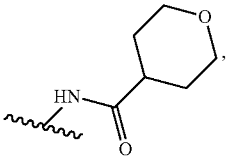
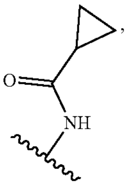
—$NHC(=O)NHCH(CH_3)_2$, —$NHC(=O)NHCH_3$, —$NHCH_2C(=O)NH_2$, —$CH_2CH_2OH$,
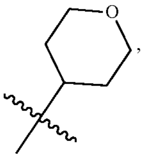 [SMILES: *C1CCOCC1]
—$NH(CH_2)_2CH_3$, —$NHCH(CH_3)_2$,
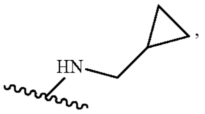
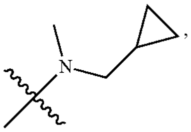
—$NH(CH_3)_2$, —$S(=O)_2CH_2CH_3$, —$CF_3$,
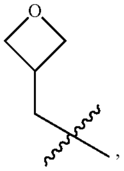 [SMILES: *CC1COC1]
—$C(=O)N(CH_3)_2$, —$SCH_3$, —$S(=O)CH_3$, —$CHOHCH_3$,
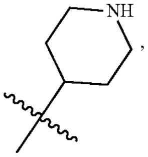 [SMILES: *C1CCNCC1]
—$S(=O)_2CH_3$, —$CH_2F$, —$CH_2NH_2$, —$NH(CH_2)_2OH$,
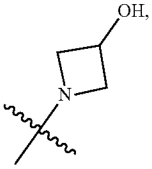 [SMILES: *N1CC(O)C1]
—$C(=O)NH(CH_2)_2OH$,
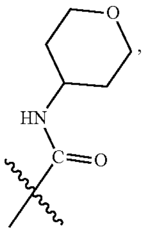
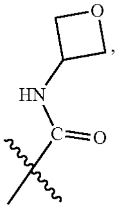
—$S(=O)_2NH_2$,
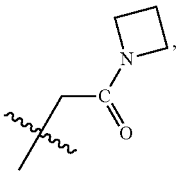 [SMILES: *CC(=O)N1CCC1]
—$CH_2C(=O)NH(CH_2)_2OH$,

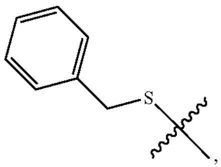 [SMILES: *SCc1ccccc1], $—S(=O)_2NHCH_3$,

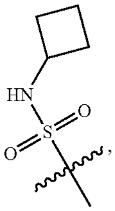, 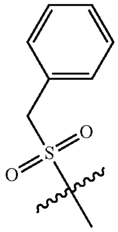, 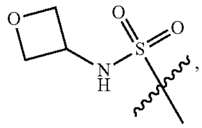,

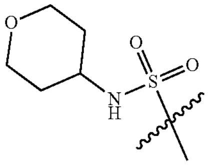, 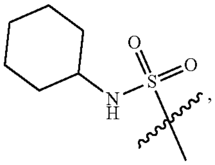,

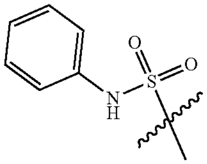, $—S(=O)_2NH(CH_2)_2OH$, $—S(=O)_2NHOCH_3$,

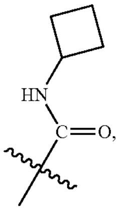

$—C(=O)NHOH$, $—C(=O)NHCNH$,

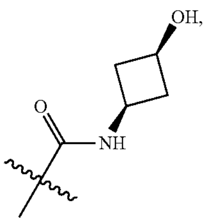 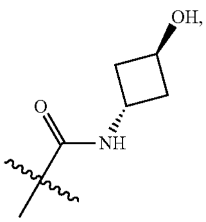

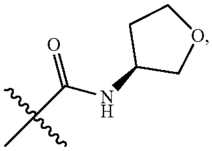 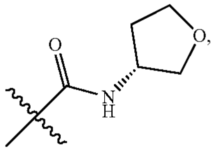

-continued

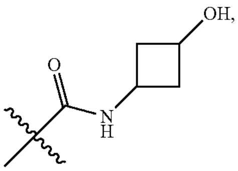 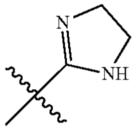, 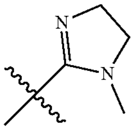,

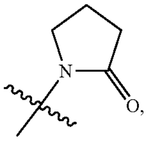

$—CH_2CN$,

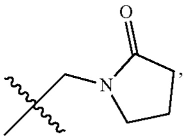 [SMILES: *CN1CCCC1=O], $—CH_2C(=O)OH$, $—C(CH_3)_2C(=O)OH$, and $—C(CH_3)_2C(=O)NH_2$.

18. The compound, salt, hydrate, or stereoisomer of claim 15, wherein R2 is substituted with 1-3 $R^a$, wherein $R^a$, for each occurrence, is independently selected from methyl, ethyl, $—NH_2$, $—NHCH_3$, —CN, $—CH_2CH_2OH$,

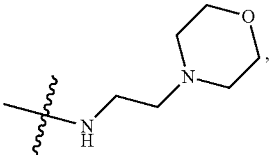 [SMILES: *NCCN1CCOCC1]

$—NHC(=O)CH_3$, $—C(=O)OCH_3$,

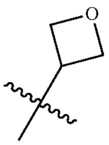, 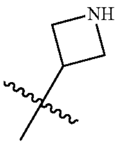, 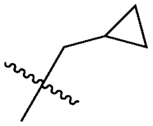

$—N(C=OCH_3)_2$, $—NHCH_2C(=O)NH_2$,

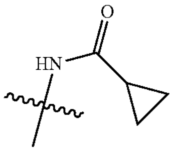, $—C(=O)OCH_2CH_3$, $—NHCH_3$, $—CH_2OCH_3$, $—CH_2CH_2OH$,

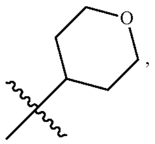 [SMILES: *C1CCOCC1]

—NHCH2CH2OCH3, —$NHCH(CH_3)_2$,

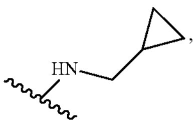 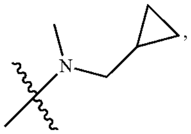

—$N(CH_3)_2$, —$C(=O)N(CH_3)_2$, —$C(=O)NH_2$, —Cl, —$SCH_3$, —$S(=O)_2CH_3$, $CH_2OH$,

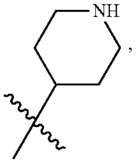

—$C(=O)NHCH_3$, $CH_2F$, —$NHCH_2OH$, —$C(=O)NHCH_2CH_2OH$,

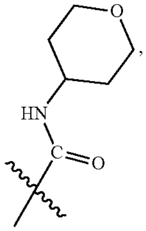 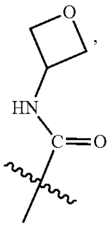

—$S(=O)_2NH_2$, —$CH_2C(=O)NH_2$,

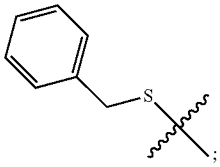 [SMILES: *SCc1ccccc1]

—$C(=O)NHCH_2CH_3$, —$C(=O)OH$,

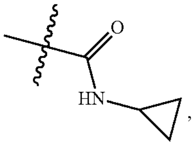 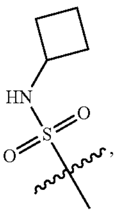 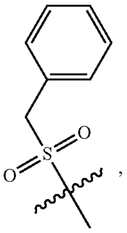

-continued

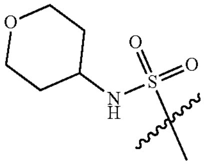 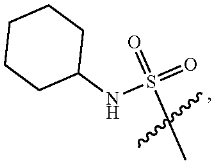

—$C(=O)NHCH_3$, —$S(=O)_2NHOCH_3$,

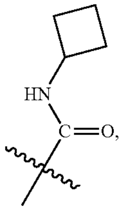 [SMILES: *C(=O)NC1CCC1]

—$C(=O)NHOH$,

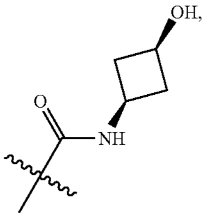 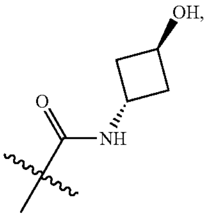

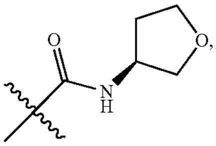 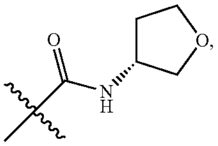

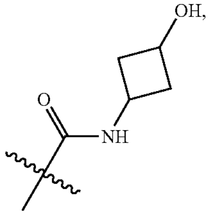

—$C(=O)NHCH_2CH_2OH$, and —$CH_2CN$.

19. The compound, salt, hydrate, or stereoisomer of claim 15, wherein R2 is substituted with 1-3 $R^a$, wherein $R^a$, for each occurrence, is independently selected from methyl, ethyl, —$NH_2$, —$C(=O)NH_2$, —$NHCH_3$, —CN, —$CH_2CN$, —$NHCH_2OH$, —$CH_2NH_2$, —$SCH_3$, $CONHCH_3$, —$SO_2CH_3$, —$CH_2OH$, —Cl, —$N(CH_3)_2$, —$NHCH(CH_3)_2$, —$NHCH_2CH_2OCH_3$, —$CH_2CH_2OH$, —$C(=O)OCH_2CH_3$, —$C(=O)OCH_3$, —$C(=O)OH$, —$S(=O)_2NH_2$, —$CH_2C(=O)NH_2$, —$C(=O)NHCH_2CH_2OH$,

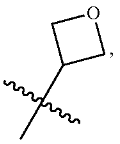 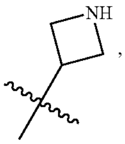 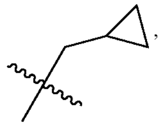

-continued
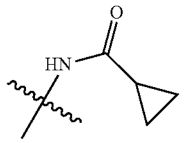, 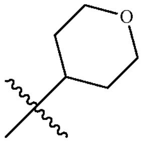, 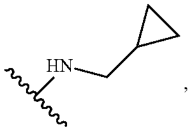,
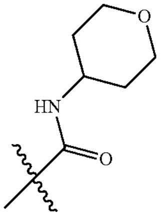, 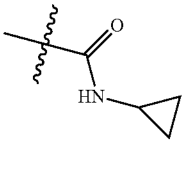, and 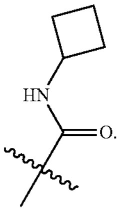.
20. The compound, salt, hydrate or stereoisomer of claim 1, wherein the compound has a structure selected from:
1
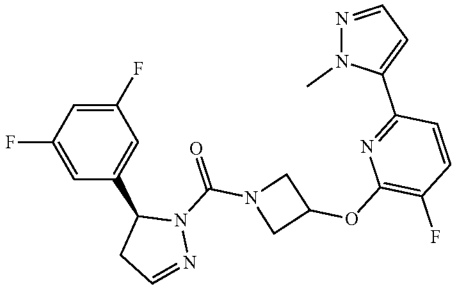
2
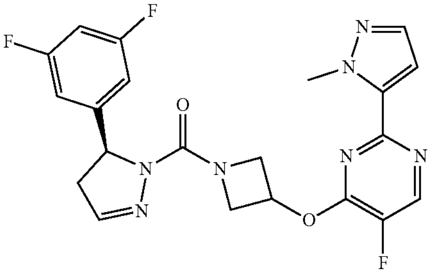
3
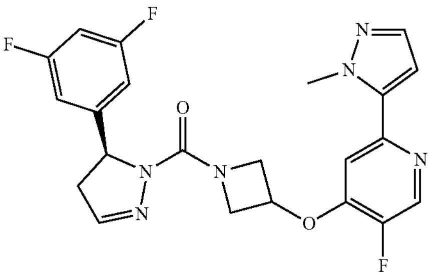
4
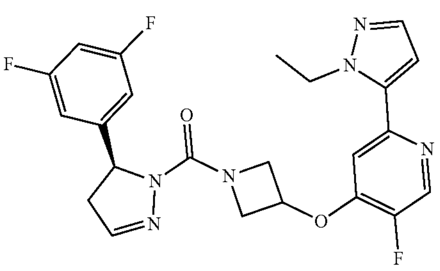
-continued
5
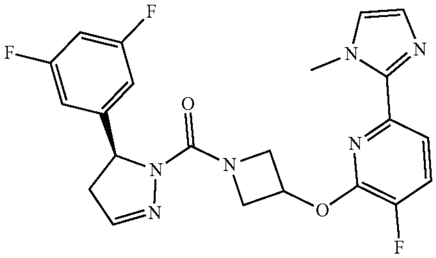
6
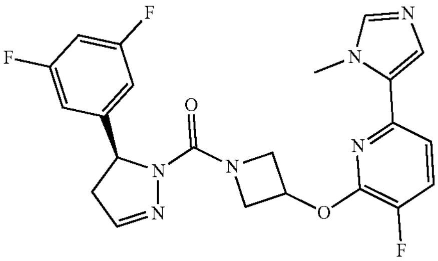
7
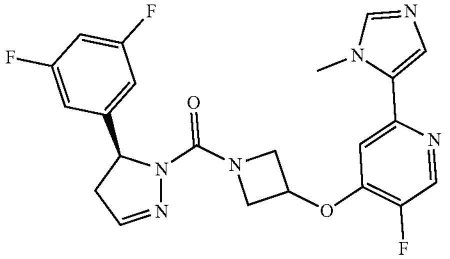
8
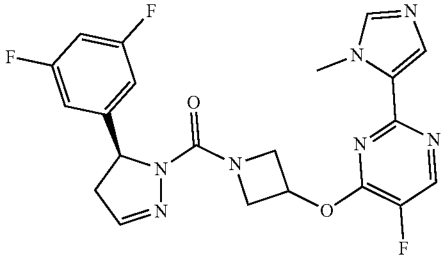
9
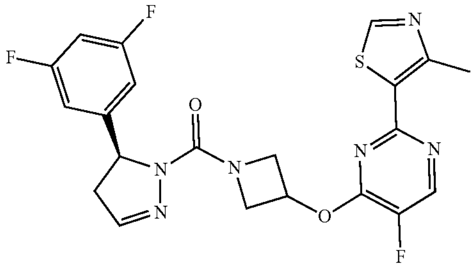
10
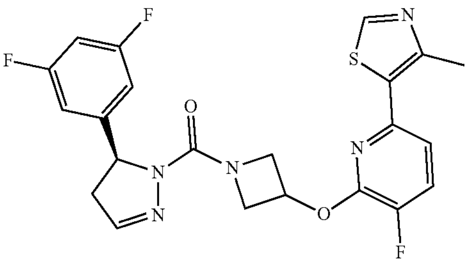

-continued
11
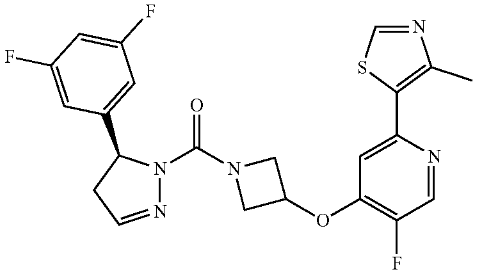
12
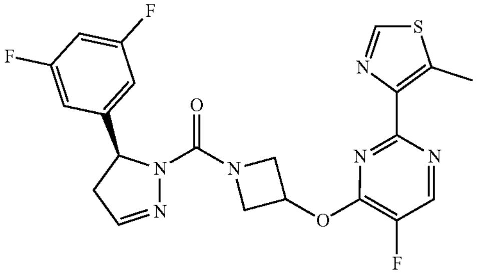
13
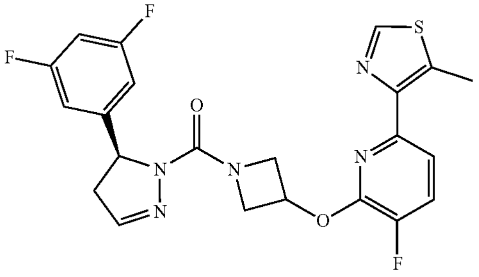
14
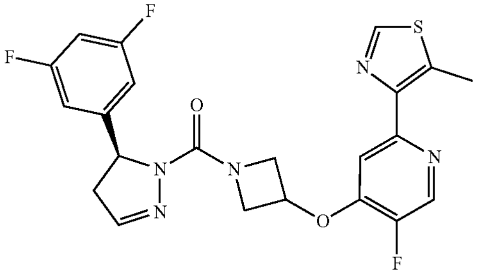
15
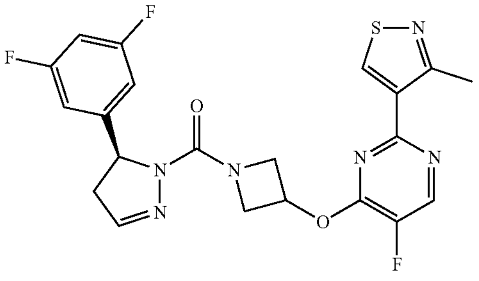
-continued
16
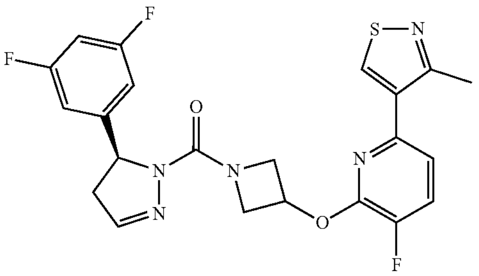
17
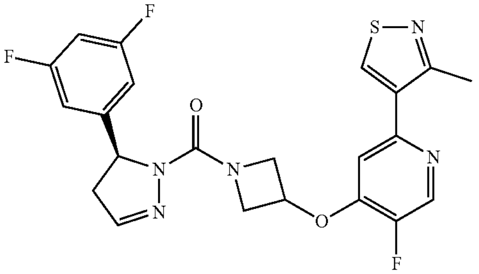
18
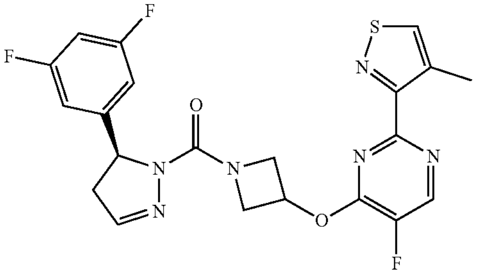
19
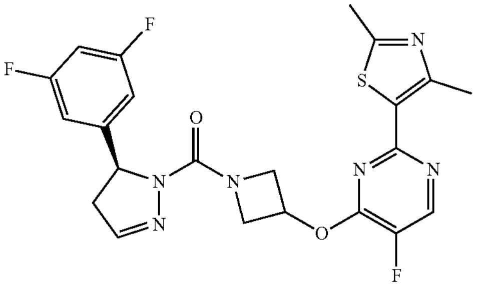
20
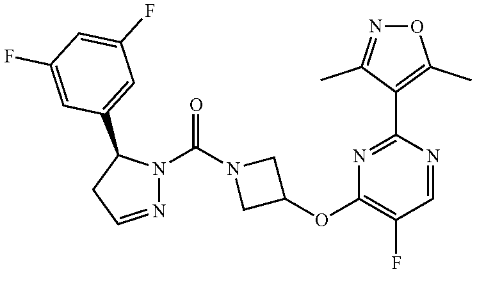

-continued
21
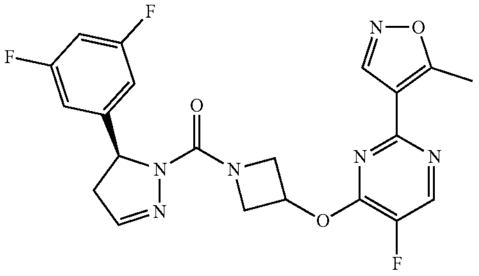
22
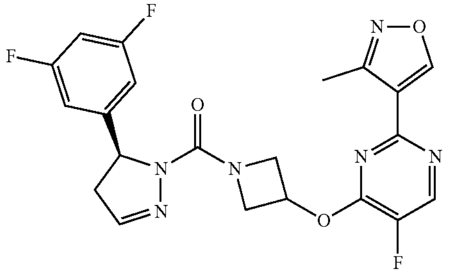
23
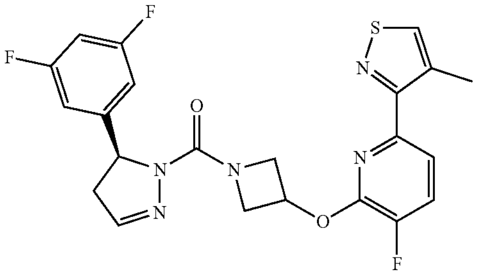
24
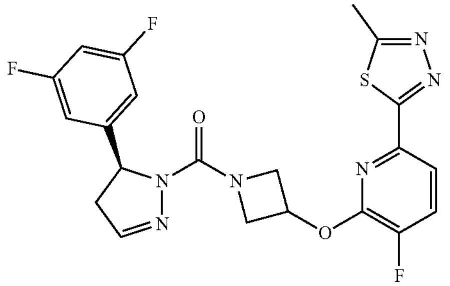
25
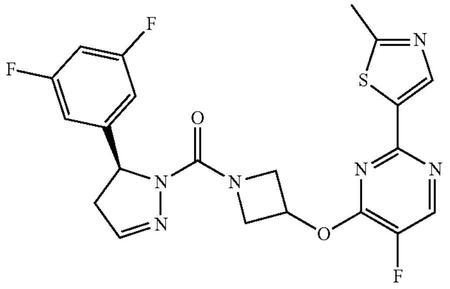
-continued
26
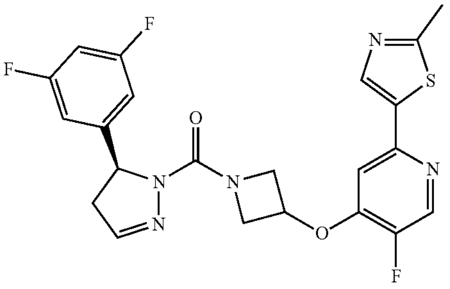
27
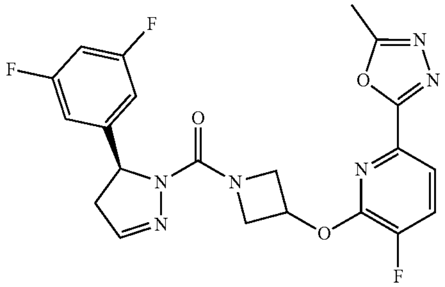
28
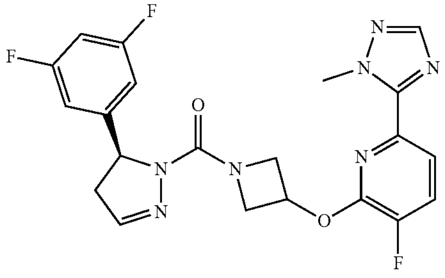
29
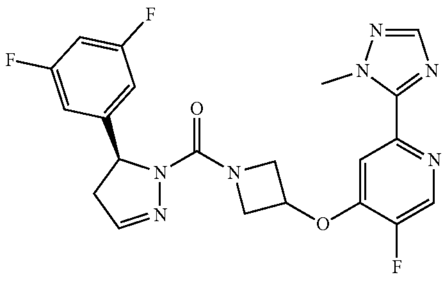
30
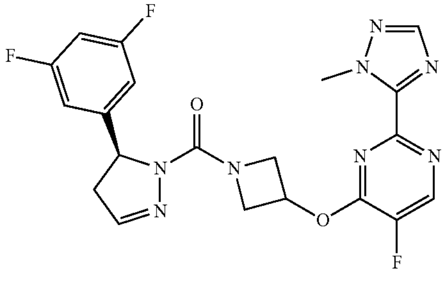

-continued
31
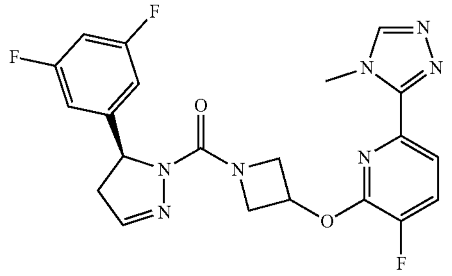
32
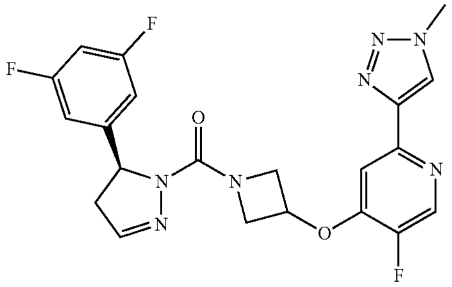
33
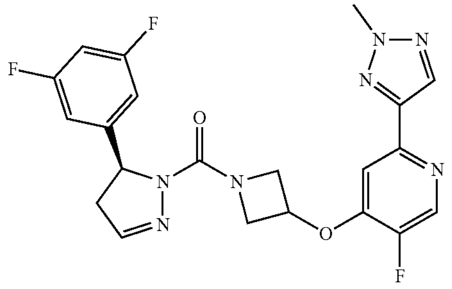
34
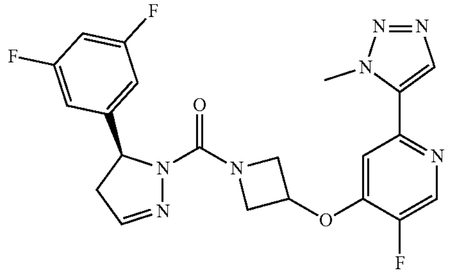
35
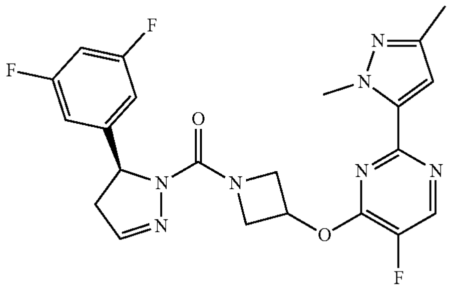
-continued
36
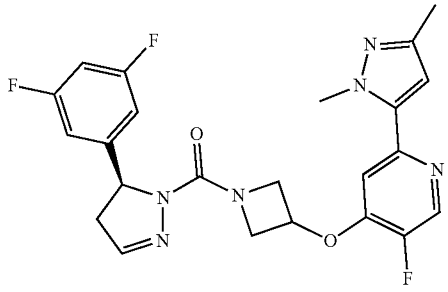
37
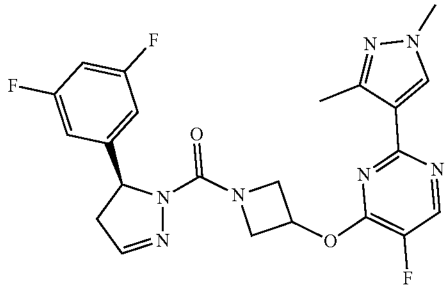
38
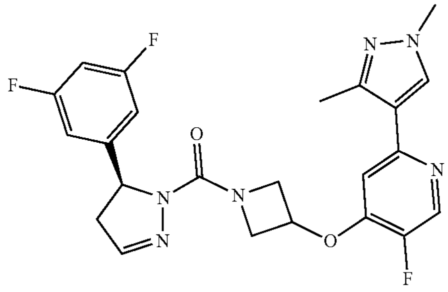
39
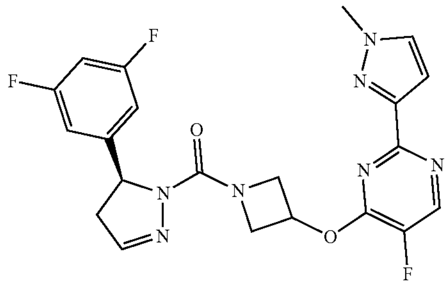
40
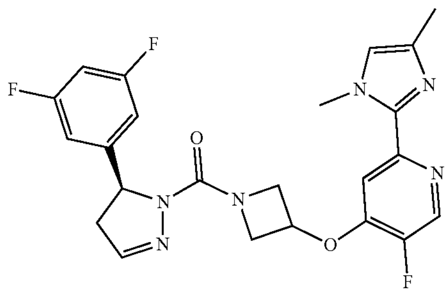

-continued
41
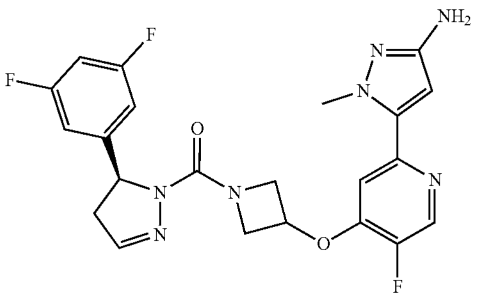
42
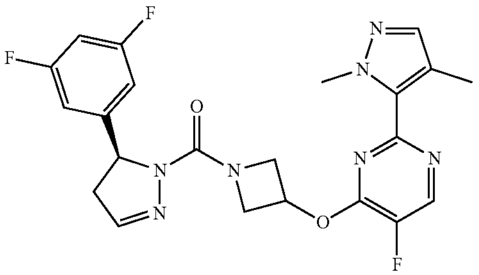
43
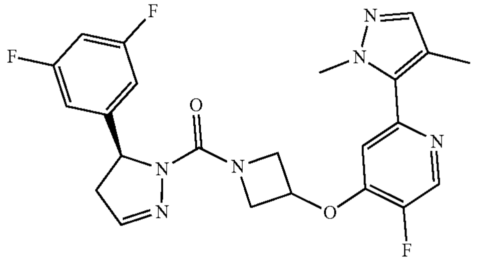
44
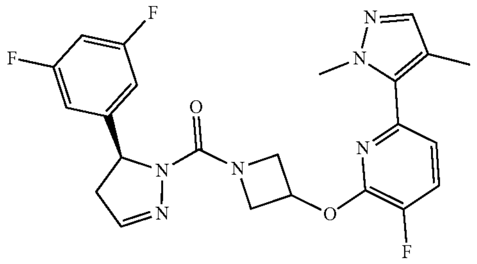
45
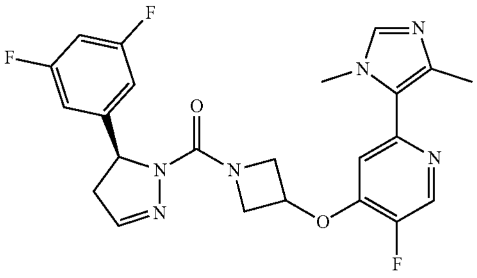
-continued
46
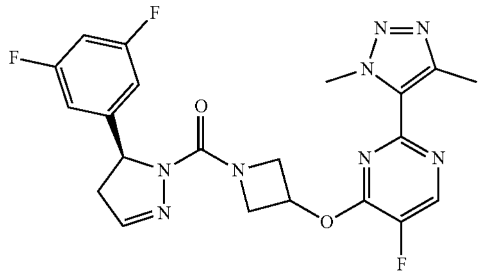
47
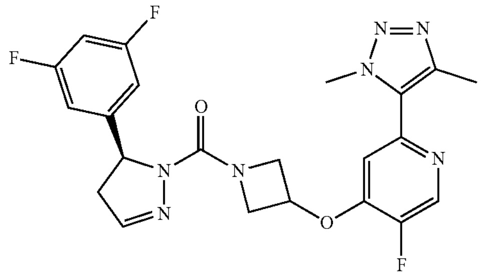
48
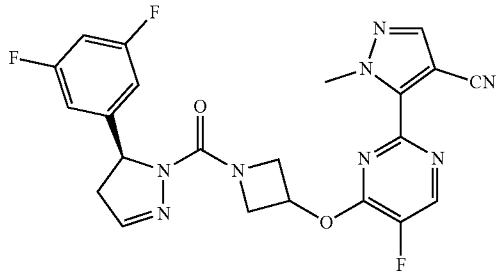
49
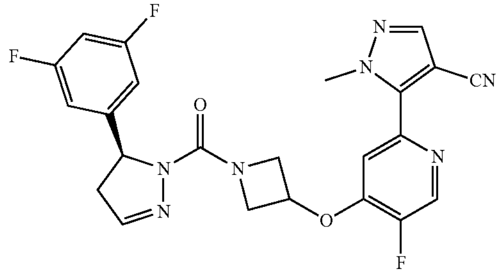
50
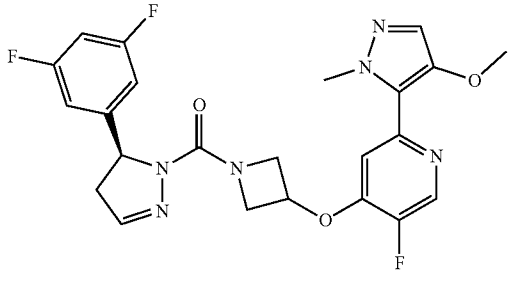

-continued
51
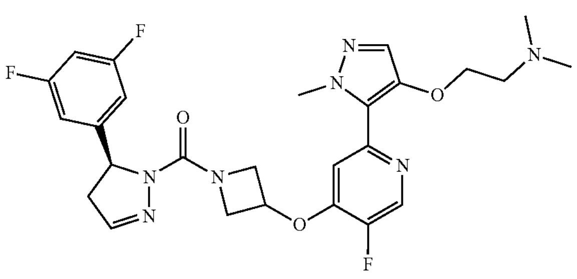
52
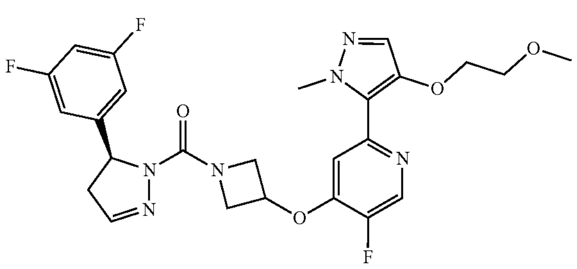
53
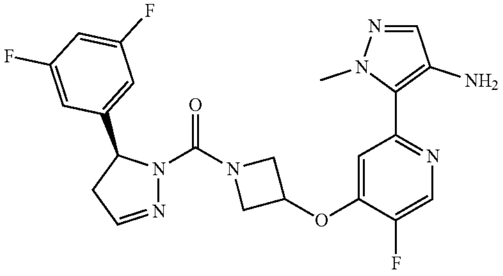
54
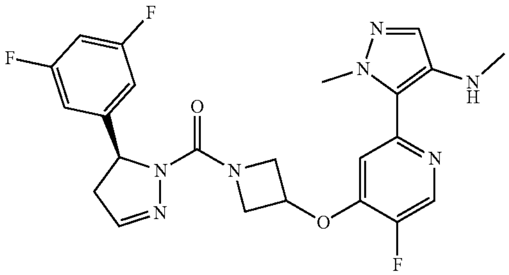
55
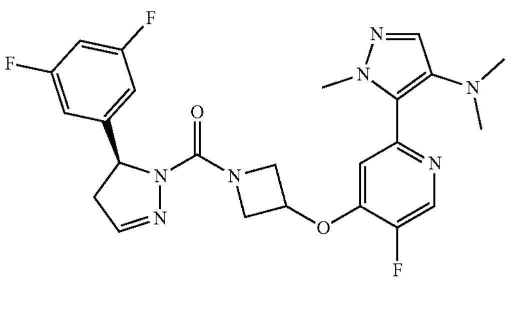
-continued
56
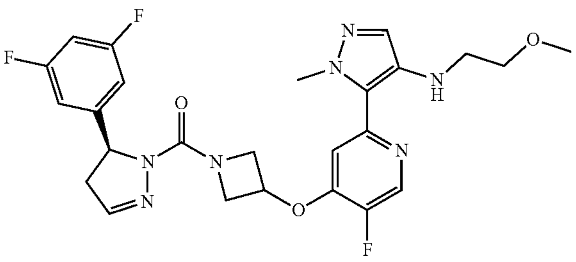
57
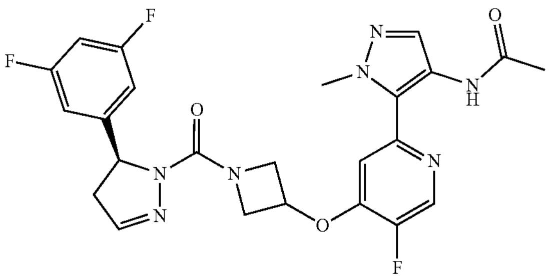
58
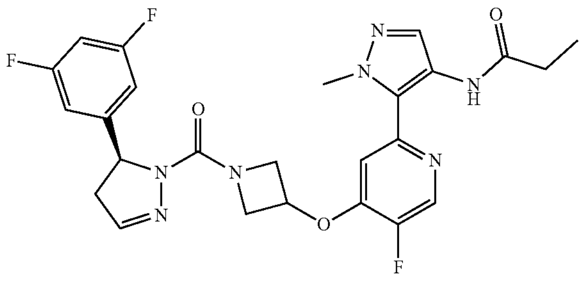
59
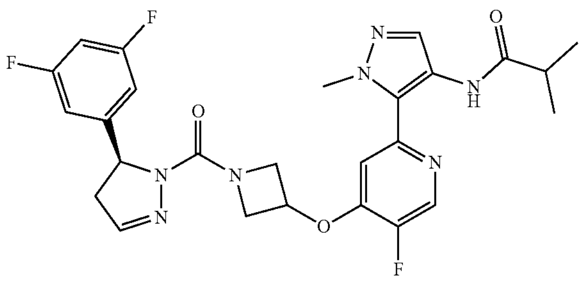
60
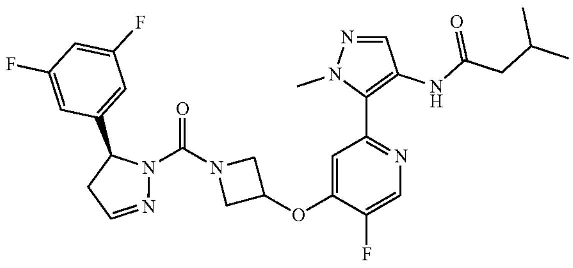

-continued
61
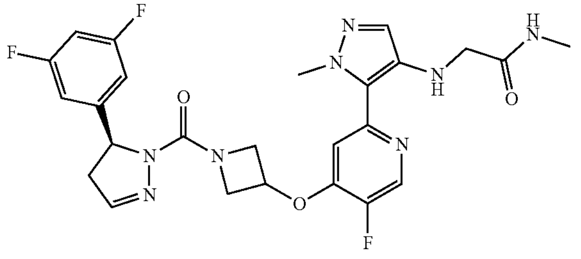
62
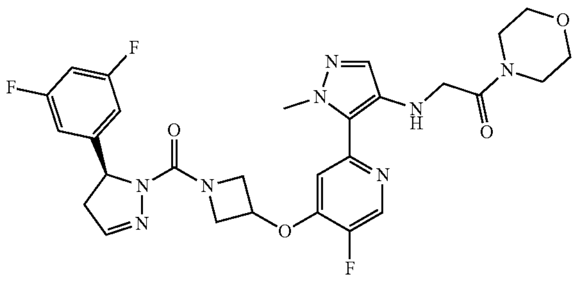
63
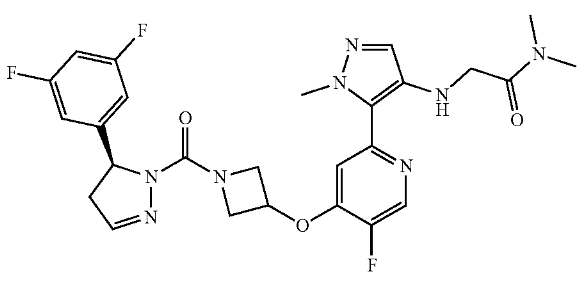
64
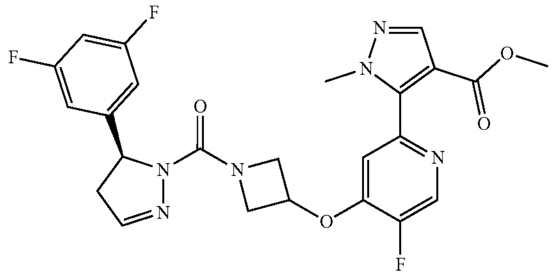
65
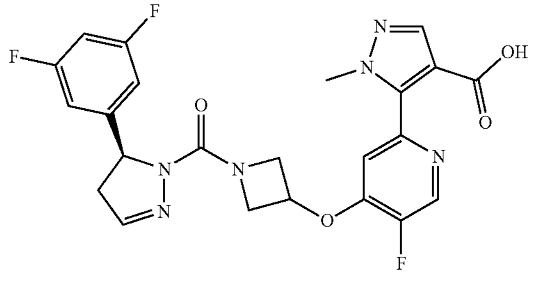
-continued
66
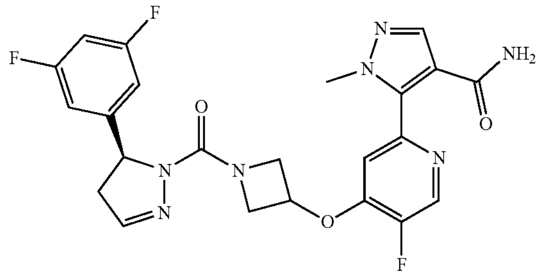
67
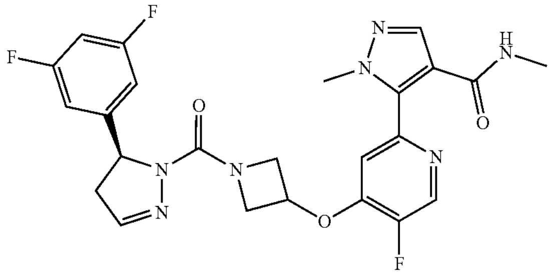
68
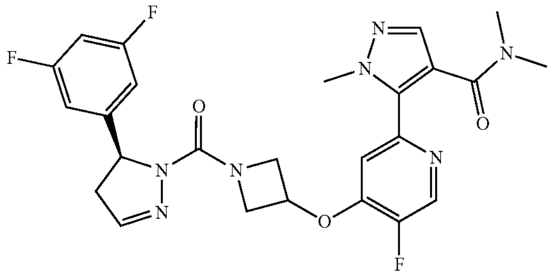
69
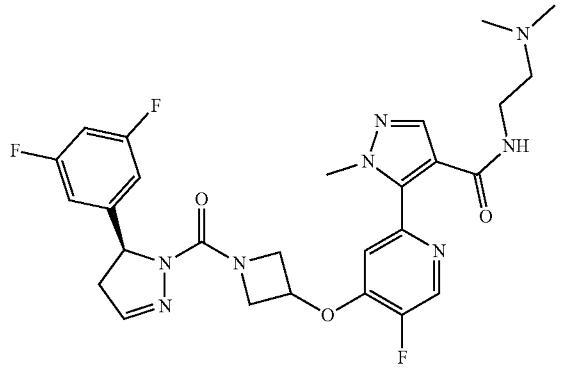
70
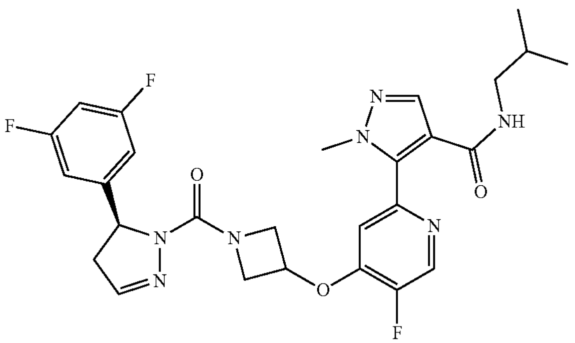

71
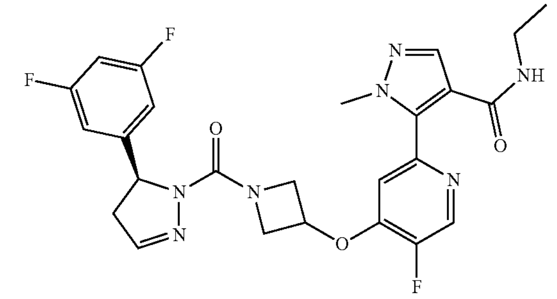
72
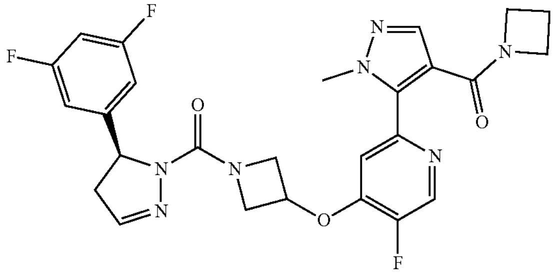
73
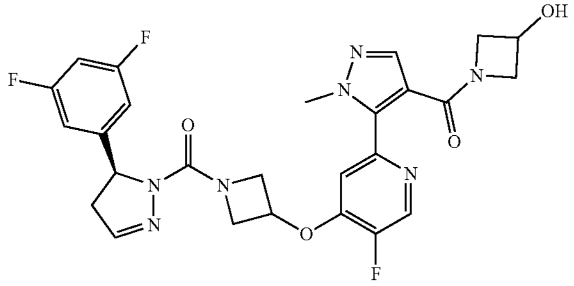
74
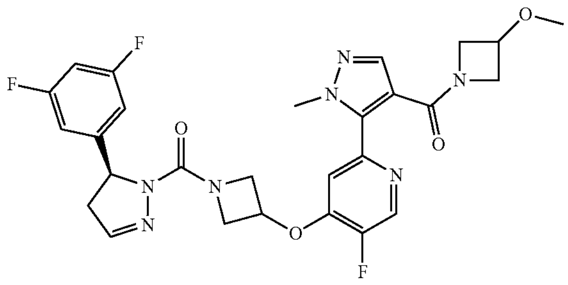
75
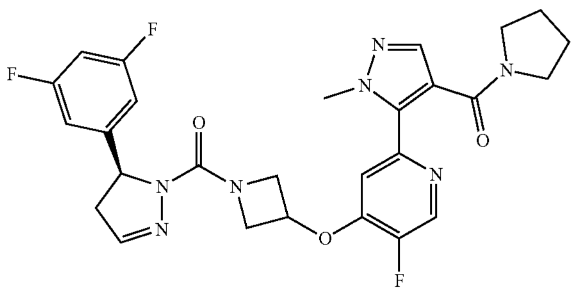
76
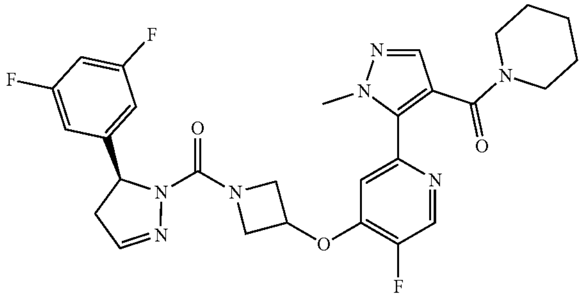
77
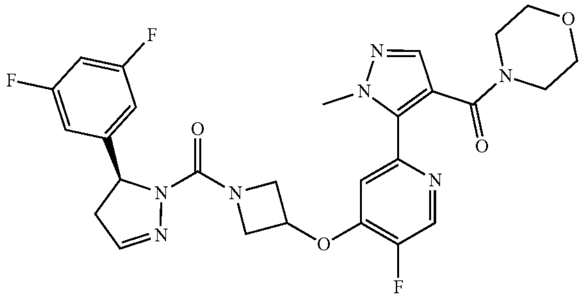
78
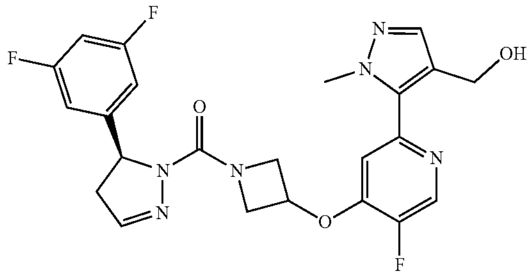
79
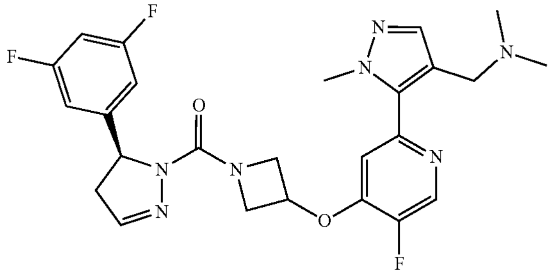
80
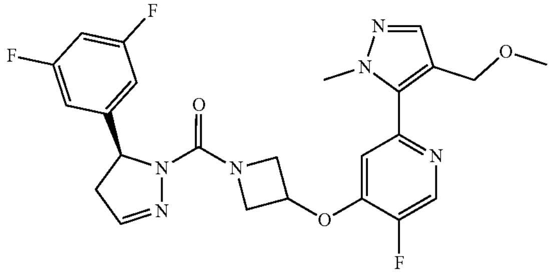

-continued
81
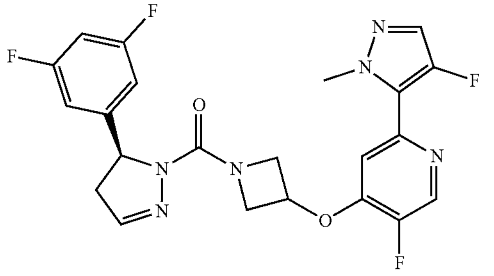
82
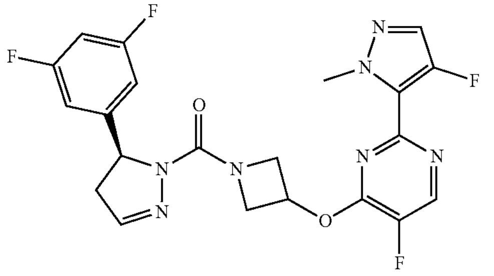
83
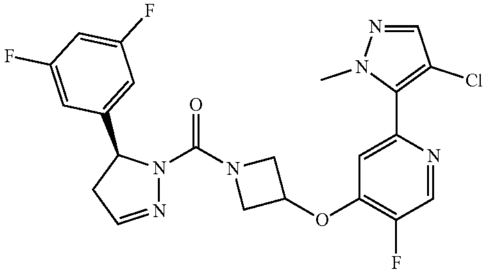
84
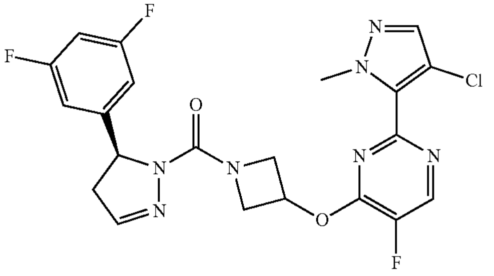
85
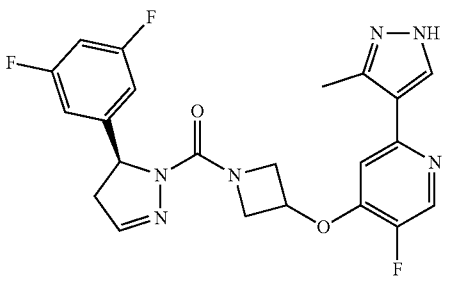
-continued
86
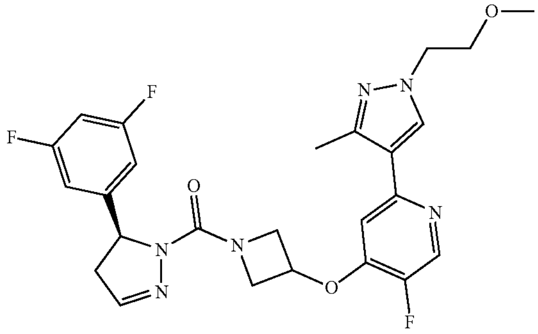
87
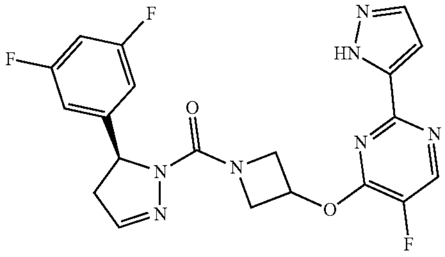
88
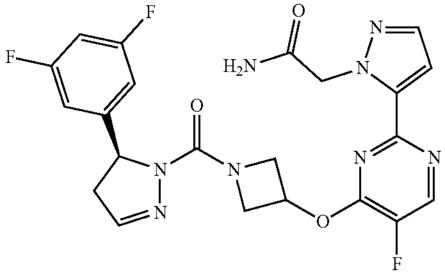
89
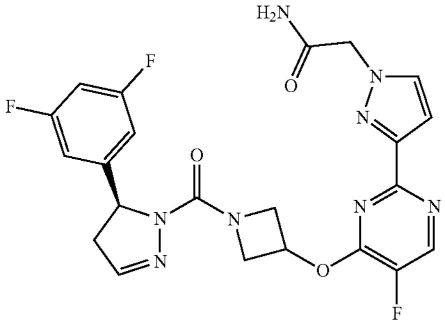
90
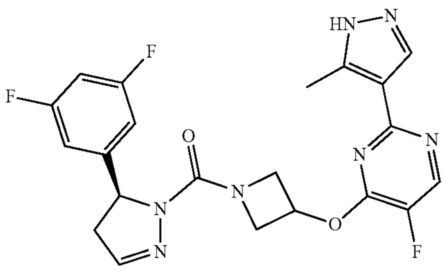

-continued
91
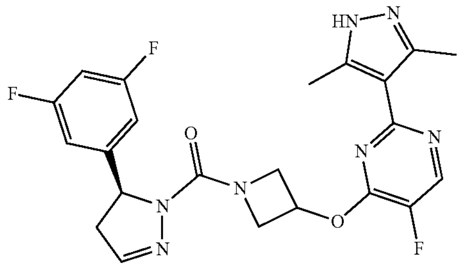
92
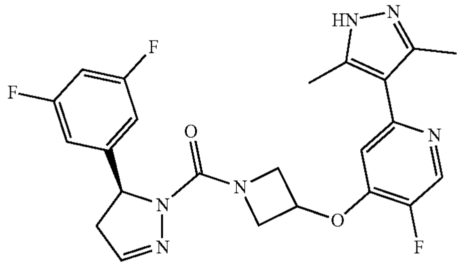
93
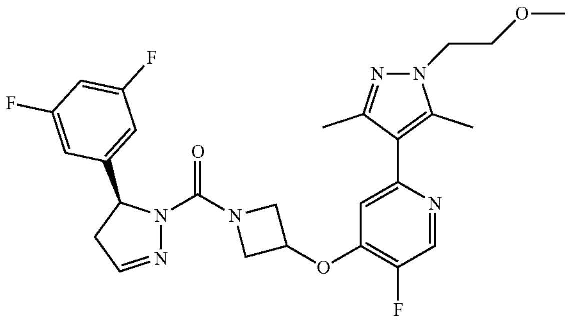
94
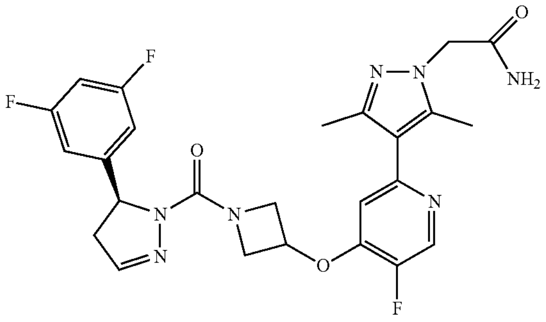
95
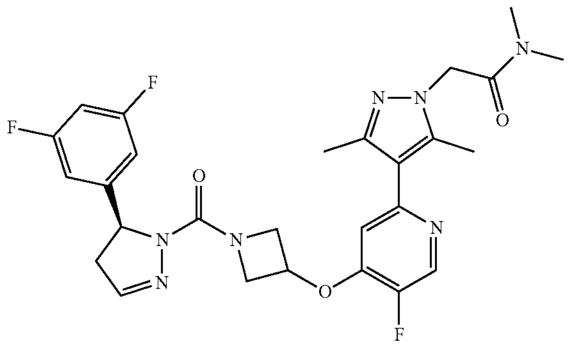
-continued
96
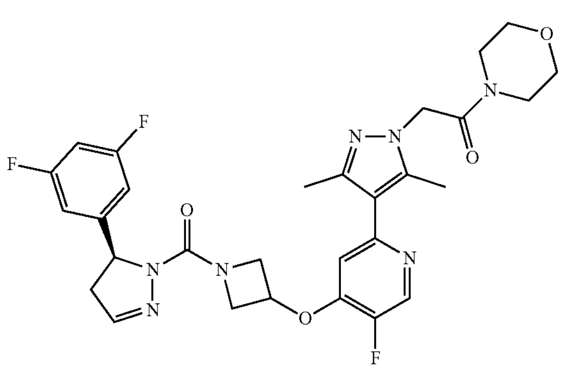
97
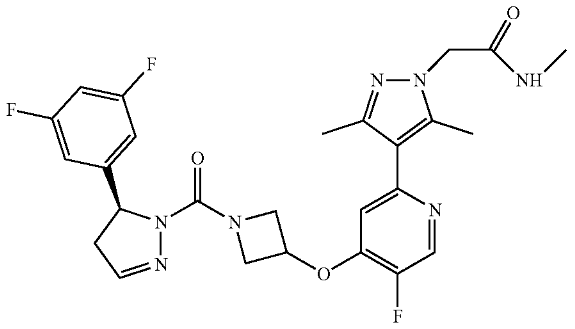
98
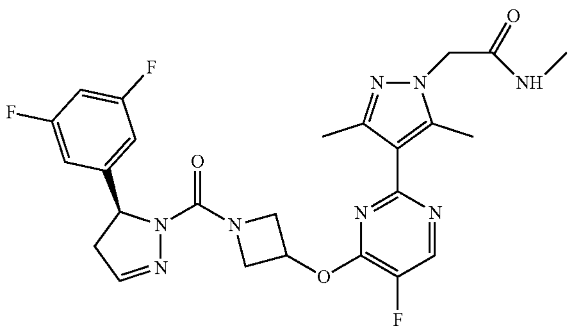
99
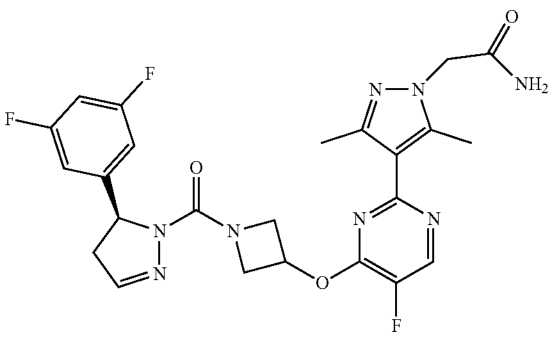

-continued
100
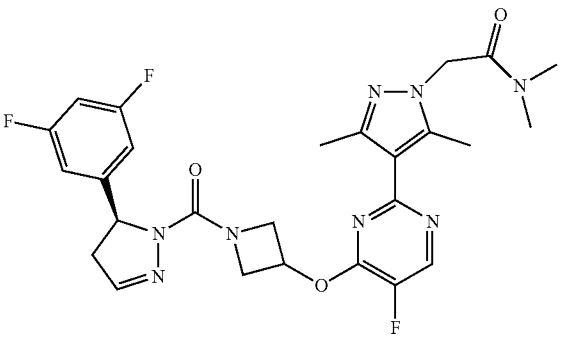
101
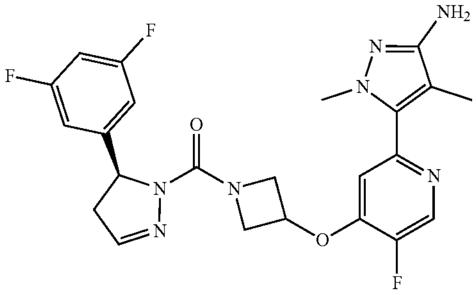
102
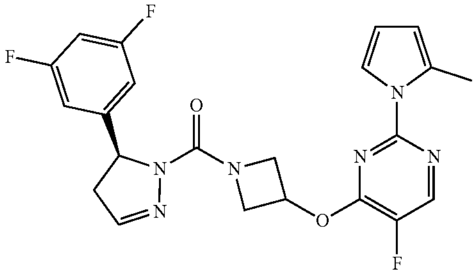
103
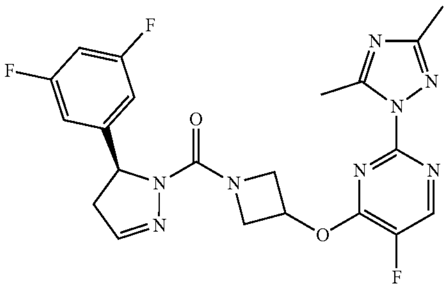
104
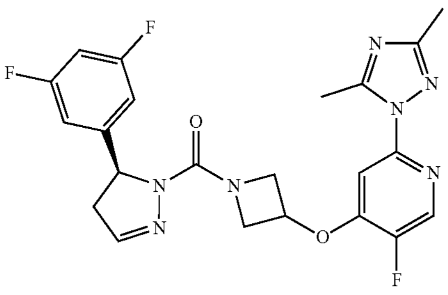
-continued
105
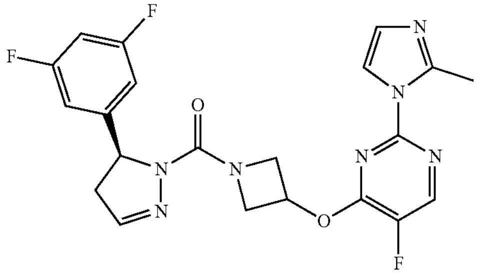
106
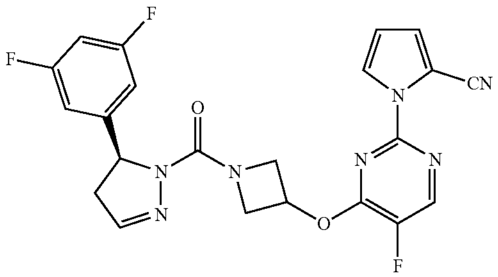
107
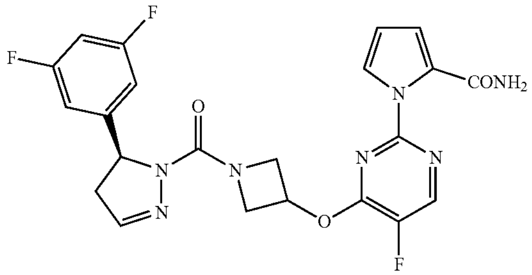
108
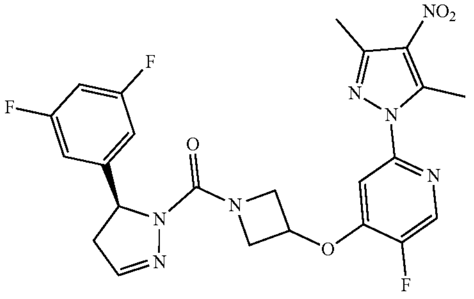
109
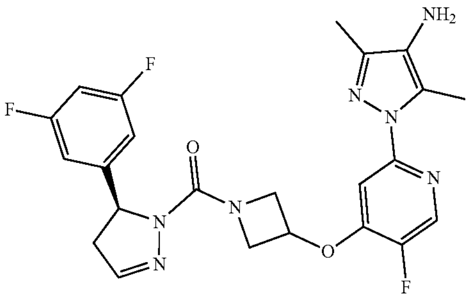

-continued
110
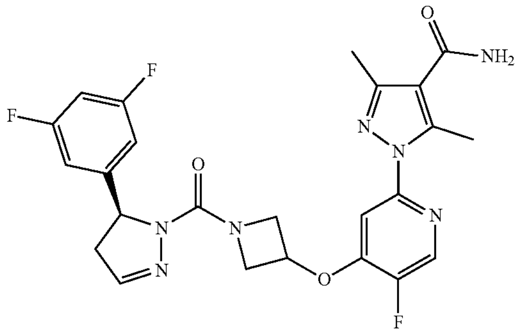
111
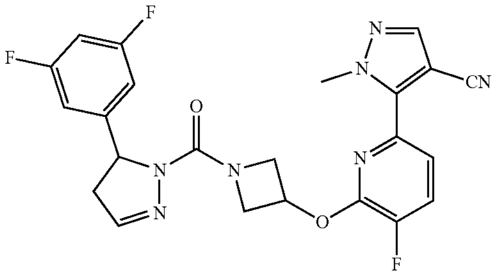
112
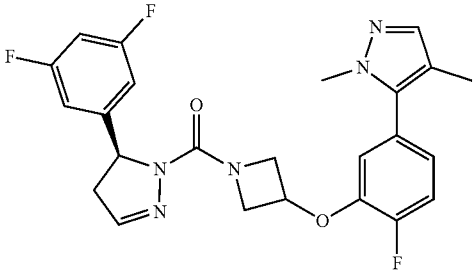
113
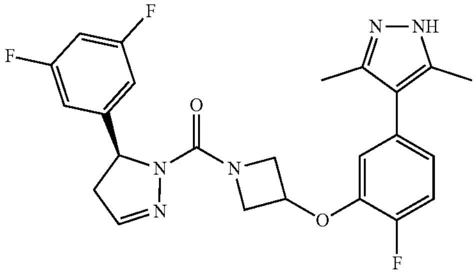
114
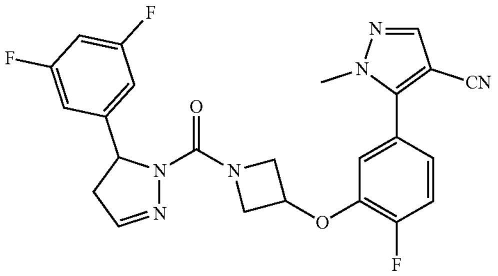
-continued
115
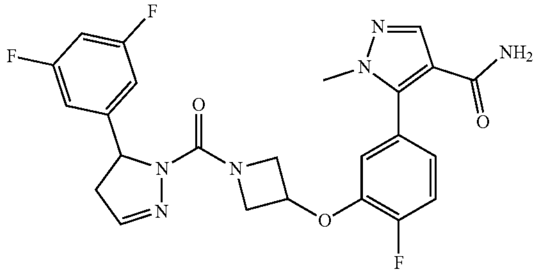
116
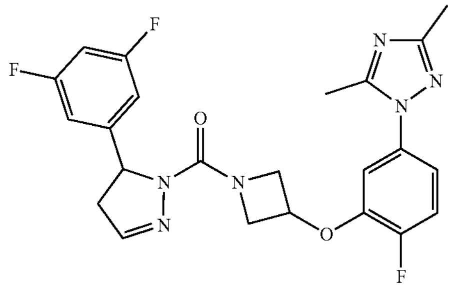
117
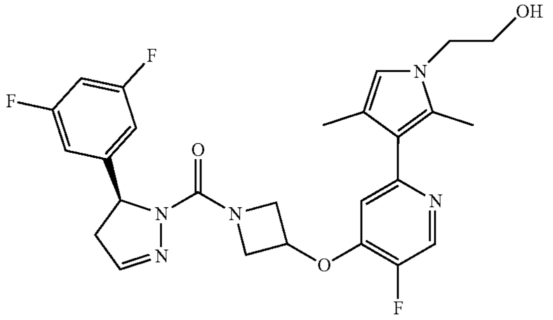
118
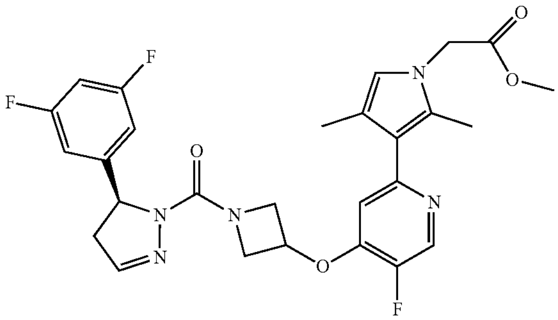
119
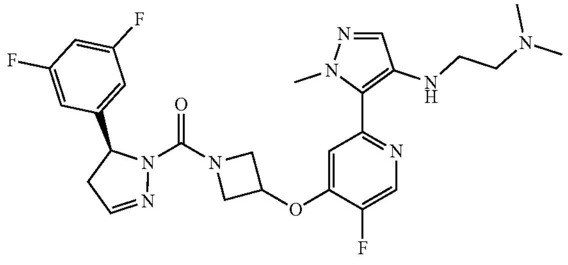

120
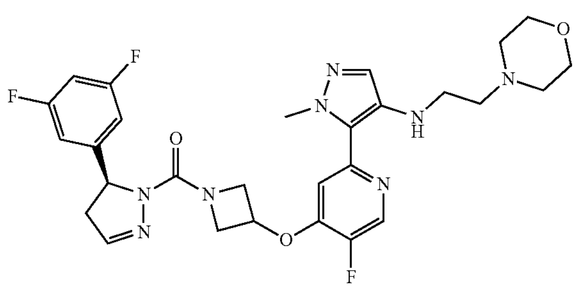
121
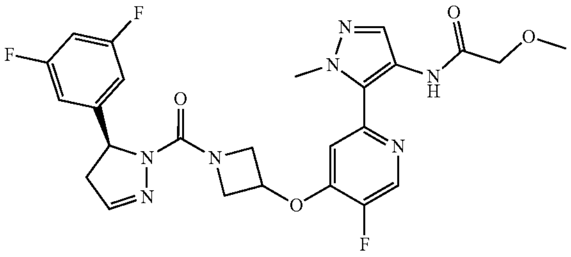
122
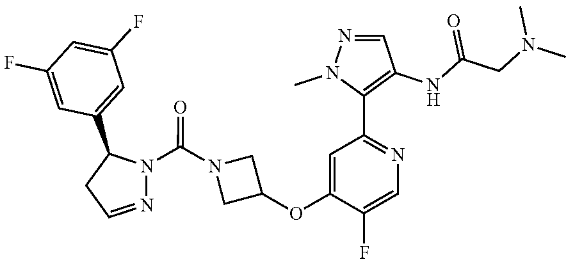
123
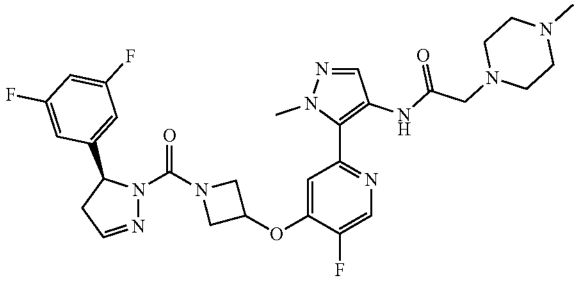
124
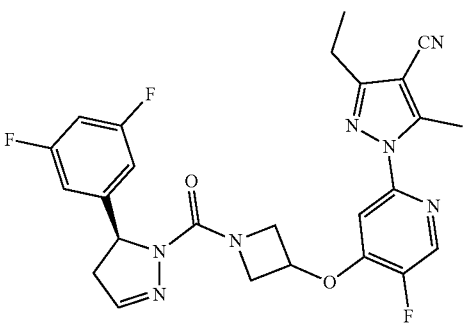
125
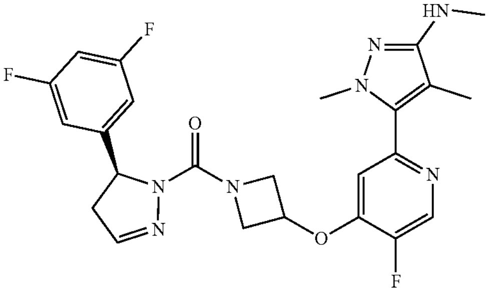
126
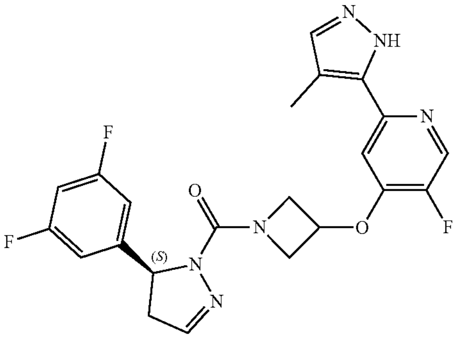
127
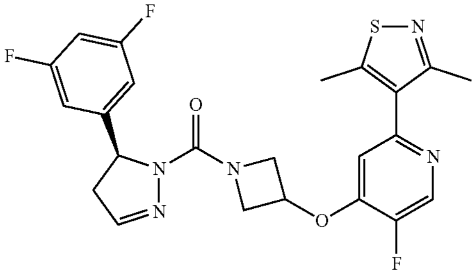
128
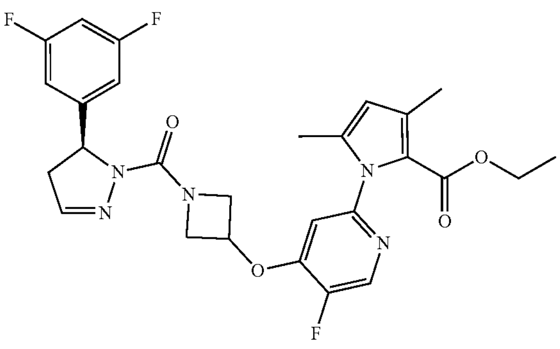
129
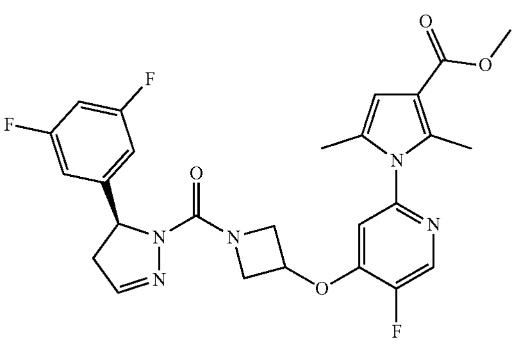

130
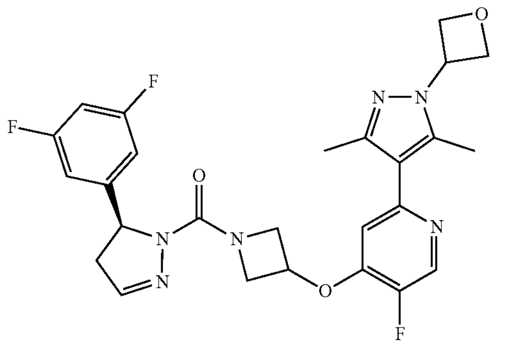
131
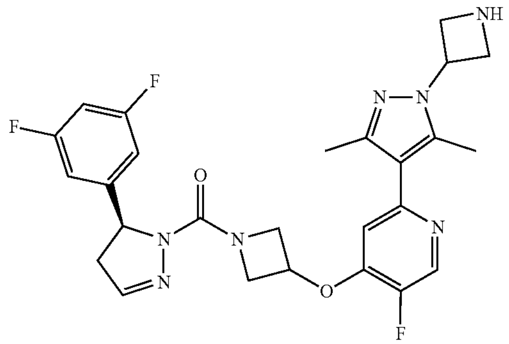
132
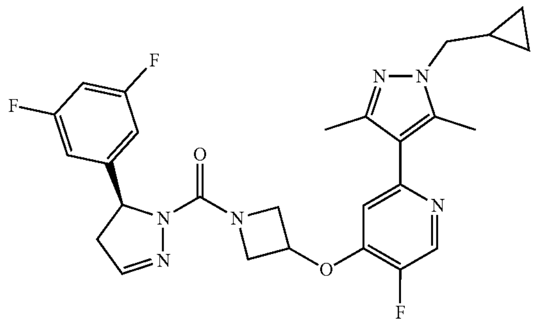
133
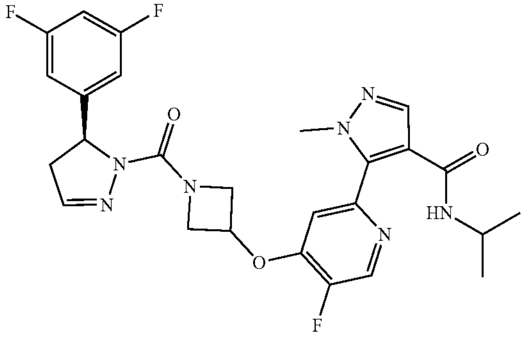
134
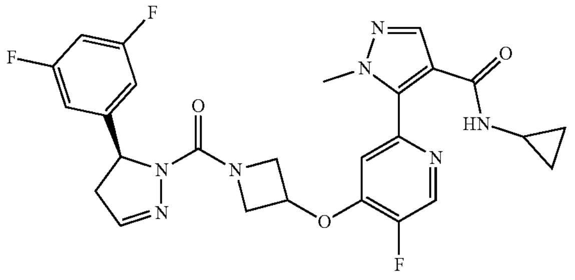
135
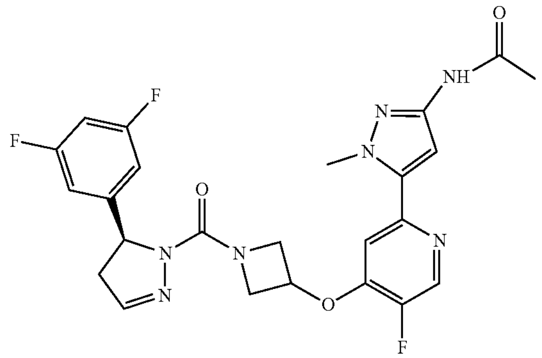
136
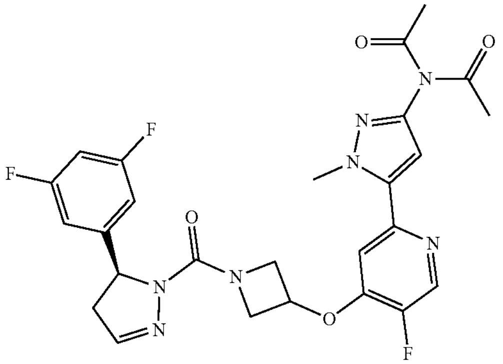
137
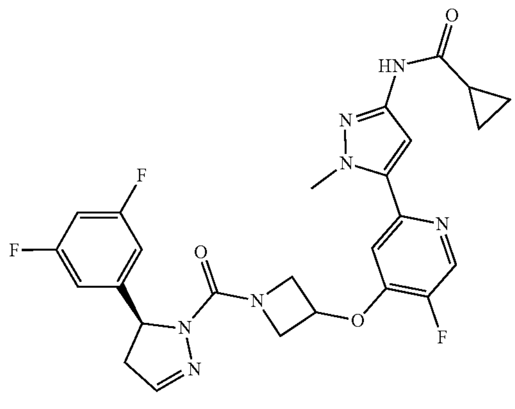

-continued
138
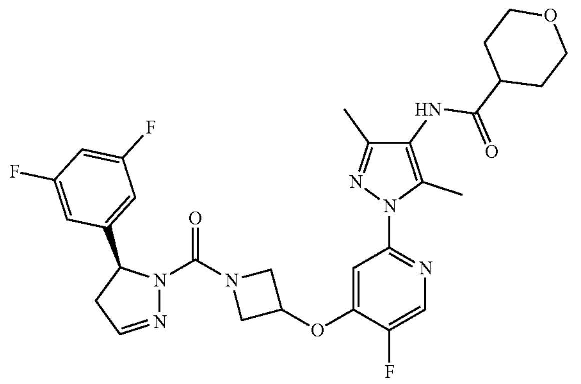
139
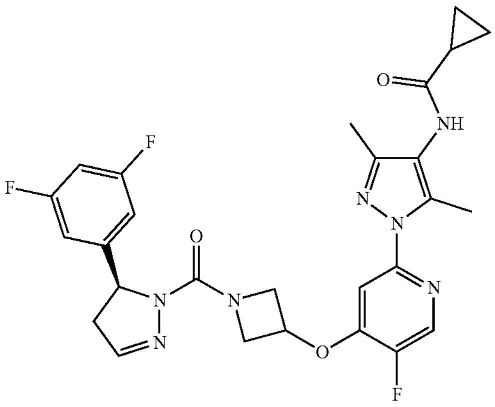
140
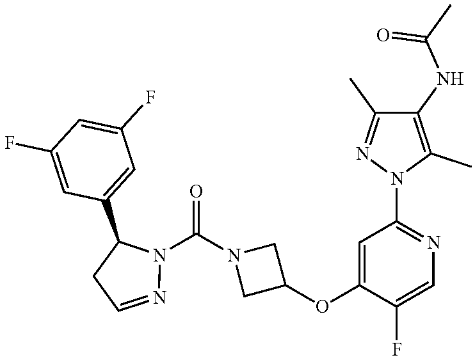
141
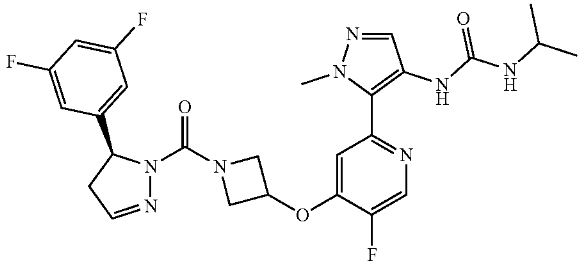
-continued
142
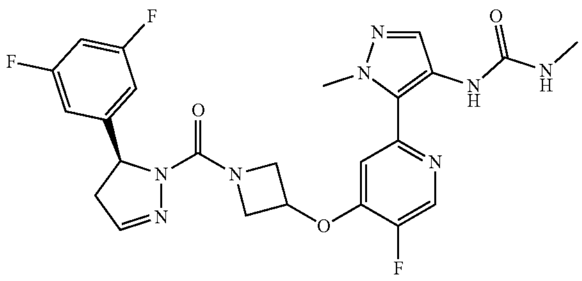
143
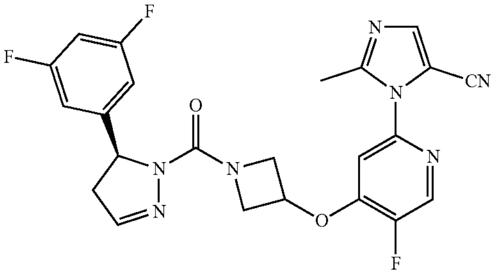
144
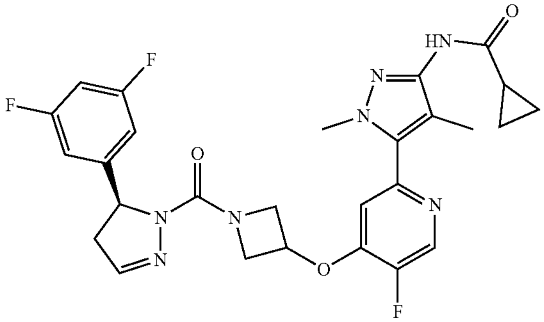
145
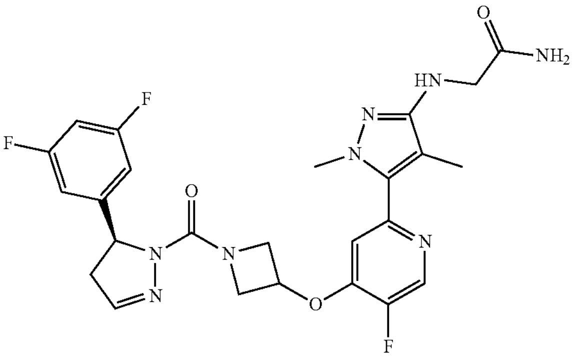
146
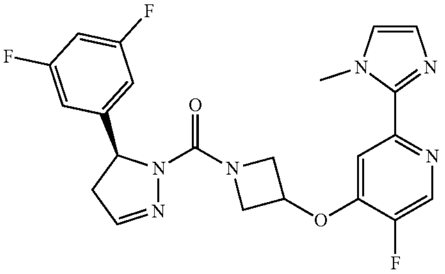

-continued
147
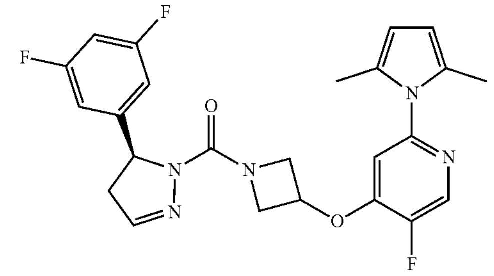
148
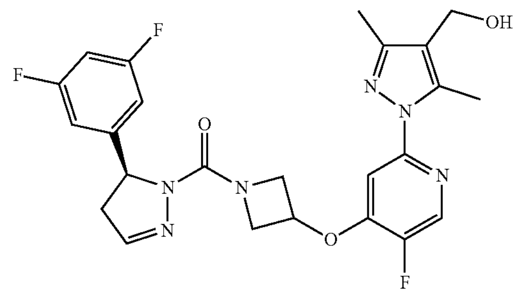
149
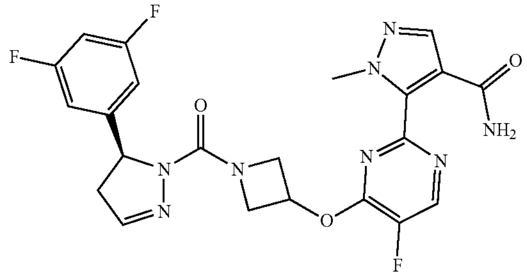
150
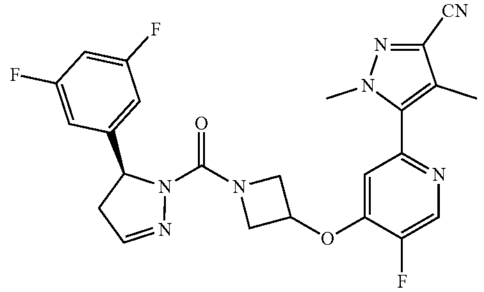
151
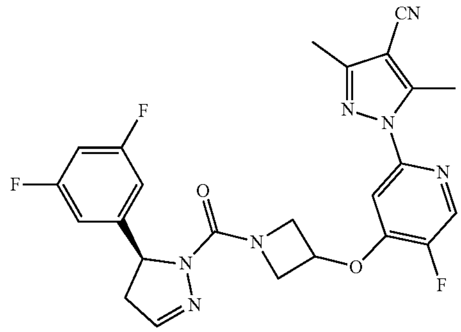
-continued
152
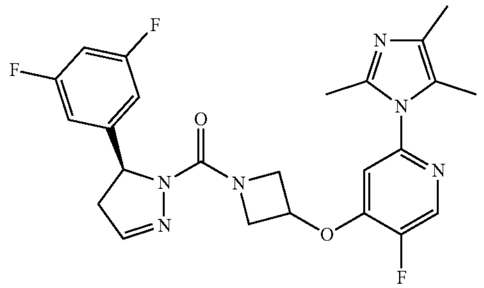
153
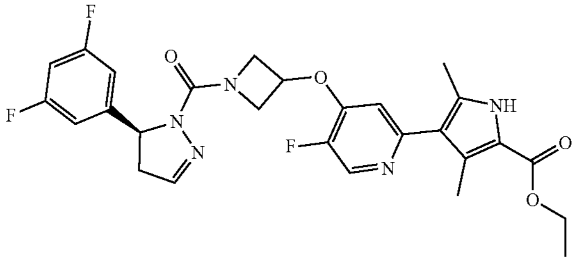
154
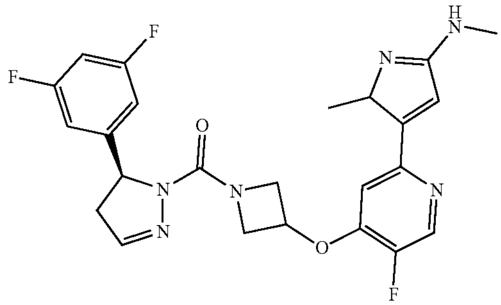
155
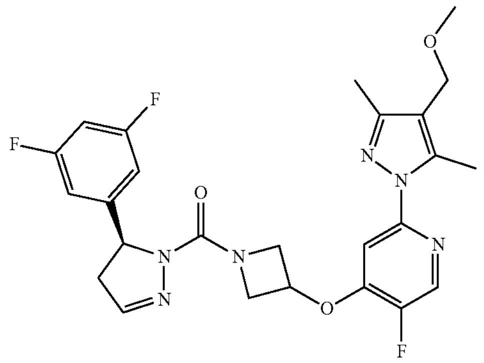
156
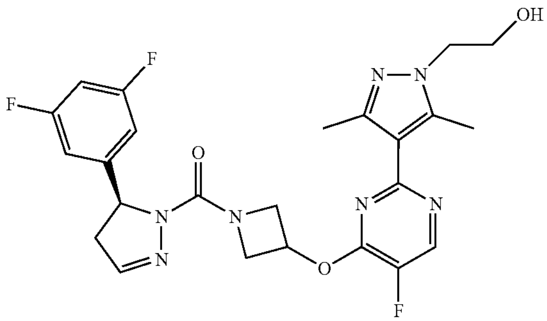

-continued
157
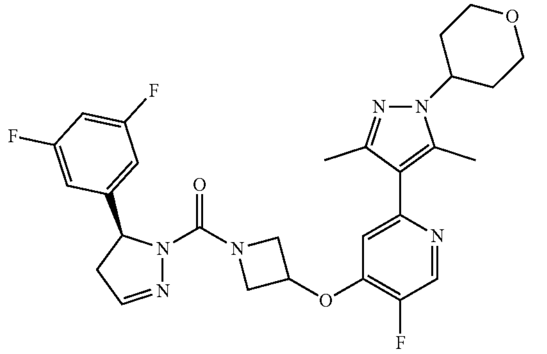
158
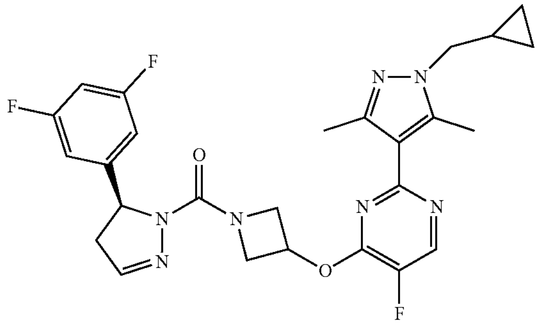
159
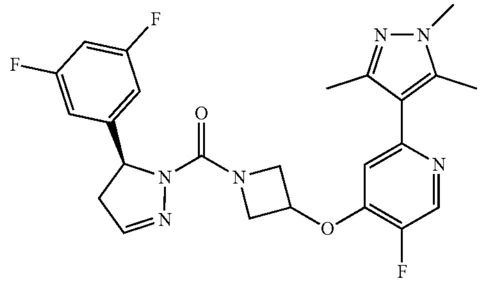
160
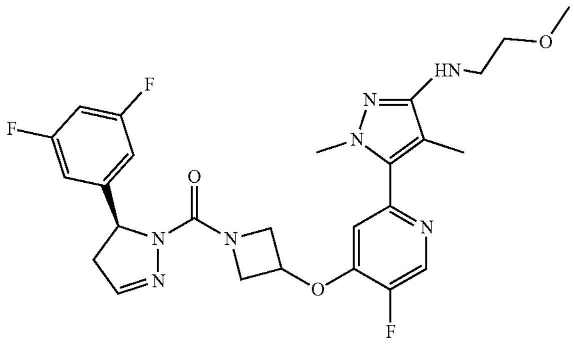
161
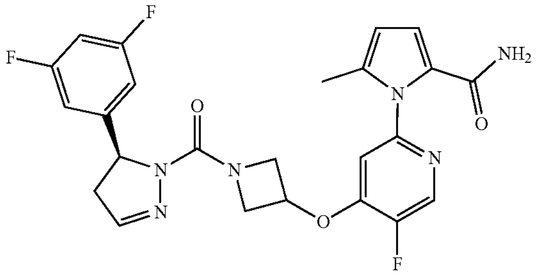
-continued
162
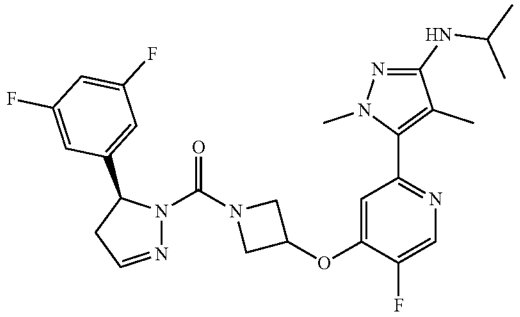
163
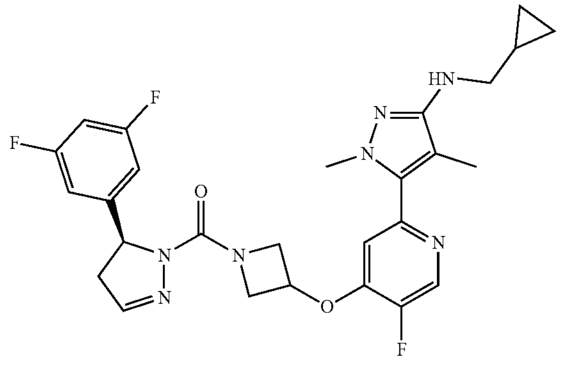
164
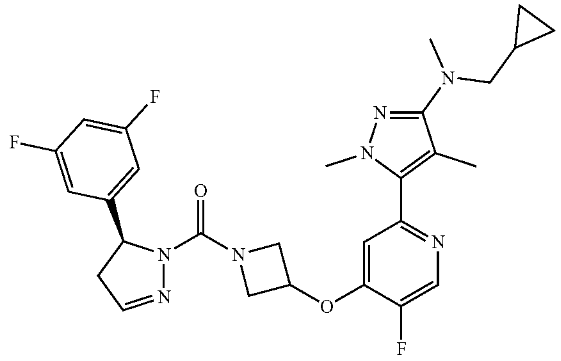
165
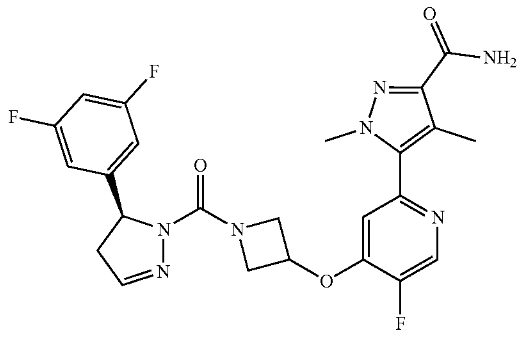

-continued
166
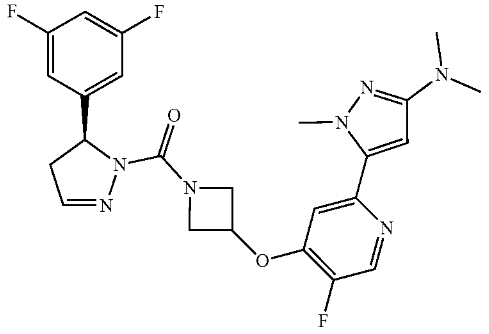
167
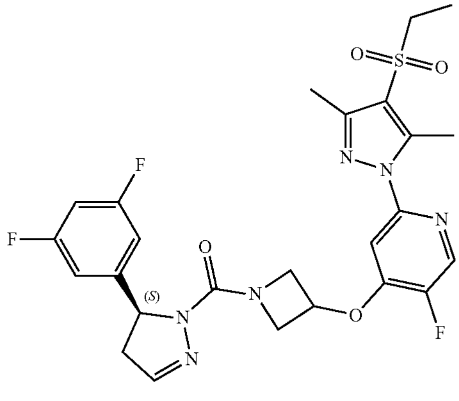
168
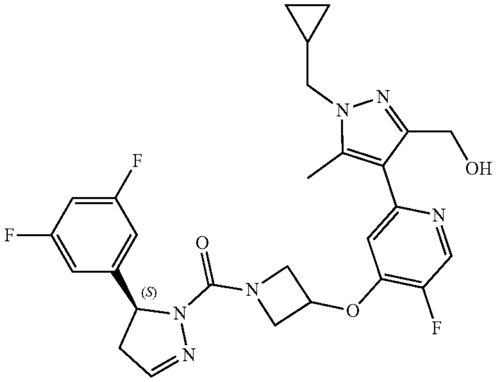
169
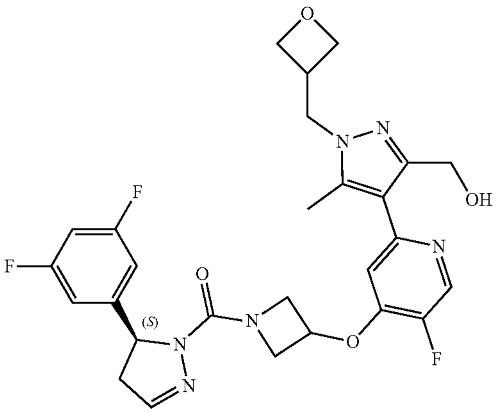
-continued
170
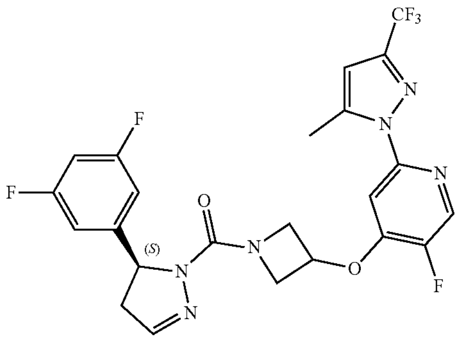
171
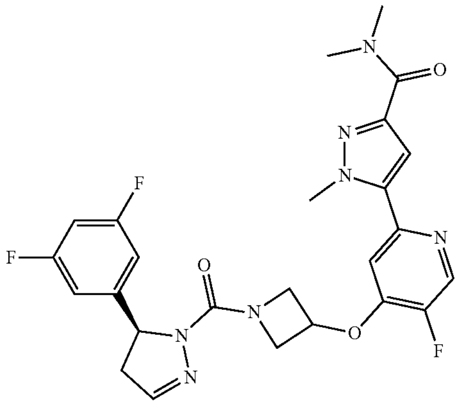
172
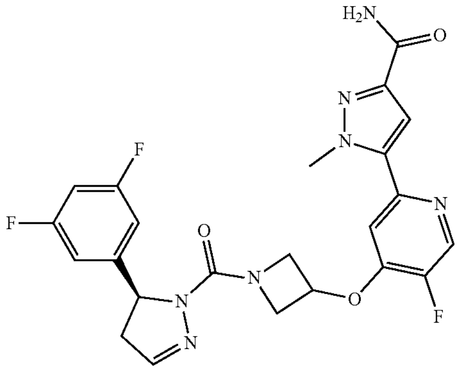
173
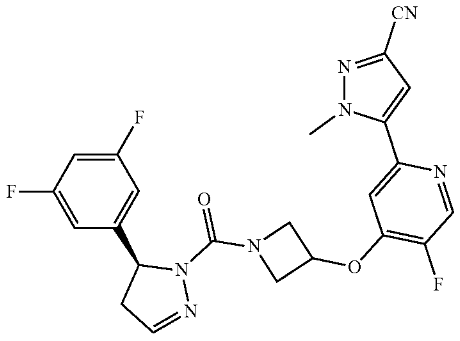

-continued
174
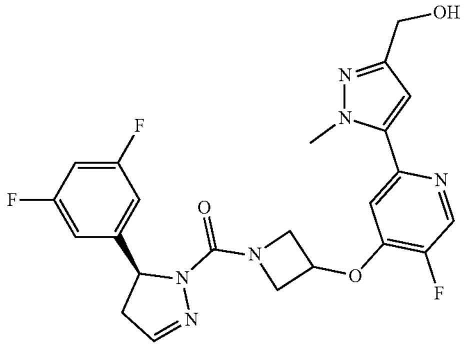
175
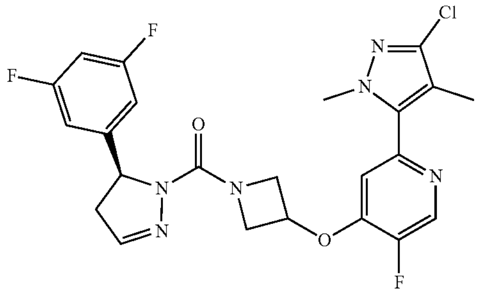
176
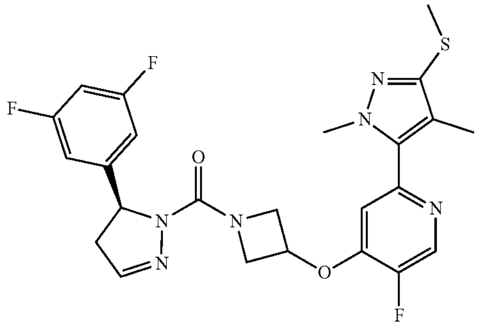
177
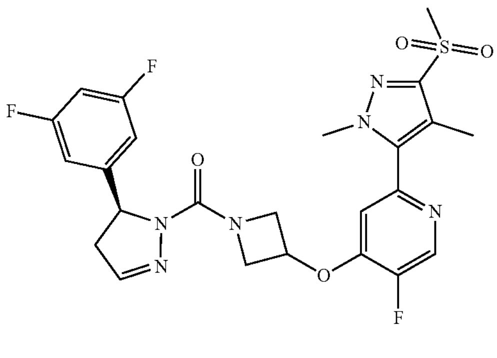
-continued
178
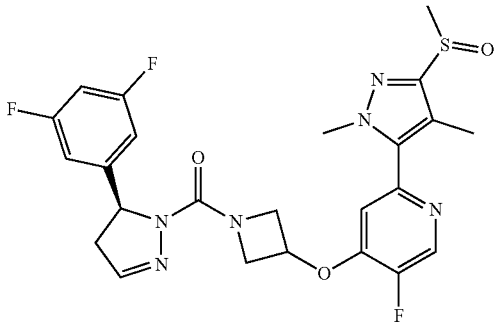
179
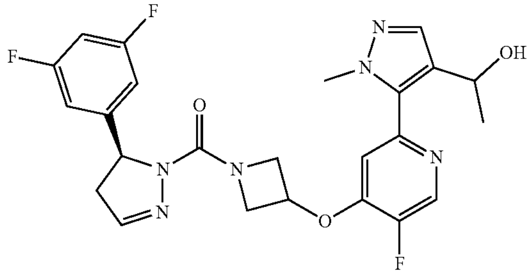
180
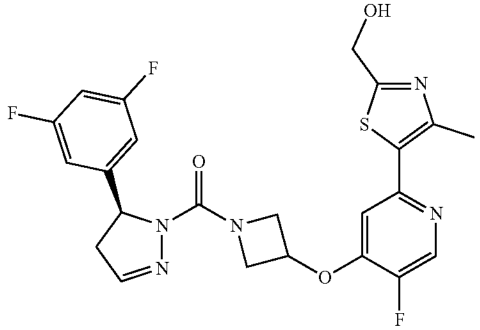
181
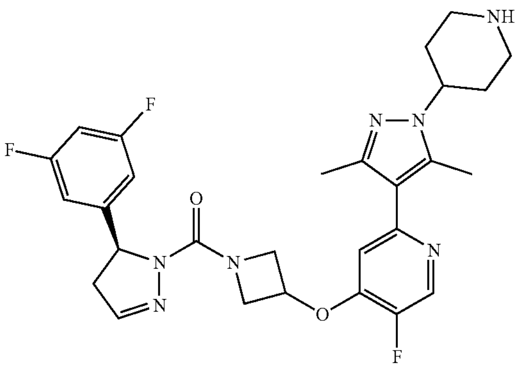
182
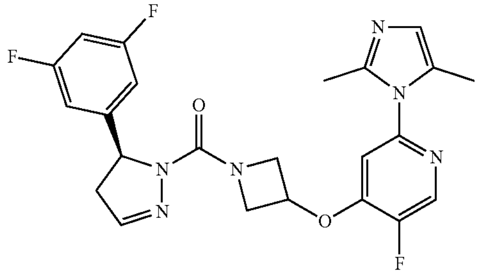

-continued
183
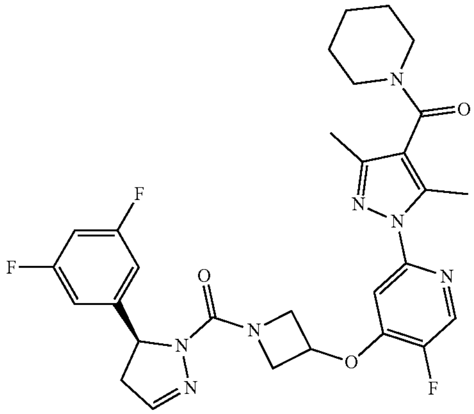
184
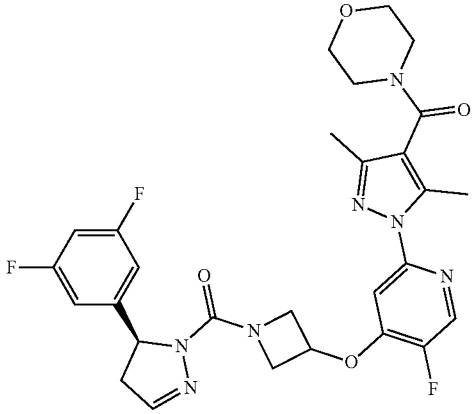
185
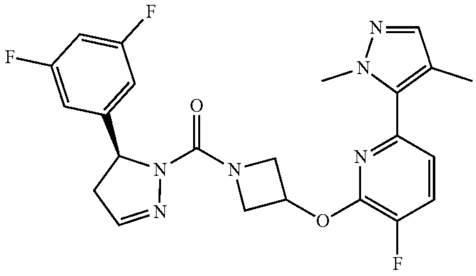
186
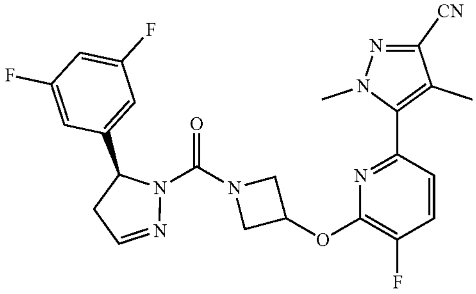
-continued
187
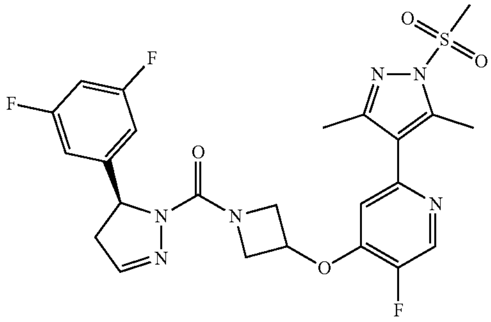
188
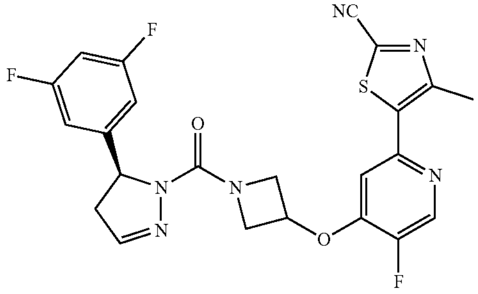
189
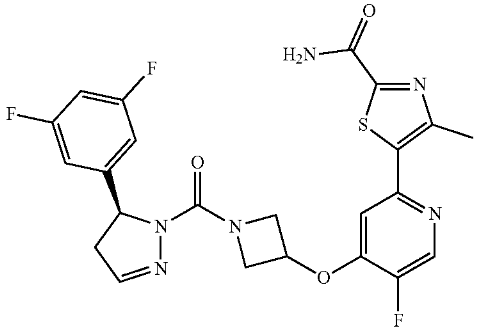
190
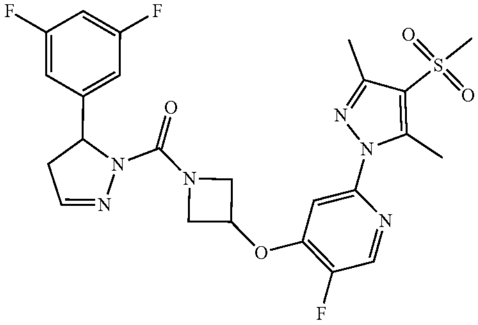

-continued
191
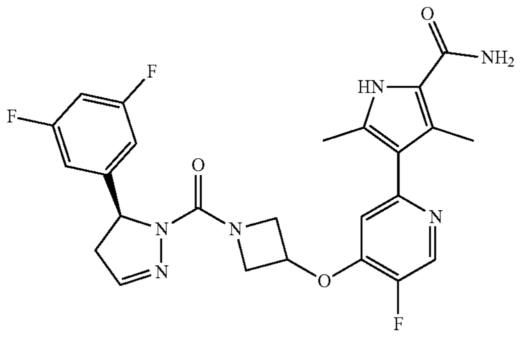
192
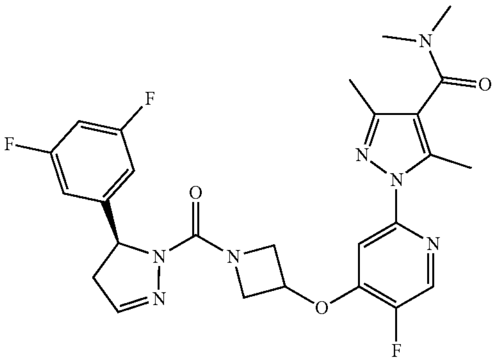
193
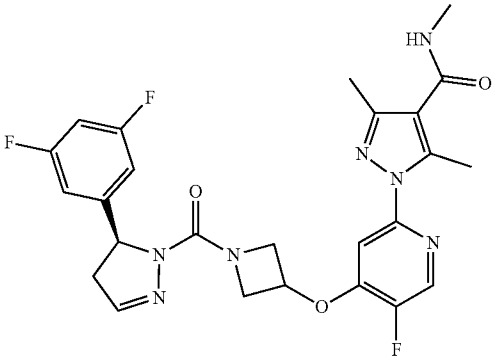
194
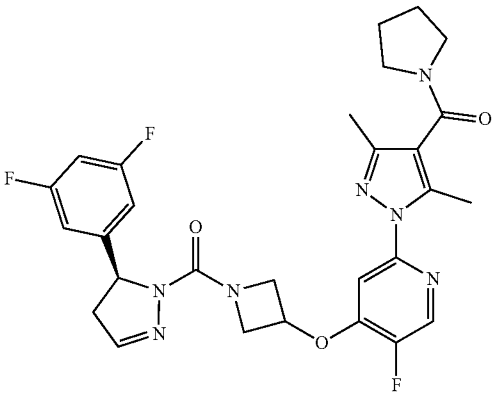
-continued
195
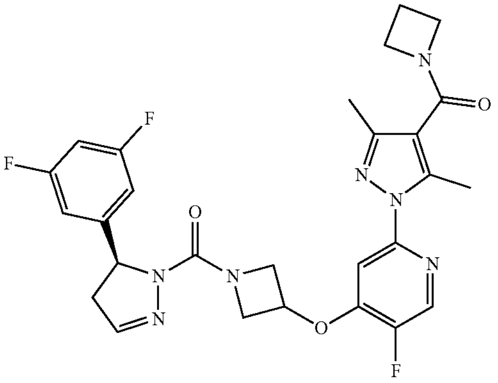
196
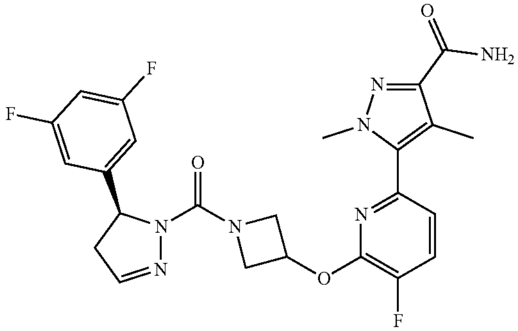
197
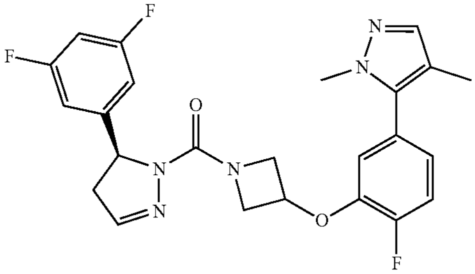
198
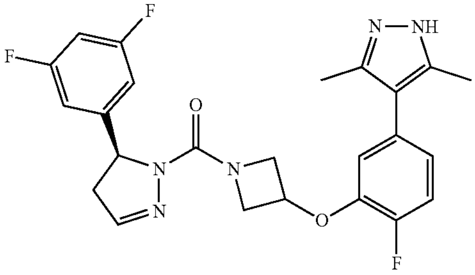
199
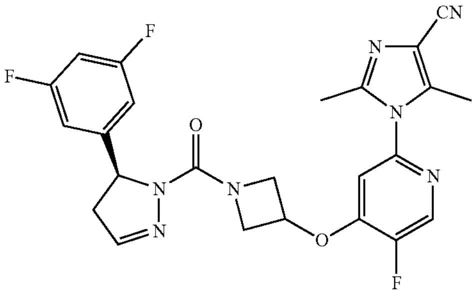

-continued
200
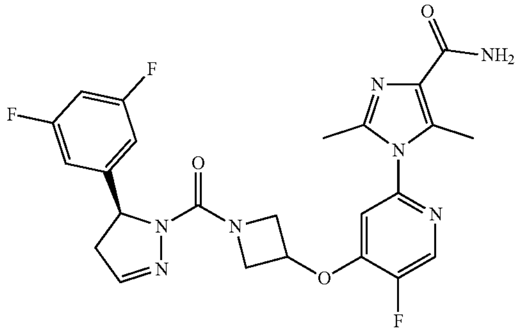
201
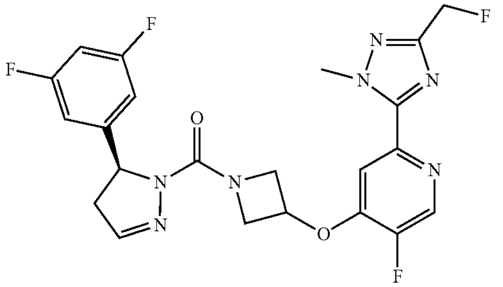
202
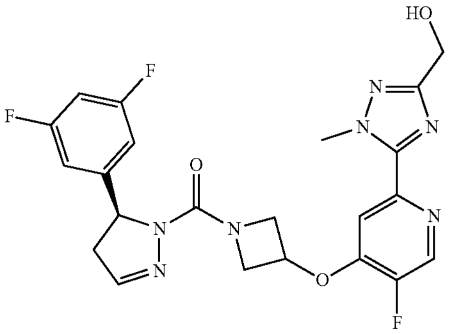
203
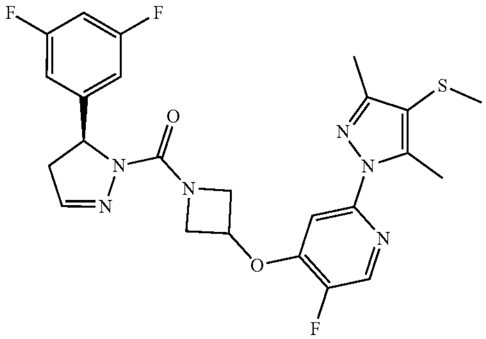
204
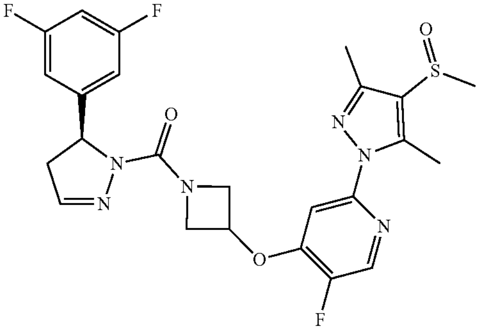
-continued
205
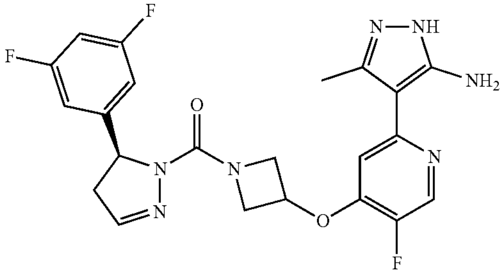
206
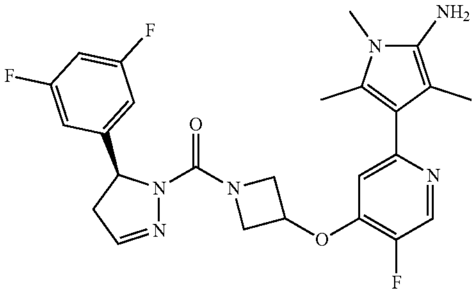
207
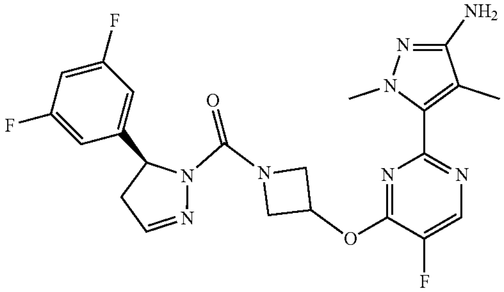
208
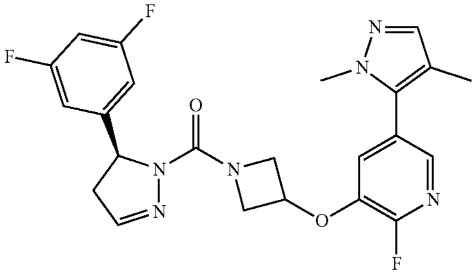
209
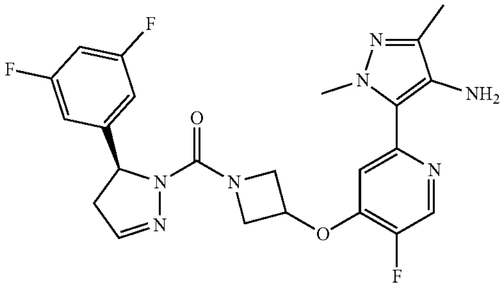

-continued
210
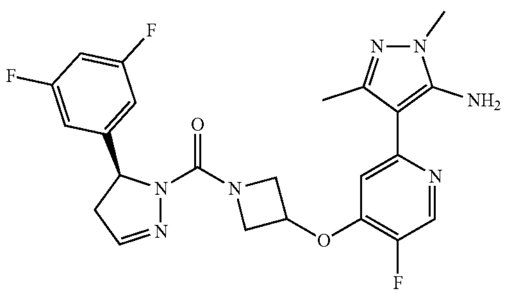
211
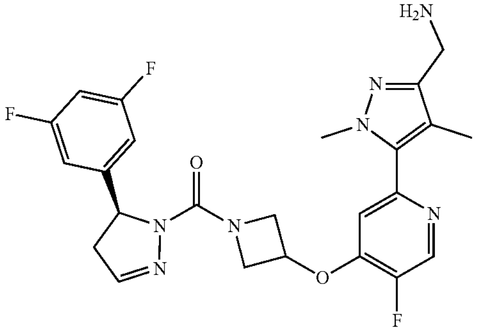
212
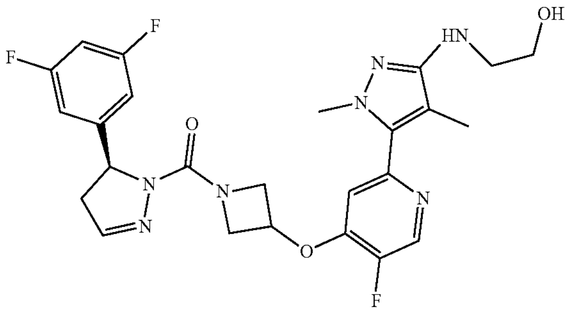
213
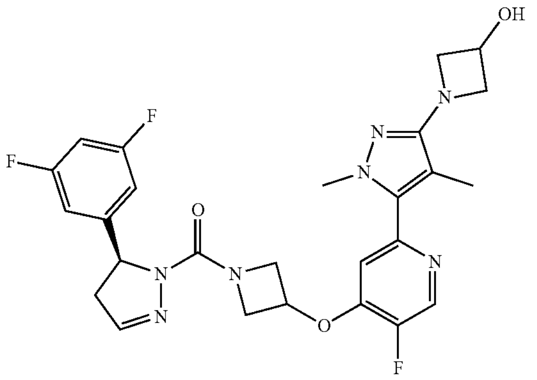
-continued
214
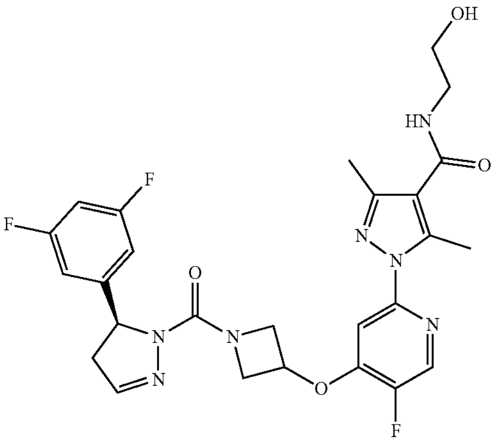
215
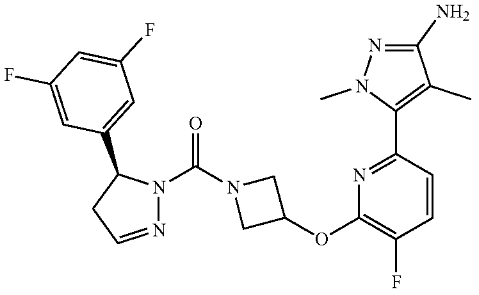
216
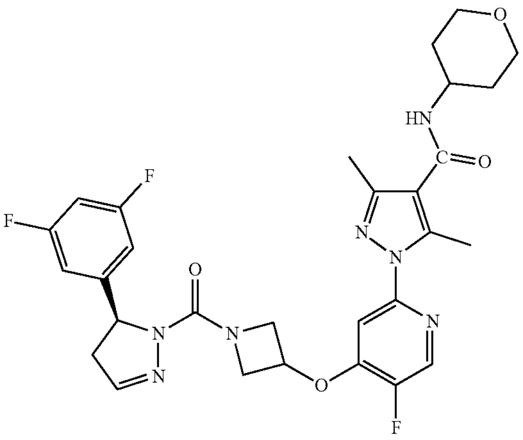
217
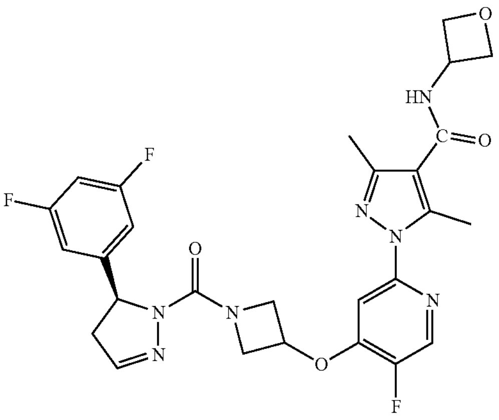

-continued
218
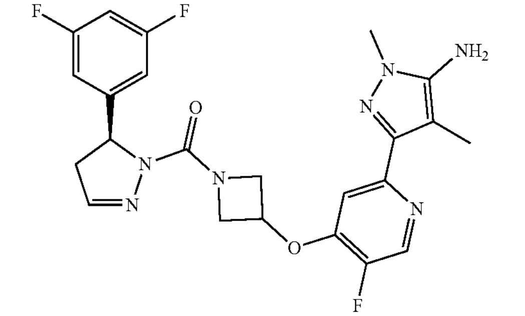
219
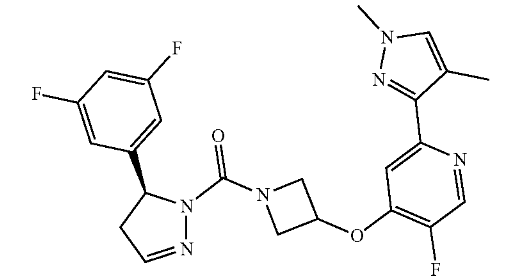
220
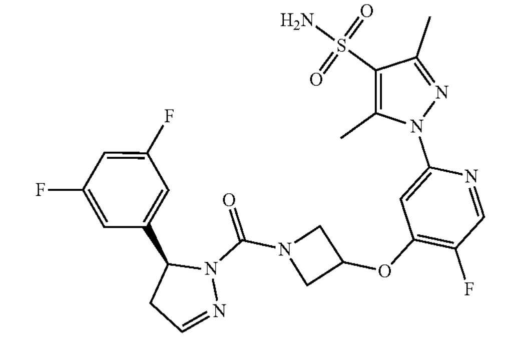
221
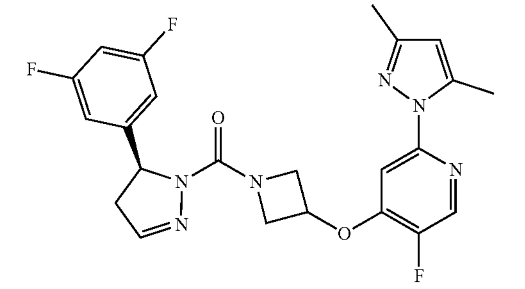
222
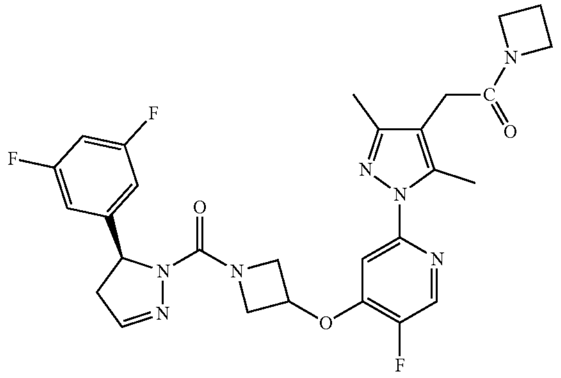
-continued
223
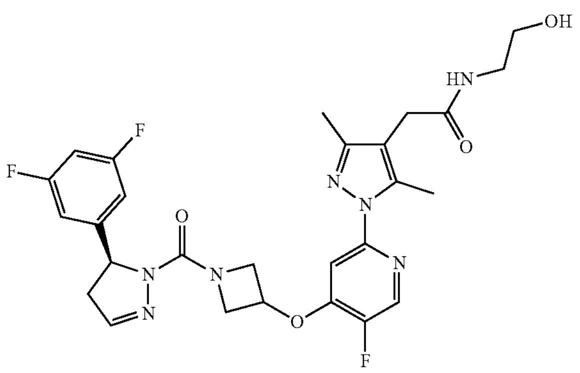
224
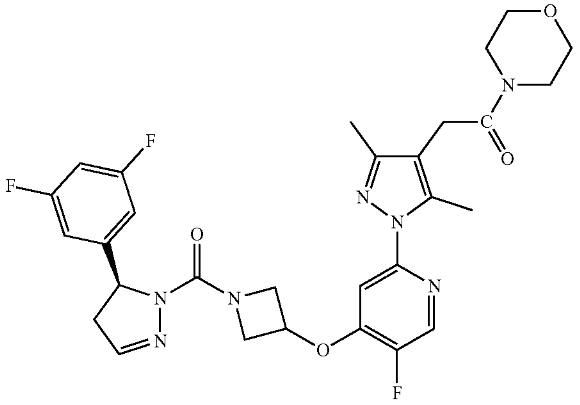
225
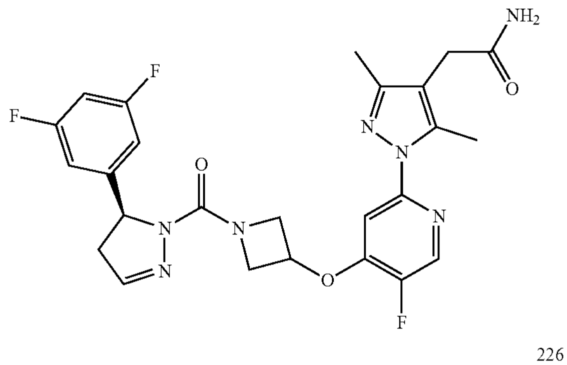
226
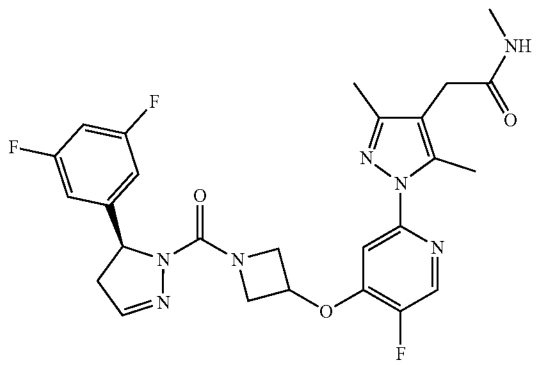

-continued
227
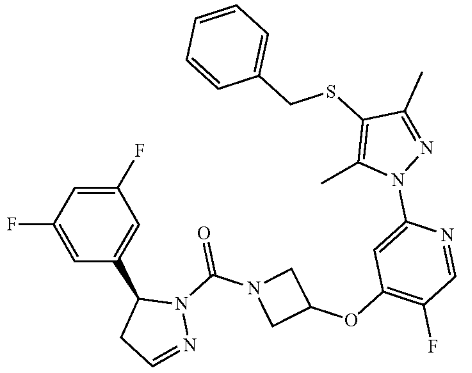
228
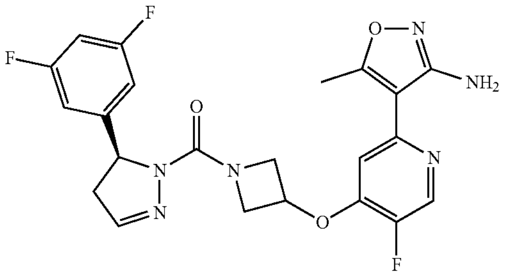
229
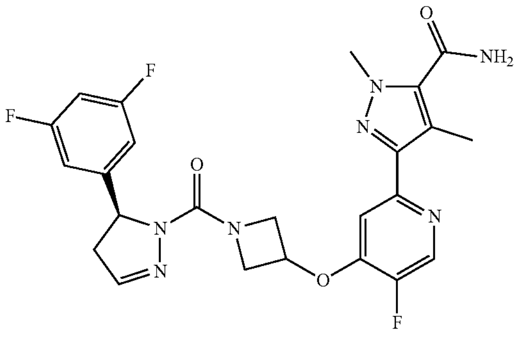
230
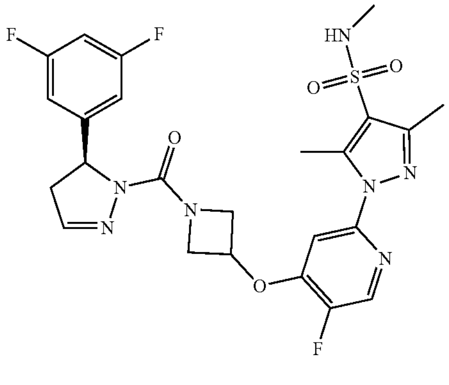
-continued
231
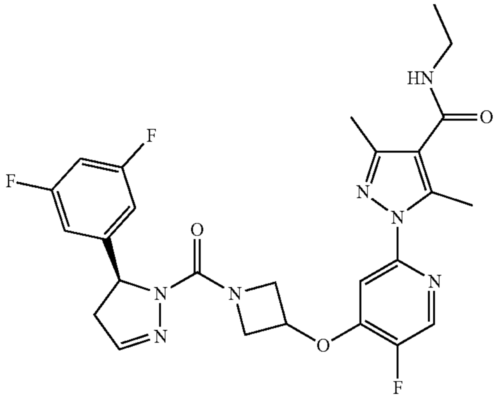
232
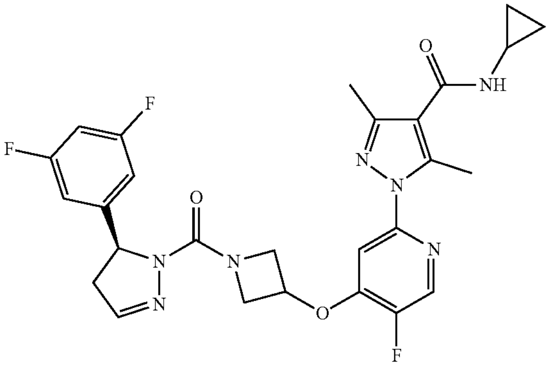
233
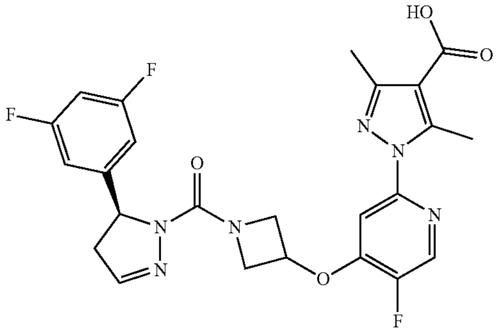
234
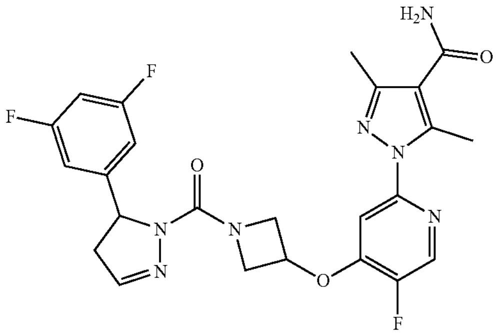

-continued
235
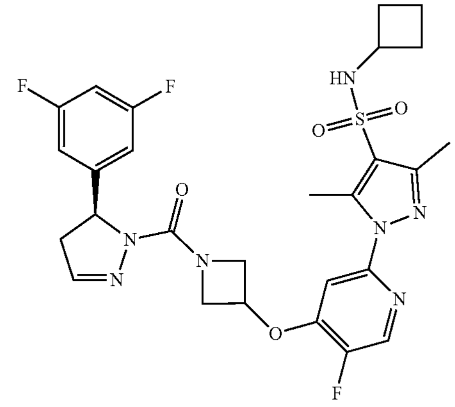
236
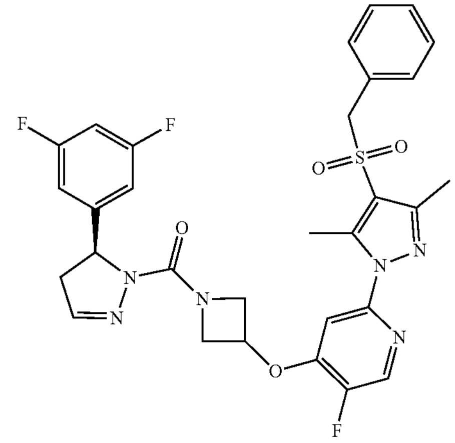
237
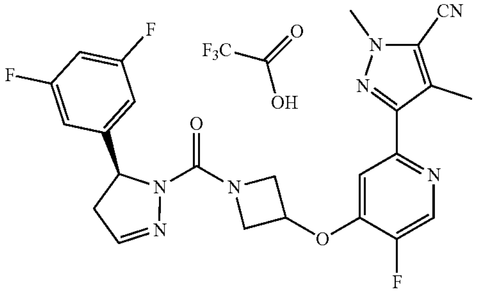
238
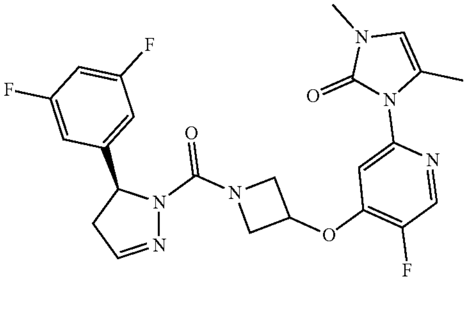
-continued
239
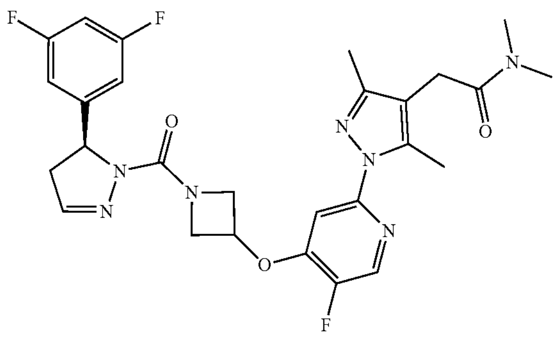
240
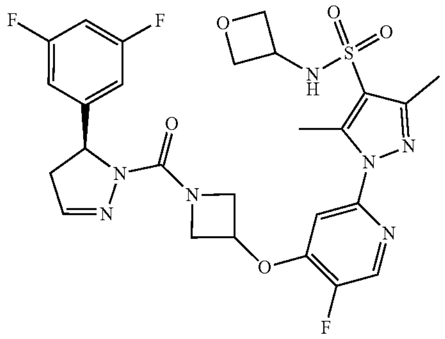
241
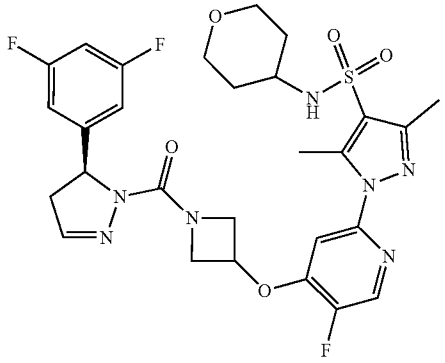
242
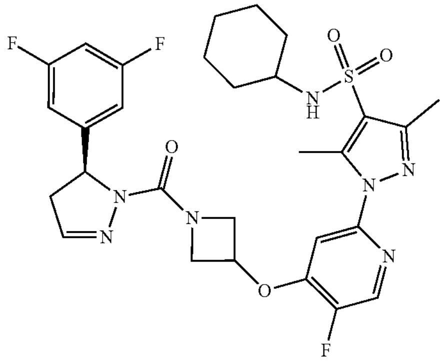

243
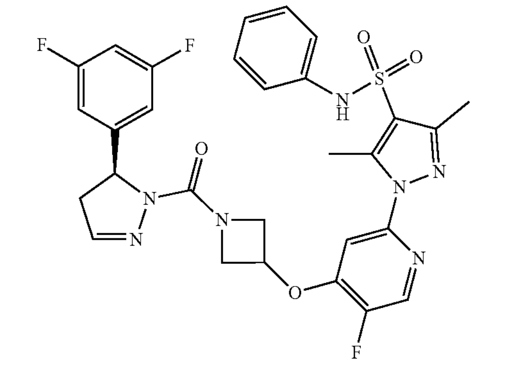
244
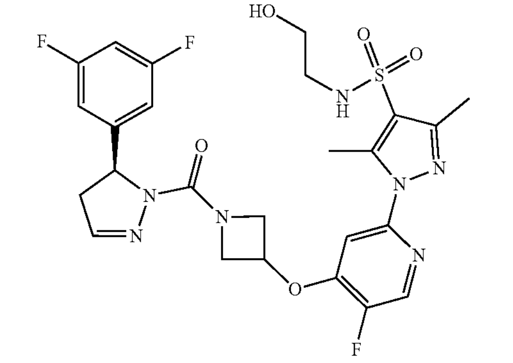
245
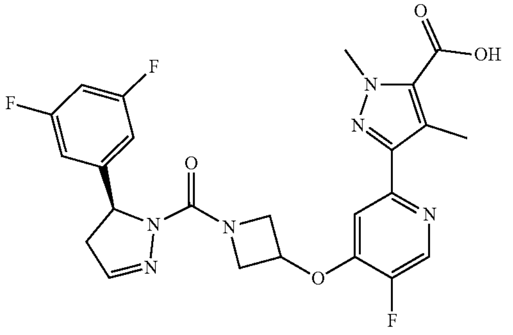
246
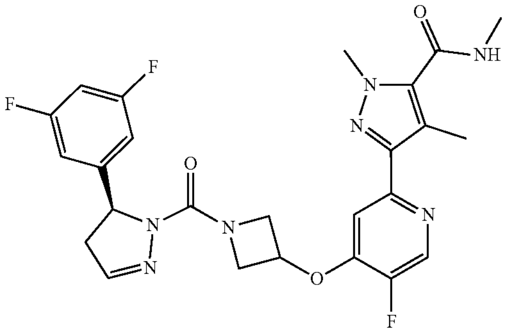
247
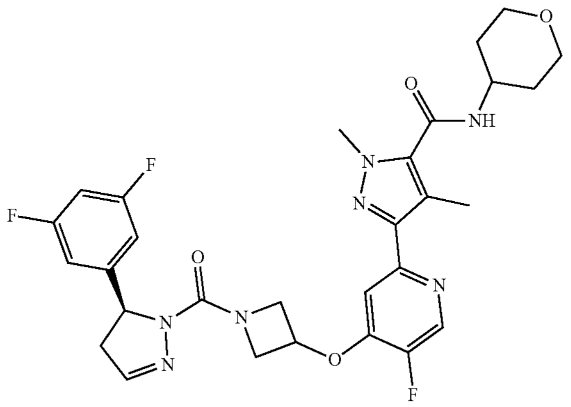
248
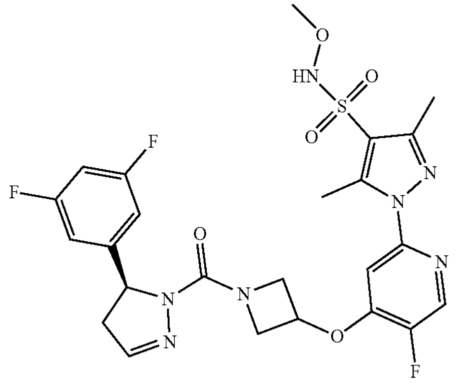
249
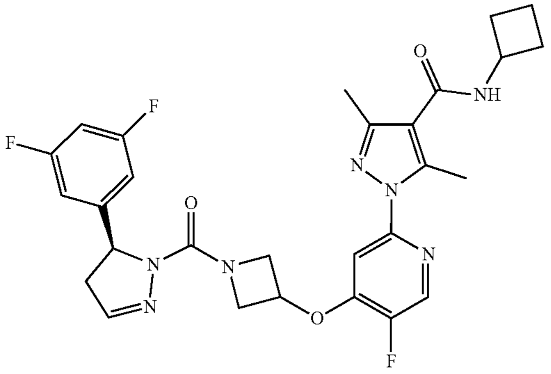
250
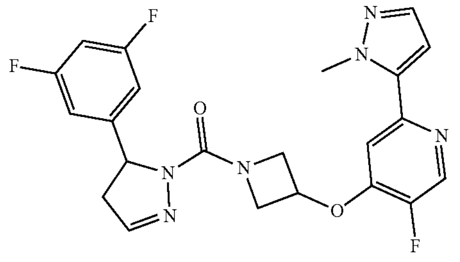

-continued
251
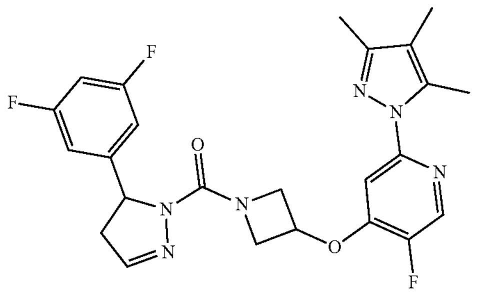
252
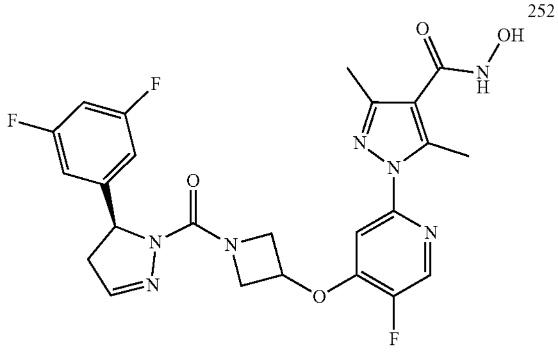
253
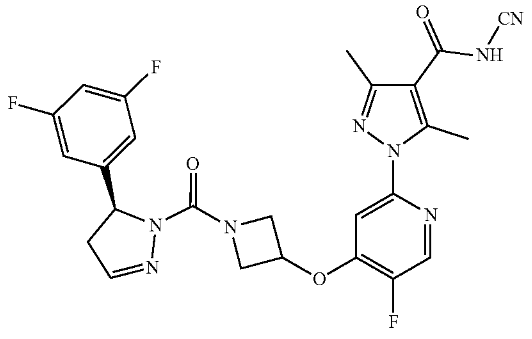
254
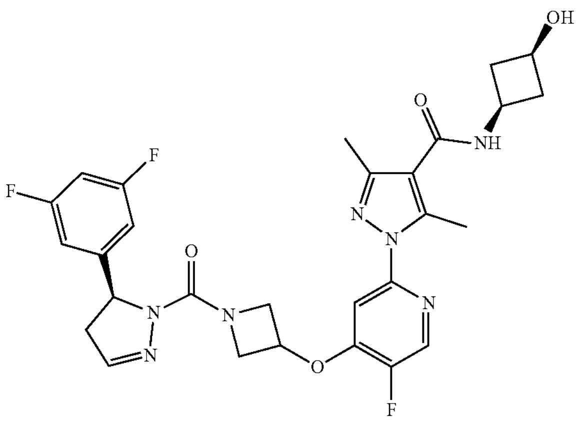
-continued
255
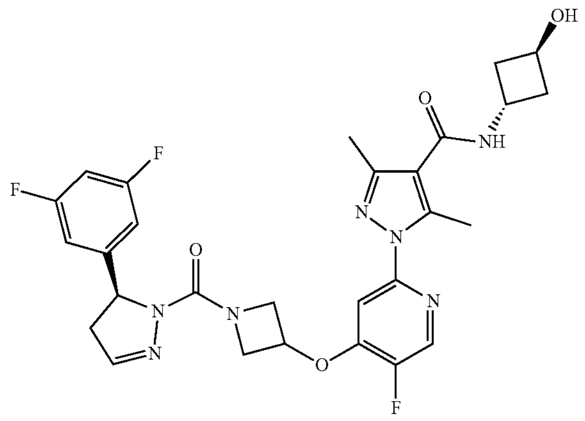
256
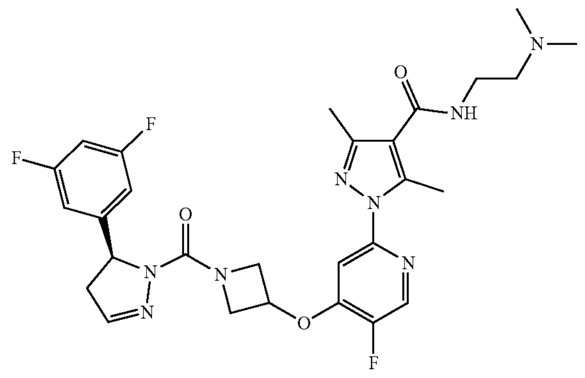
257
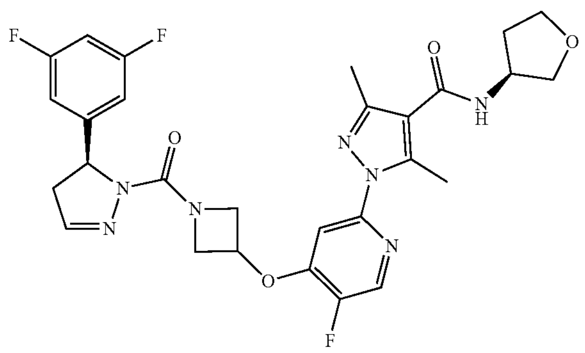
258
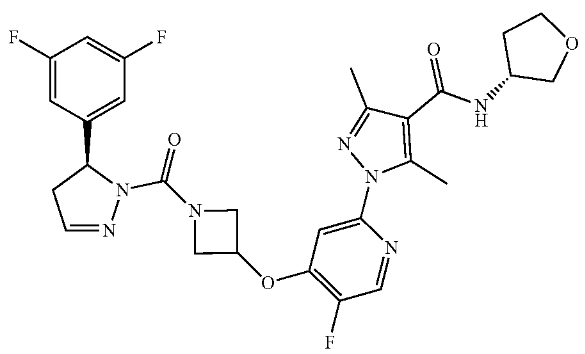

259
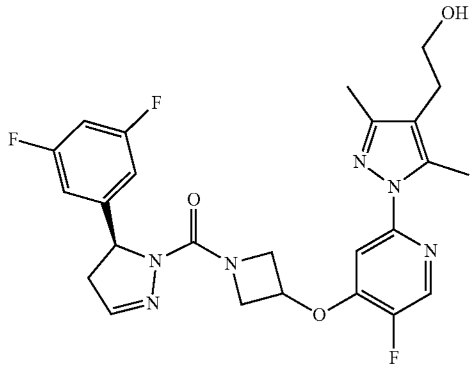
260
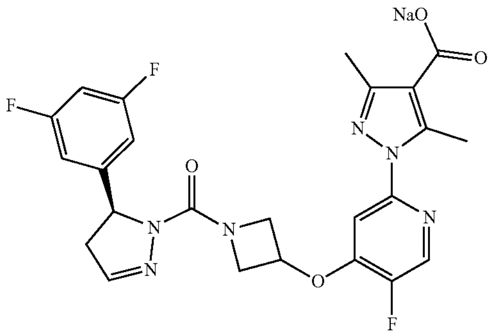
261
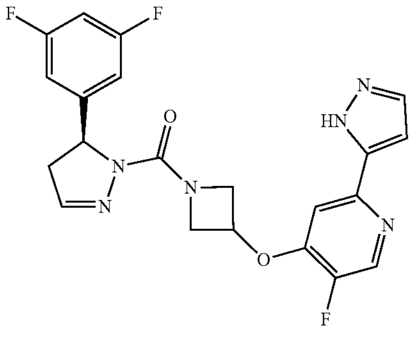
262
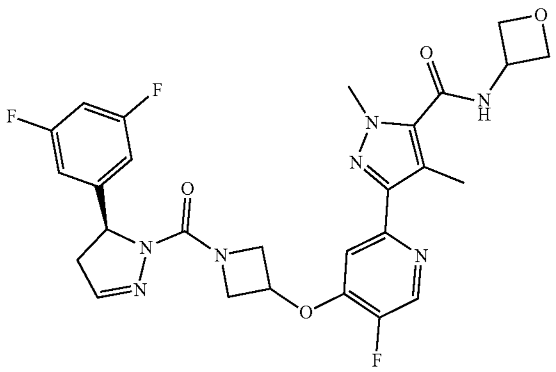
263
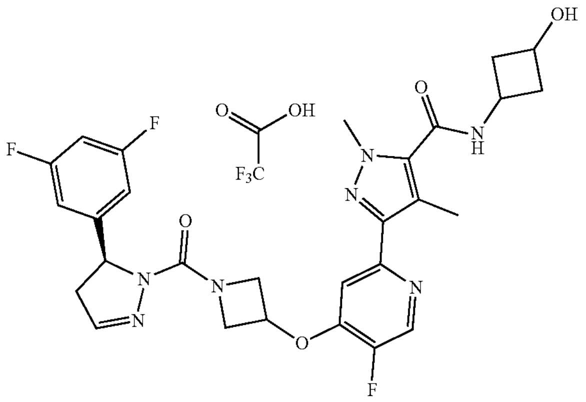
264
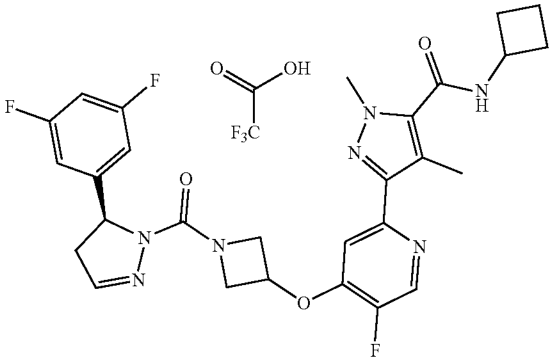
265
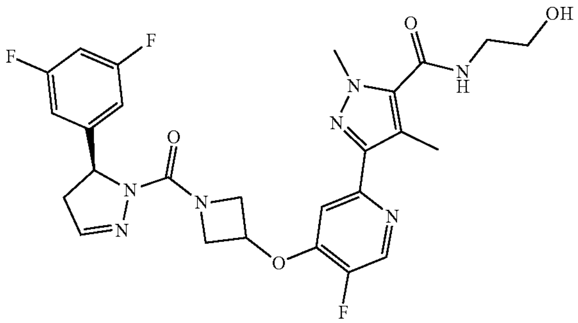
266
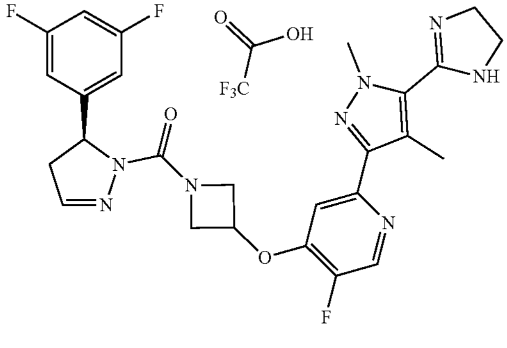

-continued
267
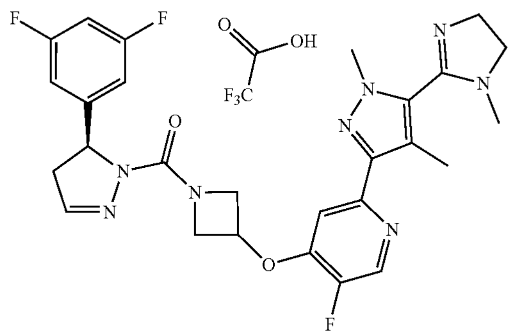
268
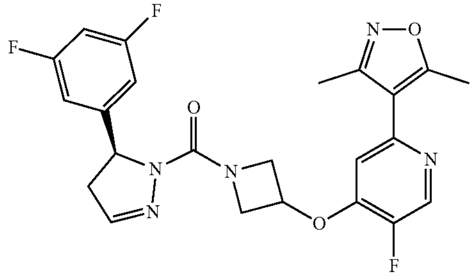
269
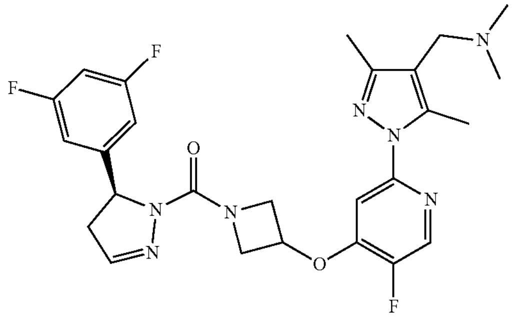
270
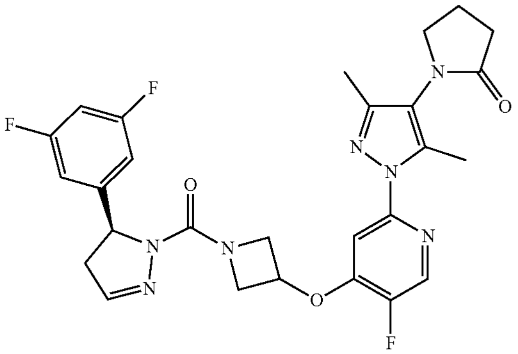
271
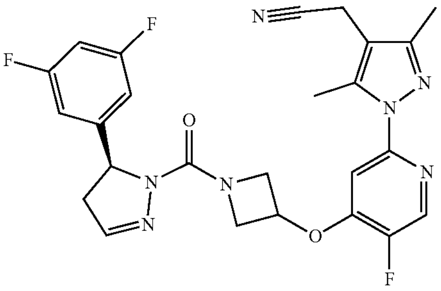
-continued
272
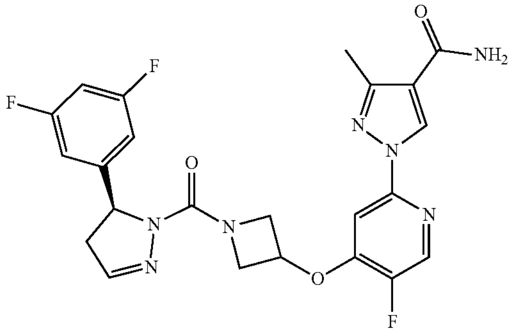
273
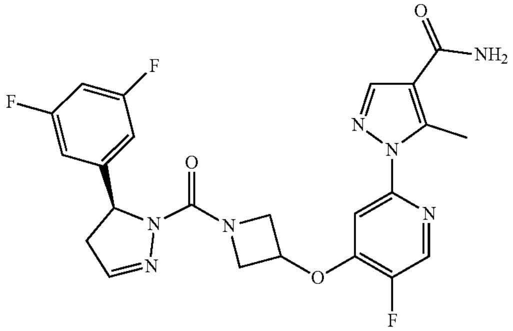
274
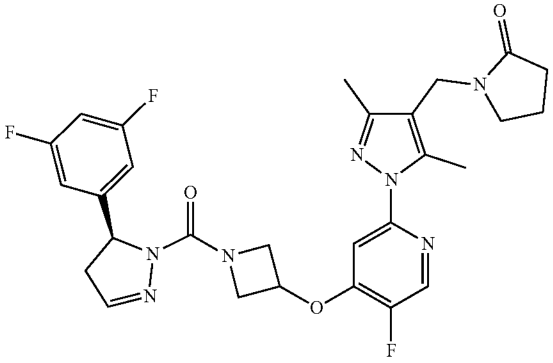
275
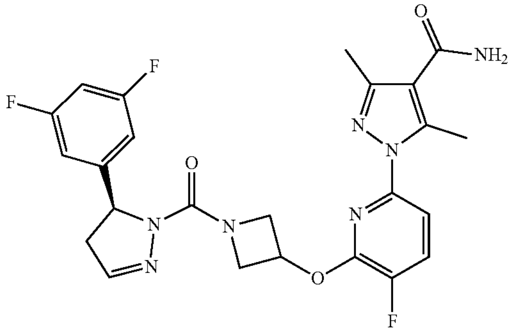

-continued
276
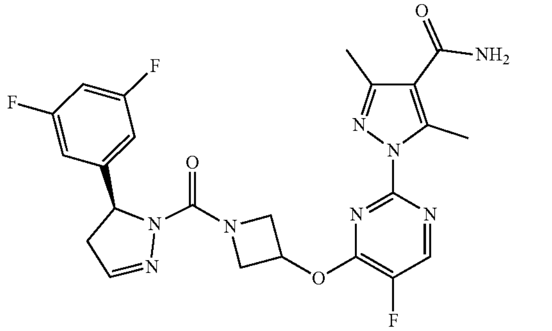
277
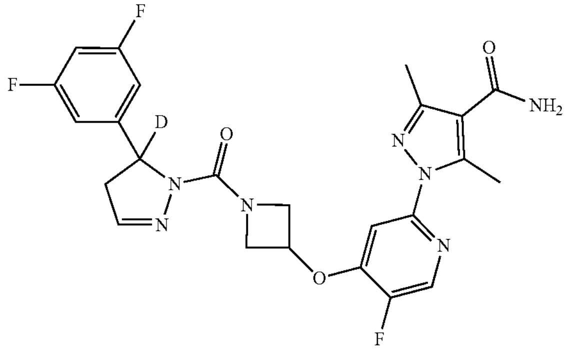
278
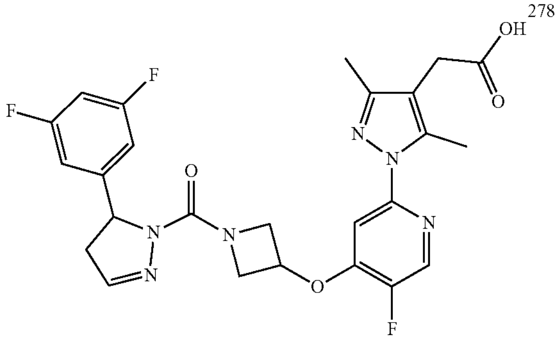
279
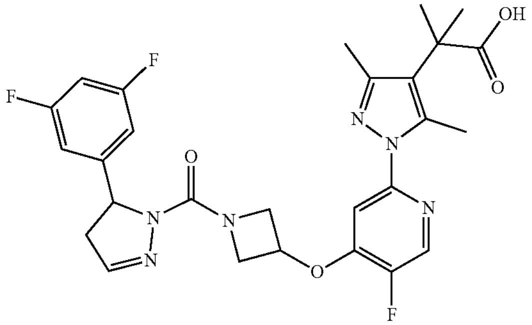
-continued
280
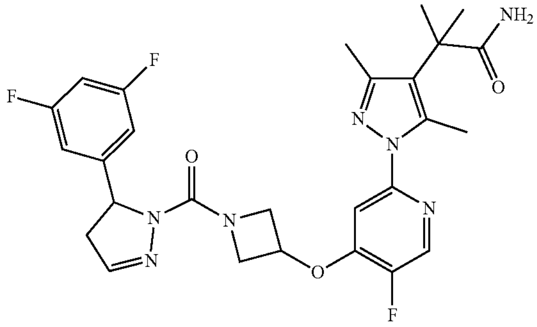
281
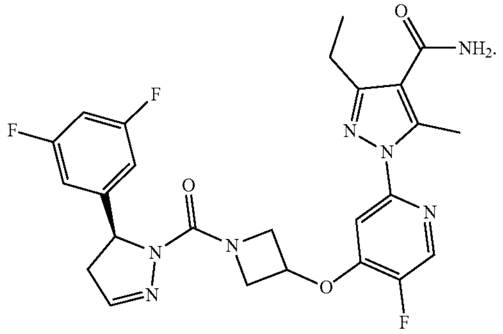
21. The compound, salt, hydrate, or stereoisomer of claim 20, wherein the compound has a structure selected from:
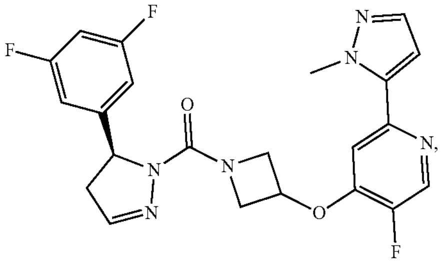
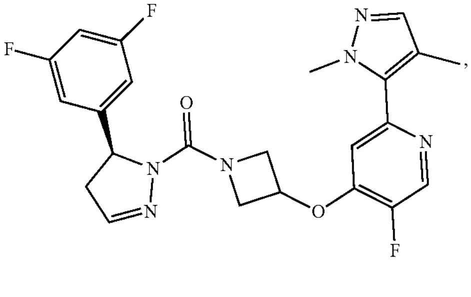

-continued

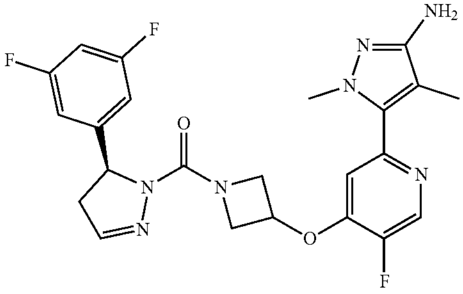

,

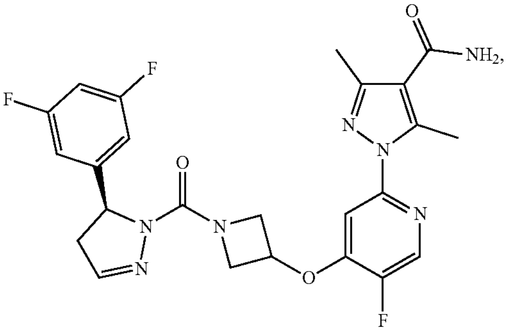

,

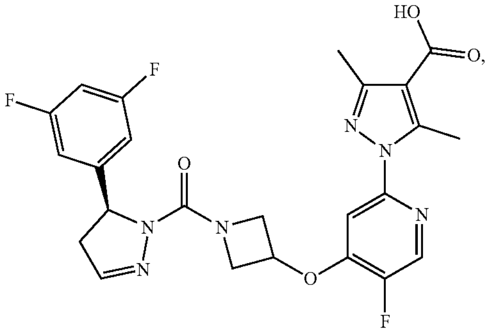

, and

-continued

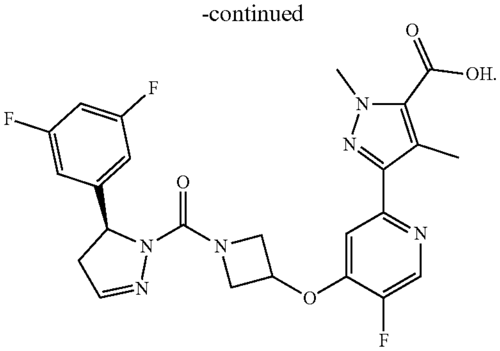

22. A pharmaceutical composition comprising a therapeutically effective amount of the compound, salt, hydrate, or stereoisomer of claim 1 and one or more pharmaceutically acceptable excipients, in predetermined, unit dosage form.

23. A pharmaceutical composition comprising a therapeutically effective amount of the compound, salt, hydrate, or stereoisomer of claim 15 and one or more pharmaceutically acceptable excipients, in predetermined, unit dosage form.

24. A method of treating an indication selected from brain injury, neurodegenerative diseases, viral infections, immune tolerance, and cancer in a person in need thereof, comprising administering to the person a therapeutically effective amount of the compound, salt, hydrate, or stereoisomer of claim 1.

25. A method of treating an indication selected from brain injury, neurodegenerative diseases, viral infections, immune tolerance, and cancer in a person in need thereof, comprising administering to the person a therapeutically effective amount of the compound, salt, hydrate, or stereoisomer of claim 15.

26. A method of inhibiting RIP1 in a person in need thereof, comprising administering to the person a therapeutically effective amount of the compound, salt, hydrate, or stereoisomer of claim 1.

27. A method of inhibiting RIP1 in a person in need thereof, comprising administering to the person a therapeutically effective amount of the compound, salt, hydrate, or stereoisomer of claim 15.

* * * * *